(12) United States Patent
Okano et al.

(10) Patent No.: US 7,569,354 B2
(45) Date of Patent: Aug. 4, 2009

(54) CELLOMICS SYSTEM

(75) Inventors: Kazunori Okano, Tokyo (JP); Kenji Yasuda, Tokyo (JP)

(73) Assignee: OnChip Cellomics Consortium, Tokyo (JP)

( * ) Notice: Subject to any disclaimer, the term of this patent is extended or adjusted under 35 U.S.C. 154(b) by 449 days.

(21) Appl. No.: 11/195,662

(22) Filed: Aug. 3, 2005

(65) Prior Publication Data

US 2007/0059763 A1    Mar. 15, 2007

(30) Foreign Application Priority Data

| Aug. 3, 2004 | (JP) | 2004-226359 |
| Aug. 3, 2004 | (JP) | 2004-226361 |
| Aug. 4, 2004 | (JP) | 2004-227640 |
| Aug. 4, 2004 | (JP) | 2004-227686 |
| Aug. 25, 2004 | (JP) | 2004-244575 |
| Aug. 30, 2004 | (JP) | 2004-249659 |
| Sep. 8, 2004 | (JP) | 2004-260501 |
| Sep. 13, 2004 | (JP) | 2004-264866 |
| Sep. 17, 2004 | (JP) | 2004-270768 |
| Sep. 24, 2004 | (JP) | 2004-276558 |
| Sep. 28, 2004 | (JP) | 2004-281347 |
| Sep. 29, 2004 | (JP) | 2004-283715 |
| Sep. 30, 2004 | (JP) | 2004-287133 |
| Sep. 30, 2004 | (JP) | 2004-287197 |
| Sep. 30, 2004 | (JP) | 2004-287249 |
| Oct. 1, 2004 | (JP) | 2004-289554 |
| Oct. 5, 2004 | (JP) | 2004-292142 |
| Oct. 12, 2004 | (JP) | 2004-297184 |
| Oct. 12, 2004 | (JP) | 2004-297194 |
| Oct. 13, 2004 | (JP) | 2004-298529 |
| Oct. 14, 2004 | (JP) | 2004-299647 |
| Oct. 20, 2004 | (JP) | 2004-305258 |
| Nov. 1, 2004 | (JP) | 2004-317701 |
| Nov. 2, 2004 | (JP) | 2004-318770 |
| Nov. 5, 2004 | (JP) | 2004-323395 |
| Dec. 2, 2004 | (JP) | 2004-349583 |
| Dec. 2, 2004 | (JP) | 2004-349609 |
| Dec. 24, 2004 | (JP) | 2004-372938 |
| Dec. 28, 2004 | (JP) | 2004-379351 |
| Mar. 7, 2005 | (JP) | 2005-062098 |

(51) Int. Cl.
*G01N 33/53* (2006.01)

(52) U.S. Cl. .......................... 435/7.1; 435/39

(58) Field of Classification Search ........ None
See application file for complete search history.

(56) References Cited

U.S. PATENT DOCUMENTS 5,372,783 A * 12/1994 Lackie ............... 422/68.1

2003/0129170 A1 * 7/2003 Iacovitti et al. .......... 424/93.21

FOREIGN PATENT DOCUMENTS

| JP | 2004-81085 | 3/2004 |
| JP | 2004-81086 | 3/2004 |
| JP | 2004-144521 | 5/2004 |
| WO | WO 2004/061131 A1 | 7/2004 |

OTHER PUBLICATIONS

Aller CB, Ehmann S, Gilman-Sachs A, Snyder AK. Flow cytometric analysis of glucose transport by rat brain cells. Cytometry. Mar. 1, 1997;27(3):262-8.*

Uldry M, Thorens B. The SLC2 family of facilitated hexose and polyol transporters. Pflugers Arch. Feb. 2004;447(5):480-9. Epub May 16, 2003.*

Nishida, Masashi, et al., Isolation and Characterization of Human and Rat Cardiac Microvascular Endothelial Cells, *Am. J. Physiol.* 264 (Heart Circ. Physiol 33): pp. H639-H652, 1993.

Takahashi, Kazunori, et al., Non-Destructive On-Chip Cell Sorting System with Real-Time Microscopic Image Processing, *Journal of Nonobiotechnology*, vol. 2, 2004.

Hoerstrup, Simon P., et al., Fluorescense Activated Cell Sorting: A Reliable Method in Tissue Engineering of a Biprosthetic Heart Valve, *The Society of Thoracic Surgeons*, vol. 66, pp. 1653-1657, 1998 (published by Elsevier Science, Inc.).

Davis, Kenneth A., et al., Staining of Cell Surface Human CD4 with 2'-F-Pyrimidine-Containing RNA Aptamers for Flow Cytometry, *Nucleic Acids Research*, vol. 26, No. 17, pp. 3915-3924, 1998.

Lupold, Shawn E., et al., Identification and Characterization of Nuclease-Stabilized RNA Molecules That Bind Human Prostate Cancer Cells Via the Prostate-Specific Membrane Antigen, *Cancer Research* 62, pp. 4029-4033, Jul. 15, 2002.

Michael E. Kamarck, "Fluorescence-Activated Cell Sorting of Hybrid and Transfected Cells", Methods in Enzymology, vol. 151, 1987.

(Continued)

*Primary Examiner*—James S Ketter
(74) *Attorney, Agent, or Firm*—Antonelli, Terry, Stout & Kraus, LLP.

(57) ABSTRACT

In labeling a cell, and separating and collecting the cell according to a degree of the labeling using a cell separator, effects on the cell is minimized and the use of the collected cell is facilitated, thereby, when labeling a cell, the cell is labeled in the state where interaction of each cell is retained. In the labeling, a specific labeling material present on a surface of a target cell is taken in the cell via a transporter, and the cell is dispersed one by one to separate the same with a cell separator. Immediately after the separation, the cell is put in a solution not containing the specific labeling substance to remove the specific labeling substance taken in the cell. This series of steps is continuously conducted with a cell separation chip.

7 Claims, 136 Drawing Sheets

OTHER PUBLICATIONS

Leslie Malmgren et al., A Sensitive Method for Histochemical Demonstration of Horseradish Peroxidase in Neurons Following Retrograde Axonal Transport., Neuropathological Laboratory, Institute of Pathology, University of Uppsala, Uppsala (Sweden), pp. 279-294.

Gary F. Blackburn et al., Electrochemiluminescence Detection for Development of Immunoassays and DNA Probe Assays for Clinical Diagnostics, Clinical Chemistry, vol. 37, No. 9, 1991, pp. 1534-1539.

Takushi Hirono et al., "Recognition of Artificial Microstructures by Sensory Nerve Fibers in Culture", 1988 Elsevier Science Publishers B.V. (Biomedical Division), pp. 189-194.

Richard E. Mains et al., "Primary Cultures of Dissociated Sympathetic Neurons", The Journal of Cell Biology, vol. 59, 1978 pp. 329-345.

Steve M. Potter, et al., "A New Approach to Neural Cell Culture For Long-Term Studies", Journal of Neuroscience Methods 110 (2001) 17-24, pp. 17-24.

Y. Jimbo et al., "Simultaneous Induction of Pathway-Specific Potentiation and Depression in Networks of Cortical Neurons", Biophysical Journal, vol. 76, Feb. 1999, pp. 670-678.

Paul C. Letourneau, "Chemotactic Response of Nerve Fiber Elongation to Nerve Growth Factor", Developmental Biology 66, pp. 183-196 (1978).

David Stopak et al., "Connective Tissue Morphogenesis by Fibroblast Traction", Developmental Biology 90, pp. 383-398 (1982).

Stephen P.A. Fodor et al., "Light-Directed, Spatially Addressable Parallel Chemical Synthesis", Research Article, Feb. 15, 1991, pp. 767-773.

Gennady Yershov et al., "DNA Analysis and Diagnostics on Oligonucleotide Microchips", Proc. Natl. Acad. Sci. USA, vol. 93, pp. 4913-4918, May 1996 Genetics.

Kazunori Okano et al., "Using Microparticle Labeling and Counting for Attomole-Level Detection in Heterogeneous Immunoassay", Analytical Biochemistry 202, pp. 120-125 (1992).

James E. Watterson et al., "Effects of Oligonucleotide Immobilization Density on Selectivity of Quantitative Transduction of Hybridization of Immobilized DNA", Langmuir 2000, 16, pp. 4984-4992.

Alexander W. Peterson et al., "The Effect of Surface Probe Density on DNA Hybridization", 2001 Oxford University Press, Nucleic Acids Research, 2001, vol. 29, No. 24, pp. 5163-5168.

Tomi Pastinen et al., "Minisequencing: A Specific Tool for DNA Analysis and Diagnostics on Oligonucleotide Arrays", Genome Research, 1997 by Cold Spring Harbor Laboratory Press, pp. 606-614.

Leslie Malmgren et al., A Sensitive Method for Histochemical Demonstration of Horseradish Peroxidase in Neurons Following Retrograde Axonal Transport., Neuropathological Laboratory, Institute of Pathology, University of Uppsala, Uppsala (Sweden), pp. 279-294, Brain Res., vol. 148 (1978).

* cited by examiner (a)

(b)

(a)

(b)

(a)

(b)

(a)

(b)

(A)

(B)

(A)

(B)

(A)

(B)

(A)

(B)

(A)

(B)

a) Set up b) Pierce the cell membrane c) Nucleus membrane shield d) Cleaning of capillary outer-wall e) Detachment of capillary (a)

(b)

(c)

(d)

(A)

(B)

(A)

(B)

(C)

(A)

(B)

(C)

(A)

(B)

(C)

(D)

(A)

(B)

(A)

(B)

(A)

(B)

Electrophoresis run (s)

(A)

(B)

(A)

(B)

(A)

(B)

(A)

(B)

SEQUENCE LISTING

<160> NUMBER OF SEQ ID NOS: 18

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ctgagcgagt gagaacctac tg                                           22

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
agccacatca gctatgtcca                                              20

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gtatgagaag gctgagataa agg                                          23

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
agctgcttat attttgagta cagg                                         24

<210> SEQ ID NO 5
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
agcaucgagu cggccuuguu ggccuacugg                                   30

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
agcatcgagt cggccttgtt g          21

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aagccacatc agctatgtcc aca          23

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aaggaacagt gatgcatgta gatt          24

<210> SEQ ID NO 9
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
aaaaucuucu ucuaugacuc agagaauccu ccugcaucag aggugcuucg          50

<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cgaagcacct ctgatgcagg aggattctct gagtcataga agaagatttt          50

<210> SEQ ID NO 11
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aaaaaaaaaa aaaaaaaaaa aaaatcttct tctatgactc agagaatcct cctgcatcag          60
aggtgcttcg aaaaaaaaaa aaaaaaaaaa          90

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 12
agaatcctcc tgcatcagag gtgcttcgaa tccagaacat tctaacagaa            50

<210> SEQ ID NO 13
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
agaatcctcc tgcatcagag gtgbttbgaa tccagaacat tctaacagaa            50

<210> SEQ ID NO 14
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (27)..(66)
<223> OTHER INFORMATION: a, c, g, t, unknown or other

<400> SEQUENCE: 14
taatacgact cactataggg agacaannnn nnnnnnnnnn nnnnnnnnnn nnnnnnnnnn     60
nnnnnnttcg acaggaggct cacaacagg                                     89

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(8)
<223> OTHER INFORMATION: Arg residue may or may not be present

<400> SEQUENCE: 15

Arg Arg Arg Arg Arg Arg Arg Arg
 1               5

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aagccacatc agctatgtcc aca                                         23

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Arg Arg Arg Arg Arg
```

-continued

```
<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tttttttttt tttttttttt tttttttttt                                      30
```

CELLOMICS SYSTEM

FIELD OF THE INVENTION

The present invention relates to promotion of researches in the field of cellomics for comprehensively understanding vital functions as those of a cell assembly, and more particularly to measurement of expression of genes in discrete cells in the state where functions of each cell structure are preserved, namely in the state where interactions between cells are preserved.

BACKGROUND OF THE INVENTION

With the active researches in the fields of genomics or proteomics from the last decade of $20^{th}$ century up to this day, data has been accumulated concerning types and quantities of genes in various cell groups each regarded as an assembly of cells. Especially, accumulation of data concerning precise comparisons among genome sequences different from species to species, or frequencies of expression of various genes in organs and tissues in one species has reached a level allowing sketchy descriptions of the life process. In the future, various active researches will be made not only for accumulation of data, but also for development of more advanced analysis methods for acquiring data allowing clarification of the life process at a higher level. This clarification of the life process at a higher level is a research scheme called cellomics, and different from the researches using homogeneous cell systems basically prepared by the cloning technique in the past, complex systems each formed with multicellular aggregate each having different functions are treated as objects for research in the field of cellomics.

For promotion of researches in the field of cellomics for comprehensively understanding vital functions as those of a cell assembly, it is necessary to measure expression of genes in discrete cells in the state where functions of each cell structure are preserved, namely in the state where interactions between cells are preserved. To achieve this objective, it is necessary to develop a technique for measuring local expressions of all concerned genes at a level of a cell, which has been impossible in the prior art.

For instance, the genes involved in the circadian rhythm have been identified, and the relation between the cycle and external factors (impetuses) such as insolation has been clarified. The researches as described above are generally carried out using DNA micro-arrays or kinetic PCR which is more quantitative (sometimes called as real time PCR). It is not too much to say, however, that there are few cases, excluding the cases fluctuating with certain cycles such as the circadian rhythm, in which precise data can be obtained from data concerning frequency of gene expressions. The main reason for this is that the relation between the sensitivity and reproducibility has not sufficiently be clarified in the researches using DNA micro-arrays.

To obtain data concerning a frequency of expression of a gene, mRNAs extracted from at least several hundreds of cells are required. By amplifying these mRNAs in the form of cRNAs or cDNAs, the mRNAs can be finally detected in the current situation. If the sensitivity is just insufficient, it is simply required to further amplify the mRNAs in the form of cRNAs or cDNAs, but in the quantitative analysis, sometimes amplifying operations cause errors. Even if it is tried to analyze gene expression (including protein translation) in discrete cells in the tissue, it is impossible to obtain a sufficient quantity of amplification products from a discrete cell with the conventional amplifying operation using, for instance, a DNA micro-array, and even when amplification is forcefully performed to a level allowing for analysis with a DNA micro-array, it is impossible to obtain data reflecting the actual abundance ratio of mRNAs.

Researchers in this field are not satisfied with the knowledge currently available in the fields of genomics and proteomics, and the many researchers are aware of the importance of analysis of a complex system formed with multiple cells at the "cell" level, namely the potential importance of cellomics described above. Further, as an expected application of the cellomics for industrial purposes, many researchers point out the importance of development of the measuring technique at the "cell" level available as an alternative for animal experiments in relation to recent developments of genomic sciences, acceleration of drug developments, and development of pharmaceuticals and chemicals which are safer as compared to those currently available in the market. At present, a vast number of laboratory animals such as guinea pigs or crab-eating macaque are used in experiments for testing the safety or effects of chemical substances such as pharmaceuticals or cosmetics.

However, it has been impossible to overcome the differences between humans and other animals, now the tendency for abolishing the animal experiments has been becoming stronger. When the circumstances as described above are taken into consideration, the preparation, along with its excellent reproducibility, of cell groups each having the minimal functions on the basis of a cell, and of a human cell, and also development of a testing system using the cell groups are conceivably essential to the industries and to realization of safer and more comfortable life of mankind. The cellomics enables researches and development of the technique for realization of the objects as described above.

SUMMARY OF THE INVENTION

In the cellomics, a cell is grasped and understood in relation to a cell assembly, and the understanding and knowledge are applied to the industrial utilization as described above, and the cellomics is not complete only with establishment of discrete techniques, and for promoting industrial utilization of cell measurement in a multicellular organism, it is necessary to build up a system satisfying the following three requirements:

1) technique for separating a specified cell,
2) technique for culturing the separated cell, and
3) analysis (or utilization) of the cultured cell.

Herein the "technique for separating a specified cell" means separation of cells involving in a specific function of an organ tissue such as a tissue stem cell. There is a case where the separated cell is immediately analyzed, and in this case, a technique is required for destructing the separated cell according to a prespecified procedure and quantitatively analyzing the mRNA or proteins included in the cell. Assuming that the cell size is about 10 µm, a means for analysis corresponding to the size is required.

Naturally the technique for achieving the object above is important, but only a passive analysis of a separated cell is insufficient for implementing the cellomics enabling breakthrough from the omics researches in the prior art. A key for development of cellomics is establishment of active analysis of a separated cell. The technique for active analysis of a separated cell as used herein indicates a cell networking technique for forming a desired pseudo tissue by placing the separated cell at a specified position or a technique making it possible for a researcher to give an electrical or chemical impetus to each discrete cell in a cell network organized by the researcher for obtaining a response from the cell. For achieving this objective, it is necessary to analyze a cell without killing the cell. Further it is necessary to establish a technique enabling analysis of proteins and mRNAs in each discrete cell in a cell network artificially constructed to clarify the differences between cells or distribution of the substances in each cell.

For achieving the cellomics as described above, the present inventors have made efforts for theoretical research and development of a technique allowing constitutively forming and measuring a cell network at a level of "one cell" on a microchip by making use of micro-fabrication of a particular cell separated from a tissue, and invented a cellomics system including a cell culture chip, measuring devices and the like. Further by using the cellomics system, the inventors found the fact that responses of cell assemblies substantially vary according to differences in "assembly network patterns" such as a spatial position, a type, and the number of the cell assemblies, and recognized the importance of the co-working phenomenon of a "cell assembly/cell network" one rank higher than the simple "cell" level.

The inventors anticipated, based on the achievements as described above, the possibility of preparation of a cell assembly (network) expectedly allowing responses similar to those by actual organ tissues, which can hardly be measured with "cell lines belonging to a single species", by controlling "patterns" of the cell assembly/cell network according to the necessity. Therefore the present inventors propose herein the screening technique based on the "cell network" cultured by means of cell-by-cell control of the "patterns" of this cell assembly as the "on-chip cellomics" measuring technique.

Outline of the cellomics system according to the present invention is shown in FIG. 1. The present invention provides a general system including the broad items as described below, and researchers are required to carry out a series of operations according to the item order as described below.

1) A method and an apparatus for separating a target cell without giving substantial damages to the cell: The method also includes the steps of reversibly labeling a target cell, separating the cell, and reproducing the original cell by removing the labeled material.

2) A method and apparatus for immediately freezing and storing the separated cell according to the necessity 3) A method of and an apparatus for handling a cell: Namely a method of and an apparatus for freely handling a cell and inserting the cell into a cell culture microchip in the next step.

4) A method of and apparatus for culturing each separated cell discretely for a long time: This technique is required to allow for not only a long time incubation of a single cell but also constitutive construction of and measurement for a cell network at a "single cell level" on a microchip.

5) A method of an apparatus for acquiring information from an incubated cell or a network-constructed cell: This technique includes a method of and an apparatus for giving a stimulus to a cell network by adding a stimulating substance to a specified cell in the cell network, or by providing an electrode on a chip to stimulate a cell, and also a method of and an apparatus for measuring a response to a stimulus as an electric signal. Further the technique includes a method and an apparatus for measuring genes and proteins expressed in a cell. For achieving the objective as described above, either a method and an apparatus for destroying a cell and measuring the contents of the cell or a method of and an apparatus for acquiring information without killing the cell are employed according to the necessity.

Many methods for analysis and separation have been proposed and put into practical use in the field of cell researches and medical examination. For instance, for separation of a cell, flow cytometer has been developed and an apparatus for optically separating a cell is now available. For measurement of a separated cell, there have been developed the DNA micro-array technique, the in situ hybridization technique for detecting distribution of mRNA expressed in each discrete cell using a tissue fragment as a sample, or the immunohistochemistry for detecting distribution of proteins, and these techniques are now used for analyzing expression of a particular cell in a tissue. These techniques are used for analyzing functions of a cell or for differentiating a normal tissue from a cancer or tumor tissue, and therefore are used for screening a cancer.

These techniques have made great contributions to medical researches and services, however, when the techniques are viewed as those based on the cellomics system, the techniques are still insufficient in the points that the techniques do not systemize a series of steps from cell separation to detection, can not be used for active measurement, and can not be used for quantitative measurement for distribution of various substances in a cell.

An object of the present invention is to develop the researches on a cell assembly or a cell network constitutively constructed in the past into a pharmaceutical and medical screening system. The present system has the potentials of not only realization of a novel measurement technique at a cell level based on new understandings and recognition of the importance of "patterns" in a "cell network" not available so far, but also provision of new understandings concerning a life system based on the findings described above. In addition, if the cellomics system enabling measurement of a cell network base in place of animal experiments is successfully industrialized, high speed and low cost measurement using only a small number of samples will be possible not only in the fundamental researches but also in the field of screening technique for medical examination and food sanitary inspection, which would make great contributions to our health control.

BRIEF DESCRIPTION OF THE DRAWINGS

FIG. 26($b$) is a cross-sectional view showing the cell culture chip 100 above taken along the line A-A in the plan view and viewed in the direction indicated by the arrow; and FIG. 26(C) is a view illustrating a method of forming a droplet;

FIG. 66(A) is an enlarged view schematically showing a tip section 3 of a biological sample chip according to the thirteenth embodiment, while FIG. 66(B) is a perspective view schematically showing the biological sample chip according to the thirteenth embodiment;

FIG. 74(A) is a view showing a tip section 53 of a needle which may be employed in Example 3, while FIG. 74(B) is a perspective view showing general configuration of the needle which may be employed in Example 3;

FIG. 80(a) is a cross-sectional view schematically illustrating outline of a method of making a biological material separation chip which can be used in a biochemical material separator in Example 1 of a sixteenth embodiment of the present invention, while FIG. 80(b) is a cross-sectional view schematically showing one example of a structure of the completed biological material separation chip;

FIG. 94(A) is a cross-sectional view showing an example in which the measuring device based on the concept described in Example 1 is formed with a substrate and a chip-like detector placed on the substrate, while FIG. 94(B) is a plan view showing outline of the relation between the substrate of the measuring device and the chip-like detector placed on the substrate;

FIG. 115B is a cross-sectional view showing the DNA probe chip 100 shown in FIG. 115(A) taken along the line A-A and viewed in the direction indicated by the arrow;

FIG. 115C is a cross-sectional view showing details of a probe fixing area of the DNA probe chip 100 advantageously applicable to the twenty third embodiment;

FIG. 116A is a cross-sectional view showing the state in which a sample liquid containing a target polynucleotide is introduced onto a surface of the DNA probe chip;

FIG. 116B is a cross-sectional view showing the state in a first step of a process for forming a concentration gradient of the target polynucleotide from a solid-liquid interface between a surface of the DNA probe chip and of a sample liquid toward a sample liquid;

FIG. 116C is a cross-sectional view showing the state in the next step for forming the concentration gradient;

FIG. 117 is a diagram showing the effect in Example 2;

FIG. 118 is a view schematically showing the state in which an edge of the probe 12-1 is configured based on the concept according to a twenty third embodiment of the present invention and is fixed to a surface of a pillar 7;

Figure 120:
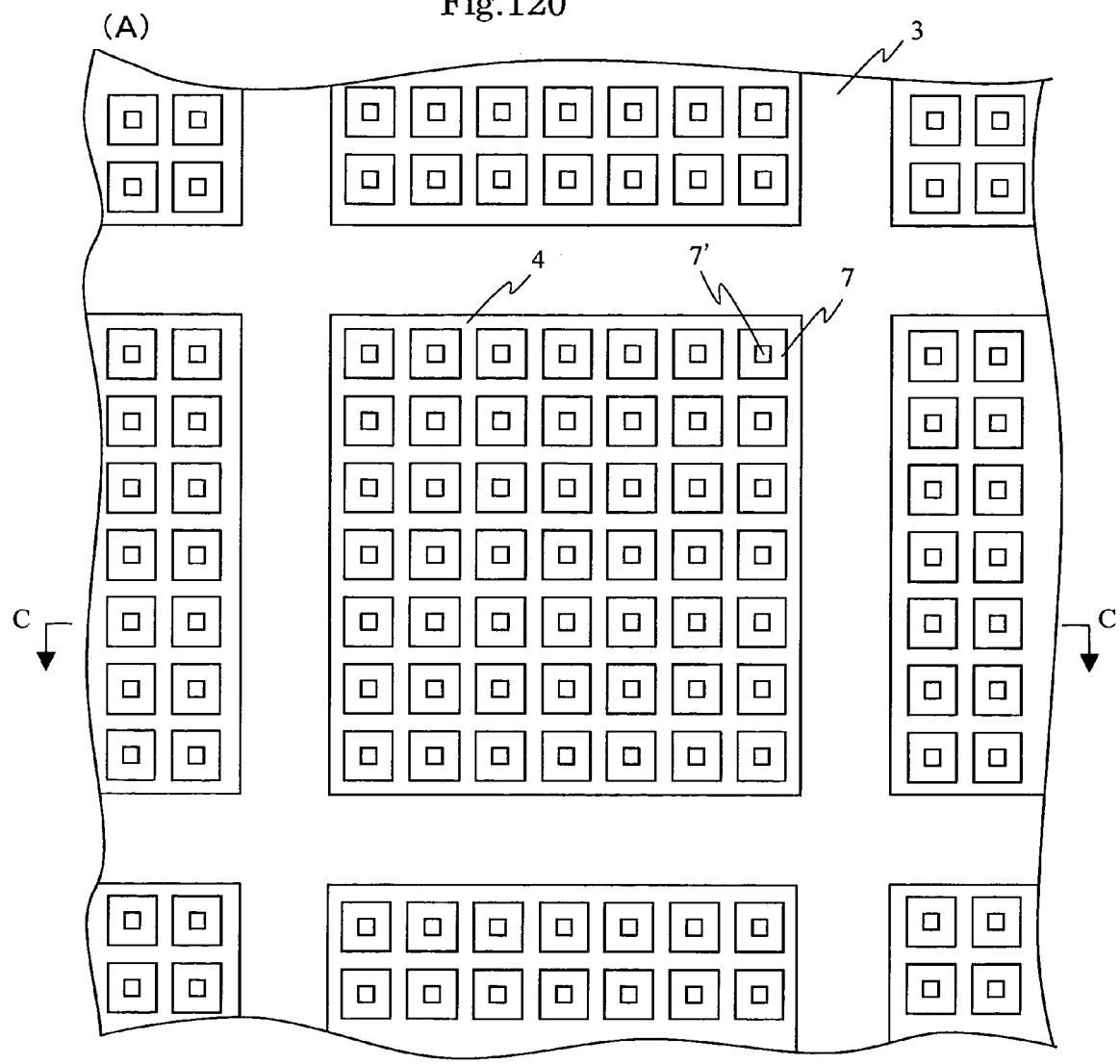
Figure 120:
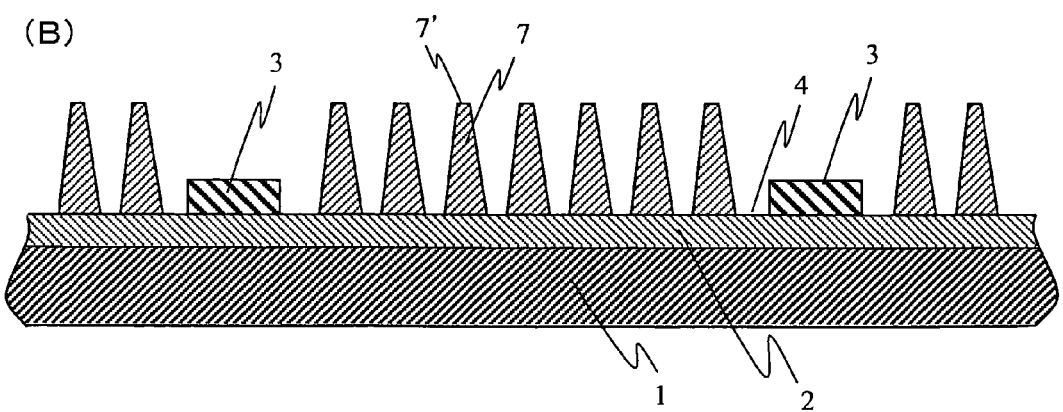
Figure 121A:
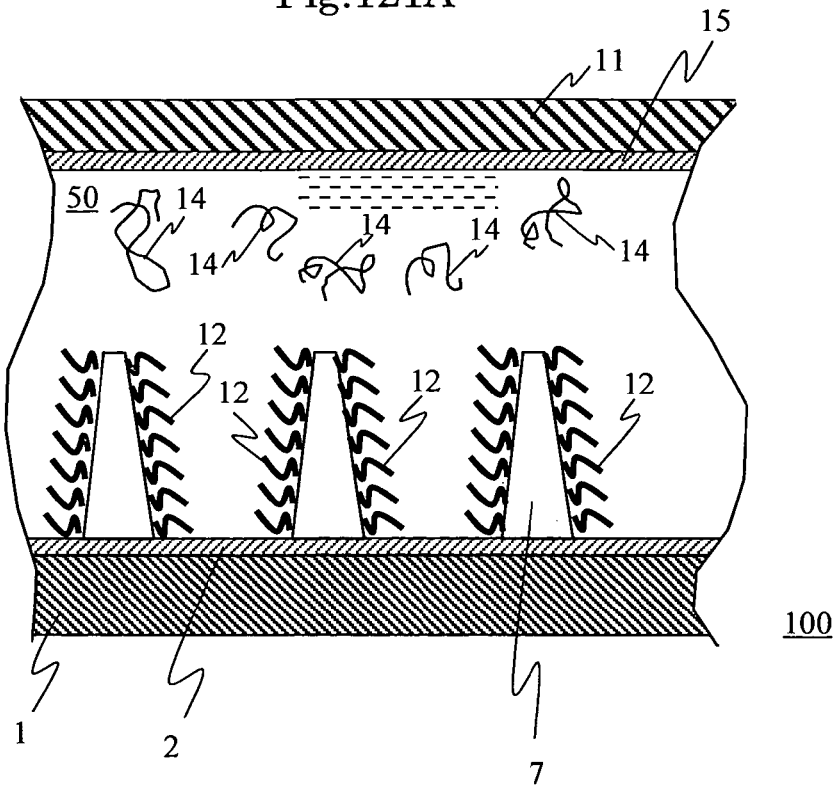
Figure 121B:
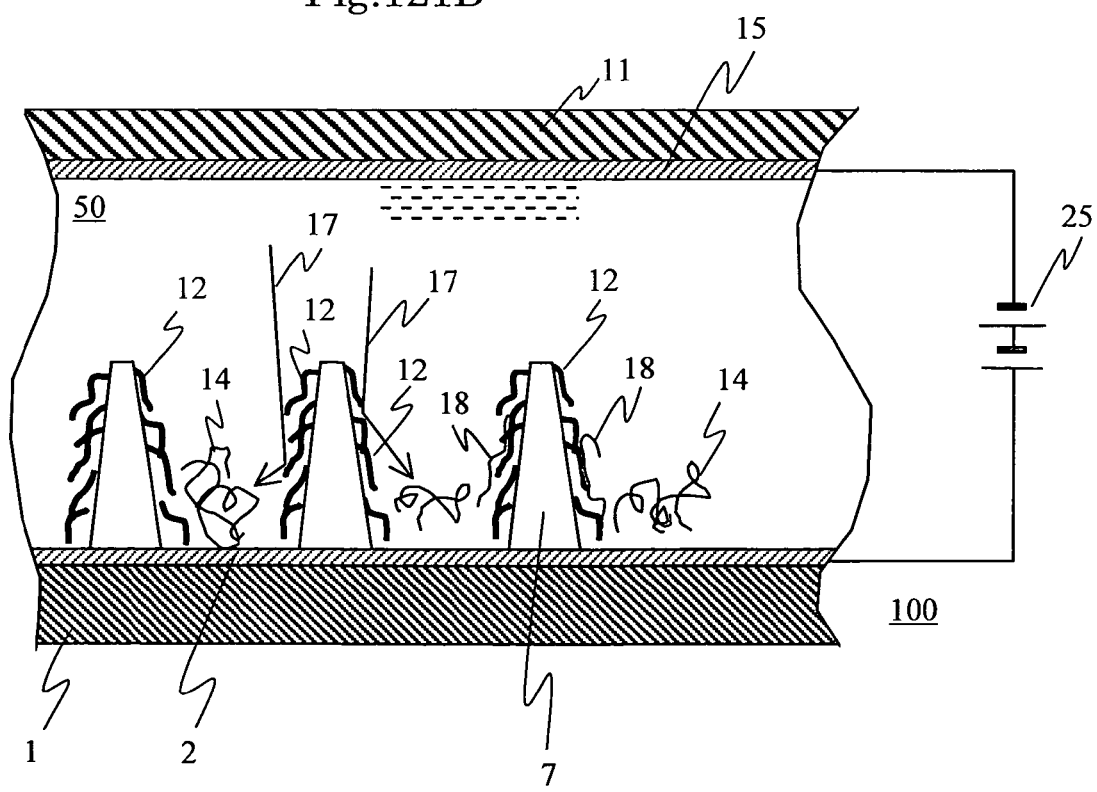
Figure 121C:
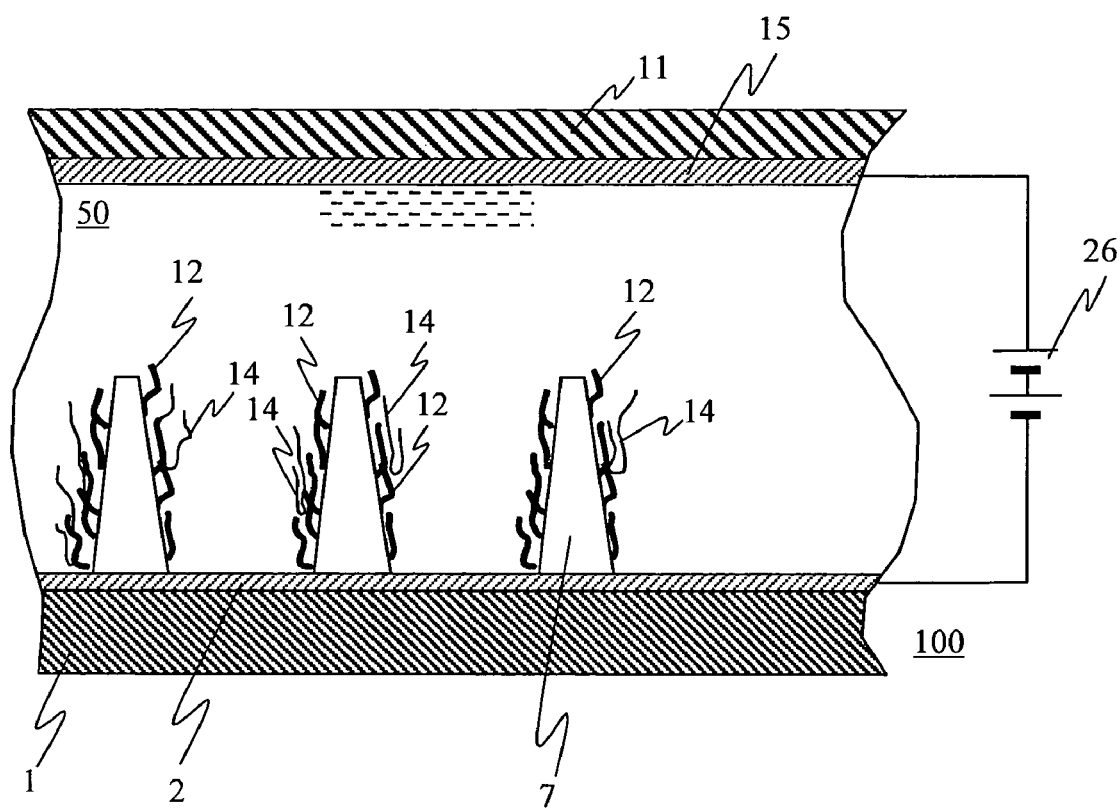
Figure 123:
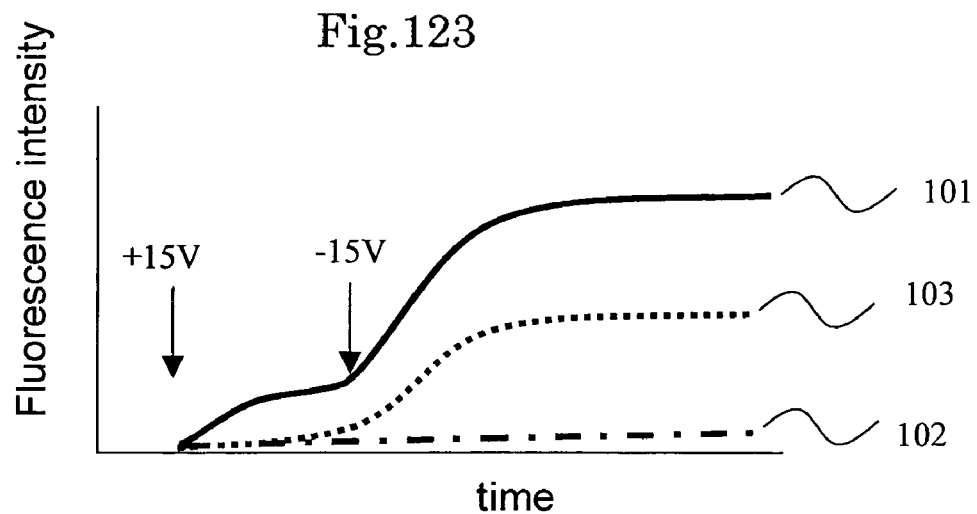
Figure 124:
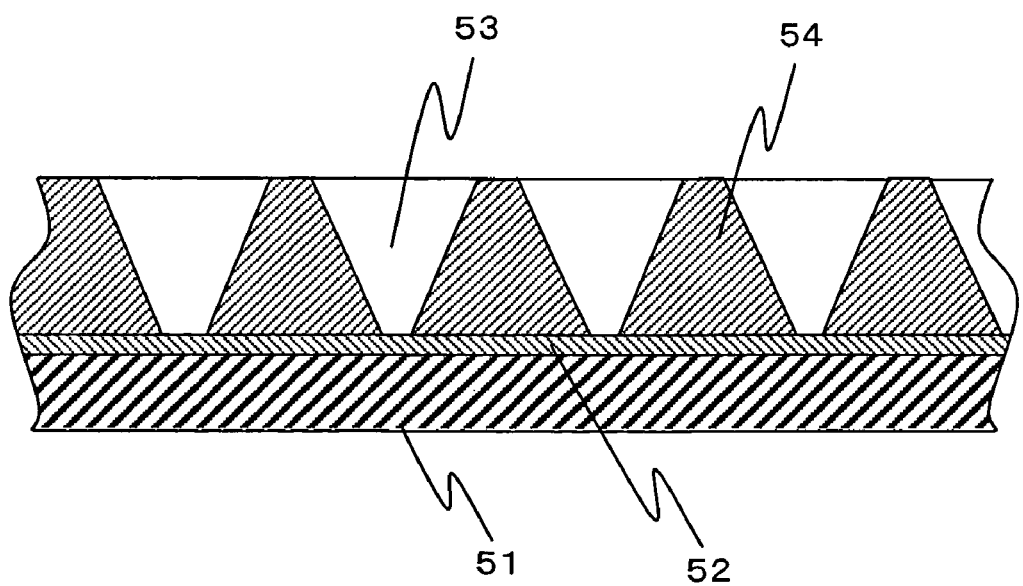
Figure 125:
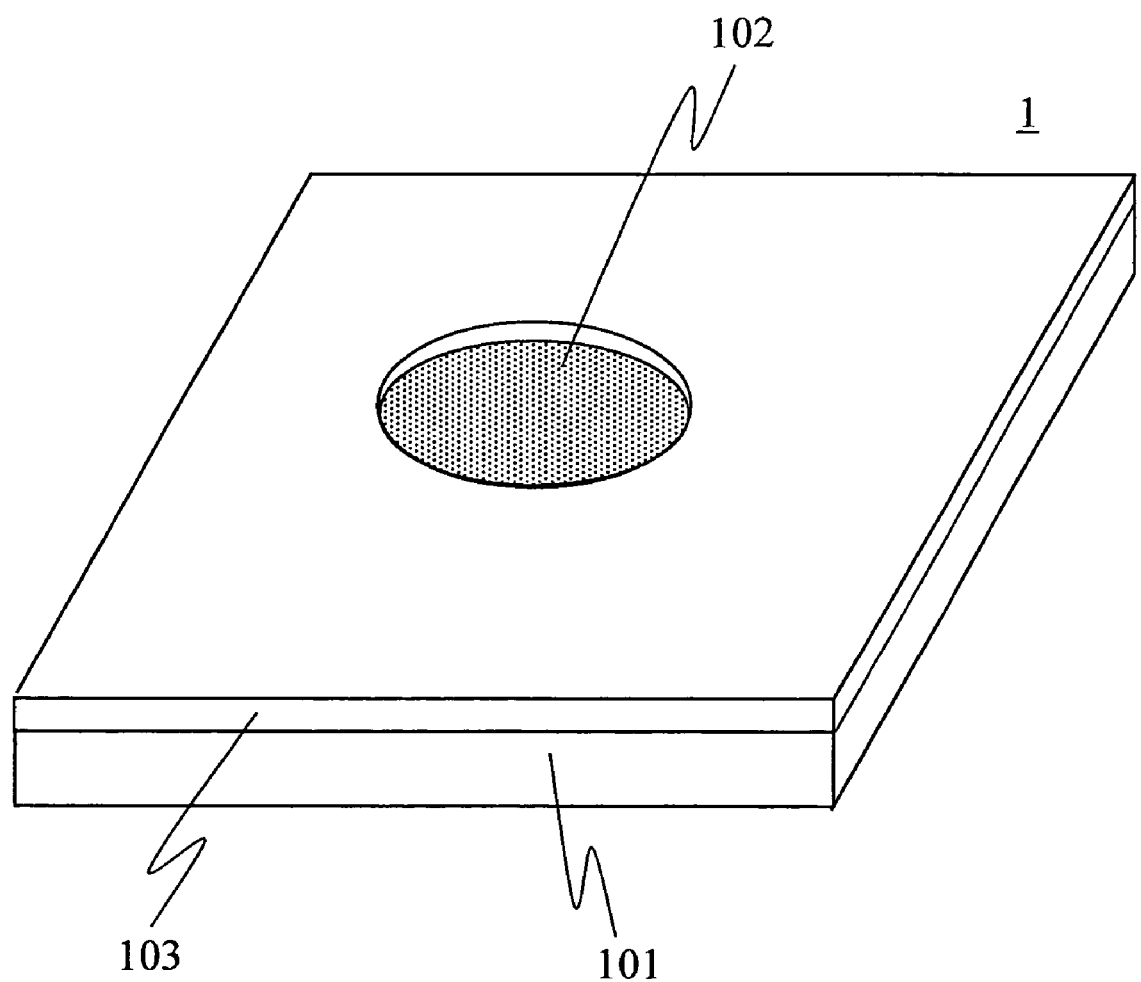
Figure 126:
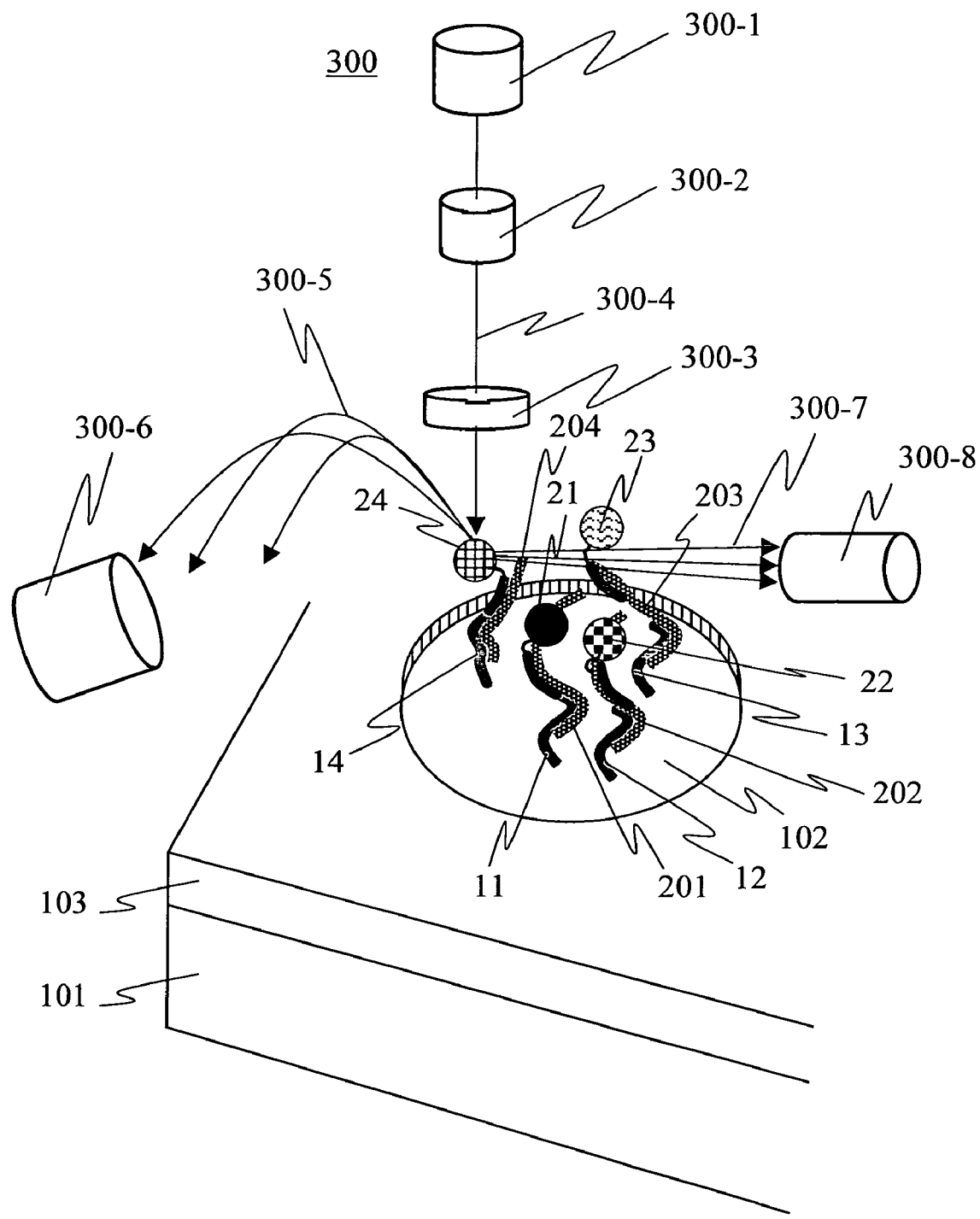
Figure 127:
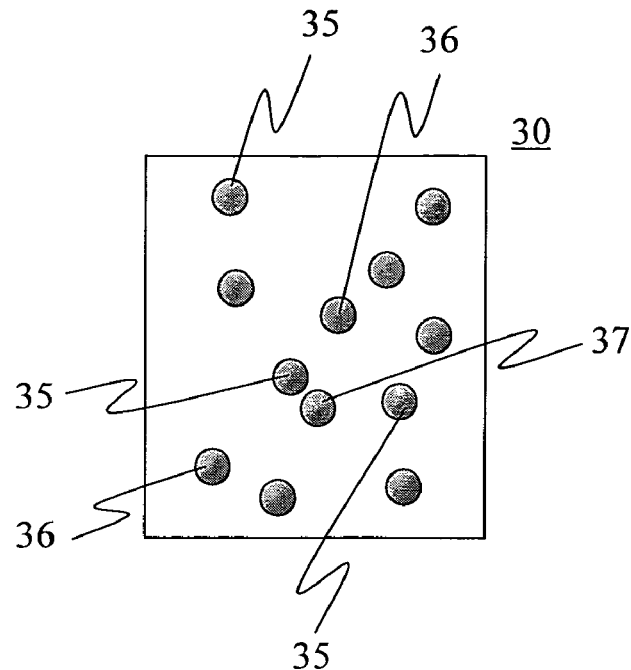
Figure 127:
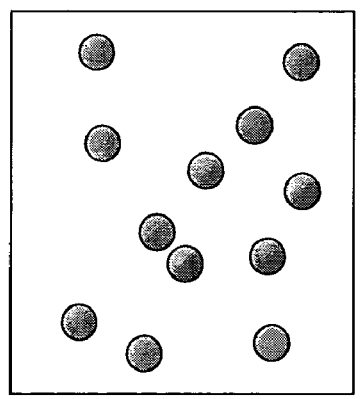
Figure 127:
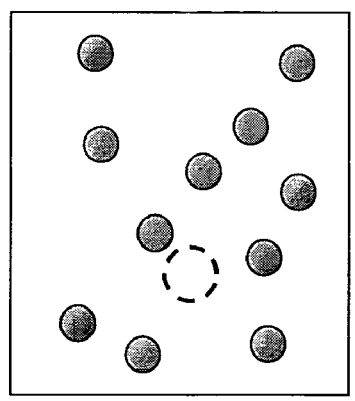
Figure 127:
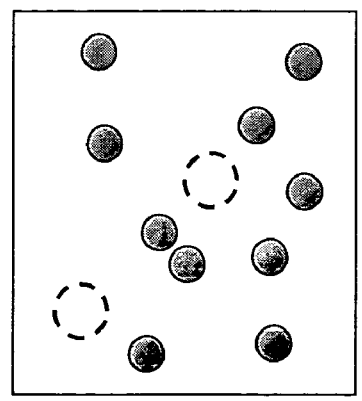
Figure 127:
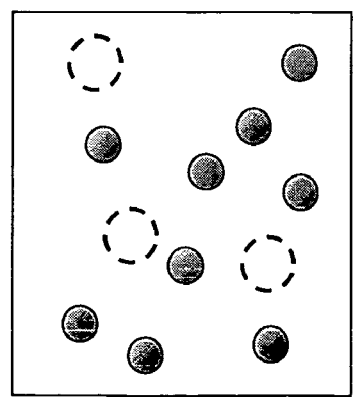
Figure 128:
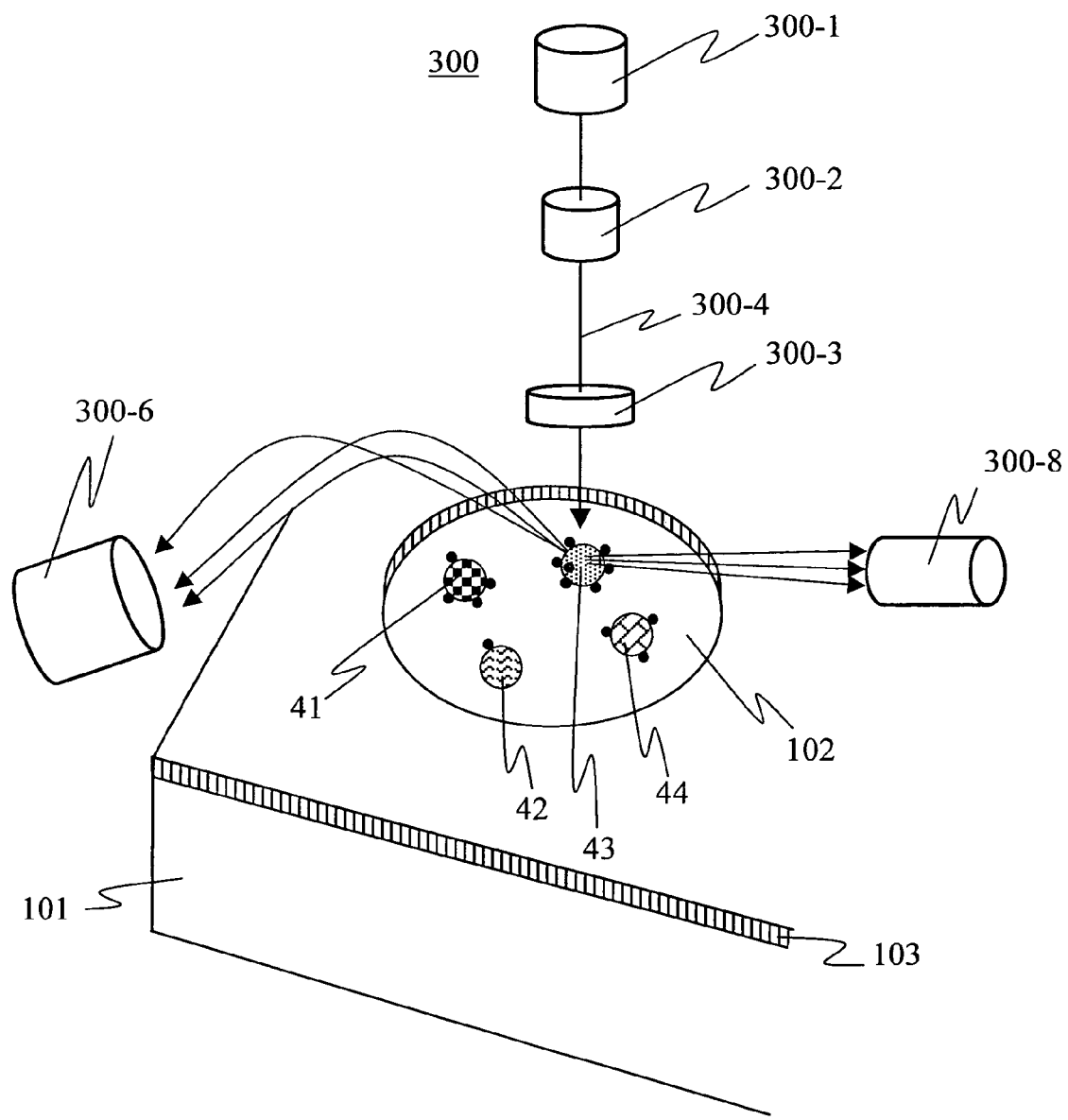
Figure 129:
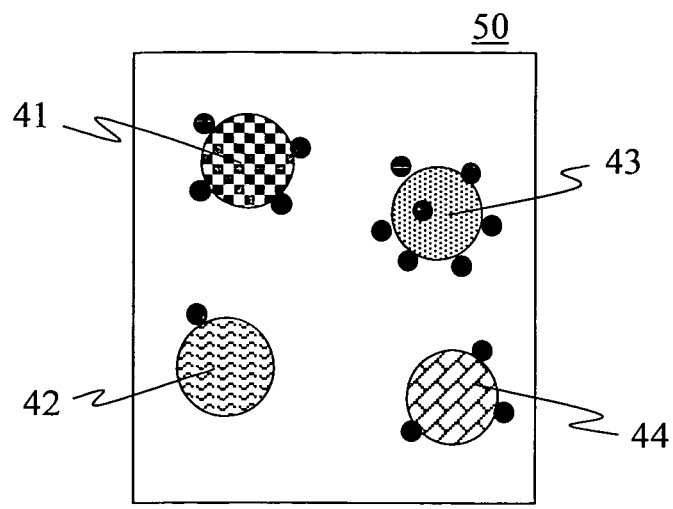
Figure 129:
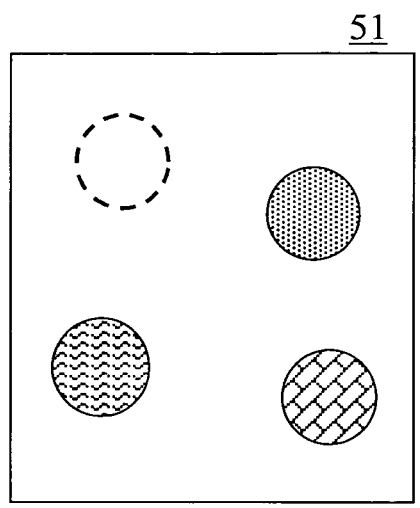
Figure 129:
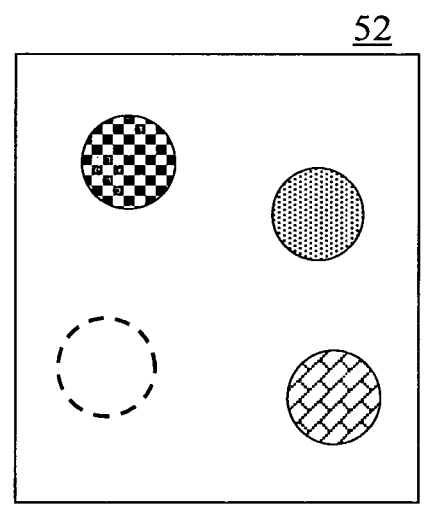
Figure 129:
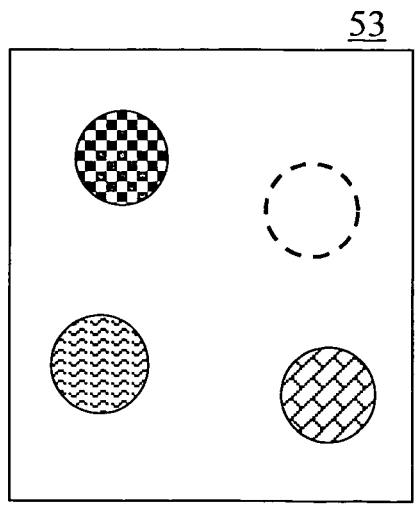
Figure 129:
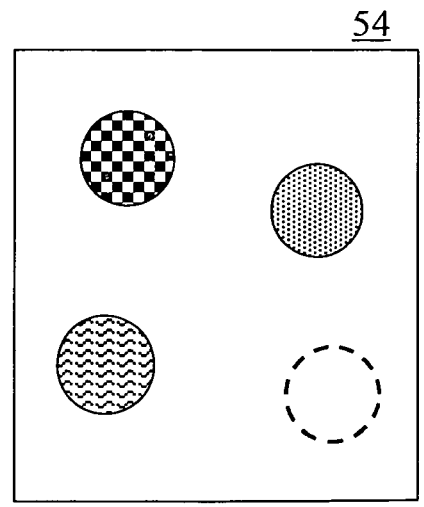
Figure 130:
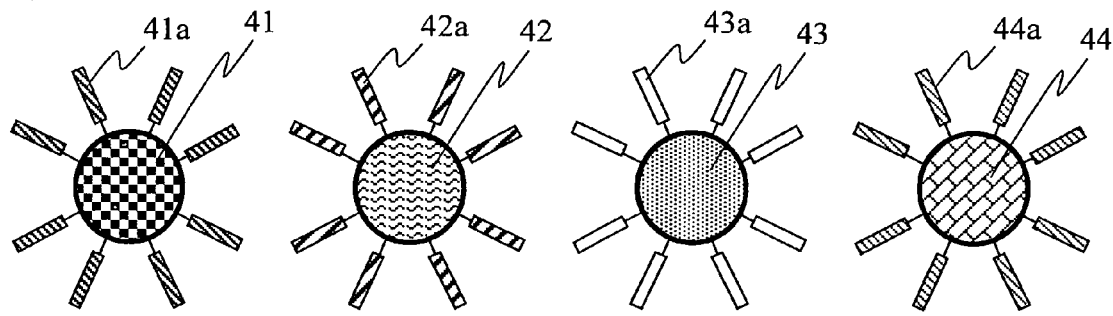
Figure 130:
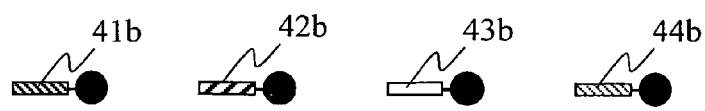
Figure 130:
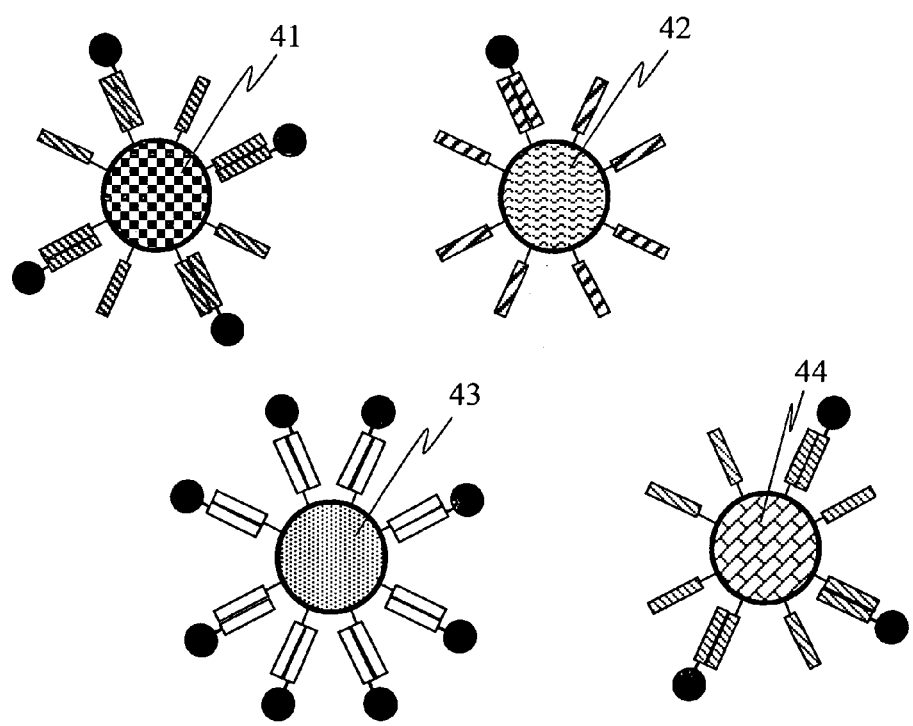
Figure 131:
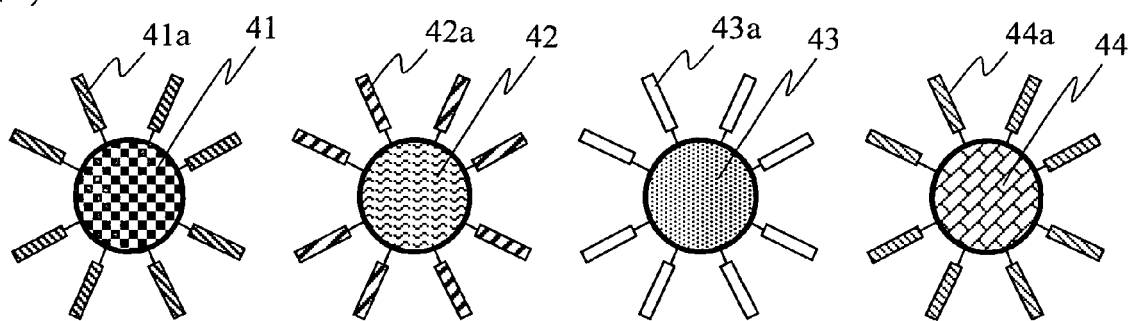
Figure 131:
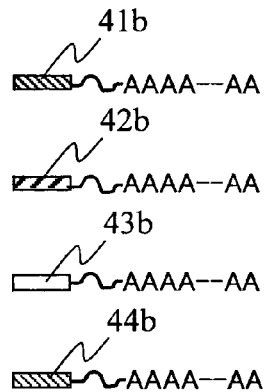
Figure 131:
Figure 132:
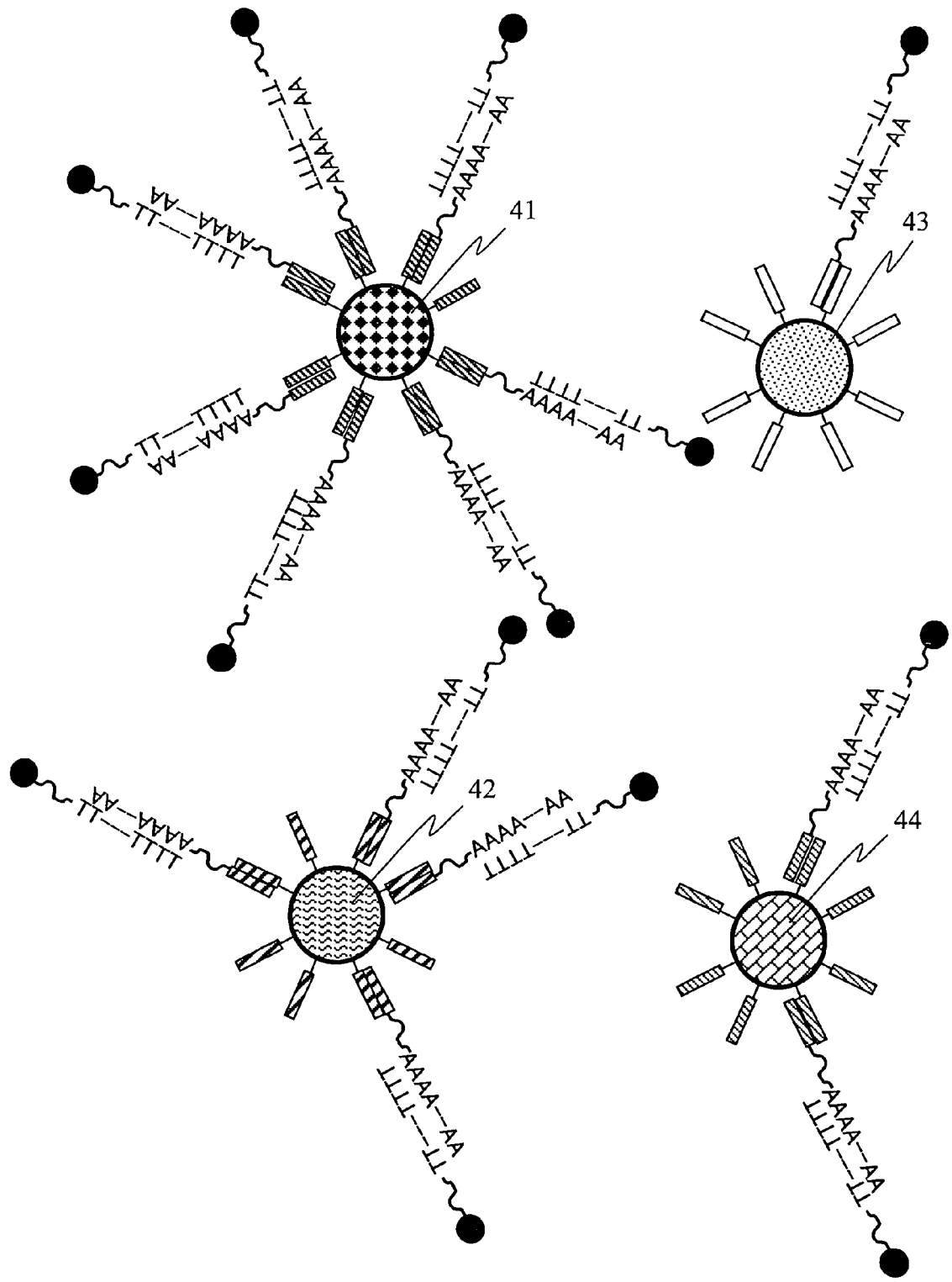
Figure 133:
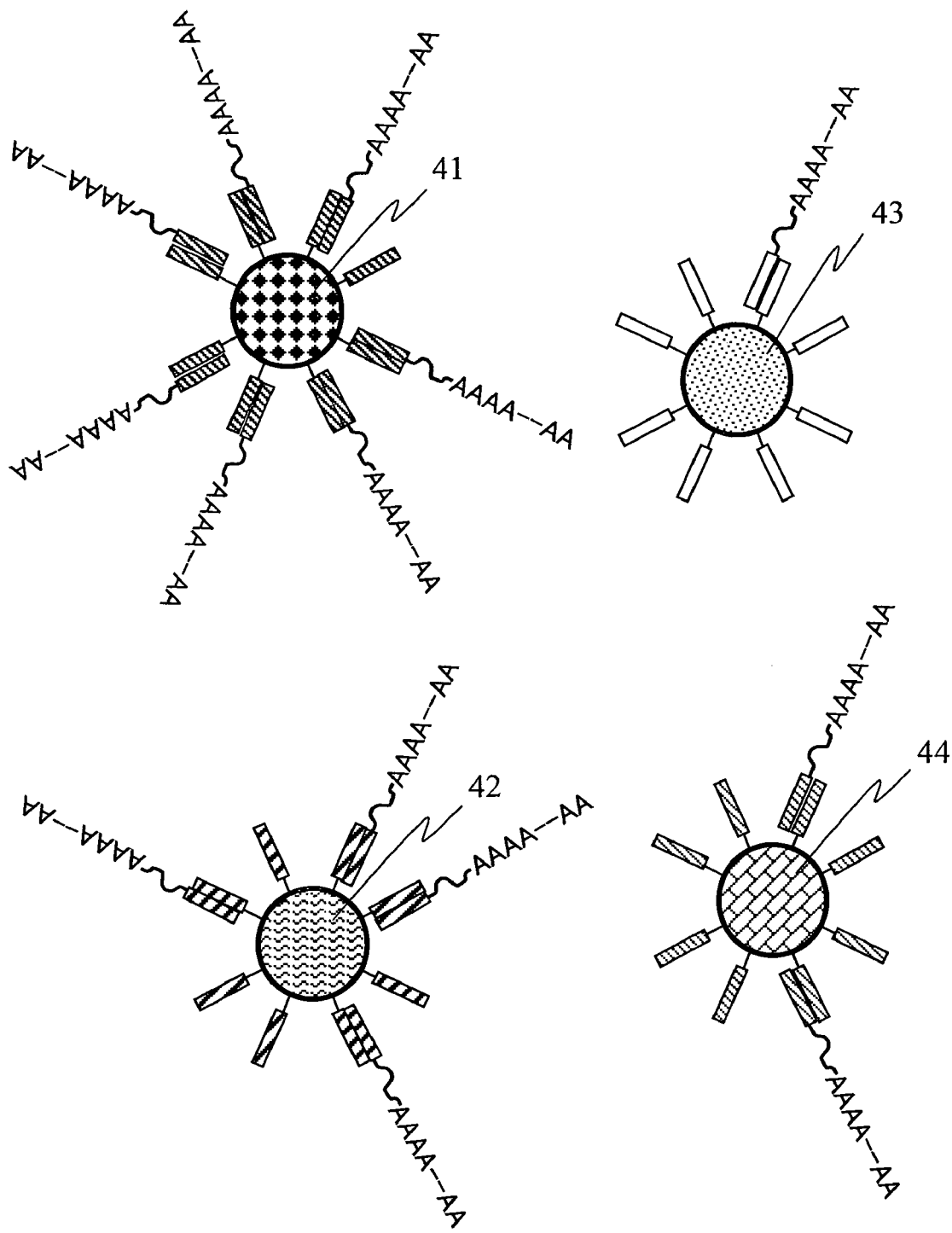
Figure 134:
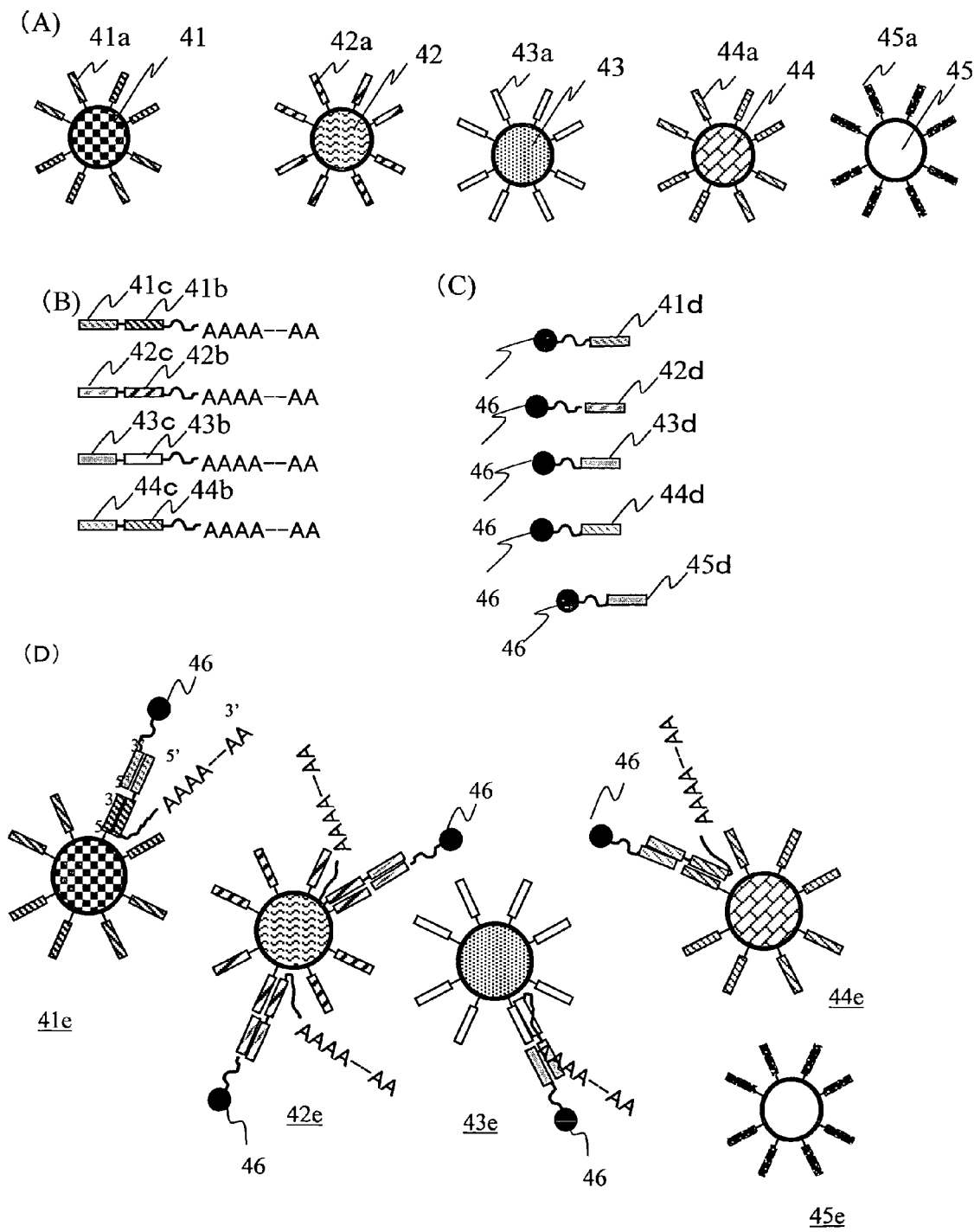
Figure 136:
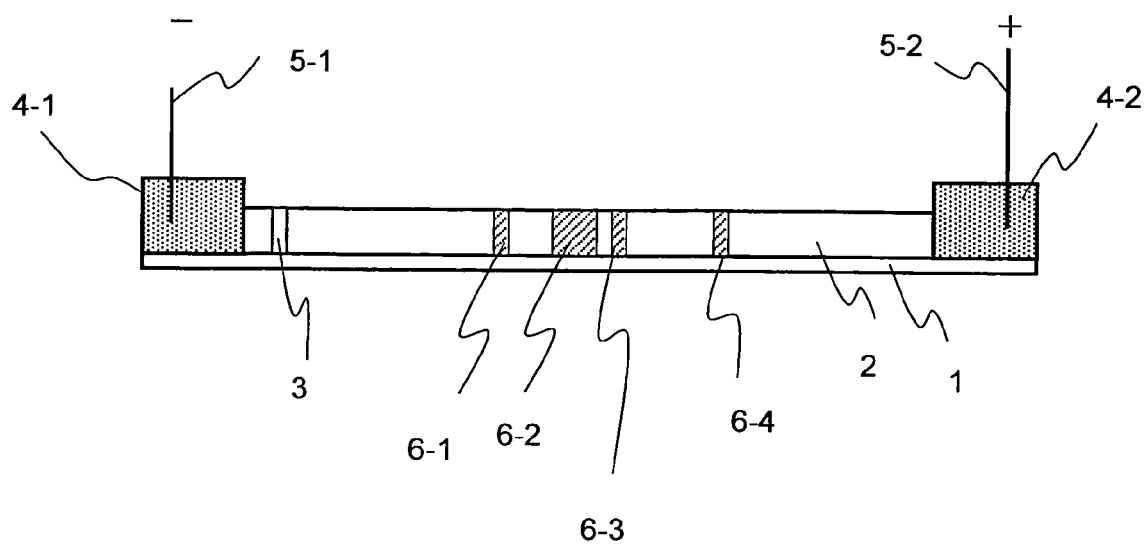
Figure 137:
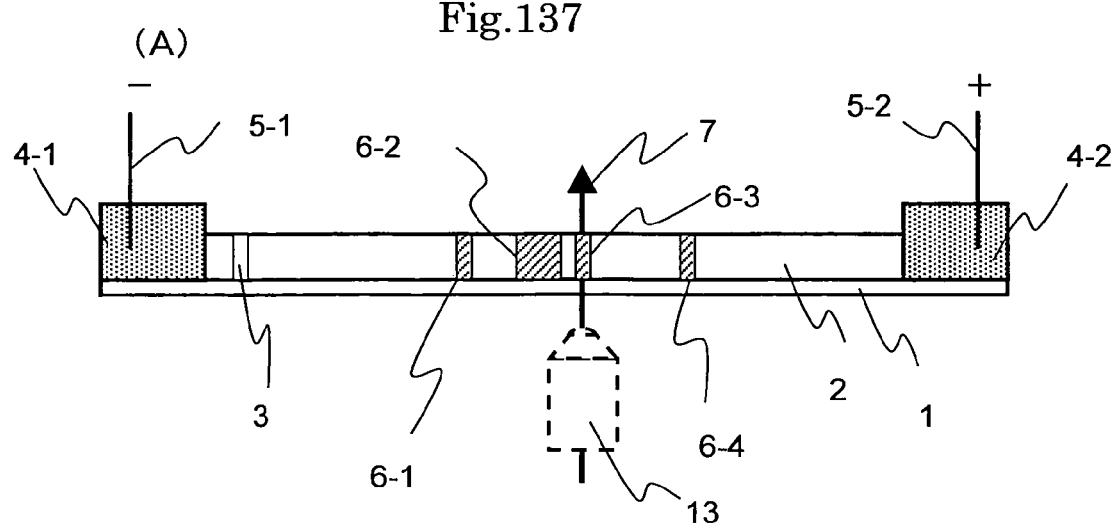
Figure 137:
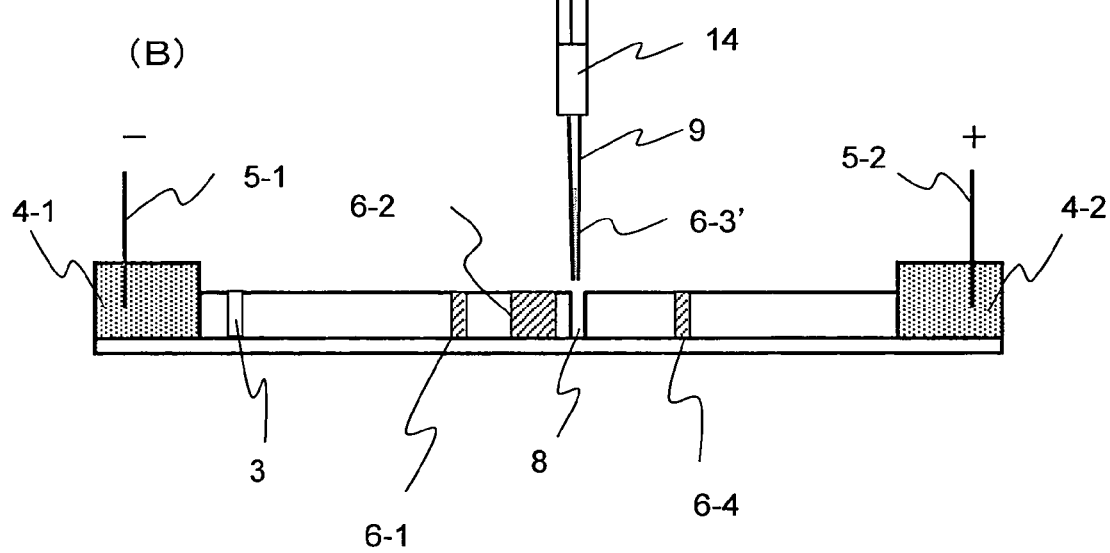
Figure 137:
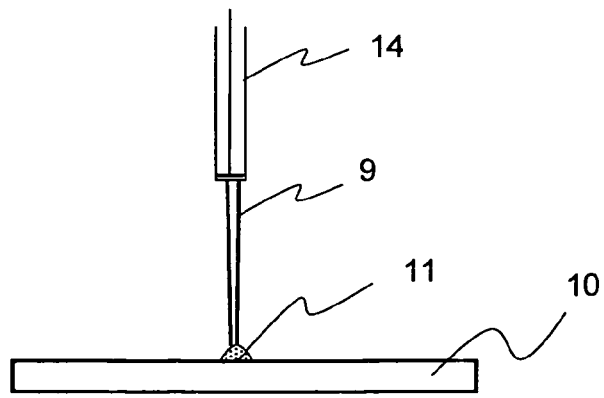
Figure 138:
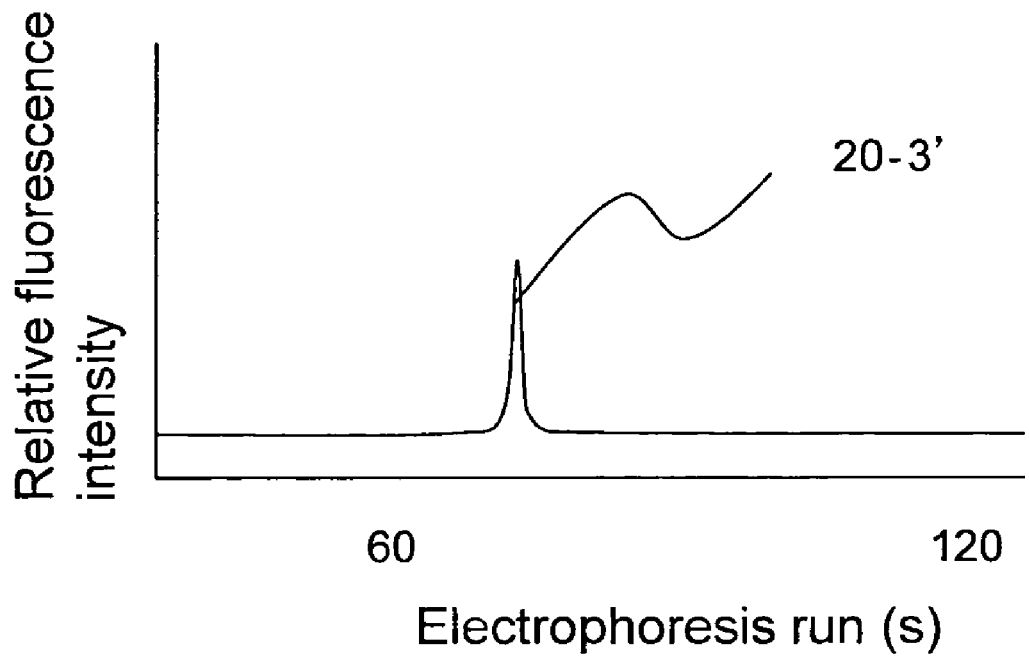
Figure 138:
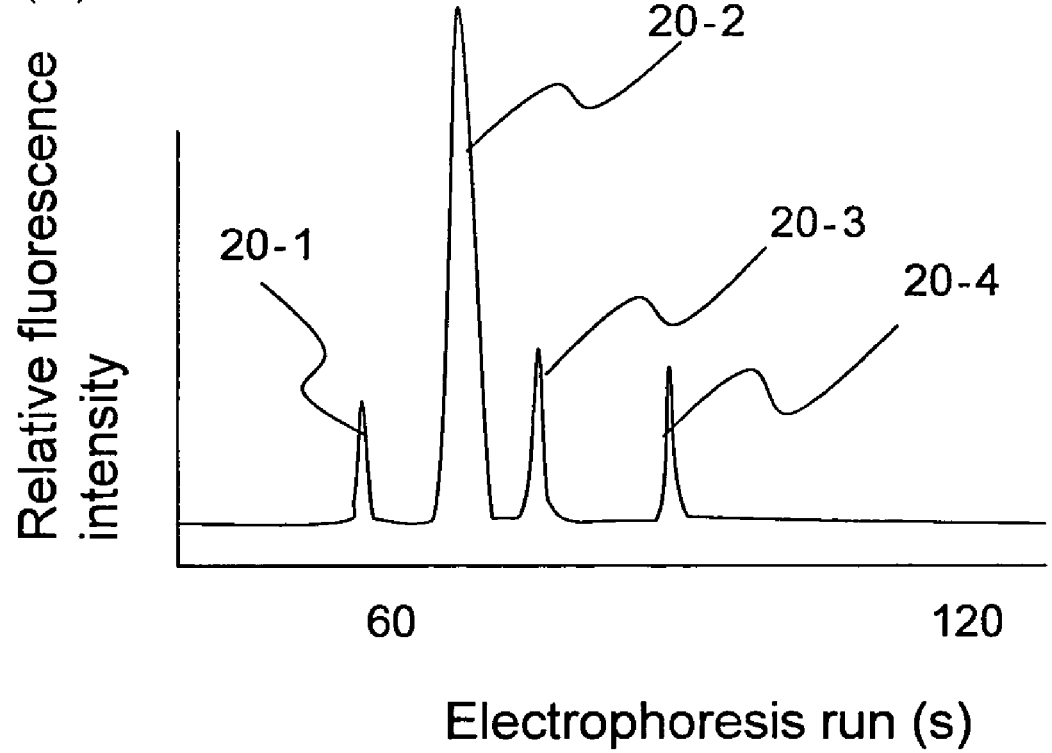
Figure 139:
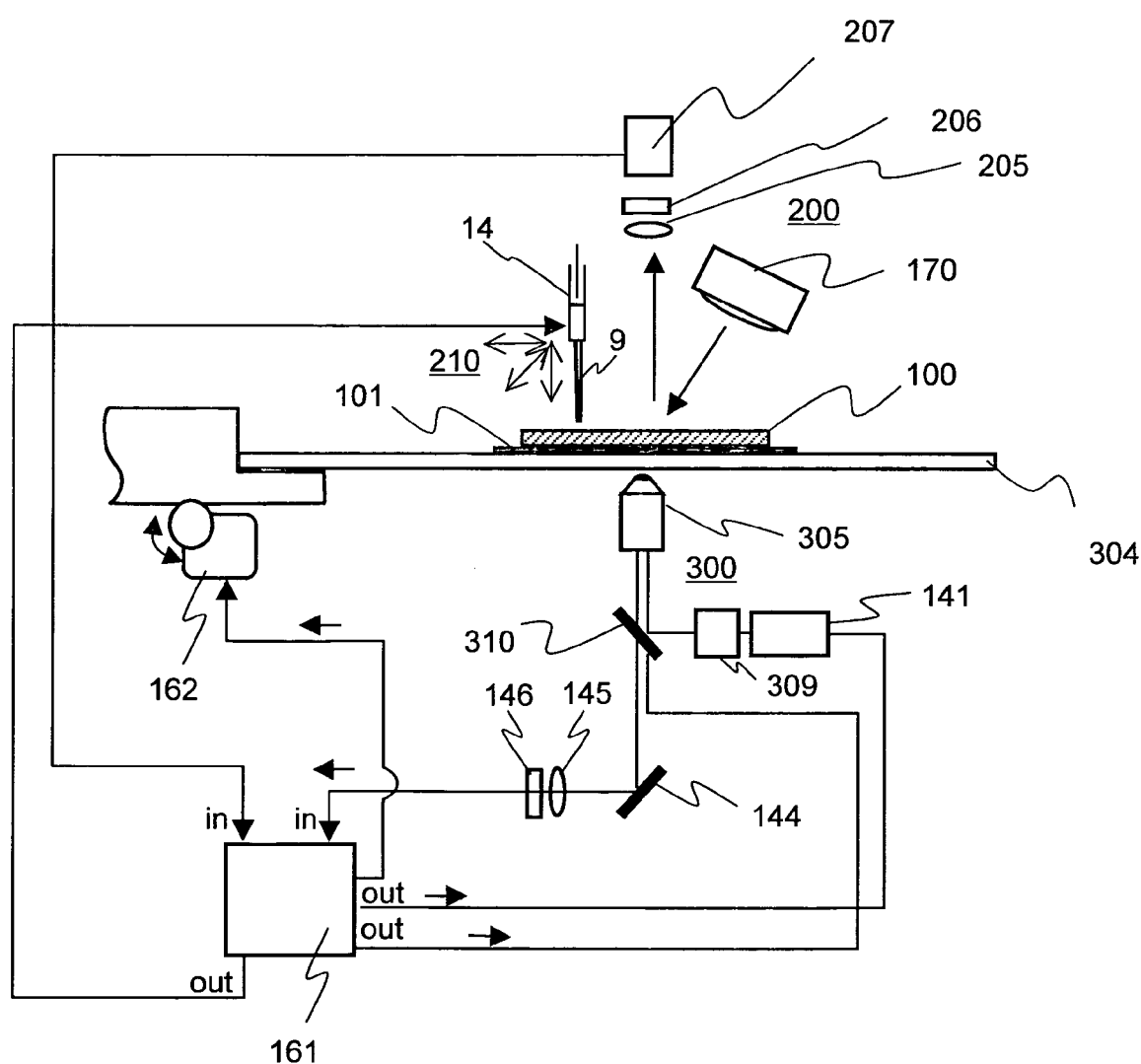
Figure 140:
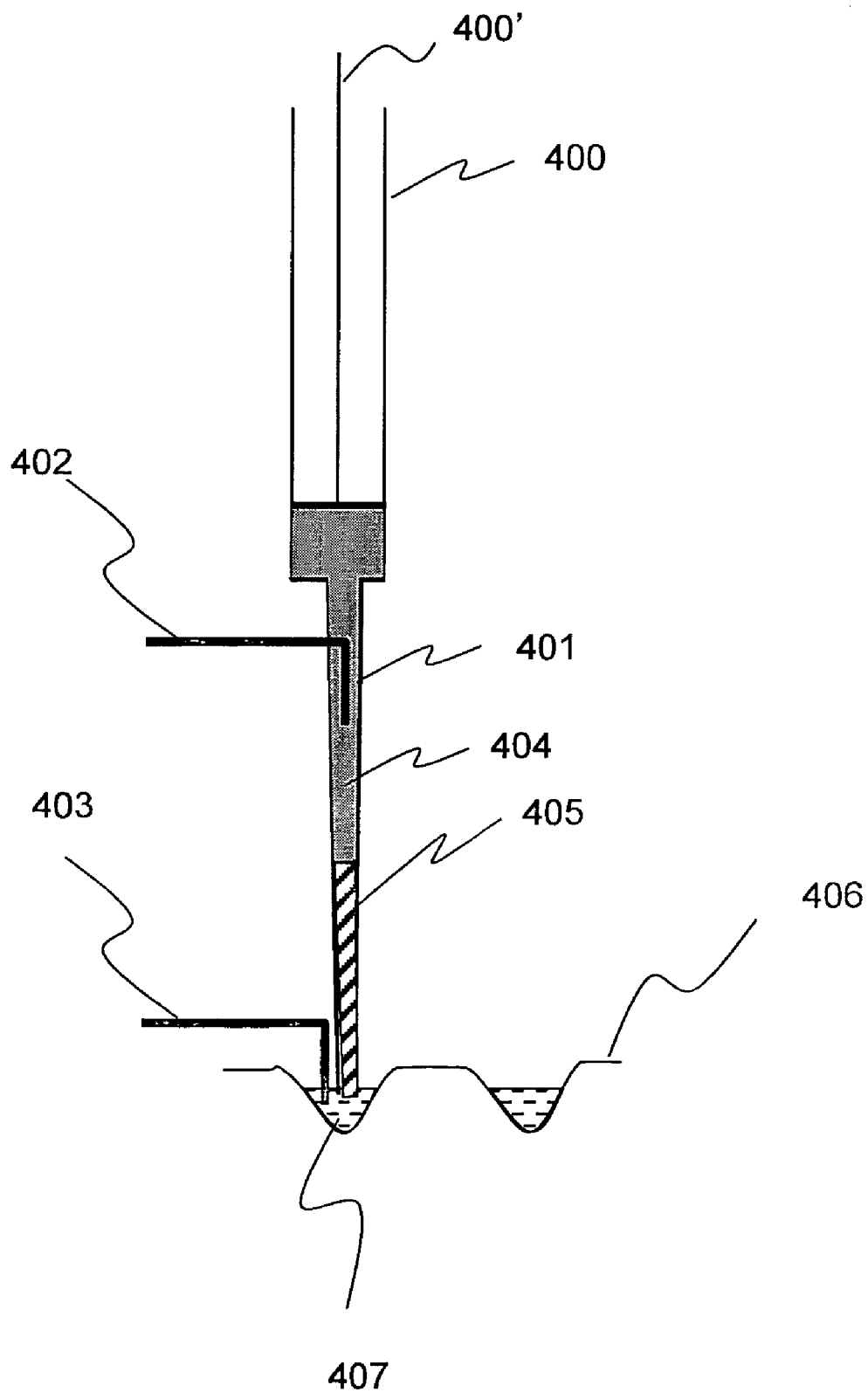
Figure 142:
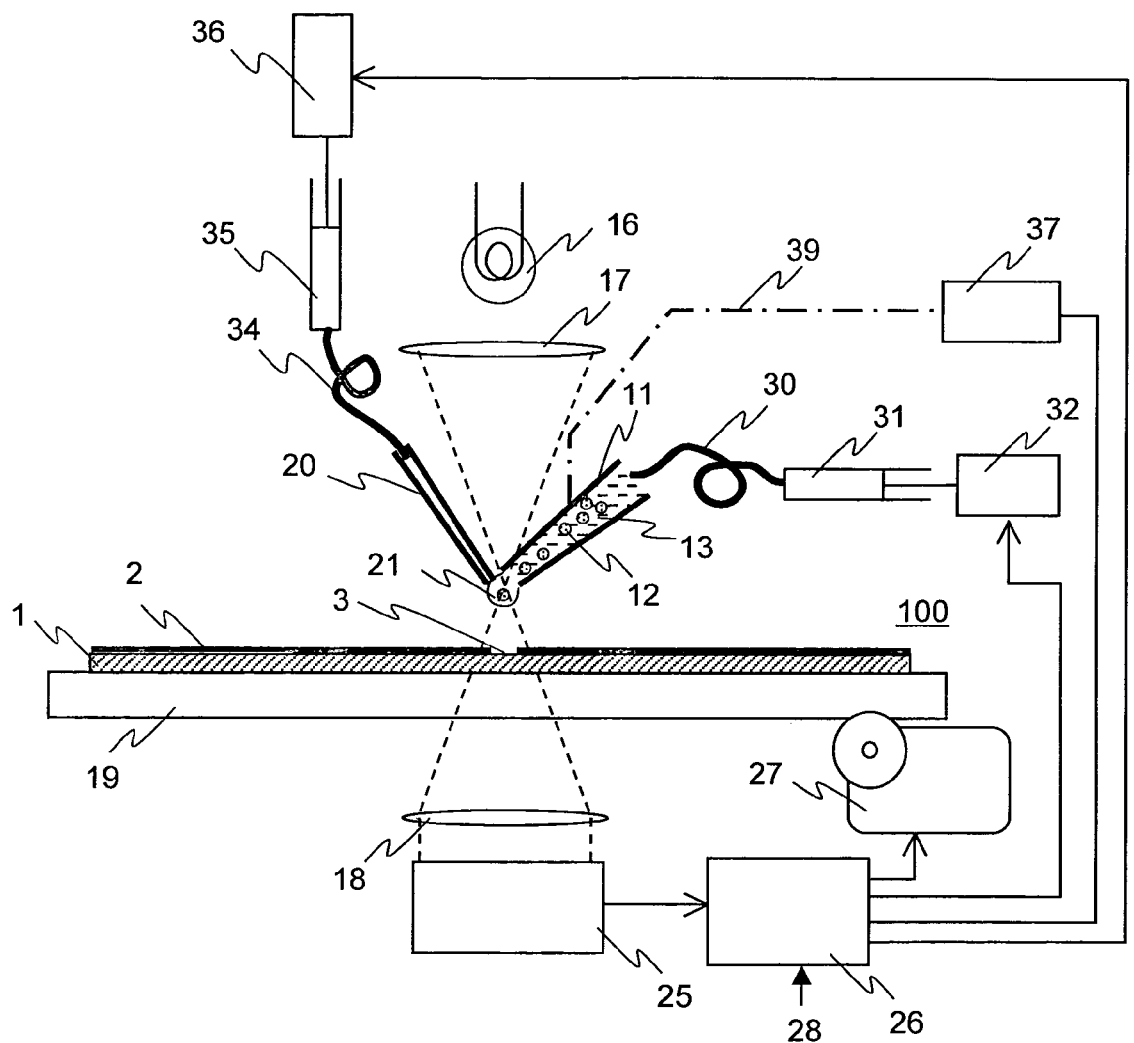
Figure 142:
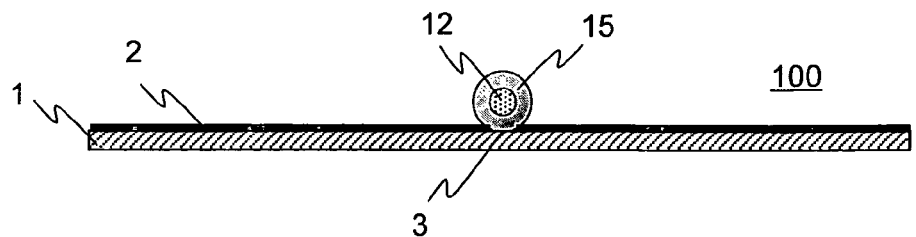
Figure 143:
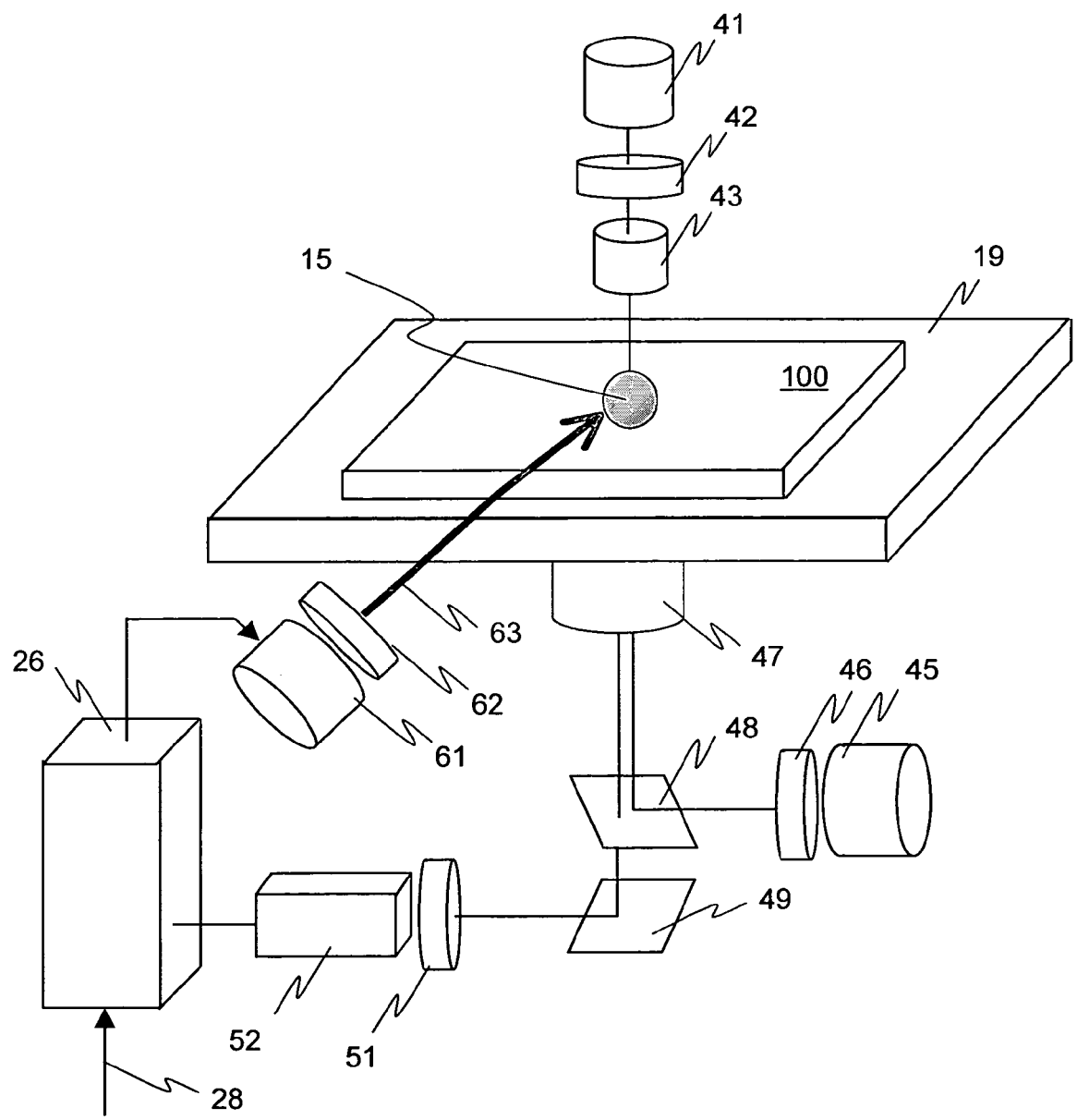
Figure 144:
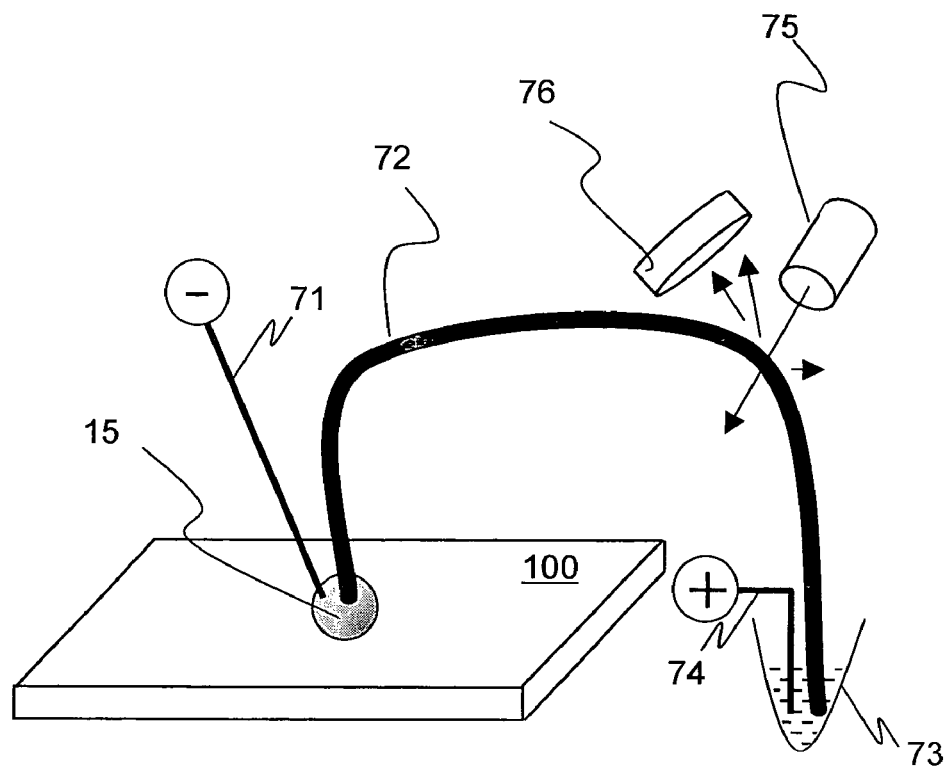
Figure 145:
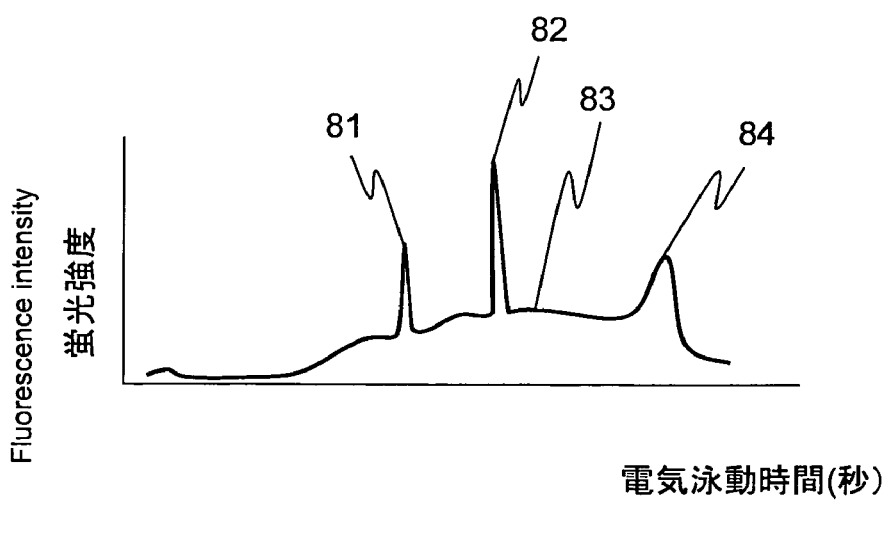
Figure 149:
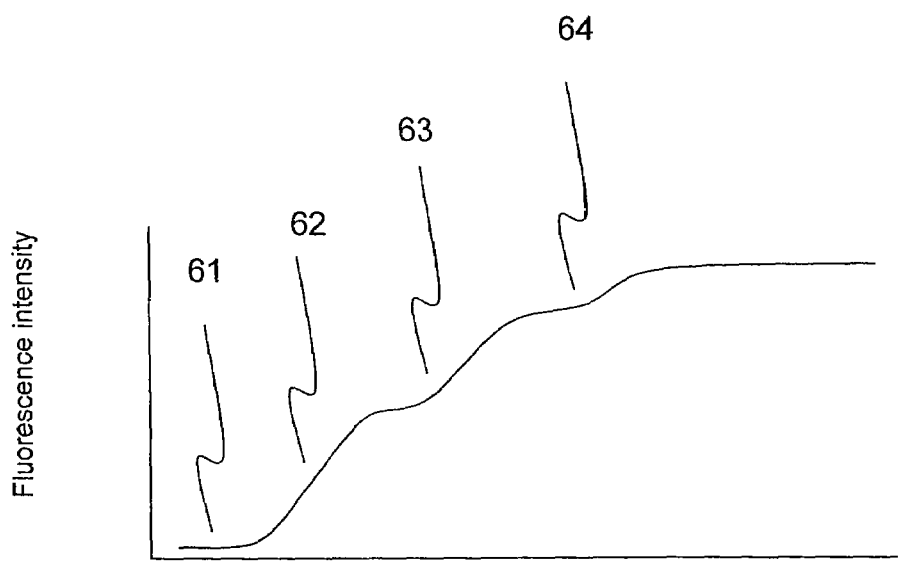
Figure 150:
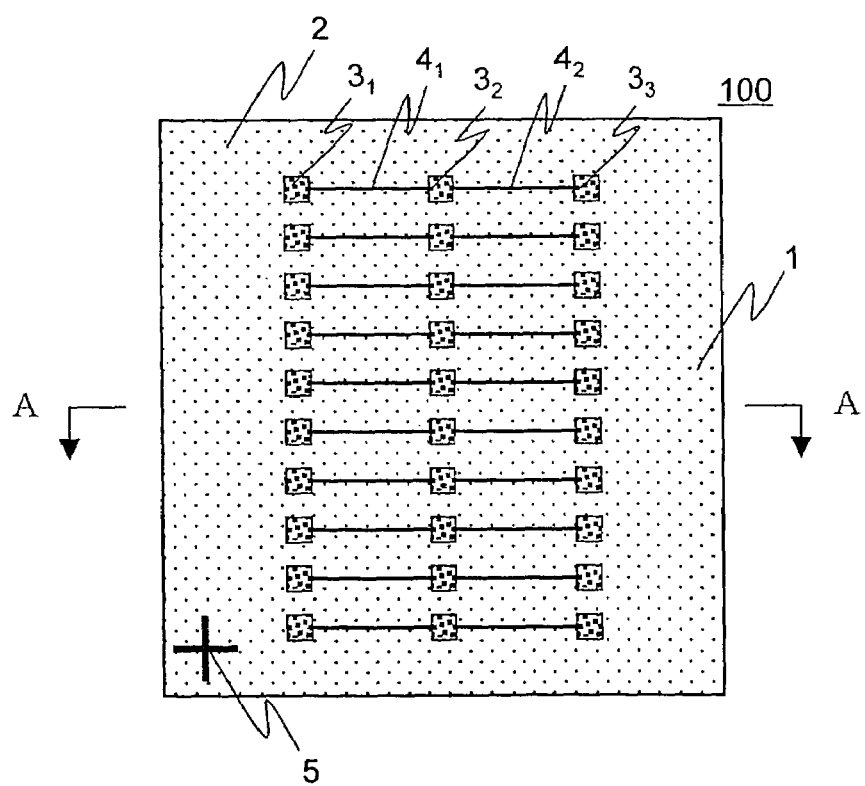
Figure 152:
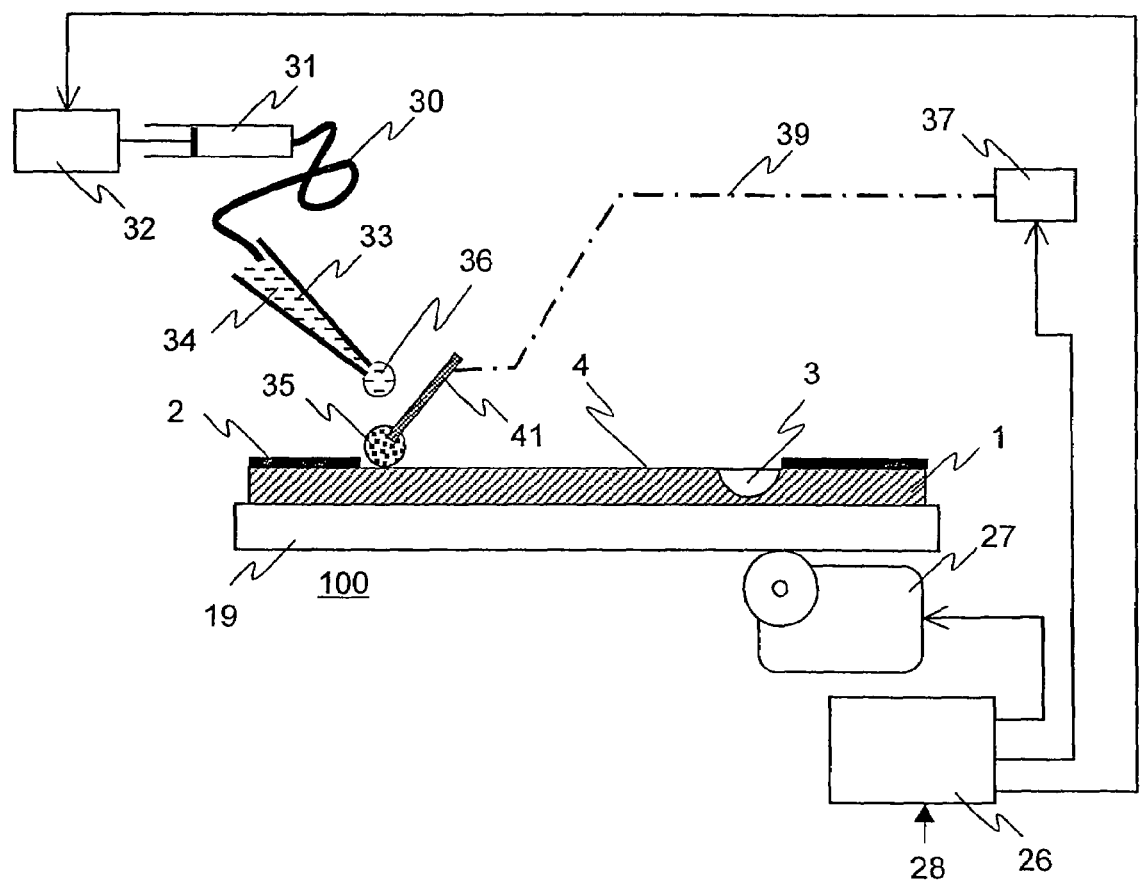
Figure 153:
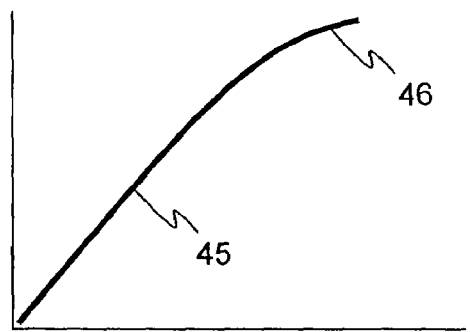
Figure 154:
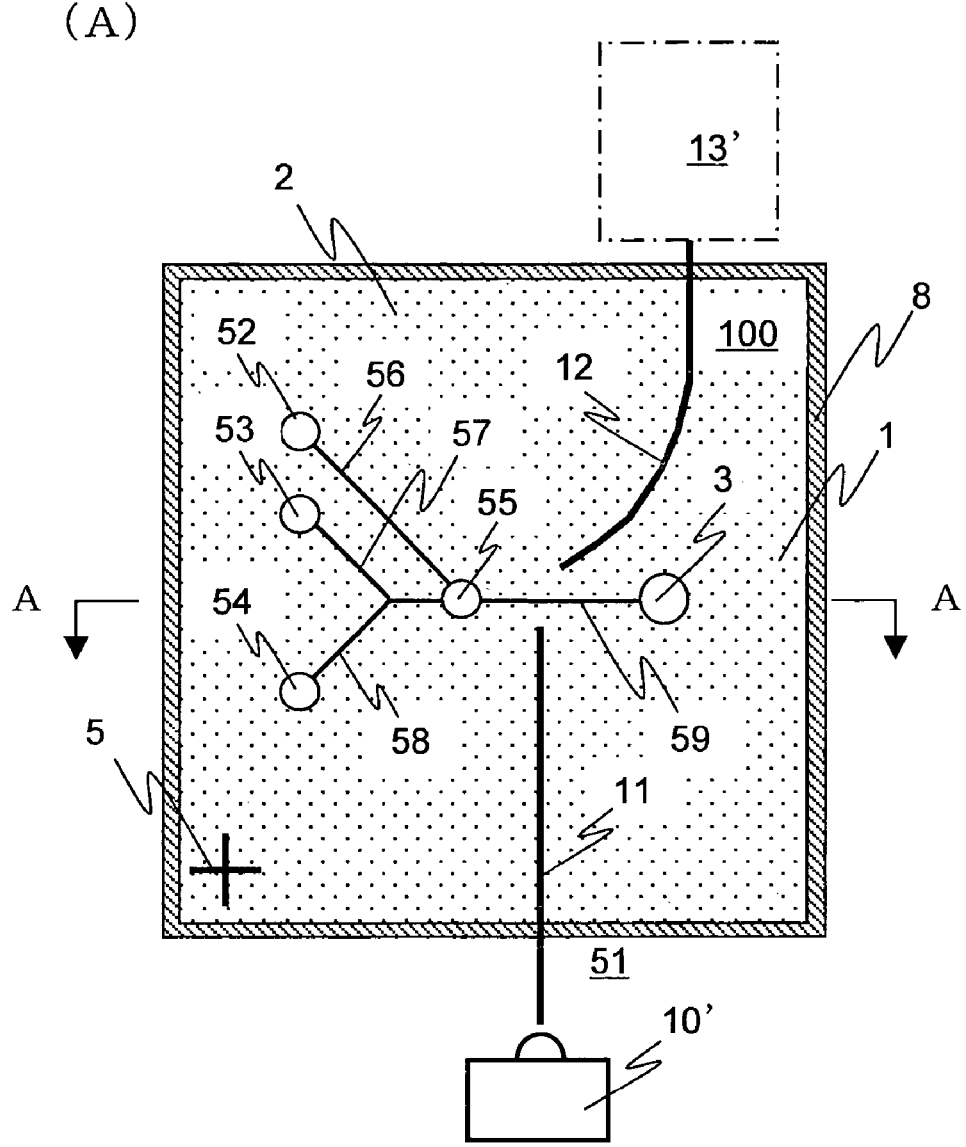
Figure 154:
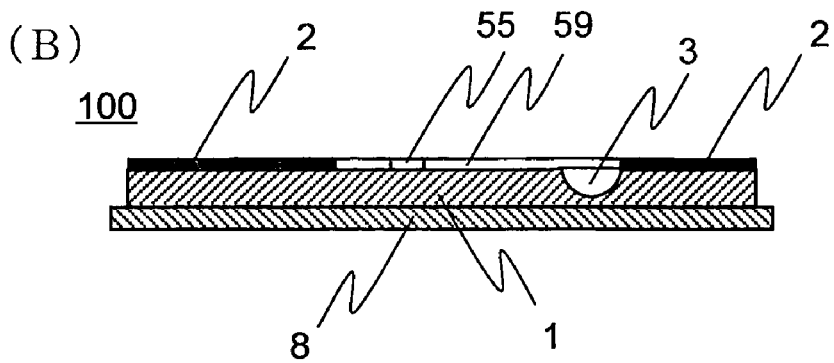
Figure 155:
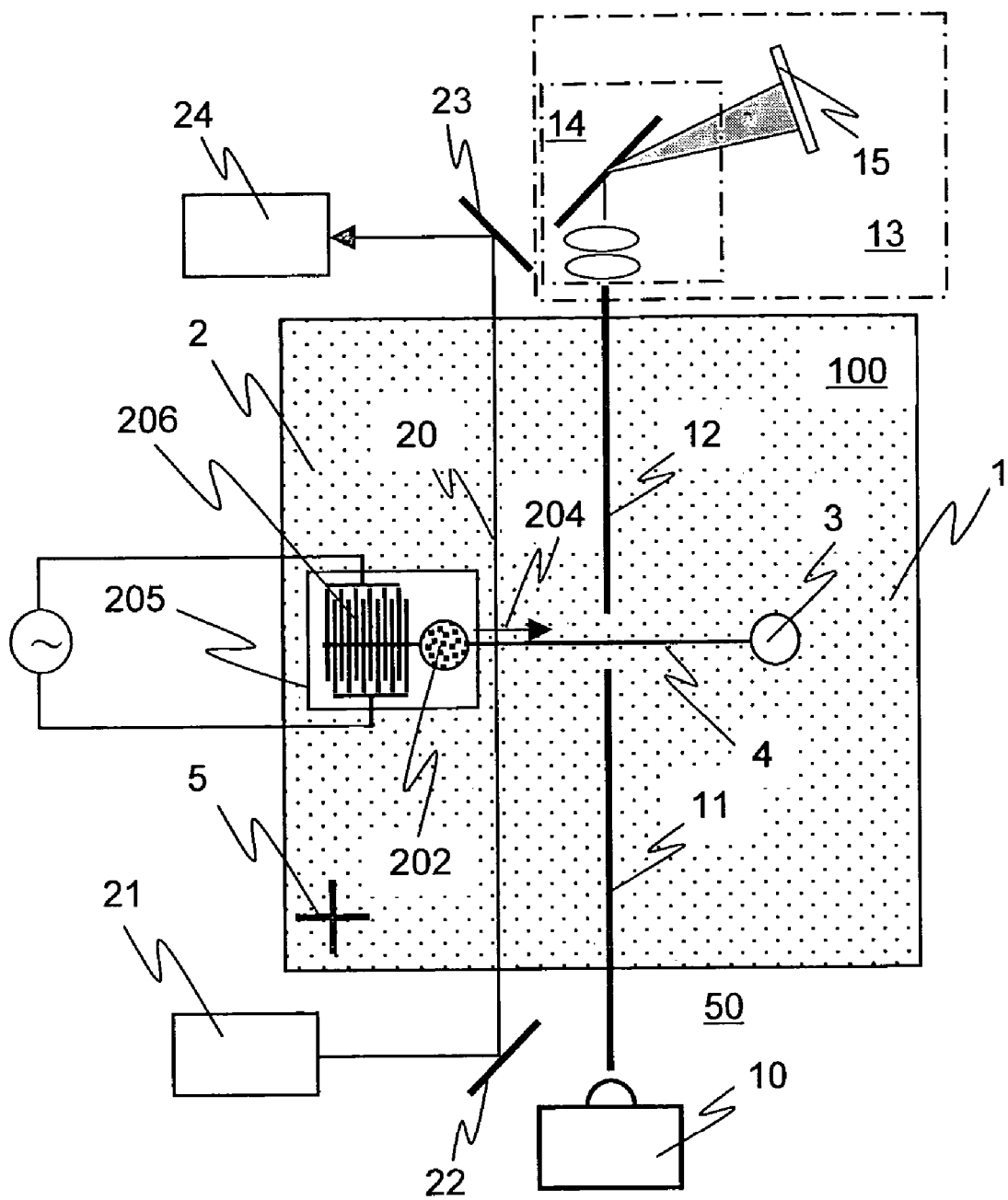

FIGS. 119(A) and 119(B) are an enlarged plan view and a cross-sectional view, respectively, showing probe fixing areas 4 according to a twenty fourth embodiment of the present invention and described in relation to FIG. 107 around one of the areas at a center;

FIGS. 120(A) and 120(B) are an enlarged plan view and a cross-sectional view, respectively, showing the probe fixing areas 4 described in relation to FIG. 107 around one of the areas at a center;

FIG. 121A is a cross-sectional view showing the state in which a sample liquid containing a target polynucleotide is introduced onto a surface of the DNA probe chip 100 described with reference to FIGS. 107, 119, and 120;

FIG. 121B is a cross-sectional view showing the state where a first step of the process for forming a concentration gradient of a target polynucleotide from a solid-liquid interface between a surface of the DNA probe chip 100 and a sample liquid toward the sample liquid is being performed;

FIG. 121C is a cross-sectional view showing the state in which the next step of a process for forming a concentration gradient is being performed;

FIGS. 122(A) to 122(F) are views illustrating the effect in Example 2;

FIG. 123 is a diagram showing an example of a result of examination concerning the fluorescence intensity by varying a period of time for capturing a target polynucleotide with reference to conditions of an electric field loaded to the DNA probe chip as parameters;

FIG. 124 is a cross-sectional view showing the DNA chip in Example 3 in which a surface area is increased by preparing a number of wells on the substrate;

FIG. 125 is a perspective view conceptually showing as a portion of the DNA chip in Example 1 of a twenty fifth embodiment of the present invention;

FIG. 126 is a conceptual diagram illustrating the situation in which the probe chip 1 described with reference to FIG. 125 is being monitored with a scanning electron microscope;

FIG. 127 is a conceptual diagram illustrating a method of identifying an mRNA to which a labeling probe of gold nanoparticle is hybridized based on a correspondence between an SEM image and an element analysis image;

FIG. 128 is a view illustrating a concept of a biological sample measurement in Example 3 of a twenty sixth embodiment;

FIG. 129 is a view illustrating identification of positions and sizes of indexing particles 41 to 44 and assessment of a specific biological material to which a labeling particle hybridized to the indexing particles 41 to 44 is added;

FIG. 130(A) is a view schematically showing the indexing particles 41 to 44 in Example 3 and probes fixed to the surface of the particles respectively, FIG. 130(B) is a view schematically showing specific biological materials hybridizing to the probes with labeling particles added thereto, and FIG. 130(C) is a view schematically showing the situation in which the probes and the specific biological materials have been hybridized to each other;

FIG. 131(A) is a view schematically showing the indexing particles in Example 4 and probes respectively fixed to the surface of the particles, FIG. 131(B) is a view schematically showing the specific biological materials each with poly A hybridizing to probes, and FIG. 131(C) is a view schematically showing a poly T with a label hybridizing to poly A added thereto;

FIG. 132 is a view showing an operation for mixing particles, a sample, and a label, and a result that hybrids of DNA probes of the respective indexing particles, respective mRNAs, and poly-T gold nanoparticles have been obtained;

FIG. 133 is a view showing the on-going situation during a process potentially providing the more precise result as compared to the homogeneous reaction illustrated in FIG. 132 in which the indexing particles, sample mRNAs, and poly T-gold nanoparticles are reacted simultaneously;

FIG. 134(A) is a view schematically showing discrete probes fixed to the surfaces of the indexing particles like in Example 4 and Example 5, FIG. 134(B) is a view schematically showing the state in which, to specific biological materials with the poly A hybridizing to discrete probes added thereto are further added probes for a sequence in another portion of the same specific biological material, FIG. 134(C) is a view schematically showing an example in which synthetic olygonucleotides (20 to 50 bases) complementary to the probes having the sequence described above is labeled with gold nanoparticles (20 nm), and FIG. 134(D) is a view showing the state of the indexing particles, the samples, and the gold nanoparticle olygonucleotide, after hybridization;

FIGS. 135(A) to 135(D) are views illustrating an example of detection of multiple biological materials by means of the antigen-antibody reaction;

FIG. 136 is a view schematically showing the situation in which a separated band is formed by electrophoresis in Example 1 of a twenty seventh embodiment of the present invention;

FIGS. 137(A), 137(B), and 137(C) are views schematically showing melting and recovery of the separated band shown in FIG. 136 with heat;

FIGS. 138(A) and 138(B) are waveform diagrams each showing a dot 11 of the separated band obtained as described above and a result of analysis of a solution obtained by PCR amplification before separation;

FIG. 139 is a schematic diagram showing configuration of a device for recovering a specific band separated by two-dimensional electrophoresis;

FIG. 140 is a view showing a recovery method in Example 2 which is different from a method of recovering a thermally melted gel of the electrophoretic spot section melted by being heated with converged light and a structure of a pipet used in the method;

FIG. 141(A) is a plan view showing a cell holding substrate 100 advantageously applicable in a twenty eighth embodiment of the present invention, while FIG. 141(B) is a cross-sectional view of the cell holding substrate 100 shown in FIG. 141(A) taken along the line A-A and viewed in the direction indicated by the arrow;

FIG. 142(A) is a conceptual diagram illustrating an example of configuration of a system for preparing a droplet containing a cell in a hydrophilic area 3 of the cell holding substrate 100 advantageously applicable to the twenty eighth embodiment, while FIG. 142(B) is a cross-section of a result of preparation of the droplet containing a cell in the hydrophilic area 3 of the cell holding substrate 100;

FIG. 143 is a perspective view showing outline of an example of a device for destroying a cell in a droplet 15 on the substrate as a target as described with reference to FIGS. 141 and 142;

FIG. 144 is a conceptual diagram illustrating a specific example of recovery of a biological material directly from a suspension of cell pieces in the droplet 15 with the cell destroyed therein;

FIG. 145 is a waveform diagram showing an example of a migration pattern obtained by electrophoresis;

FIG. 146(A) is a plan view of a reaction substrate 100 advantageously applicable in a twenty ninth embodiment of the present invention, while FIG. 146(B) is a cross-sectional view showing the reaction substrate 100 shown in FIG. 146(A) taken along the line A-A and viewed in the direction indicated by the arrow;

FIG. 147(A) is a conceptual diagram illustrating an example of configuration of a system for preparing a droplet containing a material to be reacted to the hydrophilic areas $3_1$ and $3_3$ of the reaction substrate 100 advantageously applicable in the twenty ninth embodiment, while FIG. 147(B) is a plan view showing a portion of the reaction substrate 100 with the droplet containing a material to be reacted to the hydrophilic areas $3_1$ and $3_3$ of the reaction substrate 100 formed thereon;

FIG. 148(A) is a perspective view showing outline of an example of a device for making two droplets $15_1$, $15_2$ formed on the reaction substrate 100 as shown in FIG. 147(B) run into and react with each other, while FIG. 148(B) is a plan view schematically showing the situation in which the two droplets $15_1$, $15_2$ run into each other to form one droplet;

FIG. 149 is a waveform diagram showing change over time in fluorescence intensity obtained by monitoring the fluorescence intensity of a droplet 153;

FIG. 150 is a plan view showing a example of the reaction substrate 100 which may advantageously be used for spectroscopic measurement with a microspectroscope;

FIG. 151(A) is a plan view showing a measuring substrate 100 advantageously applicable in Example 1 of a thirtieth embodiment of the present invention and a conceptual diagram showing a measuring system constructed with the measuring substrate as a basis, while FIG. 151(B) is a cross-sectional view showing the measuring substrate 100 shown in FIG. 151(A) taken along the line A-A on the plan view of the measuring substrate 100 and viewed in the direction indicated by the arrow;

FIG. 152 is a conceptual diagram illustrating an example of configuration of a system for preparing a droplet at a left edge of a hydrophilic line 4 on the measuring substrate 100 advantageously applicable in the thirtieth embodiment and also for measuring the droplet;

FIG. 153 is a characteristic diagram in which absorption of light measured in Example 1 is plotted;

FIG. 154(A) is a plan view showing a measuring substrate 100 advantageously applicable in Example 2 and a conceptual diagram showing a measuring system configured with this measuring substrate, while FIG. 154(B) is a cross-sectional view showing the measuring substrate 100 shown in FIG. 154(A) taken along the line A-A on the plan view of the substrate 100 and viewed in the direction indicated by the arrow; and FIG. 155 is a conceptual diagram illustrating an example of configuration of a system for preparing a droplet at a left edge of the hydrophilic line 4, migrating the droplet with surface elastic wave, and measuring the migration.

DESCRIPTION OF THE PREFERRED EMBODIMENT

The present invention is described below with reference to specific embodiments, and the embodiments are independent from each other, and in a case where an embodiment has some connections with another embodiment, the relation is described, for instance, with reference to the related drawings.

(A) At first, a method of and a device for separating a target cell without any substantial damage thereto are described.

[I] First Embodiment

Descriptions are provided below for a centrifugal chip and a centrifugation method enabling separation of a cell or a granule from a minute quantity of sample liquid by centrifugation as a first embodiment of the present invention.

In the first embodiment, a chip for centrifugation is attached to a rotary plate rotating around a rotary shaft. The chip for centrifugation includes flow paths for supplying a plurality of solutions having different specific gravities respectively onto a substrate, a separation chamber functioning as a separation area in which the flow paths converge, and a plurality of flow paths branching from the separation chamber. Reservoirs are provided at entrances and exits of all flow paths for supplying solutions having different specific gravities respectively to the flow paths, and in this configuration distances of all reservoirs at entrances to the flow paths from the rotary shaft are equal, and also liquid levels in reservoirs at exits from the plurality of flow paths branching from the separation chamber are equal to each other from the rotary.

EXAMPLE 1

Figure 2:
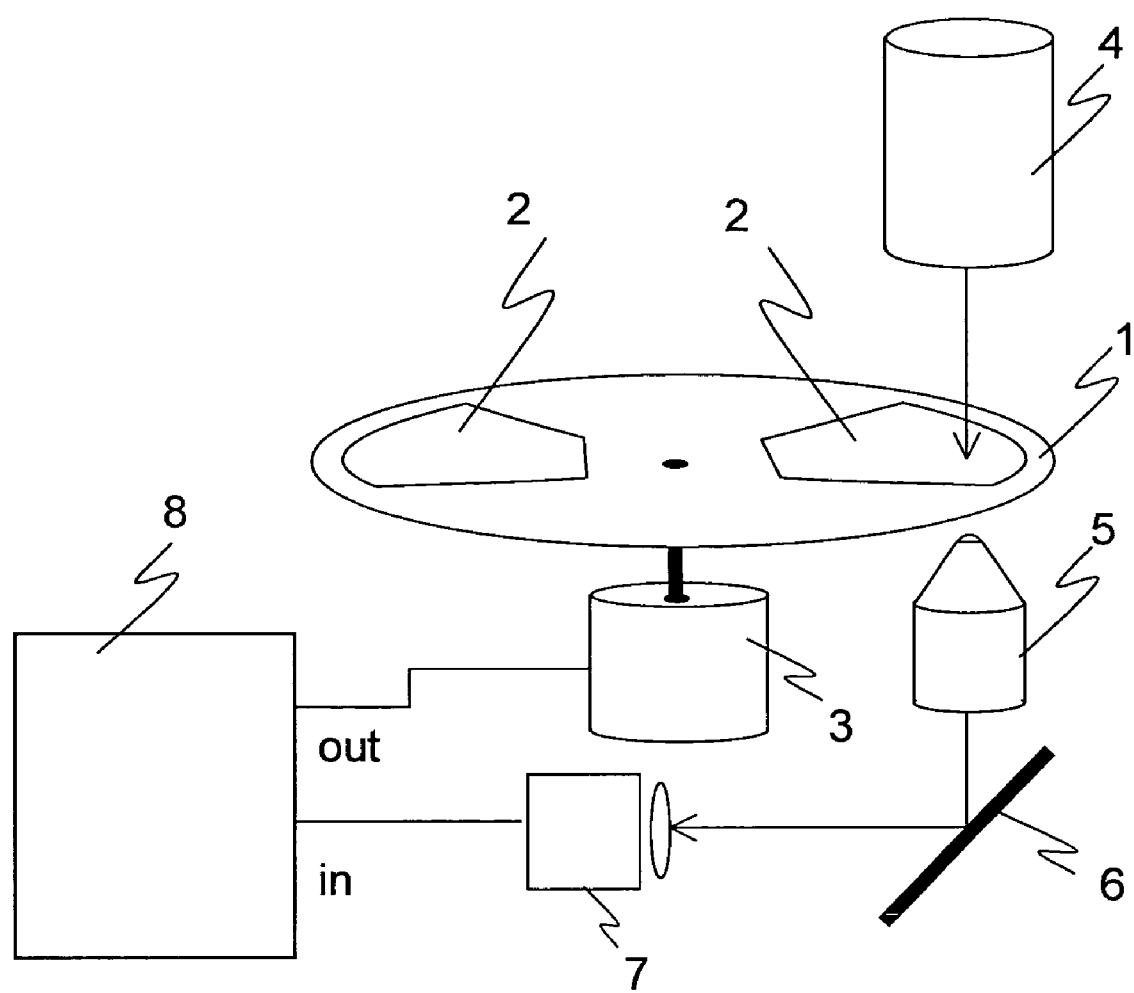
FIG. 2 is a view showing general configuration of a centrifugal separator for cell separation in Example 1 of a first embodiment of the present invention.

FIG. 2 is a view showing outline of a centrifugal separator according to a first embodiment of the present invention. In this figure, the reference numeral 1 indicates a rotary plate, and a space 2 is formed on a surface thereof for mounting a centrifugal chip according to the first embodiment. The centrifugal chip can easily be mounted to or dismounted from the space 2. The rotary plate 1 is rotated by a motor 3 at a prespecified rotational speed in the horizontal direction. The reference numeral 4 indicates a light source, which irradiates light onto a separation section of the centrifugal chip mounted on the rotary plate 1. The reference numeral 5 indicates a lens, which converges the light transmitted through the separation section of the centrifugal chip. The light converged by the lens 5 is reflected by a mirror 6, and the image is picked up by a high speed camera 7. The reference numeral 8 indicates a personal computer, which analyzes the separation section of the centrifugal chip photographed by the high speed camera 7 and computes a speed signal for the motor 3 to control a rotational speed of the motor 3.

In Example 1, a sample can be separated monitoring the separation state during centrifugation with the camera 7. Optical separation of a sample can be performed by monitoring a degree of separation with a monitor (not shown) equipped with the personal computer 8, or a controlling a rotational speed of the motor 3 with a program implemented in the personal computer 8. The observation is performed, for instance, as described below. For instance, the motor 3 is rotated at 1800 rpm and an image of the separation section of the centrifugal chip mounted on the space 2 is monitored with an optical system including the light source 4, lens 5, and camera 7. In this step, the rotational speed of the motor is controlled so that the number of passages of the centrifugal chip under the light source per second is a multiple of an image fetching rate of the high speed camera 13. With this control, an image of the rotating centrifugal chip can be picked up like a still picture. For instance, when photographing is performed with a camera operating with the image fetching rate of 30 frames per second, centrifugation should be performed by rotating the motor 3 with the rotational speed of 30×N/second (N: an integral number or a fraction of an integral number). Therefore, in the above case, by performed the centrifugation at the rotational speed of 1800 rpm described above, an image of the sample like a still image can be obtained. When a plurality of chips are photographed simultaneously, by dividing the fetched image to those for each discrete centrifugal chips with the personal computer 8, images of each chip can be obtained.

EXAMPLE 2

Figure 3:
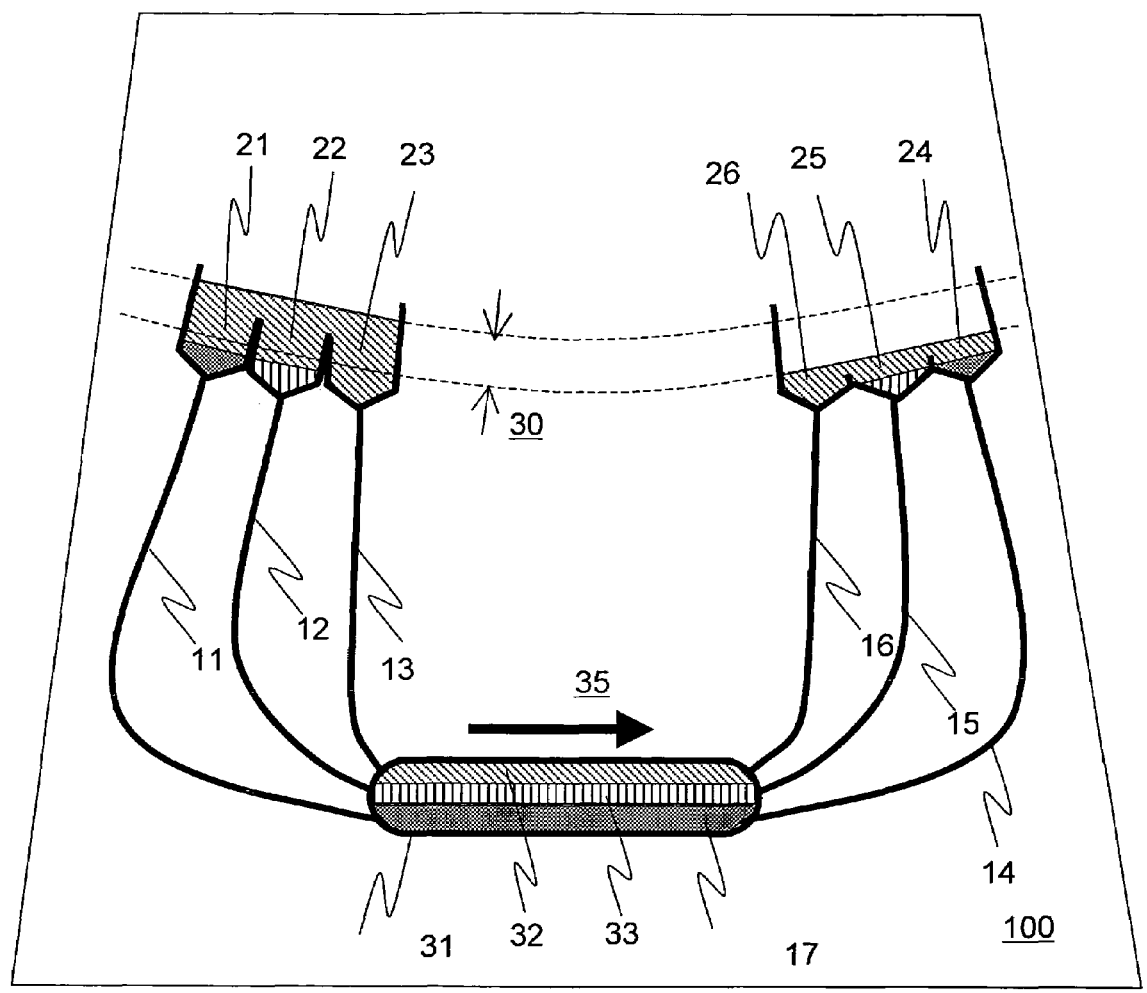
FIG. 3 is a plan view schematically showing configuration of a centrifugal chip in Example 2 of the first embodiment advantageously applicable to the centrifugal separator in Example 1.
Figure 4:
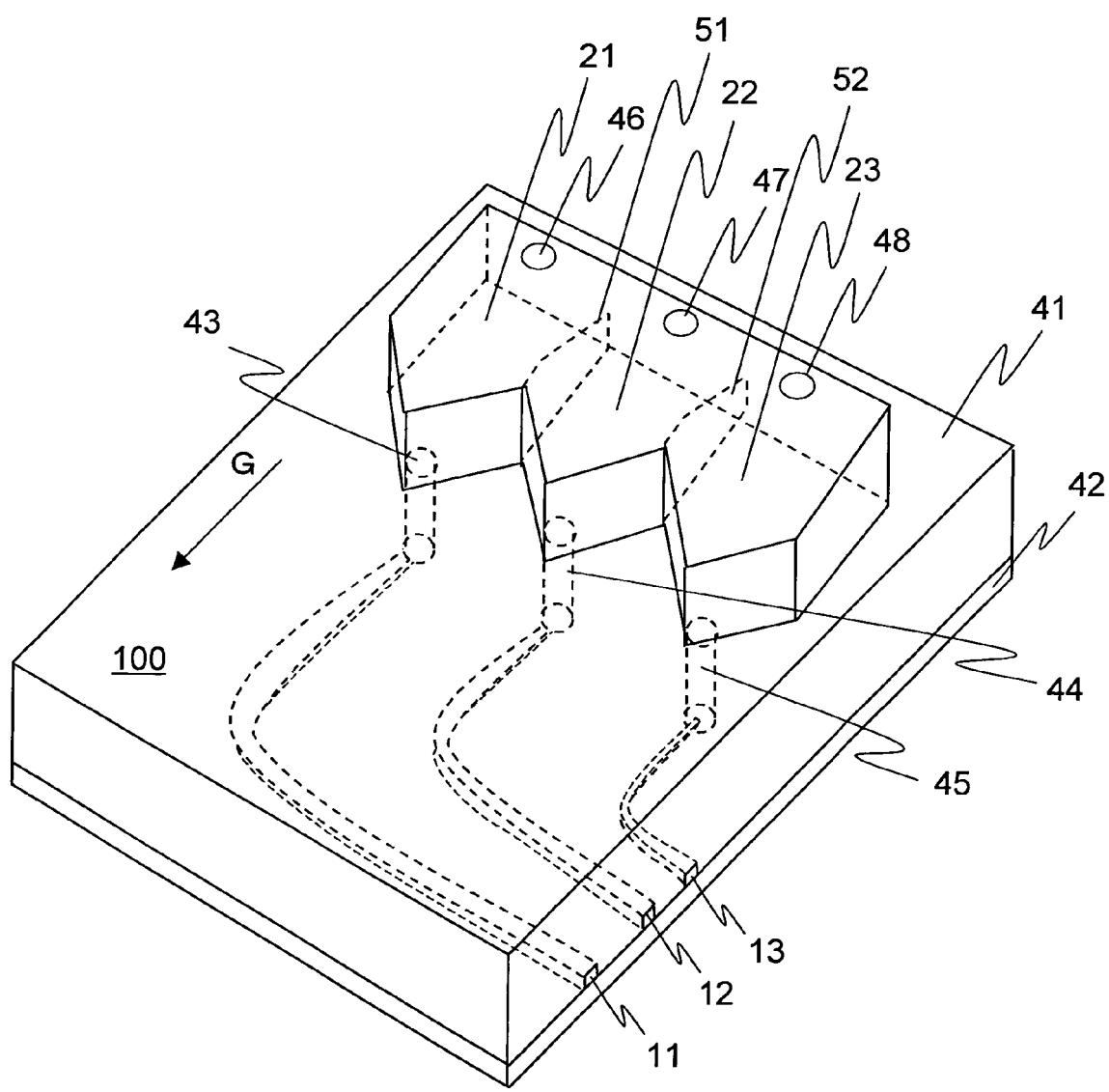
FIG. 4 is a perspective view schematically showing configuration of a reservoir section of the centrifugal chip 100 shown in FIG. 3.

FIG. 3 is a plan view schematically showing configuration of a centrifugal chip 100 advantageously applicable to a centrifugal separator in Example 1. FIG. 4 is a perspective view schematically showing cross-sectional configuration of a reservoir section of the centrifugal chip 100 shown in FIG. 3.

The reference numerals 11, 12, 13 indicate flow paths, which are independent from each other, for supplying solution having different specific gravities respectively, and edges of the flow paths are connected to reservoirs 21 to 23 on one side, and other edges of the flow paths are connected to the separation chamber 17 on the other side. The drain flow paths 14, 15, 16 are connected to the other edge of the separation chamber 17, and reservoirs 24 to 26 are connected to the other edges of the drain flow paths 14, 15, 16 respectively. Of the reservoirs 21 to 26 communicated to the flow paths respectively, the reservoir 23 contains therein a solution having the lowest specific gravity and including a sample, and reservoirs 22, 21 contain the solutions with the specific gravities in the descending order respectively. When the motor 3 is rotated in this state to perform centrifugation, layers of solutions 31, 32, 33 having the specific gravities in the descending order are formed according to the centrifugal acceleration in the separation chamber 17. Of the components of the sample, those having specified gravities higher than that of the solution 31 go into the solution layer 31, and those having the specific gravities lower as compared to those going into the solution layer 31 but higher as compared to the lowest specific gravity go into the solution layer 32, and components having specific gravities lower than the lowest one go into the solution layer 33. The components are recovered into the reservoirs 24 to 26 through the drain flow paths 14, 15, 16 corresponding to each solution layer respectively. Herein the reference numeral 30 indicates a difference between liquid levels viewed in the direction of the centrifugal acceleration in the initial state of the centrifugation. Because of the difference between the liquid levels, each solution flows in the direction 35 indicated by the arrow in the laminar flow state, and the components separated into the laminar flow in the separation chamber 17 flow into the drain flow paths 14, 15, and 16. What is important herein is the fact that the liquid levels in the reservoirs 21 to 23 and reservoirs 24 to 26 are aligned with the solution having the lowest specific gravity and therefore a liquid flow in each flow path is prevented from being disturbed.

Configuration of this centrifugal chip 100 is as described below. The flow paths 11 to 16 and separation chamber 17 are formed on one face of the PDMS substrate by casting, and the reservoirs 21 to 26 are formed with glass on the other face of the substrate and adhered thereto. The flow paths 11 to 16 and reservoirs 21 to 26 are communicated to each other with a hole penetrating the substrate. External dimensions of the chip are 30×30 mm. Although the centrifugal chip 100 is shown with a fan-like form in the figure, there is no restriction over an external form of the chip so long as the chip can be mounted on the space 2 of the rotary plate 1. At first, descriptions are provided for the casting mold for forming the flow paths 11 to 16 and the separation chamber 17 on the substrate.

A casting mold is used for mass production. At first a cleaned glass substrate or a silicon substrate is subjected to ashing for 5 minutes with oxygen plasma for removing organic materials deposited on a surface thereof. Then the substrate is spin-coated with SU 8-25 which is a photosensitive resist. Excellent spin coat can be obtained by executing the spin coating at 500 rpm for 10 seconds, and then at 2000 rpm for 30 seconds. The glass substrate with SU8-25 homogeneously coated thereon by spin coating is pre-baked for 1 minute at 75° C., and then at 100° C. for 5 minutes on a hot plate to form a layer of SU8-25 with the thickness of 25 μm. The SU8-25 layer is exposed to UV light for 15 seconds with a chromium mask with a form corresponding to the flow paths 11 to 16 and separation chamber 17 punched out thereon. Then the glass substrate is baked at 75° C. for 3 minutes and then at 100° C. for 5 minutes on a hot plate. Development is performed using a SU-8 developer according to instructions in a prespecified manual. A not-polymerized portion of the SU8-25 is removed with isopropanol, and the substrate is baked at 160° C. for 30 minutes to obtain a casting mold. As a result, a projection with the height of 25 μm for the flow paths 11 to 16 and the separation chamber 17 is formed on the glass substrate or the silicon substrate. In this case, a width of each of the flow paths 11 to 16 is 50 μm, that of the separation chamber 17 (between the positions where the inlet flow paths and outlet flow paths are attached respectively) is 4 mm, and the width of the separation chamber 17 in the centrifugal direction is 150 μm (=50 μm ×3).

Next descriptions are provided for a method of preparing a centrifugal chip using this casting mold. On the glass substrate or the silicon substrate, a wall with the height of 1.5 mm is provided to surround the casting mold for a projection with the height of 25 μm for the flow paths 11 to 16 and separation chamber 17. Internal size of this wall is 30×30 mm which is the same as the external size of the chip. A PDMS monomer mixture liquid prepared according to instructions provided in the manual is filled and then degassed and is heated at 75° C. for 30 minutes in a air constant temperature bath to polymerize PDMS. In this step, it is preferable to mount silicon wafer on a top surface of the wall and held thereon so that the thickness of the PDMS monomer mixture liquid layer is homogeneous. The wall is provided only for sustain the PDMS monomer mixture liquid, and therefore either a glass substrate or a silicon substrate may be used for this purpose. When the wall, silicon wafer, and casting mold are peeled off from the polymerized PDMS, a substrate 41 is obtained, and this substrate 41 has concaved portions formed on a surface of PDMS and corresponding to the flow paths 11 to 16 and separation chamber 17. FIG. 4 shows the state in which the flow paths 11 to 13 are formed on a surface of the substrate 41.

Then through holes 43, 44, and 45 each with the diameter of 2 mm are provided with a punch at positions where the flow paths and reservoirs are connected to each other on the substrate 41. Then a glass plate 42 with the dimensions of 30×30 mm and thickness of 1 mm is subjected to ashing for 10 seconds with oxygen plasma, and is adhered to a surface of the substrate 41 (PDMS) on which the flow paths 11 to 16 and separation chamber 17 are formed. With this operation, the concave sections formed on the surface of the substrate 41 and corresponding to the flow paths 11 to 16 as well as to the separation chamber 17 are shielded with the glass plate 42, thus the flow paths 11 to 16 and separation chamber 17 being completed.

The reservoirs 21 to 23 formed by adhering glass plates to each other are adhered to a surface of the substrate 41 contrary to that on which the flow paths and separation chamber are formed. The reservoirs and PDMS are adhered to each other with covalent bonding. In this step, the flow paths 11 to 13 are communicated to the reservoirs 21 to 23 with the through holes 43, 44, 45 formed on the substrate 41. FIG. 3 shows the state in which the flow paths 11 to 13 are communicated to the reservoirs 21 to 23 adhered on the other surface of the substrate 41 via the through holes 43, 44, 45. FIG. 4 shows only a cross-section of a portion to indicates that the two surfaces of the substrate 41 are used, and therefore the relations between the reservoirs 24 to 26 and the flow paths 14 to 16 are not shown, but it is easily understood from the figure that the relations are the same as those shown in FIG. 3. Further it is easily understood from this figure that the separation chamber 17 is formed, like the flow paths 11 to 13, on one surface of the substrate 41. The reservoirs 21 to 23 are formed with a glass plate, and therefore the reservoirs 21 to 23 should be shown with a certain thickness respectively in FIG. 3, but only a contour thereof is shown to simplify the figure. Further the reservoirs 21 to 23 are formed by adhering glass plates to each other, but the reservoirs 21 to 23 may be molded on a glass plate having a prespecified thickness, and the plate may be adhered for forming the reservoirs 21 to 23.

Holes for injecting solutions therethrough are provided on a top surface of the reservoirs 21 to 23 on the side close to the rotation center, and the reservoirs 21 to 23 are basically independent and separated with partition walls 51, 52 from each other, and the partition walls 51, 52 are lacked in the upper sections thereof at positions closed to the holes 46, 47, 48 for injection of solutions.

Now descriptions are provided for a method of feeding solutions into the reservoirs 21 to 23 of the centrifugal chip 100 to effect the state shown in FIG. 3 with reference to FIG. 4. At first, a solution with the lowest specific gravity is poured from the hole 48 for injection of a solution into the reservoir 23. In this step, a large quantity of solution is poured into the reservoirs 23 so that the solution is also poured into the other reservoirs 22, 21 through the lacks 51, 52 of on the partition wall 51, 52 for the reservoirs 21 to 23. When a centrifugal force is loaded in the state in which the reservoirs 21 to 23 are completely filled with the solution having the lowest specific gravity, all of the flow paths 11 to 16 and separation chamber 17 are completely filled with the solution with the lowest specific gravity. The liquid levels in the reservoirs 24 to 26 on the exit side are aligned to the same level, centrifugation is stopped. In this state, a solution having a higher specific gravity is poured from the holes 47, 46 into the reservoirs 22, 21 by the quantities almost equal to capacities of the respective reservoirs. As a result, the solution having the lowest specified gravity is flooded out from the reservoirs 22, 21 and is substituted with the solution having the higher specific gravity. Further a sample solution including a target for separation is poured into the reservoir 23. This step corresponds to the state shown in FIG. 3. When the centrifugal chip 100 is mounted on the space 2 of the rotary plate 1 and centrifugation is performed by driving the motor 3, the solution layers are formed according to the specific gravities of the solutions as shown in FIG. 2, and components in the sample solution are separated into the solution layers according to the specific gravities.

EXAMPLE 3

Figure 5:
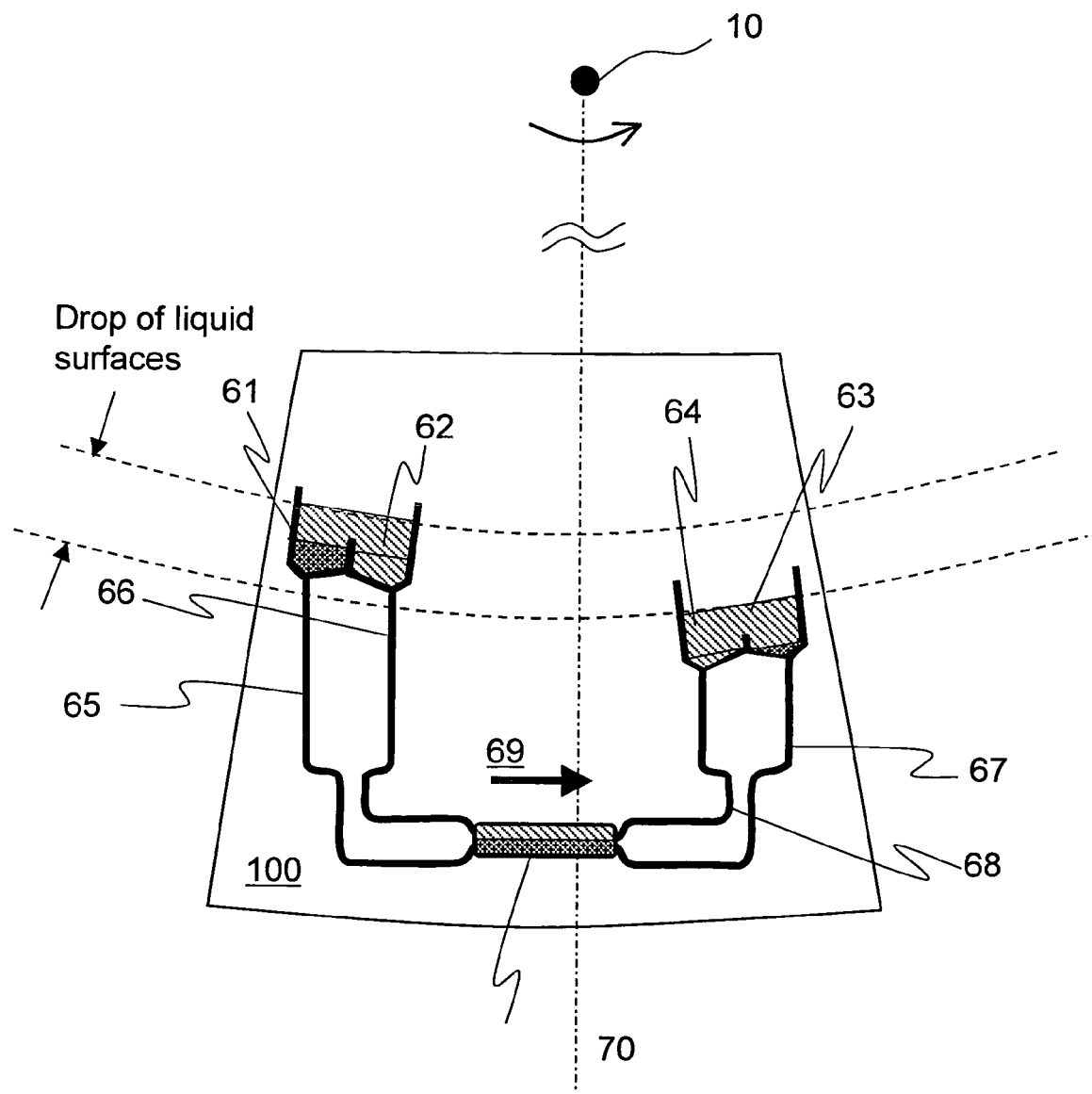
FIG. 5 is a view schematically showing configuration of the centrifugal chip 100 in Example 3 of the first embodiment.

FIG. 5 is a view schematically showing configuration of the centrifugal chip 100 in Example 3. As clearly understood when the centrifugal chip 100 in Example 3 is compared to that in Example 2 shown in FIG. 2, in the centrifugal chip in Example 3, distance of the reservoirs 61, 62 on the sample side from the rotation center 10 is different from that of the reservoirs 63, 64 on the recovery side. Because of this configuration, a larger G is loaded, during rotation, to the reservoirs 61, 62 as compared to the reservoirs 63, 64, so that the potentials at liquid levels are different from each other. Therefore the liquid flows in the direction indicated by the arrow 69. Flow paths 65 to 68 from their respective reservoirs are coupled to the separation chamber 70. In this example, two types of solutions are used, and the solutions flow from the reservoirs 61, 62 on the sample side to the reservoirs 63, 64 on the recovery side because of the difference in a centrifugal force corresponding to the drop between the liquid levels. Also in this step, it is important that distances of the levels of the solution with high specific gravity in the reservoirs on the entrance side and exit side and also distances of the levels of the solution with low specific gravity on the entrance side and exit side from the center of centrifugation are equal. To satisfy this requirements, like in Example 2, it is desirable that the solution with low specific gravity covers the solution with high specific gravity in the reservoirs 63, 64. In addition, it is necessary to align the liquid levels in the reservoirs 63, 64 on the recovery side. If there is a drop between the liquid levels, a two-liquid layer is not formed in the separation chamber 70.

Figure 6:
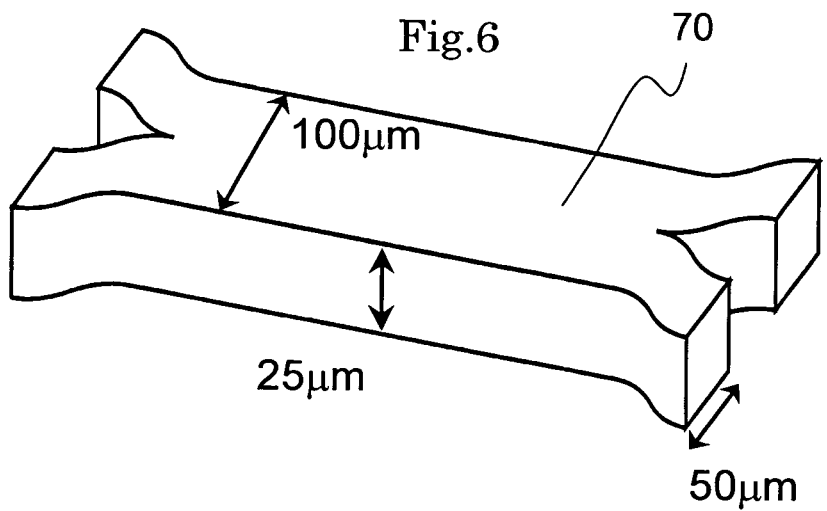
FIG. 6 is a perspective view schematically showing a separation chamber 70 in Example 3.

Also in Example 3, dimensions of the centrifugal chip 100 are the same as those in Example 2. FIG. 6 is a perspective view schematically showing the separation chamber 70 in Example 3. The width of the separation chamber 70 is 100 μm and the thickness is 25 μm in the direction in which G is loaded owing to a centrifugal force. Flow paths 65, 66, and 67, 68 each having the thickness of 25 μm and width of 50 μm are coupled to both edges of the separation section respectively. Namely the configuration is the same as that including the flow paths 11 to 13 formed on a surface of the substrate 41 shown in FIG. 4, though not shown in FIG. 5.

(Description of Operations of the Separation Section)

Figure 7:
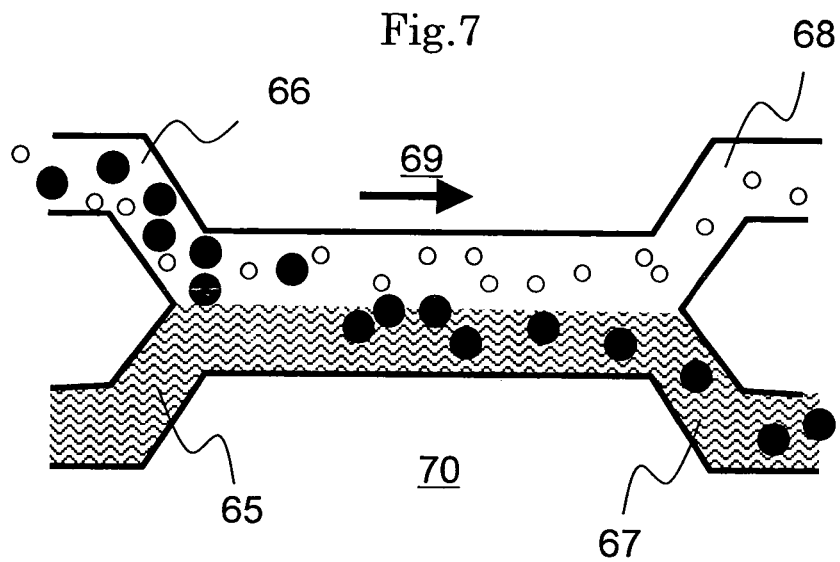
FIG. 7 is a view schematically showing the situation in which a separated materials are moving in a separation chamber 70 where two flow paths converge.

FIG. 7 is a view schematically showing the situation in which materials to be separated are moving in the separation chamber 70 to which the flow path 55 for a solution with low specific gravity and the flow path 56 for a solution with high specific gravity are coupled. Descriptions are provided below for a case in which a human erythrocyte and a human lymphocyte are separated with the centrifugal chip 100 in Example 3.

At first, a PBS containing 2-methacryloxyethyl phosphorylcholine polymer or BAS (pH 7.4) is put in the reservoirs 61, 62 of the chip to completely fill the flow paths 65 to 68 and separation chamber 70 with the PBS, and is left for 30 minutes in the state to coat surfaces of the flow paths with 2-methacryloxyethyl phosphorylcholine polymer or BSA. This operation is important for preventing non-specific absorption of cells. Then washing is performed with PBS to remove excessive BSA and the like in the flow paths 65 to 68 and in the separation chamber 70. Then PBS is filled in the reservoir 62 on the sample side (for a solution with low specific gravity) as well as in the reservoir 61 on the recovery side (for a solution with high specific gravity). In this step, the liquid is poured into the reservoirs up to a position above the lack on the partition wall between the reservoirs described above so that a constant pressure is loaded to the two flow paths (namely so that the liquid flows in the two flow paths at the same flow rate. Then a solution with the specific gravity adjusted to 1.077 is added in the reservoir 61 on the recovery side (for the solution with high specific gravity), and the reservoir is rotated at 1800 rpm to apply a centrifugal force thereto so that the solution with low specific gravity and that with high specific gravity are filled in the respective flow paths. The operations are performed at the room temperature. Then, an image of the separation chamber 70 is monitored with the optical system described with reference to FIG. 2. In this case, as shown in FIG. 7, it can be observed that the solution with low specific gravity and solution with high specific gravity form a two-layered laminar flow, and erythrocytes each shown with a large black circle moves into the solution with high specific gravity and the lymphocytes each shown with a small blank circle remain in the solution with low specific gravity.

Figure 8:
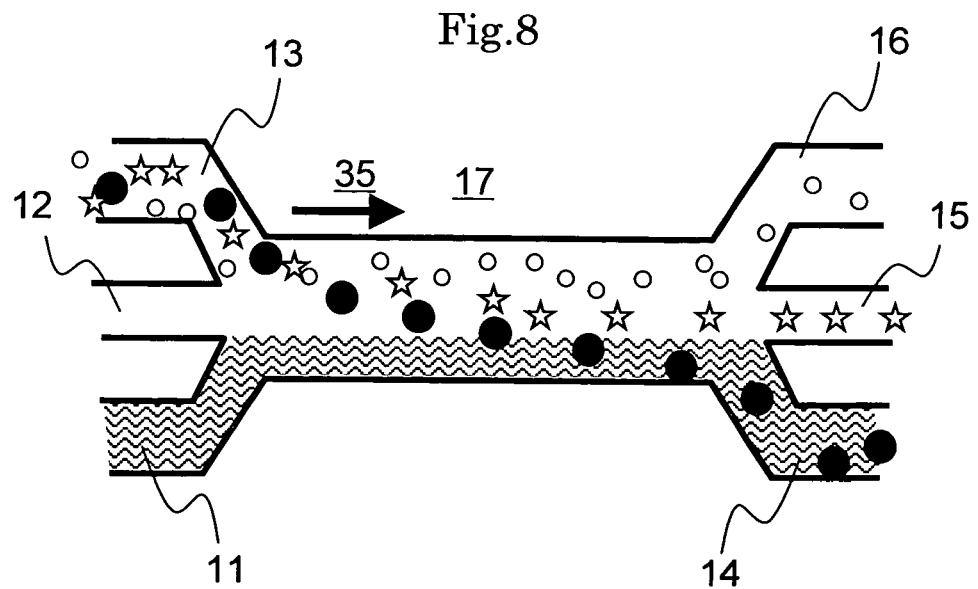
FIG. 8 is a view showing the situation in which a separated material is moving in a separation chamber 17 where three flow paths converge.

FIG. 8 is a view schematically showing the situation in which separated materials are moving in the separation chamber 17 to which a flow path 13 for a solution with low specific gravity, a flow path 12 for a solution with medium specific gravity, and a flow path 11 for solution with high specific gravity are coupled. In this case, descriptions are provided for an example in which blood serum is separated with the centrifugal chip 100 in Example 1.

At first, as described by referring to FIG. 4 above, the flow path 13 (for a solution with low specific gravity), two flow paths 12, 11 (for a solution with medium specific gravity and for a solution with high specific gravity) on the sample side, and separation chamber 17 are washed. In this case, a specific gravity of the solution with low specific gravity is adjusted to about 1, that of the solution with medium specific gravity to 1.077, and that of the solution with high specific gravity to 1.113. After washing, the solution with low specific gravity is filled in the reservoir 23 on the sample side (for the solution with low specific gravity) and in the reservoirs 22, 21 on the recovery side (for solutions with medium and high specific gravities). In this step, the solution is filled up to a position above the lack on the partition wall 51 between the reservoirs described above so that a constant pressure is loaded to the three flow paths (namely, so that the solutions will flow at the same flow rate in the three flow paths). Next, the solutions with the specific gravities adjusted to 1.077 and 1.113 are filled in the reservoirs 22, 21 on the recovery side (for solutions with medium and high specific gravities) respectively and centrifugation is performed at 1800 rpm, so that the solutions with low, medium, and high specific gravities are filled in the respective flow paths. The operations are performed at the room temperature. Then a sample (serum) mixture solution is added in the reservoir 23 on the sample side (for the solution with low specific gravity) and centrifugation is carried out at 1800 rpm. In this state, an image of the separation chamber 70 is monitored with the optical system described by referring to FIG. 2, and in this case, as shown in FIG. 8, in the separation chamber 17, the solutions with low, medium, and high specific gravities form a three-layered laminar flow, and the erythrocytes each shown with a large black circle move into the solution with high specific gravity, polykaryocytes each shown with a star mark move into the solutions with medium and high specific gravities, and a monokaryocytes each shown with a small blank circle remain in the solution with low specific gravity.

In this step, by adjusting the rotational speed of the centrifugal chip 100 and the image fetching rate of the high speed camera 101 to appropriate values, the images of the separation state can be picked up as still images.

[II] Second Embodiment

Descriptions are provided below for a method of once labeling a target cell to be separated with a particular material for identification, separating the cell, and discharging the particular material by a transporter present in the target cell after separation thereof.

At first descriptions are provided for the use of a transporter for labeling a target cell which is a feature of the second embodiment.

The transporter is generally used for transporting an amino acid such as glutamic acid, an oligopeptide such as dipeptide or tripeptide or other various types of organic materials having a low molecular weight through a cell membrane. Examples of transporters advantageously applicable to the second embodiment are shown in Table 1 each in relation to a labeling material and types of cells to be labeled. In Table 1, a transporter name is shown in item 93, a substrate moving through the cell membrane in item 94, and an organ or a cell in which the transporter is expressed in item 95.

TABLE 1

| 94 Substrate | 93 Transporter | 95 Tissue, cell, organ |
|---|---|---|
| Glucose | SLC2A1-6,8,10,11 | Erythrocyte, leukocyte |
| Fructose | SLC5A1,2 | Lever, renal, intestine, lung |

TABLE 1-continued

| Substrate | Transporter | Tissue, cell, organ |
|---|---|---|
| Galactose | | Islet of Langerhans |
| | | Brain |
| | | Fat cell |
| | | Cardiac tissue |
| | | Testis |
| | | Placenta |

It is needless to say that all of transporters present in all cells have not yet been known, and there are orphan transporters anticipated from the genome sequences, materials for which transporters are unknown, and materials which can pass through a cell membrane without using the channel as defined by the term of "transporter", such as arginine oligomer described in Table 2. For instance, the second embodiment can be implemented, if it is known that a material having the function involved in transport through a cell membrane such as steroids, chemical substances, and organic materials generally having a high lipophilicity easily fetched into a cell is present. Namely, it is desirable to confirm the presence of a substance capable of transporting various types of fluorescent molecules or the like into and out from a cell.

TABLE 2

| Substrate | Transporter | Tissue, cell, organ |
|---|---|---|
| (Arg)n (n = 6-8) | — | Nuclei of most cells |
| Lactoferrin | — | Most cells |
| Fibroblast growth factor | — | Most cells |
| Herpes simplex virus type 1 protein 22 | — | Most cells |
| HIV type 1 transactivator protein | — | Most cells |
| Engrailed | — | Most cells |

In order to label a target cell with a specific material by passing a transporter present in the target cell, the transporter is required to be exposed in a solution containing a specific labeling material to be passed for a prespecified period of time. However, in order to eliminate the specific material from the target cell by making a transporter pass therethrough after separating the target cell, the target cell is cultured in a solution not containing the specific labeling material for a prespecified period of time, so that the target cell can be separated causing little damage thereto. With the second embodiment, the target cell can be recognized and separated without damaging a cell surface thereof and a protein or a sugar chain of cytoplasm thereof.

Figure 9:
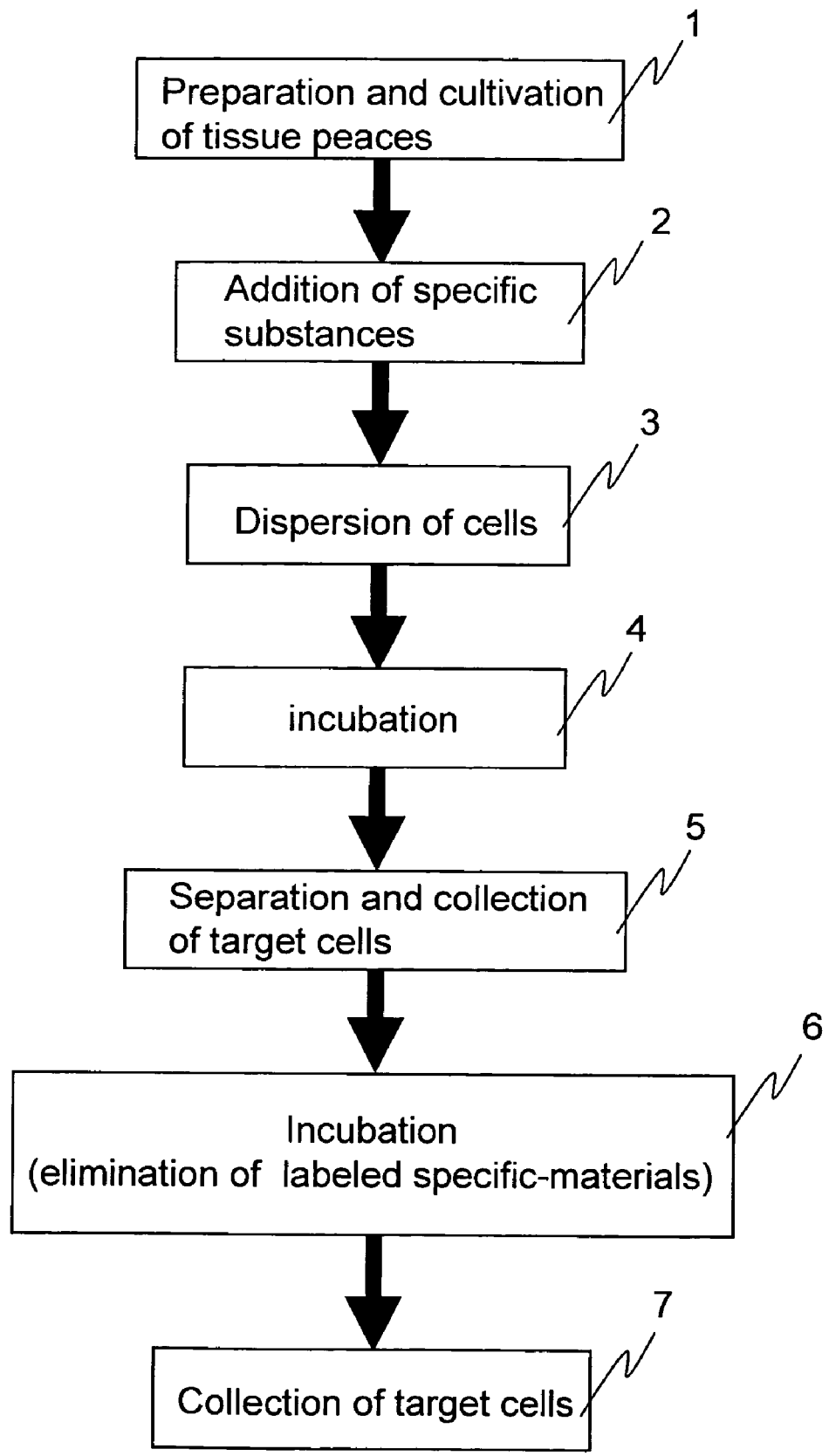
FIG. 9 is a flowchart showing processing steps in a method of separating and collecting a cell in a second embodiment.

FIG. 9 is a flowchart showing processing steps in the method of separating and collecting a cell according to the second embodiment.

In step 1, a tissue piece containing a target cell desired to be separated and collected is obtained, and is incubated in a culture solution according to the known method. It is to be noted that a targeted tissue piece may be, depending on the type thereof, subjected to conditioning for 15 to 30 minutes prior to incubation. To prevent the problem of dispersion of a specific material to be intaked into the target cell, size of the tissue piece is preferably small in general, and more preferably, the tissue piece is sliced into a thin segment having 20 layers or less of a cell. However, for instance, with an aim that a target cell present in the upper portion of epithelium existing in a large intestine tissue piece is labeled to separate the same from that reside in the deep portion the epithelium, the tissue piece is preferably sliced into a rather thick piece and is labeled via a transporter. In this case, cells on the side opposite to the upper portion of epithelium may be removed with a razor or the like after labeling.

In step 2, a specific material to be intaked into a target cell is added thereto employing a transporter presumably expressed in the target cell.

The specific material herein includes sugar substances such as glucose, fructose and galactose, amino acids such as glycine, glutamic acid and β-aminobutyric acid, an oligopeptide such as dipeptide and tripeptide, various types of medicaments, noradrenaline, dopamine, serotonin, or the like. Each specific material is labeled for an easy detection. A fluorescent material is used for labeling, and it is important that the fluorescent material does not bring about a change in a charge of the specific material. In addition, the fluorescent material with a size thereof being as small as possible is suited for the purpose, and a derivative of 6-(N-(7-nitrobenz-2-oxa-1.3-diazol-4-yl) or a derivative of 4,4-difluoro-4-bora-3a,4a-diaza-s-indacene may be employed. When an amino acid is used for labeling, in order not to change a charge thereof, a linker portion coupling the amino acid with a fluorescent material is adjusted so as not to cause a change in the number of charges after fluorescent labeling. A method of labeling without changing a charge of an amino acid may include, for instance, introducing a labeling material by modifying an amino group of the amino acid with imido esters. Imido esters react with an amino acid at pH 8.5 to 9 to turn into imido amido, namely amidine. An amidine group is protonated at a physiological pH, like an amino group prior to the reaction, so that the amidine group is not easily affected by a charge gap when the amidine group passes a transporter.

In step 3, a cell is subjected to dispersion processing by treating an issue piece with a specific material added thereto by means of, for instance, trypsin.

In step 4, a dispersed cell is generally incubated for 15 minutes to 2 hours so that a specific labeling material is intaked into a target cell. In this case, when, prior to the step of separating and collecting a target cell to be implemented in step 5, the cells are rinsed with a culture solution not containing a specific labeling material to remove the excessive one if any, reproducibility is excellent and incorrect separation is scarce owing to background noise, often leading to a good result.

In step 5, a target cell is separated and collected. A cell separation chip and a cell separator used in this step 5 are described hereinafter. Cell separation is optically recognized in the course where a labeled image is flowing down in a fluid, and cells having a prespecified level or more of fluorescent intensity are collected. In this case, image recognition can be done by recognition of a cell as a point light source, and for more advanced type of cell separation, distribution of a specific labeling material within a cell captured as an image is acquired, and only a cell having a specific organelle with a specific labeling material gathering therein can be separated. For instance, only a cell having mitochondria with a specific labeling material condensed therein can be separated.

In step 6, in order to remove a labeling material from cells having a target cell with a labeling material as a foreign material present therein, the cells are incubated in a culture solution not containing a specific labeling material to remove the specific labeling material from a target cell. Removal of the specific labeling material may include reversibly excluding the same via a transporter, excluding the same via a transporter related to a foreign material release such as an ABC transporter, and decomposing the same in lysosome.

Removal is possible with respect to a target cell obtained according to the second embodiment, unlike the case in which a labeling material is irreversibly bonded to a cell such as a CD marker commonly used so far, so that the initial state of a target cell can be advantageously preserved.

The aforementioned processing is described below more specifically.

Figure 10:
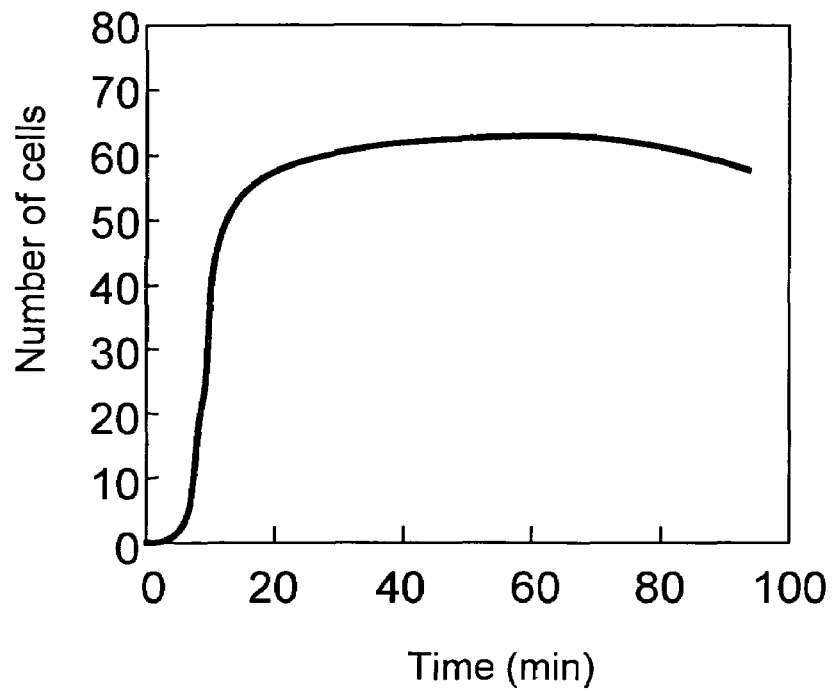
FIG. 10 is a view showing general characteristics in a case where a cell with the fluorescence intensity of 5000 or more is separated with a cell separator.

10 μM of a fluorescent labeled material is added to a tissue piece collected, and the piece is incubated at 37° C., a portion thereof is taken out at regular intervals, and the cells therein are dispersed according to the known method to be separated with a cell separator described later. FIG. 10 is a view showing general characteristics in a case where a cell with the fluorescence intensity of 5000 or more is separated with a cell separator, suggesting that intake of a fluorescent labeled material into a target cell becomes constant in about 20 minutes. It should be naturally understood that the period of time varies significantly according to the size and state of a cell piece or how to collect the same. It is needless to say that a user is required to determine how to set conditions for one's own samples.

Figure 11:
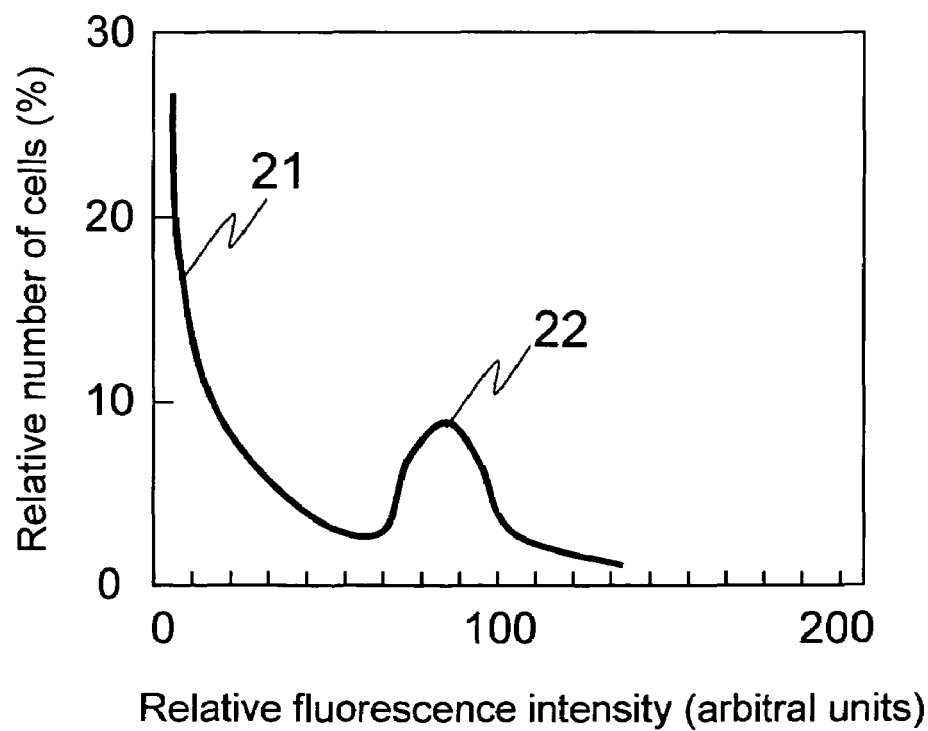
FIG. 11 is a histogram plotted with the number of cells taking a fluorescent labeled material against the fluorescence intensity.

Next is described whether separation of a target cell with a fluorescent labeled material intaked therein from a cell with the same not intaked therein is possible or not. FIG. 11 is a histogram showing fluorescence intensity of a fluorescent labeled material when the material is intaked into a target cell. The fluorescence intensity is shown on the horizontal axis, and the number of cells on the vertical axis on percentage. Two groups are generally obtained as shown in the figure with lines 21, 22. The group shown with the line 21 is regarded as a cell group not having been labeled, while the cell group shown with the line 22 as a cell group having been labeled.

Figure 12:
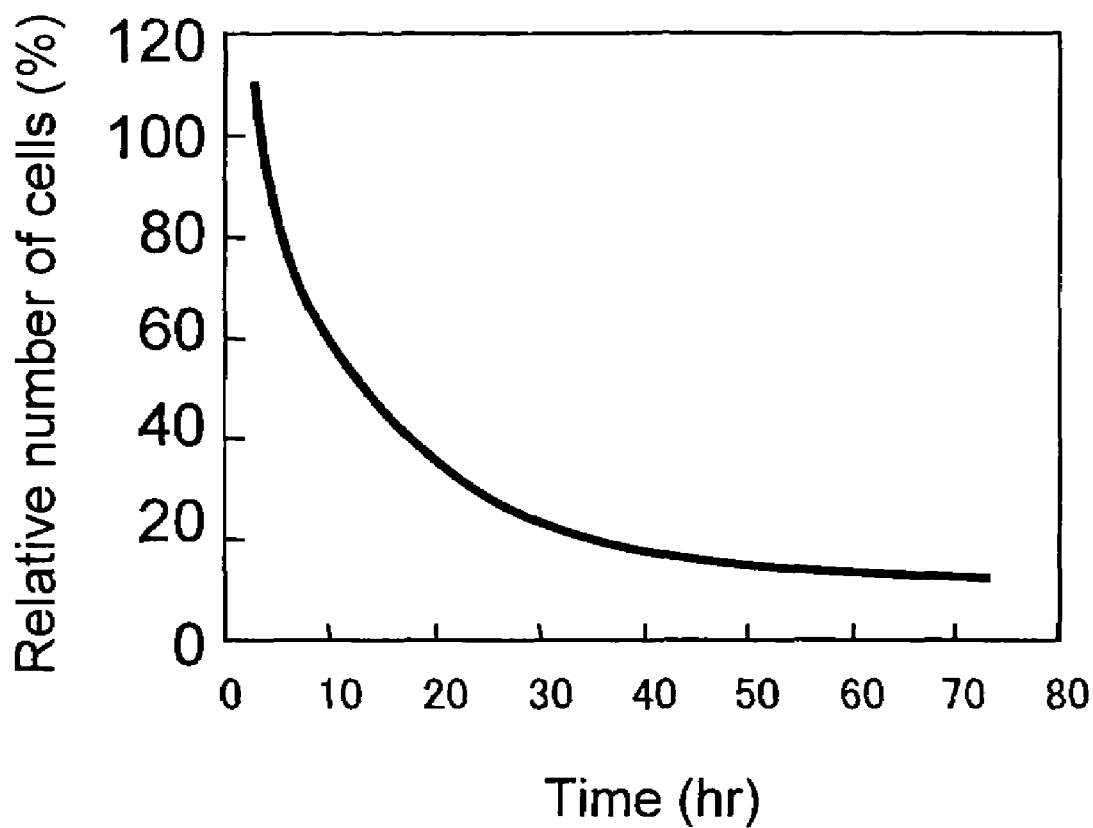
FIG. 12 is a graph showing culture time of a cell on the horizontal axis and the separated cells with the fluorescence intensity of 500 or more on the vertical axis.

Then the target cell group shown with the line 22 is continued to be incubated in a culture solution not containing a fluorescent labeled material, and a portion of the cells are taken out at regular intervals to separate cells, for instance, with the fluorescence intensity of 500 or more. FIG. 12 is a graph showing culture time of cells on the horizontal axis and the separated cells with the fluorescence intensity of 500 or more on the vertical axis. In this case, the figure demonstrates that the number of a cell with 90% of a labeling material removed therefrom reaches 70% of the total cell number in 24 hours, and in 48 hours, the labeling material is removed from almost all cells.

As described above, in the second embodiment, a material capable of passing a transporter present in a target cell is used as a labeling material, and the target cell, after separation, is incubated in a culture solution not containing a material fluorescently labeling the target cell, so that the target cell can be returned to its original state (native state). This is an important advantage because any foreign material does not get into a target cell in the case, for instance, where a separated target cell is returned to the body. Further in the cell researches, the availability of quickly removing a labeling material for cell separation makes it possible to minimize influences of the labeling material over the cell, and therefore this technique can make a great contribution to researches for accurately understanding the cellular physiology.

With regard to a transporter, it is generally contemplated that a plurality types of transporters exist in relation to one type of substrate, and a different type(s) of transporter is used according to the type or state of a cell. Therefore it is possible to modify a specific material as an original substrate of a transporter with a fluorescent material or to alter a side chain of the substrate itself, so that specificity of the specific material to a transporter can be altered. Thus the second embodiment in which a target cell is identified and separated using a transporter may be suited for identifying and separating a cell in various phases of cytodiffentiation or in the active state.

As described above, in the second embodiment, a target cell is separated and collected with the steps of: adding a specific material passing a transporter into a target cell by making use of a transporter for a target cell to be separated to introduce the specific material into the target cell; detecting a target cell with a specific material intaked therein using the cell separator described above; and separating the target cell with the specific material intaked therein by the cell separator, which makes it possible to obtain a target cell with little damage. In this case, the step of adding a specific material passing a transporter into a target cell to introduce the specific material into the target cell may be carried out, as the target cell is in just the state when it was collected, without making any major treatment thereon, which is effective for labeling a target cell in a further natural state thereof. For instance, in order to divide a tissue piece into discrete cells, treatment with an enzyme such as trypsin is available, however, the cells each having kept a specific form up to then become rounded, which may cause a trouble to the subsequent use depending on the circumstances. In this case, the second embodiment is designed to take steps for obtaining a target cell further accurately by exposing a tissue piece as it is in a solution containing a specific labeling material passing a transporter for a prespecified period of time, and then treating the tissue piece for being divided into discrete cells.

In the second embodiment, the aforementioned is applies to a culture cell, namely, a single-layer cell is incubated on a surface of a culture flask or the like, and then the cell is incubated as it is in a solution containing a specific labeling material passing a transporter, after which a cell group is divided into discrete cells using trypsin or the like to separate and collect the appropriate cells. In the conventional technology, a cell surface antigen is labeled using a labeled antibody after a cell group is divided into discrete cells, which means that labeling is conducted after a cell is treated with trypsin or the like, so that only a labeling material which is not affected even when a target cell is denatured with this operation can be used.

Moreover, if the cell dispersion treatment is forced to be executed after a cell surface antigen is labeled with a labeled antibody, a protein portion of a molecule assembly comprising the surface antigen or a labeled antigen is decomposed, thereby a state with high reproducibility can not be obtained. In the second embodiment, a material intaked in a target cell is used as a labeling material, so that, even when labeling is conducted before the cell dispersion processing, there is no possibility that the labeling material is discomposed or eliminated like in the case according to the conventional method. Further, if labeling is carried out before the cell dispersion processing, even though the subsequent operation changes the state of a cell, original characteristics of the cell are maintained at the time of labeling, enabling separation of a target cell without any problems.

A certain period of time is generally required for a labeling material to be intaked into a target cell via a transporter. Therefore a culture step may be provided in which a sample possibly containing a target cell is incubated for a prespecified period of time in a solution containing a specific material passing a transporter present in the target cell. With this step, a target cell can be labeled with a specific material passing a transporter. After the above culture step is completed and target cells each with a specific material for labeling identification intaked therein are separated, another culture step is added in which the separated target cells are exposed for a prespecified period of time to a solution not containing a specific labeling material passing the transporter described above, so that the target cells finally obtained do not contain any specific labeling material possibly having an effect on cell functions, or contains the specific material but only to the extent that the concentration of the same is reduced to have no effect on cell functions.

(Example of a Cell Separation Chip)

Figure 13:
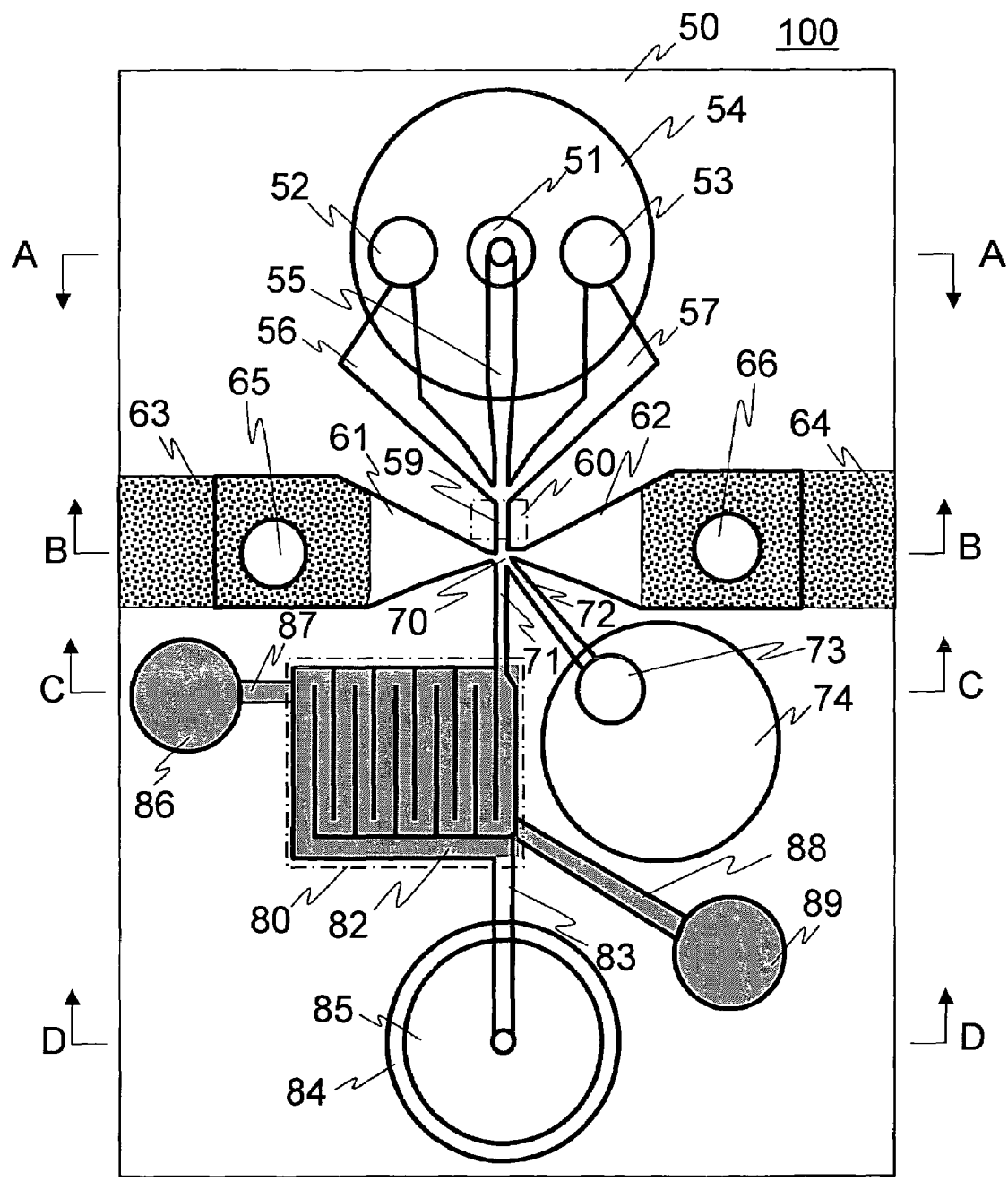
FIG. 13 is a plan view schematically showing an example of a cell separation chip adapted to implementation of a protocol for cell separation according to a second embodiment.
Figure 14:
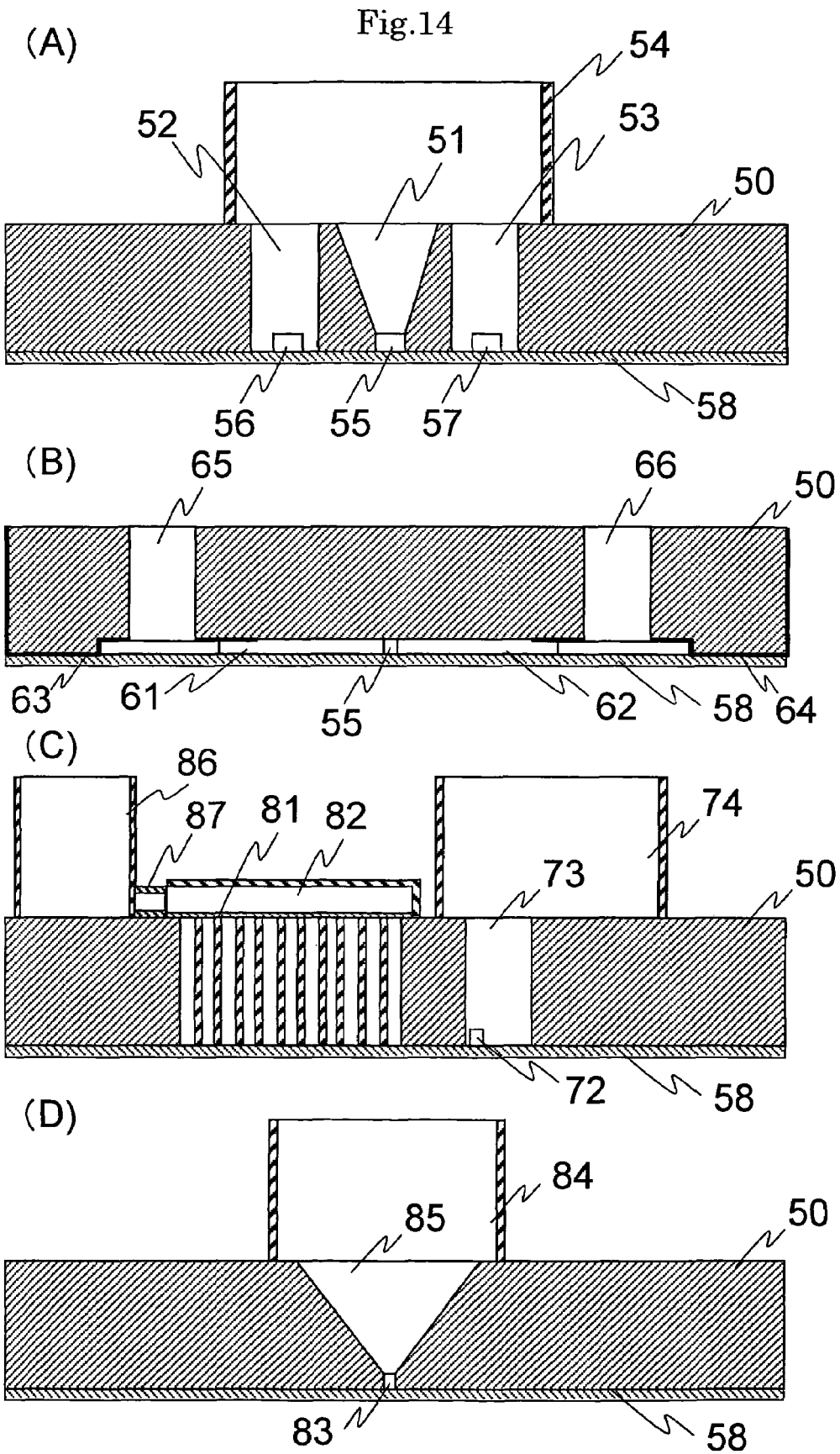
FIGS. 14(A) to 14(D) are cross-sectional views of the cell separation chip shown in FIG. 13 taken along the lines A-A, B-B, C-C, and D-D and viewed in the direction indicated by the arrows at respective positions.
Figure 15:
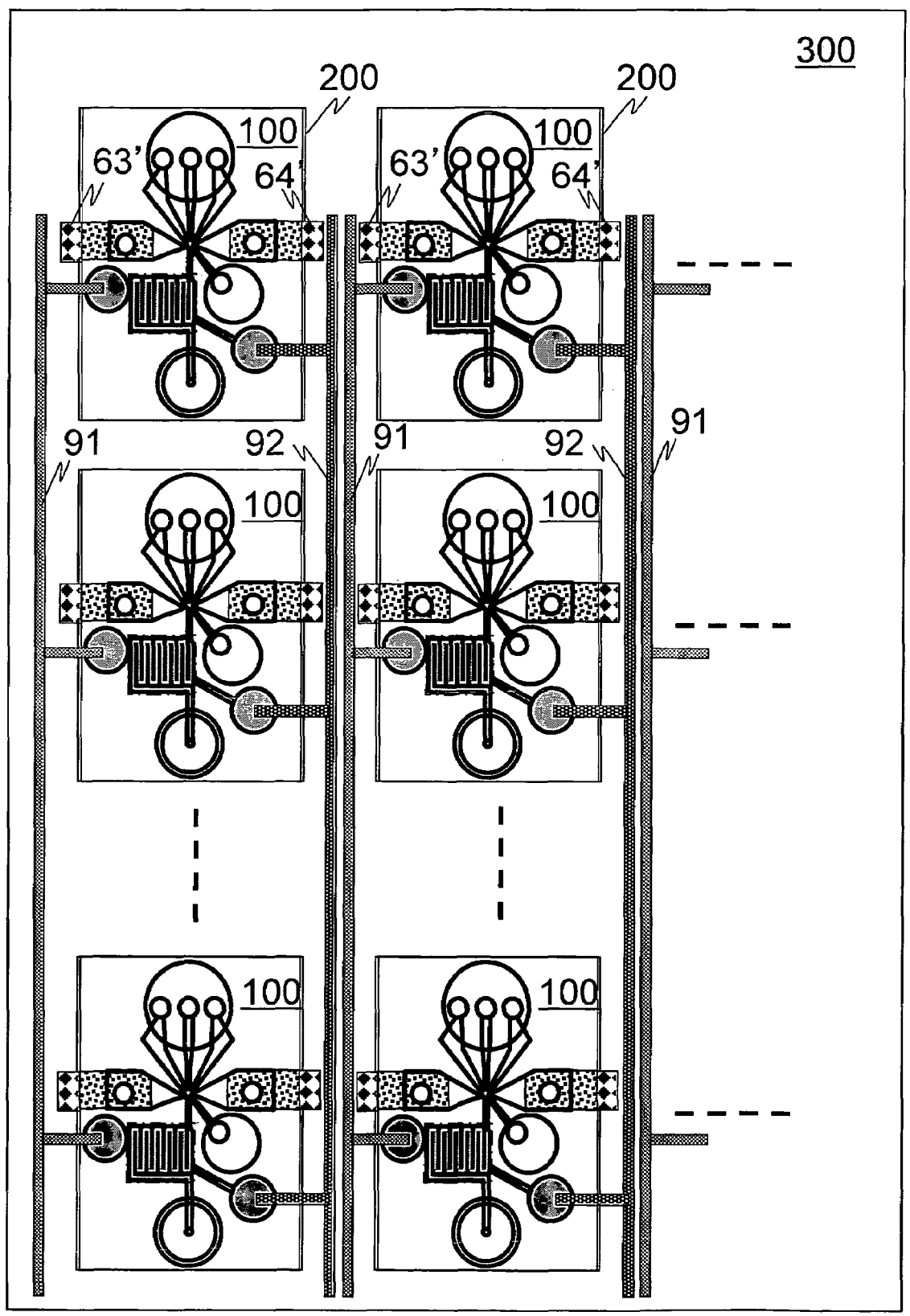
FIG. 15 is a plan view schematically showing an example of a cell separator with a plurality of cell separation chips illustrated in FIGS. 13 and 14 mounted thereon.

FIG. 13 is a plan view schematically showing an example of a cell separation chip adapted to implementation of a protocol for cell separation according to the second embodiment. FIG. 14 is a cross-sectional view of the cell separation chip shown in FIG. 13 taken along the lines A-A, B-B, C-C, and D-D and viewed in the direction indicated by the arrows at respective positions. FIG. 14 shows, to avoid excessive complexity, only those viewed in the vicinity of the cross section. FIG. 15 is a plan view schematically showing an example of a cell separator with a plurality of cell separation chips illustrated in FIGS. 13 and 14 mounted thereon.

Reference numeral 100 indicates a cell separation chip, size of which is about 30 mm×40 mm. Reference numeral 50 indicates a substrate, for instance, a mold substrate made of plastic material having a thickness of about 1 mm. Reference numeral 51 indicates a cone-shaped hole for being poured a buffer containing a target cell to be separated. Reference numerals 52 and 53 indicate holes with the buffer poured therein. The hole 51 is 0.1 mmφ in diameter of the bottom face and 5 mmφ of the top face. The holes 52 and 53 are formed to penetrate the substrate 50 and are about 3 mmφ in diameter. Reference numerals 55, 56 and 57 are flow paths, each of whose one end is open to the holes 51, 52 and 53 respectively. The flow paths 55, 56 and 57 are formed on the bottom face of the substrate 50, and have a height of about 50 μm and a width of 100 μm. On the top face of the substrate 50 is formed a buffer retention bath 54. The buffer retention bath 54 is designed to be about 10 mm in height and 10 mmφ in diameter.

The flow paths 55, 56 and 57 are converged together on the downstream side to form a flow path 59. A portion of the flow path 59 is provided to be a cell monitoring area 60, on the downstream side of which is formed a cell separation area 70. The flow path 59 has, like the flow paths 55, 56 and 57, a height of about 50 μm and a width of 100 μm. In the cell separation area 70 are provided openings of gel for two gel electrodes opposing to each other on both sides of the flow path 59. Each of the openings is placed in a position slightly deviated from the flow direction of the flow path 59. At the rear of the openings of gel for the gel electrodes are formed spaces 61, 62 for holding gel, and each of the spaces has the substantially same height as that of the flow path 59, and is provided with gel supply holes 65, 66 respectively. The gel supply holes 65, 66 are about 3 mmφ in diameter. On a portion of the spaces 61, 62 are deposited metal thin films 63, 64, and the thin films are extended from the bottom face of the substrate to a side face thereof.

A flow path 71 as a flow path for a target cell to be collected and a flow path 72 as a flow path for a target cell to be discharged are provided on the downstream side of the cell separation area 70. Each of the flow paths 71, 72 has, like the flow paths 55, 56 and 57, a height of about 50 μm and a width of 100 μm. It is assumed herein that, when a cell flowing down is determined to be labeled as a target in the cell monitoring area 60, voltage is not applied to the two gel electrodes on both sides of the flow path 59, in the meantime, when a cell flowing down is not determined to be labeled as a target, voltage is applied to the two gel electrodes when the cell reaches the cell separation area 70. In this case, the two gel electrodes are placed in a position slightly deviated from the flow direction of the flow path 59, so that the direction of force acting on a cell owing to an electrical field acted by the two gel electrodes can be turned to somewhat upper right. Consequently, force in the direction in which a cell flows down and that acting on the cell owing to an electrical field is synthesized, and the cell is thereby acted by force heading in the lower right direction, so that the flow path 72 as a flow path for cells to be discharged is provided in a position of this direction, and the cells to be discharged can be easily introduced to the flow path 72. When a cell flowing down is determined to be labeled as a target, because voltage is not applied to the two gel electrodes on both sides of the flow path 59, the flowing-down target cell flows, without delay, in the flow path 71 as a flow path for cells to be discharged.

The other end of the flow path 72 is communicated to a discharged-cell collecting hole 73. The discharged-cell collecting hole 73 is about 3 mmφ in diameter. On the top face of the substrate 50 is formed a buffer retention bath 74 communicating to the discharged-cell collecting hole 73. The buffer retention bath 74 is, like the buffer retention bath 54, designed to be about 10 mm in height and 10 mmφ in diameter. The flow path 71 as a flow path for target cells to be collected is connected to a dialysis section 80. The dialysis section 80 extends from the top face to the bottom face of the substrate 50, and forms a hooked flow path therein. The end of the hooked flow path is communicated to a collecting path 83. When the hooked flow path is designed to have a flow path width of 100 μm, a partition width of 100 μm, and the total size of 10 mm×10 mm, the total length thereof results in about 50 cm. On the top of the hooked flow path is attached a porous membrane (0.2 μm) or a dialysis membrane (molecular weight cut 100000 Da) to form a space 82 with a solution not containing a fluorescent labeled material flowing down on the top face thereof. On both ends of the space 82 are provided a buffer retention bath 86 for supplying a buffer (a solution not containing a fluorescent labeled material) and a buffer retention bath 89 for collecting a buffer flowing down in the space 82. When a target cell to be collected is flowing down in the hooked flow path in the dialysis section 80, a specific labeling material intaked in the target cell is removed by a solution not containing a fluorescent labeled material. In order to sufficiently supply a solution not containing a fluorescent labeled material, it is desirable to replenish the retention bath 86 with a solution not containing a fluorescent labeled material from a retention bath not shown, and to discharge a collected solution not containing a fluorescent labeled material from the retention bath 89. Reference numeral 87 indicates a flow path connecting the retention 86 and the space 82, while reference numeral 86 indicates a flow path connecting the space 82 and the retention bath 89. These flow paths are formed on the top face of the substrate 50. Since the retention baths 86, 89 are intermediary baths, the size of which is designed to be about 10 mm in height and 5 mmφ in diameter respectively.

The dialysis section 80 on the substrate 50 may be a lack, and in the lack may be embedded a unit with the dialysis section 80, the porous membrane or dialysis membrane 81 and the space 82 integrated therein. This has an advantage in manufacturing the substrate 50 by molding.

The other end of the collecting path 83 is communicated to a cone-shaped hole 85. On the top face of the substrate 50 is formed a buffer retention bath 84 for collecting a target cell collected via the collecting path 83 and a flowing-down buffer. The buffer retention bath 84 is designed to be 10 mm in height and 10 mmφ in diameter. Walls of various retention baths described above and the space 82 are about 1 mm thick respectively.

As seen in FIG. 14, onto the bottom face of the substrate 50 is attached a plastic thin film 58 such as PMMA to complete the flow path on the bottom face of the substrate 50. On the other hand, on the top face of the substrate 50 are formed walls of various retention baths described above and the space 82, and the walls may also be those formed with plastic made of PMMA and attached to the top face. The PMMA plastic may be substituted by polyolefin plastic. The porous membrane can be obtained by periodic acid-oxidizing a cellulose membrane (molecular weight cut off 30000 Da), partially introducing an aldehyde group therein, reacting the membrane with avidin, and reduction-stabilizing a Schiff base bonding with the hydroboration reaction, and attaching the resultant membrane to a surface of a biotin-modified chip with the biotin-avidin bonding. Biotinylation of a chip surface is introduced by, in the case of plastic, treating the surface with oxygen plasma to generate a radical, and immediately soaking the chip in a solution containing a biotin derivative having a double bond residue.

Additionally, as shown in FIG. 15, a cell separator 300 having a number of cell separation chips 100 can be configured to raise the throughput for cell separation as a whole. In the figure, reference numeral 91 indicates plumbing for replenishing the retention bath 86 with a solution not containing a fluorescent labeled material, and the plumbing is branched out to thereby replenish the retention bath 86 on the cell separation chip 100 with a solution not containing a fluorescent labeled material. Reference numeral 91 indicates plumbing for discharging a solution not containing a fluorescent labeled material collected from the retention bath 89, and the plumbing is branched out to thereby discharge the solution from the retention bath 89 on the cell separation chip 100. The cell separation chip 100 is inserted in a position for a cell separation chip holder 200 provided by hollowing a surface of the cell separator 300, so that, when a chip is exchanged with another, the new chip can be provided in the same position. With a configuration in which voltage is applied to the gel electrodes via electrodes 63, 64 provided in a position corresponding to metal thin film 63, 64 on the plane of the cell separation chip holder 200 extended from the plane of the cell separation chip 100, labor of connecting an electrode can be saved in exchanging a chip. It is needless to say that, in place of providing metal thin films 63, 64 on the cell separation chip 100, terminals for connection may be provided in a position adjoining to the cell separation chip 100 on a surface of the cell separator 300, so that voltage can be applied to the gel electrodes by inserting the terminals into the gel supply holes 65, 66.

Whether a cell separator is configured with a single cell separation chip 100 or with a plurality of cell separation chips 100 incorporated therein, it is necessary to provide an optical system for determining whether a cell flowing in a flow path in the cell monitoring area 60 is a target cell to be collected or a cell to be discharged, and voltage is applied to the gel electrodes by means of a signal from the system according to the necessity.

Figure 16:
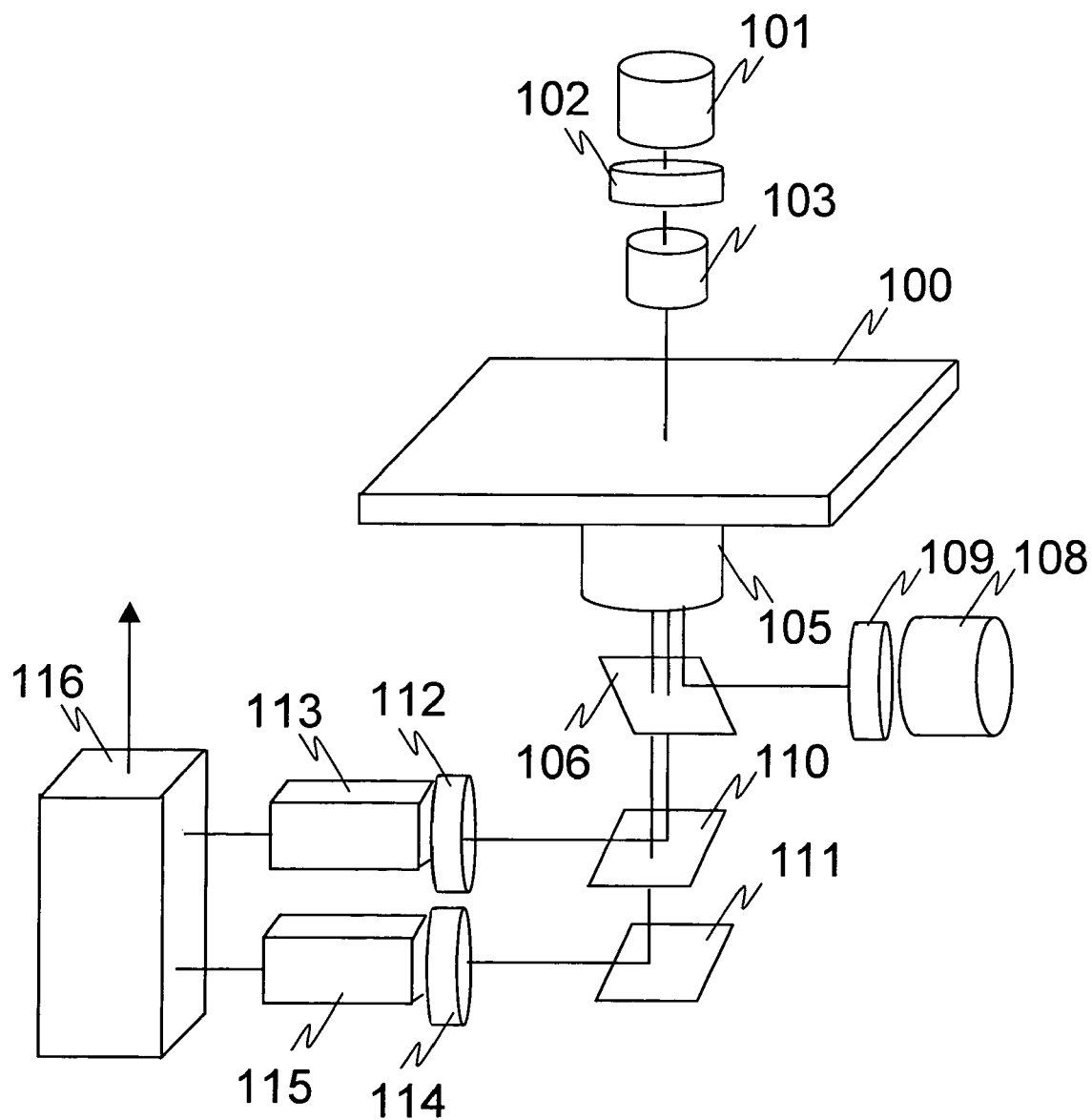
FIG. 16 is a view for illustrating an optical system of the cell separation chip.

FIG. 16 is a view for illustrating an optical system provided in a cell monitoring section 60 of the cell separation chip. Although the optical system is omitted and not shown in FIG. 13 to FIG. 15, it is necessary to monitor a cell flowing down the flow path 59, determine that the cell is a target cell to be collected or a cell to be discharged, as well as to measure the flowing speed, and to provide controls so that, when a target cell is recognized and reaches the cell separation area 70, voltage is applied to the gel electrodes, or otherwise, voltage is not applied to the gel electrodes. The optical system is used for the purposes described above.

Reference numeral 101 indicates a light source of a stereomicroscope, for which is generally used a halogen lamp. Reference numeral 102 indicates a band pass filter for transmitting only light at a specific wavelength from light of the light source 101 for the stereomicroscope. Reference numeral 103 indicates a condenser lens, to which is introduced a phase contrast ring in the case of a phase contrast observation, and a polarizer in the case of a differential interference observation. Reference numeral 100 indicates a cell separation chip. The state of the flow path 59 in the cell monitoring area 60 on the cell separation chip is observed with an objective lens 105. What is observed hereupon with the objective lens 105 is a stereoscopic image of a cell in the flow path 59 reflected by light transmitted from the light source 101, and a fluoroscopic image reflecting fluorescence emitted by a target cell labeled with excitation light in which only a wavelength of excitation light of light from the light source 108 through the band pass filter 109 is eradiated from the objective lens 105 by a dichroic mirror 106. In this step, it is desirable that the wavelength of light used for a stereomicroscopic observation is sufficiently shorter or sufficiently longer than a fluorescent wavelength area to be observed, and, if possible, is different from the excitation light wavelength area.

Only a stereoscopic image in a flow path is observed with a camera 113 utilizing a dichroic mirror 110 and a band pass filter 112 reflecting light at the same wavelength as that transmitting the band pass filter 102 described above. On the other hand, a fluoroscopic image is observed with a camera 115 by selectively transmitting the wavelength band for the fluoroscopic observation of light passing through the objective lens 105 utilizing a mirror 111 and a band pass filter 114. Images picked up by the two cameras 113, 115 are subjected to image data processing for analysis, and comparison of the relative positional relation between the two images makes it possible to compare and identify fine structures and fluorescence emitting positions of a cell. According to this result, a computing machine 116 determines whether voltage is applied to gel electrodes or not, and, when voltage is applied to gel electrodes, sends a voltage applying signal at a prespecified timing as indicated by the arrow. It is to be noted that in this case, stereoscopic images in a single wavelength band and fluoroscopic images in a single wavelength band are observed for comparison and analysis, and similarly, stereoscopic images in two or more wavelength bands may be compared to each other, or fluoroscopic images in two or more wavelength bands may be compared and analyzed. In doing so, one or more dichroic mirror and a light source or a camera observation system may be further provided in the light path as described above.

Descriptions are made in more detail for a case in which a CCD camera is used in an optical system. In this case, the cameras 112, 115 illustrated in FIG. 16 are integrated into a single camera.

As a prerequisite, suppose that a cell is moving in the flow path 59 at an average of 1 mm per second, and that a cell is flowing while turning around approximately once in 0.5 second in some cases, though depending on a shape of the cell. Assuming that 10 frames are required for recognizing a cell, detection of a cell image at intervals of 50 microseconds allows measurement of a shape of the cell or the like, even when the cell is turning around. Thus, on this condition, a system of observing an image at the rate of at least 20 frames/ second will suffice. Assuming that one cell is picked up in the same frame on average, cell recognition becomes possible at the rate of 20 cells/second, however, a CCD camera capable of picking up an image at the rate of 200 frames/second is used herein to be on the safe side. Thus, cell recognition and separation at the rate of several ten thousands of cells/10 minutes is actually possible.

Such a camera has the cell monitoring area 60 as an imaging range, and observes an area of 100 μm along the flow path 59 in a position 0.5 mm upstream of the cell separation area 70 in the flow path 59 of the cell monitoring area 60. A cell observed in the area reaches the cell separation area 70 in 0.1 second. As the cell is flowing at 1 mm per second, 20 frames of a cell image are fetched while the cell passes the observation area, and the shape of a cell and fluorescent images are observed.

The camera recognizes a cell as an image by operating scanning lines of the camera in the orthogonal direction against the direction in which a cell flows. The camera constitutes an optical system in which a cell is subjected to incident light from a lens 105, fluorescence emitted by the cell returns to the lens 105, and the fluorescence is separated according to the wavelength through a band pass filter for image formation, and another optical system in which light from the light source 101 irradiates a cell, and a transmission image thereof is detected. The optical system may be designed so that a transmission image and a fluorescent image are projected in different sections on the same CCD imaging screen of the camera, which enables measurement of both transmission image and fluorescent image with a single unit of an upmarket high-speed low-light camera.

How to use the cell separation chip 100 described above is outlined. First, the cell separation chip 100 is warmed to about 60° C., and material for gel electrodes is supplied by applying prespecified pressure from holes 65, 66 on the material for gel electrodes in the amount corresponding to the space for gel electrodes 61, 62. Consequently, the material for gel electrodes reaches the openings of the gel electrodes 61, 62. Further, the holes 65, 66 are almost filled with the material for gel electrodes. Nevertheless, on the assumption that the chip according to the second embodiment is brought on the market, material for gel electrodes may be filled in the chip beforehand.

Next, a tank 54 is filled with a buffer. As a result, the buffer sequentially flows in the flow path 59, cell separation area 70, flow path 71, flow path 72, dialysis section 80 and flow path 83 via a sample hole 51 for supplying a fluid containing cells and the buffer holes 52, 53 for supplying a buffer and via flow paths 55, 56 and 57. Then the buffer also flows in holes 73, 85. In this state, when a fluid containing cells is fed into a sample hole 51, the cells get lined up as passing in the tapered flow path 55, and become a laminar flow in the position where the cells converges with the flow paths 55, 56 to then reach the flow path 59 in the cell monitoring area 60. Each flowing down cell is sequentially identified as a target cell to be collected or that to be discharged, since cells are monitored with the optical system flowing down the flow path 59. The optical system applies or does not apply voltage to the gel electrodes 61, 62 according to the result of identification. When prespecified voltage is applied to the gel electrodes 61, 62, force owing to an electric field acts on a cell to introduce the cell to the flow path 72. When voltage is not applied to the gel electrodes 61, 62, force owing to an electric field does not act on a target cell, allowing the cell to flow down in the flow path 71. The target cell flowing down in the flow path 71 flows down in the flow path of the dialysis section 80. In the upper section of the dialysis section 80 is provided a porous membrane 81, on which a buffer fed from a buffer retention bath 86 flows, so that the target cell flowing down in the flow path of the dialysis section 80 has a reduced amount of a fluorescent labeled material having been intaked into the target cell. Because only a capacity of a tank 86 is insufficient for the quantity of a buffer to be fed in the dialysis section 80, buffer is to be fed also from other source, and a buffer collected into the buffer retention bath 89 is to be discharged. The buffer retention baths 86, 89 are intermediary tanks for a buffer.

Taking a length of the flow path of the dialysis section 80 and a passing speed of a cell into consideration, it is contemplated that, in some cases, a sufficient dialysis effect is not achieved with the cell separation chip described above. In such cases, it is desirable that a target cell is collected from a hole 85 for holding a fluid containing the target cell, and then dialysis is performed separately.

Several specific examples are described below in which a protocol for cell separation according to the second embodiment is implemented with the cell separation chip shown in Examples.

(Example of Cell Separation 1)

Descriptions are provided below for a case, as a specific example, in which cerebrum tissue piece cut off from a cerebral corium of a mouse is used. Tissue cells (in this case, a cerebral tissue piece) are directly put in an isotonic culture fluid, and are incubated at 37° C. for 15 minutes in atmosphere containing 5% carbon dioxide for conditioning. Substances and labeling materials presumably available in a neural cell system are descried with reference to Table 3. The transporters are disclosed in http://www.bioparadigms.org/slc/intro.asp.

TABLE 3

| 94 Substrate | 93 Transporter | 95 Tissue, cell, organ |
|---|---|---|
| γ-aminobutylic acid (GABA) | SLC6A1 | Brain (neuron) |
| Noradrenaline | SLC6A2 | Peripheral nerve system |
| Dopamine | SLC6A2, 3 | |
| Serotonin | SLC6A4 | |
| Glycine | SLC6A5 | |

More specifically, in the neural cell system, such transporters as γ-aminobutylic acid (GABA), noradrenaline (4-tetrahydro-N-methyl-1-naphthylamine), dopamine (2-dihydroxyphenylethylamine), serotonin have been known, and these amino acid sequences share homology with each other, and form a type of family. It is known that any of these transporters has a structure 12-times transmembrane structure. For instance, when labeled serotonin is added in the state of tissue piece, the labeled serotonin is taken into the neural cell system via a transporter which may be regarded as a serotonin transporter. Serotonin is labeled with a fluorescent material in use. Not only in the transporters each having homology with GABA, but also in a glutamic acid transporter which can be regarded as one belonging to a different transporter family, a labeling material can be introduced into a target cell by using a glutamic acid with a fluorescent body bonded thereto with a linker. In this example, a membrane-permeable transporter having a relatively small molecule size and no electric charge such as various derivatives of 4,4-difluoro-4-bora-3a,4a-diaza-s-indacene is used. As a label, a fluorescent material can be introduced by using, for instance, an amino group of serotonin through the amidic group of serotonin.

At first, 10 μM serotonin labeled with the fluorescent material (described as labeled serotonin hereinafter) is added to the tissue piece and incubated at 37° C. for 30 minutes, and the cells are dispersed according to the known method, and are analyzed with a cell sorter independently developed by the inventors. Cell with the fluorescence intensity of 5000 or more obtained with this device are separated. 1000 cells are used as starting cells, and when operations are performed up to this step, 26% of the cells are separated in this process. When a group of labeled target cells are cultured in a culture fluid not containing labeled serotonin for 18 hours and then cells with the fluorescence intensity of 500 or below are separated, 156 target cells are recovered. This technique prevents foreign materials from being intaked, and provides an important merit, for instance, in a case where the separated target cells are returned to a human body. Further in the cell researches, the availability of quickly removing a labeling material for cell separation makes it possible to minimize influences of the labeling material over the cell, and therefore this technique can make a great contribution to researches for accurately understanding the cellular physiology.

(Example of Cell Separation 2)

Cell separation is performed by using any of the sugar-related transporters shown in Table 1. The glucose labeling method described in Cytometory 27, 262-268 (1997) may be used for labeling the sugar. This document suggests that cells can actually be stained by fluorescent material-labeled glucose and detected with a cell sorter (not separated and recovered in this document).

In Example 2 for cell separation, a case is described in which differences of cells are recognized by measuring differences in cell permeability of a plurality of substrates and then discrete cells are separated. In this example, cells are identified and separated by observing the cell permeability of galactose or fructose against the glucose described in the aforementioned document. Generally, glucose is often used as an energy source for cells, but galactose or fructose is not directly consumed. For instance, when *Escherichia coli* is cultured in a mixed culture medium of glucose and fructose, glucose is consumed at first, and then galactose is consumed when glucose decreases. Therefore, for instance, by measuring cell permeability of various types of substrates using a quantity of intaked glucose as control data, cell separation reflecting the state of cell more accurately can be performed.

In this example, a glucose labeling derivative of 6-(N-(7-nitrobenz-2-oxa-1.3-diazol-4-yl)amino) sugar (Ex465/Em540) (NBD-labeled sugar) is used. As a labeling fluorescent material for galactose or fructose, a membrane-permeable material having a relatively small molecular size and not electrically charged such as various derivatives of 4,4-difluoro-4-bora-3a,4a-diaza-s-indacene may be used. Various types of NDM-labeled sugars are added to the culture fluid, and cells dispersed in the culture fluid via the brain tissue pieces (the cut-off site unknown) are trisected, and then the three types of NBD-labeled sugars are added to the culture fluids respectively and incubated for 15 minutes at 37° C. The culture fluid is exchanged with that not containing the NBD-labeled sugar, and the sample is immediately added to a cell sorter independently developed by the inventors, and cells with the relative fluorescence intensity of 500 or more are separated. 200 cells were processed with the sorter, and 66 cells using the NBD-labeled glucose and 13 cells using the NBD galactose were obtained respectively, and any cell using the NBD-labeled fructose could not be obtained. Similarly in a case of a sample in which cells from a lever tissue were suspended, 46 cells using the NBD-labeled glucose as an index, 37 cells using the NBD-labeled fructose, and 8 cells using the NBD-labeled galactose were obtained, and this result is different from that obtained using the brain-derived cells.

The glucose, fructose, and galactose are expressed by various transporters on cell surfaces, and substrate-specificity of each transporter is not so high, but actually the cells can be divided into several groups. This fact suggests that change in specificity due to a fluorescent material bonded to each transporter causes change in easiness of fetching glucose, fructose, and galactose into the cell.

(Example of Cell Separation 3)

In Example of cell separation 3, descriptions are provided for a case in which difference of cells are identified and discrete cells are separated by measuring the difference in cell permeability of a plurality of labeling amino acids or labeling peptides.

In Example 2 for cell separation, glucose is used as a control, but it is better to use herein substrates of transporters expressed in various organs. As shown in Table 4, thiamine, folic acid, eicosanoids, prostaglandin, L-ascorbic acid, arginine, and nucleoside may advantageously be used for this purpose. The transporters are ubiquitously present in various cells.

TABLE 4

| Substrate | Transporter | Tissue, cell, organ |
|---|---|---|
| Thiamine | SLC19A2, 3 | Nonspecific |
| Folic acid | SLC19A1 | |
| Eicosanoids | SLC2A1 | |
| Prostaglandin | SLCO3A1, 4A1 | |
| L-ascorbic acid | SLC2O3A2 | |
| Arginine | | |
| Nucleoside | SLC28A, 29A | |

Alternatively, a material such as arginine oligomer, a transporter for which is still unknown (intaked into a cell via another mechanism), but which is always intaked into a cell is used. As a substrate for measurement against a control, for instance, substances based on amino acid-related peptides and transporters corresponding to the substances as shown in Table 5 may be used.

TABLE 5

| Substrate | Transporter | Tissue, cell, organ |
|---|---|---|
| L-Glu<br>D/L-Asp | SLC1A1-3,6,7 | Cerebral cells such as neuron and astrocyte<br>Purkinje cell in cerebellum<br>Retina<br>Small intestine, kidney, lever, skeletal muscle, placenta |
| L-Ala | SLC1A5 | Lung |
| L-Ser | | Skeletal muscle |
| L-Thr | | Intestine, kidney, testis |
| L-Cys | | Fatty tissue |
| L-Gln | | |
| L-Asn | — | Asparagin-demanding tumor cell |

TABLE 5-continued

| 94 Substrate | 93 Transporter | 95 Tissue, cell, organ |
|---|---|---|
| | | (Acute leukemia, malignant lymphoma, various types of cancerous cells) |
| Dipeptide Tripeptide | SLC15A | — |

L-Glu or D/L-Asp is used for identification and separation of cell groups consuming much energy such as cerebral cells such as neuron or astrocyte, Purkinje cell of cerebellum, retina, small intestine, kidney, lever, skeletal muscle, and placenta. L-Ala, L-Ser, L-Thr, L-Cys and L-Gln are used for identification and separation of cells in lung, skeletal muscle, intestine, kidney, testis, and fatty tissue. L-Asn is effectively used for detection and separation of asparagines-demanding tumor cells in acute leukemia or malignant lymphoma. L-Asn may also be used for examination of the acute leukemia. For labeling, for instance, a fluorescent material modified by using isodiamido binding is used to prevent an electric charge of the amino group from being lost.

(Example of Cell Separation 4)

Descriptions are provided below for a case in which cells causing leukemia are separated by applying the technique in Example 3 for cell separation. NDB folic acid (Ex465/Em540), 4,4-difluoro-1,3,5,7-tetramethyl-4-bora-3a,4a-diaza-s-indacene-8-propionate labeled ASn, and 4,4-difluoro-5-(2-pyrrole)-4-bora-3a,4a-diaza-s-indacene-3-propionate labeled Thr are added to blood from a patient suffering from leukemia, and the mixture is incubated for 30 minutes at 37° C. Using the NDB folic acid (Ex465/Em540) as a control, the amounts of intaked 4,4-difluoro-3,5,7-tetramethyl-4-bora-3a,4a-diaza-s-indacene-8-propionate labeled ASn (Ex493/Em503) and intaked 4,4-difluoro-5-(2-pyrrole)-4-bora-3a,4a-diaza-s-indacene-3-propionate labeled Thr are measured by detecting the fluorescent intensities of various derivatives of 4,4-difluoro-4-bora-3a,4a-diaza-s-indacene against the fluorescence intensity generated by NDB-labeled folic acid, and cells having high fluorescence intensity with the fluorescence wavelength of around 503 nm, namely cells having a large intake amount of the 4,4-difluoro-1,3,5,7-tetramethyl-4-bora-3a,4a-diaza-s-indacene-8-propionate labeled ASn are sorted with a cell sorter. Histological examination of the sorted cells with a microscope shows that 95% or more of the sorted cells are cancerous leukocytes. An intake rate of the 4,4-difluoro-5-(2-pyrrole)-4-bora-3a,4a-diaza-s-indacene-3-propionate labeled Thr in normal cells against cancer cells is not so remarkable as compared to the intake rate of 4,4-difluoro-1,3,5,7-tetramethyl-4-bora-3a,4a-diaza-s-indacene-8-propionate labeled Asn.

(Example of Cell Separation 5)

In Example of cell separation 5, descriptions are provided for a case in which a substance taken into a target cell via an unknown mechanism is used. In this case, arginine oligomer is herein used as a substrate. The arginine oligomer can be intaked into a target cell even by conjugating, in addition to various fluorescent materials, a giant molecule such as an enzyme thereto. Further the arginine oligomer shows the cell membrane permeability to any cell (J. Mol. Recognit. 16, 260-264 (2003)). The mechanism of arginine oligomer intake into a cell is still unknown, but it is clear that the mechanism is not endocytosis nor phagocytosis, and now discussions are made for a model in which a guanidil residue of arginine forms a hydrogen binding to phospholipids present in a cell membrane and the molecule directly overcomes the membrane gap and also for the influence by a strong base in the guadinil group. The present inventors speculate, in addition to the assumptions described above, the possibility that the arginine oligomer acts as a weak denaturing agent because of the influence by chaotropic ions and the cell membrane is partially denatured.

(Example of cell Separation 6)

In this example, sulforhodamine 101-labeled arginine octamer (Em605) and NBD-labeled Asn (Em540) are sent into a target cell, and cancerous cells are separated according to a different in intake rates of the two labeling materials. The sulforhodamine 101-labeled arginine octamer ($Arg_8$-Cys-S-sulforhodamine 101) is ether-bonded to an SH group of Cys using a reagent having a maleimide group (produced by Molecular Probe Corp., Texas Red $C_2$ maleimide). Actions of the arginine oligomer to a cell are specific, and additional descriptions are provided below. J. Mol. Recognit. 16, 260-264 (2003) suggests that there is an optimal value for length of arginine oligomer, and the optimal value is in the range from 6 to 8. When the length is too short, the oligomer hardly permeates a cell membrane, and when the length is too large, the oligomer tends to be bonded to the cell membrane. Further, when the length is several tens mer, the oligomer may be cytotoxic. In this Example, an octamer is used. Actually, Cys is conjugated to a COOH terminal of arginine octamer for binding a fluorescent material, and a fluorescent material having a maleimido group is conjugated to the SH group of this Cys. Alternatively, the fluorescent labeling may be performed by using, in place of Cys, Lys with a fluorescent material previously conjugated to the e-amino group thereof when synthesizing peptide. In this case the arginine oligomer is $Arg_8$-Lys-e-NH-sulforhodamine 101. A concentration of the arginine oligomer is 1 μm, and the processing time may be 0.5 hour. When labeled with arginine oligomer with the length of 6 to 8, strong fluorescence is generated in an internal structure of the nuclear, and therefore it is conceivable that the fluorescent material is specifically migrated to the nuclear. However, in which portion of the nuclear the fluorescent material is concentrated is still unknown. Fluorescence can be observed also from cytoplasm, although the intensity is not so strong as that in the nuclear. In any way, a percentage of a projection area of a nuclear in a cell can be measured. In addition to the materials described above, it is possible to use, as a fluorescent material, fluorescein, tetramethylrhodamine, sulforhodamine 101, pyrene derivatives, Cy3, Cy5, europium complexes of $N,N,N^1,N^1$-[2,6-bis(3'-aminomethyl-1'-pyrazolyl)-4-phenylpyridine], and various types of fluorescent nanoparticles (with the diameter of 30 nm). Therefore, an excitation wavelength and a fluorescence wavelength can be obtained according to the necessity.

(Example of Cell Separation 7)

In this example, descriptions are provided for cell separating operations using a tissue cut off from the overhead colon in intestine with the epithelium partially being cancerous. The two types of fluorescent substrates described above are mixed in the medium as the tissue piece, and are incubated for 30 minutes at 37° C. After the tissue is washed with 0.15 M NaCl not containing the substrate, and the cells are dispersed in a solution containing trypsin. Then immediately the dispersion is processed with an image analysis type of cell sorter according to the second embodiment of the present invention to measure fluorescence intensity distribution around the fluorescence wavelength of 605 nm from the sulforhodamine 101-labeled arginine octamer for each cell. To identify a cancer cell by making use of the fact that cancer cells have a larger size, a percentage of the nuclear in each cancer cell becomes larger as compared to that in normal cells, so that cells, in which an area ratio of the portion having high fluorescence intensity against to the total area of the cell is 20% or more, are detected. However, sometimes it is hard to make a determination only with the operation above because the actually stained structural body is not known, and a ratio of false negative may disadvantageously increase. Therefore, at the same time, by making use of the fact that a cancer cell has a high demand for Asn, the fluorescence intensity at and around the wavelength of 540 nm from the NBD-labeled Asn is observed. Then, cells showing a positive reaction with either sulforhodamine 101-labeled arginine octamer or NBD-labeled Asn are sorted with a cell sorter. The separated cells vary according to a type of tissue piece, and in this case, of 1000 cells in the tissue piece, 16 cells are separated. The separated cells are visually and histologically compared to cells (presumably not cancerous) in another portion of intestine of the same person, and based on the result of the operation above, it can be guessed that all of the separated cells are cancerous. The separated cells can be proliferated by culturing, and when cultured according to the known method, the cells can be proliferated infinitely. As described above, the cancerous cells can be separated more accurately by checking the two facts that nuclei of cancerous cells are substantially stained by the sulforhodamine 101-labeled arginine octamer, and that the NBD-labeled Asn is intaked into the cytoplasm of the cells.

(Example of Cell Separation 8)

In Example of cell separation 8, descriptions are provided for the availability of conjugating a substrate which specifically permeates to mitochondria in a cell like a mitochondria transporter and using the substrate for specifically staining mitochondria. Most arginine compounds often show the cell membrane permeability and also specifically reach mitochondria. Actually, Arg-specific transporters are present on a surface of mitochondria (See http://www.bioparadigms.org/slc/intro.asp). Therefore, it can be anticipated that the arginine oligomer conjugated to sulforhodamine 101 described in Example 5 for cell separation is taken into mitochondria. By introducing sulforhodamine 101-$Arg_6$ into a cell and observing the situation in the cell with an optical system using a water-submerged lens with the resolution of 100 times shown in FIG. 16 as an object lens 105, spotted patterns can be observed in the cytoplasm. This result of observation suggests that the sulforhodamine 101-$Arg_6$ has migrated into mitochondria.

Therefore, sulforhodamine 101-$Arg_6$ is added to the cells, and the cells are sorted checking localization of fluorescence in the cells. For observing mitochondria with high resolution, the water-submerged lens with the resolution of 100 times is used as an object lens 105 in the optical system shown in FIG. 16. In this case, a degree of distribution of fluorescent light emitting points in each cell are checked, and cells with the fluorescence intensity of 40 times or more from the cytoplasm against the background are sorted as ones having taken the fluorescent material into the mitochondria. The sorted cells are transferred into a culture liquid to remove the intaked sulforhodamine 101-$Arg_6$. The cells having lower fluorescence intensity ratio as compared to the value described above has a low survival rate after sorting, while most of cells having high fluorescence intensity can be cultured. This fact suggests that apoptosis is induced in cells with low mitochondria staining intensity, or that the cells are substantially damaged. With the second embodiment of the present invention, fresh cells can easily be sorted from damaged ones.

[III] Third Embodiment

As a third embodiment, a method is disclosed for adding a labeling substance to a cell for separation based on a certain characteristic of the cell and after isolation removing the labeling substance, for the purpose of avoiding degeneration of the target cell to be separated by the labeling substance to the extent as much as possible, by selecting as the labeling substance to a surface antigen a substance degradable under a mild condition and by degrading and removing the labeling substance to the surface antigen under a physiological condition without impacts to the cell.

Before describing an example of the third embodiment, a method of preparing aptamer to a cell surface antigen CD4 is described as an example of the labeling substance useful in the third embodiment.

As aptamer for use as the labeling substance, aptamer to the cell surface antigen CD4 disclosed in an article "Staining of cell surface human CD4 with 3'-F-pyrimidine-containing RNA aptamers for flow cytometry" (Nucleic Acids Research 26, 3915-3924 (1998)). The aptamer is of type ribonucleotide, that is, RNA aptamer. In the above article, GDP-β-S is introduced to the 5' end of the RNA aptamer as an identification substance by in vitro transcription, for the purpose of identifying the aptamer with fluorescence. At this stage, a thiophosphoric acid group is inserted to the 5' end of the aptamer. A 5' biotinylated RNA aptamer is obtained by reacting biotin introduced with an iodine acetyl group to the thiophosphoric acid group.

As a fluorescent pigment, a conjugate of phycobiliprotein and streptavidin is reacted to the 5' biotinylated RNA aptamer and through biotin/avidin reaction phycobiliprotein-modified RNA aptamer is obtained. Of types of phycobiliprotein, β-phycoerythrin is a fluorescent substance of type fluorescent protein, characterized by a high light absorbance at $2.41 \times 10^6$ $M^{-1}$ $cm^{-1}$ as well as a high quantum yield at 0.98 and is suitable for high-sensitive detection, but a large size thereof at a molecular weight of 240K daltons as well as nonspecific adsorption and instability characteristic to proteins proves problematic occasionally. In one of the examples of the third embodiment, the phycobiliprotein-modified RNA aptamer is used. Since the molecular weight is as large as 240K daltons, it is equivalent, in terms of size, to using particles of about 10 nm in diameter as a marker substance. In addition to phycobiliprotein, therefore, a particle containing fluorescent pigment, a gold nanoparticle and a magnetic particle, all 10 nm in diameter, are also used.

An example of identification element with phycobiliprotein or a nanoparticle as the marker substance is described hereinafter.

(i) Phycobiliprotein-modified RNA aptamer: A method described in the article hereinabove may be used, but another method is used hereinafter. Synthesis of RNA aptamer is securely achieved by chemical synthesis. An amino group is introduced to the 5' end of the synthesized RNA aptamer. The amino group is introduced at the time of chemical synthesis of the RNA aptamer. A bifunctional reagent such as N-(8-Maleimidocapryloxy)sulfosuccinimide is reacted to the amino group introduced at the 5' end, and as a result, an SH-reactive maleimide group is introduced to the 5' end of the RNA aptamer. Separately β-phycoerythrin with an SH group introduced thereinto is prepared. For the introduction of the SH group, an amino group of the β-phycoerythrin is modified with 2-iminothiolane. β-phycoerythrin-modified RNA aptamer is obtained by mixing the maleimide group-introduced RNA aptamer and the SH group-introduced β-phycoerythrin through 2-iminothiolane modification at pH 7.

(ii) Gold nanoparticle-modified RNA aptamer: A method of preparing gold nanoparticle-modified RNA aptamer is described hereinafter, with reference to methods disclosed by Tonya M. Herne and Michael J. Tarlov (J. Am. Chem. Soc. 1997, 119, 8916-8920) and by James J. Storhoff (J. Am. Chem. Soc. 1998, 120, 1959-1964). In a suspension of gold nanoparticles (20 nm φ) are added synthetic RNA aptamer with an SH group at the 5' end and 6-mercapto-1-hexanol, and the mixture is left for an hour. The molar ratio of the synthetic RNA aptamer and 6-mercapto-1-hexanol is 1:100, but if gold nanoparticles get agglomerated, or the synthetic RNA aptamer does not bond with the gold nanoparticles, it is necessary to change the ratio according to the necessity until an optimal ratio is found. The gold nanoparticles easily get agglomerated, and hence it is necessary, at the time of adding synthetic RNA aptamer, to stir the liquid, so that concentration gradients of potassium carbonate buffer or the synthetic RNA aptamer do not result. The synthetic RNA aptamer and the gold nanoparticles are reacted under a condition where the molecular ratio of the synthetic RNA aptamer to the gold nanoparticles is 100 times. That is, the reaction takes place where the ratio between the number of the gold nanoparticles and the number of synthetic RNA aptamer molecules is 1:1000. The synthetic RNA aptamer with an SH group are chemically synthesized. After the reaction the solution is centrifuged at 8000 G for an hour and the supernatant is discarded. The aptamer is suspended again in 10 mM potassium carbonate buffer with 0.1 M NaCl added (pH 9), then is centrifuged again, the supernatant is discarded again, and the aptamer is finally suspended in 10 mM potassium phosphate buffer with 0.1 M NaCl added (pH 7.4) to make stock.

(iii) RNA aptamer modified with nanoparticles other than gold: Nanoparticles like quantum dot is generally inorganic nanoparticles. A product covered with biotin-introduced polyethyleneglycol is already in the market, for example, under the trade name of EviFluor from Evident Technologies, Inc. RNA aptamer bonded with streptavidin can be used together with nanoparticles with biotin introduced thereinto. A method of preparing RNA aptamer bonded with streptavidin is described hereinafter. RNA aptamer with a maleimide group introduced at the 5' end and streptavidin introduced with an SH group by a 2-iminothiolane modification is mixed at pH 7 with the method (i) and streptavidin-bonded RNA aptamer is obtained. Mixing the streptavidin-bonded RNA aptamer with the nanoparticles with biotin results in nanoparticle-modified RNA aptamer as identification element.

From nanoparticles with a carboxyl group introduced thereinto is obtained nanoparticle-modified RNA aptamer as identification element with a well-known method of first reacting carbodiimide to the carboxyl group to obtain active ester and then reacting 5'-aminated RNA aptamer thereto.

Methods of preparing nanoparticle-modified RNA aptamer have been described above, and similar methods are applicable for preparation of DNA aptamer of type deoxyribonucleotide: phycobiliprotein-modified DNA aptamer, gold nanoparticle-modified DNA aptamer and DNA aptamer-modified with nanoparticles other than gold may be prepared each as identification element in a similar fashion, because an SH group, an amino group and the like may be introduced to the 5' end at a time when the DNA aptamer is synthesized in a synthesizing machine, as in the case of RNA aptamer.

In addition to methods as described hereinabove, RNA aptamer may be synthesized according to a commonly used method of first synthesizing single-chain DNA with a T7-promoter at the 5' end and then transcribing the synthesized DNA to RNA with RNA polymerase.

EXAMPLE

An example is described hereinafter with identification element made up of RNA aptamer as a labeling substance to label cell surface antigen CD4 and β-phycoerythrin as a marker substance in isolating and collecting cells bonded with the RNA aptamer. That is, cells presenting the cell surface antigen CD4 is specifically labeled with the β-phycoerythrin-modified RNA aptamer as described hereinabove, and then a cell isolation chip, which is a cell sorter formed on a plastic chip substrate as disclosed in Japan Patent Application 2004-379327.

Figure 17:
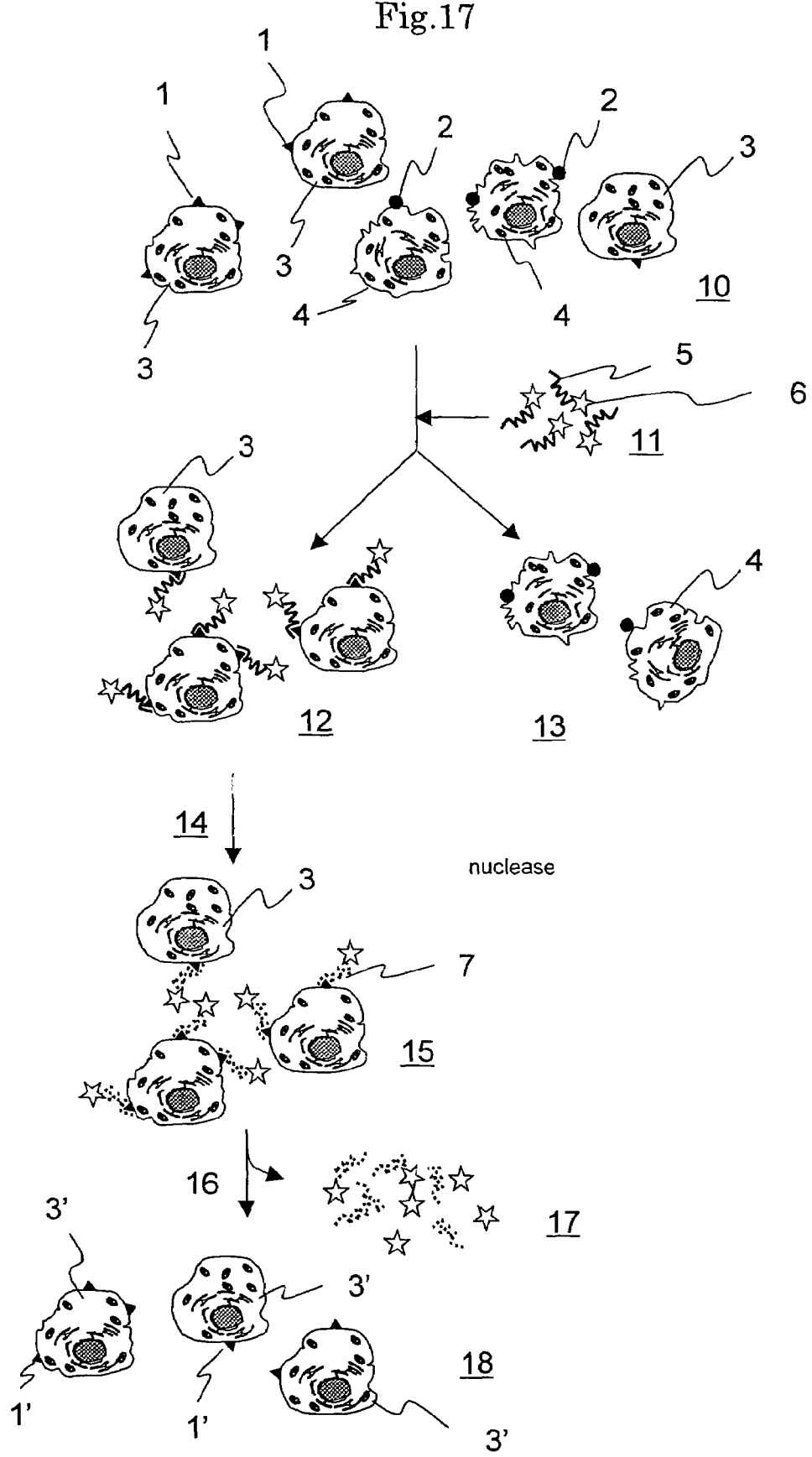
FIG. 17 is a view showing a process flow of specifically labeling a cell surface antigen with the β-phycoerythrin-modified RNA aptamer for separating a cell according to a third embodiment of the present invention.

FIG. 17 is a view showing a process flow of specifically labeling a cell presenting the cell surface antigen CD4 with the β-phycobiliprotein-modified RNA aptamer and thereafter isolating the cell with a cell sorter. The top-most part of FIG. 17 shows a sample 10 with two kinds of cells 3 and 4 in a mixed manner. The cells 3 present a cell surface antigen CD4 indicated by a triangular marked out in black with a reference numeral 1. The cells 4 present a surface antigen 2 other than CD4 indicated with a circle marked out in black. With the sample is mixed β-phycoerythrin-modified RNA aptamer 11 as described hereinabove. The RNA aptamer is indicated with a reference numeral 5 while the β-phycoerythrin is indicated with a numeral 6. Concentration of labeling substance 11 is 100 nM.

As a result, to the antigen 1, which is CD4 present on a surface of the cells 3, is bonded the labeling-substance RNA aptamer modified with β-phycoerythrin as an identification substance. To the antigen 2, which is not CD4, the labeling-substance RNA aptamer is not bonded. The identification substance β-phycoerythrin, modifying the labeling-substance RNA aptamer, yields a strong fluorescence at around 575 nm when excited with 532-nm second harmonic of YAG laser. In the cell isolation chip, therefore, cells presenting CD4 can be isolated from the other cells through detection of this fluorescence. In the top-most part of FIG. 17, an arrow leading to the vertical line of a reverse "Y" shape extending from the sample 10 indicates that such isolation is carried out with the cell sorter. Reference numeral 12 at the end of one of the diagonal lines of the reverse "Y" shape indicates a group of the cells 3 bonded to the labeling-substance RNA aptamer. Reference numeral 13 at the end of the other diagonal line of the reverse "Y" shape indicates a group of the cells 4 not bonded to the labeling-substance RNA aptamer.

Next the cells presenting CD4 and isolated with the cell sorter are collected into a microtube and are immediately reacted with nuclease 14. Since the RNA aptamer has a three-dimensional structure, types of nucleases like ribonuclease A that breaks down single-chain RNAs alone may not decompose the aptamer sufficiently. A nuclease that breaks down both single- and double-chained RNAs can be used effectively. For the purpose of this example, Benzonase (registered trademark) is used, a nuclease derived from Serratia marcescens as described in "The Journal of Biological Chemistry 244, 5219-5225 (1669)" mass produced genetically (European patent No. 0229866, U.S. Pat. No. 5,173,418). The enzyme works at a temperature of 37° C., and has a working pH range at a neutral range between 6 and 9, and is therefore easy to use on cells. Highly concentrated phosphoric acid or monovalent metal ion reduces activity of the enzyme, hence buffer liquid of type non-phosphoric acid is used, for example, 10 mM HEPES at pH 7.4 with 0.15 M NaCl, 2 mM $MgCl_2$ and 1 mg/ml BSA contained therein. If buffer liquid of type phosphoric acid must be used, then concentration of potassium phosphate/sodium phosphate should be held down to 5 mM, and the liquid should be used with 0.15 M NaCl, 2 mM $MgCl_2$ and 1 mg/ml BSA contained therein. Benzonase (registered trademark) nuclease is used at a concentration of 10~100 u/ml. Alternatively, a mixture of ribonuclease A and ribonuclease T1 may be used, but nuclease derived from *Serratia marcescens* has wider applications.

If necessary, blood serum may be substituted with buffer liquid, although it may be necessary to adjust the concentration of Benzonase (registered trademark) nuclease for each blood serum lot, because of the effect of nuclease inhibitor found in blood serum. Generally, if, blood serum is used, concentration between 100~400 u/ml gives a good result.

In FIG. 17, an arrow representing the nuclease leading to another arrow indicated on the lower side of the group 12 of the cells 3 bonded with the labeling-substance RNA aptamer indicates a process of adding the nuclease. This process is given a reference numeral 14. As a result of the nuclease acting on the aptamer, the labeling-substance RNA aptamer 6 bonded with the CD4 antigen 1 on the surface of the cells 3 is degraded. In FIG. 17, the degraded labeling-substance RNA aptamers are indicated as a group of dots and are given a reference numeral 7. A reference numeral 15 indicates a mixture of the cells 3, the degraded labeling-substance RNA aptamers 7, and the identification-substance β-phycoerythrin 6.

Next, by changing cell supernatant of this mixture and removing the decomposed substance 17 (the mixture of the degraded labeling-substance RNA aptamers 7 and the marker-substance β-phycoerythrin 6), only the cells 3 with CD4 antigen 1 on the surface are collected. In changing the cell supernatant, centrifugal action is used. The mixture is centrifuged for 15 minutes at 3000 rpm, the cells are precipitated, and thereafter the decomposed substance 17 can be removed by discarding the supernatant. The precipitated cells are resuspended. This process is given a reference numeral 16. A reference numeral 18 indicates a group of the collected cells 3 with the CD4 antigen 1 on the surface. A reference numeral 3' is given to the cells 3 and a reference numeral 1' to the surface antigen CD4 1, indicating that, as a result of acting the nuclease on the cells 3, there is a chance, be it slim, that the cells 3 and the antigen 4 are affected in some way, and that they may not be exactly the same as before.

Figure 18:
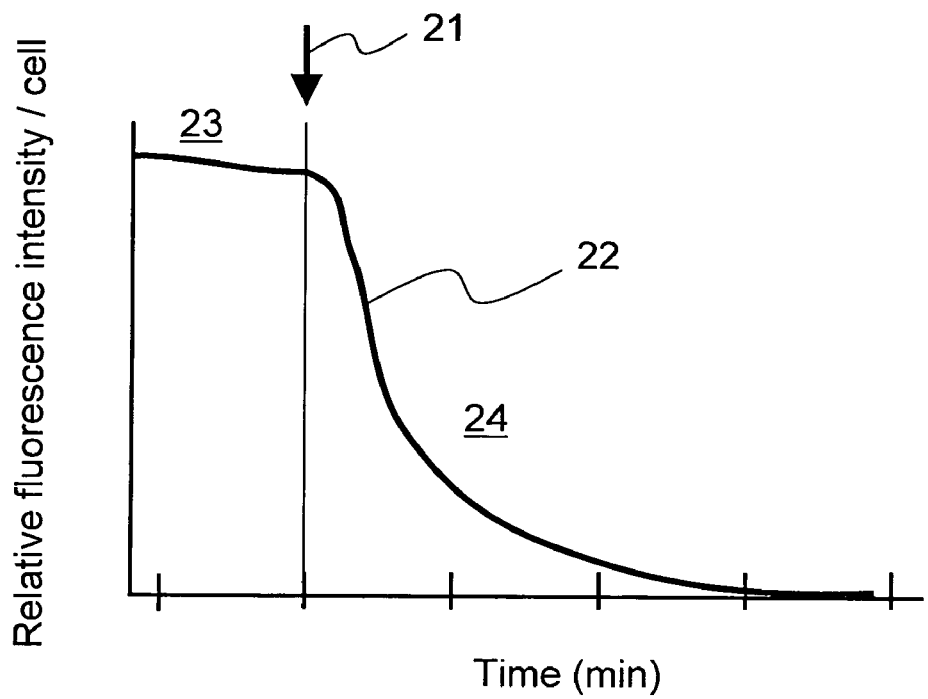
FIG. 18 is a diagram showing an effect of removal of the β-phycoerythrin-modified RNA aptamer used for identifying a cell by adding nuclease.

FIG. 18 is a view showing a time change of fluorescence intensity of the identification-substance β-phycoerythrin bonded to the cell surface with the addition of the nuclease. Herein, the cells are placed on a preparation, the cell surface is observed under a fluorescence microscope, and an integrated value of the fluorescence intensity obtained from the entire cell is observed. When the aptamer is degraded with the nuclease, the identification-substance β-phycoerythrin is diffused from the cell surface and turns unobservable, hence by following the fluorescence intensity, progress in degradation of the aptamer by the nuclease can be followed. In FIG. 18, the horizontal axis represents time, while the vertical axis indicates integrated value of the fluorescence per cell shown as the fluorescence intensity per cell. The figure is a result of time course observation under the fluorescence microscope of the fluorescence intensity (excitation wavelength at 532 nm, fluorescence wavelength at 575 nm, a band pass filter in use) of the cell surface of the cells presenting the cell surface CD4 bonded with the β-phycoerythrin-modified RNA aptamer (the group 12 in FIG. 17 of the cells 3 bonded with the labeling-substance RNA aptamer) isolated with the cell sorter. In order to avoid fluorescent degradation, radiation time of the excitation light is limited to a minimum length: for instance, the light is radiated for a second at a minute interval for the fluorescence observation.

Reference numeral 22 is a line indicating the time change of the fluorescence intensity. An arrow 21 indicates the timing at which the Benzonase (registered trademark) nuclease is added. It is difficult to completely prevent the fluorescence degradation, even if the radiation time of the excitation light at excitation wavelength at 532 nm is kept short, and upon the defection of the Benzonase (registered trademark) nuclease (time area 23), the fluorescence intensity slightly reduces over time. Upon the addition of the Benzonase (registered trademark) nuclease at the timing 21, the fluorescence intensity detectable from the cells reduces rapidly in the time zone 24, although with some delay in timing.

This indicates that during the isolation process, with the cell sorter, of the cells presenting the cell surface CD4 bonded with the β-phycoerythrin-modified RNA aptamer, the functionality of the β-phycoerythrin as the identification substance remains intact, but that when the nuclease is added, the portion of the RNA aptamer (the reference numeral 5 in FIG. 17) of the β-phycoerythrin-modified RNA aptamer bonded with the cell surface is decomposed, and that the fluorescence-substance β-phycoerythrin 6 is diffused into the solution.

Figure 19:
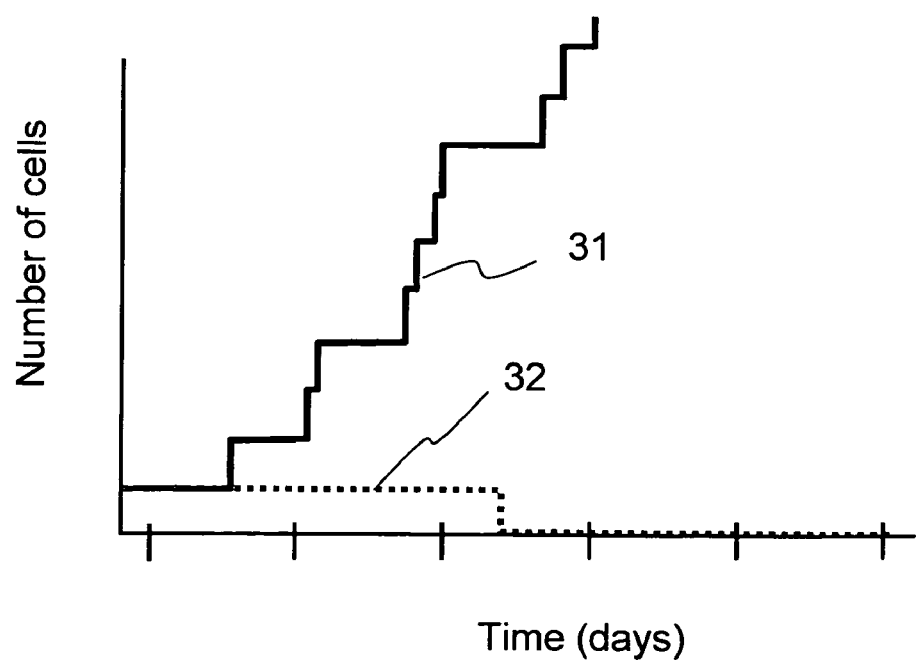
FIG. 19 is a diagram indicating the fact that a cell obtained after the β-phycoerythrin-modified RNA aptamer is removed can be cultured.

FIG. 19 is a diagram indicating culturability of the cells presenting the surface CD4 obtained by removing the β-phycoerythrin-modified RNA aptamer according to the third embodiment. The horizontal axis represents time, while the vertical axis indicates the number of cells. From the characteristics in FIG. 18, the time necessary for the β-phycoerythrin-modified RNA aptamer to be regarded as sufficiently removed by adding Benzonase (registered trademark) is evaluated beforehand. The cells with the β-phycoerythrin-modified RNA aptamer removed are obtained after waiting for the time described hereinabove after adding the nuclease to the cells isolated with the cell sorter. The cells thus obtained are incubated in, for example, a microchamber for cell incubation disclosed in Japanese Patent Application No. 2004-305258 filed by the inventors of the present invention. The microchamber for cell incubation is made of agarose and made up of an array of microchambers, has a structure allowing changes of culture liquid at any time through a semipermeable membrane, and allows a long-term incubation of cells on an individual cell basis. Upon incubation of the cells presenting the surface CD4 with the β-phycoerythrin-modified RNA aptamer removed therefrom, the cells divide, as shown in Graph 31. Graph 31 shows a stepwise increase, indicating that, as the process starts with a single cell, the number of cells grows each time the cells divide. The cells not subjected to the Benzonase (registered trademark) nuclease process are unable to divide as is shown in Graph 32, and become extinct over time.

When surface antigen is recognized by bonding an RNA aptamer to a cell marking and, when the cell marking is no longer required, the RNA aptamer is degraded and removed with ribonuclease, the cells can be returned to a state as natural to the extent as allows them to divide, like before the cell marking. This technique, as described in the first example, brings about a revolutionary impact to the cell isolation with a cell sorter. In the conventional method of cell separation by labeling a surface antigen with an antibody, the labeling substance cannot be removed from the cell after the separation of target cells, and in most cases damages to the cells are fatal. The third embodiment allows a reversible removal of the labeling substance to the surface antigen, therefore the separated cells can be used.

(Other Example of Aptamer 1)

In the previous example, a detailed description is given to a case in which RNA aptamer is used as the aptamer as the labeling substance and a cell surface antigen CD4 is used as the labeling target. In this example a use of aptamer of type DNA as the labeling substance for micro separation of a live cell tissue is described.

In preparation of the DNA aptamer, a sequence of about 40 bases long and random to the CD4 antigen, with priming sequences for PCR amplification attached to both ends, is prepared in advance, and is affinity-separated with CD4 antigen fixed to a magnetic particle. The affinity-purified fraction is PCR-amplified using the priming sequences at both ends, and is once again affinity-separated with CD4 antigen fixed to a magnetic particle. By repeating this process, DNA aptamer bonding to the CD4 antigen is obtained, although the bonding strength is weaker than that of RNA aptamer. Finally, by using primer with an SH group having a blocking group at 5' end as one of the primers through PCR amplification, DNA aptamer with the 5' end modified with an SH base is obtained. Thereafter, by using a method similar to that described in the example is applied: the DNA aptamer is reacted to gold nanoparticle β-phycoerythrin, and β-phycoerythrin-modified DNA aptamer is obtained as identification element.

A biopsy sample is lightly crushed up on a slide glass and fixed thereto. The sample is added with the β-phycoerythrin-modified DNA aptamer; is left for 30 minutes and cells in the sample presenting the CD4 are labeled with the β-phycoerythrin-modified DNA aptamer; then the labeled part is cut out (or the unlabeled part is removed by laser killing); the part is treated in culture fluid with Benzonase (registered trademark) nuclease or DNaseI added at pH 7; and part of the tissue rich in CD4 is obtained as the tissue remains alive.

(Other Example of Aptamer 2)

In this example, labeling-substance aptamer is of type RNA bonding to EpCAM, and magnetic particles around 100 nm in diameter are used as the identification substance. The object is to identify and separate tumor-originated cells circulating in the blood and having EpCAM as surface antigen.

In preparation for RNA aptamer bonding to EpCAM, a sequence 90 bases long is synthesized by introducing a sequence of 26 bases, including a sequence for T7 promoter, to the 5' end of a single-chain DNA random sequence of 40 bases, and a priming site for PCR made up of 24 bases to the 3' end of the single-chain DNA. The sequence is from the 5' end:

TAATACGACTCACTATAGGGAGACAAN(40)TTCGACAGGAGGCTCACAACAGG.

The T7 sequence is used for transcription to RNA with RNA polymerase. For the transcription to RNA, a quantity of 500 μl of DNA at 100 pmol is reacted with 100 u of T7 polymerase. For the bases, 3 mM each of 2'-F-CTP and 2'-F-UTP as well as 1 mM each of ATP and GTP are used, and the polymerase is acted on at 25° C. for 10 hours. After the RNA transcription is completed, the DNA is degraded with DNaseI and the transcribed RNA products are collected with electrophoresis. The collected transcribed RNA products are heat-denatured, and then are passed through a sepharose CL4B column, fixed with EpCAM, in PBS (at pH 7.4) added with 2 mM of $MgCl_2$. The bonded transcribed RNA elements are eluted in solution containing 7M urea. The resultant transcribed RNA elements are reverse-transcribed and PCR-amplified with a pair of primers each complementary to each of the known sequences at both ends. The resultant PCR products are again transcribed with T7 promoter, the transcribed RNA is captured with a sepharose CL4B column fixed with EpCAM, in a similar fashion as before, and the bonded transcribed RNA elements are collected. By repeating the process of transcription, capture, collection and PCR amplification 15 times, RNA aptamer specifically reactive to EpCAM is obtained.

At the 5' end of the resultant RNA aptamer is inserted a thiophosphoric acid group through in vitro transcription, as described in an article "Staining of cell surface human CD4 with 3'-F-pyrimidine-containing RNA aptamers for flow cytometry" (Nucleic Acids Research 26, 3915-3924 (1998)). To the thiophosphoric acid group is reacted biotin with an iodine acetyl group introduced thereinto, and 5' biotin-modified RNA aptamer is obtained. Magnetic beads conjugated with streptoavidin are reacted, and RNA aptamer specifically reactive to EpCAM with a magnetic particle as the identification substance is obtained.

Reaction of a magnetic particle with RNA aptamer label to an EpCAM-positive tumor cell is described hereinafter. 10 ml of blood is suspended in culture solution 5 times the quantity of the blood, the RNA aptamer specifically reactive to EpCAM with the marker-substance magnetic particle is added, and is stirred slowly for 30 minutes. The suspension fluid is sent through a tube with 2 mm in inner diameter, and magnetic particles are captured with an array of neodymium magnets spaced at an interval of 1 cm. The collected magnetic particles are washed with culture fluid, and cells are separated using the cell sorter in example 1. To the separated cells is added Benzonase (registered trademark) nuclease for degradation of the RNA aptamer, and live cells are obtained. The separated live cells are incubated in the microchamber disclosed in Japanese Patent Application No. 2004-305258. Tumor-derived cells, if any, can endure incubation for a prolonged period, and some of them start dividing shortly.

Generally most of live cells circulating in the blood are, apart from hematopoietic cell groups, derived from tumor. Cells other than tumor cells do not normally break off the surface of vascular endothelium alive, and if they do, they are degraded in blood with the work of host defense mechanism. On the other hand tumor cells do break off alive, resist to degradation in blood as well, and circulate in the blood alive. The number of such cells, however, is small, making it unsuitable for biopsy. If tumor-derived cells circulating in the blood are collected alive in a large number and are incubated for a certain period of time, it can be known that there is a tumor somewhere in the body, although it is not possible to identify the tumor site.

If particles or magnetic particles are used as identification substance of the identification element as used in the above example, such methods as particle imaging, scattered light detection or magnetic detection can be used in identifying cells bonded to the marker substance of the identification element.

(B) A method of and an apparatus for immediately freezing and storing the separated cell according to the necessity is described hereinafter.

[IV] Fourth Embodiment

A fourth embodiment discloses a method and a means of freezing a sample cytoplasm without destroying the same; in the fourth embodiment a freezing rate of a cell is quickened to the utmost limit, namely, water mixed with a sample is cooled in a pressurized state to a temperature of a little under 0° C. so that it won't freeze; the water is then frozen by reducing pressure rapidly, while at the same time the sample is frozen quickly. By instantly skipping over a zone of maximum ice crystal formation, and by freezing the sample cytoplasm amorphously, the cytoplasm of the sample can be frozen without being destroyed.

In general, it is difficult to freeze water mixed with a sample in a very short time by controlling outside temperature because temperature transmission depends on heat conduction of a substance and convection of a solvent. Therefore, in general, a thinly sliced section of a sample is cooled in liquid nitrogen to cope with it. However, when a thicker section is used, a heat conduction influence emerges, making it difficult to cool it at a high rate. On the other hand, because the fourth embodiment is a method dependent on pressure transmission of a substance, it is possible to cool at a much higher rate than a heat conduction method. In respect to a relationship between pressure and temperature, a pressure transmission rate can be equivalent to that of a pressurized substance itself; therefore it is possible to transmit virtually at the speed of sound.

In the fourth embodiment, water and the sample are put into a pressure-resistant vessel so that no gas phase exists. Namely, the sample is put inside the vessel so that there will be no bubbles or air space; while applying pressure slowly so that a temperature doesn't go up, the water is cooled at a temperature of not more than 0° C. in such a condition as no sample in the water freezes. After reaching the prescribed pressure and temperature, the pressure is instantly reduced. Then a temperature in the sample goes down according to a decompressing time, and finally the sample freezes. Of course, water consumes latent heat to change its phase into ice, which has to be taken into consideration. Instant freezing is made possible by reducing pressure right before the water changes its phase into ice, after the water reaches the prescribed temperature with the prescribed pressure. A phrase, "no gas phase exists" means that water is degassed; and it means that no bubbles can be seen on the walls of the pressure-resistant vessel or the outside surface of the sample.

EXAMPLE 1

Figure 20:
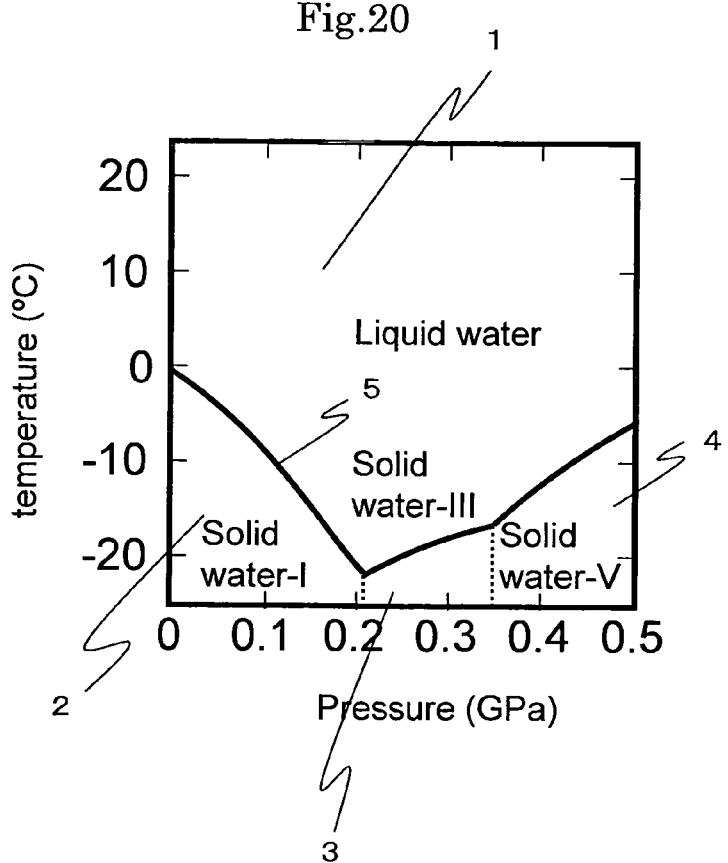
FIG. 20 is a diagram showing the generally known water phases.

FIG. 20 indicates a diagram of water which is commonly known. The horizontal axis indicates pressure applied on water, while the vertical axis indicates temperature; information on a high temperature region is skipped because there is no need for it. The triple point of water coincides with the pressure 0 point on line segment 5 (on the vertical axis of FIG. 20) which divides liquid water region 1 and ice-I region 2. Ice changes into various phases depending on pressure and temperature; there are ice-III region 3 and ice-V region 4, but here the relationship between the ice-I region 2 and the liquid water region 1 is important.

Figure 21:
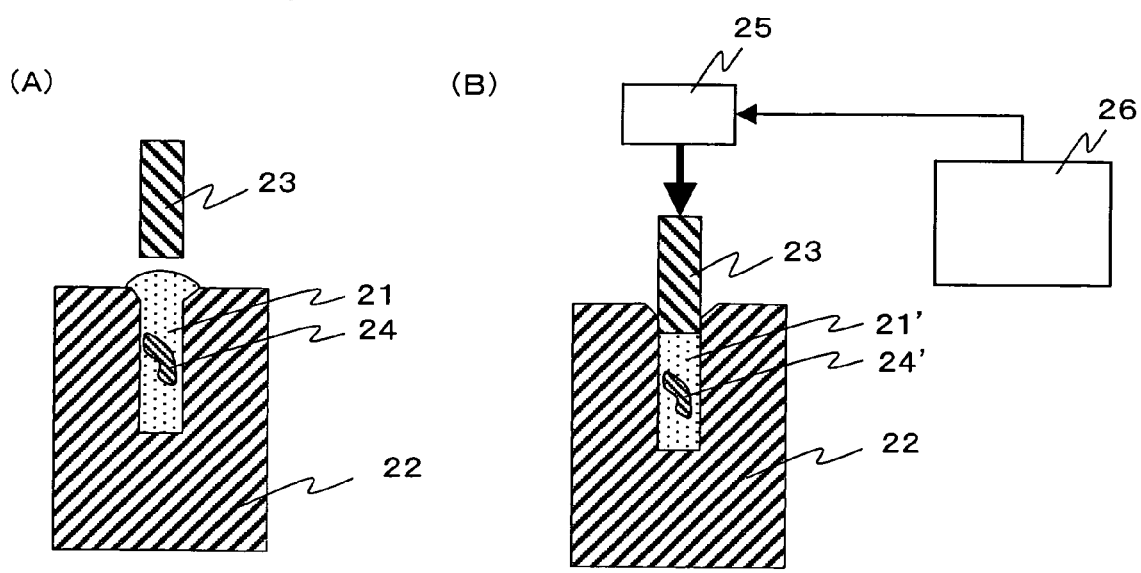
FIGS. 21(A) and 21(B) are cross-sectional views illustrating outlines of a cell freezer and a method of freezing a cell according to a fourth embodiment of the present invention respectively.

FIGS. 21 (A) and (B) indicate a cross-sectional view showing an outline of examples for describing a cell freezing method and a cell freezing apparatus according to the fourth embodiment. In FIG. 21 (A) the reference numeral 22 indicates a stainless pressuring vessel having, in the middle, a cylinder, for example, with an 8 mm-bore and a 10 mm height, with its top end open for putting water 21 and a sample 24. The cylinder has a tapered top end. A pressurizing vessel 22 is supposed to be sturdy enough to sustain the pressure applied on water. The numeral number 23 indicates a piston, which is inserted into the cylinder of the pressurizing vessel 22. The surface of the piston 23 and the inside of the cylinder of the pressurizing vessel 22 are mirror surfaces; and both of them have to be large enough for the piston 23 to move inside the cylinder, but at the same time they have to have tight space in which a tight built-in can be realized so that no water leaks out from a contact surface of the piston 23 and the cylinder of the pressurized vessel 22.

A 0.1 g of liver cell tissue sample is put into the water 21 as a sample 24 (herein, it is regarded as a culture solution and is called a sample solution 21). The sample solution 21 is poured into the cylinder so that there will be no gas phase; that means the solution 21 is poured to a degree that the solution is spilt from the cylinder so that no bubbles stick on the surface of the cylinder. Then the sample 24 is put into the cylinder.

As described in FIG. 21 (B), the piston 23 is slowly inserted into the pressurizing vessel 22. As a matter of fact, this insertion is conducted with a pressurizing device 25 utilizing hydraulics and the like. The pressurizing device 25 is controlled with a control device 26. At this time, by pouring a plenty of sample solution 21 so that the sample solution overflows from the top of the pressurizing vessel 22, it is possible to prevent air from coming inside the cylinder when the piston 23 is inserted.

When the piston 23 is inserted into the cylinder of the pressuring vessel 22, pressure is applied slowly up until 0.1 GPa while paying attention so that the temperature of the sample solution 21 inside the cylinder doesn't go up. A signal given by the control device 26 to the pressuring device 25 is programmed so that a scope of temperature drop and pressurization fall is within the range of not under the line segment 5 as well as in the range of the line segment 5 plus 4° C. In this case, it is permissible to write a program according to a previous experiment, and it is permissible to mount a thermometer not shown in the cylinder, in order to control this signal while feeding back the signal to the control device 26. At a time when the pressure inside the cylinder, namely the pressure applied by the pressurizing device 25, reaches 0.1 GPa; namely when the pressure reaches a state of almost the lowest temperature in the relationship between the ice-I region 2 and the liquid water region 1, the control device 2 6 releases hydraulic pressure, reducing the pressure rapidly. That makes a liver cell tissue sample 24' inside the cylinder freeze.

Due to a latent heat influence of the pressurizing vessel 22, it is in fact impossible to reduce a temperature of the sample to −20° C., but it can be cooled to around −10° C. According to molecular dynamic calculation of ice, it takes 250~350 nanoseconds for water to change its phase into ice with only molecular reorganization, while ignoring heat conduction. Assuming that a slice of the sample 24 is around 5 mm thick, and a pressure transmission rate is 1500 m/second, it takes about 3μ seconds to transmit pressure. It is assumed that a time needed for the freezing of the invention is from several μ seconds to several dozen μ seconds. Because of that, it is possible to freeze cells instantly.

(C) Next, a device and a method for handling separated cells in a cell-by-cell way are described.

[V] Fifth Embodiment

Descriptions are provided below for example cases where, in order to place a prespecified number of the separated cells each in a prespecified position on a cell culture chip, hydrophilic areas are separately formed with a prespecified distance between one another on the surface of the cell culture chip, a suspension of cells is dropped as a droplet of an appropriate size containing a required number of cells from the tip of a pipet having sucked the suspension, and the size of a droplet and the number of cells are monitored and controlled by monitoring the tip of the pipet with an optical system.

EXAMPLE 1

FIG. 22(a) is a plan view showing a cell culture chip 100 advantageously used in Example 1, and FIG. 22(b) is a cross-sectional view showing the cell culture chip 100 taken along the line A-A in the plan view and viewed in the direction indicated by the arrow. The reference numeral 1 indicates a silicon substrate, for instance, with a thickness of 1 mm and with a size of 20 mm×20 mm. 2 indicate walls, which are made of silicon substrates, with a thickness of, for instance, 1 mm, and with a height of 0.5 mm. An area surrounded by the walls 2 is a hydrophobic area 3, in which hydrophilic areas 4 are regularly placed. The size of the hydrophilic area 4, which is determined from the size or the number of cells to be placed in one of these areas, is approximately 400 µm×400 µm. Spacing between the hydrophilic areas 4, which should have a distance sufficient for droplets containing the cells not to contact and not to be mixed one another, is preferably about 2000 to 4000 µm for convenience of handling. 5 indicates a marker for positioning, which is formed on one side of the silicon substrate 1.

In a method of producing hydrophilic areas and a hydrophobic area, for instance, the upper side of the hydrophobic silicon substrate 1 is oxidized once to turn the entire area into a hydrophilic $SiO_2$ thin film. Then, a hydrophobic area may be produced by dissolving and removing the $SiO_2$ thin film in the area to be hydrophobic with hydrofluoric acid.

EXAMPLE 2

FIG. 23(a) is a conceptual diagram for illustrating configuration of a system for distributing a cell to the cell culture chip 100 in Example 2, and FIG. 23(b) is a cross-sectional view showing the state in which the cell has been placed in a hydrophilic area 4 of the cell culture chip 100.

In Example 2, a cell 12 is placed in a hydrophilic area 4 on a cell culture chip 100 while optically monitoring a droplet formed at the tip of a pipet 11 for distributing the cell 12. In FIG. 23(a), 19 indicates a stage to be driven in the direction of XY, and 27 indicates a driving unit for the stage 19. A heater 22 for controlling the temperature of the cell culture chip 100 is provided on the upper side of the stage 19, on which the cell culture chip 100 is placed. Above the cell culture chip 100, the pipet 11 is placed, in which a suspension 13 containing the cell 12 to be distributed has been sucked up in advance and held. At the root of the pipet 11, a syringe pump 31 is provided via a tube 30, and the syringe pump 31 is attached with a driving unit 32. When the syringe pump 31 is driven by the driving unit 32, the suspension 13 in the pipet 11 is squeezed out together with the cell 12. It is to be noted that a joint between the root of the pipet 11 and the tube 30 is illustrated as like they are separated because it is intended to show the pipet 11 in an enlarged view, but they are not actually separated.

On the other hand, at the tip of the pipet 11, the tip of another pipet 20 for supplying a culture solution to the tip of the pipet 11 is placed. At the root of the pipet 20, a syringe pump 35 is provided via a tube 34, and the syringe pump 35 is attached with a driving unit 36. When the syringe pump 35 is driven by the driving unit 36, the culture solution in the syringe pump 35 is squeezed out from the pipet 20.

Also, a driving unit 37 for vertical motion of the pipet to transfer a droplet formed at the tip of the pipet 11 into a hydrophilic area 4 of the cell culture chip 100 is provided. Herein, the vertical motion driving unit 37 is correlated to the pipet 11. When a signal to lower the pipet 11 is given to the vertical motion driving unit 37 by a user, the pipet 11 is moved downward and the droplet formed at the tip of the pipet 11 is transferred into a hydrophilic area 4 of the cell culture chip 100. When a signal to restore the pipet 11 is given to the vertical motion driving unit 37 by the user, the pipet 11 is moved back to the position shown in the figure. Restoration of the pipet 11 to the position shown in the figure may be carried out time-sequentially after the downward operation using a PC 26. An alternate long and short dash line 39 denotes a correlation between the vertical motion driving unit 37 and the pipet 11.

Further, a light source 16 and a condenser lens 17 are provided, which construct an optical system for monitoring the size of a droplet formed inside the pipet 11 adjacent to the tip and formed at the tip of the pipet 11, while in the opposite position to the light source and the condenser lens, a collimate lens 18 and a monitor 25 are provided below the cell culture chip 100. Accordingly, the cell culture chip 100, the heat regulator 22, and the stage 19 must be optically transparent. 26 indicates a PC, which provides a control signal obtained from a prespecified program stored in advance in response to an input signal from the monitor 25, and necessary signals for the driving units 27, 32 and 36 in response to an operation input signal 28 which the user gives while watching the display screen of the monitor 25. Although it is not shown in the figure here, it is convenient that the same display as the screen of the monitor 25 detecting are displayed on the monitor screen of the PC 26. Thus, the monitor 25 can be a small CCD camera. The operation input signal 28 is to be given via an input device of the PC 26.

Consideration about the size of the pipet 11 is provided as follows. The pipet 11 must be able to form a droplet of an appropriate size containing a required number of cells, at the tip thereof. On the other hand, in the pipet 11, the suspension containing cells is sucked up by the pipet prior to its use, and when forming a droplet, the cells passing through the tip of the pipet 11 must be detected by the monitor 25 without error. Therefore, the diameter of the tip of the pipet 11 allows only a cell or a mass of a prespecified number of cells to pass through, but does not allow cells to pass through at once so many as uncountable. Namely, unlike pipets for culture with a large diameter currently used for general purpose, it is preferable to be transparent and to have a diameter at the tip of 20 to 100 µm for general animal cells, or of about 5 µm for microbes such as bacteria.

An operation to distribute a cell 12 into a hydrophilic area 4 of the cell culture chip 100 is described below. Firstly, when the system is started-up, the user positions the cell culture chip 100 to lie in a prespecified start-up position by focusing attention on the marker 5 described in FIG. 22(a). Next, in response to the operation input signal 28 which transfers the first distribution position of the cell 12 to the position corresponding to the tip of the pipet 11 and pipet 20, the stage 19 is operated with the driving unit 27. When the cell culture chip 100 reaches a prespecified position, an operation is carried out to eject the suspension 13 in the pipet 11 together with the cell 12. In this step, the outside of the tip and the inside adjacent to the tip of the pipet 11 are monitored with the optical system including the light source 16 and the monitor 25. Output from the monitor 25 is captured into the PC 26, and the driving unit 32 is activated based on a result of image computing by the PC 26, to control a transfer of liquid in the syringe pump 31.

While monitoring the tip of the pipet 11 with the monitor 25, the driving unit 32 is moved by activating the driving unit 32, and a droplet 21 is formed at the tip of the pipet 11 by ejecting the suspension 13 containing the cell 12 from the tip of the pipet. In this step, the PC 26 determines through the monitor 25 that a prespecified number of cells are inserted into the droplet 21, and sends a stop command to the driving unit 32 to stop the syringe pump 31.

To simplify descriptions, it is described below as the number of cells 12 to be inserted into a droplet 21 is one, but the number of cells may be discretionally determined by the user according to a purpose. For instance, it may be 10 cells. Identification of the cell 12 may be carried out just by directly detecting the cell 12 present in the droplet 21 at the tip of the pipet 11, but more efficiently, the syringe pump 31 may be controlled by monitoring the cell 12 passing inside the pipet 11 with the monitor 25, and by calculating the cell's position and passing speed inside the pipet with the PC 26 to predict a timing of ejecting the cell into the droplet 21 from the tip of the pipet 11. Using the latter identification method, it is advantageous for inserting just one cell into the droplet, for instance, when a plurality of cells is passing inside the pipet 11 at a short interval.

When the cell concentration of the cell suspension 13 is low, each droplet 21 can be made in a certain size by starting to form the droplet 21 just before a cell being ejected from the tip of the pipet 11 and then stopping droplet formation after a prespecified time period. When a droplet is not required to be formed, for instance, liquid being ejected from the tip of the pipet 11 may be blown off with a blower. Alternatively, a drain may be provided outside the substrate 1 to eject the unwanted liquid thereto.

On the other hand, when the cell concentration of the cell suspension 13 is high, quantities of drops ejected from the pipet 11 are varied. Namely, since the frequency of ejection of a cell 12 being ejected from the pipet 11 increases, if the time period for ejecting liquid is fixed at a prespecified time period, the next cell may possibly be inserted into the same droplet 21 within the time period. In such a case, the pipet 20 is to be used. In the pipet 20 and the syringe pump 35 correlated thereto, only culture solution or cell dilution is held. Namely, when via the monitor 25 the PC 26 checks that a cell 12 enters a droplet 21, it issues a stop command to the driving unit 32 to stop the syringe pump 31 as well as it calculates the volume of the droplet 21 at that moment based on the fed quantity until that moment by the syringe pump 31 driven to form droplets 21. The difference between this volume and the desired volume of a droplet 21 is calculated with the PC 26. According to this calculation result, the PC 26 sends an operation signal to the driving unit 36 so as to add culture solution or cell dilution with the pipet 20 to the droplet 21 which has been already formed, so that liquid is added to the droplet 21 using the pipet 20 by driving the syringe pump 35 until the volume of the droplet 21 reaches a prespecified value.

In this step, in order to prevent the cell in the droplet from flowing back to the pipet 20, the tip of the pipet 20 preferably has a size unavailable for a cell to pass through, for instance, with a diameter of 0.2 μm. Alternatively, the tip may preferably have a structure with 0.2 μm filter.

The droplet 21 containing a single cell produced in this way is contacted with a hydrophilic area 4 on the substrate 1 placed on the stage 19 using the vertical motion driving unit 37 for the pipet 11, then the droplet 21 is transferred into the hydrophilic area 4 on the substrate 1. When the transfer is checked of the droplet 21 containing the cell 12 into the hydrophilic area 4 on the substrate 1, namely, the hydrophilic area 4 of the cell culture chip 100, the user gives an operation signal 28 to move a stage driving unit 10, and moves the cell culture chip 100 so that the tip of the pipet is to be positioned in a position for the next droplet to be placed. This movement can be automatically carried out by the PC 26 as positional information of the hydrophilic areas 4 has been provided to the PC 26. Then, in this new position, a new droplet is formed at the tip of the pipet 11 as described above, and transferred into another hydrophilic area 4 of the cell culture chip 100. By repeating this step, droplets are placed in required positions in hydrophilic areas 4 of the cell culture chip 100. All of these operations are carried out in a moist atmosphere in order to avoid drying. When placement of droplets 21 is finished, the whole area surrounded by the walls 2 is filled with silicon oil 38.

FIG. 23(b) is a cross-sectional view showing the state in which the cell has been placed in a hydrophilic area 4 of the cell culture chip 100, by a system for distributing a cell to the cell culture chip 100 in Example 2, as described with reference to FIG. 23(a). A cell 12 and a droplet 15 enveloping thereof are placed in a hydrophilic area 4 within the area surrounded by the walls 2 on the silicon substrate 1. The area surrounded by the walls 2 is fully filled with silicon oil 38. Since each droplet 15 is about 0.2 to 2 μl, the droplet 15 is protected from drying by filling silicon oil 38 inside the walls 2 of 0.5 mm in height.

The reason for using silicon oil here is because silicon oil has excellent gas permeability. This allows to supply oxygen constantly to the cell 12 in the droplet 15, and to keep the cell 12 alive in a very small quantity of culture solution. The thickness of the silicon oil is preferred to be thinner, but thick enough to cover the droplet 15, for instance, so as to be 0.5 mm in depth, the silicon oil being poured softly. Depending on kind and state of the cell, for instance, in a case of epithelial cells, this allows them to be observed usually for several hours. For cell observation, the monitor 25 may be used, or alternatively the chip may be transferred to another device for observation.

EXAMPLE 3

In order to observe the cells by incubating for longer hours, ensuring oxygen permeability is not enough and a droplet 15 enveloping a cell 12 must be exchanged with a new culture solution.

Figure 23:
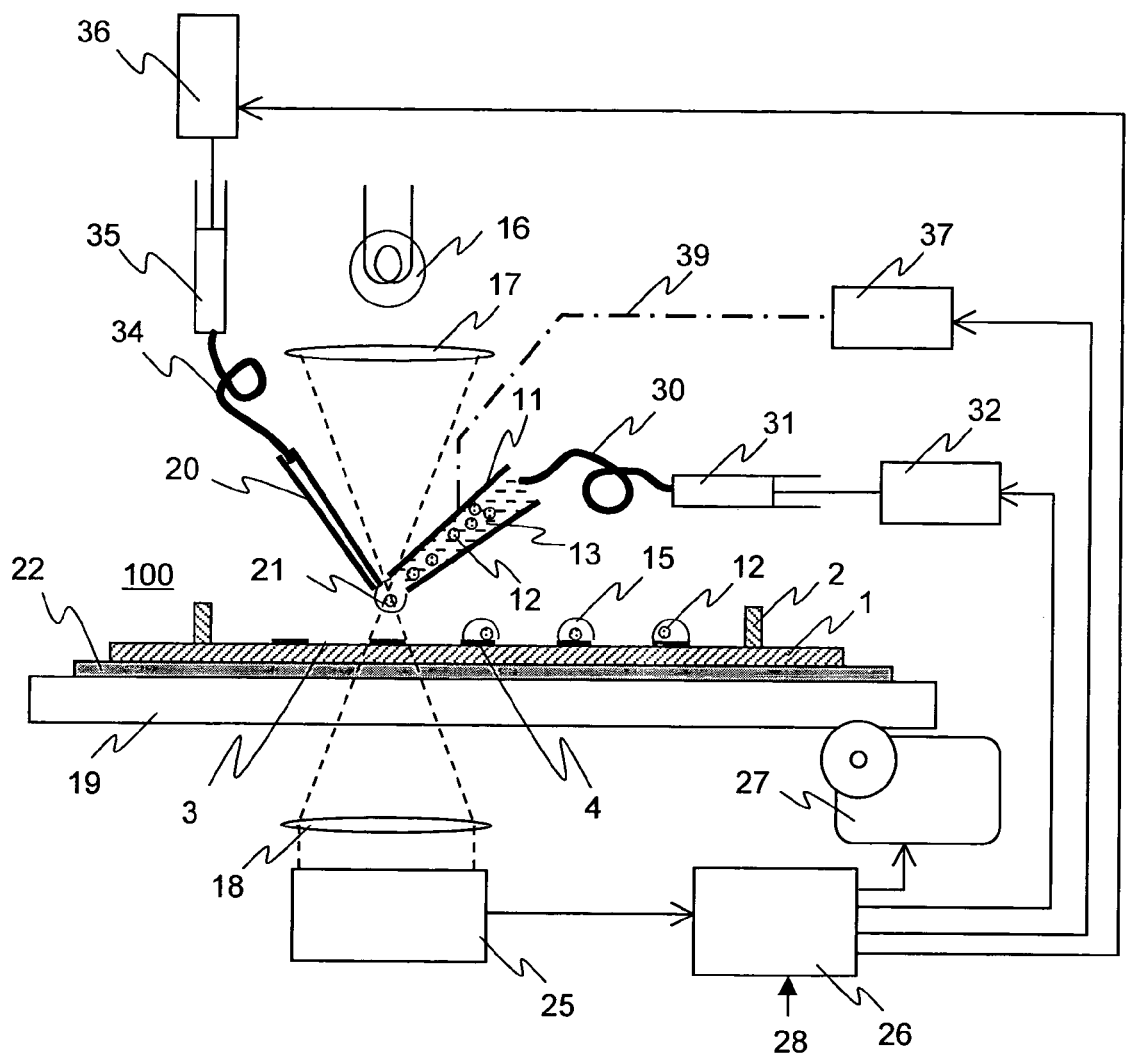
FIG. 23($a$) is a conceptual diagram for illustrating configuration of a system for distributing a cell to the cell culture chip 100 in Example 2, and FIG. 23($b$) is a cross-sectional view showing the state in which the cell has been placed in a hydrophilic area 4 of the cell culture chip 100.
Figure 23:
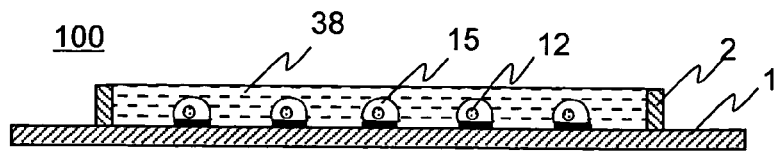
Figure 24:
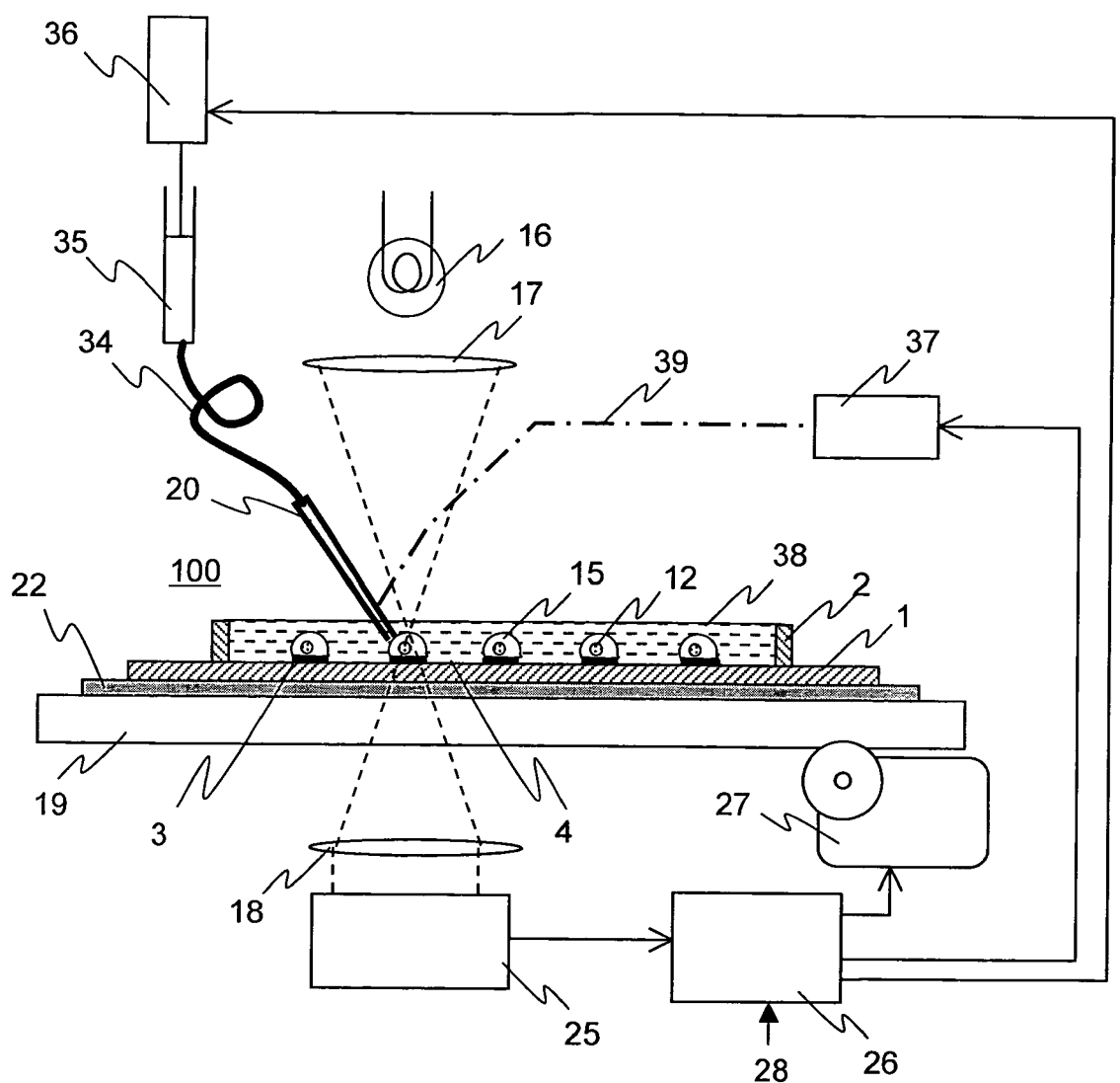
FIG. 24 is a conceptual diagram illustrating system configuration in Example 3 in which the function for exchanging a droplet 15 enveloping a cell 12 with a new culture fluid in the system configuration in Example 2 is emphasized.

FIG. 24 is a conceptual diagram illustrating system configuration in Example 3 in which the function for exchanging a droplet 15 enveloping a cell 12 with a new culture solution in the system configuration in Example 2 is emphasized. In practice, a pipet 20 and a tube 34 correlated thereto, a syringe pump 35, and a driving unit 36 in the system configuration in Example 2 can be used, therefore descriptions are provided with reference to FIG. 23 but without irrelevant parts deleted from the configuration. It is needless to say that a pipet 20 and a tube 34 correlated thereto, and a syringe pump 35 may be exchanged with new ones from a point of view to avoid contamination or the like.

The stage 19 is moved so that the tip of the pipet 20 comes in a position of the droplet 15 to be exchanged with a new culture solution, and the droplet 15 in question is monitored with the monitor 25. While monitoring the droplet 15; and the tip of the pipet 20 with the monitor 25, the pipet 20 is inserted into the droplet 15. Here, the vertical motion driving unit 37 is to be correlated to the pipet 20. To the vertical motion driving unit 37, a signal to lower the pipet 20 is given by the user, then the pipet 20 is moved downward and the tip of the pipet 20 is inserted into the droplet 15.

After it is checked via the monitor 25 that the tip of the pipet 20 is inserted into the droplet 15, the user gives a signal 28 to exchange culture solution to the PC 26. If the PC 26 has been given with information about the size of the droplet 15 and the number and size of cells enveloped therein, in response to the signal 28 to exchange culture solution, the PC 26 can automatically and time sequentially carry out operations to eject (to absorb and throw away) a prespecified amount of old culture solution and to supply a new culture solution containing such as substrates and growth factors by driving the syringe pump 36. In this step, it is important that the cell 12 enveloped in the droplet 15 must not be ejected together with the old culture solution, and unwanted bacteria must not contaminate with the new culture solution.

For this purpose, the tip of the pipet 20 preferably has an inner diameter not to suck in any cell, for instance, 0.2 μm. Alternatively, the tip may have a structure with 0.2 μm filter. Further, the pipet 20 and the tube 34 correlated thereto, and the syringe pump 35 should be treated to keep them sufficiently clean.

EXAMPLE 4

Operations to incubate cells for a prespecified period of time, to complete observation by the monitor 25, and to recover only a prespecified cell are described.

Figure 25:
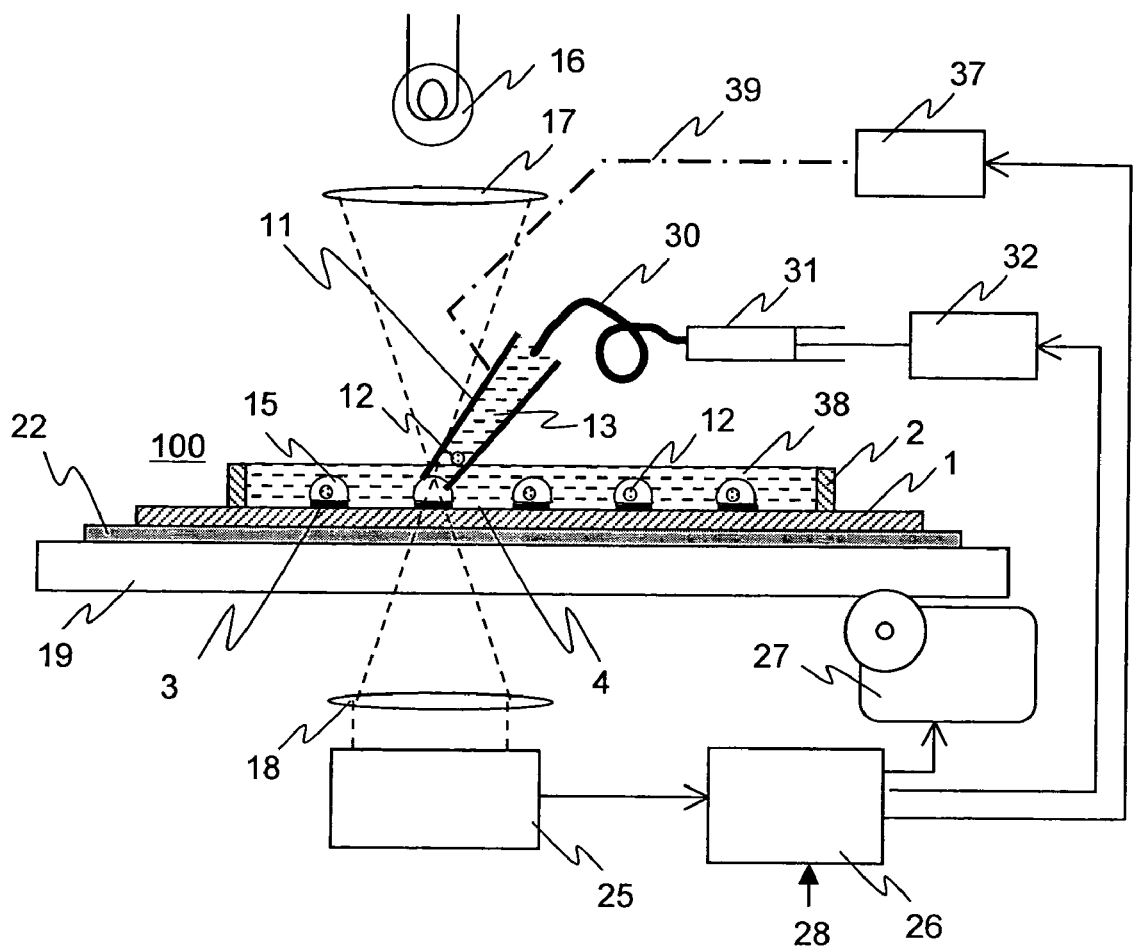
FIG. 25 is a conceptual diagram showing system configuration in Example 4 in which the function for recovering a cell from inside of the droplet 15 enveloping a prespecified cell 12 in the system configuration shown in Example 2 is emphasized.

FIG. 25 is a conceptual diagram showing system configuration in Example 4 in which the function for recovering a cell from inside of the droplet 15 enveloping a prespecified cell 12 in the system configuration shown in Example 2 is emphasized. In practice, a pipet 11 and a tube 30 correlated thereto, a syringe pump 31, and a driving unit 32 in the system configuration in Example 2 can be used, therefore descriptions are provided with reference to FIG. 25 but without irrelevant parts deleted from the configuration. It is needless to say that a pipet 11 and a tube 30 correlated thereto, and a syringe pump 31 may be exchanged with new ones from a point of view to avoid contamination or the like. Further, considering for recovering a cell, a pipet 11 may have a larger diameter.

By moving the stage 19 so as to lie in a position of the droplet 15 enveloping the cell to be recovered, the droplet 15 in question is monitored with the monitor 25. While monitoring the droplet 15 and the tip of the pipet 11 with the monitor 25, the pipet 11 is inserted into the droplet 15. Herein, the vertical motion driving unit 37 is to be correlated to the pipet 11. To the vertical motion driving unit 37, a signal to lower the pipet 11 is given by the user, then the pipet 11 is moved downward and the tip of the pipet 11 is inserted into the droplet 15, to recover the cell 12 in the droplet 15 by sucking it up into the pipet 11.

After it is checked via the monitor 25 that the tip of the pipet 11 is inserted into the droplet 15, the user gives a signal 28 to suck the cell 12 in the droplet 15 to the PC 26. If the PC 26 has been given with information about the size of the droplet 15 and the number and size of cells enveloped therein, in response to the signal 28 to suck in the cell 12, the PC 26 can automatically and time sequentially carry out an operation to suck the cell 12 into the pipet 11 together with the culture solution by driving the syringe pump 31. Herein, since sucking is carried out by inserting the pipet 11 into the droplet 15 enveloping the cell 12 through the silicon oil 38, more or less the silicon oil 38 is sucked up together, but it can be ignored without problem.

The cell 12 sucked into the pipet 11 is ejected to a prespecified recovery container to recover the targeted cell.

After recovering the targeted cell, when recovering a cell 12 from another droplet 15, the stage 19 is moved so that a droplet 15 enveloping a new cell to be recovered lies in a position able to be monitored with the monitor 25, while monitoring the new droplet 15 in question with the monitor 25, the new cell is sucked into the pipet 11 and ejected into a prespecified recovery container to recover the new targeted cell, according to the procedure as described above.

Consideration about the size of the pipet 11 suitable for Example 4 is provided as follows. When producing a droplet in Example 2, the pipet 11 preferably has a diameter at the tip of 20 to 100 μm for general animal cells, or of 5 μm for microbes such as bacteria, however, considering ejection of cells after a prespecified time period of incubation in Example 4, the pipet needs a sufficiently large diameter to suck up a mass of cells made by cell division. Specifically, it is approximately 100 to 400 μm.

EXAMPLE 5

Figure 26:
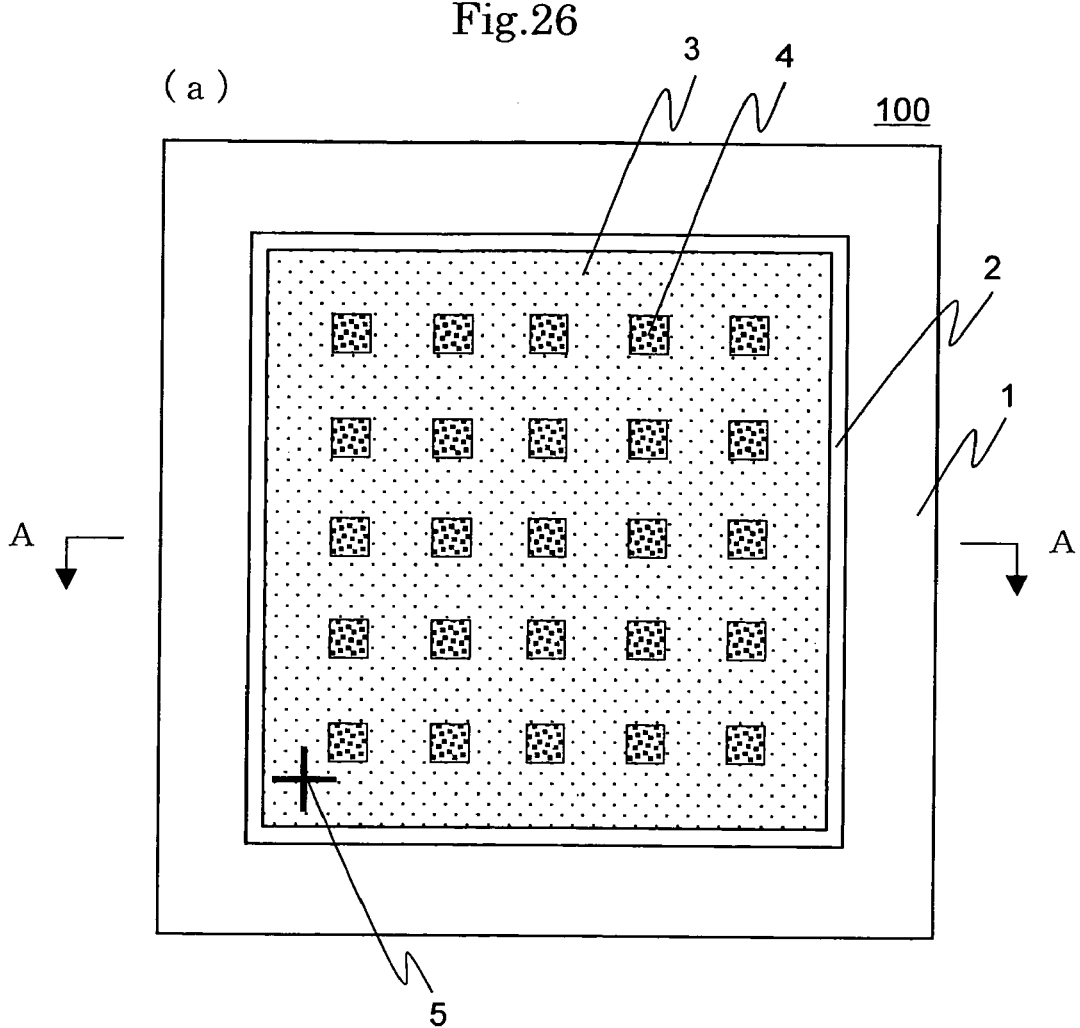
FIG. 26($a$) is a plan view showing another configuration of the cell culture chip 100 in Example 5 advantageously applicable to a fifth embodiment of the present invention.
Figure 26:
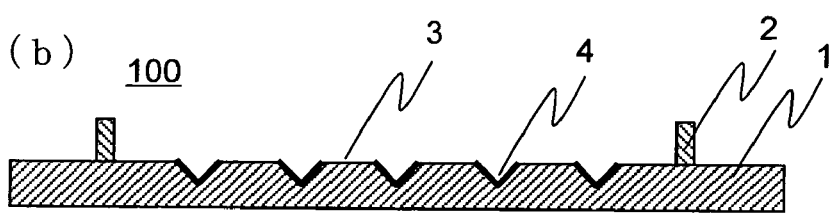
Figure 26:
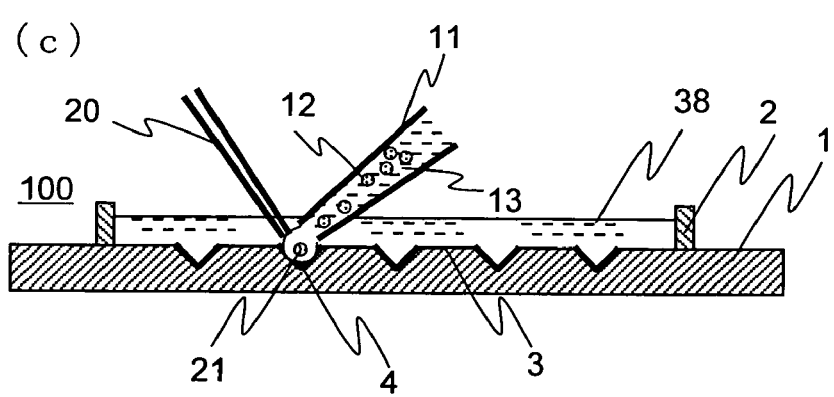

FIG. 26(*a*) is a plan view showing another configuration of the cell culture chip 100 in Example 5 advantageously applicable to a fifth embodiment of the present invention; FIG. 26(*b*) is a cross-sectional view showing the cell culture chip 100 above taken along the line A-A in the plan view and viewed in the direction indicated by the arrow; and FIG. 26(C) is a view illustrating a method of forming a droplet. By comparing FIG. 26(*a*) and FIG. 22(*a*), it is obvious that the cell culture chip 100 in Example 5 has the same planar structure as that in Example 1. Also materials, size and a producing method are the same. The cross-sectional structure of the cell culture chip 100 in Example 5 is different from that in Example 1. Namely, hydrophilic areas 4 are formed as wells, while it is the same that the area surrounded by the walls 2 is the hydrophobic area 3, in which hydrophilic areas 4 are regularly placed. The size of the well is to be 400 μm in diameter (or 400 μm×400 μm) and 100 μm in depth.

As shown in FIG. 26(*c*), in this Example 5, silicon oil 38 is applied in advance over the area surrounded by the walls 2. Passing through the layer of silicon oil 38, the pipet 11 and the pipet 20 in Example 2 as described with reference to FIG. 23 are inserted, and within the well 4, by supplying the cell suspension 13 from the pipet 11 and dilution from the pipet 20, a droplet 21 is formed directly in a well in a hydrophilic area 4. By contacting the tips of the pipets 11 and 20 with walls of the well on the substrate 1, the formed droplet 21 is automatically formed inside the well, to be used as the droplet 15 in Example 2.

Also in Example 5, the well area to form the droplet 21 and the tips of the pipets 11 and 20 have to be controlled while monitoring with the monitor 25, but the figures and descriptions are simplified because it can be understood easily from the description in Example 2.

EXAMPLE 6

In the examples as described above, a pipet is described in each case as it has one function, while in Example 6, an example of a pipet having two functions is described.

Figure 27:
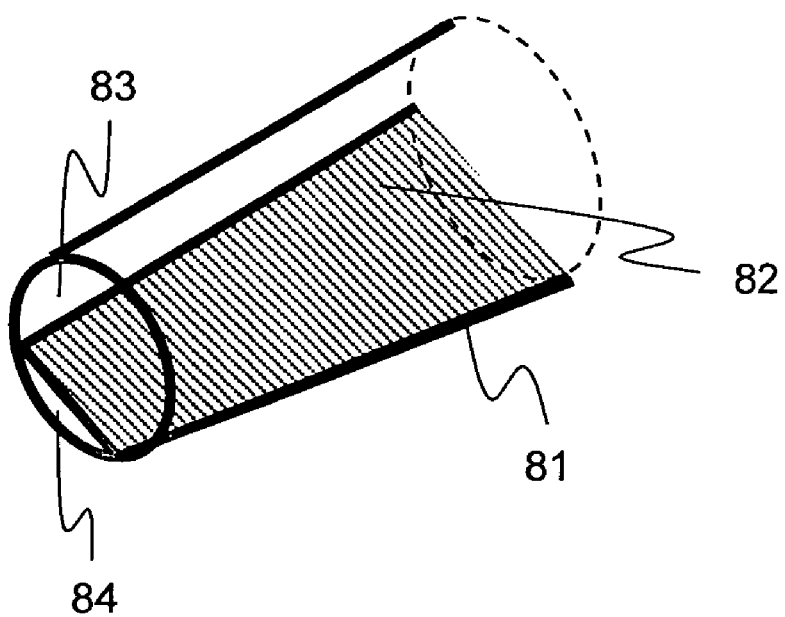
FIGS. 27($a$) and 27($b$) are views showing a tip of a pipet having two flow paths.
Figure 27:
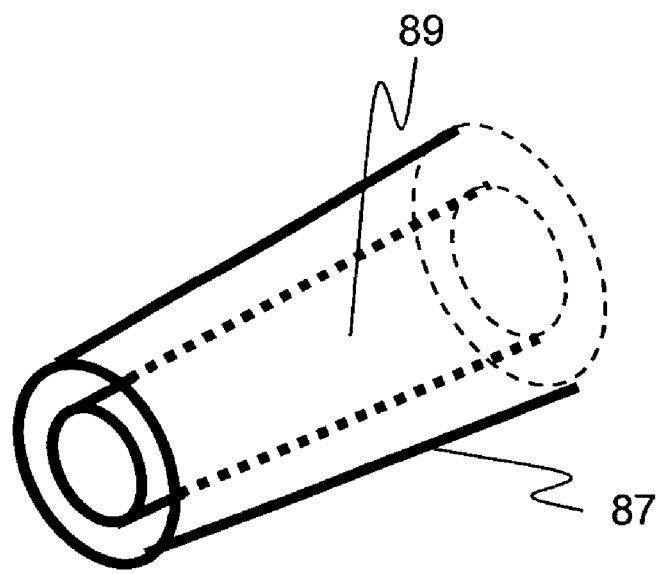

FIG. 27(*a*) is a view showing a tip of a pipet 81 having two flow paths separated by a partition plate 82, and FIG. 27(*b*) is a view showing configuration in which a pipet 89 is provided inside a pipet 87 to form two flow paths.

In the configuration shown in FIG. 27 (*a*), by making a first flow path 83 sufficiently larger than a second flow path 84, and by designing a structure in which cell suspension can be supplied from the first flow path 83 and dilution can be supplied from the second flow path 84, the pipet 11 and the pipet 20 described in Example 2 can be integrated. It is needless to say that controls of the respective flow paths are carried out with respective independent syringe pumps.

In the configuration shown in FIG. 27(*b*), the inner pipet 89 has an inner diameter of 50 μm, and spacing therefrom to the inner wall of the outer pipet 87 is up to 8 μm. This allows cell suspension to be supplied from the inner pipet 87 and dilution to be supplied from the outer pipet 89, so that the pipet 11 and the pipet 20 described in Example 2 can be integrated. It is needless to say that controls of the respective flow paths are carried out with respective independent syringe pumps.

In each case, the size of a pipet for supplying dilution is determined so as to avoid getting mixed with cells from the pipet for supplying cell suspension, so that the pipet 11 and the pipet 20 described in Example 2 can be integrated.

OTHER EXAMPLES

In any example described above, underneath the substrate 1, there is a device 22 for controlling a substrate temperature in case of incubation of cells. Incubation is basically carried out while observing cells via microscope, the substrate 1 itself should be transparent. The heater 22 for controlling temperature should also be transparent, for which ITO element may be preferably used. When it is not ITO element, for instance, a structure inside which transparent and thermally controlled circulation fluid flows may be used. In this case, limitations may occur in the optical system of the monitor 25, but it is to be solved by using long-focus objective lens.

With respect to measurement of the number of cells passing through the tip of a pipet, it can be measured by checking a cell being ejected from the pipet, for instance, via installation of a pair of electrodes at the tip of the pipet to capture an electrical change when ejecting a cell from the pipet, or via irradiation of laser light to the tip to detect light scattering when a cell passing through.

By using a function of exchanging a droplet 15 enveloping a cell 12 with a new culture solution, which is described with reference to FIG. 24, influences on cells can be assessed by injecting various materials influential on cells, for instance, substrates for culturing cells, growth factors, chemical substances such as cytokine or endocrine disrupting chemicals.

[VI] Sixth Embodiment

A reliable droplet manipulation is disclosed as a sixth embodiment in which any droplet selected from a droplet group arranging densely on the substrate are transferred to a predefined position. In particular, droplet transfer lines with hydrophilic property are arranged in the shape of matrix on the substrate with an insulating surface having water-repellent property, and a droplet holding area is provided at both ends of the droplet transfer lines. A droplet is formed at the droplet holding area and only a targeted droplet to be transferred is charged. When an electrode with the same polarity as the electricity charged to the targeted droplet closes to the targeted droplet, the targeted droplet is transferred by a repulsion force generated between the electrode and the targeted droplet along the droplet transfer line with hydrophilic property. The transferred droplet is stopped in the droplet holding area with hydrophilic property, and then discharged to keep stable at the position. The transferred droplet is contacted with any other droplet in the droplet holding area to be reacted thereto.

EXAMPLE 1

Figure 28:
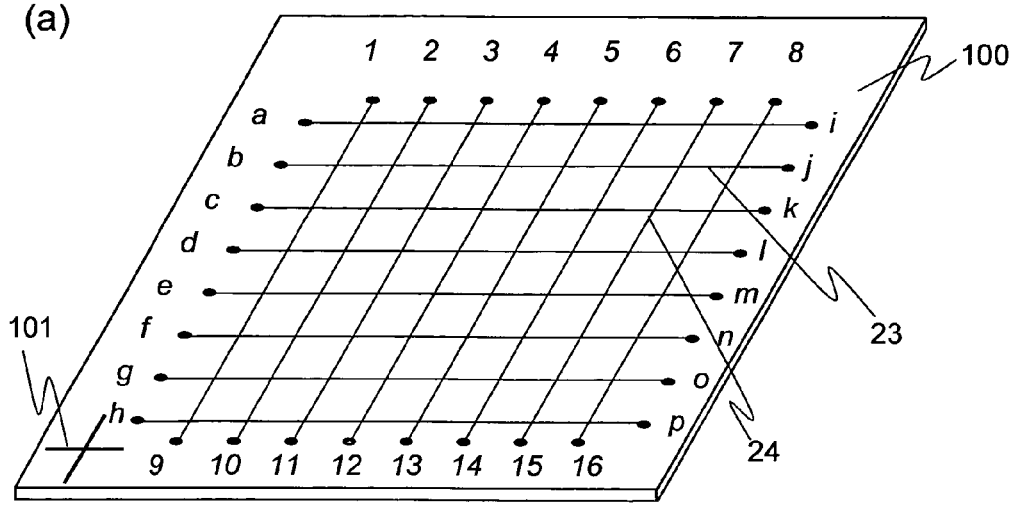
FIG. 28($a$) is a perspective view showing a substrate applicable to the droplet manipulation according to a sixth embodiment of the present invention, FIG. 28($b$) is a perspective view showing the substrate in which discrete droplets to be reacted are placed on a surface of the substrate, and FIG. 28($c$) is a perspective view schematically showing the substrate during the droplet manipulation.
Figure 28:
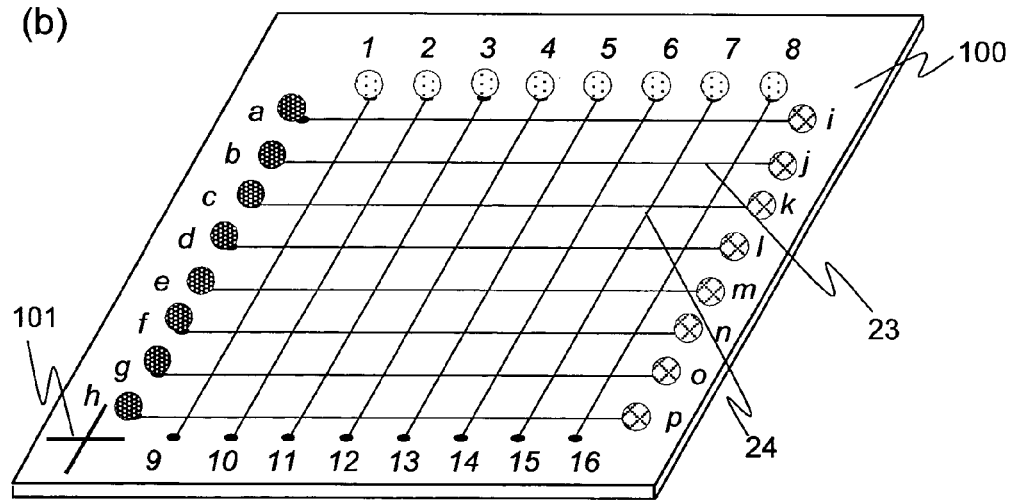
Figure 28:
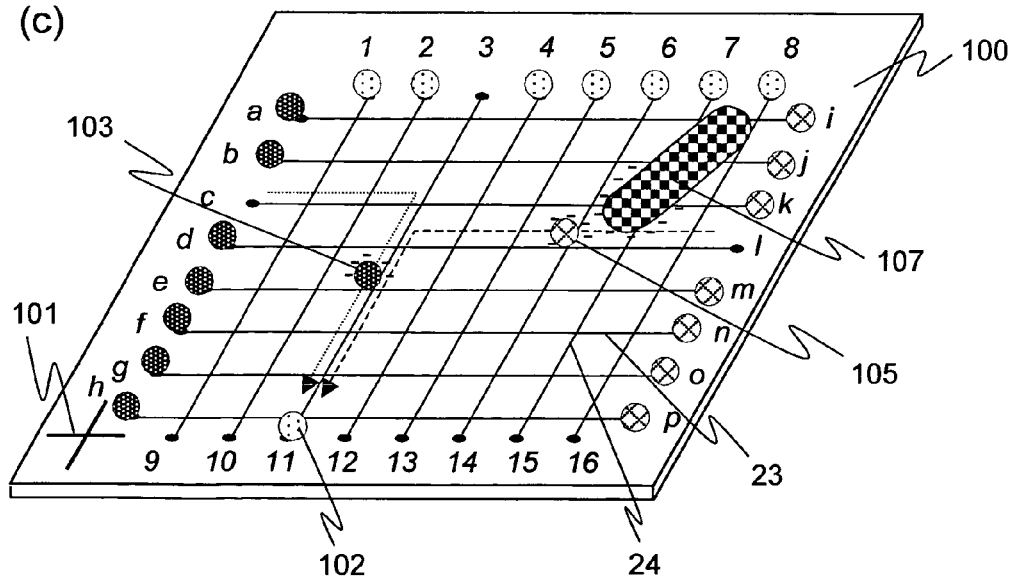

FIG. 28 (*a*) is a perspective view showing a substrate applicable to the droplet manipulation according to the sixth embodiment of the present invention; FIG. 28(*b*) is a perspective view showing the substrate in which discrete droplets to be reacted are placed on a surface of the substrate; and FIG. 28(*c*) is a perspective view schematically showing the substrate during the droplet manipulation.

In FIG. 28(*a*), a reference numeral 100 denotes a substrate made of an insulating material, the whole surface thereof having water-repellent property; droplet transfer lines 23 and 24 with hydrophilic property are formed in a shape of matrix on the surface thereof; droplet holding areas with hydrophilic property a, b, . . . , p and droplet-holding areas with hydrophilic property 1, 2, . . . , 16 are formed on both ends of the droplet transfer lines 23 and 24 in shape of matrix, in this example the droplet holding areas with hydrophilic property a, b, . . . , p and the droplet holding areas with hydrophilic property 1, 2, . . . , 8 are used as a droplet holding area for holding a droplet to be reacted, whereas the droplet-holding areas with hydrophilic property 9, 10, . . . , 16 are used as a droplet holding area for holding a droplet after two droplets are collided and reacted to each other. It is assumed in this example that the droplet is 0.1 to 1 µl in quantity, the droplet holding area is for instance 30 µmφ dot with hydrophilic property, and the hydrophilic lines 23 or 24 used as a path for droplet transfer is 2 µm in width. The droplet can be pushed out from the droplet holding area onto the hydrophilic lines 23, 24 by the repulsion force generated by the static electricity, and role along the line. The reference numeral 101 denotes a positioning mark.

Figure 29:
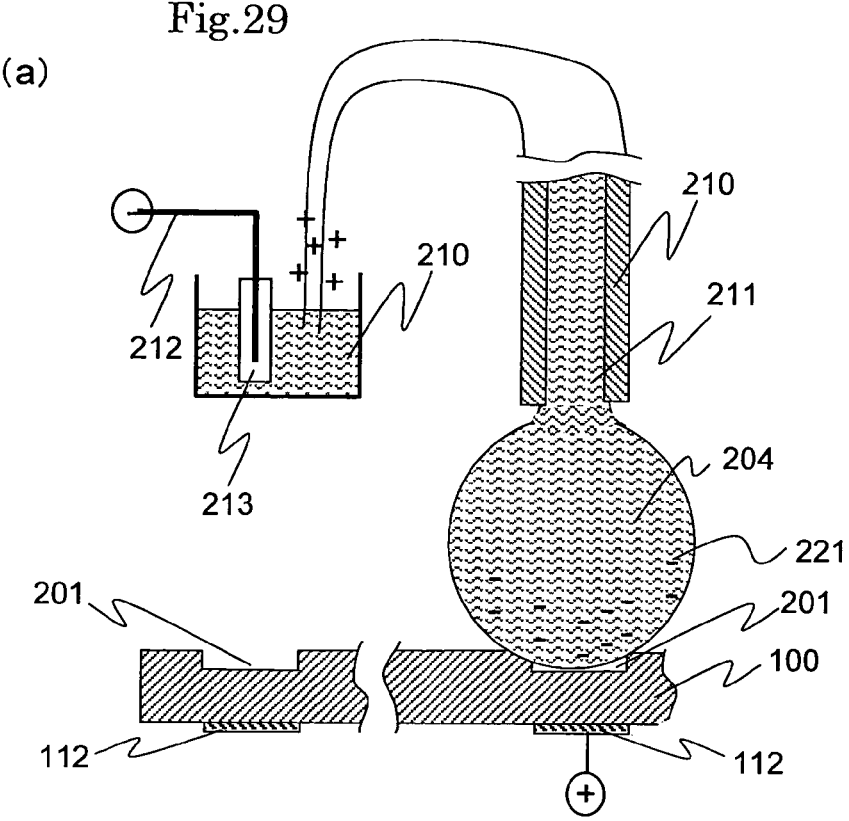
FIGS. 29($a$) and 29($b$) are views each illustrating a procedure for charging a droplet in a droplet holding area, FIG. 29($a$) is a view showing the initial state in the process for charging the droplet, and FIG. 29($b$) is a view showing the state in which the charged droplet has been removed to the droplet holding area.
Figure 29:
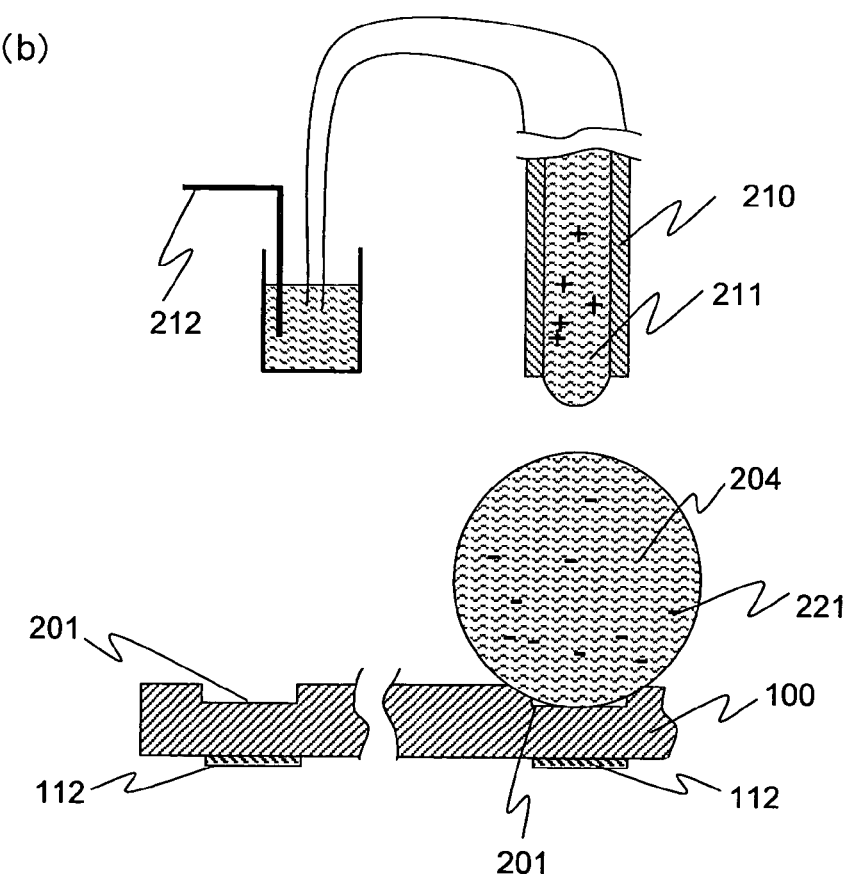

In order to make the droplet on the droplet holding area receive the repulsion force generated by the static electricity, the droplet is required to be charged. This charging manipulation is a modification based on a method described on Micro Total Analysis Systems 2004, vol. 1, pp. 144-146 (Proceedings of µ TAS 2004, 8th International Conference on Minituialized Systems for Chemistry and Life Sciences, ISBN 0-85404-643-7 or the like. FIGS. 29(*a*) and 29(*b*) are views showing a process for making the droplet on the droplet holding area to be charged, in which FIG. 29(*a*) shows an initial stage of making the droplet charged, and FIG. 29(*b*) shows a state in which the charged droplet is transferred to the droplet holding area.

In this example, the substrate 100 is made of an insulating material, and a reference numeral 201 is the droplet holding area described in FIG. 28 with a droplet 204 is formed therein. There is provided an electrode 112 on an area in the back of the substrate 100 corresponding to the droplet holding area 201. A capillary 210 is provided on the droplet holding area 201, capable of contacting the droplet 204 freely, with a conductive solution 211 filled therein, and contacting the electrode 212 at the opposite side thereof. A predetermined voltage is applied to the electrodes 112 and 212, and then the solution 211 on the edge of capillary 210 contacts with the droplet 204. As a result, when the voltage is loaded so as to make the electrode 112 positive and the electrode 212 negative, the droplet 204 and the solution 211 within the capillary are polarized generally, where the droplet 204 carries excessive negative electricity 221. In the state described above, when the capillary 210 is lifted away from the droplet 204 immediately, the droplet 204 is charged with negative electricity as shown in FIG. 29(*b*). On the contrary, in a case where a voltage is loaded so as to make the electrodes 112 negative and the electrode 212 positive, the droplet 204 can be charged with positive electricity. As described hereinafter, the voltage applied to between the electrodes 112 and 212 can be determined whether it is applied or not via a switch 115 on a switchboard 74.

Figure 30:
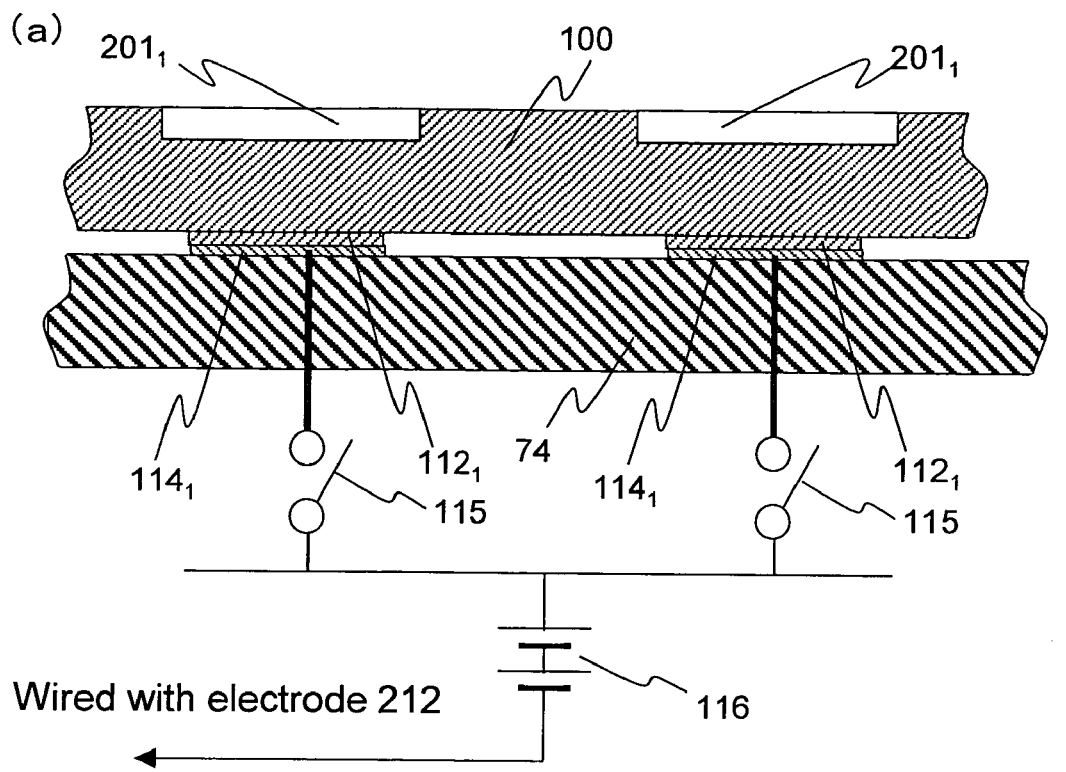
FIG. 30($a$) is a cross-sectional view showing the relation between an electrode portion for charging in the droplet holding area of a substrate 100 and a switchboard 74, and FIG. 30($b$) is a cross-sectional view showing the relation between an electrode portion for discharging in the droplet holding area of the substrate 100, and the switchboard 74.
Figure 30:
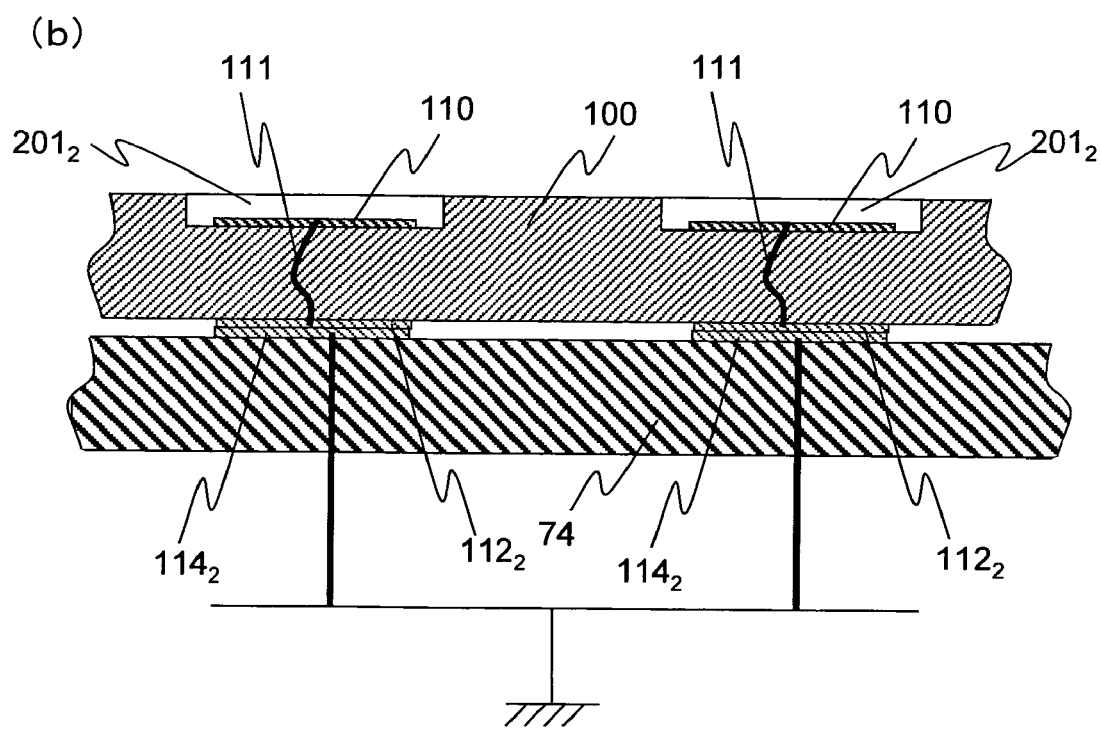

FIG. 30(*a*) is a cross-sectional view showing a relation between an electrode portion for charging in the droplet holding area of the substrate 100 and the switchboard 74; and FIG. 30(*b*) is a cross-sectional view showing the relation between an electrode portion for discharging in the droplet holding area of the substrate 100 and the switchboard 74. Namely, FIG. 30(a) is a cross-sectional view showing the electrode portion of the hydrophilic droplet holding areas a, b, . . . , p or the hydrophilic droplet holding areas 1, 2, . . . , 8, each area holding a droplet to be reacted; and FIG. 30(b) is a cross-sectional view showing the electrode portion of the hydrophilic droplet holding areas 9, 10, . . . , 16 each holding a droplet to induce reaction by colliding droplets or a resulted droplet after reaction and integration.

As shown in FIG. 30(a), an electrode $112_1$ is provided at an area on the back face of the substrate 100 corresponding to the droplet holding area $201_1$ with the droplet to be reacted. When the droplet is formed on the droplet holding area $201_1$, the droplet faces to the electrode $112_1$ provided in a position on the back face of the substrate 100 corresponding to the droplet. The switchboard 74 is provided on the back of the substrate 100. The switchboard 74 has a connecting electrode $114_1$ in a position corresponding to the electrode $112_1$ on the back face of the substrate 100. When the substrate 100 is mounted on the switchboard 74, the electrode $112_1$ and the connecting electrode $114_1$ corresponding thereto are connected each other. The connecting electrode $114_1$ is connected with a power supply 116 through the switch 115 capable of switching open or close selectively. As described above in FIGS. 29(a) and 29(b), when the switch 115 is closed and the voltage is applied to between the droplet on the droplet holding area $201_1$ and the electrode $112_1$, the droplet is charged. In the Figs. the switch 115 is described as an independent part, however, it can be acceptable that the switchboard 74 is a silicon substrate including semiconductor circuits and the on-off switching operation thereof is controlled with a personal computer 76 as described hereinafter.

As shown in FIG. 30(b) similarly, in the droplet holding area $201_2$ for holding the resultant droplet after two droplets are collided and reacted to each other to be integrated, electrodes 110 are provided to be contacted with the droplet. The electrodes 110 are connected with an electrode $112_2$ provided in a position corresponding to the back of the substrate 100 by a connecting line 111. A connecting electrode $114_2$ is provided in a position corresponding to an electrode $112_2$ of the switchboard 74, therefore, when the substrate 100 is mounted on the switchboard 74, the electrode $112_2$ and the connecting electrode $114_2$ corresponding thereto are connected to each other. The connecting electrode $114_2$ is grounded. As a result, when a droplet enters the droplet holding area 201, the droplet is discharged and kept stable in the area. Needless to say that capacitance of the switchboard 74 or circuits in the example should be minimized.

FIG. 28(b) shows a state in which a droplet is formed on the droplet holding areas a, b, . . . , p and the hydrophilic droplet holding areas 1, 2, . . . , 8 on the substrate 100. The droplet forming is carried out, for instance, with a method described below.

Figure 31:
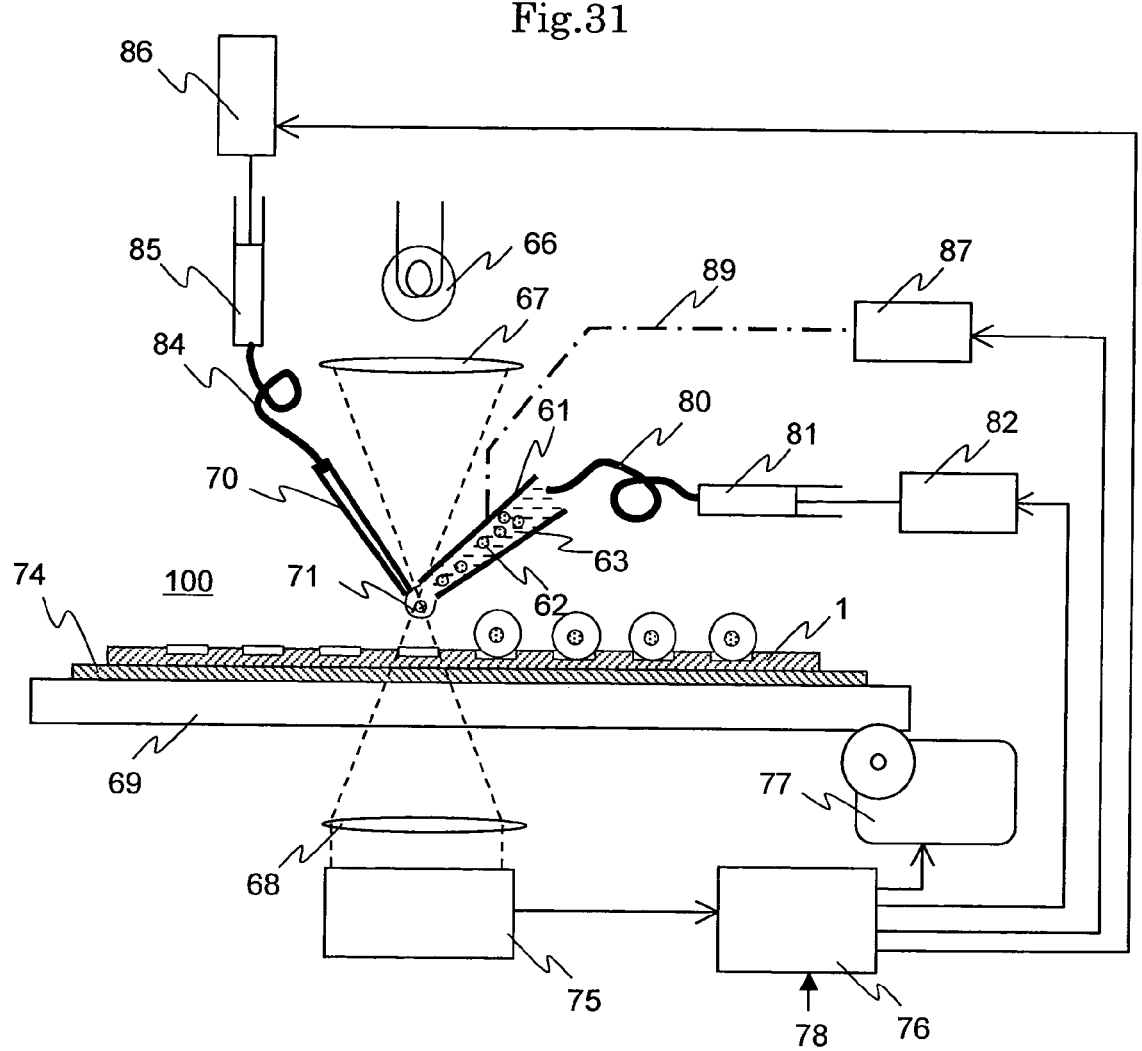
FIG. 31 is a view schematically showing the configuration in which a droplet including a cell 62 is formed at a tip of a pipet 61, and the cell is distributed, while optically monitoring, to the droplet holding area of the substrate 100.

FIG. 31 is a view schematically showing a configuration in which a droplet with a cell 62 is formed at a tip of a pipet 61, and the cell is distributed, while optically monitoring, to the droplet holding area of the substrate 100. A reference numeral 69 indicates a stage to be driven toward X or Y directions; and a reference numeral 77 indicates a driving device for driving the stage 69. The switchboard 74 is provided on an upper surface of the stage 69, and the substrate 100 is mounted on the upper surface thereof. On an upper part of the substrate 100, the pipet 61 is provided with a suspension 63 including the cell 62 prepared therein. When the cell to be put in the droplet is changed, the pipet 61 is exchanged for a new one in order to prevent contamination. At a root of the pipet 61, a syringe pump 81 is provided via a tube 80 with a driving device 82 attaching to the syringe pump 81. When the syringe pump is driven by the driving device 82, the suspension 63 in the pipet 61 is pushed out accompanying the cell 62.

While at the tip of pipet 61, a tip of a pipet 70 for supplying a culture solution to the pipet 61 is provided. At a root of the pipet 70, a syringe pump 85 is provided via a tube 84, with a driving device 86 attaching to the syringe pump 85. When the syringe pump 85 is driven by the driving device 86, the culture solution in the syringe pump 85 is pushed out from the pipet 70.

A vertical motion driving device 87 for a pipet is provided to place the droplet formed on the tip of the pipet 61 to the substrate. In this example, the vertical motion driving device 87 is connected with the pipet 61. When the vertical motion driving force 87 receives a signal for lowering the pipet 61 by a user, the pipet 61 moves downward and the droplet formed on the tip thereof is transferred to the droplet holding area on the substrate 100. When the vertical motion driving device 87 receives a signal for returning to the normal position by the user, the pipet returns to the normal position as described in the figure. Restoration of the pipet 61 to the position shown in the figure may be carried out time-sequentially after the downward operation using a personal computer 76. An alternate long and short dash line 89 denotes a correlation between the vertical motion driving unit 37 and the pipet 61.

Further, in order to monitor a size of the droplet formed on the tip of the pipet 61 and inside near the tip thereof, there is provided an optical system including a light source 66, a condenser lens 67, a collimating lens 68, and a monitor 75, the latter two provided on the bottom of the substrate 100 in a position opposing to the former two. The substrate 100, the switchboard 74, and the stage 69, therefore, are required to be optically transparent. In this example, reference numeral 76 indicates a personal computer, which transmits controlling signals according to prespecified program stored therein responding to an input signal via the monitor 75 by a user and necessary signals to the driving devices 77, 82, 86 and 87 responding to the operational input signals 78 given by the user while monitoring a display screen of the monitor 75. Though not shown in the figure, it is convenient to display the same screen on a monitor on the personal computer 76 as that being detected by the monitor 75, the monitor 75 can operate as a small CCD camera. Also, the operating input signal 78 is transmitted via an input device of the personal computer 76.

With regard to the size of the pipet 61, a transparent pipet is preferable having a tip thereof with the diameter of around 20 to 100 μm for a general animal cell and of around 5 μm for a microorganism such as bacteria, based on the same reason as described in Example 2 of the fifth embodiment.

A process is described as follows in which a cell 62 is distributed to the droplet holding area on the substrate 100. At first when the system starts up, the user positions the substrate 100 at a predefined starting-up position with reference to the marker 101 shown in FIG. 28. Secondly the user operates the stage 69 by the driving device 77 responding to an operating input signal 78 to adjust an initial distributing position for the cell 62 to a position corresponding to the tips of pipet 61 and 70. When the substrate 100 moves to the predefined position, an operation for discharging a cell suspension 63 within the pipet 61 accompanying the cell 62, while monitoring the outside of the pipet 61 at the tip thereof and the inside of the pipet 61 near the tip thereof with the optical system including the light source 66 and the monitor 75. Controls of sending the solution from the syringe pump 81 can be provided by capturing the output from the monitor 75, and operating the driving device 82 based on computed results of images by the personal computer 76.

The droplet is formed on the tip of the pipet 61 by operating the driving device 82 while monitoring the tip of the pipet 61 through the monitor 75 to operate the syringe pump, and discharging the suspension 63 including the cell 62 from the tip of the pipet 61. At that time, after the personal computer 76 recognizes through the monitor 75 that the predefined number of cells is inserted in the droplet, the personal computer 76 commands the driving device 82 to stop for stopping the syringe pump 81.

In order to make the description simple, the number of the cell 62 inserted in the droplet is assumed to be one in this example. However, the user can change the number thereof according to a user's purpose to, for instance, 10 or the like. In order to recognize the presence of the cell 62, the method of directly detecting the cell 62 present in the droplet 71 formed at the tip of the pipet 61 may be enough. However, more effective method is allowable such as, monitoring the cell 62 moving inside the pipet 61 with the monitor 75, computing the position of the cell 62 and a moving velocity thereof in the pipet 61 with the personal computer 76, and controlling the syringe pump 81 based on the calculated timing of discharging the cell 62 into the droplet 21 from the tip of the pipet 61. The latter recognizing method may bring advantages in a case where only one cell is inserted into a droplet when several cells are moving inside the pipet at a short interval.

In a case where the cell suspension 63 has a low cell density, a droplet can be formed of a prespecified size by forming the droplet 71 just before the cell comes out from the tip of the pipet 61, and stopping the droplet forming after a predefined period of time. When formation of the droplet is not desired, the suspension coming out from the tip of the pipet 61 may be blown out. Alternatively, the liquid may be discharged to a drain provided outside the substrate 1.

On the other hand, in a case where the cell suspension 63 has a high cell density, the amount of suspension discharged from the pipet 61 is not varied. Namely, as the cell 62 is discharged from the pipet 61 more frequently, if the time for discharging the suspension is fixed, the next cell may be disadvantageously inserted into the droplet 71 within such period of time. To deal with the case described above, the pipet 70 is used. The pipet 70 and the syringe pump 85 connected thereto are filled only with the culture solution or the cell diluted solution. Namely when the personal computer 76 recognizes via monitor 75 the cell 62 inserted in the droplet 71, the personal computer 76 commands the driving device 82 to stop for stopping the syringe pump 81, calculates the volume of the droplet 71 at that time based on a fed amount from the syringe pump 81 driven to form the droplet 71, and computes the difference between the calculated volume of the droplet 71 and the desired volume. According to the computed result, the personal computer 76 sends an operational signal to driving device 86, so that a culture solution or a cell diluted solution is added to the droplet 71 being produced at that time with a pipet 70, makes the syringe pump 85 drive, and adds the solution to the extent that the volume of droplet 71 becoming the predefined value using the pipet 70.

To prevent the cell in the pipet 70 from going backward, the pipet 70 is preferably of the size through which the cell can not pass, for instance 0.2 $\mu m \phi$, or has a filter structure with the size of 0.2 $\mu m$ provided at the tip thereof.

The droplet 71, which is formed with the method described above and contains a single cell, is contacted with a cell holding area on the substrate 100 placed on the stage 69 by the vertical motion driving device 87 of the pipet 61, and moves to the cell holding area on the substrate 100. When it is confirmed that the droplet 71 including the cell 62 moves to the cell holding area, namely the droplet holding area on the substrate 100, the user operates the stage driving device 77 by giving an operational signal 78, and moves the substrate 100 to the position where the tip of the pipet is set to a position for placing a next droplet. The personal computer 76 can automatically operate the process, if positional information concerning placement of the hydrophilic area 4 has been stored in the personal computer 76 in advance. In the new position, the next droplet is formed at the tip of the pipet 61 and is moved to the droplet holding area on the substrate 100 as described above. By repeating this process, the droplet is placed to the correct position in the droplet holding area on the substrate 100. In a case where the formed droplet does not include a cell or the like, the pipet 70 for adjusting the size of the droplet and the related device thereto is not necessary.

FIG. 28(c) shows conceptually a process for integrating to react any of droplets selected from a droplet formed in the droplet holding areas a, b, . . . , p and the hydrophilic droplet holding areas 1, 2, . . . , 8 on the substrate 100. Also FIG. 28(c) shows a state where the droplet 102 is transferred from the droplet holding area 3 to the droplet holding area 11 and discharged, the droplet 103 charged with negative electricity is transferred from the droplet holding area c to a point where two droplet transfer lines crossing each other, one line extending from the droplet holding area e and the other extending from the droplet holding area 3, and the droplet 105 charged with negative electricity is transferred from the droplet holding area 1 along the droplet transfer line extending from the droplet holding area 1. Of those droplets, the droplets charged with negative electricity are transferred by a manipulation rod 107. Because the manipulation rod 107 is charged with electricity in the same polarity as droplets to be transferred, the droplets can be transferred just by making the manipulation rod 107 close to the droplets from the opposite side to the direction the droplets transferred thereto, without touching the droplets. The other droplets do not move because they are not charged, even being adjacent to each other. In the figures, the droplets 103 and 105 are transferred at the same time, though in the actual operation, the droplet is moved one by one. The detailed process for transferring a droplet by the manipulation rod is described below.

Figure 32:
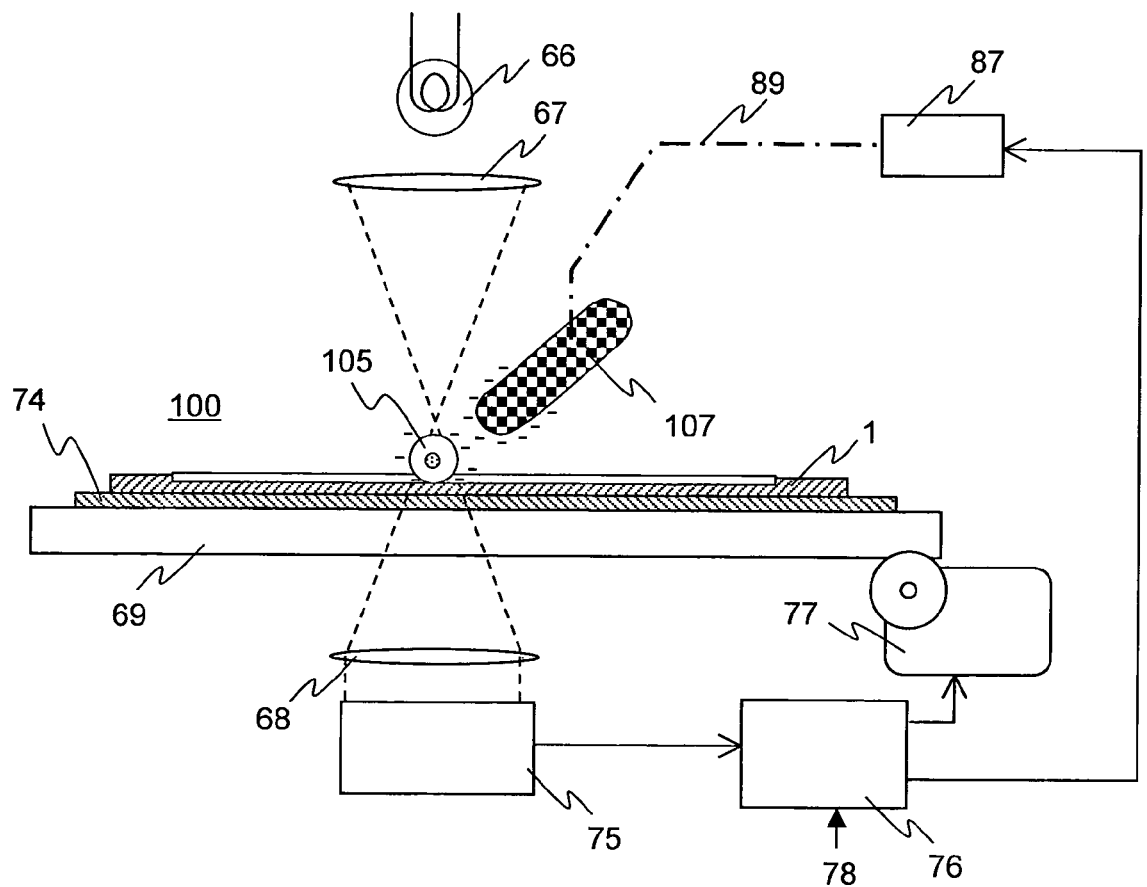
FIG. 32 is a view schematically showing the state in which a droplet 105 is being transferred with a manipulation rod 107 on a droplet transfer line shown in FIG. 28.

FIG. 32 is a view schematically showing a state where the droplet 105 is transferred with the manipulation rod 107 on one of the droplet transfer lines shown in FIG. 28. In this case, the pipet 61 is replaced by the insulating manipulation rod 107 charged with electricity, as similar to the case of forming a droplet described above in FIG. 31, the manipulation rod 107 is moved upward or downward under the control by the vertical motion driving device 87 with an operational signal 78 while monitoring the tip of the manipulation rod 107 and the droplet 105 via monitor 75, and the direction to which the stage 69 moves is also controlled, paying attention not to contacting the manipulation rod 107 with the droplet 105. With this case described above, the vertical motion driving device 87 simply controls upward or downward operations, however, as is obvious with reference to FIG. 28(c), the driving device preferably deals with operations for the other directions because the droplet to be moved may need to be turned. Namely, desirable positioning and formation should be made for the driving device 87, so that a droplet receives a repulsion force from backside at any time.

While the droplet 105 is transferred between the hydrophilic droplet holding areas after pushed away by the repulsion force generated between the manipulation rod 107 and the droplet 105, the droplet 105 is discharged due to contacting the electrode to be grounded, and stops automatically in a position with lower energy. The driving device 87 lifts up the manipulation rod 107 and prevents it from contacting with the droplet 105.

Figure 33:
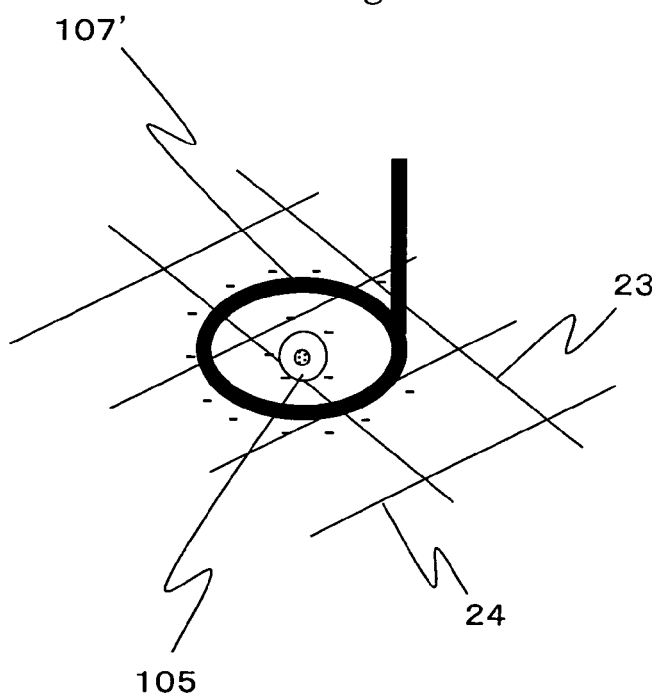
FIG. 33 is another view schematically showing the state in which a droplet 105 is being transferred with a manipulation rod 107 on a droplet transfer line shown in FIG. 28.

The droplet manipulation with the manipulation rod 107 in shape of a bar is described in FIG. 32, though it is more practical to use a manipulation rod 107' with a shape of ring in FIG. 33. For instance in a case where the droplet 105 charged with negative electricity is transferred along the hydrophilic lines 23 and 24, the ring of the manipulation rod charged with negative electricity is pulled down from above the droplet so as to make the droplet placed inside the ring. As both of the droplet 105 and the ring of manipulation rod 107' are charged with negative electricity, the droplet keeps within around the center of the ring stably. Therefore when the ring is transferred, the droplet is also transferred, keeping within around the center thereof. With the manipulation rod described in the FIG. 32, the droplet unavoidably swings side to side during its transfer because the rod pushes the droplet from the back thereof. As a result when the speed of transfer is too high, the droplet to be transferred may deviate from the hydrophilic line. Also, the droplet usually stops in a stable position associating with the substrate, however, in a case where the speed is too high, the droplet may not stop in the position by inertial force. With the manipulation rod with a shape of a ring, on the other hand, the droplet is transferred with support from all horizontal directions, therefore the accidents such as deviating from the hydrophilic line or passing over the stop position due to the inertial force may decrease, which enables more reliable droplet transfer.

In Example 1, to confirm the droplet position on the substrate, the optical system is used for observing the substrate with a configuration including the light source 66, the condenser lens 67, the collimating lens 68, and the monitor 75, the latter two placed at the bottom of the substrate 100 opposite to the former two. Therefore the substrate 100 is required to be made of a transparent material. A thin-layer silicon substrate is also applicable, in this case the infrared rays, which can be absorbed into water, are used for an observation so as to confirm the droplet position easily. Of course, the optical system such as a stereo microscope from the top surface of the substrate can also be used, which allows less limited substrate compositions. The optical system is used similarly in Examples 2 and 3 described below.

Various reactions can be generated by similarly transferring and colliding another droplet to the droplet being stopped. Or other usages are possible like preparing a cell store with droplets each including a cell arranging in a shape of array and a droplet array including various chemical materials to examine an effect of a chemical material against a cell by transferring a cell and a reaction liquid assorted from any of cells and droplets to a reaction section.

EXAMPLE 2

Another method of charging a droplet is described in Example 2. As in the method used in Example 2, a charged particle is launched into a droplet, those equipments used in Example 1 for charging are not required such as the electrode 100 and the related equipments like the connecting line, the electrode, the switchboard or the power supply.

Figure 34:
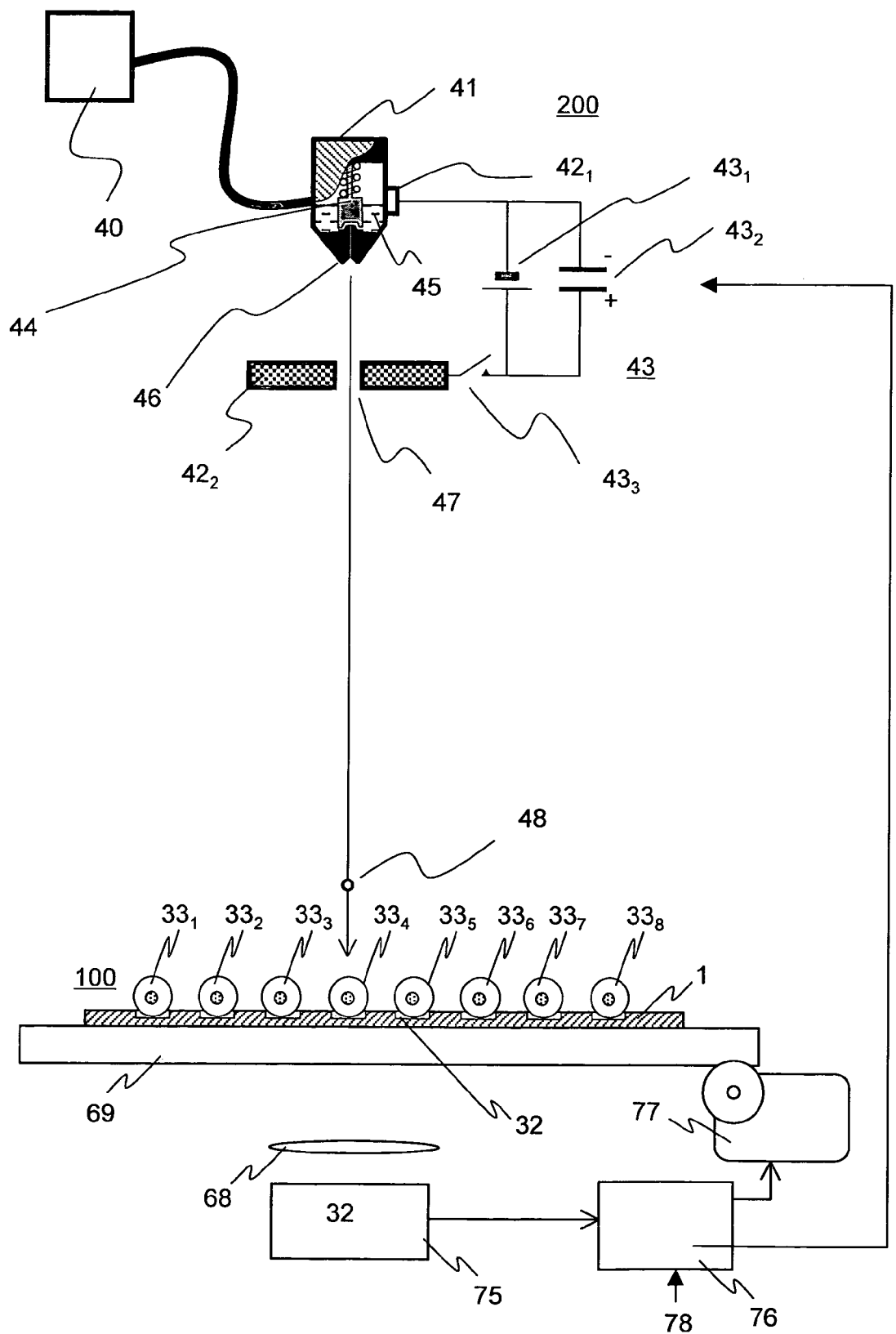
FIG. 34 is a view illustrating configuration and manipulation method for giving electric charge to a droplet.

FIG. 34 is a view showing a configuration of and manipulating method for making a droplet formed similarly to the method described in FIG. 31 in the droplet holding area on the substrate 100 shown in FIG. 28 charged with electricity. In this state, droplets $33_1$, $33_2$, ... $33_8$ are still on a hydrophilic droplet holding area 32 with no electricity. The droplet $33_4$, which is selected arbitrary from the droplets, is charged with electricity with a charged particle launching device 200. The charged particle launching device 200 includes a gas compressor 40, a solution holding container 41, electrodes $42_1$ and $42_2$, power supply section 43, and a solenoid valve 44. While the solution holding container with a conductive outlet 46 at an edge thereof is connected with the power supply 43 by the electrode $42_1$, the solution holding container and the entire circuit keep an electrically floating state and are isolated from grounding. Inside of the solution holding container 41 is partially shown in the figure. The power supply includes a power supply $43_1$, a condenser $43_2$, a blockage section $43_3$, and other circuits. As the charged particle launching device 200 is provided on an upper stage of the droplet forming measure, the configuration shown in FIG. 34 is realized after forming a droplet and putting the droplet forming measure aside. Though only the bottom parts below the substrate of the optical system in the droplet forming measure is used in this example, when the upper parts have a configuration which is not obstructive to the charged particle launching device 200, the optical system can be used in both.

The solenoid valve 44 and the blockage section $43_3$ are synchronously carried out sequence operations by an instruction of the personal computer 76 described in FIG. 31. At first, the condenser $43_2$ is charged with static electricity from the power supply $43_1$ by an instruction of the personal computer 76. Because the blockage section $43_3$ is open, an electric field is not loaded on between the electrode $42_1$ and the electrode $42_2$. Though the solution holding container 41 is applied pressure at all times by the gas compressor 40, as the outlet 46 is closed by the solenoid valve 44, a solution 48 does not come out in this state. When the solenoid valve 44 is opened in an instant by an instruction of the personal computer 76, the solution comes out from the outlet 46 because the solution holding container 41 is applied pressure. The blockage section $43_3$ is closed by an instruction of the personal computer 76, just before the droplet 45 leaves the outlet 46. Then the outlet 46 is charged with negative electricity and the electrode $42_2$ is charged with positive electricity. Therefore the droplet 48 leaving the outlet 46 is charged with negative electricity. As the positive electrode $42_2$ has a slit 47 opened thereto, the charged droplet 48 gets together with the droplet $33_4$ on the substrate 100 passing through the slit 47. Therefore the droplet $33_4$ is also charged with negative electricity. After the droplet is charged, the stage moves while monitoring though the monitor 75 and a next droplet to be charged is charged.

As the series of the droplets 33 is 0.1 to 1 μl in volume, the charged droplet 48 to be put in the droplet 33 should be significantly smaller than the droplet 33. The conventional technique can be used to form an extremely small droplet. The method with the solenoid valve 44 can form a droplet in size of nanoliter level, which has already been commercialized as a DNA micro-array forming device. Such technique can be used directly. Or another technique can also be used like a technique for forming a droplet with an oscillator like piezo instead of a solenoid valve used in an existing cell sorter.

EXAMPLE 3

The charged droplet 48 is put in a droplet directly under the charged particle launching device 200 in the example 2, so that, the stage should shift (or the charged particle launching device 200 should shift) to select the targeted droplet 33 to be put in the charged particle. While in the example 3, using a fact that the particle to be put in the droplet is charged, a method for controlling flight of the charged droplet is described.

Figure 35:
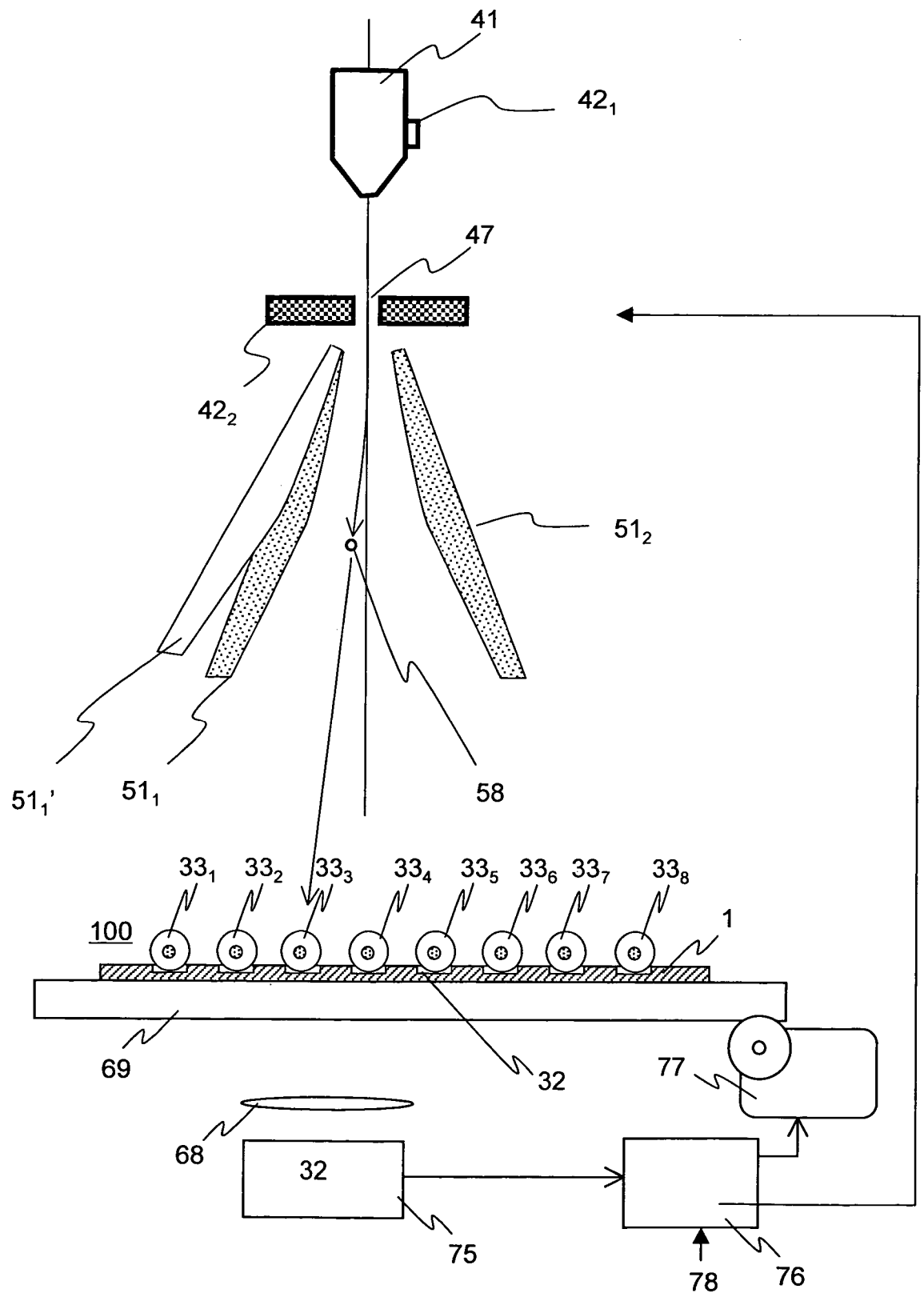
FIG. 35 is a view for illustrating configuration and a manipulation method for controlling flight of a charged droplet 58 to give an electric charge to a droplet.

FIG. 35 is a view for illustrating configuration and a manipulation method for controlling flight of a charged droplet 58 to give an electric charge to a droplet formed by a method similar to that illustrated in FIG. 31, in a droplet holding area of the substrate 100 shown in FIG. 28. The droplets $33_1, 33_2, \ldots, 33_8$ in which the charged droplet 58 is put are placed on the hydrophilic droplet holding area 32 in a state of rest. Then the charged droplet 58 is put out in a state where the electric field is loaded on between the electrodes $42_1$ and $42_2$, and the electric field is also loaded on a plate spanned between biased electrodes $51_1$ and $51_2$. In a case, for instance, where the droplet 58 is charged with negative electricity, the electric field is loaded to make a state in which the bias electrode $51_1$ become positive. By controlling the size of electric field loaded on the plate between the biased electrodes $51_1$ and $51_2$ depending on the droplet position at which the charged droplet is launched, a droplet to be launched into the charged droplet 58 therein can be selected arbitrary. Another method is allowed such as controlling an angle, for instance changing the biased electrode $51_1$ to $51_1'$ in a state where the electric field is loaded keeping a voltage of 3000. In this method, when the biased electrode $51_1$ is at $51_1$, the charged droplet is applied the stronger electric field, so that the droplet 58 is launched into the droplet $33_1$ placed at outside. On the other hand when the biased electrode $51_1$ is at $51_1'$, the charged droplet is applied the weaker electric field, so that the droplet 58 is put in the droplet $33_2$. Similarly, by changing the position of electrode $51_2$, it can be controlled which droplets $33_4$ or $33_5$ the charged droplet 58 should be put in. The user controls via the personal computer 76 the voltage applied to the electrode 51, the angle of the electrode 51, the timing of releasing the charged particle, or the like. (D) The method for and device of culturing separated cell one by one in a long time are described below.

[VII] Seventh Embodiment

A seventh embodiment of the present invention provides a method of and a reliable system for conducting various reactions in the droplet(s) placed on a substrate. This embodiment enables to make a reaction more reproducible by keeping the volume or size of a droplet at constant values on the substrate. Further in this embodiment, a series of chemical reactions and cell culture can be carried out without unnecessary delays by freely changing the size of a droplet on a substrate in the substantially non-contact state to control concentrations of a matrix or reaction products in the droplet.

EXAMPLE 1

Detailed descriptions are provided below for a method of controlling the size of a droplet when an operation takes so long a time that a droplet on a substrate may be affected by vaporization thereof and some specific operations are required to prevent this phenomenon.

The basic idea of the seventh embodiment is to realize a balance between vaporization and agglutination by making use of the that fluctuation in the size of a droplet occurs due to the difference between a vaporization rate of the solvent from the droplet in a small area on a phase boundary between the droplet and a gas phase and an agglutination rage from the gas phase to the droplet in the same area. Generally, a droplet grows when the vapor pressure of water as a solvent increases, and the size of a droplet becomes smaller when the vapor pressure thereof decreases. Because of this, the size of a droplet can be controlled, for instance, by increasing the humidity or controlling the temperature according to the saturation vapor pressure curve of the solvent.

Figure 36:
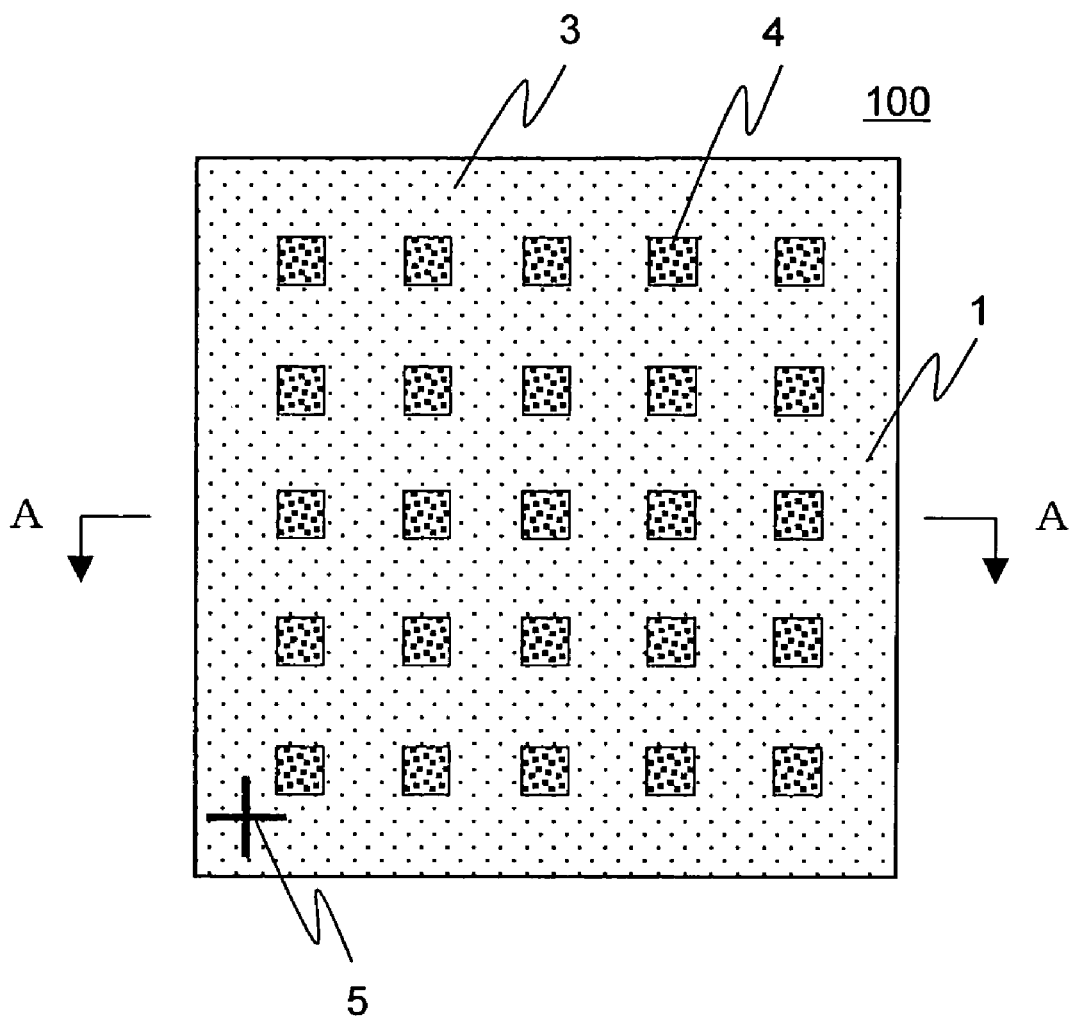
FIG. 36($a$) is a plan view showing the cell culture chip 100 advantageously applicable in Example 1 of a seventh embodiment of the present invention, and FIG. 36($b$) is a cross-sectional view showing the cell culture chip 100 taken along the line A-A in the plan view and viewed in the direction indicated by the arrow.
Figure 36:
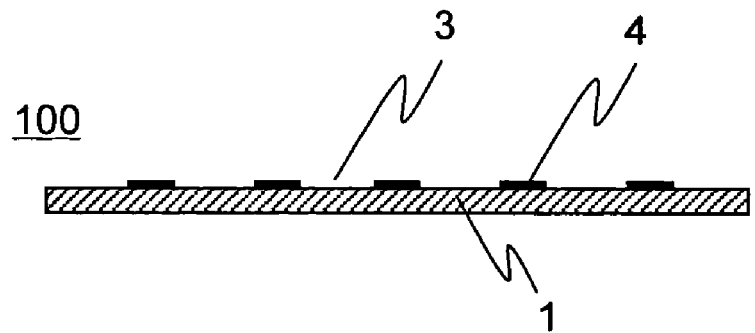

FIG. 36A is a plan view illustrating a cell culture chip 100 advantageously applicable to the embodiment 1, while FIG. 36B is a cross-sectional view showing the cell culture chip shown in FIG. 36A taken at the line A-A and viewed in the direction indicated by the arrow. The reference numeral 1 indicates a silicon substrate, for instance, with the thickness of 1 mm and the size of 20 mm×20 mm. The region of the top surface of the silicon substrate 1 is a hydrophobic region 3 with some hydrophilic regions 4 regularly provided at intervals therein. The size of the hydrophilic region 4 may be approximately 400 μm×400 μm depending on the size of cells or the number of the cells placed on the region. The interval between the hydrophilic regions should be wide enough so that droplets including cells are not contacted and mixed with other cells on neighboring hydrophilic regions, and is preferably approximately 2000 μm when convenience in operations dealing with the droplet(s) is taken into consideration. When the diameter of the droplet is less than 100 μm, the interval between two hydrophilic regions 4 may be approximately 500 μm. In general, the size of a droplet, the size of the hydrophilic region, and an interval between two hydrophilic regions should be determined in accordance with the intended use thereof. FIG. 36 shows an example where hydrophilic regions are provided at a regular interval. But, in some cases when, for instance, a number of droplets are need to be mixed and reacted on a substrate as described below, it may be more effective to provide hydrophilic regions with various intervals therebetween. Basically, positions of the hydrophilic regions on a surface of the substrate should be decided assuming the case where the interval between the droplets is narrowest and also by providing the interval which is two times or larger than the size of a droplet. The reference numeral 5 denotes an alignment marker, and the markers 5 are formed on the entire surface of the silicon substrate 1.

For preparing hydrophilic regions and hydrophobic regions, for instance, the top surface of the hydrophilic silicon substrate 1 is oxidized to cover the surface with a hydrophilic $SiO_2$ film. Then portions of the $SiO_2$ film to be changed to hydrophobic regions are melted and removed by using hydrofluoric Acid. Alternatively, in a case where the $SiO_2$ film is previously formed to provide a hydrophilic surface on the surface of the material of the substrate 1, hydrophobic regions can be formed by placing hydrophobic material like fluorocarbon resin or silicon resin thereon. In this case, the height of the hydrophilic region placed on the hydrophobic region is higher than that of the hydrophobic region by the thickness of the hydrophobic material.

Another method of forming hydrophilic regions on a surface of the substrate 1 is to make a fractal structure on the surface of the substrate 1 by mixing powders of fluorinated carbon having super water-shedding property (fluoride pitch) during metal plating to form various Figures of fluoride pitch on the surface to make super-hydrophobic surface having 145-170 degrees of contact angle. In this case, it is also possible by treating only necessary portions on hydrophilic surface so that it will have the water-repelling property. Also the other technique generally called the super-hydrophilic treatment may be used for portions on which water drops are to be formed. The super-hydrophilic treatment is performed by forming a thin (10-20 nm) coating film with $SiO_2$ component on the surface of $TiO_2$ multilayered film. For using the film of titanium oxide ($TiO_2$), it is necessary to irradiate the substrate 1 with ultraviolet rays in advance and to introduce a hydroxyl group into the surface of the $TiO_2$. By this previous treatment, $TiO_2$ on the surface is converted to TiOH with the super-hydrophilic property. With this method, a super-hydrophilic region with less than 10 degrees of contact angle can be retained for several weeks.

Figure 37:
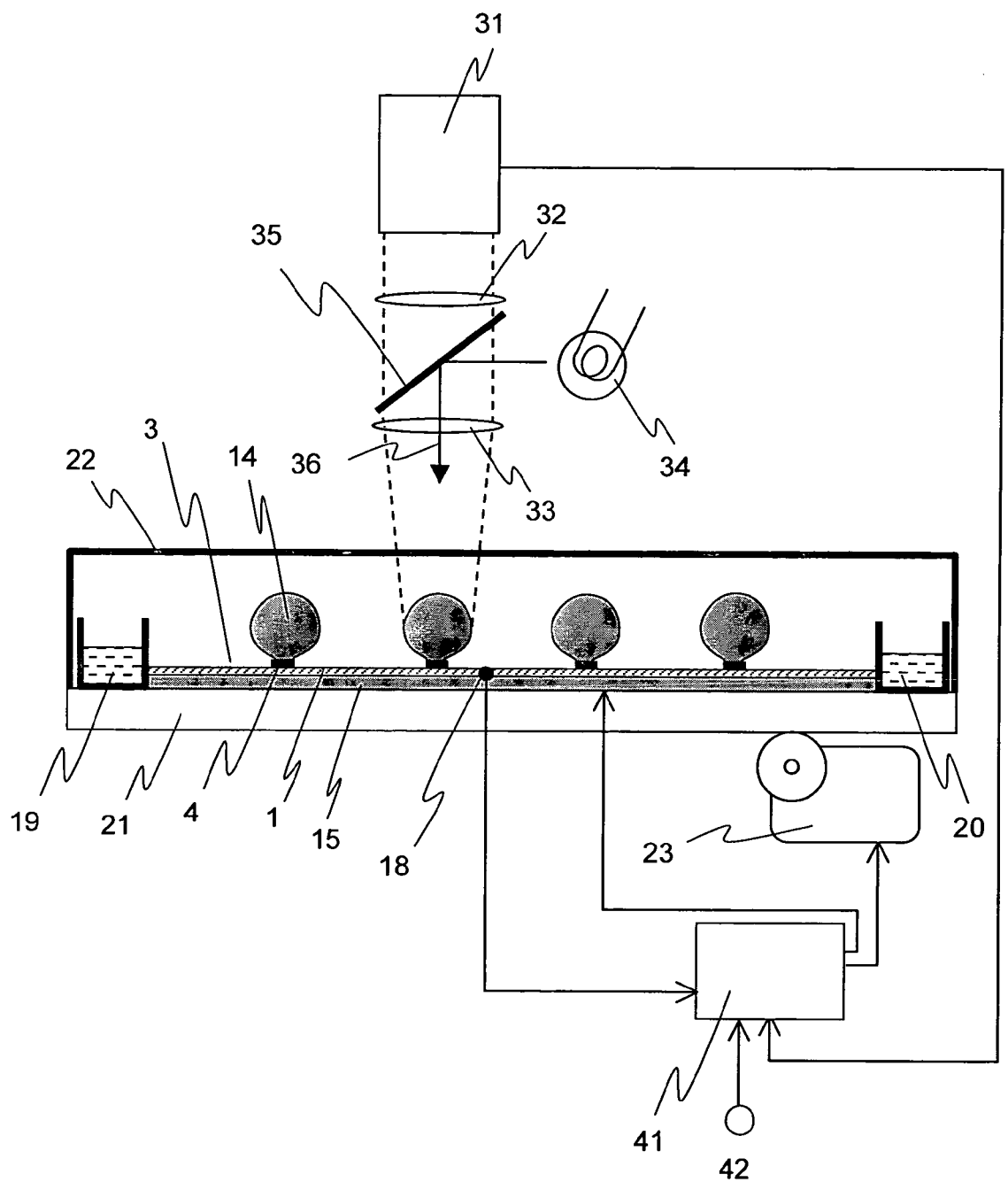
FIG. 37 is a schematic diagram showing an outline of a device for controlling size of a droplet in Example 1.

FIG. 37 is a schematic diagram view illustrating the outline of a device capable of controlling the size of droplet in Example 1 of the seventh embodiment. The substrate 1 in FIG. 37 is prepared by oxidizing the upper surface of the silicon substrate 1 with the above-mentioned hydrophilic property to form a hydrophilic $SiO_2$ thin film over the whole surface, and then by melting and removing the $SiO_2$ thin film from the portions, where hydrophobic regions are to be formed, with a fluorinated acid. The hydrophilic region 4 on the substrate 1 is higher than the surface of the substrate 1. The peripheral area around the hydrophilic region 4 is the hydrophobic region 3. A droplet 14 is placed on the hydrophilic region 4. The reference numeral 15 denotes a temperature regulator provided on the bottom surface of the substrate 1 to control the temperature of the substrate 1. The reference numeral 18 denotes a temperature sensor installed on the contact surface between the substrate 1 and the temperature regulator 15. The reference numerals 19 and 20 denote water tanks for hydration, which are provided on both sides of the substrate 1. The reference numeral 21 denotes a stage on which the temperature regulator 15 and water tanks 19 and 20 are placed. On the stage 21, there is an upper cover 22 in the shape of a reversed transparent vessel. The temperature regulator 15, substrate 1, water tanks 19, 20 and droplet 14 on the substrate 1 are all covered with this upper cover 22. The space defined by the upper cover 22 and the stage 21 is not sealed off, but is closed. Because of this feature, the inside is filled with saturated steam. The reference numeral 23 denotes a drive unit capable of receiving a signal from a personal computer 41 and moving the stage 21 in both X and Y directions.

As the above temperature regulator 15, for instance, a Peltier device may be used. With the Peltier device, it is possible to control either heating or cooling according to the direction of a current flowing through the device, and, in addition, the heating or cooling rate can be controlled by amplitude of the current flowing through the device.

The reference numeral 31 denotes a camera, for instance, a CCD camera, for picking images of the droplet 14 via lenses 32, 33. In addition, a light source 34 is used to illuminate in the direction indicated by the arrow 36 via a half mirror 35 placed between the lenses 32 and 33. It is also allowable to illuminate the droplet 14 directly from above the upper cover 22 without using the half mirror 35.

The reference numeral 41 denotes the so-called personal computer capable of storing therein a necessary program and also receiving a temperature signal from the temperature sensor 18 on the substrate 1 and information concerning the size of the droplet 14 from the camera 31. In addition, the personal computer receives input operation-related signal inputted by a user. When the personal computer 41 recognizes based on the information described above that the size of the droplet 14 is not appropriate, or when the user monitors the display device (not shown) and then sends the operation signal 42 to adjust the size of the droplet 14, the personal computer provides controls so that an appropriate current will flow through the Peltier device constituting the temperature regulator 15. When the user changes the droplet 14 to be monitored by the camera 31 to the other droplet, the user can send the operation-related signal 42 to the personal computer 41, and then the personal computer 41 sends a drive signal to the drive unit 23 to move the stage 21.

Descriptions are provide below for outline of the operations of the control device for controlling the droplet size according to the example 1 in FIG. 37. The personal computer 41 analyzes the image data sent from the camera 31, and then calculates successively the size of droplet 4 on the substrate 1. When it is observed that the droplet is growing, the personal computer 41 gives an instruction so that the temperature in the temperature regulator 15 will rise, and when it is observed that the droplet is shrinking, the personal computer gives an instruction so that the temperature in the temperature regulator 41 will decline.

Temperature of the substrate 1 can be monitored with a temperature sensor 18, and the temperature data is sent to the personal computer 41 together the size data for the droplet 14 from the camera 31 to be used for the temperature control. In a case where there are provided a plurality of hydrophilic regions 4 and also there are a plurality of droplets 14, sometimes the camera 31 may not be capable to simultaneously monitor all of the droplets with a scope thereof. In this case, only the representative droplets 4 should be monitored. If a more accurate result is necessary, the stage 21 on which the substrate 1 is placed may be moved with the drive unit 23 to measure the sizes of all the droplets to obtain the average, minimum, and maximum diameters of the droplets for controlling the temperature. In this step, if it is expected that droplets having the maximum or minimum diameters are not covered within the control range, the temperature may be controlled so that the droplets having the maximum or minimum diameter are included within the control range even if the droplets having the other diameter go out of the control range.

Since fluctuation in the temperature of a droplet may affect the chemical reaction rate on the droplet, it is preferable that the temperature fluctuation in the droplets should be controlled within about $\pm 3°$ C. at the maximum. Even when the temperature fluctuation is controlled within this range, the chemical reaction rate may fluctuate by tens percent, but even in this case, a better result can be obtained as compared to a case where a diameter of a droplet changes while cell culture is performed in the droplet and a concentration of salt changes by tens percent. A temperature change rate can easily and freely be controlled in either heating or cooling by using the Peltier device as the temperature regulator 15. But since the Peltier device is not transparent, it is impossible to build up an optical system allowing for transmission of light.

An example of the practical data is described below. For instance, the space enclosed by the vessel 22 is filled with steam and the temperature is kept at 25° C. A sufficient quantity of water is stored in the water tanks 19,20 for hydration. Assuming that the capacity enclosed with the vessel 22 is 100 mm×100 mm×50 mm (height), the volume is $5 \times 10^{-4}$ $m^3$. Therefore, the saturated steam pressure and the volume of saturated steam are 31.7 hPa and 23.1 $g/m^3$ respectively. Therefore, 11.6 mg of water exists as the steam in the space enclosed by the vessel 22. When the temperature of the space enclosed by the vessel 22 is 23° C., the values of saturated steam pressure and the volume of saturated steam are 28.1 hPa and 20.6 $g/m^3$ respectively. Therefore, When the temperature in the space enclosed by the vessel lowers from 25° C. to 23° C. within a short period of time, 1.25 mg of water is vaporized due to the difference in the saturated steam pressure between 25° C. and 23° C. (because $(23.1-20.6)$ $g/m^3 \times 5 \times 10^{-4}$ $m=1.25$ mg). As a result, the size of the droplets will shrink.

As an example, the temperature of the substrate 1 is set to 25° C., and four pieces of 1 µl droplets 14 are placed on the substrate. In this situation, it is assumed that also the temperature of the space enclosed by the vessel 22 is at 25° C. Also it is assumed that the droplet is in the stable condition under the saturated steam pressure at 25 degrees Celsius and also the size of the droplet 14 is stable. Next the temperature of the substrate 1 is changed to 23° C. The temperature of the droplet 14 changes rapidly because the droplet 14 contacts the substrate 1, but there is no substantial change in the temperature of the space enclosed by the vessel 22 because the thermal conductivity of the air is substantially low. As the result, because of the temperature change of the droplet 14 due to the temperature change of the substrate 1, the diameter of the droplet 14 changes from 1.24 mm to 1.31 mm within a few minutes (it becomes larger because the surrounding water is agglutinated into the droplet 14 as the temperature declines) and then the equilibrium is achieved.

In other words, when the temperature of the substrate 1 is controlled, the temperatures of the droplet 14 contacting thereto can also be changed within a short period of time, and therefore, also the size of the droplet 14 can be changed flexibly. On the other hand, as described above, if the temperatures in the space enclosed by the vessel 22 is changed rapidly, the size of the droplet 14 will also be changed due to the subsequent change of the saturated steam pressure. But the temperature of the space enclosed by the vessel 22 is not changed rapidly unless an external large influence is loaded to the space. On the contrary, when the temperature in the space enclosed by the vessel 22 gradually changes according to changes in the external conditions and any change in the size of the droplet 14 is observed, it is possible to suppress the changing rate of the size of the droplet 14 by controlling the temperature of the substrate 1 so that the temperature of the droplet 14 changes in the direction reverse to the direction of size change of the droplet 14.

Therefore, to keep the size of a droplet constant, when the growing trend of the droplet 14 in the size is detected with a camera 31 by monitoring the diameter of the droplet 14, the temperature of the board is raised by 1 or 2° C. so as to vaporize the water so that the droplet 14 will shrink. This means that, by raising the temperature of the space enclosed by the vessel 22, it is possible to cancel the growing trend of the droplet in the size so that the size of the droplet should not exceed the predetermined size. On the contrary, if the shrinking trend of the droplet in the size is observed, the temperature of the substrate is lowered so as to help the growth of the droplet. That is to say, the data relevant to the droplet size can be used as the feedback data to control the temperature of the substrate 1 so as to keep the diameter of the droplet 14 substantially constant.

In a humidity control device for a microscope, generally temperature of the atmosphere in which the test sample is placed is controlled. But in this case, the response of the response to control of the atmospheric temperature is rather low. On the contrary, in the system in which an extremely small quantity of droplets is used and temperature of the droplets is directly controlled as described above, real time control of the droplet size is possible.

EXAMPLE 2

Figure 38:
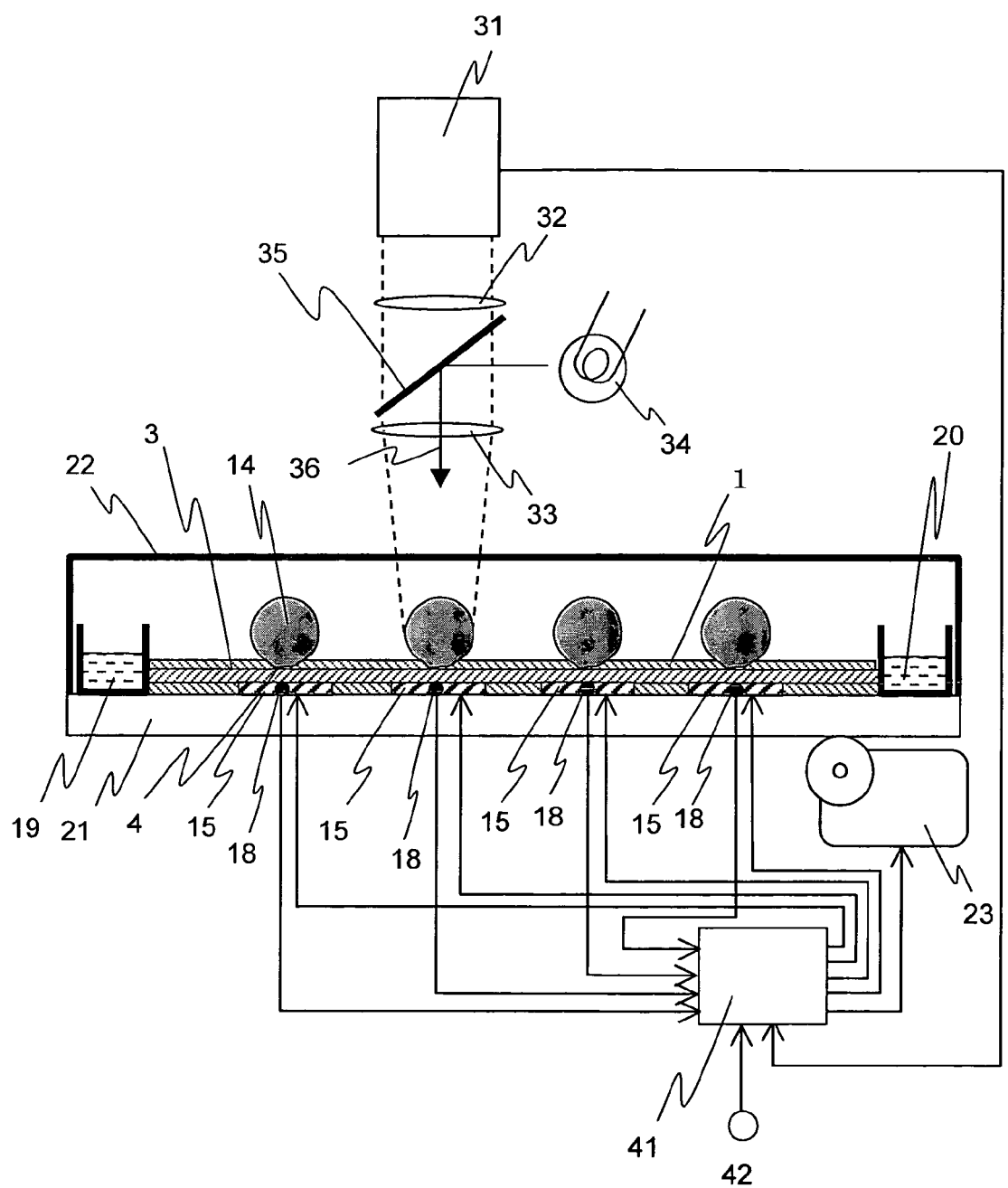
FIG. 38 is a schematic diagram showing Example 2 in which size of each discrete droplet among a plurality of droplets on a substrate 1 is controlled.

FIG. 38 is a schematic diagram illustrating Example 2 in which the size of one droplet among a plurality of droplets on the substrate 1 is controlled discretely. The configuration employed in Example 2 is the same as that employed in Example 1 described above excluding the points that independent temperature regulators 15 are placed on each hydrophilic regions on the substrate 1 respectively and also independent temperature sensors 18 are placed at the positions where droplets 14 are placed, and that temperature control signals are sent from the personal computer 41 to each temperature regulator respectively. In FIG. 38, however, the surface of the hydrophilic regions 4 is lower than the surface of the substrate 1. All the surrounding are of the hydrophilic region 4 are the hydrophobic region 3. An appropriate spacer having a low thermal conductance is provided between adjoining temperature regulators 15.

In Example 2, the size of each droplet is always monitored concurrently by a camera 7. The personal computer 41 then calculates the diameter of each droplet from the images sent from the camera 7, and the data is used to give feedback data to control each temperature regulator 15 for the relevant droplet respectively. With this method, it is possible to limit a fluctuation range of the diameter of each droplet within 10 percents.

EXAMPLE 3

Figure 39:
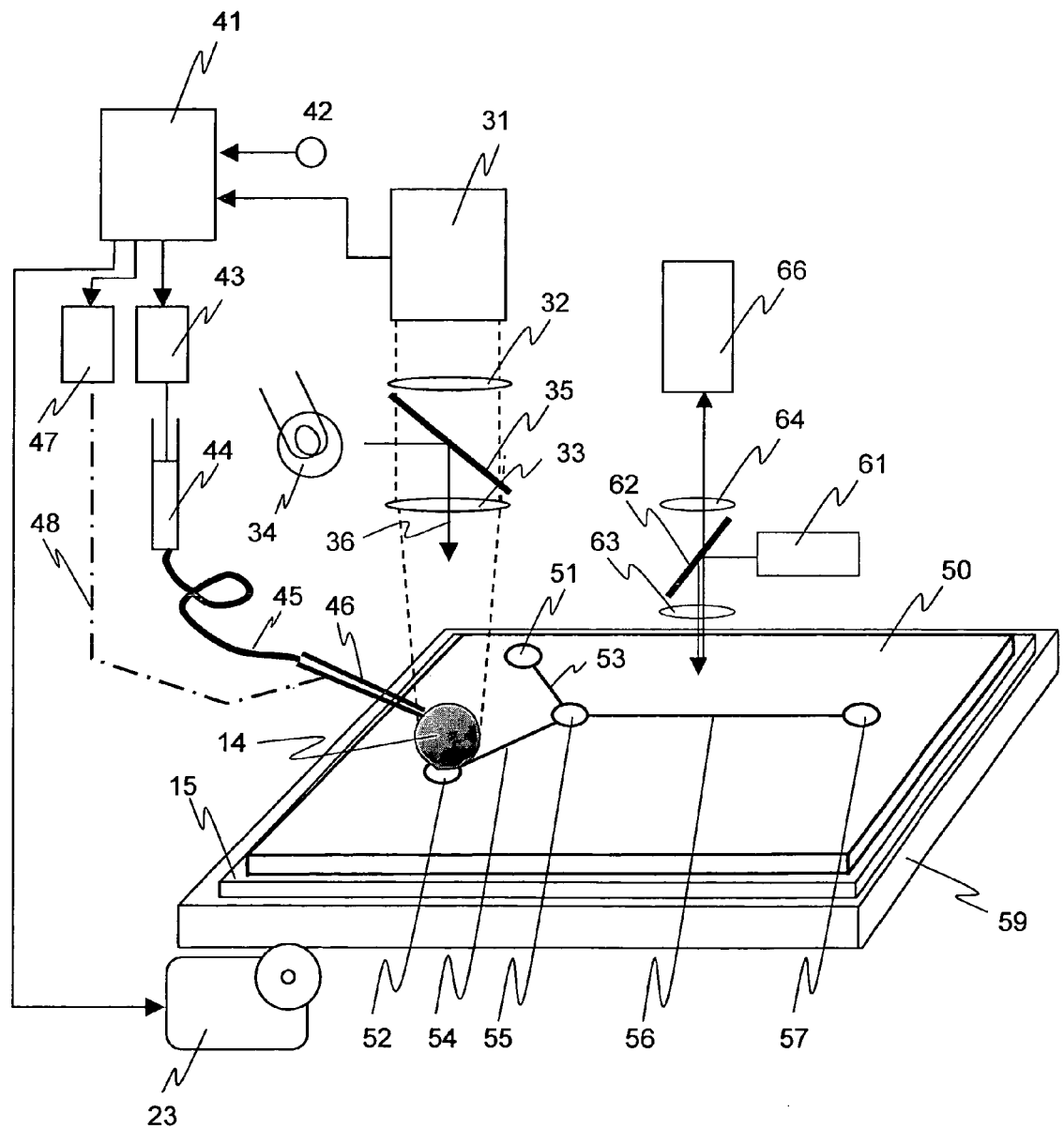
FIG. 39 is a schematic diagram showing Example 3 in which operations of forming two types of droplets on a substrate 50, mixing the droplets to each other, and transferring the mixture droplet to a prespecified position can be easily performed.

FIG. 39 is a schematic diagram illustrating Example 3 in which such operations as, for instance, forming two types of droplets, mixing them, and then transporting the mixture droplet to a predefined position can easily be performed.

In FIG. 39, the entire surface of a substrate 50 has the hydrophobic property. On this surface, two hydrophilic regions 51,52 for forming two types of droplets, one hydrophilic region 55 for mixing the two types of droplets, one hydrophilic region 57 for holding the mixture droplet in a position after the droplet is moved are provided, and further the hydrophilic lines 53, 54, 56 connecting those hydrophilic regions to each other are provided. The substrate 50 has a super water-shedding property with the size of 20 mm×20 mm. The sizes of the hydrophilic regions 51,52,55,57 are decided according to the size of a droplet formed in each of the regions and are about 200 μm×200 μm square. The width of the hydrophilic lines 53,54, 56 is 2 μm. The substrate 50 is provided on the temperature regulator 15 placed on the stage 59. The stage 59 is driven in both X-axial and Y-axial directions with a drive unit 23 operating according to a drive signal from a personal computer 41. The temperature regulator 15 is provided to control the temperature of the substrate 50 like in example 1 and 2. In this example as well, the temperature sensor is necessary to monitor the temperature of the substrate 50, and the sensor is placed on the contact surface between the substrate 50 and the temperature regulator 15, but is not shown in the figure for simplification. Also the signal transactions with personal computer 41 are not shown.

The reference numeral 31 denotes a camera such as, for instance, a CCD camera, for taking pictures of the droplet 14 formed on the hydrophilic regions 51, 52 via lenses 32, 33. In this case, a light source 34 is used to illuminate in the direction indicated by the arrow 36 through a half mirror 35 placed between the lenses 32 and 33. The light may directly be illuminated from above the substrate 50 without using the half mirror 35. The reference numeral 41 denotes the so-called personal computer with necessary software stored therein and capable of receiving the size information relevant to the droplet 14' from the camera 31 and operation-related signals from a user. The personal computer 41 has a display device (not shown in the figure), and an image of the droplet 14' inputted from the camera 31 is displayed thereon.

The reference numeral 46 denotes a pipet for forming a droplet 14'. The pipet 46 contains therein the solution used for forming as the droplet sucked therein in advance. At the root section of the pipet 46, a syringe pump 44 is provided via a tube 45, and a drive unit 43 is attached to the syringe pump 44. When a user gives an instruction to prepare a droplet to the personal computer 41, the drive 43 unit starts operating, the syringe pump 44 is driven by the drive unit 43, and then the solution inside the pipet 46 is pushed out to form a droplet at the tip of the pipet 46. While optically monitoring the droplet at the tip of the pipet 46, the user stops forming the droplet when the droplet is grown to a prespecified size.

When the droplet 14' is formed in the state where the pipet 46 is contacted to the substrate 50, if a user gives an instruction to the personal computer 41 to lift the pipet 46, the instruction to lift the pipet 46 is given to a lift up/down drive unit 47, and then the pipet 46 goes up and separates from the droplet. A dashed line 48 shows coordination between the lift up/down drive unit 47 and the pipet 46. When the droplet 14' is formed with the pipet 46, a user lowers the pipet 46 once and moves the droplet to a hydrophilic region on the substrate 50, and raises the pipet 46 to separate the pipet form the droplet.

Next, to form a new droplet, the user gives an instruction to the personal computer 41 to move the stage. In response to this instruction, the personal computer 41 gives a drive signal to the drive unit 23 to move the stage 59. While monitoring the header portion of the pipet 46, the user stops movement of the stage when the header of the pipet 46 reaches the hydrophilic region where the droplet is formed. At the new position, as described above, a droplet is formed at the tip of the pipet and then on a hydrophilic region on the substrate 50. It is needless to say that, in this step, the pipet 46 has been already replaced by a new pipet containing a new solution for forming a new droplet.

Next, the user moves the droplets on the hydrophilic regions 51, 52 to the hydrophilic region 55 to mix them up. In this step, each droplet is moved on the hydrophilic line 53 or 54 which connects the hydrophilic regions 51 and 55 and hydrophilic region 52 and 55 to each other. In other words, the droplet is moved in a manner that they are dragged on the hydrophilic line with the tip of the pipet 46 contacting the droplet 14. As a result, the droplet can be moved smoothly on the hydrophilic line to a new hydrophilic region.

After each droplet formed on the hydrophilic regions 51, 52 is moved to the hydrophilic region 55, a specific chemical reaction occurs. In some cases, the chemical reaction may take a longer period of time as compared the time required forming or moving the droplets. Therefore the moisture content of the droplet may vaporize because of the circumstances as described above. So, like in Examples 1 and 2 described above, while the size of a droplet is monitored, the temperature of the substrate 50 is controlled so that the diameter of the droplet is kept at the substantially constant level by controlling the temperature regulator 15. This control is also applicable when a droplet is formed. In addition, although not shown, like in Examples 1 and 2 described above, it is preferable to install water tanks 19,20 for hydration and an upper cover 22 having a shape like a reversed transparent vessel to prevent the change in environments for the droplet during the chemical reactions.

When the two droplets are DNA and fluorochrome SYBR Green I for intercalating to the DNA, for instance, the droplets are moved to the hydrophilic region 55 and merged with each other and left at the position for two minutes. During this process, the diameter is monitored for controlling the temperature of substrate 50 so that the diameter of the droplet is kept substantially constant. Then the droplet is moved from the hydrophilic region 55 to the hydrophilic region 57 on the hydrophilic line 56. Light is illuminated from the laser source 61 through the half mirror 62 to the droplets which has been merged and finished the chemical reaction on the hydrophilic line 56 or on the hydrophilic region 57. The fluorescence from the reactants in the droplet can be measured by detecting the fluorescence emitted from the droplet with a detector unit 66. The reference numerals 63, 64 denote lenses constituting the optical system. Also in this case, it is preferable to move and slide a droplet on the hydrophilic line with the tip of the pipet 46 contacting the droplet with the chemical reactions already finished therein. However, since it is not possible to provide both the optical system for monitoring the diameter of the droplet and the other optical system for measuring the fluorescence volume from reactants in the droplet at the same place, and therefore it is preferable to use the lift up/down drive unit 47 capable of moving the pipet 46 also in the X-axial and Y-axial directions.

In FIG. 39, there are two hydrophilic regions 51, 52 to form two types of droplets. But a single hydrophilic may be enough when the following procedure is employed. In this case, a first droplet formed on a hydrophilic region is moved to the hydrophilic region 55 for merging the two types of droplet later, and then another droplet is formed on the same hydrophilic region and, in the same manner, moved to the hydrophilic region 55 to be merged with the first droplet there.

If three types of droplets needs to be merged with each other, it is allowable to prepare three hydrophilic regions instead of two hydrophilic regions 51,52, or to form droplet one by one on a single hydrophilic region and to move the droplets to the next hydrophilic region one by one to merge the droplets each other there.

[VIII] Eighth Embodiment

In an eighth embodiment of the present invention, descriptions are provided below for a structure allowing for long term electric measurement of changes in responses of a cell network to stimulus while completely controlling a shape of the intercellular network shape to clarify functions of the cells. This structure has a plurality of cell culture zones each to confine the cell in the specific space arrangement and each zone is interconnected with a groove that the cell may not pass through reciprocally, and a plurality of electrode patterns to measure the change in the electric potential of the cell are provided in the groove. The electrode pattern is provided in the groove between adjoining cell culture zones, and has a structure suited for measurement of the difference of intercellular potential. When the measured cell is a neurocyte, the cell extends the axon. Therefore the change in the electric potential of an intercellular axon itself which is coupled with adjoining cell at synapse is measured.

EXAMPLE 1

Figure 40:
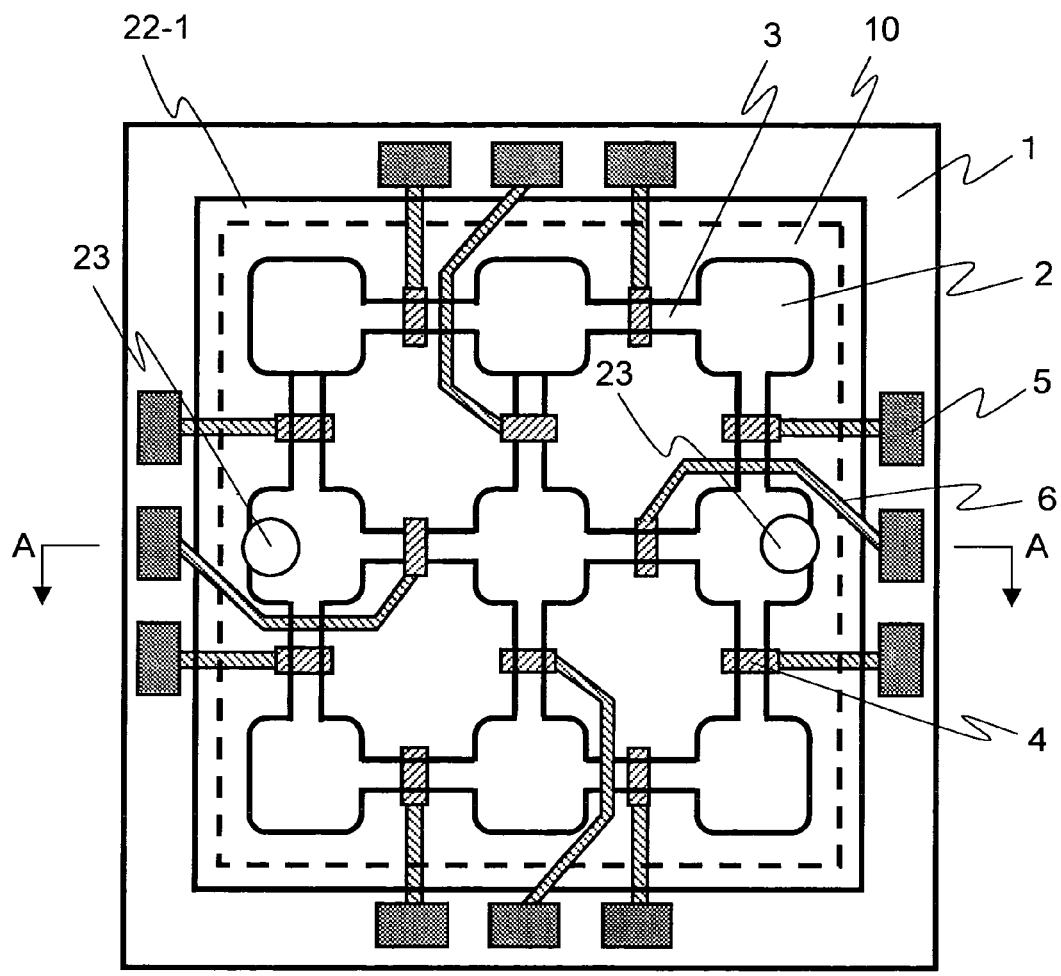
FIG. 40 is a plan view schematically showing an example of a structure of a cell culture micro-array with an electrode according to Example 1 of an eighth embodiment of the present invention.
Figure 41:
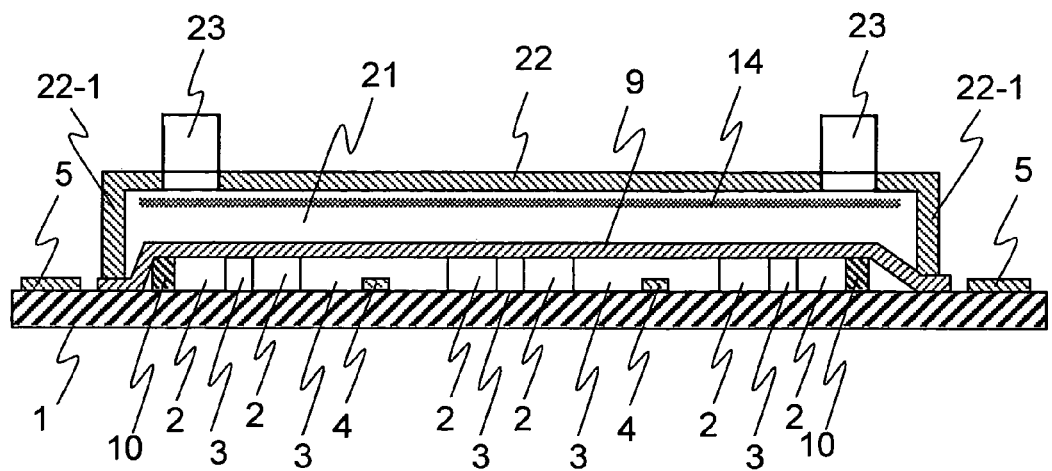
FIG. 41 is a cross-sectional view showing the cell culture micro-array shown in FIG. 40 taken along the line A-A and viewed in the direction indicated by the arrow.

FIG. 40 is a plan view schematically illustrating an example of a structure of cell culture micro-array with electrode in Example 1 of the eighth embodiment of the present invention, and FIG. 41 is a cross-sectional view showing the cell culture micro-array shown in FIG. 40 taken along the line A-A and viewed in the direction of indicated by the arrow. The reference numeral 1 indicates a substrate, and all the structures are constructed on substrate 1. The reference numeral 2 indicates a cell culture zone, and a plurality of cell culture zones 2 are regularly constructed with a prespecified interval. The reference numeral 3 indicates a groove which interconnects the adjoining cell culture zones. The reference numeral 10 indicates a resin layer formed on substrate 1, and the cell culture zones 2 and the groove 3 interconnecting the cell culture zones 2 are formed by removing the resin layer 10. The reference numeral 4 indicates an electrode for measuring the electric potential, and is installed in each of the grooves 3. Electrode 4 is gold deposited with the thickness of 100 nm onto the surface of substrate 1. The reference numeral 5 indicates an external terminal, and is installed near substrate 1 at a position corresponding to the electrode 4. The reference numeral 6 indicates wiring and the wiring connects the electrode 4 to the external terminal 5.

The reference numeral 9 indicates a semipermeable membrane, and is formed tightly on the upper surface of the resin layer 10 with the grooves 3 each interconnecting the adjoining cell culture zones 2 formed thereon. The reference numeral 22 indicates an upper housing which covers the entire area of the resin layer 10 with an appropriate space on the semipermeable membrane 9. The reference numeral 22-1 indicates a falling section of the upper housing 22. The reference numeral 21 indicates a culture fluid bath formed between the semipermeable membrane 9 and the upper housing 22. The reference numeral 23 indicates an opening 23 provided on the upper housing 22, and the culture fluid is provided to the bath 21 therethrough. The reference numeral 14 indicates a common electrode, which is provided in the culture fluid bath 21.

In Example 1, each cell culture zone 2 has an edge of 30 μm and depth of 25 μm for the purpose of measuring a human cell while culturing the cell. The groove 3 has the width of 5 μm and depth of 25 μm. The distance between each cell zone is in the range from 30 to 200 μm.

Descriptions are provided below for a method of preparing the substrate 1. The substrate 1 is made of non-luminescent glass with the thickness of 0.18 mm, which enables the observation with an object lens having the resolution of 100 times, and at first, layers for the electrode 4, wiring 6 and terminal 5 are formed by deposition. Secondly the areas of the electrode 4 and terminal 5 are masked, and the insulating layer is formed to cover the areas. Then, the surface of electrode 4, insulating layer, and terminal 5 is covered with photo-curing resin SU-8 (an epoxy type photoresist material, produced by Micro Chem. Inc., U.S. Pat. No. 4,882,245) having the degree of viscosity adjusted so that the thickness of the layer may become 25 μm and resin layer 10 is formed. Then portions of the resin layer 10 corresponding to cell culture zones 2 and grooves 3 are locally eliminated. As a result, the cell culture zone 2 and grooves 3 are formed. The electrode 4 is provided in the groove 3 in the exposed state, but the wiring 6 crossing the groove 3 is isolated with the insulating layer. Also the terminal 5 is exposed.

A cytophilic substance such as laminin and collagen is applied on the surfaces of the cell culture zone 2 and groove 3, and further the cell culture zone 2 and groove 3 are filled with a buffer fluid buffer, and then a cell is put into the cell culture zone 2. After that, a lid made of semipermeable membrane 9 is placed on the upper surface of the area for the cell culture zone 2 and groove 3 in order to confine the cell within the cell culture zone 2. Then, the upper housing 22 is set to completely cover the lid made of semipermeable membrane 9 (the entire area of resin layer 10). In this step, the upper housing 22 has a suitable falling section 22-1, and covers the semipermeable membrane 9 with an appropriate space to form the culture liquid bath 21. The common electrode 14 is formed with a light-transmissible electrode such as ITO on an inner wall of upper housing 22 of culture fluid bath 21. The reference numeral 23 indicates an opening of the culture fluid bath, and a fresh culture fluid is constantly supplied to the culture liquid bath 21 through this opening 23, and also the used culture fluid is exhausted therethrough.

For the aforementioned semipermeable membrane 9, a transparent cellulose film is used so as not to interrupt optical observations. Cellulose with the molecular weight cut off of 30,000 Daltons is used in this example. The upper housing 22 is also made of a transparent material, such as plastics to avoid interruption of the optical observation by the upper housing 22.

The cell culture micro-array accommodating a plurality of cells discretely is prepared as described above. A number of methods are conceivable for putting a cell in each cell culture zone 2. For instance, there is a method in which a micro capillary is inserted into the liquid solution including the cells, a cell is captured with the distal end thereof and put into the cell culture zone 2. Alternatively, when the size of the cell culture zone 2 is substantially the same as that of a cell, the cell can be set in the cell culture zone 2 by dripping a droplet including the cell onto a top surface of the area with the cell culture zone 2 and groove 3 formed thereon and sliding the micro-capillary along the surface of the area to push out the surplus liquid.

The independent bonding formation based the biotin-avidin reaction is used to stabilize the cell in the cell culture zone 2. Since the photo-curing resin SU-8 possesses a reactive epoxy group, the photo-curing resin SU-8 is subjected to pre-baking before irradiation of light thereto to form the base SU-8 layer, and then immediately a solution containing biotin hydrazide is applied to the layer to react the epoxy group to the hydrazide group for fixing biotin. By exposing to light to solidify the resin and forming a structural body, the SU-8 pattern with biotin introduced on the surface thereof is obtained.

Extension of axon in the groove 3 can be detected by measuring an impedance between terminal 5 connected to electrode 4 and provided in the groove 3 and the common electrode 14, or by measuring an electromotive force by the cell itself detected in the terminal 5 that is connected to electrode 4 by referring to an electric potential in the common electrode 14 as a reference value.

All of the operations described above can be performed observing the cell with a microscope. Further, in the cell culture micro-array with electrodes according to the eighth embodiment, it is possible to provide the stimulus to the specific cells with the same electrode or to measure a response of the cell to the stimulus by selecting a desired electrode among the plurality of electrodes provided therein.

For instance, as a result of incubation of a rat cerebellar granule cell in the cell culturing micro-array with the electrode according to the eighth embodiment, the cell confined in the cell culture zone 2 was observed to form a network without cutting itself free from the cell culture zone 2. It is also confirmed that the electromotive force is generated, before and after the axon extends and cells are contacted to each other, in the electrode 4 provided in the groove 3 between the cell culture zones 2 where the axon extends and the cells are connected to each other, and also in the electrode 4 provided in the groove 3 that the axon in the opposite side of the cell does not extend. It is understood based on a result of these observations that the structure of the cell culturing micro-array with an electrode according to the eighth embodiment has the expected performance.

Furthermore, it is possible to measure responses of the cells by checking a change in electrical potential by adding a biological material, such as peptide or amino acid, and a chemical substance having suspected endocrine disrupting or toxic property.

EXAMPLE 2

Example 2 are described below with reference to a case where the cell culture zone 2 or groove 3 is formed by using agarose gel 100 in place of the photo-curing resin SU-8.

Figure 42:
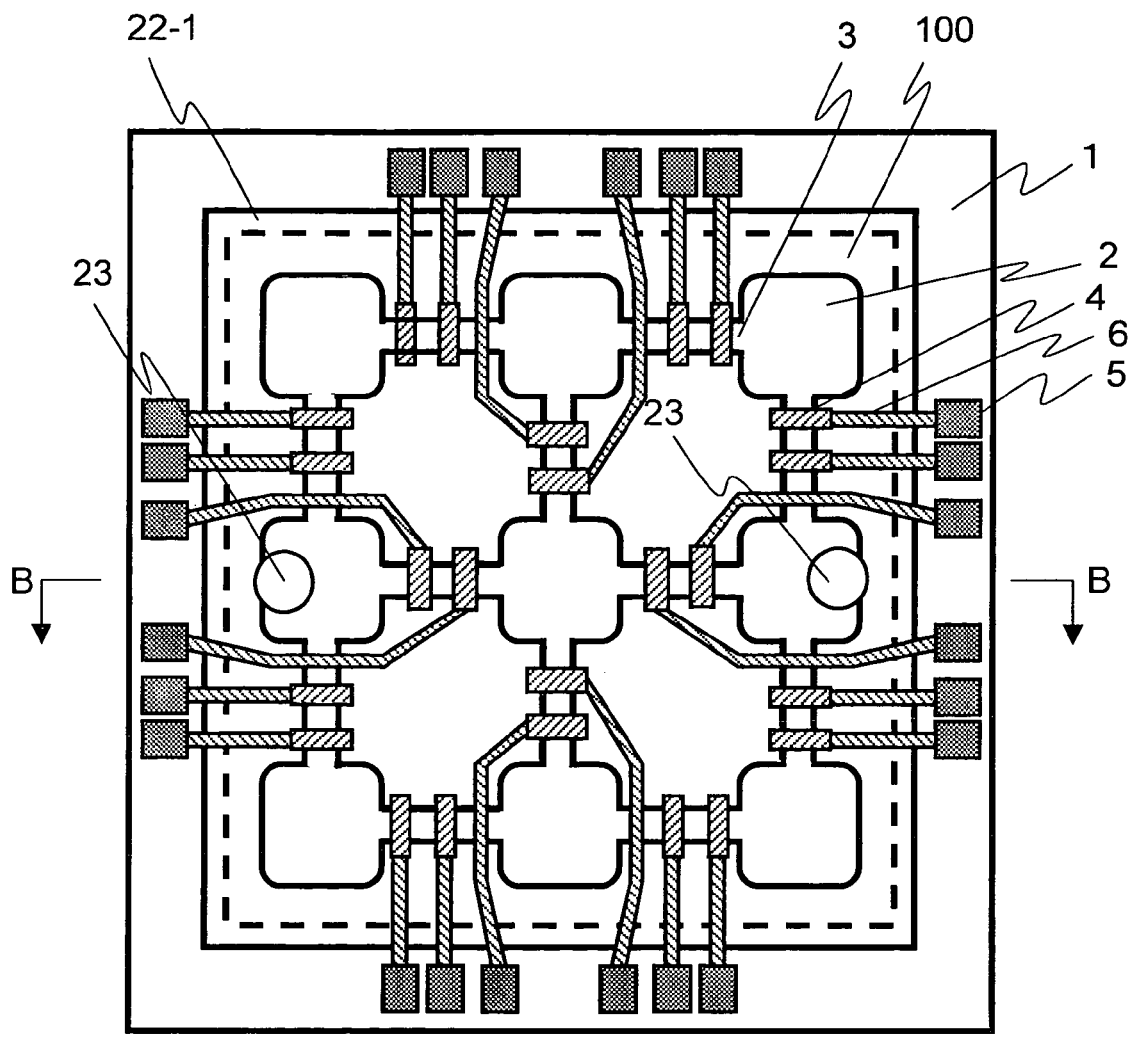
FIG. 42 is a plan view showing Example 2 of the eighth embodiment.
Figure 43:
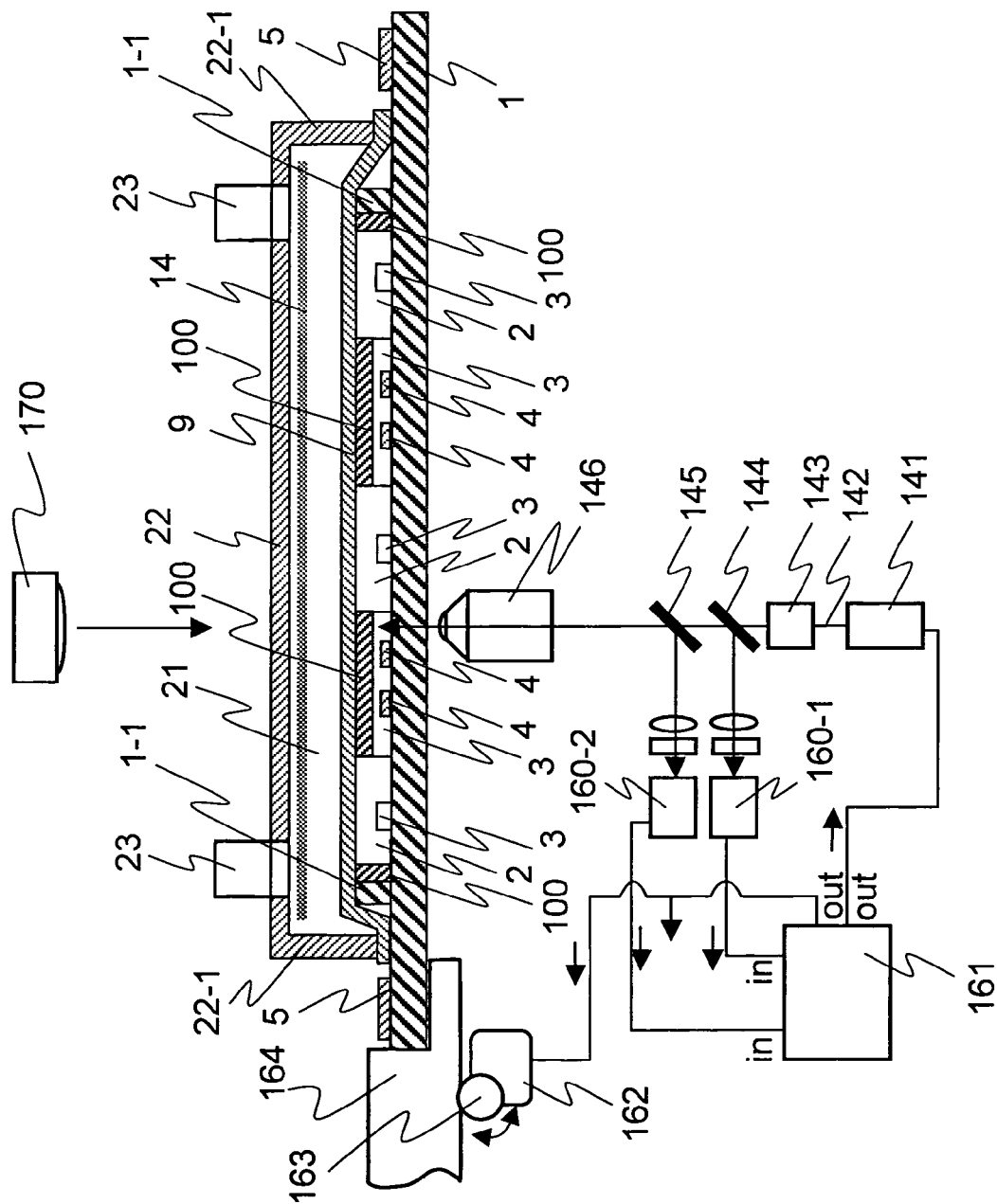
FIG. 43 is a cross-sectional view showing the cell culture micro-array shown in FIG. 42 taken along the line B-B and viewed in the direction indicated by the arrow.

FIG. 42 is a plan view showing Example 2 of the eighth embodiment, and FIG. 43 is a cross-sectional view illustrating the cell culture micro-array shown in FIG. 42 taken along the line B-B position and viewed in the direction indicated by the arrow. As clearly understood from comparison of FIGS. 40 and 41 to FIGS. 42 and 43, the structure in Example 2 is the same as that in Example 1 excluding the points that that the groove 3 interconnecting the cell culture zones 2 is changed to a tunnel 3, that a plurality of electrodes 4 are provided in the tunnel 3, and that the tunnel 3 is provided only on the bottom surface of agarose gel 100. The reference numeral 1-1 indicates a wall provided on the substrate 1, and an area surrounding agarose gel 100 is formed with and sustained by this wall.

In Example 2, the electrode 4, wiring 6, and terminal 5 are formed on the substrate like in Example 1, and then the wall 1-1 is adhered to the upper face of the substrate 1 and agarose gel 100 is put inside the wall 1-1. The 2% agarose gel (with the melting temperature of 65° C.) is heated with a microwave oven and melted therein. The melted agarose solution is added to inside the external wall of the lower part of the substrate 1 heated to 65° C., and immediately spread homogeneously with a spin coater. An amount of added agarose gel and a rotational speed of the spin coater are adjusted so that the agarose gel membrane will have the thickness of 1 mm. The thickness differs according to devices used and lots of agarose gel, but a good result has been obtained with the rotational speed of 50 rpm for 15 seconds, and followed by 200 rpm for 10 seconds. The agarose gel membrane 100 is formed with leaving the melted agarose solution in the moistening box for one hour at 25° C. At this point, the agarose gel membrane is formed on the inner side of the external wall of the substrate 1. Next, after the agarose gel 100 is formed, a portion corresponding to the cell culture zone 2 is removed to form the cell culture zone 2 with agarose gel 100.

FIG. 43 is a cross-sectional view illustrating an agarose made cell culturing micro-array with electrodes when the cell culture zone 2 prepared thereon and an optical system and a control system using for preparing the tunnel 3 in the agarose gel 100. A cellulose membrane is adhered to the upper surface of agarose gel like in Example 1. For instance, the heated and melted agarose is applied on the cellulose membrane with a spin coater to prepare a cellulose membrane with the agarose membrane formed on one surface thereof. Then the cellulose membrane is placed, after a cell is put in the zone 2, on the agarose gel 100 so that the agarose-applied surface thereof contacts the agarose gel 100. Alternatively, while the agarose gel 100 is formed, a small amount of streptoavidin-conjugated agarose may be added and solidified. The streptoavidin is exposed on the surface of this agarose gel derivative. Separately, in the same way like in Example 1, the cellulose membrane with an aldehyde group introduced by oxidization with periodic acid is reacted with biotin hydrazide, and the biotin-modified cellulose membrane obtained from reducing by the hydroboration reaction is prepared. By using the biotin-avidin reaction to fix the agarose gel derivatives and biotin-modified cellulose membrane, a structural body with a cell confined therein can be formed.

A laser 141 is used to irradiate a beam with the wavelength of 1480 nm which is absorbed by water. A laser beam 142 passes through an expander 143, and also passes through a filter 144 reflecting rays with the wavelength of 740 nm or more but allowing transmission of light with the wavelength of 1480 (±20 nm), and further passes through a deposition filter 145 that transmits the light with the wavelength of 700 nm or more, and is focused by a condenser 146 onto the surface of substrate 1. The converging light with the wavelength of 1480 nm is absorbed by water contained in the agarose layer, and the temperature in the neighboring area rises to a level close to the boiling point. When the laser power is at 20 mW, agarose is melted with approx 20 μm of the line width in the neighboring area where the convergent light is irradiated and removed by thermal convection. The problem is that the amplitude of the convergent light absorbed by agarose changes depending upon the presence of an electrode on the substrate 1. To solve this problem, there has been introduced in the present invention a contrivance enabling constant temperature control with irradiation of converging light by estimating a temperature of the agarose gel and feeding back the expected temperature value. The converging light having reached the agarose portion is converted to heat and simultaneously irradiates infrared rays. The infrared rays pass through the filter 145 is reflected by the filter 144, and reaches the infrared ray camera 160-1. The image data picked by the infrared ray camera 160-1 is fetched into a computing device 161 with a video recorder, the temperature is estimated from the detected amplitude, and power of the laser 141 is adjusted. In the case when it is difficult to control temperature only by adjusting the laser power, the moving speed of stage 164 is controlled according to an output from computing device, so that the agarose temperature in the portion exposed to the converging light is constantly maintained at the same level. More specifically, rotation of stepping motor 162 is controlled by the computing device 161, and rotation of the stepping motor is delivered by power transmission device 163 to move the state 164.

The substrate 1 is set on the stage 164, and the tunnel 3 can freely be formed in the agarose gel. An ITO transparent electrode is previously formed in the tunnel 3. Moreover, also the optical system for detecting the transmitted light from the light source 170 is incorporated to monitor the progress of the cell observation as well as of agarose processing. Light from the light source 170 transmits the transparent upper housing 22, transmits the objective lens 146 scattering in the agarose section, and is fetched as an image with the CCD camera 160-2 through the deposition filter (mirror) reflecting visible light. The image data is sent to the computing device 161, overlapped with images taken the infrared ray camera 160-1, and used, for instance, for confirmation of the portions heated by laser beam irradiation and the structure pattern.

On the upper surface of the agarose gel, the culturing solution that is supplied and discharged through the opening 23 is constantly circulating. Alternatively, stimulating substances to the cell or various chemicals including endocrine disrupting chemicals and the like are added through the opening 23, and the state of the cell can be monitored by the electrodes by observation with a microscope.

In Example 2, two electrodes are provided in one tunnel 3, so that it is easy to capture fluctuation in impedance or inductance in the tunnel 3. Each electrode is connected to the terminal 5 respectively with the wiring 6, and therefore it is possible to measure a single electrode or a pair of electrodes. For instance, when an axon of the neurocyte extends and the cell couples with the neighboring cell, an electrical potential of electrode 5 can be measured by referring to that in another electrode as a reference potential.

Moreover, in Example 2, since it is possible to additionally engrave the tunnel 3, activities of a cell can be assessed by monitoring the current situation and changing the tunnel configuration.

EXAMPLE 3

Figure 44:
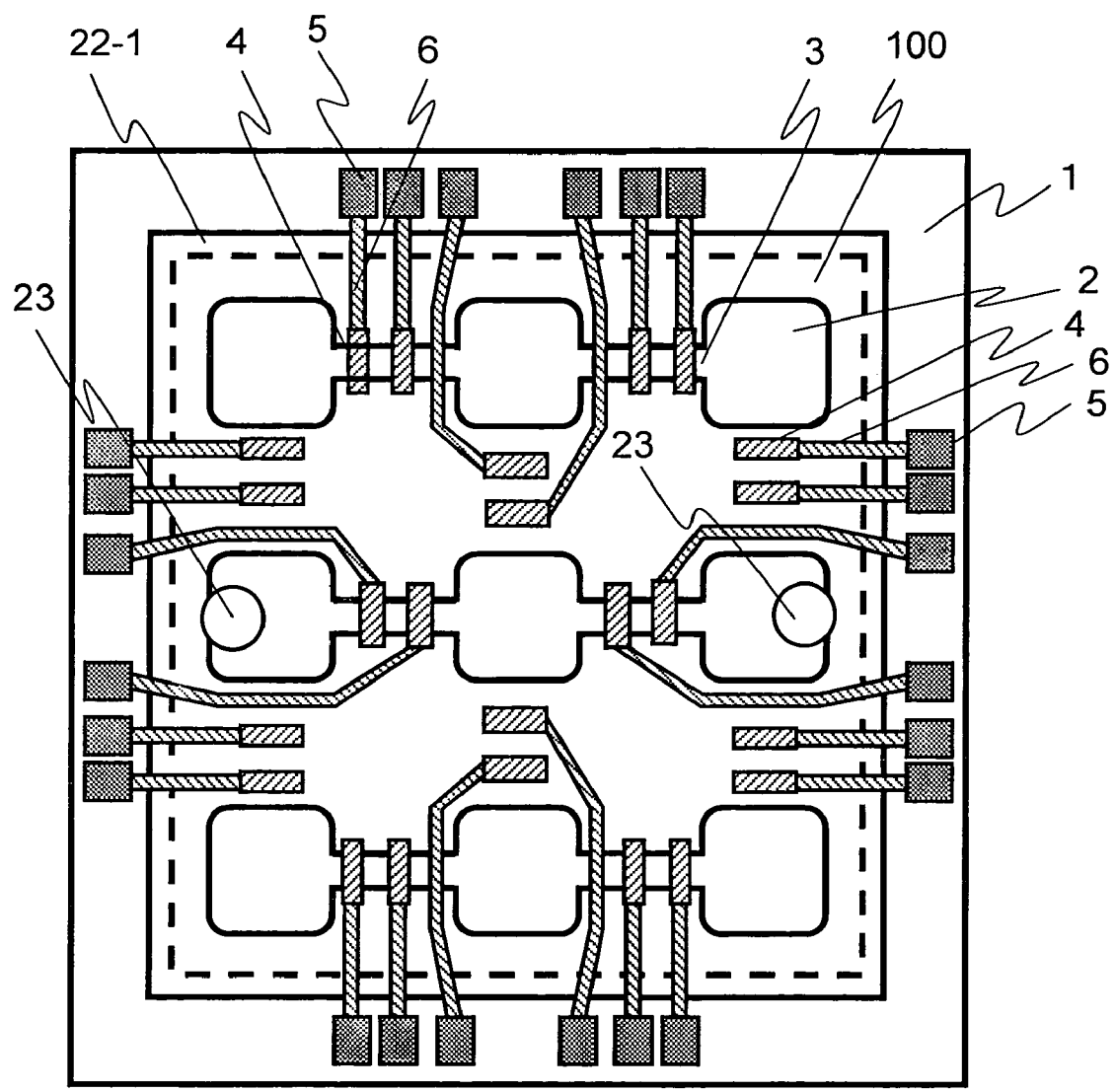
FIG. 44 is a plan view showing Example 3 in which a plurality of cell culture zones 2 most important in the practical use are adjoined to each other and formed as a one-dimensional array.

FIG. 44 is a plan view illustrating Example 3 in which a plurality of cell culture zones 2, which is most important in practical use, are connected each other for form a one-dimensional array. As it is clearly understood from comparison of FIG. 44 to FIG. 42, configuration in Example 3 is the same as that in Example 2 excluding the point that the cell culture zones 2 formed with the agarose gel 100 and the tunnel 3 interconnecting the cell culture zones 2 are formed in the lateral direction. Also in Example 3, the tunnel 3 interconnecting the cell culture zones 2 is not always required to be formed previously, and may be opened, for instance, only in the direction in which the axon of the neurocyte is required to extend at a point of time when the axon is formed. All electrodes 4 should be made in the tunnels or at positions where tunnels are to be formed when practically used.

The cross-section of the device in Example 3 is the same as that in Example 2, and descriptions thereof are omitted herefrom.

(Others)

The aforementioned examples are all described as completed cell culturing micro-array. However, a researcher as a user of the cell culture micro-array is required to put in a cell or the like in the cell culture zone 2. Accordingly, it is practical to provides the substrate 1 with the electrode 4, external terminal 5, wiring 6, cell culture zone 2 and groove 3 formed thereon, semipermeable membrane 9, and upper housing 22 as a cell culturing micro-array kit. In this case the researcher having purchased the kit prepares a culture fluid, puts a cell or the like in the cell culture zone 2, sets the semipermeable membrane 9 and upper housing thereon to complete the kit. Also in Examples 2 and 3, it is practical to use the cell culturing micro-array kit depending on the purposes of researches. The kit includes, as in Example 1, the substrate 1 on which the agarose gel is placed and such as electrode, the cell culture zone 2 and a necessary tunnel are formed on the agarose gel, the semipermeable membrane 9, and the upper housing 22.

[IX] Ninth Embodiment

A ninth embodiment of the present invention discloses a structure for configuring a network consisting of the minimum number of cells in which a plurality of heterogeneous cells are interacted, on a chip, for measuring a change in responses to stimulus in the cell network, by controlling a few heterogeneous intercellular network. Namely a plurality of cell culture zones are formed for keeping heterogeneous cells in the state where the cells adjoin each other within a specific space, and adjoining zones are communicated to each other with a groove or a tunnel through which the cells can not pass through. If required, a collective cell micro-array (bioassay chip) having a plurality of electrode patterns for measuring an electric potential in a cell is provided in the groove or tunnel, or in the cell culture zone.

EXAMPLE 1

Figure 45:
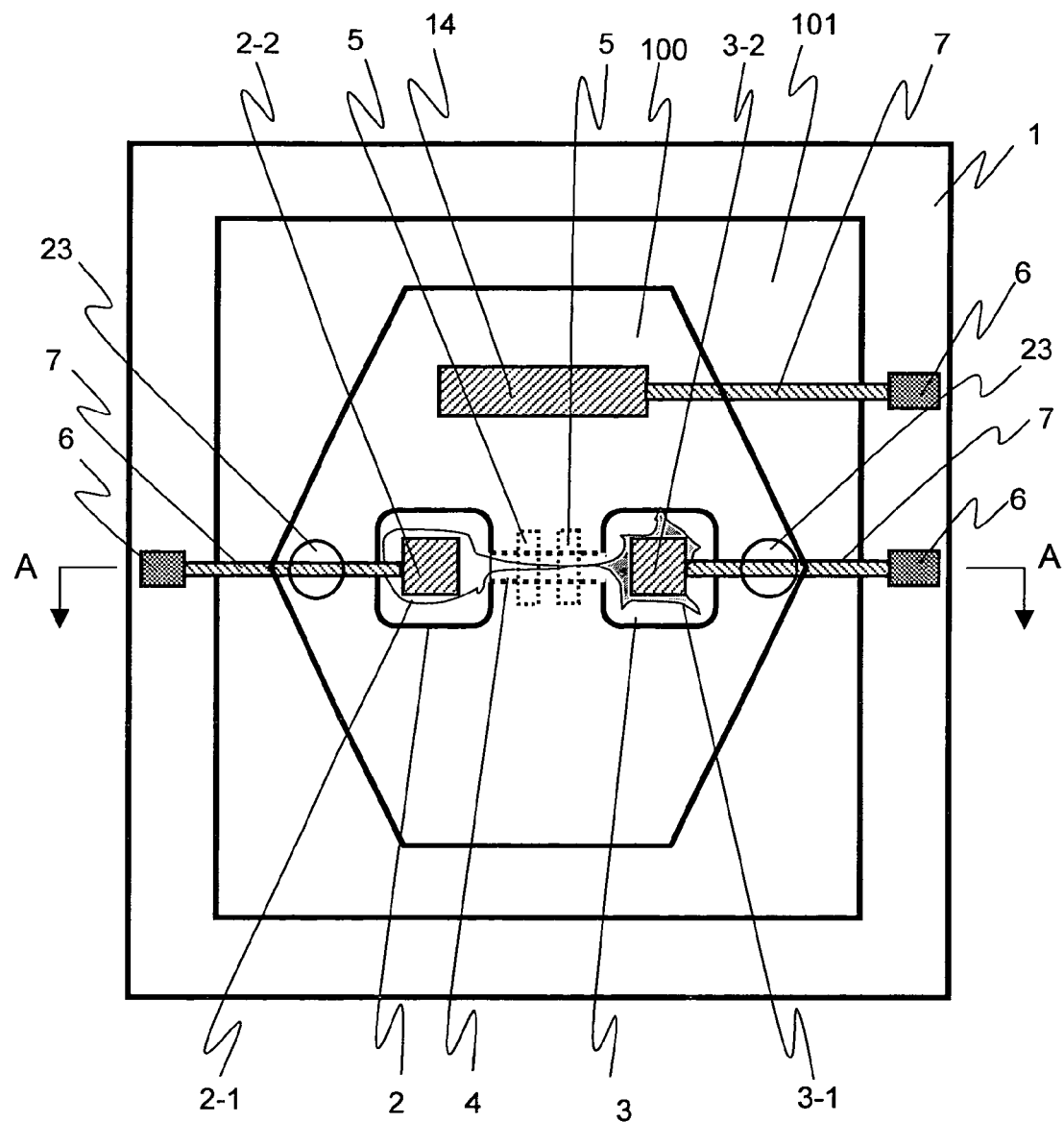
FIG. 45 is a plan view schematically showing one example of a structure of a cell reconstituting device having a circuit between different types of cells according to Example 1 of a ninth embodiment of the present invention.
Figure 46:
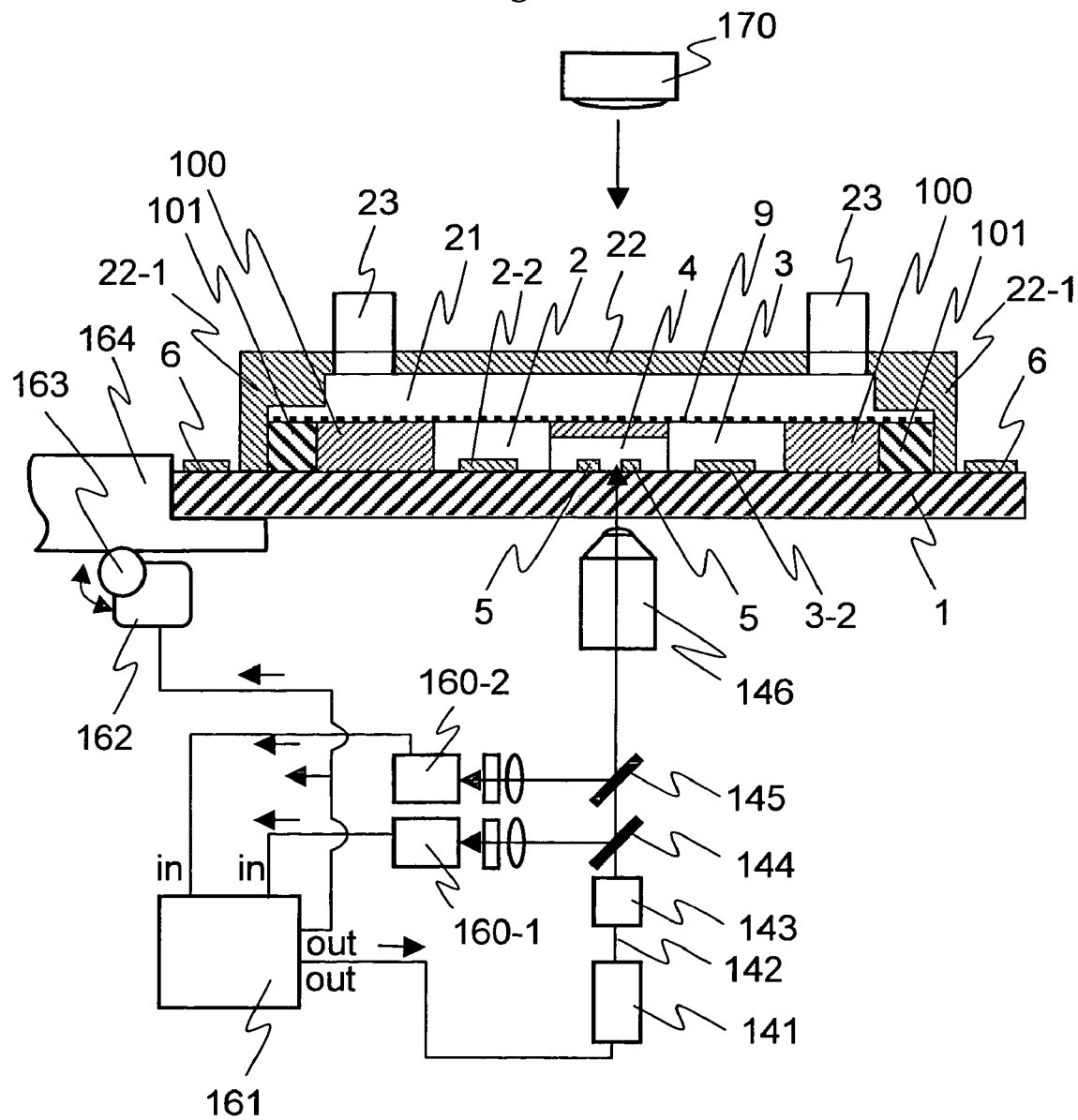
FIG. 46 is a view schematically showing a cross section of a cell reconstituting device shown in FIG. 45 taken along the line A-A and viewed in the direction indicated by the arrow, and also showing an optical system for forming a tunnel communicating between cell holding zones in the device as well as a control system for the optical system.

FIG. 45 is a plan view schematically showing an example of a structure of a cell reconstituting device having a circuit among heterogeneous cells according to the ninth embodiment of the present invention. FIG. 46 is a view schematically showing a cross section of the cell reconstituting device taken along the line A-A and viewed in the direction indicated by the arrow, and an optical system for forming a tunnel communicating adjoining cell holding zones in the device as well as a control system for the same.

The reference numeral 1 indicates a substrate and all of the constructions are provided on the substrate 1. The reference numerals 2, 3 indicate cell holding zones respectively, which are provided at a prespecified gap in-between and are communicated to each other via a groove 4. The reference numeral 100 indicates an agarose gel formed on the substrate 1, and the cell holding zones 2, 3 and the tunnel 4 communicating the zones to each other are formed by removing a portion of the agarose gel 100. The reference numerals 2-2, 3-2 indicates electrodes respectively, which are provided in the cell holding zones 2, 3. If required, plural electrodes 5 are provided on the tunnel 4. The electrodes 2-2, 3-2, and 5 are formed each with a transparent electrode (indium-tin oxide: ITO) and is deposited on a surface of the substrate 1 with the thickness of 100 nm. The reference numeral 6 indicates an external terminal, and is provided around the substrate 1 at a position corresponding and adjacent to the electrode. The reference numeral 7 indicates wiring, which connects the electrode to the external terminal. Both the external terminal 6 and wiring 7 have the thickness of about 100 nm and are made from transparent ITO. The wiring 7 is complicated and is not shown in FIG. 46. The reference numeral 101 is a bank for holding the agarose gel and is made from SU8 or glass. When the bank is made from SU8, the SU8 is coated on the substrate 1 with the thickness of 100 μm, and UV ray is irradiated onto the SU8 for curing. When the bank is made from glass, a glass sheet with the thickness of 100 μm is adhered to the substrate 1. The bank 101 is made after the electrodes are prepared.

The reference numeral 9 indicates a semipermeable membrane and is provided in adhesion to a top surface of the agarose gel 100 with the cell holding zones 2, 3 and the tunnel 4 connecting the zones 2, 3 to each other formed thereon. The reference numeral 22 indicates an upper housing, which is provided on the semipermeable membrane 9 with a proper space and entirely covers the top face of the agarose gel 100. When the cells are not floating ones, the cells tend to be deposited on a bottom surface of the substrate, and therefore the diffusion shell is not necessarily required. The reference numeral 22-1 indicates a fall section of the upper housing 22. The reference numeral 21 indicates a culture fluid bath formed between the semipermeable membrane 9 and the upper housing 22. The reference numeral 23 indicates an opening provided on the upper housing 22, and the culture fluid is supplied through this opening 23 into the culture fluid bath 21. The reference numeral 14 in FIG. 45 is a common electrode. Because the culture fluid is supplied through the diffusion shell to cells held on the cell holding zones 2, 3, change of conditions during culture is prevented. In Example 1, a pulsating myocardial cell 2-1 is held in the cell holding zone 2 and a neurocyte 3-1 in the cell holding zone 3. The two cells are coupled to each other to form a gap-junction via the tunnel 4 between the heterogeneous cells.

As for the procedure for preparation, after the electrodes 2-2, 3-2, 5, wiring 7, and terminal 6 are formed on the substrate 1, the bank 101 is formed on a top surface of the substrate 1, and thermal-melted agarose 100 is poured into the bank 101. A 2% agarose gel (with the melting point of 65° C.) is heated and melted in a microwave oven. The melted agarose gel solution heated to 65° C. is added to inside of the bank 101 on the substrate 1, and is immediately spread to a coat with the homogeneous thickness by a spin coater. In this step, by adjusting a quantity of added agarose solution and the rotational speed of the spin coater so that the agarose gel coating film has the thickness in the range from 0.005 mm to 0.5 mm, an agarose solution layer having the same height as that of the bank 101 is formed. A good result is obtained by operating the spin coater at the rotational speed of 50 rpm for 15 seconds, and then at the rotational speed of 200 rpm for 10 seconds. When the agarose layer is left in a moist box for one hour at 25° C., an agarose gel film 100 is formed. At this point of time, the agarose gel film is formed on the entire inner surface of the bank 101 on the substrate 1.

Then for forming the cell holding zones 2,3 with the agarose gel 100, at first the agarose gel 100 is formed, and then portions corresponding to the cell holding zones 2, 3 and tunnel 4 are removed. This operation can easily be performed by using a laser 141 in the wavelength band (for instance, 1480 nm) which can be absorbed by water. A laser beam 142 passes through an expander 143, then passes through a filter 144 which reflects the IR rays with the wavelength of 740 nm or more but allows transmission of the IR rays with the wavelength of 1480 nm (+20 nm), further passes through a deposition filter 145 which allows transmission of the light with the wavelength of 700 nm or more, and is focused onto a top face of the substrate 1 by a converging lens 146. The converging light with the wavelength of 1480 nm is absorbed by water contained in the agarose gel 100, and the temperature of the adjacent area goes up to that close to the boiling point. When the laser power is 20 mW, the agarose gel 100 is melted in the area irradiated by the converging light with the width of about 20 μm, and is removed by thermal convection. The problem is that intensity of the converging light absorbed by the agarose gel 100 changes according to the presence of an electrode on the substrate 1. Therefore, the temperature in the area irradiated by the converging light can be adjusted by controlling a laser power by means of feedback control based on estimation of the temperature of the agarose gel 100. The converging light having reached the agarose gel 100 is converted to heat and generates the IR rays. The IR ray passing through the filter 145, is reflected by the filter 144, and reaches an IR camera 160-1. Image data picked by the IR camera 160-1 are fetched into a computing device 161 with a video recording mechanism, and the temperature is estimated from the detected intensity of the light to adjust a required power of the laser 141. When it is difficult to control the temperature only by adjusting the laser power, a moving velocity of a stage 164 is controlled according to an output from the computing device so that the temperature of agarose gel in the irradiated section is kept within the prespecified range. Namely, a rotational speed of a stepping motor 162 is controlled by the computing device 161 so that a stage 164 is moved according to rotation of the stepping motor transferred through a driving force transfer device 163. When the tunnel 4 is to be formed, it is necessary to control the laser power to keep the agarose gel from being penetrated.

As the dispersion shell 9 provided on a top surface of the agarose gel 100, for instance, a cellulose membrane (with the molecular cutoff of 30000 Daltons) is used. Streptoadivin is previously fixed on the bank 101. When the bank 101 is made from SU8, the surface is oxidized by an oxygen plasma or ozone. Then an activated silane solution prepared by leaving a 1% 3-glycidoxypropyltrimethoxysilane (0.5% acetic acid aqueous solution) for 30 minutes in the atmosphere is applied on the surface of the agarose gel for making the activated silane and agarose react to each other for one hour, and the product of the reaction is heated and dried in the atmosphere for 30 minutes at 105° C. with the glycidoxy group introduced onto the surface thereof. When the material is made from glass, it is not necessary to carry out the surface oxidization processing, and it is required only to directly apply the 3-glycidoxypropyltrimethoxysilane on the surface. Then 50 mM boric acid buffer liquid with streptoavidin dissolved therein (pH 10) is coated and fixed on the surface. Separately, a biotin-modified cellulose membrane is prepared by reacting biotin hydrazide to a cellulose membrane with aldehyde group introduced by oxidization with periodic acid and reducing the reaction product by means of hydroboration.

The culture fluid is filled in the cell holding zones 2, 3 and tunnel 4 formed on the agarose gel 100, and one pulsating myocardial cell 2-1 and one neurocyte 3-1 are inserted into the cell holding zones 2 and 3 respectively with a micro-pipet under observation with a microscope. Then the entire top faces of the bank 101 and agarose gel 100 are covered with the biotin-modified cellulose membrane 9. By fixing the agarose gel derivative and the biotin-modified cellulose membrane to each other by biotin-avidin reaction, a structure, in which a cell is kept in the agarose gel structure, can be formed.

ITO-permeable electrodes 2-2, 3-2 and ITO-permeable electrode 5 are previously formed in the cell holding zones 2, 3 and in the tunnel 4 respectively. Further to observe beating of cells or to monitor progression of agarose machining, also an optical system for detecting transmitted light from a light source 170 is incorporated. The light from the light source 170 transmits the upper housing 22, further transmits an object lens 146 being scattered by the agarose gel 100, and is picked up as an image by a deposition filter (mirror) reflecting visible light and with a CCD camera 160-2. The image data is transmitted to the computing device 161 and is overlapped with the image taken by the IR camera 160-1, and the synthesized image is used, for instance, for checking a portion heated by laser beam irradiation and a pattern of a structure. In other words, with this system, electric potentials of the pulsating myocardial cell 2-1 and neurocyte 3-1 kept in the cell holding zones 2, 3 respectively can be measured with the electrodes 2-2, 2-3, and also the beating state of the pulsating myocardial cell can be picked up as an image by observing with a microscope. Further by using the electrode 5 provided in the tunnel 4, signal transaction between the two cells can be measured.

A top surface of the agarose gel 100 functions as a culture fluid bath 21, and the culture fluid supplied from the opening 23 always circulates therein. Further various types of chemical substances such as a cell-stimulating material or an endocrine disrupter are added in the culture fluid from the opening 23, for instance, to monitor the beating state of the pulsating myocardial cell or changes of electric potentials in the pulsating myocardial cell or neurocyte by using any of the electrodes or by means of observation with a microscope. In this step, for bioassay of an ionic material affecting measurement with an electrode, observation with a microscope is employed, and for bioassay of materials not suited to observation with a microscope such as a coloring matter, an electrode may be used.

Main dimensions of a structure of the heterogeneous cell bioassay chip in Example 1 shown in FIG. 45 are as described below. The size of the cell holding zone 2 is 30 μm×30 μm, and the depth is 0.1 mm, which is equal to that of the agarose gel 100. There is no specific restriction over the thickness of the cell holding zone, and in a case where a cell is set on a surface of the substrate, the thickness is required to be in the range from 0.005 to 0.5 mm. A distance between adjoining cell holding zones 2, 3 is generally 50 μm, and the tunnel 4 communicating to the cell holding zones 2, 3 to each other has the height in the range from 50 μm to 300 μm, and the width of 5 μm. When the tunnel 4 has the height of 100 μm and the thickness of the agarose gel 100 is 0.1 mm, not a tunnel but a groove is provided.

Example 2

Figure 47:
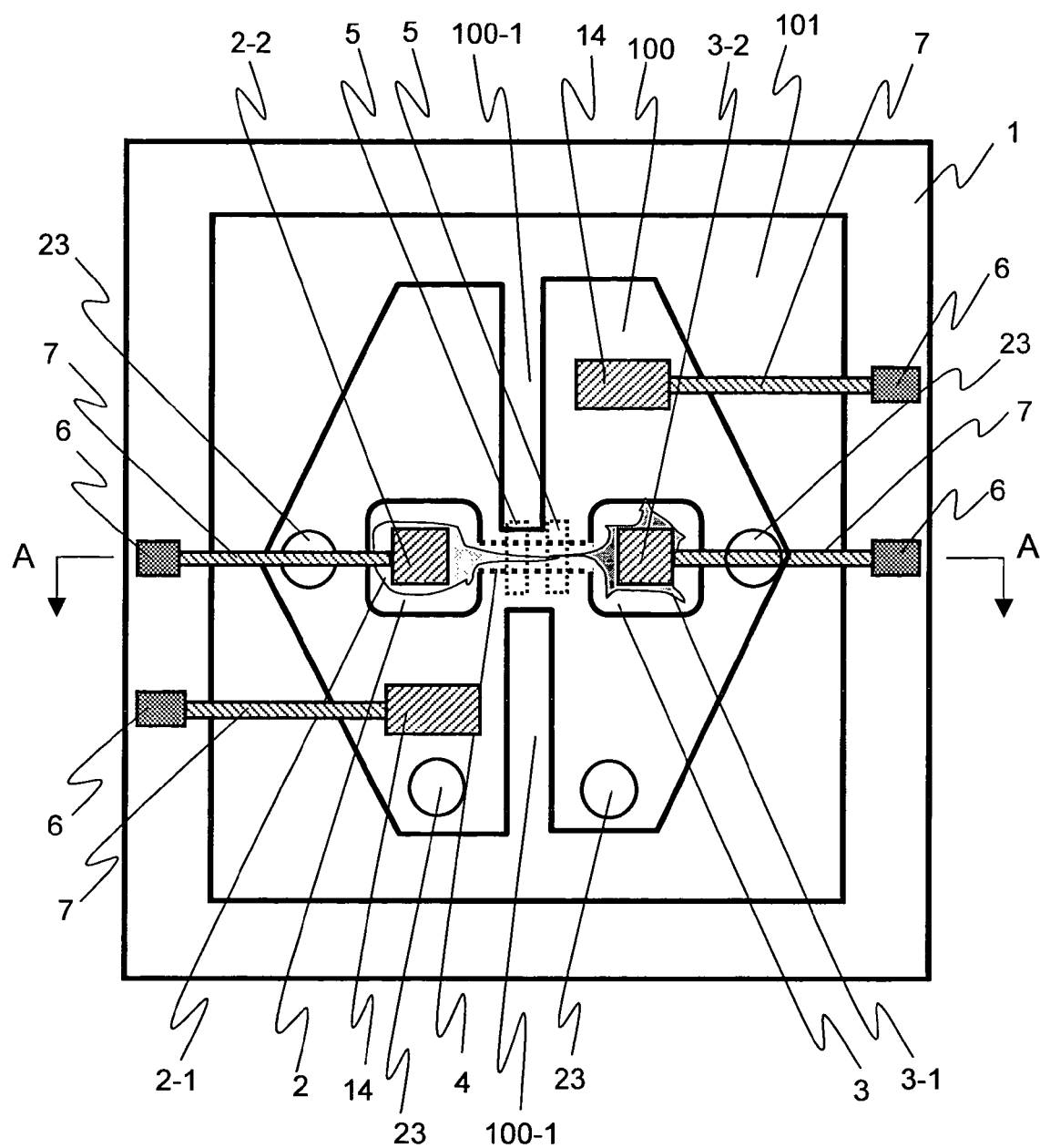
FIG. 47 is a plan view schematically showing an example of the cell reconstituting device having a circuit between different types of cells according to Example 2 of the ninth embodiment.
Figure 48:
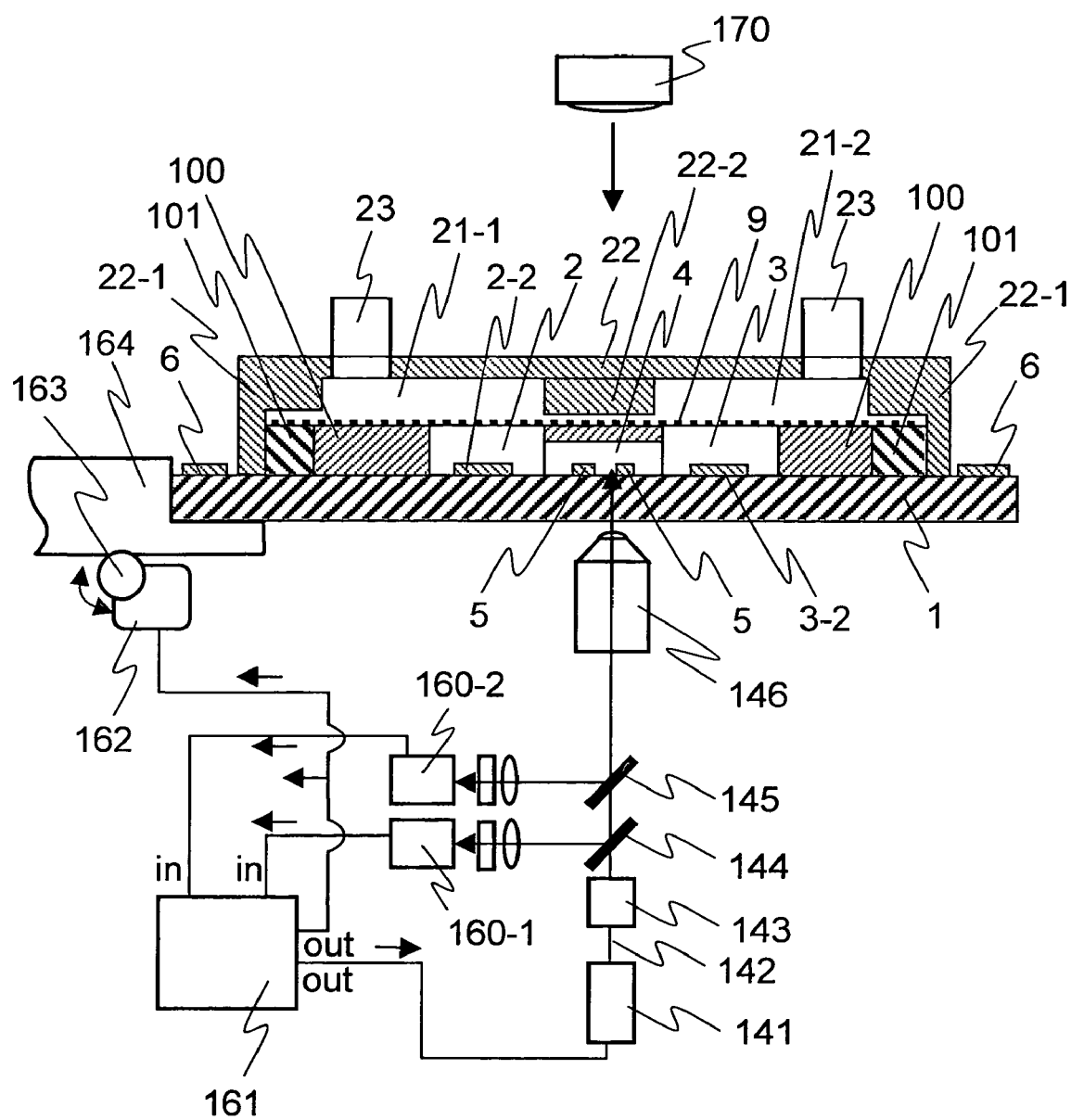
FIG. 48 is a view schematically showing a cross section of a cell reconstituting device shown in FIG. 47 taken along the line A-A and viewed in the direction indicated by the arrow, and also showing an optical system for forming a tunnel communicating between cell holding zones in the device as well as a control system for the optical system.

Example 2 proposes a heterogeneous cell bioassay chip having the basically same structure as that described in Example 1, but allowing for independent modification of an environment for each of the cell holding zones 2 and 3. FIG. 47 is a view schematically showing a structure of a cell reconstituting device having a circuit between heterogeneous cells in Example 2 of the ninth embodiment of the present invention. FIG. 48 is a view schematically showing a cross section of the cell-reconstituting-device shown in FIG. 47 taken along the line A-A and viewed in the direction indicated by the arrow, and also showing an optical system and a control system for forming a tunnel communicating adjoining cell holding zones in the device.

As easily understood by comparing FIG. 45 to FIG. 47, in Example 2, a projection section 101-1 which is a protrusion of the bank 101 is provided not only around the agarose gel 100, but also in a central portion of the agarose gel 100 to device in half the agarose gel 100 and reaches a point close to the tunnel 4. As easily understood by comparing FIG. 46 to FIG. 48, a partition 22-2 is provided to divide in half the culture fluid bath 21 to a section 21-1 and a section 21-2. Further, as shown in FIG. 47, an opening 23 for supplying a culture fluid into the culture fluid baths 21-1 and 21-2 is additionally provided.

In Example 2, even though the cell holding zones 2, 3 are communicated to each other with the tunnel 4, the culture fluid bath includes the two culture fluid baths 21-1 and 21-2 partitioned by the projection section 101-1 of the bank 101 and the partition 22-2 of the housing 22. Two openings for supplying a culture fluid are provided in the culture fluid baths 21-2, 21-2, so that a culture fluid can independently be supplied into each of the culture fluid baths 21-2, 21-2. In other words, bioassay of heterogeneous cells can be performed by culturing cells kept in the cell holding zones 2, 3 in the different environments respectively.

Example 3

Figure 49:
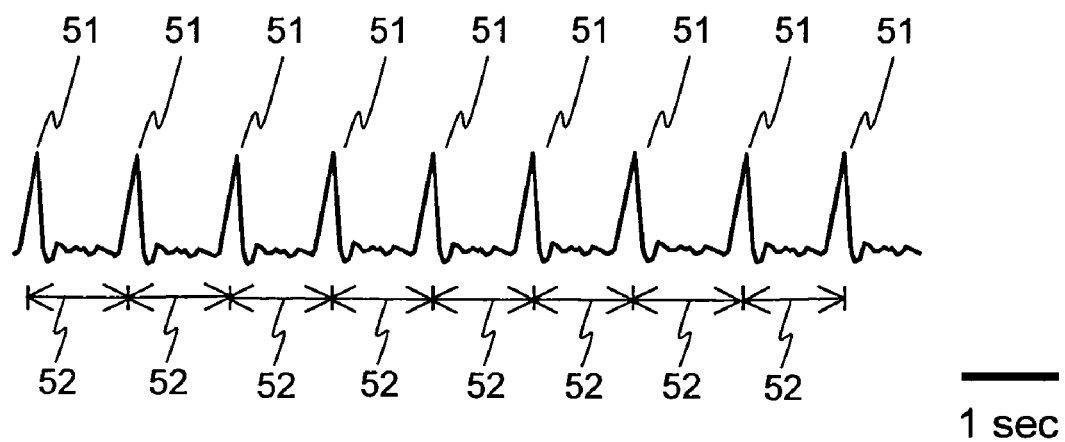
FIGS. 49(A) and 49(B) are waveform diagrams each showing a result of assessment for influences, in a case that a network consists of a socillating myocardial cell and a neurocyte, when an electric stimulus is given to the neurocyte.
Figure 49:
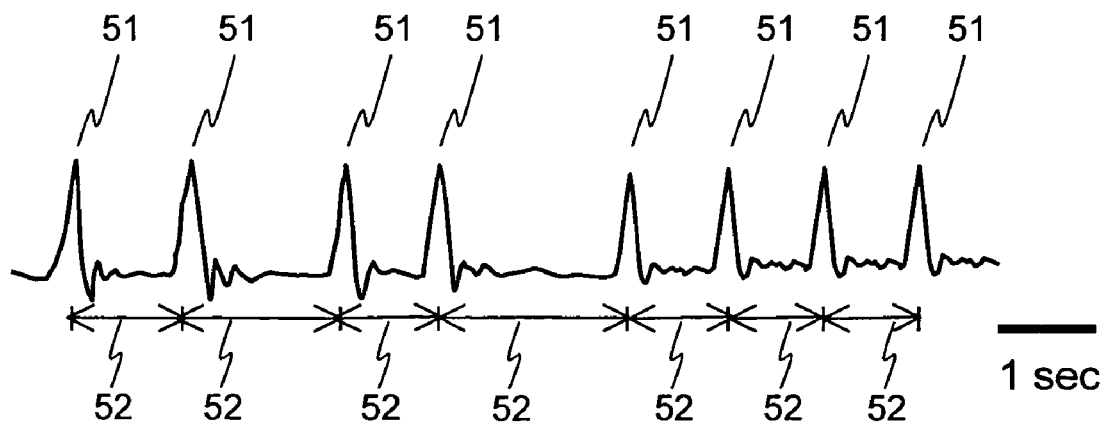

In Example 3, a network consisting of a pulsating myocardial cell and a neurocyte is formed by using the heterogeneous cell bioassay chip described in Example 2, and assessment is made for influence when an electric impact is given to the neurocyte. FIGS. 49(A) and 49(B) are waveform diagrams each showing a result of the assessment for the influence when an electric stimulus is given to the neurocyte.

In Example 3, examination is made for whether a beat cycle of the pulsating myocardial cell 2-1 kept in the cell holding zone 2 changes when potassium or glucose, or suspected endocrine disrupter is added to the culture fluid of the neurocyte 3-2 in the cell holding zone 3, or the content is increased.

At first, the same culture fluid is filled in the culture fluid baths 21-1, 21-2, and a beat cycle of the pulsating myocardial cell 2-1 is checked to obtain a myocardial pulsation pattern showing the substantially same cycle as shown in FIG. 49(A). Then, for instance, when dopamine is added to the culture fluid in the culture fluid bath 21-2 in the cell holding zone 3 without changing the culture fluid in the culture fluid bath 21-1 in the cell holding zone 2, the disturbance in the beat cycle as shown FIG. 49(B) is expected to be observed. This phenomenon occurs because a chemical substance give influences to the neurocyte and a beat cycle of the pulsating myocardial cell is fluctuated when an electric potential on a surface of the neuron changes.

In this experiment, the number of object cells for measurement is only one, so that the dispersion is around 50%. To suppress this dispersion, four or more cells and more preferably eight cells should be put in each of the cell holding zones 2 and 3 to suppress the dispersion of observed beat cycles of the cells to around 10%.

Example 4

Figure 50:
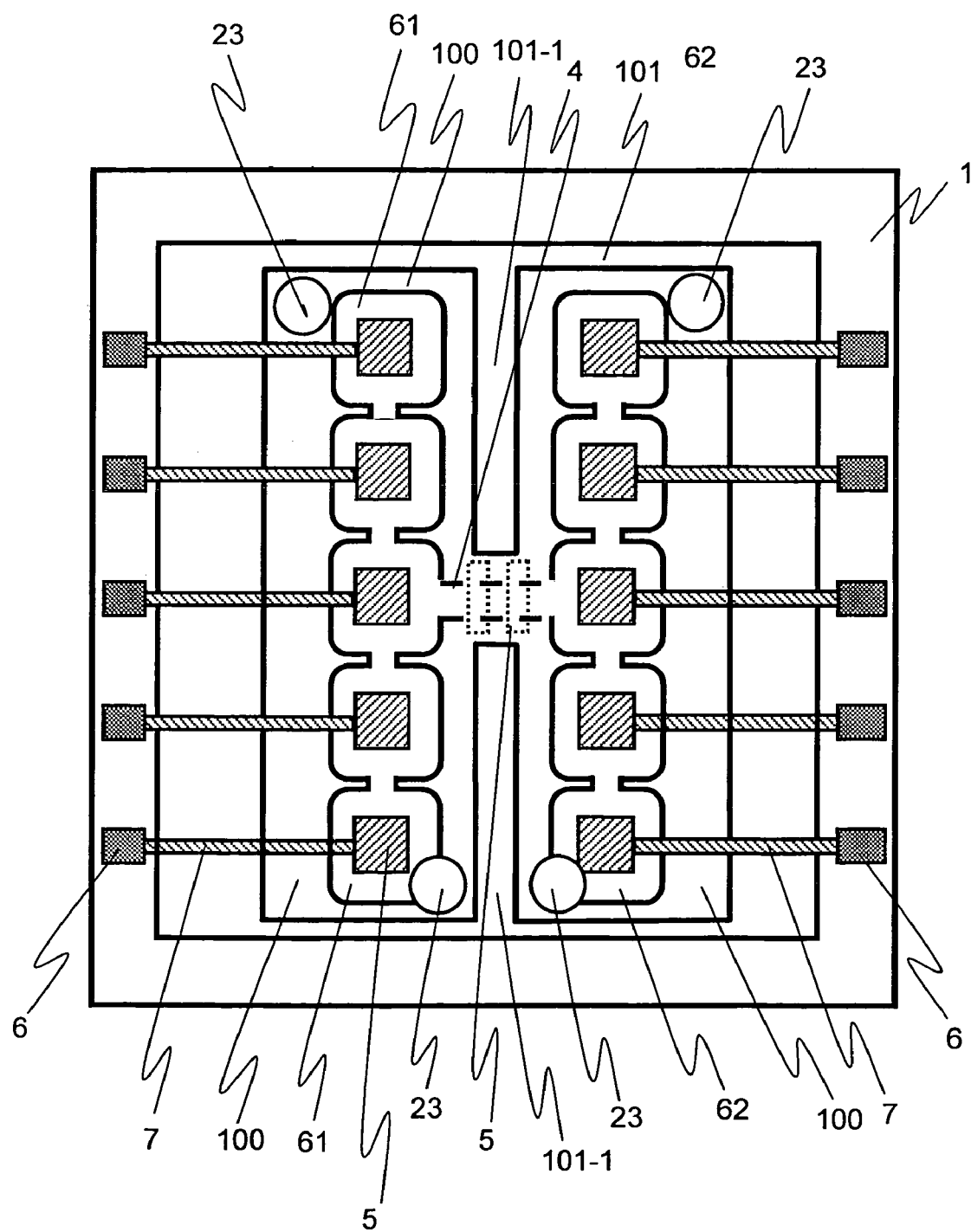
FIG. 50 is a plan view showing a different type cell bioassay chip in which cell holding zones are placed in the array state and the zones are correlated to each other.

FIG. 50 is a plan view showing an example of the heterogeneous cell bioassay chip in which cell holding zones each communicated to adjoining ones with a tunnel or a groove are placed side by side like an array, in place of a block of cells in each cell holding zone, and this array of cell holding zones functions like a block of cells. In FIG. 50, the number of cells in each species is five. The same reference numerals are assigned to the same or equivalent components as those in Examples 1 and 2. The reference numerals 61 and 62 each indicates five arrays, which house heterogeneous cells, in the cell holding zone. Electrodes are provided in each of the cell holding zones in the heterogeneous cell arrays 61, 62 and also in the tunnel 4 between the heterogeneous cell arrays 61, 62. In this case, only one tunnel 4 is provided between the heterogeneous cell arrays 61, 62. AS described in Example 2, the heterogeneous cell arrays 61, 62 are divided by cell type by the projecting section 101-1 of the bank 101, and naturally the culture layers (not shown) corresponding to the heterogeneous cell arrays 61, 62 are divided by the partition 22-2 (not shown) of the housing 22 as described in Example 2, so that different culture fluids can be used for different types of cells respectively.

Examples 2 and 3, combination of a pulsating myocardial cell and a neurocyte is described, but the combination may be changed according to an application, and for instance, a sensor cell such as an olfactory cell or a taste receptor cell or a cell with various types of receptors incorporated therein may be used to communicate with the pulsating myocardial cell or an epithelial cell of small intestine to perform a heterogeneous cell bioassay. Therefore, with this technique, there is provided the possibility of measuring influence of even a substance lethal to a particular cell and not allowing for measuring influence thereof to other cells with the conventional technique by communicating a cell having the durability to the substance and a cell not having the durability to the substance.

As described above, in the ninth embodiment of the present invention, various influences which a cell receives from the environment can objectively be examined by making use of the community effect between heterogeneous cells. Therefore the influence of medicaments, which have been expressed with the subjective words such as "feeling bad or good when a medicament is administered", or effects of environmental conditions to a human body may be expressed digitally.

As described above, a groove may be provided in place of the tunnel 4 in this example. Instead of measuring an electrical response of a cell, change of a form of the cell may be observed by adding a specific testing sample in a culture fluid of the cell. Further, instead of measuring an electrical response of a cell, a specific cell is stimulated using electrodes to measure a response of the cell by adding a specific testing sample in a culture fluid of the cell.

As for the industrial utilization of the heterogeneous cell bioassay chip according to the ninth embodiment of the present invention and bioassays with the bioassay chip, there are the possibilities that researches in academic research organizations or drug manufacturing companies utilize the heterogeneous cell bioassay chip, and also that people concerned in manufactures of heterogeneous cell bioassay chips use the chip. From the user's view point, the chip should preferably be provided in the state in which heterogeneous cells are accommodated in the heterogeneous cell holding zones respectively. However, a cell accommodated in the heterogeneous cell holding zone of the chip can not live for a long period of time, the chip manufactures are required to supply chips clearly showing the expiration date, or to supply a kit including the substrate 1, electrodes, wiring, banks and agarose gel on the substrate 1, dispersion shell 9, and upper housing 22. When a chip is supplied as a kit, the user is required to perform accommodation of heterogeneous cells in heterogeneous cell holding zones and assemble the kit components for building up the bioassay chip.

[X] Tenth Embodiment

A tenth embodiment of the present invention discloses a method allowing for easy exchange of a medium for cell culture and separation of cell culture from a vessel wall without giving any damage to the cultured cell. A cellulose membrane is used as a material for the vessel, and a cell is attached to the cell membrane for culturing. After culturing, the vessel is processed with cellulase to dissolve, melt, and remove the cellulose membrane, so that damages to the cultured cell can be reduced.

In the ninth embodiment, a cell to be cultured is attached to the cellulose membrane for cell culturing. The cellulose membrane may previously be coated with an extra-cell matrix such as gelatin or laminin. After culturing, the cellulose membrane is processed with cellulase to decompose the cellulose membrane and the cultured cell is recovered. The cell membrane is spread on an ordinary dish and culturing is performed on the cellulose membrane. Finally cellulase is slowly poured along a rim of the dish so that the cellulase is spread over the dish. By decomposing the cellulose as described above, it is possible to recover, for instance, an epithelial cells in the sheet state, namely with the inter-cellular adhesion intact.

Further, by spreading the cellulose membrane on a substrate having fine flow paths, the cellulose membrane is preserved, and by feeding a cellulase solution into the fine flow path structure between the cells and the substrate, the cellulose membrane can selectively be decomposed and removed. What is important in this step is that cellulase does not decompose animal cells. For, an animal cell does not have a cell wall like that in cellulose. This fine flow path structure may be used not only for adding cellulose, but also for exchanging a medium during cell culture. Because of this feature, by using a cellulose filter with the molecular weight cut off of 10,000 to 100,000 Daltons as the cellulose membrane according to the necessity, proliferating factors in serum or metabolic decomposition products from cells can be exchanged and removed.

Example 1

FIG. 51(A) to (D) are views schematically showing a case in which cell culture is performed on a cellulose membrane in Example 1 of the ninth embodiment of the present invention, cultured cells are recovered in the sheet state, and further a multi-layered cell sheet is formed.

Figure 51:
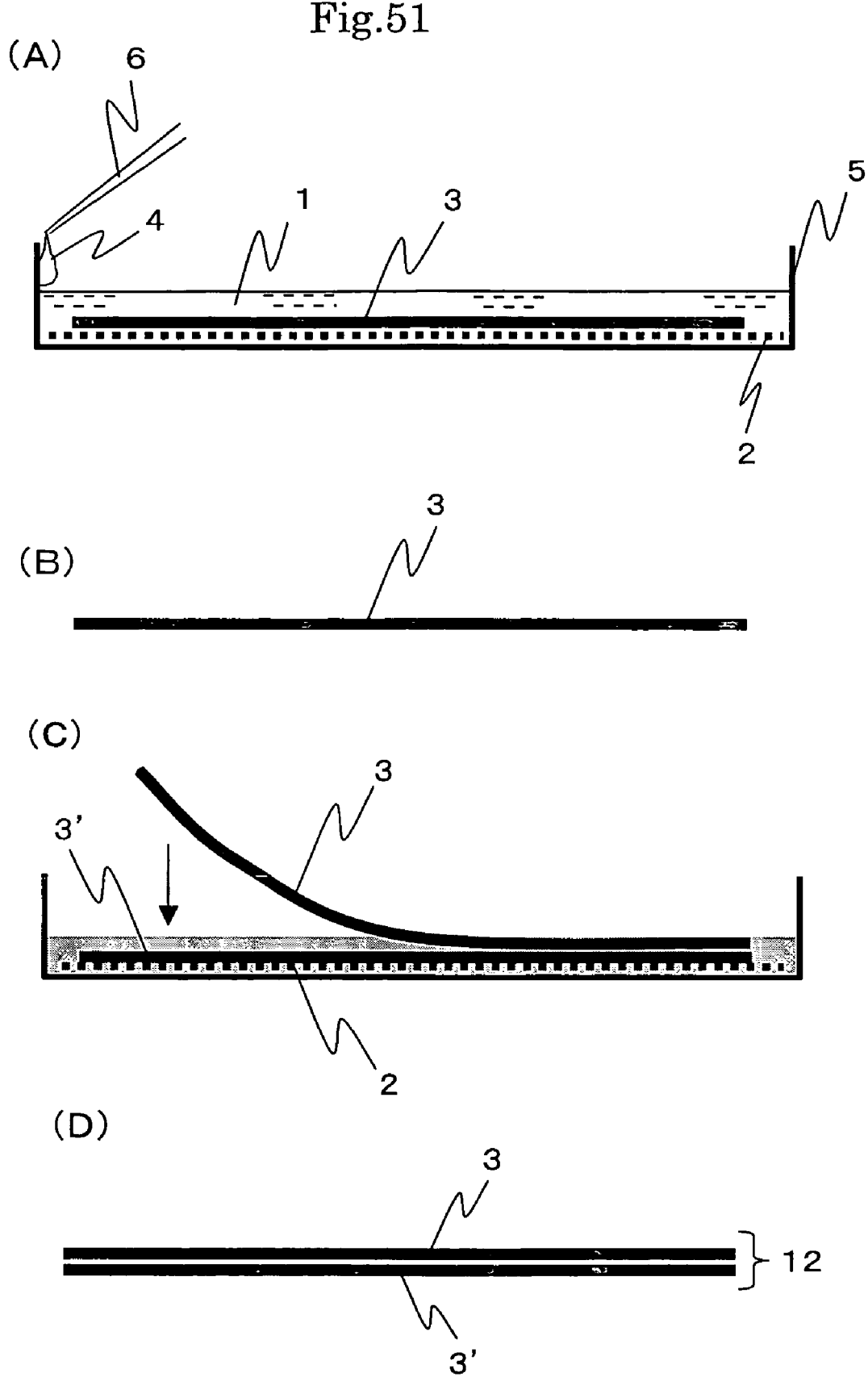
FIGS. 51(A) to 51(D) are views each showing an example in which a cell is cultured on a cellulose membrane according to Example 1 of a tenth embodiment of the present invention, the cultured cells are recovered in the sheet state, and further a multi-layered cell sheet is formed.

As shown in FIG. 51(A), a cellulose membrane 2 (with the molecular weight cut off of 30,000 Daltons, and having the diameter of 55 mmφ) with gelatin coated thereon is spread on a dish (60 mm) 5 storing therein 5 ml of a medium 1 with serum. Preincubation is performed for 30 minutes in 5% $CO_2$ at 37° C. for assimilating the cellulose membrane 2 to the medium 1. A suspension of pulsating myocardial cell is added to the medium by 0.5 ml, and incubation is performed in a $CO_2$ incubator at 37° C. During this incubation, the medium 1 may be exchanged with a new one, if necessary. When the incubation proceeds, the pulsating myocardial cells spread over the substantially entire cell membrane 2 in the sheet form. The reference numeral 3 indicates the pulsating myocardial cells spread in the sheet form.

When the pulsating myocardial cells are spread into the sheet form, the medium 1 is sucked and removed with an aspirator, and immediately a 10 mg/ml cellulase solution 4 (1 ml) is spread along a rim of the dish 5 with a pipet 6. Then the dish is tilted mildly to spread the cellulase solution to the entire bottom surface of the dish for rinsing the cells 3 in the sheet form. Then the cellulase solution is removed with the aspirator, and again the cellulase solution is added by 1 ml. Processing with the cellulase solution is performed twice, because it is assumed that some cellulose inhibitors may be present in the medium. The cells in the sheet form is put in a $CO_2$ incubator at 37° C. to incubate the cells until the cellulose membrane 2 is decomposed and the cell sheet 3 floats. Decomposition of the cellulose membrane can easily be observed with a microscope.

FIG. 51(B) shows the mono-layered cell sheet 3 separated from the cellulose membrane 2 as described above.

FIG. 51(C) shows the state in which the cell sheet 3 already prepared is overlaid on a cell sheet 3' newly prepared as described in relation to FIG. 51(A).

In FIG. 51(C), after the cell sheet 3' is formed, it is important to overlay the cell sheet 3 already prepared and continue incubation before a cellulase solution 4 is added. Incubation after the already prepared cell sheet 3 is overlaid should be performed under the same conditions as those described above. After the incubation is continued, the cellulase solution 4 is added as described in relation to FIG. 51(A) to process the cell sheet with cellulase, a two-layered cell sheet 12 as described in FIG. 51(D) can be obtained.

By repeating the operation steps described above, the cell layers can be laminated up to about four layers. Further, by overlaying the four-layered cell sheets on each other, it is possible to prepare an 8-layered cell sheet. Specifically, at first the four-layered cell sheet is prepared according to the procedure described above and is processed with cellulase to obtain a four-layered cell sheet. Then a four-layered sheet is prepared according to the procedure described above, and the four-layered cell sheet is overlaid on the four-layered cell sheet newly prepared, and incubation is continued. Then the cellulase solution is added as described above to process the cell sheet with cellulase, thus an 8-layered cell sheet being obtained.

Example 2

FIG. 52(A) is a plan view showing a cell culture support body having a structure for preventing cellulase from contacting the entire surface of the cell sheet. FIG. 52(B) is a cross-sectional view showing the cell culture support body shown in FIG. 52(A) taken along the line A-A and viewed in the direction indicated by the arrow. FIG. 52(C) is a cross-sectional view showing the cell culture support body shown in FIG. 52(A) taken along the line B-B and viewed in the direction indicated by the arrow.

A substrate 100 is a vessel with the diameter of 60 mmφ, and has two-staged bottom surfaces 101, 102 on the internal surface. A depth of the higher bottom surface 101 from a top surface of the vessel is about 10 mm, and that of the lower bottom surface 102 from the top surface of the vessel is about 12 mm. Beams 105 each with the width of 1 mm are provided on the lower bottom surface 102. As for a height of the beam 105, a top of the beam is at the same level as the bottom surface 101, so that the beam 105 is located at a relatively lower position. A space between the adjoining beams 105 is about 1 mm. Recesses 103 for sucking or pouring a culture fluid or the like are provided on the bottom surface 102. Further, diffusion plates 106 are provided between the recesses 103 and beams 105 respectively so that the fluid is homogeneously spread into spaces between the beams when a liquid is distributed from the recesses 103. A height of the diffusion plate is about ¾ of that of the beam so that the liquid is leaked over the plate and is spread homogeneously. If the diffusion plate is not provided, a liquid flows only in the shortest flow path, for instance, when a solution such as a culture medium is exchanged, and sometimes the liquid does not homogeneously flow into spaces between the beams.

Figure 52:
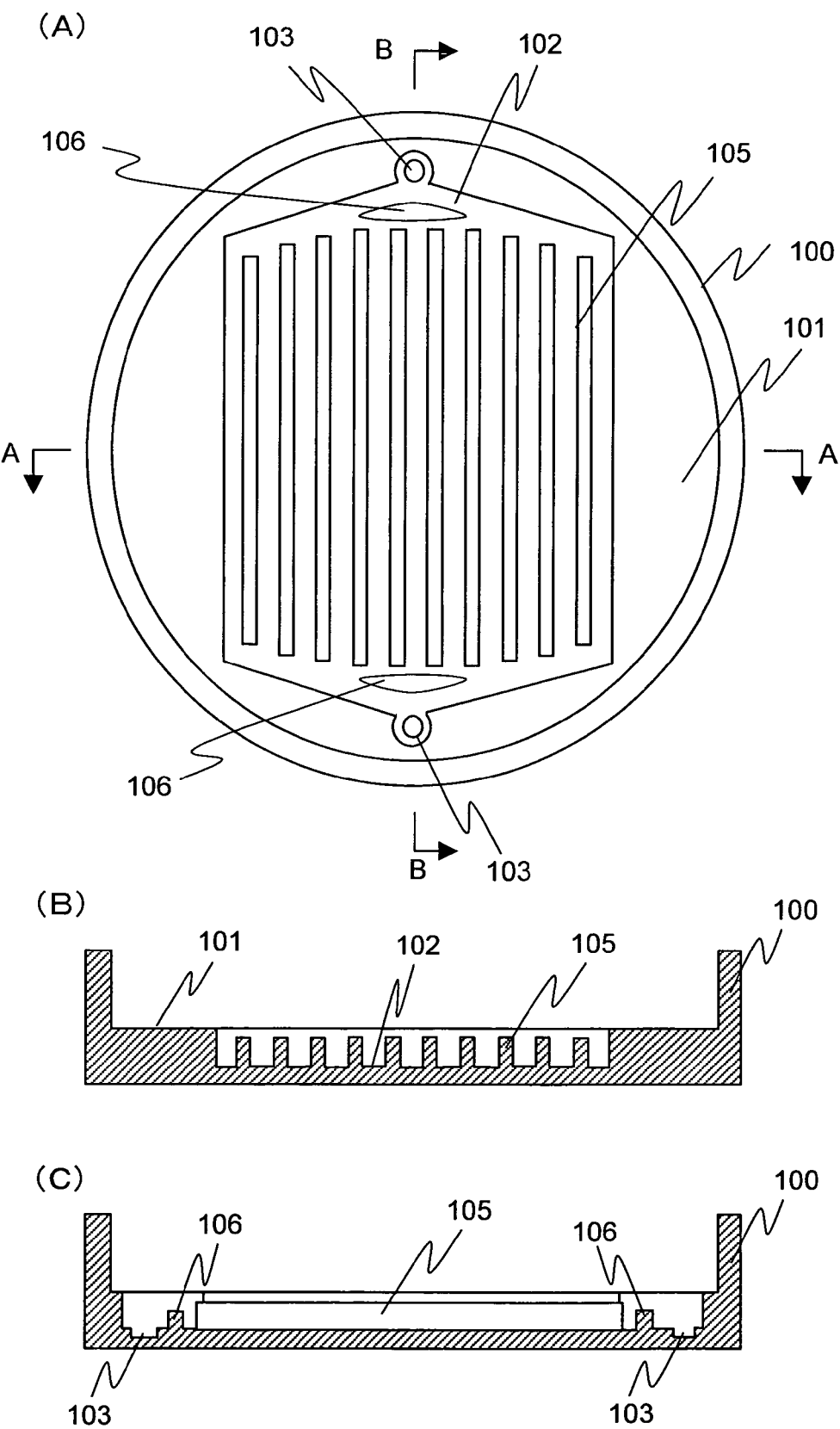
FIG. 52(A) is a plan view showing a cell culture support body functioning as a support body for holding a cellulose sheet.
FIG. 52(B) is a cross-sectional view showing the cell culture support above taken along the line A-A in FIG. 52(A) and viewed in the direction indicated by the arrow.
FIG. 52(C) is a cross-sectional view showing the cell culture support above taken along the line B-B in FIG. 52(A) and viewed in the direction indicated by the arrow.
Figure 53:
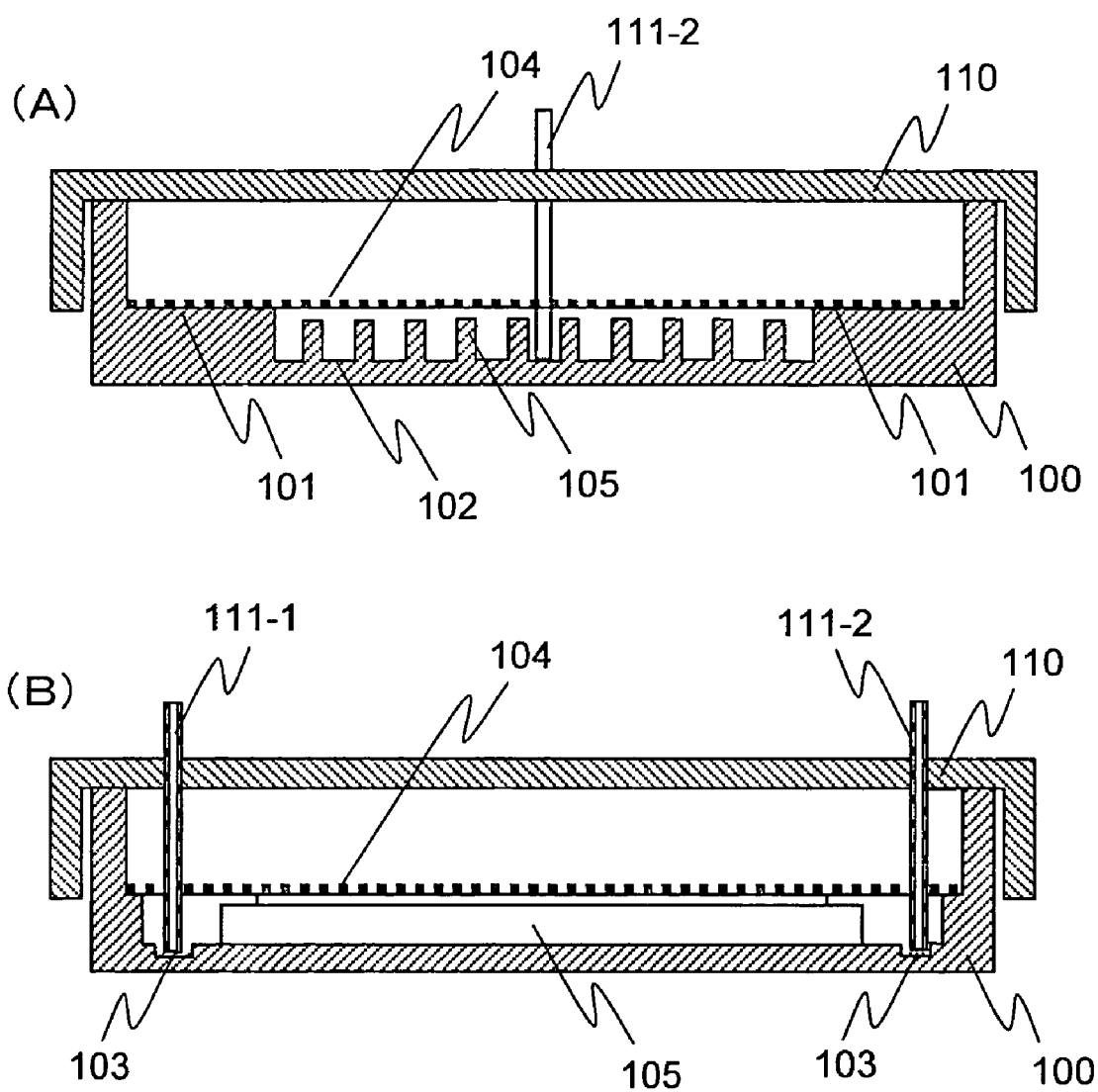
FIG. 53(A) is a cross-sectional view corresponding to a view taking along the line A-A in FIG. 52 and viewed in the direction indicated by the arrow, illustrating the situation in which the cell sheet described in Example 1 is formed by using the substrate 100 illustrated in FIG. 52.
FIG. 53(B) is a cross-sectional view showing the same situation taken along the line B-B and viewed in the direction indicated by the arrow.

FIG. 53(A) is a cross-sectional view illustrating the situation in which the cell sheet described in Example 1 is prepared by using the substrate 100 described with reference to FIG. 52, and is a cross-sectional view showing the substrate shown in FIG. 52 taken along the line A-A and viewed in the direction indicated by the arrow. FIG. 53(B) is a cross-sectional view showing the substrate shown in FIG. 52 taken along the line B-B and viewed in the direction indicated by the arrow. The cellulose membrane 104 is placed on a top face of the face formed with the beams 105 and the bottom surface 101. A cover 110 is placed on a top face of the substrate 100, and tubes 111-1, 111-2 extending to bottom surfaces of the recesses 103 are attached to the cover. When the cover 110 is set, tips of the tubes descend into spaces inside the recesses 103.

The procedure for culturing cells using the substrate 100 in Example 2 is described below. At first, a medium is added up to a top edge of each beam on the substrate 100. In other words, the medium is added until a surface of the higher bottom surface 101 is wetted by the medium. Then the cellulose membrane assimilated to the medium is sunk and is placed on the beams 105 and the higher bottom surface 101. Then the cover 110 is set, and the medium is fed from the tube 111-1 and is exhausted from the tube 111-2. The medium is previously heated to 37° C. Then preincubation is performed for 30 minutes in a $CO_2$ incubator (5% $CO_2$, 37° C.).

Then the substrate 100 is taken out from the $CO_2$ incubator, the cover is opened, the pulsating myocardial cells are spread as described in Example 1, the cover 110 is set, and the medium is exchanged with a new one to continue incubation. When the pulsating myocardial cells are spread to the substantially entire surface of the cellulose membrane, a 10 mg/ml cellulase solution is continuously supplied from the tube 111-1 in place of the medium until top faces of the beams 105 are wetted by the solution. As the cellulose membrane 4 and top faces of the beams 105 are not adhered tightly, the cellulase solution is spread into recesses sections between the beams 105. When the incubation is continuously performed at 37° C., the cellulose membrane 104 is decomposed, and the cultured cells are peeled off in the sheet-like state.

[XI] Eleventh Embodiment

An eleventh embodiment of the present invention discloses a method of constructing a cell network by controlling a small number of heterogeneous cells to form a network for clarifying functions of discrete cells, for examining responses of discrete cells to a medical agent or the like (for bioassay), or for forming an assembly of cells.

For achieving the object as described above, the various types of micro-chambers as described below are required:

1) a cell culture micro-chamber in which homogeneous or heterogeneous cells are arrayed at any positions according to any order, 2) a culture micro-chamber based on a structure enabling free and easy administration of medical agents, induction of physiological activities of each cell, and easy exchange of a culture fluid with a fresh one and including a mechanism for adding a given material during cell culture, 3) a culture micro-chamber including a mechanism enabling easy administration of a medical agent and control for cultural environment, 4) a micro-chamber for cell culture including a recovery mechanism, with which an operation can recover, after a cell network is formed, the formed cell network by removing the culture chamber used for cell culture, and also a method of constructing a cellular structure with the micro-chambers as described above is required.

In the eleventh embodiment, a support body having the structure in which an agarose gel membrane is formed on a cellulose membrane is used as a material for the cell culture chamber. The agarose gel can be melded by heating, and a space for cell culture is formed by making use of this property. For instance, an agarose membrane is provided in a sufficient quantity of aqueous solution, and a converging beam from a laser having the wavelength allowing for absorption by water, for instance, with the wavelength of 1480 nm is irradiated, the converging laser light is absorbed by the agarose gel, generates heat, and melts the agarose gel. The melted agarose gel is dispersed in the solution and the concentration drops to the level below a threshold value required for gelatinization, so that the agarose gel once melted never be gelatinized.

By using this technique, a cell holding well having the resolution of about 1 μm or a connection flow path between the wells can be formed. What is important in this technique is that, when a specified number of specified cells are cultured in each well and a portion of the cell membrane extends to form a junction with an adjoining cell, a direction in which the cell membrane extends and an order of cells with which the junction is to be formed can be controlled. In other words, it is important that a form of a micro-chamber for cell culture can freely be changed during cell culture. With the availability of this kind of technique as described above, for instance, when three types of cells, namely types A, B, and C of cells are cultured in independent wells and the number of cells belonging to each type is four, for instance, such as an operations are possible in which at first four cells belonging to type A are conjugated to four cells belonging to type B independently, then one of the four cells belonging to type A is conjugated to one of the four cells belonging to type B, and then one of the four cells belonging to type A is conjugated to one of the four cells belonging to type C. With the operations as described above, the objective 1) described is achieved.

The agarose gel membrane can easily be processed by heating the gel with converging light when the agarose gel is formed on a cellulose membrane and is present in a solution, or when the agarose gel is placed on a transparent substrate such as a glass sheet. When the agarose gel is placed on an opaque structural body, another technique according to the present invention is required. The opaque structure is, for instance, one made from a material which absorbs or scatters the converging laser beam having the wavelength employed for processing the agarose gel membrane.

When there is an opaque structural body, a flow path having a desired pattern is formed on the agarose gel by contacting a tip of a light-absorbing needle to the agarose gel and focusing the converging light beam not to the opaque structural body but to a portion of the needle. With this operation, regardless of the type of the substrate on which the agarose gel is placed, it is possible to form a desired cell circuit by linking specified cell culture wells according to a desired order. The silicon or SU8 is a structural body which is not completely transparent is disadvantageous for being irradiated by a converging laser beam, but still the materials are used because application of the micro-fabrication technique is advantageous for addition of a reagent or for formation of a micro-structural body for medium exchange.

The objectives 2) and 3) can easily be achieved by not only using a cellulose membrane and but also placing the cellulose membrane on a micro-structure made from silicon or SU8. In cell culture, it is necessary to employ a semipermeable membrane which structurally separates inside of a well accommodating cells therein from a cell fluid bath and also allows for transmission of a cell fluid. When irradiating a converging light beam onto an agarose gel membrane through this semipermeable membrane, it is necessary to make the semipermeable membrane with a material which can hardly be damaged by the converging light beam. As this material, for instance, a cellulose membrane may be used.

The micro-chamber for cell culture in the eleventh embodiment is formed on a semipermeable membrane, and further a micro flow path prepared by the micro fabrication technique contacts the semipermeable membrane, so that it is possible to exchange a culture fluid with a new one via the semipermeable membrane from the micro flow path, to add any additive for bioassay, or to recover molecules released from a cell in response to addition of the additive. Because of this configuration, the objectives 2) and 3) are achieved.

Finally the cell circuit formed as described above is separated from the substrate. Adhesion between cells is not so strong, so that cell circuits can not be mechanically separated from the substrate. It may be considered that a cell bites into a cellulose membrane. Taking into considerations the fact that a volume of the agarose gel is larger and the cells are damaged when heated, the agarose gel is used as a support body as it is. It is necessary to remove the cellulose membrane and separate the cells together with the agarose gel, but the cellulose itself can be decomposed by cellulose. In this state, the cell circuit is held by the agarose gel, and therefore by laminating a plurality of agarose gel sheets prepared as described above, it is possible to three-dimensionally form a cell network structure.

Example 1

FIG. 54(A) is a perspective view showing a micro-chamber for cell culture in Example 1, while FIG. 54(B) is a cross-sectional view showing the micro-chamber in FIG. 54(A) taken along the line A-A and viewed in the direction indicated by the arrow. An agarose gel membrane 1 is integrally formed on a cellulose membrane 2, and is placed on a glass substrate 3. A plurality of wells 5 each for holding a cell thereon are formed on the agarose gel membrane 1. The micro-chamber for cell culture 1 is placed in a vessel 6. A culture medium 7 is present in the vessel, and the micro-chamber 1 is immersed in the culture medium. In FIG. 51(A), the agarose gel membrane 1, cellulose membrane 2, and glass substrate 3 are separated from each other for the purpose of simplification, but actually the components are closely attached to each other as shown in FIG. 54(B).

The agarose gel 1 is made as described below. At first, the water-swelling cellulose membrane 2 (with the molecular weight cut off of 100000 Daltons) is placed on the glass substrate 3 with the dimensions of 20 mm×20 mm×1.1 mm(t), and is provided on a chuck of a spin coater. Size of the cellulose membrane 2 must be larger than that of the glass substrate 3, and the peripheral portions are cut off after the agarose is gelatinized. Then 0.5 ml of 50 mM sodium phosphate buffer liquid with pH of 7.4 containing 0.15 M NaCl in 1.5% agarose gel (previously heated in a microwave oven to dissolve the agarose and then cooled to about 60° C.) is applied to the agarose gel, and the agarose gel is rotated for 10 seconds at 100 rpm. Then the agarose is left in a moisture box for 30 minutes to gelatinize the agarose. With this operation, an agarose gel membrane with the thickness of about 100 μm is formed. Thickness of the gel membrane is decided by conditions for forming the membrane, so that the thickness is adjusted by changing the rotational speed and a temperature of the gel.

In this state, wells 5 for accommodating cells therein, grooves each connecting adjoining wells 5 to each other, and the like have not been formed yet. Size of the well 5 as expressed by a diameter thereof is, for instance, 30 μm, and the agarose gel is removed only in portions corresponding to the well 5. For forming the well 5, the agarose gel is heated, melted, and removed by irradiating a converging laser beam with the wavelength adapted for absorption by water, for instance, 1480 nm to the agarose gel membrane 1. Because a sufficient quantity of culture medium 7 is present in the vessel 6, the melted agarose gel is diffused, and therefore the agarose gel is not again gelatinized because the concentration is lower than the threshold value for gelatinization of the agarose gel. A desired number of wells 5 are formed at desired positions by the method.

Figure 55:
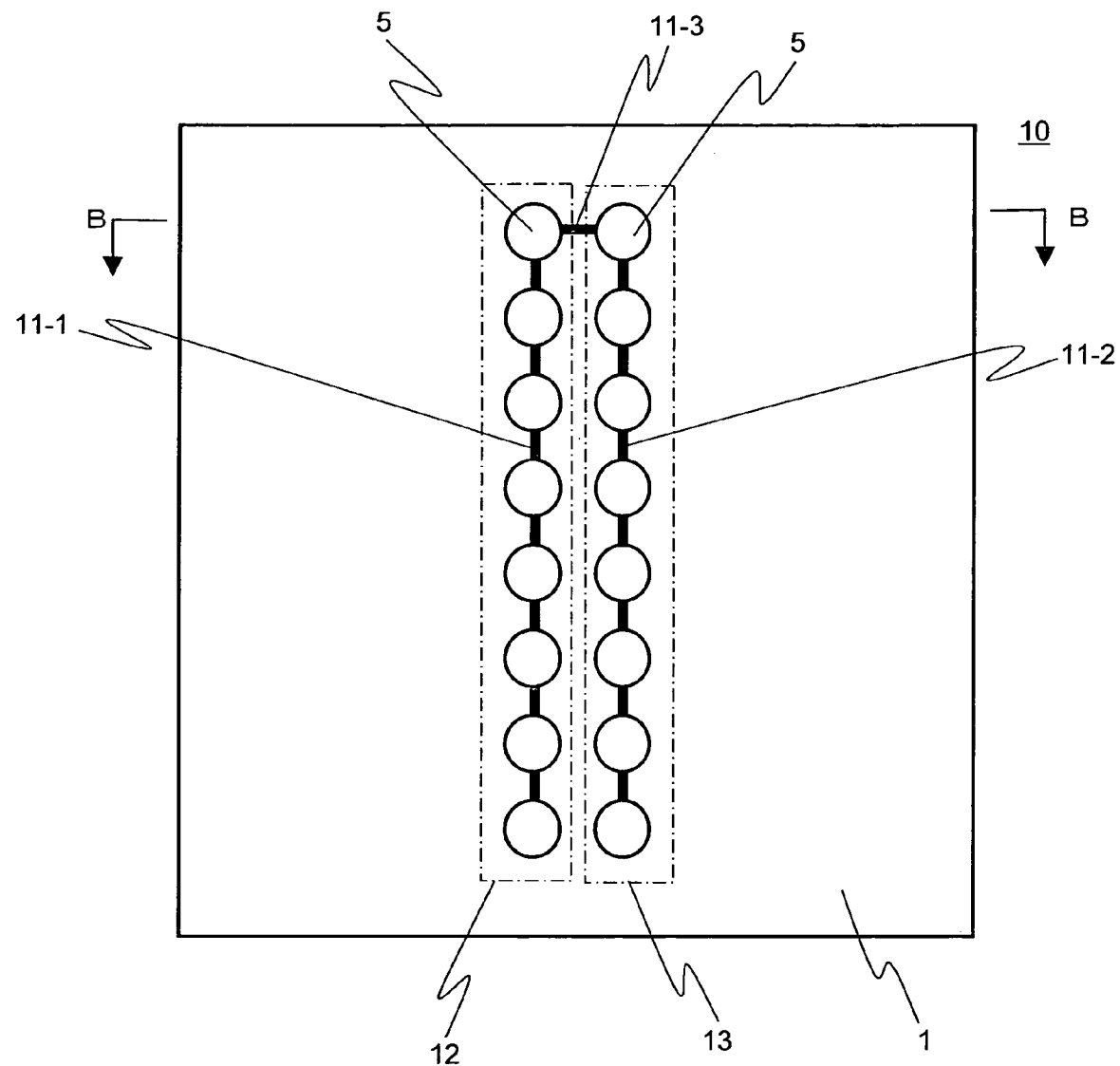
FIG. 55 is a plan view showing an example of a cell culture micro-chamber with a cell circuit formed thereon.

FIG. 55 is a plan view showing an example of the micro-chamber for cell culture with a cell circuit formed thereon. The reference numeral 10 indicates the micro-chamber for cell culture with a cell circuit formed thereon. A cell is put in the well 5 with a micro pipet (not shown). For instance, of 8×2 wells (with the clearance between adjoining wells of 100 μm), a neurocyte is inserted into each of the wells. A pulsating myocardial cell is put in each of the remaining eight wells. The reference numeral 12 indicates a group of wells 5 each with a neurocyte inserted therein, and the reference numeral 13 indicates a group of wells 5 each with a pulsating myocardial cell put therein. When cell culture is continued for a prespecified period of time, the neurocyte and the pulsating myocardial cell generate projections respectively. The projections start extending in random directions, but at this point of time, generation of junctions between cells is prevented by the agarose gel membrane 1.

At first, like in the case in which a well is prepared on the agarose gel membrane 1 between the wells 5 in the group 12 of eight wells each containing a neurocyte therein, a converging laser beam having the wavelength of 1480 nm is irradiated to link the wells 5 with a groove 11-1 for guiding the projections generated on each neurocyte into the groove 11-1 formed on the agarose gel membrane 1. With this operation, gap junctions between neurocytes are formed. Likely, the agarose gel membrane between each well 5 in the group 13 of 8 wells each containing a pulsating myocardial cell therein are linked to each other by a group 11-2 to form a circuit between pulsating myocardial cells. Cell culture is started, only before the grooves are formed between the cells, to prevent the cells from generating projections in random directions with one cell jointing to a plurality of cells, and also for forming a series of cell circuit. If the grooves 11-1, 11-2 are previously formed, projections generated on the cell extend over the well 5 and the cell may be jointed to the adjoining cell. Namely, when a cell has the high activity, the cell generates projections in random directions. On the other hand, when the cell in the adjoining well has the low activity, the cell does not substantially extend the projections. In this case, a cell having the high activity may be jointed to a plurality of cells. To prevent the phenomena as described above, the grooves are not prepared previously, and the grooves should be prepared when the cells are jointed to each other. Further, for instance, when different types of neurocytes are put in the wells 5 in the well group 12, it is necessary to strictly manage an order of linkage between the cells. Therefore, it is more effective to dig a groove after projections are generated on the cells.

Finally, for forming a circuit between the neurocytes in the well group 12 and the pulsating myocardial cells in the well group 13, a converging laser beam is irradiated onto the agarose gel between the two groups. With this operation, the eight neurocytes and eight pulsating myocardial cells are connected with the groove 11-3 to form a cell circuit. In this example, for testing, in a case where a signal flows one-dimensionally, namely in a case a signal from a neurocyte in the well 5 in the well group 12 goes into a pulsating myocardial cell in the well 5 in the well group 13, to check how the signal is transferred to the pulsating myocardial cell in the well 5 in the well group 13, data analysis is easier by connecting the wells 5 at edges of the well groups 12 and 13. When it is necessary to analyze signal transfer in a more complicated circuit between a neurocyte in the well 5 in the well group 12 and a pulsating myocardial cell in the well 5 in the well group 13, any selected wells 5 may be connected according to the object.

In the cell circuit network as described above, for instance, when an electric stimulus is given to or the ionic state is changed in any of the neurocytes, it is observed that a change occurs in a cyclic beat of the pulsating myocardial cells. In other words, this cell circuit may be used in bioassay of various types of medical agents. Each group contains eight cells, because, in a pulsating myocardial cell or a neurocyte, the cooperativeness between cells can be obtained when four or more cells are linked to each other with the projections as compared to the phenomenon observed in a single cell. Especially, when there are eight cells or more, dispersion of myocardial pulsation is suppressed to about 10% (in contrast to about 50% in a test with a single cell).

In Example 1, a top face of the well 5 formed on the agarose gel membrane 1 is open, and with this configuration no problem occurs, because generally an animal cell can not move over a wall with the height of even several μm. Further unnecessary migration of cells can be prevented by placing a cellulose membrane on the entire opening of the well, if necessary.

Finally descriptions are provided for a method of removing the cellulose membrane 2 and adhering fibroblast over the section with the cellulose membrane 2 having been removed.

Figure 56:
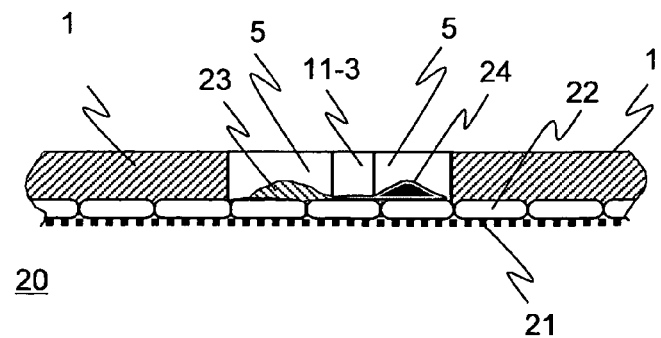
FIG. 56 is a cross-sectional view showing an example of a cell structure construct 20 in which a circuit formed with a neural cell 23 and a oscillating myocardial cell 24 is fixed on a fibroblast sheet 22 on a cellulose membrane 21.

FIG. 56 is a cross-sectional view showing an example of a cell structure construct 20 in which a circuit consisting of a neuron 23 and a pulsating myocardial cell 24 is fixed on a fibroblast sheet 22 on the cellulose membrane 21 taken along the line B-B in FIG. 55 and viewed in the direction indicated by the arrow.

Figure 54:
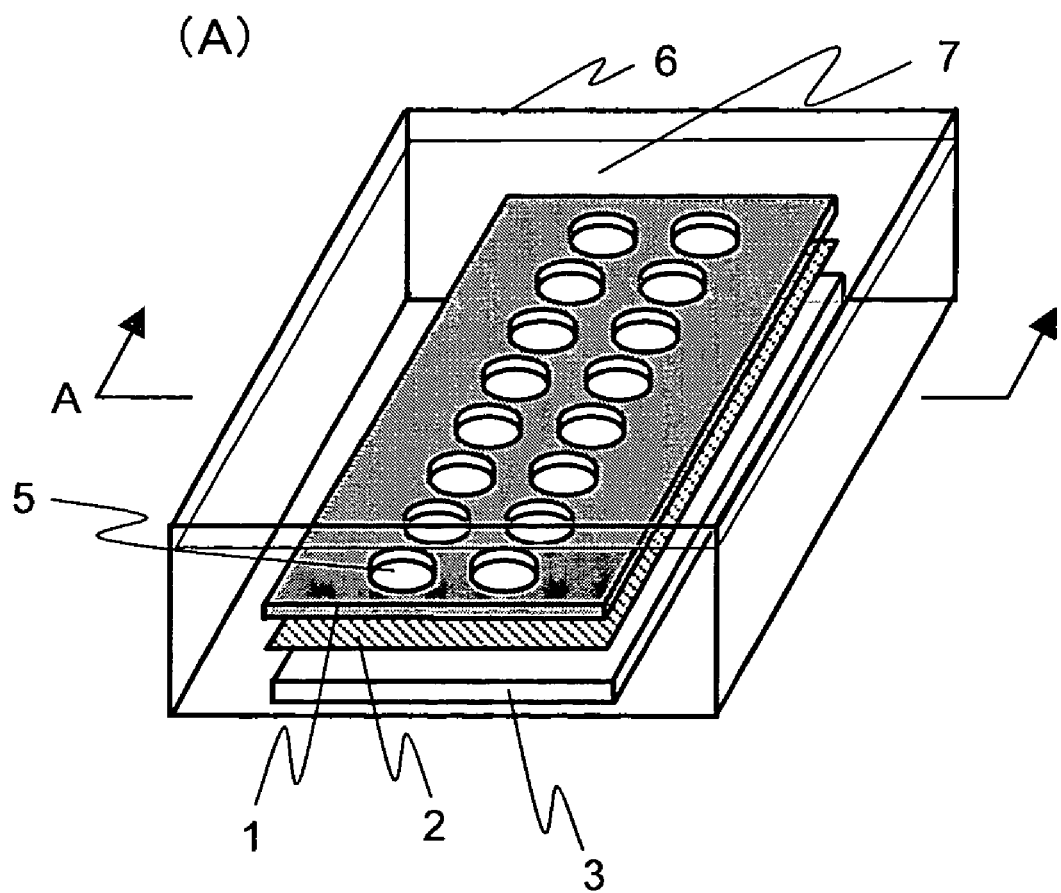
FIG. 54(A) is a perspective view showing a cell culture micro-chamber according to Example 1 of an eleventh embodiment of the present invention.
FIG. 54(B) is a cross-sectional view showing the cell culture micro-chamber taken along the line A-A and viewed in the direction indicated by the arrow.
Figure 54:
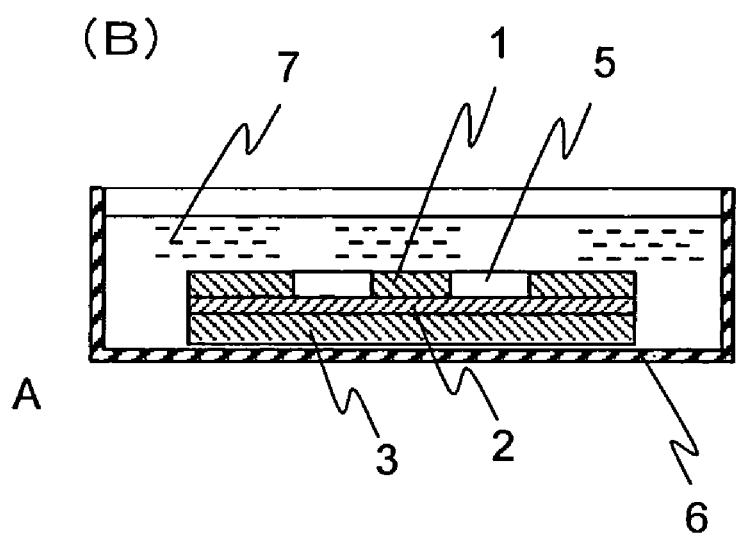

At first, the cellulose membrane 2 formed on the glass substrate 3 described with reference to FIG. 54 and a structural body based on the agarose gel 1 are separated from the glass substrate 3 and are floated in the vessel 6. For this purpose, cellulase is added in the culture medium 7 in the vessel 6 accommodating therein the cell culture micro-chamber 10 on which the cell circuit has been prepared, and a quantity of cellulase is adjusted to 50 mg/ml as expressed by the final concentration. When the sample is incubated at 37° C., the cellulose membrane 2 on the glass substrate 3 is gradually decomposed.

Separately, fibroblast cultured into a sheet form is prepared, and a surface of the agarose gel membrane 1 with the cellulose membrane 2 melted thereof is contacted to the fibroblast. When the cell culture is continued in this state, the cell structure construct 20, in which the agarose gel membrane 1 is directly adhered to the fibroblast layer 22, is obtained. A neurocyte 23 is put in the left well 5, and a pulsating myocardial cell 24 is put in the right well 5, and the two cells extend projections to joint to each other with the groove 11-3. In FIG. 56, the reference numeral 21 indicates a cellulose membrane, and as understood from the following description concerning construction of the sheet-formed fibroblast, the cellulose membrane 21 is different from the cellulose membrane 2 used for forming the agarose gel membrane 1.

As described above, in the eleventh embodiment, a groove is formed between wells containing cells to be conjugated to each other during cell culture, and therefore after a structural body in which the cellulose membrane 2 and the agarose gel membrane 1 are placed on the glass substrate 1 is formed, the wells 5 are formed on the agarose gel membrane 1 with cells put therein respectively, and then grooves each connecting adjoining wells 5 to each other are formed. In other words, cell network containing cells is formed at first, and then the cellulose membrane 2 is melted with cellulase, and the cellulose membrane 2 is contacted to the fibroblast sheet 22. The neurocyte 23 and the pulsating myocardial cell 24 extend projections to the fibroblast sheets 22 and are attached thereto.

Figure 22:
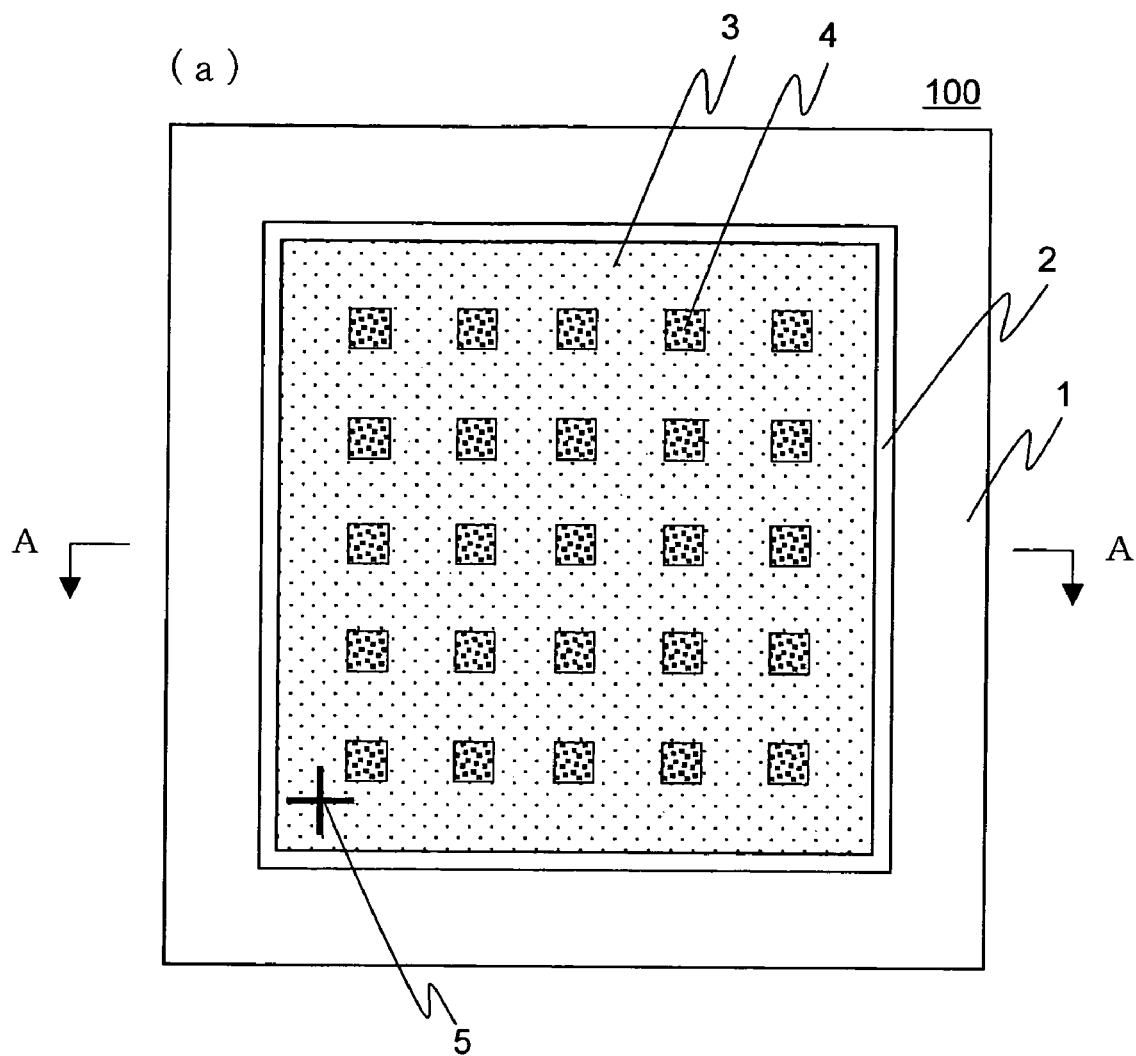
FIG. 22($a$) is a plan view showing a cell culture chip 100 advantageously used in Example 1 of a fifth embodiment of the present invention, and FIG. 22($b$) is a cross-sectional view showing the cell culture chip 100 taken along the line A-A in FIG. 22($a$) and viewed in the direction indicated by the arrow.
Figure 22:
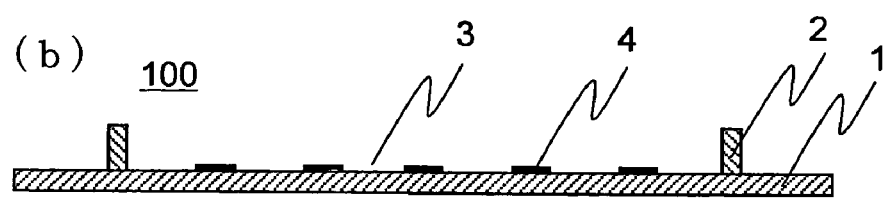

To culture the fibroblast into the sheet state, a cellulose membrane 21 (with the molecular weight cut off of 30,000 Daltons, 55 mmφ) with gelatin applied thereof is spread on a dish (60 mm) with 5 ml medium 1 including serum accommodated thereon. Incubation is performed for 30 minutes in 5% $CO_2$ atmosphere at 37° C. to assimilate the cellulose membrane to the medium. 0.5 ml suspension of fibroblast cells is added to the medium, and incubation is further continued in the $CO_2$ incubator at 37° C. During this incubation, the medium is exchanged with a new one, if necessary. When the cell culture proceeds, the fibroblast pulsating myocardial cells spread like a sheet on the entire surface of the cellulose membrane 21. FIG. 22 schematically shows the state in which the fibroblast has spread into the sheet state on the cellulose membrane 21.

Example 2

In Example 1, the cellulose membrane 2 is placed on a top surface of the flat glass substrate 3, but in Example 2, a support body for supporting the cellulose membrane 2 is more improved, and a cell can more easily be controlled during incubation in the state in which the cell is placed in the well 5 formed on the agarose gel membrane 1.

Figure 57:
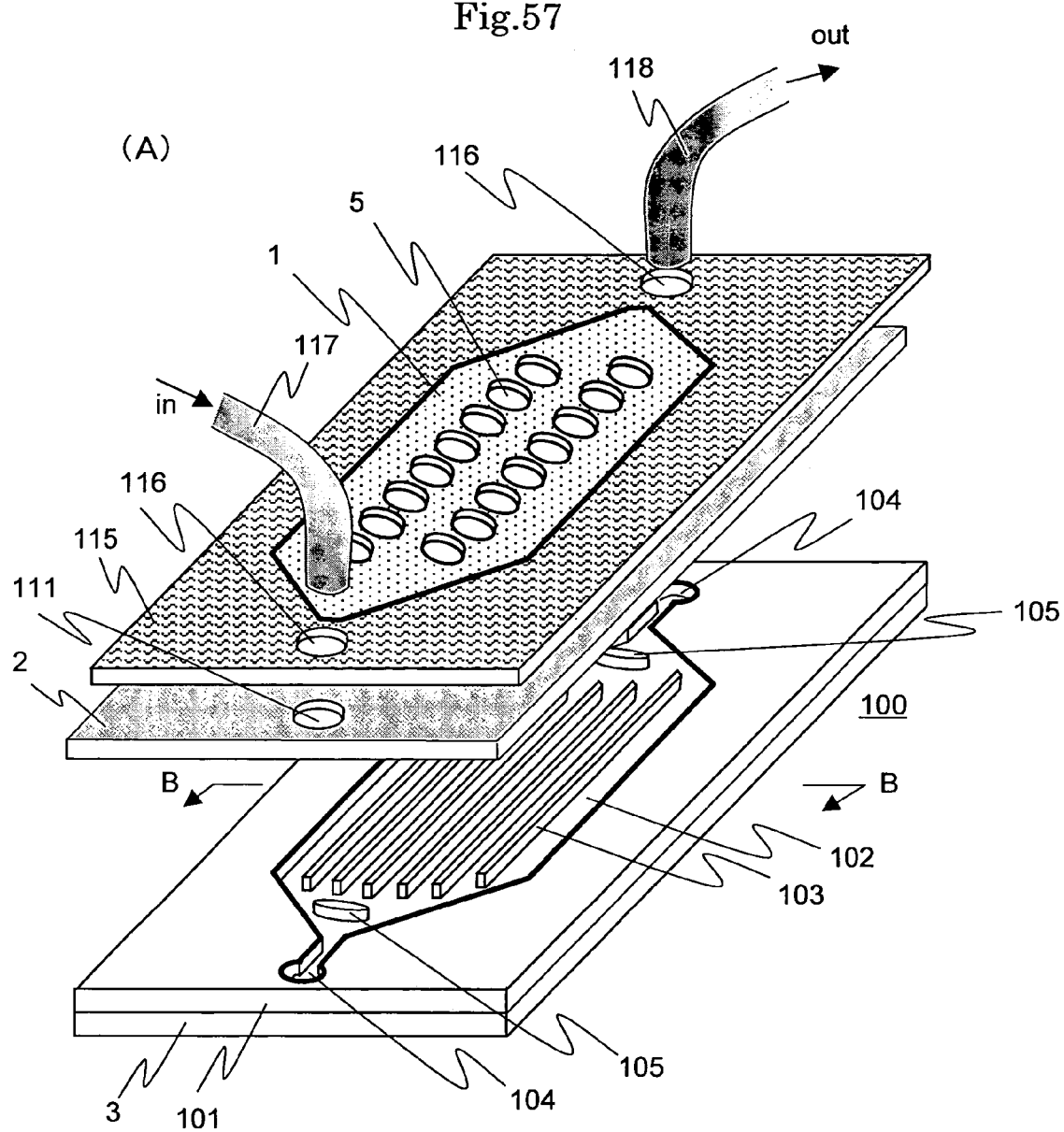
FIG. 57(A) is a perspective view showing the cell culture micro-chamber.
FIG. 57(B) is a cross-sectional view showing the cell culture micro-chamber shown in FIG. 57(A) taken along the line B-B and viewed in the direction indicated by the arrow.
Figure 57:
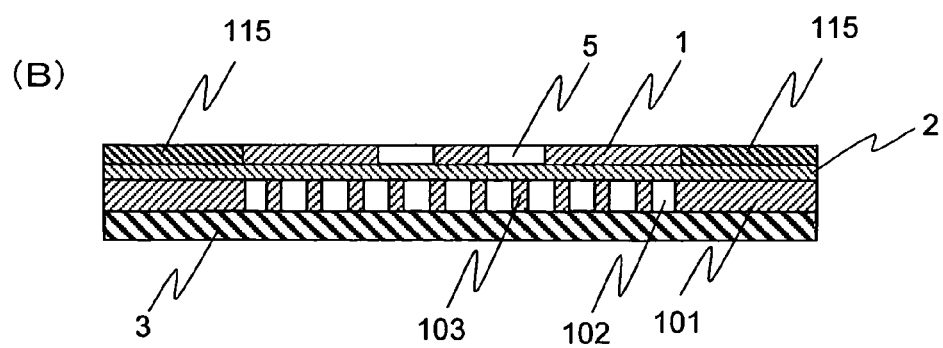

FIG. 57(A) is a perspective view showing a micro-chamber for cell culture, while FIG. 57(B) is a cross-sectional view showing the micro-chamber shown in FIG. 57(A) taken along the line A-A and viewed in the direction indicated by the arrow. The substrate 100 is based on a structural body 101 with the thickness of 2 mm placed on a top surface of the glass plate 3 with the size of 60×60 mm. The structural body 101 may be shaped into a specific form at first with polydimethylsiloxane polymerized. Alternatively the structural body may be cut off from a plastic sheet employed in place of the glass plate 3. Also the structural body 101 may be made with SU 8. A rhombus pool 102 with the depth of 2 mm, in which a solution such as a culture medium flows, is formed, and then a plurality of beams 103 with the width of 1 mm and height of 2 mm are formed in the pool 2. Space between the adjoining beams 103 is about 1 mm. End sections of each beam are off from the periphery of the pool 102. Spaces 104, through which a solution is introduced or exhausted, are formed at positions opposite to the pool 102. A dispersion plate 105 with the height of 1.5 mm is formed between the space 104 and beam 101 so that the solution is homogeneously spread into spaces between the means 103.

The reference numeral 2 indicates a cellulose membrane, which has the size sufficiently covering the top surface of the structural body 101, and the thickness varies from product to product, but is generally in the range from 30 to 100 µm. The reference numeral 111 indicates an opening, which is provided at a position corresponding to the space 104 through which a solution is introduced or exhausted.

The reference numeral 115 indicates a thin plastic plate with the thickness of about 100 µm. The thickness of the thin plastic plate 115 is preferably the same as that of the agarose gel membrane. The thin plastic plate 115 is used as a support body for the cellulose membrane 2, and is also used as a wall material for forming the agarose gel membrane 1. The agarose gel membrane 1 is formed at a position corresponding to the rhombus pool 102 at a central portion of the thin plastic plate 115 (which hereinafter described). Further openings are formed at positions corresponding to the spaces 104, through which a solution is introduced or exhausted, provided at two edge sections of the thin plastic plate 115. In FIG. 57(A), the cellulose membrane 2 and the thin plastic plate 115 are separated from each other, and also are off from a top surface of the structural body 101, but actually the components are overlaid on each other as shown in FIG. 57(B).

The cellulose membrane 2 may be adhered to the thin plastic plate 115 with an adhesive before the agarose gel membrane 1 is formed, and also may simply be placed on the structural body 101 made from SU8 with the thin plastic plate 115 overlaid thereon. In any case, the cellulose membrane 2 and thin plastic plate 115 are placed and assembled in the integrated state on a top surface of the structural body 101 before the agarose gel membrane 1 is formed.

In this process, agarose with the melting temperature of about 65° C. and a concentration of 1.5% is used. The agarose is melded in a microwave oven and is coated on a region for forming the cellulose membrane 2 integrated with the thin plastic plate 115, and is left for 30 minutes in the wet state at the room temperature. As a result, the thin plastic plate 115 with the agarose gel membrane 1 adhered on the cellulose membrane 2 can be obtained.

Next descriptions are provided for a method of forming a groove 11 between adjoining wells 5. Different from Example 1, in this example, the substrate 100 is not always required to be transparent to the converging light beams with the wavelength of 1480 nm. Therefore, in this example, the groove 11 between the adjoining wells 5 can not be formed by irradiating the converging light beam.

When the cellulose membrane 2 is adhered to the thin plastic plate 115 with an adhesive before the agarose gem membrane 1 is formed, the wells 5 can be formed on the glass substrate transparent to the converging light beam by removing the thin plastic plate 115 with the agarose gem membrane 1 formed thereon from the substrate 100. However, another technique is required when the cellulose membrane 2 is placed on a top surface of the structural body 101 and held by the thin plastic plate 115. Also another technique is required for forming a groove to be prepared after the cell culture is started.

As described above, when wells 5 can not be formed on the glass substrate transparent to the converging light beams, a converging light beams with the wavelength, absorption of which by water can substantially be ignored, (for instance a converging light beam with the wavelength of 1064 nm) is used. When the converging light beams with the wavelength, absorption of which by water can substantially be ignored, is employed, even if the light beams is irradiated onto the agarose gel membrane 1, the agarose gel membrane 1 can not absorb the light beams and convert the energy to heat, so that the agarose gel membrane 1 can not be processed. To overcome this problem, the light beam is irradiated to a micro needle functioning as a transducer to convert energy of the converging light beam to heat, and the agarose gel membrane 1 is processed by making use of this heat.

Figure 58:
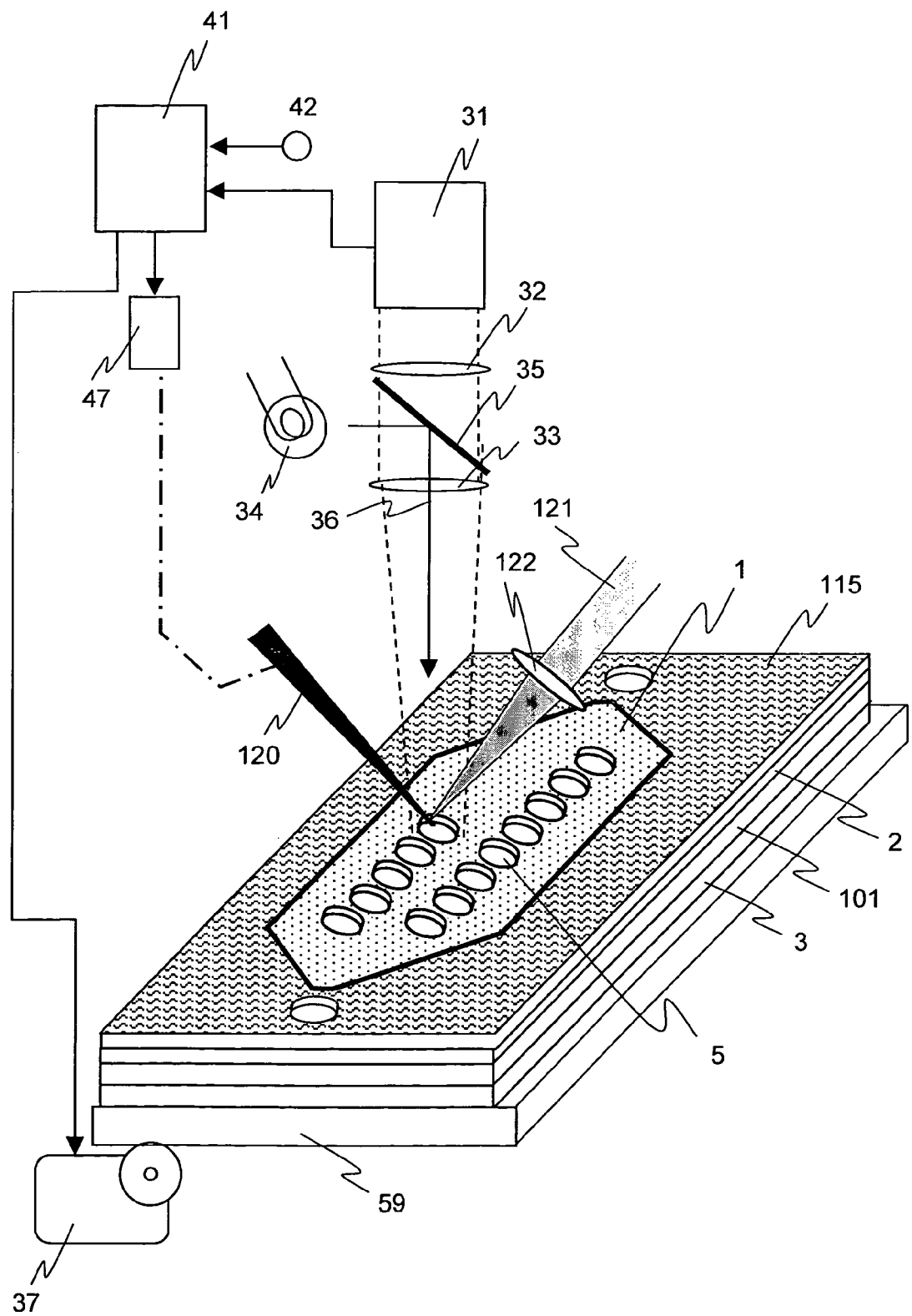
FIG. 58 is a schematic view for illustrating a system in which a converging light is converted to heat with a micro-needle and an agarose gel film 1 is processed with the heat.

FIG. 58 is a schematic view illustrating an outline of the system for converting a converging light beam to heat with a micro-needle and processing the agarose gel membrane 1 with the heat. A micro-chamber for cell culture integrated with a thin plastic plate 115 having a glass substrate 3, the structural body 101, the cellulose membrane 2 and the agarose gel membrane 1 formed thereon is put in a chamber (not shown) containing a culture medium and is placed on a stage 59. The stage 59 is driven in any of directions X and Y by a driving device 35 operating according to a drive signal from the personal computer 41. The reference numeral 31 indicates camera which is, for instance, a CCD camera, and picks up images of a processed surface of the agarose gel membrane 1 via lenses 32, 33. In this step, a light source 34 is prepared, a light beam is introduced through a half mirror 35 provided between the lenses 32, 33 and irradiated in the direction indicated by an arrow 36. The light beam may directly be irradiated from above the micro-chamber for cell culture without using the half mirror 35. The reference numeral 41 indicates a so-called personal computer, which stores therein necessary programs, receives information concerning a surface to be processed from the camera 31, and also receives an operation-related signal 42 from a user. Although not shown in the figure, a display unit is provided on the personal computer 41, and an image of the surface to be processed from the camera 31 is displayed thereon.

The reference numeral 120 indicates a micro-needle used to process the agarose gel membrane 1. A laser beam 121 is focused by a lens 122 and irradiated as a converging light beam to the micro-needle 120. The micro-needle 120 is made from, for instance, silicon or carbon, and a diameter of a tip section thereof should preferably 2 µm. The laser beam 121 with the wavelength of 1064 nm is irradiated through the lens 122 onto a tip section of the micro-needle. Then a temperature of the tip portion of the micro-needle 120 rises, so that the agarose gel membrane 1 can be melted. An agarose gel in a necessary range can be melted and removed by moving the stage 59 in the directions X and Y, while monitoring the processed surface of the agarose gel membrane 1.

The micro-needle 120 can be separated upward from the processed surface of the agarose gel membrane 1 according to a user's instruction via the personal computer 41. When the micro-needle 120 is separated in the upward direction, irradiation of the converging light beam 121 should preferably be stopped. When a user forms one well 5 monitoring the processed surface of the agarose gel membrane 1 with the micro-needle 120 and converging light beam 121, the user gives an instruction to move the micro-needle 120 in the upward direction to the personal computer 41, when the instruction to move the micro-needle 120 in the upward direction is given to an up-down driving device 47 of the micro-needle 120, so that the micro-needle 120 moves in the upward direction and goes off from the processed surface of the agarose gel membrane 1. A chain line 48 indicates coordination between an up/down movement device 47 and the micro-needle 120. In the state where the micro-needle 120 has been separated from the processed surface of the agarose gel membrane 1, the user gives an instruction for movement of the stage 59 to the personal computer 41 to form the next well 5. In response to this instruction, the personal computer 41 gives a drive signal to the driving device 37; thus the stage 59 being driven.

The user monitors a tip of the micro-needle 120 and stops the stage 59 when the tip of the micro-needle 120 reaches a position at which the next well 5 is to be formed. At the new position, the micro-needle 120 is moved downward as described above, and the converging light beam 121 is irradiated to form the next well 5.

Figure 59:
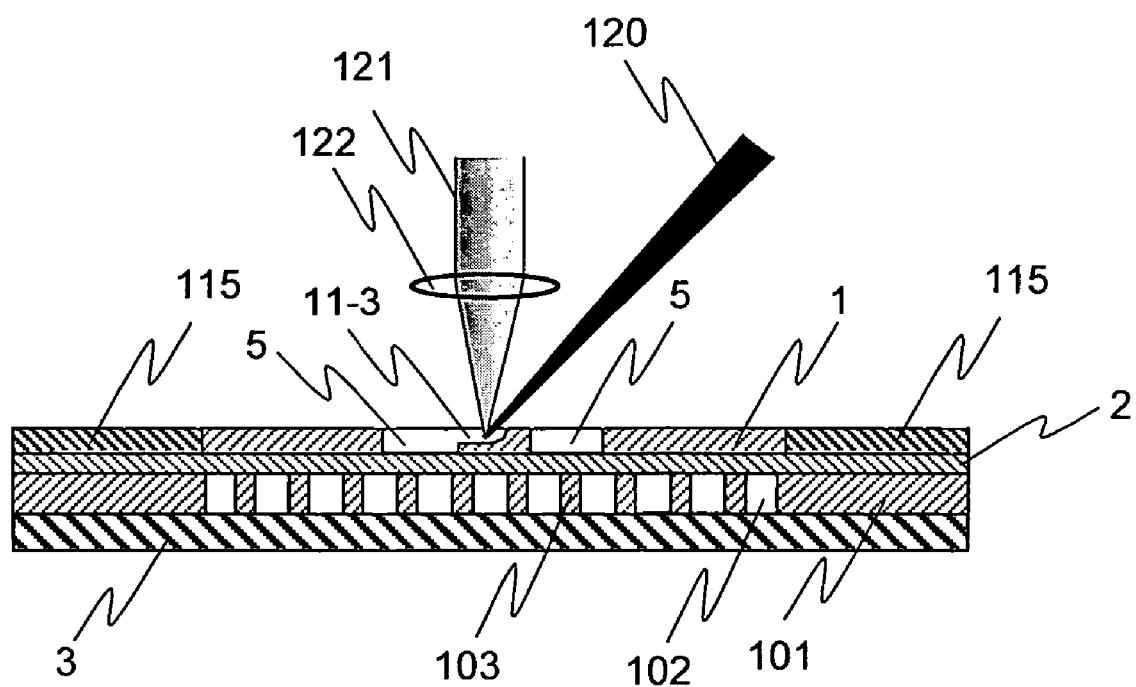
FIG. 59 is a schematic view illustrating outline of the situation in which a groove between wells 5 is formed on the agarose gel film 1, during cell culture, with a micro-needle in the same way as that illustrated in FIG. 58.

FIG. 59 is a schematic view showing an outline of the situation in which a groove between the wells 5 on the agarose gel membrane 1 is formed during cell culture. FIG. 59 schematically shows the situation in which a groove 11-3 between the wells 5 shown in FIG. 55 is being formed. The micro-chamber for cell culture integrated with the thin plastic plate 115 with the glass substrate 3, the structural body 101 made from SU8, the cellulose membrane 2, and the agarose gel membrane 1 formed thereon is described with reference to FIG. 57(B). An operator is required only to engrave the groove 11-3 from one side of the adjoining well 5 with the micro-needle 120 and converting light beam 121. With the method as described above, regardless of a type of the substrate on which the agarose gel is placed, a desired cell circuit can be formed by connected selected cell culture wells according to a specified order.

In Example 2, as understood from FIG. 57(A), tubes 117, 118 of the micro-chamber for cell culture integrated with the thin plastic plate 115 with the glass substrate 3, the structural body 101 made from SU8, the cellulose membrane, and agarose gel membrane 1 formed thereon can be inserted into the space 104 through which a solution can be introduced into or exhausted from the rhombus pool 102 formed in the structural body 101 made from SU8 through openings 116, 111. Therefore, the cellulose membrane 2 can efficiently be decomposed by pouring cellulase from the contrary side of the agarose gel membrane 1 via the tubes 117, 118 and directly contacting the cellulase to the cellulose membrane 2, and also the culture medium can easily be exchanged with a new one or any additive can be added to or removed from the medium during cell culture.

Others

In the examples above, the micro-chamber for cell culture is described as a completed one in any case. However, the micro-chamber for cell culture is required only to allow for placement of a cell or the like in the cell culture zone 5 and formation of a groove or grooves by a researcher using the micro-chamber. Therefore, for instance, in Example 1, it is practical to provide the gel membrane 1 formed with the semipermeable membrane (cellulose membrane) 2 and agarose or agarose derivative formed thereon, or the gel membrane with cell culture zones 5 formed thereof is provided as a market product. In this case, a researcher or other persons having purchased the product places the product on an appropriate glass substrate, prepares a culture fluid, puts in a cell or the like in each of the cell culture zones 5, and forms a groove during cell culture.

Also in Example 2, it is practical to provide an assembly prepared by adhering the cellulose membrane 2 to the thin plastic plate 115 with adhesive and also forming a agarose gel membrane in an area of the thin plastic plate 115 for forming the agarose gel membrane 1, or an assembly prepared by forming cell culture zones 5 on the gel membrane as a market product. Further a structural body 101 with a plurality of beams 103 for forming a rhombus pool 102 through which a solution such as a culture medium flows and also functioning support materials for the agarose gel membrane 1 and the tubes 117, 118 may be provided as a kit for cell culture micro-chamber. In this case, a researcher or other persons prepares a culture fluid, puts a cell or the like in the cell culture zone 5, and forms a groove between wells during cell culture.

[XII] Twelfth Embodiment

A twelfth embodiment of the present invention discloses, like in the ninth embodiment, a structure in which a network consisting of a minimum number of cells with a plurality of heterogeneous cells interacting therein on a chip for measuring change in responses of the cell network to a stimulus controlling the network consisting of a small number of heterogeneous cell.

Example 1

Figure 60:
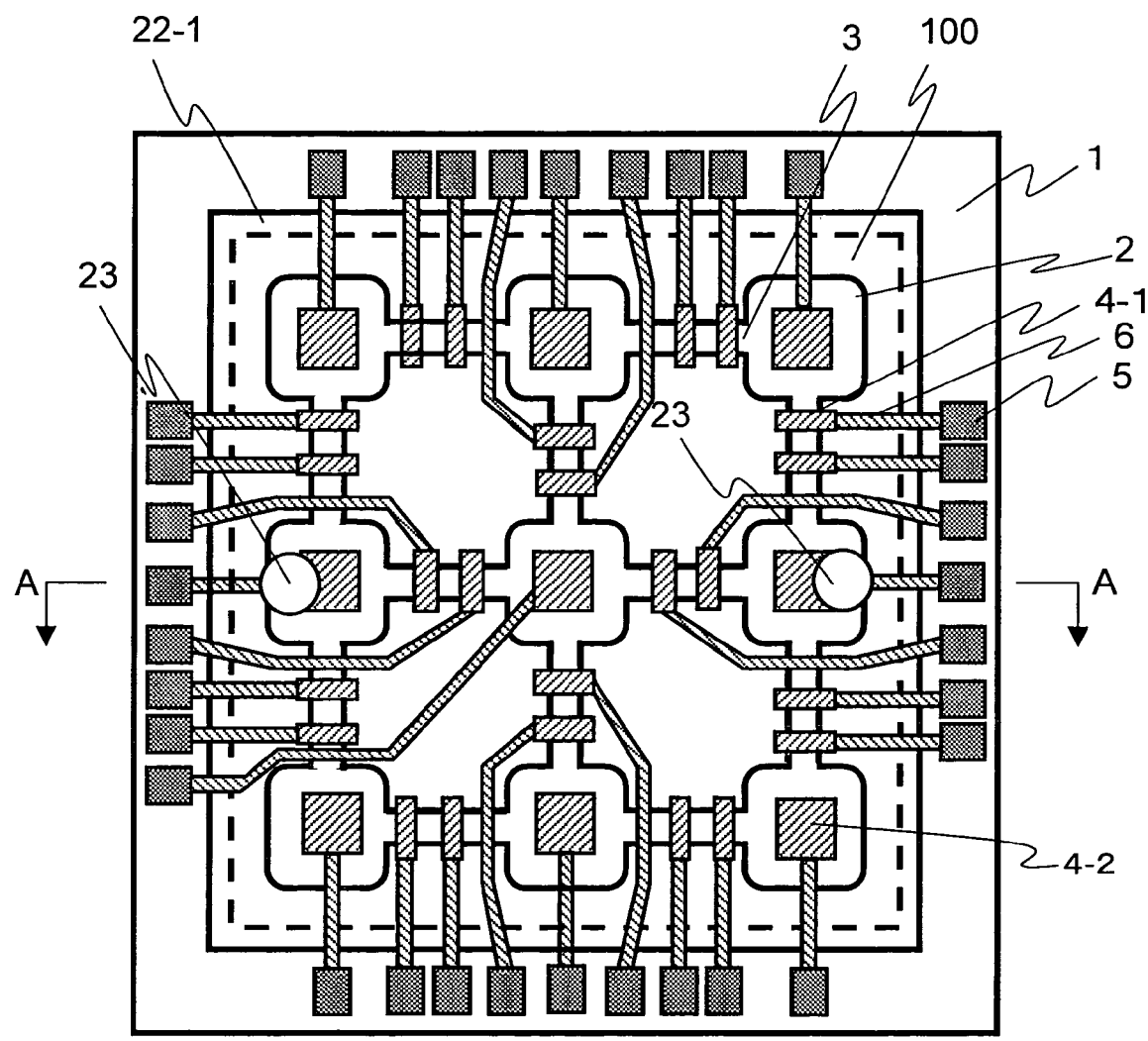
FIG. 60 is a plan view schematically showing an example of a structure of a cardiac-myocyte-cell bioassay chip in Example 1 of a twelfth embodiment of the present invention.
Figure 61:
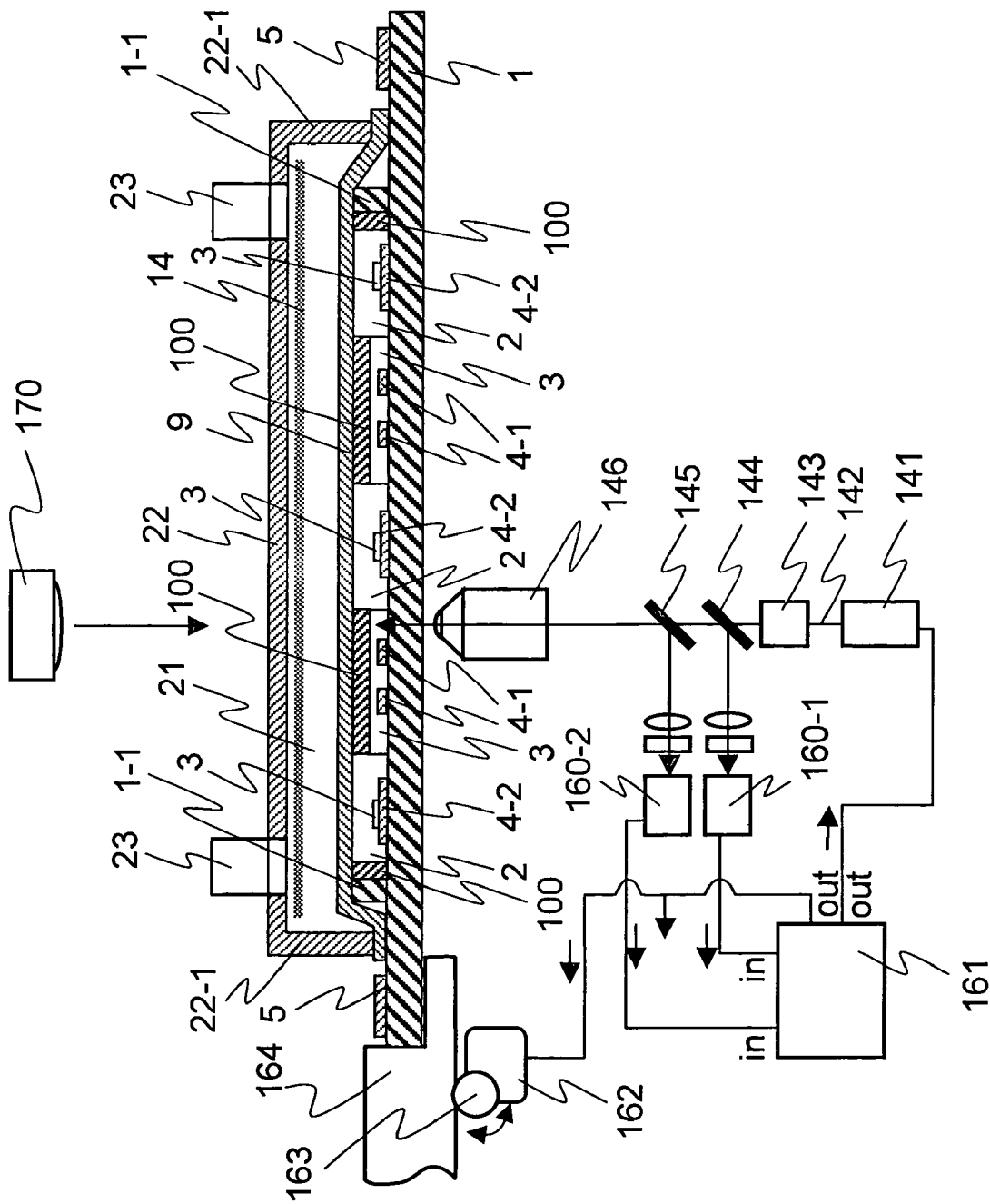
FIG. 61 is a cross-sectional view showing the cardiac-myocyte-cell-bioassay chip shown in FIG. 60 taken along the line A-A and viewed in the direction indicated by the arrow.

FIG. 60 is a plan view schematically showing an example of a cardiac muscle cell bioassay chip in Example 1 of the twelfth embodiment of the present invention. FIG. 61 is a cross-sectional view showing the bioassay chip shown in FIG. 60 taken along the line A-A and viewed in the direction indicated by the arrow. The cardiac muscle cell is not shown now. The reference numeral 1 indicates a substrate, and all constructs are provided on the substrate 1. The reference numeral 2 indicates a cardiac muscle cell holding zone, and a plurality of zones 2 are regularly formed thereon. The reference numeral 3 indicates a groove or a tunnel, which connected adjoining cardiac muscle cell holding zones 2 to each other. The cardiac muscle cells extend the projections through the groove or tunnel 3 to contact each other and form a gap junction. The reference numeral 100 indicates an agarose gel, which is formed on the substrate 1, and the cardiac muscle cell holding zones 2, the groove or tunnel 3 connecting the zones 2 to each other are formed by partially removing the agarose gel 100. The reference numerals 4-1, 4-2 indicate electrodes respectively, and the electrode 4-1 is provided in all of the groove or tunnel 3, while the electrode 4-2 is provided in all of the cardiac muscle cell holding zones 2. The electrode 4 comprises a transparent electrode (ITO) and is adhered by deposition on a surface of the substrate 1. The reference numeral 5 indicates an external terminal, and is provided around the substrate 1 at a position corresponding to and close to the electrode 4. The reference numeral 6 indicates wiring, which connects the electrode 4 to the external terminal 5. The wiring 6 is not shown in FIG. 61 for simplification. The electrode 4 and wiring 6 have the thickness of about 100 nm, and is made from transparent ITO. The reference numeral 1-1 indicates a wall provided on the substrate 1, which defines and holds a peripheral section of the agarose gel 100. The reference numeral 9 indicates a semipermeable membrane, which is provided and adhered to a top surface of the agarose gel 100 with the cardiac muscle cell holding zones 2 and the groove or tunnel 3 communicating the zones 2 to each other formed thereon. The reference numeral 22 is an upper housing, which covers the entire top surface of the agarose gel 100 and is provided on the semipermeable membrane 9 with a proper space in-between. The reference numeral 22-1 indicates a fall section of the upper housing 22. The reference numeral 21 is a culture fluid bath formed between the semipermeable membrane 9 and the upper housing 22. The reference numeral 23 indicates an opening provided on the upper housing 22, and a culture fluid is supplied through this opening into the culture fluid bath 21. The reference numeral 14 indicates a common electrode, which is provided in the culture fluid bath 21. Because the culture fluid is supplied to cells held in the cardiac muscle cell holding zones 2 through the semipermeable membrane 9, which prevents change in conditions during culturing.

As for the procedure for preparing the structure, at first the electrode 4, wiring 6, and terminal 5 are formed on the substrate 1, and then the wall 1-1 is adhered to the substrate 1, and hot-melted agarose 100 is poured into the wall 1-1. The 2% agarose gel (with the melting point of 65° C.) is heated and melted in an microwave oven. The melted agarose solution is added to inside of the external wall 1-1 of the substrate 1 heated to 65° C., and is immediately spread into a sheet with the homogeneous thickness with a spin coater. An addition rate of the agarose gel and a rotational speed of the spin coater are added so that the agarose gel membrane with the thickness in the range from 0.05 mm to 0.5 mm will be obtained. Although the required thickness varies according to a device or a lot of the agarose gel, a good result is obtained with the operating conditions of 50 rpm for 15 seconds, and 200 rpm for 10 seconds. When left in a moistening box for 1 hour at 25° C. At this point of time, the agarose gel membrane is formed on the entire inner surface of the external wall 1-1 of the substrate 1. Then, for forming the cardiac muscle cell holding zones 2 on the agarose gel 100, the agarose gel 100 is formed, and then portions corresponding to the cardiac muscle cell holding zones 2 are removed. The portions can easily be removed by using a laser beams in the wavelength band adapted for absorption by water (for instance, 1480 nm).

FIG. 61 is a cross-sectional view showing a cardiac muscle cell bioassay chip with an agarose-made electrode on which the cardiac muscle cell holding zones 2 have been formed, and this cross-sectional view also schematically shows an optical system and a control system used for preparing the groove or tunnel on the agarose gel 100. A cellulose membrane (with the molecular weight cut off of 30,000 Daltons) is used as the semipermeable membrane 9 on a top surface of the agarose gel 100. For instance, heated and melted agarose gel is applied on a surface of the cellulose membrane with a spin coater, and an agarose film is formed on one surface thereof. After cells are put in the cardiac muscle cell holding zone 2 respectively, the cellulose membrane previously prepared as described above is placed the agarose gel 100 so that a surface of the cellulose membrane with agarose applied thereon contacts the agarose gel 100. Alternatively, when the agarose gel 100 is formed, a small quantity of streptoavidin conjugated agarose is added for solidification. Streptoavidin is exposed on a surface of the agarose gel derivative. Further alternatively, biotin hydrazide is reacted to a cellulose membrane with an aldehyde group introduced therein by oxidization with periodic acid, and a biotin-modified cellulose membrane is prepared by reducing the reaction product above by hydroboration reaction. By fixing the agarose gel derivative and biotin-modified cellulose membrane to each other with the biotin-avidin reaction, a structural body with a cell shielded in the agarose-made structural body can be formed. The peripheral portion of the cellulose membrane may also be adhered outside the wall 1-1 and on the substrate 1 by the biotin-avidin reaction. Namely, because the cellulose membrane is biotin-modified, streptoavidin may be fixed to the wall 1-1 and to a surface of the substrate 1 at an outer side from the wall 1-1. For fixing streptoavidin, for instance, a glycidoxy group is introduced into the substrate by the silane coupling reaction so that the glycidoxy group will directly react with an amino group of streptavidin, or aminosilane is introduced into the substrate and a the aminosilane and an amino group of streptoavidin is bridged with a bifunctional reagent. Further the fall section 22-1 of the upper housing 22 may be adhered thereto.

A Laser 141 with the wavelength of 1480 nm adapted to absorption by water is used for irradiation. The laser beam 142 passes through an expander 143, and passes through a filter 144 which reflects IR rays with the wavelength of 740 nm or more but allows for transmission of the light with the wavelength of 1480 nm (±20 nm), further passes through a deposition filter which allows for passage of light with the wavelength of 700 nm or more, and is focused by a conversing lens 146 on a top surface of the substrate 1. The converged light beam with the wavelength of 1480 nm is absorbed by water contained in the agarose layer, and the temperature rises up to a degree near the boiling point. With the laser power is 20 mW, the agarose is melted with a line width of about 20 μm near the section irradiated by the converging light beam, and is removed by thermal convection. The problem is that amplitude of the converging light beam changes absorbed by agarose according to whether the electrode is present on the substrate 1 or not. To solve the problem as described above, in the present embodiment, a contrivance is introduced so that a temperature caused by irradiation of a converging light beams can be controlled by controlling a laser power by means of feedback control based on estimation of a temperature of the agarose gel. The converging light beam having reached the agarose section is converted to heat and generates IR rays. The IR rays pass through the filter 145, are reflected by the filter 144, and reach an IR ray camera 160-1. Image data picked up by the IR camera 160-1 is fetched into a computing device with a video recording mechanism 161, and the temperature is estimated based on amplitude of detected light, which is used for adjusting a power of the laser 141. When it is difficult to control the temperature only by adjusting the laser power, a moving velocity of the stage 164 is controlled according to an output from the computing device so that a temperature of agarose in the section irradiated by the converging light beam is kept at a constant level. Namely, a rotational speed of the stepping motor 162 is controlled by the computing device 161, and a torque of the stepping motor is delivered by the driving force delivering device 163 to the stage 164.

The substrate 1 is set on the stage 164, and the groove or tunnel 3 can freely be formed on the agarose gel. An ITO-made transparent electrode 4-1 is previously formed in each groove or tunnel 3. Further to monitor beat of the cardiac muscle or the progress of agarose engineering, also an optical system for detecting transmitted light from a light source 170 is also incorporated therein. The light from the light source 170 passes through the transparent upper housing 22, also passes through the object lens 146 being scattered in the agarose section, and is fetched by a deposition filter (mirror) reflecting visible light and a CCD camera 160-2 as an image. The image data is sent to the computing device 161, overlapped with the image taken by the IR camera 160-1, and the synthesized image is used for checking temperature-raised portions by laser irradiation and a pattern on the structural body. Namely the system can measure beat of cardiac muscle using both or either one of a microscope and the electrode.

A top surface of the agarose gel 100 forms the culture fluid bath 21, and a culture fluid fed from the opening 23 is always circulating therein. Further by adding various types of chemical substances such as those stimulating cells or endocrine disrupting chemicals can be added from the opening 23, and a beating state of the cardiac muscle can be monitored with the electrode or with a microscope. In this step, observation with a microscope is employed for bioassay of an ionic substance which may affect a result of measurement with the electrode, while observation with the electrode is employed for bioassay of a substance such as a coloring matter not suited to observation with a microscope.

Main dimensions of the cardiac muscle cell bioassay shown in FIG. 60 are as shown below. The size of the cardiac muscle cell holding zone 2 is 30 μm×30 μm with the depth in the range from 0.05 mm to 0.5 mm which is the same as that of the agarose gel 100. A distance between the adjoining cardiac muscle cell holding zones 2 is 50 μm, and the tunnel 3 communicating the adjoining cardiac muscle cell holding zones 2 has the height in the range from 50 μm to 300 μm and the depth of 5 μm. When the height of the tunnel 3 is 50 μm and thickness of the agarose gel 100 is 0.05 mm, the tunnel is not a tunnel, but a groove. There are several methods available for placing a cell in each of the cardiac muscle cell holding zones 2. For instance, there is the method in which a micro-capillary is inserted to capture a cell with a tip thereof and the cell is removed into the cardiac muscle cell holding zone 2. There is another method available for the same purpose in which a droplet containing cells is dropped onto a top surface of a region for the cardiac muscle cell holding zone 2 and agarose gel 100, and the top surface of the region is slid so that an odd liquid is extruded therefrom to set the cell in the cardiac muscle cell holding zone 2. In the latter case, the size of the cardiac muscle cell holding zone 2 is required to be substantially the same as that of the cell.

Because two electrodes are provided in each cardiac muscle cell holding zone and in one groove or tunnel 3, so that fluctuation of an electric potential in the cardiac muscle cell can easily be captured. Each electrode is connected with the wiring 6 to the terminal 5, so that electric measurement can be carried out by each single electrode or a pair of the electrodes.

Figure 62:
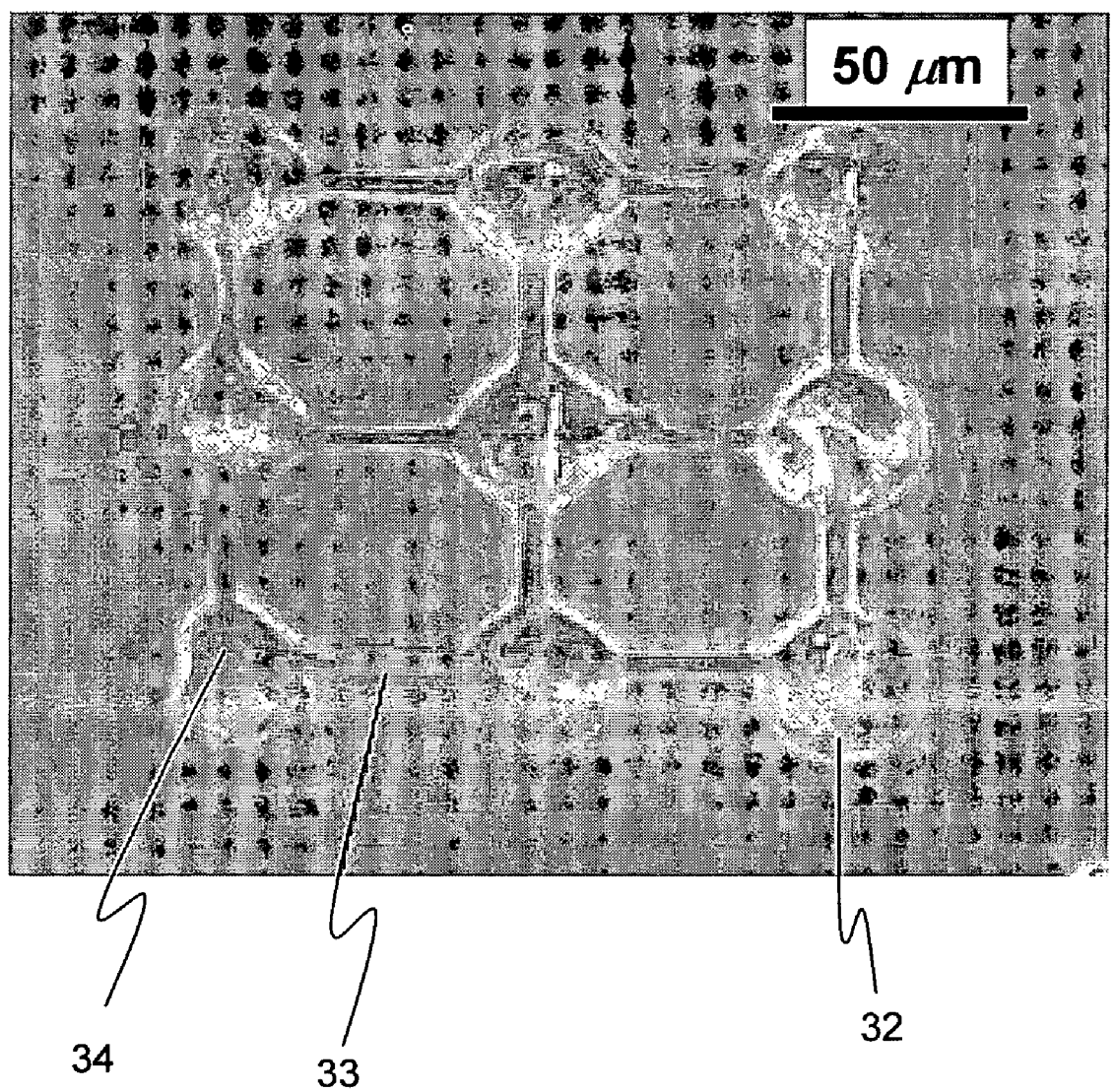
FIG. 62 is a view showing a transmission microscope image accommodating oscillating myocardial cells in all of zones in the cardiac-myocyte-cell chip in Example 1.

FIG. 62 is a view showing an image taken by a transmission microscope and showing the state where cardiac muscle cells are accommodated in all zones on the cardiac muscle cell chip in Example 1. This microscopic image shown in FIG. 61 shows a result of observation of light irradiated from the cardiac muscle cell chip and transmitting therethrough with the CCD camera 160-2. The IR laser 140 or IR camera 160-1 is not used in this observation. It is needless to say that the observation can be made with an assembly in which the CCD camera 160-2 is attached to an inverted microscope. The reference numeral 32 indicates the cardiac muscle cell holding zone 2, which is the same as that indicated by the reference numeral 2 in FIG. 60. The reference numeral 33 indicates a groove or a tunnel, which corresponds to the tunnel 3 shown in FIGS. 60 and 61. In FIG. 62 (photograph), cardiac muscle cells 34 are previously set in all of the cardiac muscle cell holding zones 32, and the cells extend the projections through the tunnel 33 to contact each other and form a gap junction. Namely the cells contact each other in this state.

Example 2

In Example 2 of this embodiment, descriptions are provided for a result of examination on a number of cells required for configuring a network of pulsating myocardial cells as a cardiac muscle cell bioassay chip.

With the cardiac muscle cell bioassay chip shown in FIGS. 60 and 61, a network consisting of up to nine oscillating myocardial cells can be formed by placing a oscillating myocardial cell in each of the cardiac muscle cell holding zones. In this case, an electric potential or transfer imaging of a cardiac muscle cell while beating, which was described with reference to FIGS. 49(A) and 49(B), are obtained, and a similar analysis result can be obtained.

Figure 63:
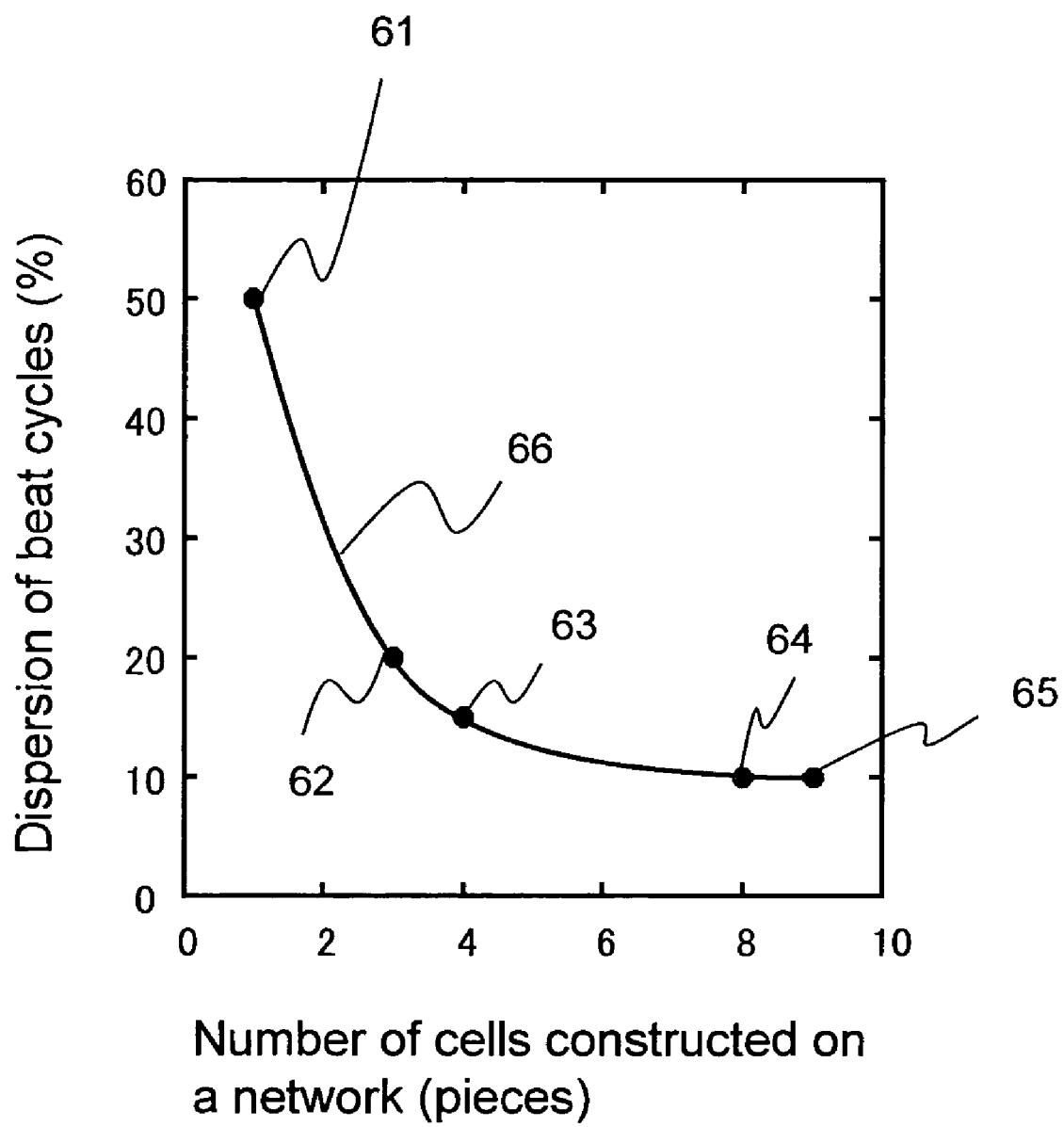
FIG. 63 is a diagram showing a measuring result of the variation of palmic intervals in the cells in the cardiac-myocyte-cell chip.

FIG. 63 is a view plotted by accommodating a oscillating myocardial cell in each of 1, 3, 4, 8 and 9 cardiac muscle cell holding zones respectively, measuring a beat interval of each cell 64 times to obtain CV (a value obtained by dividing the standard deviation by the average value). Plots 61, 62, 63, 64, and 65 are CVs for beat interval measurement values measured with 1, 3, 4, 8 and 9 pulsating myocardial cells respectively, and the curve 62 is a curve obtained by supplementing sections between the plots. It was found that sometimes dispersion of beat may reach even 50% in a case of a single oscillating myocardial cell, but that the beat dispersion lowers when the oscillating myocardial cells form a network. When a number of oscillating myocardial cells forming a network is eight or more, the dispersion in beat drops to about 10%, which indicates that the cells beat in the stable state.

This result suggests that bioassay data with high reproducibility can be obtained by performing a bioassay with a network consisting of eight or more pulsating myocardial cells. A number of cells at a cross point between a string passing through dispersed points obtained with one and three cells and those obtained with eight and ten cells is four. From this point, it can be guessed that, when a network consists of four or more cells, dispersion of beat intervals drops to a substantially constant value.

When the number of cells is too large, dispersion in beat interval is more stabilized, but other negative factors increase in association with increase of a number of cells, which is not preferable. For instance, it is possible to prepare a bioassay chip consisting of 1000 cells, but the obtained result indicates only an average as described in the description of the background technology, and responses of each cell to a medical agent can not be obtained accurately, which is disadvantageous. Further when the number of cells forming network increases, also the number of electrodes and other components increase, which disadvantageously leads to increase in cost for preparing a chip or cost for a measuring device, and further a longer time is required for preparing the bioassay chip, which is also disadvantageous. Up to 32 cells are sufficient for bioassay.

As for arrangement of pulsating myocardial cells in the cardiac muscle cell bioassay chip and the number of cells therein, when viewed from the view point of the necessity to build up an environment similar to that for cells in a living organism, the space should be as compact as possible, or should be as close to a square as possible. Therefore, when the number of cells is four, the number of cardiac muscle cell holding zones should be 2×2, and when the number of cells is 32, the number of cardiac muscle cell holding zones should be 6×6 with four cells at four corners removed. Namely it is preferable that the number of cells for forming a cardiac muscle cell network is in the range from 4 to 32. For obtaining more accurate data with small dispersion, it is preferable to form a cardiac muscle cell network with cells in the range from 8 to 32.

Descriptions are provides below for a procedure to carry out bioassay with a cardiac muscle cell bioassay chip with a cardiac muscle cell accommodated in each of eight cardiac muscle cell holding zones.

An additive to be measured is put in the culture fluid bath 21 shown in FIG. 61, monitoring an electric signal between each electrode 4-1 or 4-2 and the common electrode 14 shown in FIG. 61, or measuring change in brightness of each oscillating myocardial cell by monitoring the microscopic images. An interval 52 between beat signals 51 generated in each cell is measured as a beat cycle. With an additive not affecting a cell, no change is observed in the beat cycle. With an additive affecting a cell, the beat cycle fluctuates. An electrode used for monitoring the electric signal may be either the electrode 4-1 or the electrode 4-2 in the cardiac muscle cell holding zone, but when it is necessary to monitor beat of each cell, it is better to use the electrode in the cardiac muscle cell holding zone 2.

The beat cycle data obtained with the cardiac muscle cell bioassay chip according to the twelfth embodiment has a dispersion of 10% or below, and therefore, if the data values fluctuate by 20% or more as 2SD (a value indicating a range of twice of standard deviation), it can be determined that there are actual influences. With a single cell, the dispersion is 50%, unless the beat cycle fluctuates, it can not be determined that there is any influence by the additive. Therefore, when the cardiac muscle cell bioassay chip based on a cardiac muscle cell network consisting of eight or more cells, there is provided the merit that influences by the additive can be measured with high precision. On the other hand, in a bioassay using a large number of cells, a concentration of an additive against each discrete cell drops, and dispersion due to differences in the characteristics between cell groups becomes larger, which is disadvantageous.

Example 3

Example 3 shows a case where a cardiac muscle cell bioassay chip is formed with a glass substrate. In this case, size of each cardiac muscle cell holding zone has a diameter of 30 μm and the depth of 20 μm, and the cardiac muscle cell holding zones are prepared with a pitch of 50 μm on the glass substrate 1 by etching, and also a groove with the width of 5 μm and depth of 10 μm is formed between adjoining cardiac muscle cell holding zones. An amino group is introduced into a surface of the glass substrate by means of the silane coupling reaction, and further a carboxylic group is introduced into the amino group by reacting succinic anhydride, and this carboxylic group and streptoavidin are bonded to each other by condensation with water-soluble carbodiimide. A cell is inserted into each cardiac muscle cell holding zone 2 with a capillary pipet, and each zone may be covered with biotinated cellulose membrane. An upper circulation bath 21 similar to that shown in FIG. 61 is attached thereon to prepare a structure in which a fluid in the upper circulation bath is always circulated or a reagent for assay is added therein.

Example 4

Figure 64:
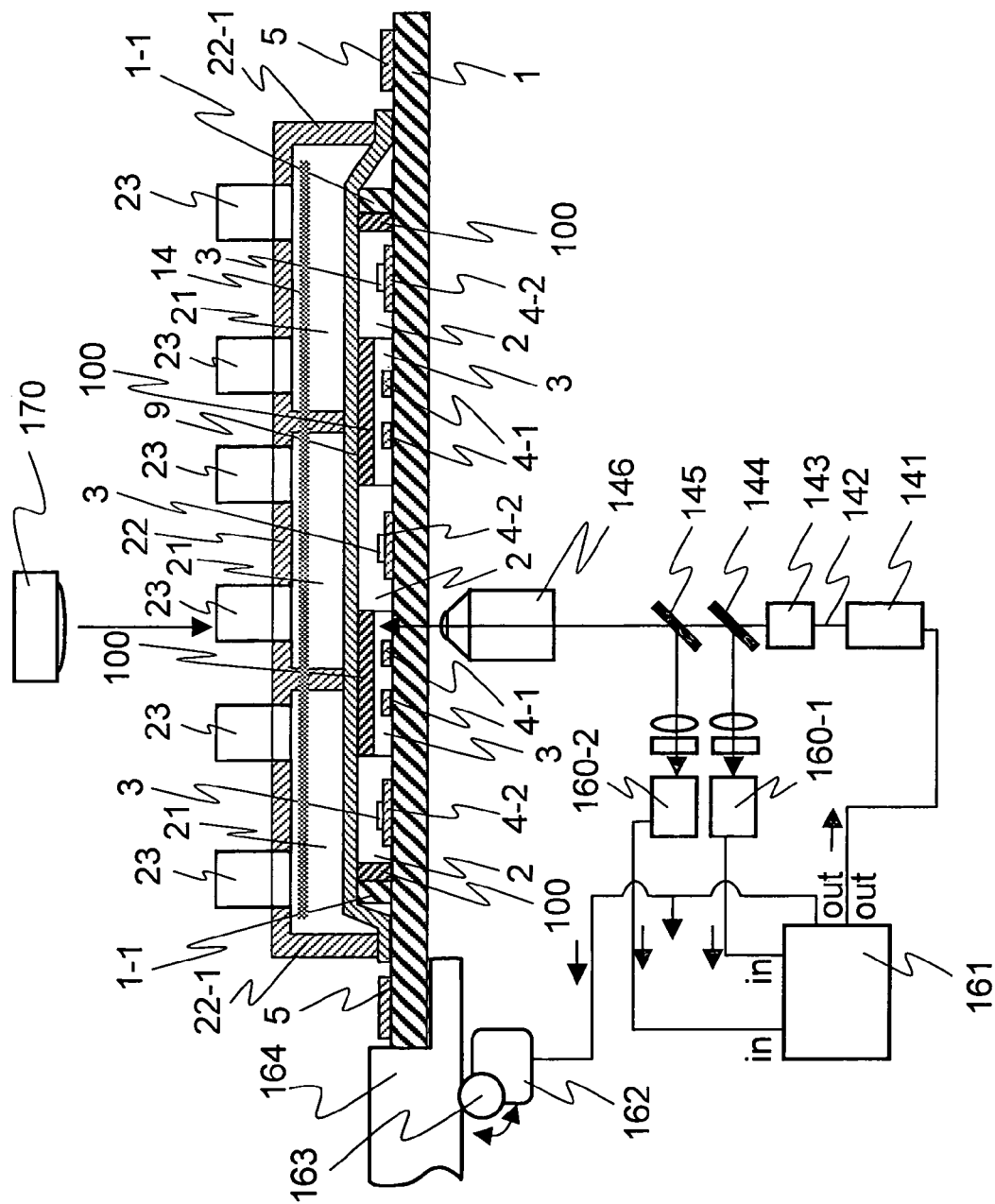
FIG. 64 is a cross-sectional view showing an example of a structure of the cardiac-myocyte-cell bioassay chip in Example 4 with the cross section corresponding to that shown in FIG. 61.

FIG. 64 is a cross-sectional view showing the cardiac muscle cell bioassay chip in Example 4 and shown in FIG. 61. As clearly understood by comparing FIG. 64 to FIG. 61, the cardiac muscle cell bioassay chip in Example 4 is the same as that in Example 1 excluding the point that the circulation bath 21 is divided to three sections by setting a partition for three cardiac muscle cell holding zones which are perpendicular to a view plane. As described above, the circulation bath 21 is divided to three sections each consisting of three cardiac muscle cell holding zones. In this configuration, different solutions may be circulated in the three sections respectively, and therefore measurement of myocardial oscillation may be performed, for instance, by adding a bioassay reagent only in the middle circulation zone and filling an ordinary buffer liquid (culture fluid) in other upper circulation zones. In this figure, the opening 23 provided on the upper housing 22 are shown side by side for convenience, but it is needless to say that the openings should be provided in the three cardiac muscle cell holding zones perpendicular to the view plane respectively so that each solution can be circulated more smoothly.

By measuring oscillation of cardiac muscle by adding a reagent for bioassay only in the middle circulation bath and also flowing an ordinary buffer liquid (culture fluid) in other upper circulation baths, disturbance of a beat synchronization signals from the adjoining cells can easily be measured. Namely, in addition to the direct cytotoxity when a medical chemical is administered, the effect over the inter-cellular community can be measured, and therefore the effects which have been expressed with subjective expressions such as "physical conditions are good or not good when a medicine is drunk" may be expressed with digital values.

Others

As described in Example 3, a communication route between adjoining cardiac muscle cell holding zones in the cardiac muscle cell bioassay chip according to the twelfth embodiment is not limited to a tunnel, and may be a groove.

As for the potentials in industrial utilization of the cardiac muscle cell bioassay chip according to the twelfth embodiment, various possibilities are conceivable from the viewpoint of utilization thereof by researchers or in pharmaceutical companies and from the viewpoints of utilization by manufacturers supplying cardiac muscle cell bioassay chips. From the user's point of view, the chip should preferably be supplied in the state where cardiac muscle cells have been accommodated in the cardiac muscle cell holding zones respectively to form a cardiac muscle cell network. However, the cardiac muscle cells accommodated in the cardiac muscle cell holding zones can not live for a long time in the state as described above, a manufacturer/supplier of bioassay chips preferably supplies chips each with the duration of effective use limited to a short period of time. Alternatively the bioassay may be separated to a portion including the substrate 1, electrodes and related portions 4, terminals 5, wiring 6 and agarose gel 100 on the substrate 1, and to a portion including the semipermeable membrane 9 and upper housing 22, and a set comprising these two portions may be supplied as a kit. When the bioassay chip is supplied as a set (kit), the user must be responsible for accommodation of a cardiac muscle cell into a cardiac muscle cell holding zone and assembly of the kit.

(E) Now descriptions are provided for a device and a method for obtaining information from cultured cells and those formed into a network.

[XIII] Thirteenth Embodiment

In a thirteenth embodiment of the present invention, a method is described in which mRNA or proteins present in cytoplasm are recovered without killing the cell and in-vitro analysis is performed for the purpose to successively obtain information over time from a single cell. In this method, a tip portion of a living organism sampling chip with the tip diameter of 2 nm or below is inserted into a cell to recover the contents. An oligo T for hanging up the mRNA is fixed to the tip portion of the living organism sampling chip. Alternatively, a tip portion of the living organism sampling chip is partitioned into several areas in the sagittal direction, and the oligo based on two to four different sequences is fixed to the 3' terminal side of the oligo T, and the mRNA is preparatively isolated being classified by the two to four bases adjoining the poly A.

As a probe used in this step, PNA or synthetic polynucleotide not having any minus electric charge like PNA is used.

For the ordinary polynucleotide based on the phosphodiester bond is easily decomposed by endonuclease in a cell and the proving sequence portion of the mRNA is easily blocked due to holding. When a specific protein is to be analyzed, the RNA aptomer or DNA aptomer to specific protein groups described in the third embodiment is fixed to a tip of the living organism sampling chip, and the conjugate is used to hang up the specific protein.

When a tip of the living organism sampling chip is inserted into a cell, for reducing physical damages to the cell, a diameter of the tip portion (inserted into the cell) should be 1/5 of the cell size or below. Further the tip portion should previously be coated with titanium oxide $TiO_2$. Alternatively the entire tip portion inserted into the cell may be coated with arginine in place of titanium oxide $TiO_2$ to facilitate interactions with phospholipids in the cell membrane on a surface of a cell and also to facilitate smooth insertion of the tip portion of the living organism sampling chip. If necessary, the entire portion inserted into a cell is coated with arginine, and only the tip portion is coated with titanium oxide $TiO_2$.

In this embodiment, a tip portion of the living organism sampling chip is inserted into a cell, and then the tip portion of the living organism sampling chip with an object for measurement on a surface of the prove tip is pulled off from the cell, and a quantity of the specified substance captured on a surface thereof is measured. In this step, at first the specific substance is bonded to nanoparticles by using the so-called sandwich reaction. By scanning the nanoparticles remaining on a surface of the tip portion of the living organism sampling chip with a scanning microscope, an amount of the recovered substance is quantitatively measured. Alternatively, the nanoparticles remaining on a surface of the tip portion of the living organism sampling chip is measured with an atomic force microscope.

Example 1

Figure 65:
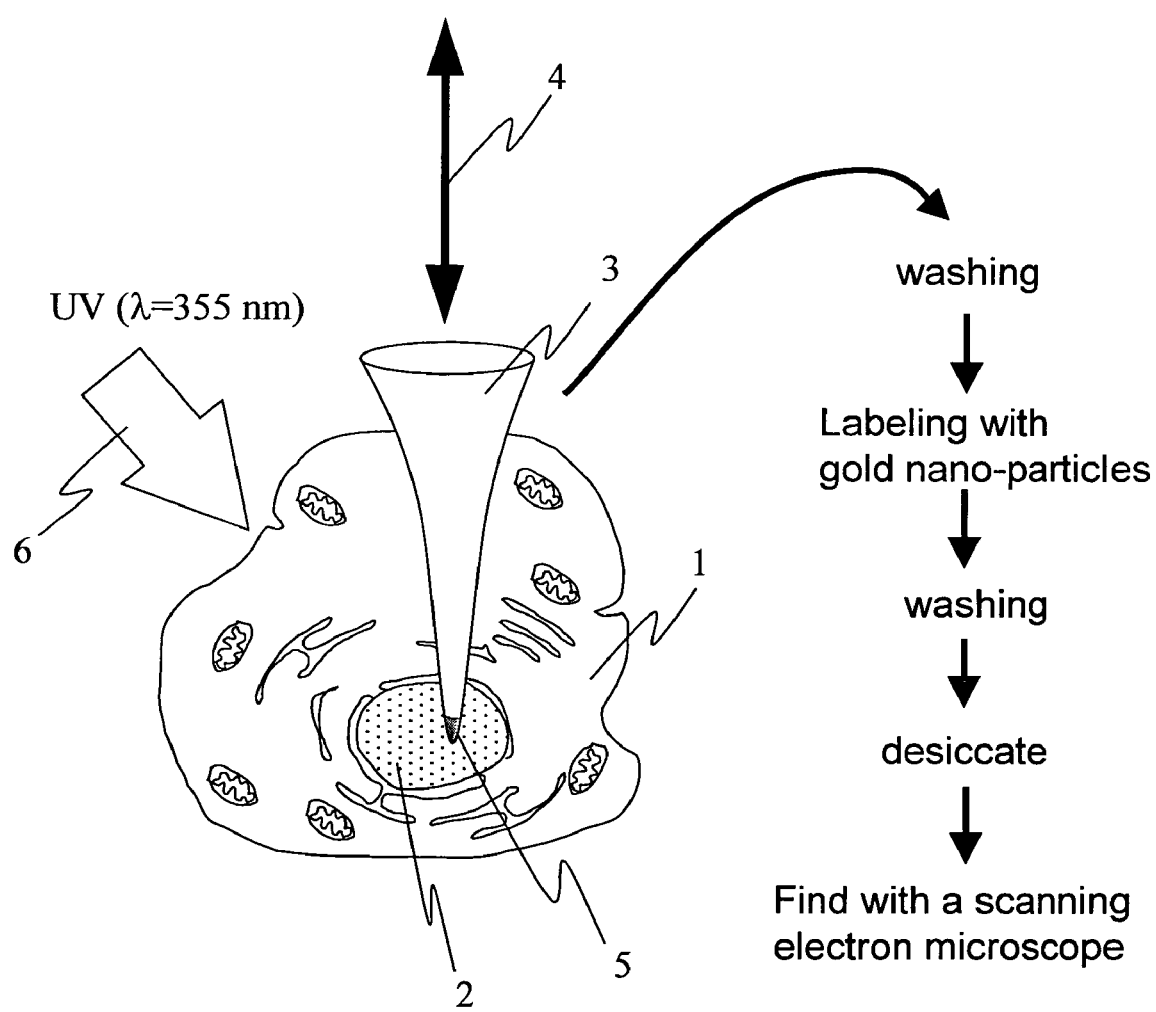
FIG. 65 is a view illustrating an operation flow in a method of recovering and analyzing biological materials in a cell according to a thirteenth embodiment of the present invention.
Figure 66:
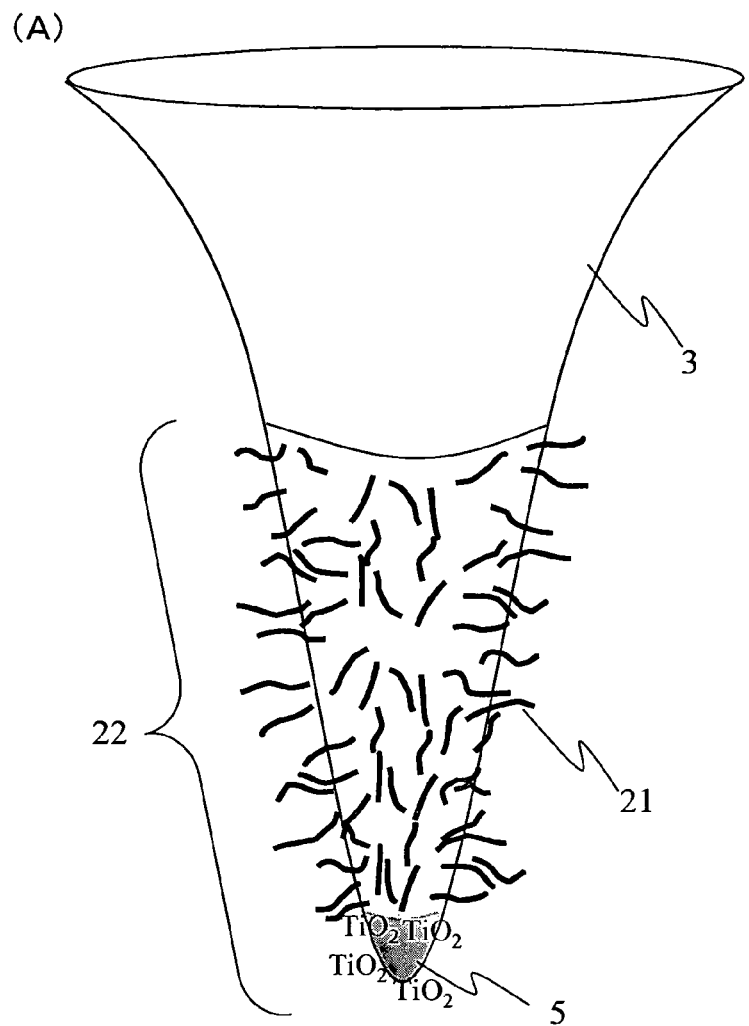
Figure 66:
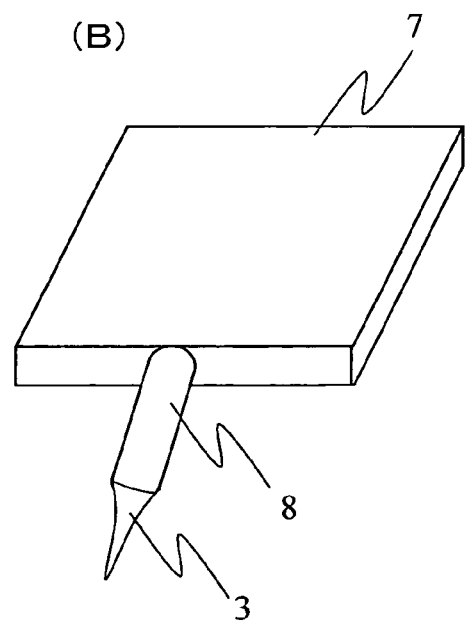

FIG. 65 is a flow chart showing an operation flow in the method of recovering and analyzing organic substances in a cell according to the thirteen embodiment shown in FIG. 65, while FIG. 66(A) is an enlarged view schematically showing a living organism sampling chip tip portion 3, and FIG. 66(B) is a perspective view schematically showing the entire image of the living organism sampling chip according to the thirteenth embodiment.

In FIG. 65, the reference numeral 1 indicates a cell, while the reference numeral 2 is a nucleus of the cell 1. The reference numeral 3 is a tip portion of the living organism sampling chip according to the thirteenth embodiment. The living organism sampling chip tip portion 3 has a diameter with the size of about 1/5 of the size of cell 1, and is a sharp needle. The reference numeral 5 is titanium oxide $TiO_2$ coated on the living organism sampling chip tip portion 3, while the reference numeral 6 is ultra-violet rays with the wavelength of 335 nm, and irradiated to the living organism sampling chip tip portion 3 when inserted into the cell 1. By irradiating the ultra-violet rays with the wavelength of 335 nm to the living organism sampling chip tip portion 3 when inserting into the cell 1, the tip portion 3 can easily be inserted into the cell 1 due to the organic material decomposing action of the titanium oxide $TiO_2$ use for coating. When prematured mRNA or core protein is to be analyzed, the living organism sampling chip tip portion 3 is inserted into a core 2 of the cell 1.

The living organism sample obtained with the living sample chip tip portion 3 is washed after the living organism sampling chip tip portion 3 is pulled off from the cell 1, and is labeled with gold nanoparticles. Then the sample is again washed and dried, and then measurement is performed. The arrow 4 indicates that the living organism sampling chip tip portion 3 is moved up and down against the cell during the operation.

As shown in FIG. 66(A), the probe 21 is fixed to the probe area 22 of the living organism sampling chip tip portion 3. The probe 21 is a substance having affinity to an intracellular biological material to be recovered. Size of the probe area 22 may be decided by taking into consideration the cell's size, and is at most 10 μm, and 4 μm at the root of the probe area 22. The living organism sampling chip tip portion 3 is coated with titanium oxide $TiO_2$ 5. As described above, the living organism sampling chip tip portion 3 is extremely small. To make treatment thereof easier, as shown in FIG. 66(B), the living organism sampling chip tip portion 3 according to the thirteenth embodiment has a living organism sampling chip tip portion holder 8, and the holder 8 is connected to the operation board 7. A diameter of the holder 8 is, for instance, 1 mmφ, while size of the operation board 7 is 4 mm×5 mm. The cell 1 is placed under an object lens of a microscope and the living organism sampling chip tip portion 3 is inserted into the cell by operating the operating section supporting the operation board 7, so that the operation can be performed in the stable condition with safety. Further, even when measurement is performed with an SEM or an AMF, the living organism sampling chip tip portion 3 can be operation with the operating section supporting the operation board 7.

In Example 1, descriptions are provided for a case in which the living organism sampling chip tip portion 3 is inserted into a cell from a tissue sample of colon cancer and a specific mRNA present in the cell is analyzed. A 5-base random sequence oligo DNA conjugated to the 3' terminal of a 26-base poly T is used as the probe 21. This conjugate is used as the probe, because only the poly T is insufficient for achieving stability in mRNA hybridization. The probe 21 is made of PNA (peptide nucleic acid) for easy interaction with the mRNA in the cell. Different from the ordinary DNA, the PNA does not have a minus electric charge originated from the phosphodiester bond, and therefore an electrostatic repelling force does not work with a DNA as a target.

Because of the feature, when the probe area 22 of the living organism sampling chip tip portion 3 is inserted into a cell, the probe 21 efficiently hybridizes the specific mRNA present in the cell, which is advantageous. Also, repulsion force is not generated between phospholipid and the living organism sampling chip tip portion 3, the tip portion 3 can be inserted into the cell membrane smoothly. In a case where the probe 21 is tightly fixed to a solid phase surface of the probe area 22 like in Example 1, if an ordinary DNA is used as the probe 21, the target DNA is required to move toward the probe 21 overcoming a barrier of minus electric charge generated by the probe area 22, which is disadvantageous from the both viewpoints of chemical kinetics and thermodynamics. Also the target mRNA is required to be a single chain, but is actually three-dimensionally held in a molecule, and therefore sometimes a probing site, to which the probe conjugates, may be blocked.

When a probe not having minus electric charge like PNA is used, an electric charge of the probe itself can be eliminated, so that a barrier of minus electric charge is not generated by the probe area 22, and because of the feature, the speed and yield in hybridization can be improved. Further the PNA having no electric charge does not generate an electrostatic repelling force, so that the prove can competitively creep into the target DNA even when the target DNA is double-stranded to achieve competitive hybridization.

Further also the cell membrane is covered with negatively charged phospholipids, and therefore if a surface of the living organism sampling chip tip portion is negatively charged, a repulsion force works between the living organism sampling chip tip portion and the cell, so that insertion of the living organism sampling chip tip portion into the cell becomes difficult. In contrast, the living organism sampling chip tip portion with a PNA probe fixed thereto can easily be inserted into a cell.

The living organism sampling chip tip portion 3 is inserted into the cell 1, and the probe area 22 is left in the cell for 30 seconds. Then the living organism sampling chip tip portion 3 is pulled off from the cell 1, and is immediately washed with 2×SSC. Then a second probe labeled with gold nanoparticles with the diameter of 8.3 nm is hybridized with the mRNA hybridized to the probe 21 in the probe area 22. In this step, an oligo PNA having a specific sequence is used as the second probe. PNA is used for the same reason as that described above. For instance, the 28-base sequence specific to EpCAM, which is reportedly expressed a lot in epithelial cell cancer, is used. The conjugate is again washed and cleaned with deionized water. In Example 1, because the PNA probe is used, the hybridized probe is never de-hybridized even when washed with deionized water.

When the ordinary DNA is used as the second probe, the hybridization is substantially affected by a dielectric constant of a solvent due to the repulsion force between the molecules generated by minus charge in the phosphodiester bond. Therefore, hybridization can not be achieved unless decreasing the repulsion force between the phosphoric acid groups at a high concentration of salt. The double-stranded bond becomes lose in deionized water, and when the ordinary oligonucleotide structure is used in a complex of oligo A and oligo T like in Example 1, it is difficult to maintain a stable double-stranded structure. In Example 1, PNA is used as the second probe, the electrostatic repelling force does not work between the probe and the mRNA as a sample. Because of the feature, the double-stranded structure of RNA and PNA hybridized to each other can be preserved in the stable state even in deionized water.

Then the gold nanoparticles labeling the second probe are dried to fix the particles on a surface of the probe area 22 of the living organism sampling chip tip portion 3. Because the Brownian motion of the gold nanoparticles occurs in the liquid phase state, and in that case, for instance, precision of measurement with an AFM drops, and observation by an SEM is impossible. By observing the probe area 22 of the dried living organism sampling chip tip portion 3 with an SEM or an AFM, the number of gold nanoparticles captured on a surface of the probe area 22 is counted. The number of gold nanoparticles captured on a surface of the probe 22 depends on a quantity of mRNAs captured on the surface of the probe area 22, and the quantity of mRNAs captured on the surface of the probe area 22 depends on a quantity of mRNAs hanged up from inside of the cell with the probe 21 in the probe area 22, and therefore the quantity correlates to a quantity of mRNAs present around a position of the cell into which the living organism sampling chip tip portion 3 is inserted.

With the method described above, a quantity of mRNAs of EpCAM in a cell can be measured without killing the cell.

Figure 67:
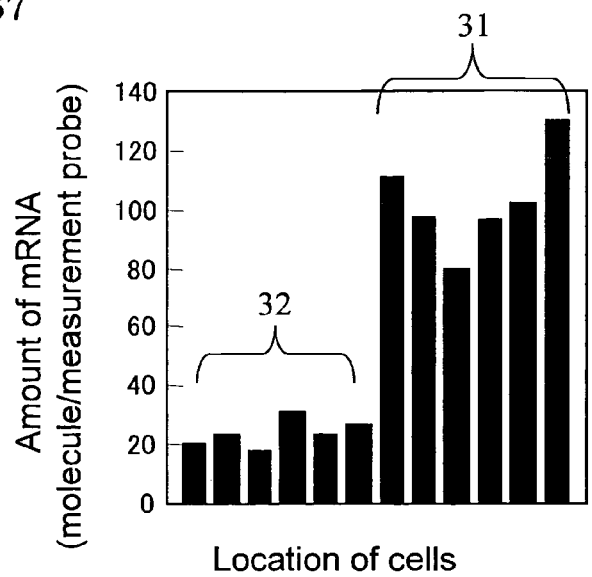
FIG. 67 is a diagram showing a quantitative comparison of EpCAMs alternatively expressed in a cancerous focus cell in a cancerous colon tissue piece and in adjoining cells along the cancer focus cell line.

FIG. 67 is a view showing quantitative comparison among quantities of EpCAM which can be obtained from the cell in a cancer focus in a colon cancer tissue sample and from each of adjoining cells. In this case, the living organism sampling chip tip portion 3 is inserted into the colon cancer tissue sample changing the inserting positions by and by and also exchanging the living organism sampling chip tip portion 3 with a new one to assess a quantity of EpCAM expressed at each position. From this assessment, it can be understood that there are a highly EpCAM-expressing cell group 31 and a not-highly EpCAM-expressing cell group 32, and that the two groups are bordered by a specific cell. It can be guessed that the portion with a high EpCAM expression rate is a group of cancer cells and the portion with a low EpCAM expression rate is a group of noncancerous cells.

Example 2

In Example 2, descriptions are provided for a case in which PNA having different sequences labeled with gold nanoparticles having different diameters is used as the second probe in Example 1, and a plurality of different mRNAs captured on a surface of the probe area 22 are simultaneously detected.

Figure 68:
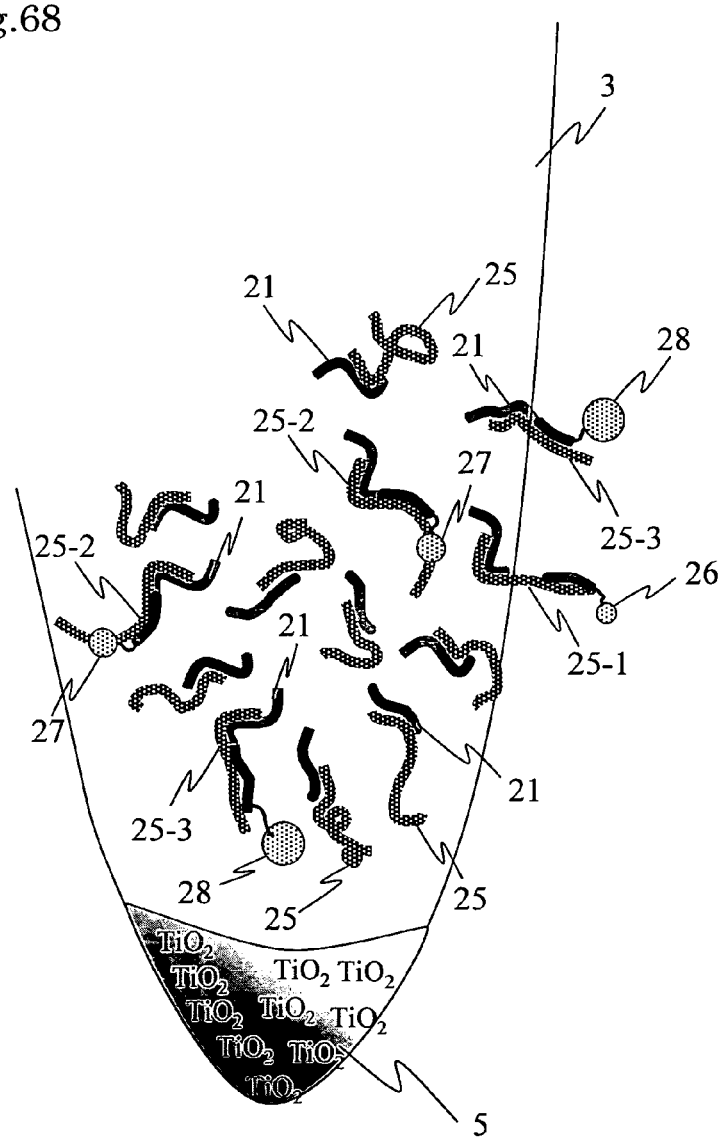
FIG. 68 is a schematic view showing the situation in which a plurality of PNAs having different sequences respectively labeled with nanoparticles of gold having different diameters are hybridizing at a tip section of the biological sample chip.

FIG. 68 is a schematic view showing the situation in which a plurality of PNAs each having a different sequence respectively and labeled with gold nanoparticles having different diameters are being hybridized to the probe 21 fixed on a surface of the probe area 22 of the living organism sampling chip tip portion 3.

Like in Example 1, the 5-base random sequence DNA probe 21 is fixed to the 3' terminal of the 26-base poly T on the surface of the probe are 22 of the living organism sampling chip top portion 3. Also line in Example 1, the living organism sampling chip tip portion 3 is inserted to the cell 1 to hand up the mRNA with the probe 21 of the probe area 22 from a cell in a tissue sample of colon cancer, and the mRNA is cleaned.

As shown in FIG. 68, second probes having different sequences respectively and labeled with the gold nanoparticles 26, 27, and 28 having different diameters respectively are being hybridized to the plurality of mRNAs 25-1, 25-2, and 25-3 hybridized to the probe 21 on the probe area 22 of the living organism sampling chip tip portion 3. The reference numeral 25 in FIG. 68 indicates a plurality of mRNAs being hybridized to the probe 21, but has not been hybridized to the second probe. Gold nanoparticles 26 with the diameter of 8.3 nm and gold nanoparticles 27 with the diameter of 11 nm, and gold nanoparticles 28 with the diameter of 17 nm are conjugated to 5' terminal of oligo PNA (28-base) having the EpCAM sequence and PNA probe sequences including 26 bases and 29 bases corresponding to the CD 44 and CEA mRNA sequences which are reportedly expressed a lot in a cancer cell, and the conjugates are used each as the second probe. The reference numerals 25-1, 25-2, and 25-3 are the captured mRNA sample pieces for EpCAM, CD44, and CEA.

Like in Example 1, measurement of quantities of the three types of mRNAs included in the cells near the cancer focus cell provides the result as shown in FIG. 67 for EpCAM and CEA, but all of the sample cells give values of about 250 molecules/living organism sampling chip tip portion for CD44, and therefore a substantial difference is not observed. There is a report in relation to the CD44 that splicing variants are generated in the colon cancer, but a total quantity of mRNA for the CD44 may not change. The probe sequence used for CD44 is that in exon present at the closest position to the poly-A tail, and there is the possibility that the exon is used in any splicing variant, the detail is still unknown.

Example 3

In Example 3, the probe area 22 of the living organism sampling chip tip portion 3 is divided to a plurality of areas in the longitudinal direction, and different probes are fixed to the areas respectively.

Figure 69:
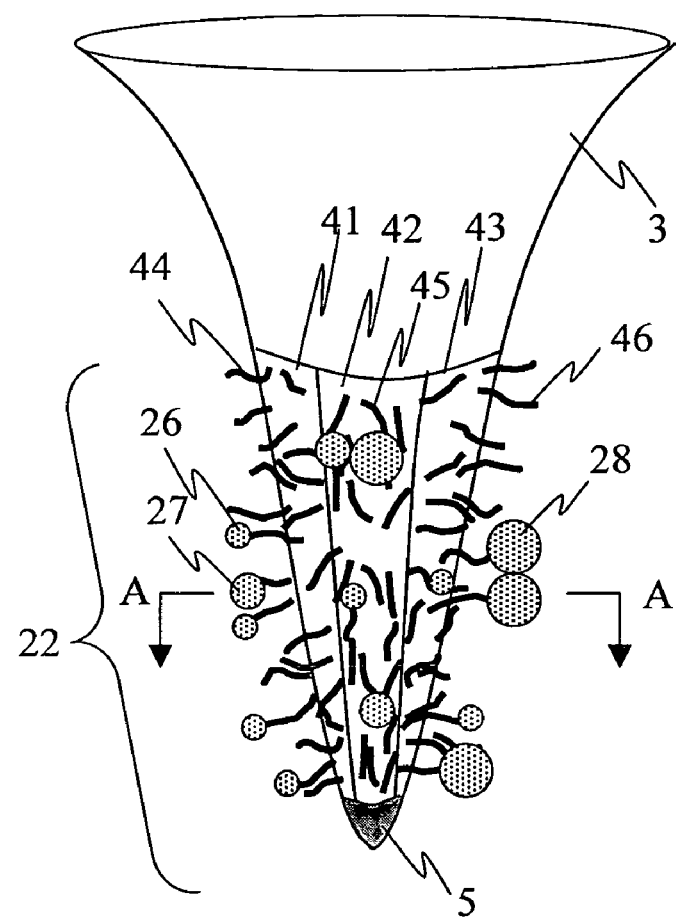
FIG. 69(A) is a schematic view showing a tip section of a biological sample chip measuring targets.
FIG. 69(B) is a cross-sectional view showing the tip section shown in FIG. 69(A) taken along the line A-A and viewed in the direction indicated by the arrow.
Figure 69:
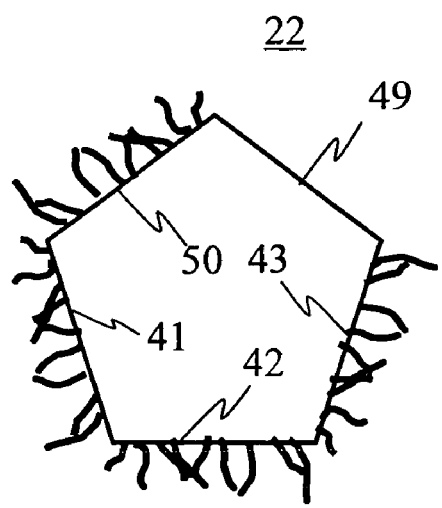

FIG. 69(A) is a schematic view showing the state in which the probe 22 of the living organism sampling chip tip portion 3 is divided to five areas 41, 42, 43, 49, and 50 along the longitudinal direction (the areas 49 and 50 are present in the rear side and therefore are not shown in FIG. 69(A)) and the probes 44, 45, and 46 are fixed to the surfaces of the areas. FIG. 69(B) is a cross-sectional view showing the living organism sampling chip tip portion 3 shown in FIG. 69(A) taken along the line A-A and viewed in the direction indicated by the arrow.

Complementary sequences extending over a final exon and that just ahead in each of EpCAM, CD44, and CEA (having the lengths of 28, 26, and 29 bases respectively) is fixed to each of the areas 41, 42, and 43. The area 49 is used as a negative control, and nothing is fixed thereto. The area 50 is used as a positive control, and TTTT-T and base T each having the 26-base length are fixed thereto. For fixing the sequences, a glycidoxy group is introduced into a surface of the living organism sampling chip tip portion 3 by means of the silane coupling reaction, and PNA having an amino group is fixed to the 5' terminal. The probe area is divided to a plurality of subareas and different types of PNA are fixed to the subareas by suspending the PNAs to be fixed in DMSO, applying the suspension onto a support piece having a sharp tip like that of the living organism sampling chip tip portion 3, and smoothly sliding a tip portion of the support piece only a surface of each discrete zone of the probe area 22 of the living organism sampling chip tip portion 3. By setting the living organism sampling chip tip portion 3 with the surface having the suspension applied thereon downward and heating the surface for five minutes at 50° C., the probes can be fixed. After drying, another probe is fixed to another surface thereof. With the operations as described above, different probes can be fixed to the four different surfaces respectively.

When there are provided a plurality of surfaces to which different probes are fixed thereon as in Example 3, specific living biological materials are captured on each surface respectively, which ensures higher precision in measurement.

Example 4

In Example 4, arginine is fixed to the probe area 22 of the living organism sampling chip tip portion 3.

Figure 70:
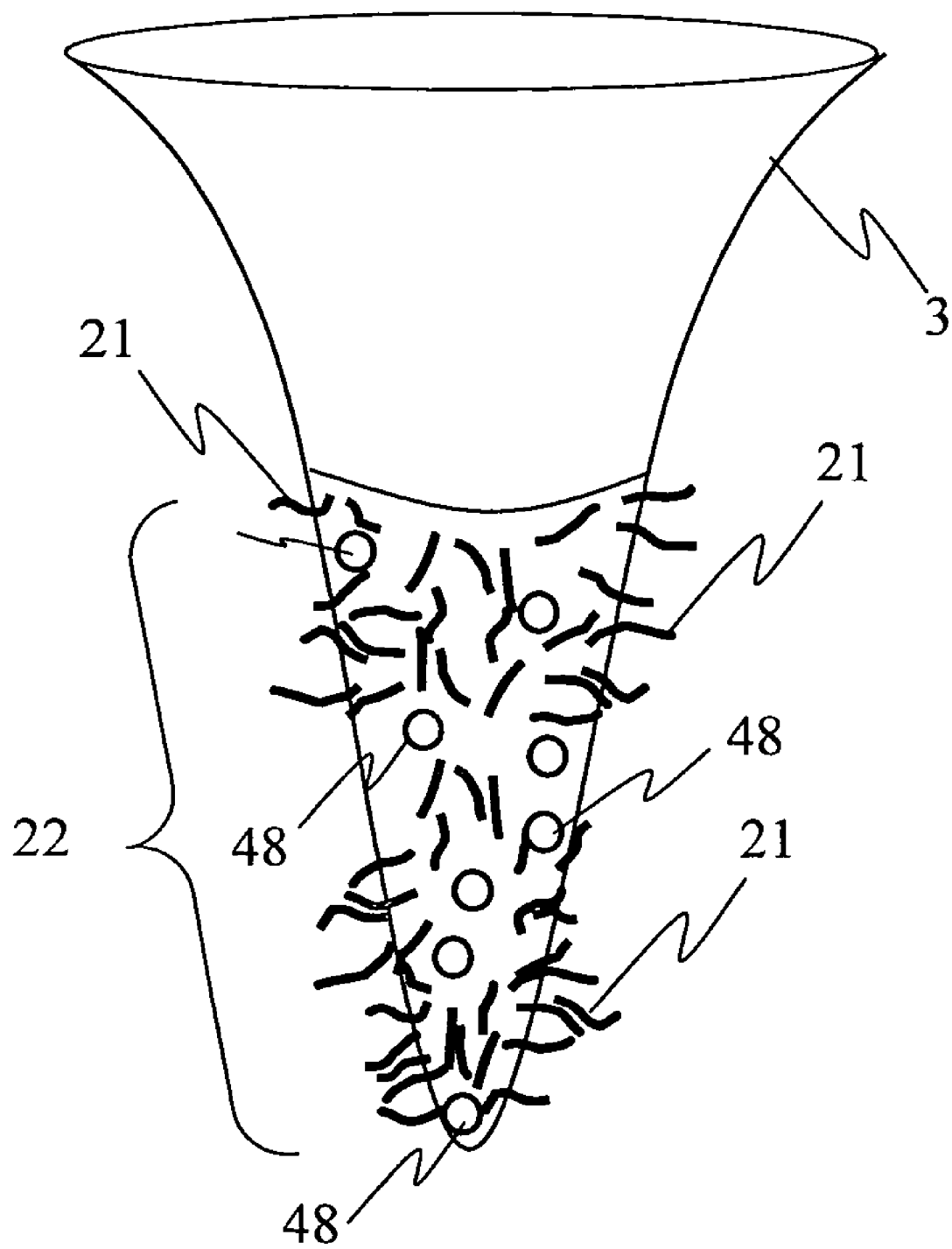
FIG. 70 is a view schematically showing a tip section 3 of the biological sample chip in Example 4.

FIG. 70 is a view schematically showing the living organism sampling chip tip portion 3 in Example 4. Arginine 48 is fixed, in addition to the probe 21, to a surface of the probe area 22. The fixed arginine may be a single amino acid, and also the length of up to an octamer is allowable. The arginine is added to a solution to which the PNA is fixed at the molar ratio of 1/40, and the solution is homogeneously applied on the entire living organism sampling chip tip portion 3.

The method of fixing the probe is as described below. At first 0.5% aqueous solution of γ-glycidoxypropyltrimethoxysilane (with acetic acid added therein by 0.5% or until the silane coupling agent is dissolved) is left for 30 minutes at the room temperature (25° C.) to hydrolyze the methoxy group, thus active silanol group being generated.

The living organism sampling chip tip portion 3 made from silicon and having an oxide film on a surface thereof is immersed into the activated silane coupling agent, and left in the state for one hour. Then rinsing is performed with deionized water for five seconds. At this point of time, a silanole group in the silane coupling agent reacts to a silanole group on a surface of the silicon oxide to form a partially dehydrated compound. Further a silanole group in the silane coupling agent and oxygen on a surface of the silicon oxide form a compound by hydrogen bond. The compound formed through the hydrogen bond is in the metastable state. This mixture is heated for 30 minutes in the air at the temperature in the range from 105 to 110° C. With this operation, dehydrating condensation between the silanol group in the silane coupling agent and oxygen molecules on a surface of silicon is completed. Further dehydrating condensation proceeds between the silane coupling agents present on the silicon surface. Finally the glycidoxypropyl group is introduced into the silicon surface. A portion of the atomic group constituting the glycidoxy group is an epoxy group having high reactivity to an amino group. PNA having the amino group with the concentration of 50 pmol/μl is reacted to 1.25 μM L-Arg or arginine oligomer ((L-Arg)$_n$ (n: 2 to 8))(SEQ ID NO: 15) are reacted to each other in the aqueous solution with pH 10 for one hour at 50° C. With this reaction, the PNC fixed living organism sampling chip tip portion with arginine partially fixed thereto can be obtained.

The living organism sampling chip tip portion 3 prepared in Example 4 can be inserted into a cell with a slight force substantially not requiring support of the cell. Because of this feature, the living organism sampling chip tip portion 3 can relatively easily be inserted into not only the tissue cells described in Examples 1 to 3, but to a floating cell under incubation. By using a sequence originated from the mRNA of EpCAM is used to PNA, the substantially same result as that obtained in Example 1 can be obtained.

In Example 4, no comment is provided for the necessity that the living organism sampling chip tip portion 3 is coated with titanium oxide $TiO_2$ 5, and when the coating with titanium oxide $TiO_2$ 5, the living organism sampling chip tip portion 3 can be inserted into the cell 1 more easily.

[XIV] Fourteenth Embodiment

In a fourteenth embodiment of the present invention, a method is disclosed in which mRNAs, DNA or proteins can easily and instantly be taken out from a living cell several times for analysis without killing the cell. In this method, in order to obtain contents of a cell keeping the cell alive, a needle having a tip diameter substantially smaller than a cell is inserted into the cell to have the contents deposited on the needle's tip for sampling the contents.

To obtain mRNA, an oligo T is fixed as a probe to the needle's tip for sampling mRNA. Alternatively, an oligo including two to about four different sequences is fixed to the 3' terminal of the oligo T to ensure stability in hybridization between the mRNA and poly A, and the conjugate is used as a probe. Because polynucleotide having the phosphodiester bond is easily decomposed by endonuclease in a cell, and also for the purpose to prevent the probing sequence portion of mRNA, which easily causes holding, from being blocked, PNA or synthetic polynucleotide not having minus electric charge like the PNA is used as a probe in this step.

To obtain a particular protein, an antibody fixed on the needle's tip is used for sampling the particular protein. The Fc moiety of the antibody may non-selectively absorb substances other than a target substance, so F(ab')$_2$ not including the Fc moiety is used as a probe. Alternatively, a molecule having the avidity such as the RNA aptamer or DNA aptamer like an antibody is used.

When a needle is inserted into a cell, to minimize physical damages to the cell, a diameter of the needle's tip (a portion inserted into a cell) should be ⅕ of the cell size or below. Further a region 5 coated with titanium oxide $TiO_2$ is provided on the living organism sampling chip tip portion 3. Alternatively, a tip portion of the needle is coated with arginine to facilitate interactions with phospholipids in a cell membrane of a surface of the cell so that the needle can smoothly be inserted into the cell. In a case of arginine, about 6 arginine monomer molecules should preferably be present in a narrow area. Alternatively, oligo arginine may be used in the fixed state.

The particular biological material captured on a surface of the needle is sampled by pulling off the needle from the cell, and when the sample is mRNA, the needle is immersed in the PCR reaction solution as it is to amplify and obtain a specific sequence portion of the particular mRNA. Alternatively, the mRNA is once reversely transcribed to obtain the cDNA, and then the particular gene may be subjected to PCR amplification. In a case of a protein, amplification is impossible, so that the sample is used as it is, and in this case measurement of q quantity of a particular substance in a cell can be made most effectively.

Example 1

Figure 71:
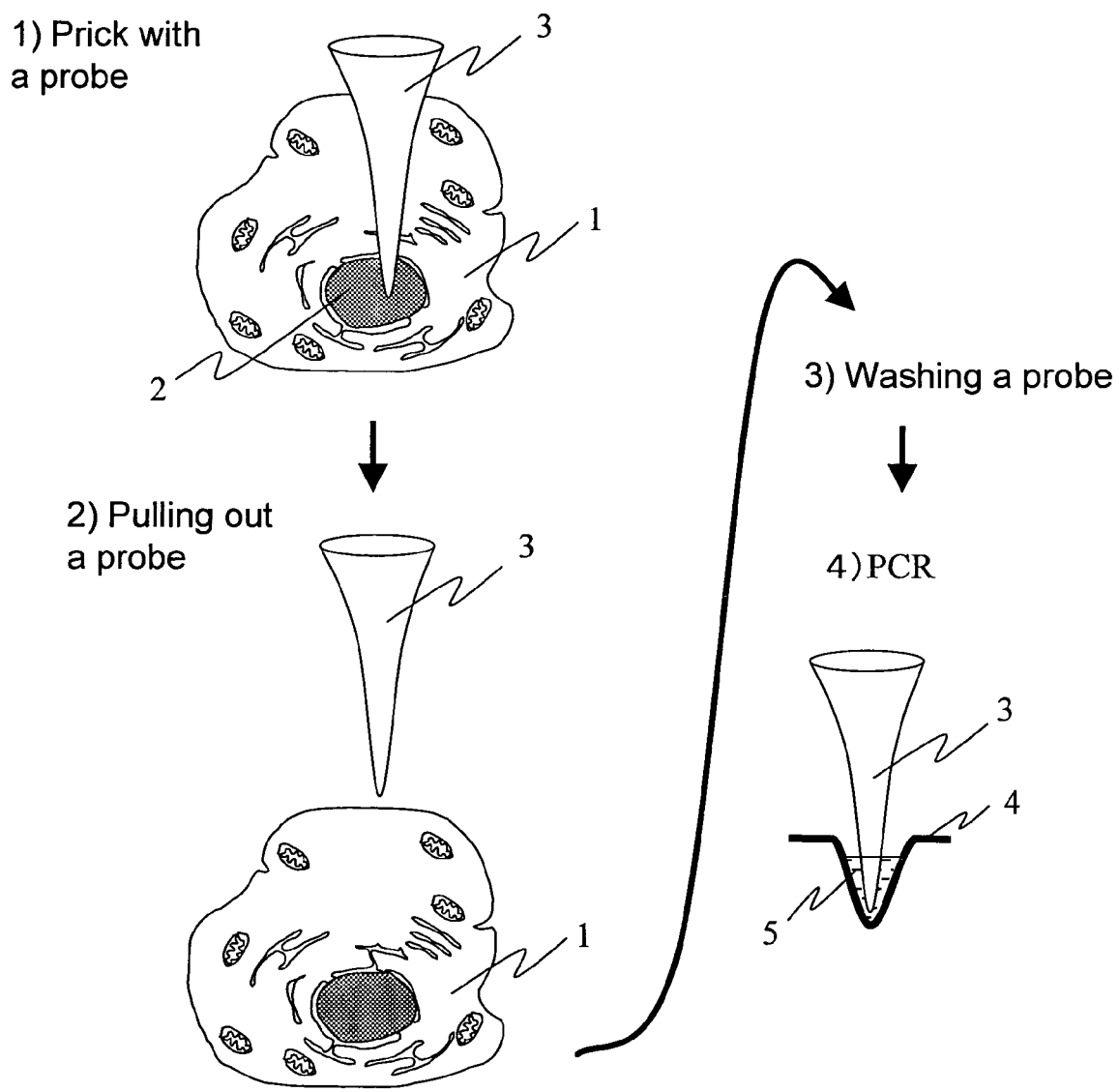
FIG. 71 is a view showing outline of a flow of operations for sampling mRNA which is an intracellular biological material in Example 1 of a fourteenth embodiment of the present invention.

FIG. 71 is a view showing outline of a flow of operations for sampling mRNA which is an intracellular biological material in Example 1. Configuration of a tip portion of a needle used in Example 1 is the same as that shown in FIG. 66.

In FIG. 71, designated at the reference numeral 1 is a cell, at 2 a cell core, at 3 a tip portion of the needle, at 4 a vessel, and at 5 a reaction liquid for PCR method. As shown in FIG. 66(A), the probe 21 is fixed to the tip portion 22 of the needle 3. The needle 3 is supported by the base section 7 via the support section 8 as shown in FIG. 66(B). The tip portion of the needle 3 is extremely small. To facilitate treatment of this needle, the tip portion of the needle 3 has a holder 8, and the holder 8 is connected to an operation board 7. A diameter of the holder 8 is, for instance, 1 mmϕ, and size of the operation board 7 is 4 mm×5 mm.

In Example 1, descriptions are made for a method of inserting a needle into a colon cancer cell for sampling particular mRNA present in the cell. 5-base length random sequence oligo DNA conjugated to the 3'-terminal of 26-base length poly T is used as the probe 21. The probe 21 is made of PNA (peptide nucleic acid) to facilitate interactions with mRNA in a cell. Further, there is provided a region 5 with $TiO_2$ coated thereon, and therefore when the living organism sampling chip tip portion 3 is inserted into the cell 1, UV ray with the wavelength of 335 nm is irradiated so that the living organism sampling chip tip portion 3 can easily be inserted into the cell 1 because of organic material decomposing reaction of the titanium oxide 5 coated thereon.

As shown in step 1), the needle 3 with the tip portion having a diameter of ⅕ or below of size of a cell is inserted into the cell 1 as a target from which an intracellular biological material is sampled. For sampling premature mRNA or a nucleic protein, the needle 3 is inserted into the core 2. The needle 3 is kept in the state for 30 seconds.

In step 2), the needle 3 is pulled off from the cell 1.

In step 3), the tip portion 22 of the needle 3 is washed with 2×SSC immediately.

In step 4), particular mRNA among those capture by the probe 21 on the tip portion 22 of the needle 3 is amplified. A 2 µl reaction liquid 5 including a primer pair corresponding to the particular mRNA, heat-resistant DNA polymerase, dNTP which is a matrix for polymerase, Mg, and pH9 Tris buffer solution is contained in a vessel 4. 2 µl mineral oil is poured onto a top surface of the reaction liquid to prevent evaporation thereof during the operation.

In Example 1, the sequence segment specific to the *Homo sapiens* tumor-associated calcium signal transducer 1 (TACSTD1) is amplified. TACSTD1 is mRNA with the full length of 1528 bp which is reportedly expressed a lot when an epithelial cell cancer occurs. As for the mRNA sequence of human TACSTD1, refer to HUGO Gene Nomenclature Committee, "SLC new solute carrier superfamily proposed members (SLC) HGNC approved", "HGNC Gene Grouping/Family Nomenclature", [online], HUGO [searched on Aug. 1, 2004], Internet <URL: http://www.gene.ucl.ac.uk/nomenclature/genefamily.shtml>.

Synthetic oligo DNAs having the sequences SEQ No. 1 and SEQ No. 2 respectively (concentration: 0.2 pmol/µl) are employed as primers, and PCR amplification is formed by the known method. PCR is repeated 35 times with the cycle of denaturing for 5 seconds at 94° C., annealing for 10 seconds at 55° C. and then for 10 seconds at 72° C. A quantity of reaction liquid is 2 µl as described above. The solution obtained by PCR amplification is analyzed with Hitach i-chip (micro electrophoresis chip) and Cosmo-i chip electrophoresis device. As a result, a substantially single electrophoresis separation band is obtained at the position of 230 bp. The base length of the PCR product estimated from the database is 233 bp.

```
CTGAGCGAGT GAGAACCTAC TG        (SEQ ID NO: 1)

AGCCACATCA GCTATGTCCA           (SEQ ID NO: 2)
```

The mRNA obtained by the second insertion of needle is subjected to amplification with a primer having another sequence segment from the same human TACSTD1. This primer is formed with the sequences SEQ No. 3 and SEQ No. 4 respectively.

```
GTATGAGAAG GCTGAGATAA AGG:      (SEQ ID NO: 3)

AGCTGCTTAT ATTTTGAGTA CAGG:     (SEQ ID NO: 4)
```

To carry out PCR amplification, a cycle of denaturing for 5 seconds at 94° C., annealing for 10 seconds at 52° C. and then 10 seconds at 72° C. is repeated 35 times.

Like in a case of the mRNA obtained by the first insertion of needle, the solution obtained by the PCR amplification is analyzed with Hitach i-chip (micro electrophoresis chip) and Cosmo-i chip electrophoresis device. As a result, a single electrophoresis separation band of 215 bp is obtained. The base length computed from the sequence is 216 bp. Any band is not observed at the position of 230 bp of the solution obtained by PCR amplification of the mRNA obtained by the first insertion of needle.

This fact indicates that the cell is still alive in 16 hours after the first needle insertion. In other words, if the cell 1 is killed when the needle is inserted first, mRNA is immediately decomposed by RNase in cytoplasm, and therefore the mRNA can not be amplified. In this Example 1, the mRNA sampled by the second needle insertion can be amplified by PCR, which indicates that the cell 1 is not killed when the needle is inserted first into the cell 1.

Example 2

In Example 2, descriptions are provided for a case in which mRNA is taken out from a living cell by inserting a needle into the cell once, and then a plurality of cDNAs are obtained from the mRNA. In this example, mRNA is sampled with the needle 3 with the PNA-made probe 21 like in Example 1.

Figure 72:
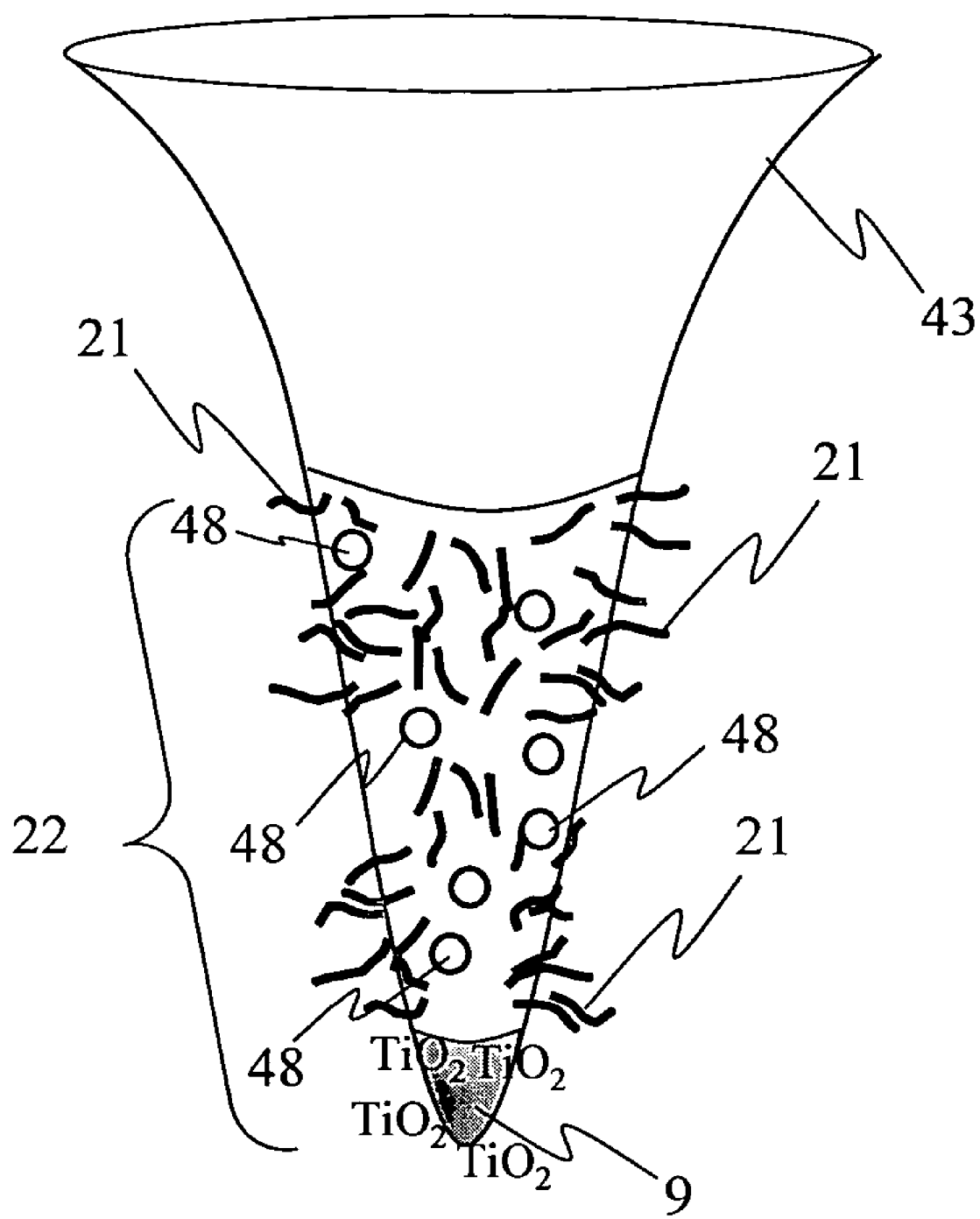
FIG. 72 is a view showing a specific example of a needle 43 used in Example 2.

FIG. 72 is a view showing an example of a needle 43 used in Example 2. Like in Example 1, in addition to the probe 21, $TiO_2$ is fixed to a region 9 at a tip portion of the needle 43, and further arginine 48 is added thereto. The fixed arginine may be one amino acid molecule, or an amino acid sequence with the length of up to an octamer. Arginine is added to a solution to be fixed to PNA at the molar ratio of 1/40, and is homogeneously coated on the entire needle. Configuration of a support section of the needle 43 is not shown, but is the same as that shown in FIG. 66(B).

The method of fixing the probe 21 and arginine is the same as that described in Example 4 of the thirteenth embodiment.

When the needle 43 prepared in Example 2 is used, the needle 43 can be inserted into the cell 1 with a force requiring substantially no force for supporting the cell 1. Because of the feature, the needle can relatively easily be inserted, not only into a tissue cell, but also into a floating cell.

Figure 73:
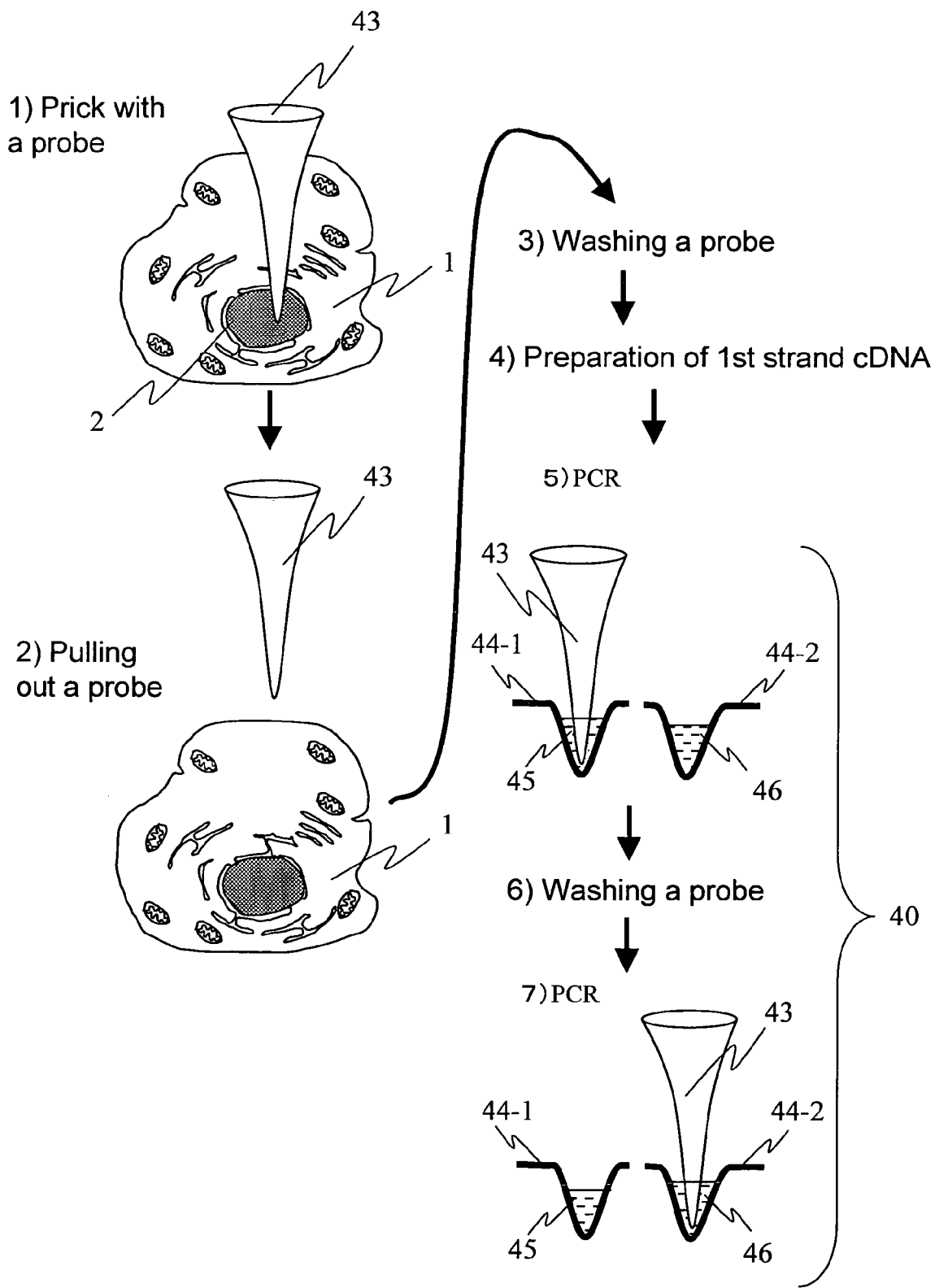
FIG. 73 is a view showing outline of a method of sampling mRNA which is an intracellular biological material in Example 2.

FIG. 73 is a view showing outline of a method of sampling mRNA which is an intracellular biological material in Example 2.

In step 1), the needle 43 is inserted into the living cell 1, and is kept in this state for 30 seconds.

In step 2), the needle 43 is pulled off from the cell 1.

In step 3), the needle 43 is immediately washed in a solution with RNase inhibitor contained therein. The matter having been hybridized to a surface of the needle 43 is conceivably poly A-RNA.

Step 4) is a step of obtaining a $1^{st}$ strand cDNA. Because the complementary poly T, which is the probe 21, is fixed to a surface of the needle 43, when a complementary chain is synthesized with a reverse transcriptase in this state, the complementary chain is synthesized at poly T as the base. Then RNase H is reacted to decompose the RNA chain, thus the $1^{st}$ strand cDNA being obtained.

In step 5), the first PCR amplification is carried out. In Example 2, a first pair of primers having the sequence SEQ No. 1 and sequence SEQ No. 2 corresponding to the human TACSTD1 used in Example 1 respectively and a second pair of primers having the sequence SEQ No. 3 and sequence SEQ No. 4 are prepared in vessels 44-1 and 44-2.

In the first PCR amplification, the needle 43 is inserted into a vessel 44-1 containing a PCR solution 45 including a first pair of primers having the sequence SEQ No. 1 and sequence SEQ No. 2 respectively, and PCR is carried out. The conditions for reaction are the same as those in Example 1.

In step 6), the needle 43 is pulled off from the vessel 44-1, and is fully washed.

In step 7), the second PCR amplification is carried out. In the second PCR amplification, the needle 43 is inserted into a vessel 44-2 containing a PCR solution 46 including a second pair of primers having the sequence SEQ No. 3 and sequence SEQ No. 4 respectively, and PCR is carried out. The conditions for reaction are the same as those in Example 1.

After completion of the second PCR, the solutions obtained by the respective PCR amplifications and stored in the vessels 44-1 and 44-2 are analyzed with Hitachi i-chip (micro electrophoresis chip) and Cosmo-i chip electrophoresis device. A signal electrophoresis separation band with 230 bp length is detected from the solution obtained after the first PCR amplification and stored in the vessel 44-1, while a single band with 215 bp length is detected from the solution obtained after the second PCR amplification and stored in the vessel 44-2.

The process 50 from the steps 5 to 7 can be carried out in repetition to the $1^{st}$ strand cDNA obtained in the step 4 and stored in the vessel containing a PCR solution prepared properly.

In Example 2, mRNA can easily be sampled from a living cell, and cDNA from the mRNA hybridized to the needle tip can be synthesized in the fixed state. Because the mRNA is preserved as a library on a surface of the needle, and therefore a target sequence segment of a target gene can be obtained by means of PCR. The needle with the mRNA library fixed in the form of cDNA can be preserved for a long time, and therefore a transcription product obtained when the needle is inserted into the cell can be preserved as a master library.

Example 3

Figure 74:
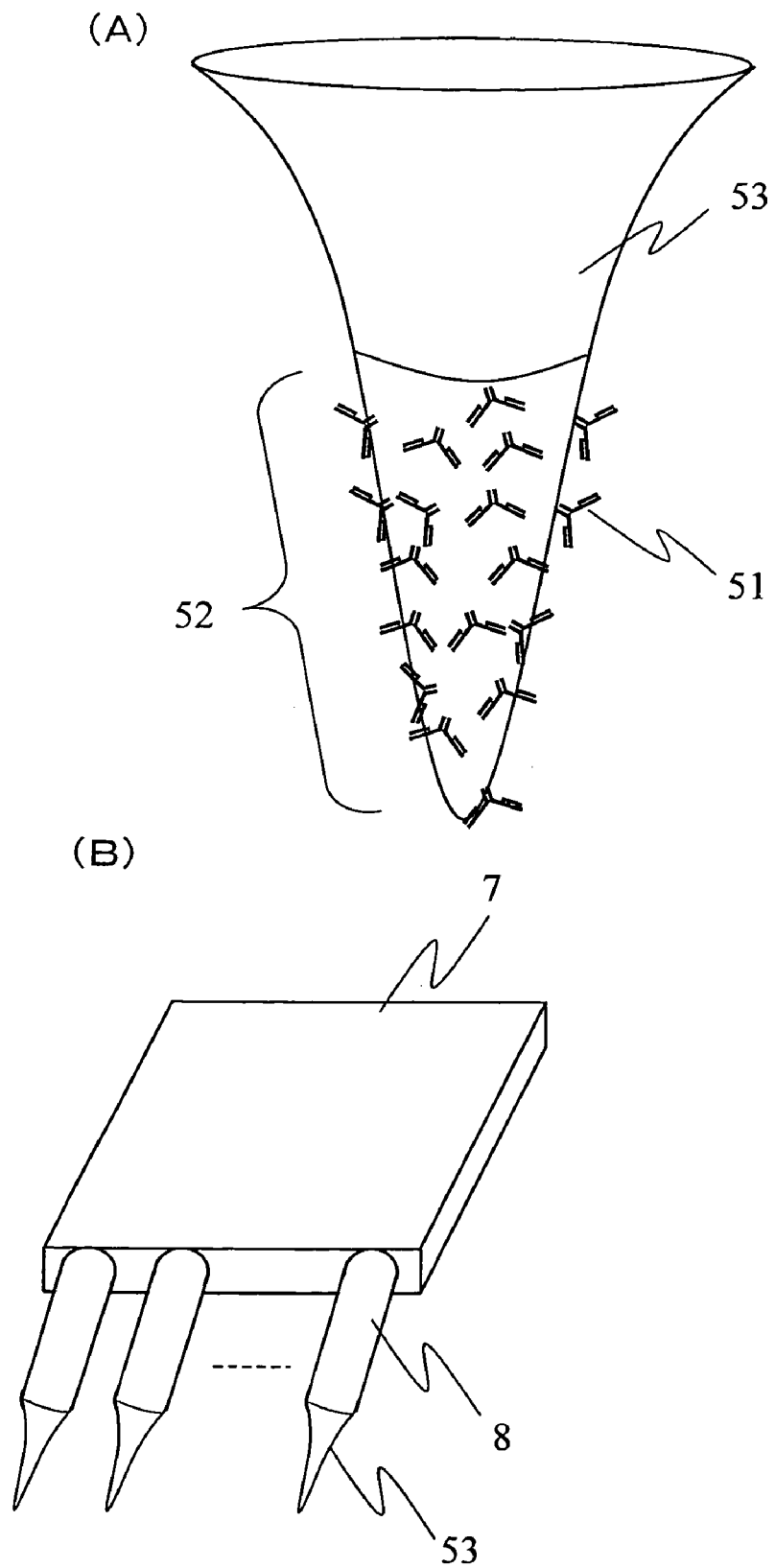

In Example 3, descriptions are provided for a case in which a needle with an antibody having affinity to a particular protein fixed thereon is used to sample the particular substance. FIG. 74(A) is a view showing a needle tip portion 53 which can be employed in Example 3, while FIG. 74(B) is a perspective view illustrating general configuration of a needle which may be employed in Example 3.

The polyclonal anti-mitochondria antibody separated from the human mitochondria membrane and having sensitivity to rabbit is used as an antibody in this example. This antibody reacts to a plurality of proteins or sugar chain antigens in mitochondria.

The needle with the anti-human mitochondria body fixed on the needle tip portion 53 is prepared as described below. At first, an SH group is introduced into the F(ab')$_2$ fragment obtained by subjecting the antibody to papain decomposition. A number of SH groups introduced as described above is 3 to 4 molecules per one F(ab')$_2$ molecule. Then the needle tip portion 53 is subjected to silane coupling processing to previously introduce an amino group into the surface thereof. Then 0.5% N-(β-aminoethyl)-γ-aminopropyltrimethoxysilane aqueous solution is left for 30 minutes at the room temperature to obtain an activated silane coupling solution. A silicon-made needle with the surface oxidized is immersed in the solution and left in the state for one hour. After the needle tip portion 53 is rinsed with deionized water, the needle tip portion 53 is dried in the air at a temperature in the range from 105 to 110° C. With this operation, an amino group fixed by covalent bond to a surface of the needle tip portion 53 is obtained.

Then N-(maleimidoundecanoyl)sulfosuccinimide, which is a bivalent reagent having a succinimide residue in on side and a maleimide residue in the other side, is reacted to the sample above for 30 minutes at the room temperature at pH 8. 0.1 M anti-oxidation buffer solution, pH 8.5 is used. After rinsing, F(ab')$_2$ with SH group having been introduced therein is reacted for one hour at the room temperature at pH 6.5. 0.1M sodium phosphate buffer solution, pH 6.5 is used as a buffer solution. The obtained needle with F(ab')$_2$ fixed thereon is preserved in PBS containing 5% trehalose (pH 7.4). FIG. 74(A) schematically shows the situation in which the F(ab')$_2$ is fixed on an area 52 of a surface of the needle tip portion 53. As shown in FIG. 74(B), the needle tip portion 53 with the F(ab')$_2$ fixed thereon is supported by the support section 8 and is jointed to the based section 7.

In the state where the needle tip portion 53 is jointed to the base section 7, the needle tip portion 53 with the F(ab')$_2$ fixed thereon is inserted into cytoplasm and then the needle tip portion 53 is pulled off. When the needle is pulled off observing the situation with an object lens with the resolution of 100 times, sometimes the situation is observed in which mitochondria comes near the needle and moves together with the needle. The needle tip portion 53 is mildly rinsed. The substances remaining on the surface is eluted with 3M guanidine, and the eluate may be used for analysis of proteins or mRNAs included therein.

[XV] Fifteenth Embodiment

A fifteenth embodiment of the present invention discloses a method and a device for sampling matured mRNA from a living cell without giving substantial damages.

Figure 75:
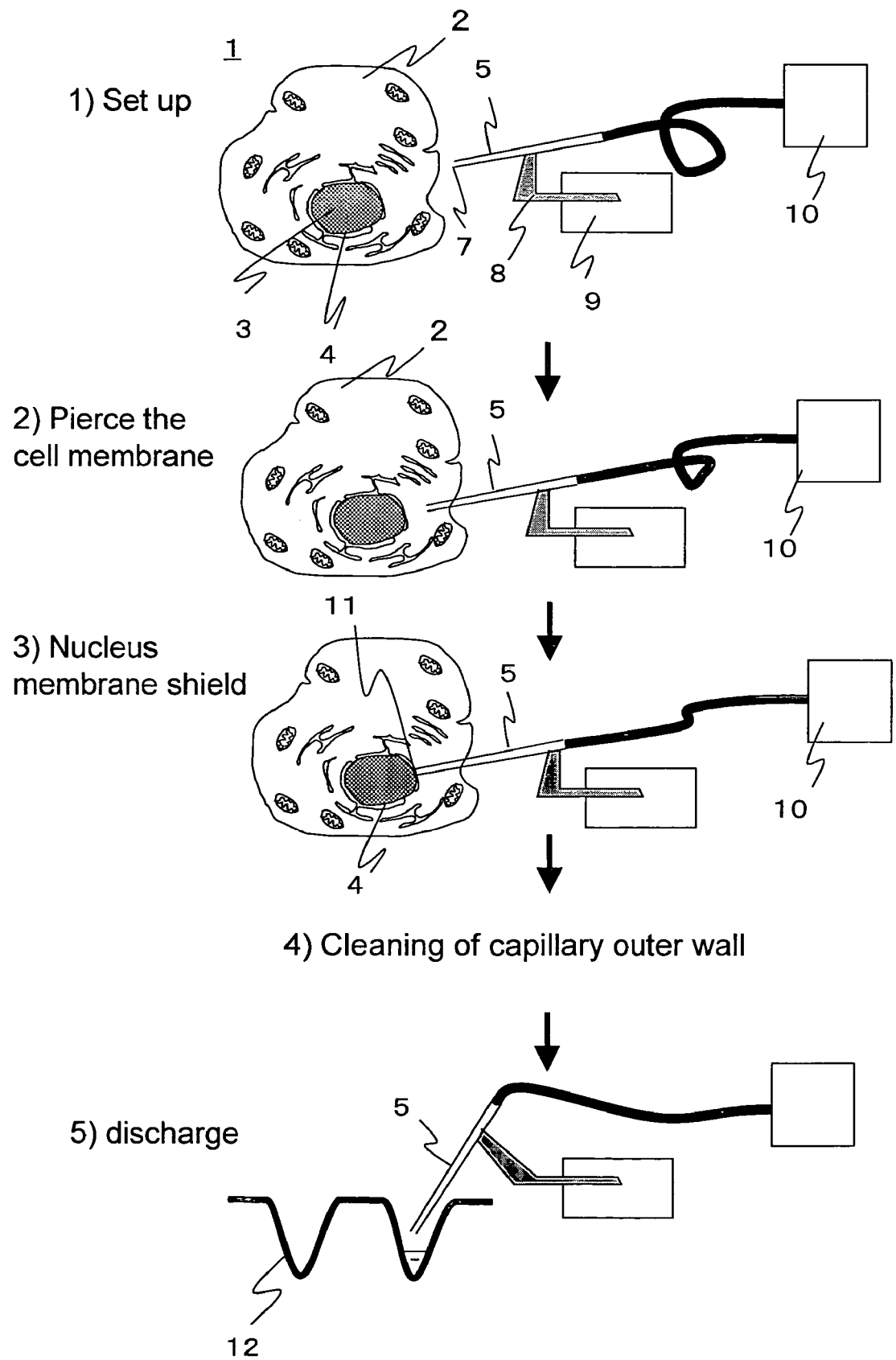
FIG. 75 is a schematic diagram showing a process flow for acquiring matured mRNAs in Example 1 of a fifteenth embodiment of the present invention.

FIG. 75 is a schematic diagram showing a processing flow for sampling matured mRNA in Example 1 of the fifteenth embodiment.

Example 1

Step 1 in the figure is a preparation process, and the figure shows the situation in which a living cell as a target from which mRNA is to be sampled and a capillary of an mRNA sampling device are set in a view field of a microscope. Designated at the reference numeral 1 is a cell (herein a cell having a nuclear like that of a human, a mouse, or a plant), at 2 a cytoplasm, at 3 a cell nuclear, and at 4 a nuclear membrane separating the cytoplasm from the nuclear. The reference numeral 5 indicates a capillary, and a diameter of a tip 7 (a portion to be inserted into a cell) is ⅕ of the cell size or below to reduce physical damages to the cell. The capillary 5 is set to a tool 8 allowing for movement thereof in the X- and Y-axial directions and also allowing for change of an angle of the tip. Further a buffer generally used for cell culture is filled inside the capillary. The tool 8 is attached to a driving device 9 driven by water pressure. Water pressure is used for delivery of a driving force from the driving device 9 to the tool 8. Further a micro syringe pump 10 is attached to the capillary 5, and a positive pressure state or a negative pressure state can be realized inside the capillary.

Although not shown, to prevent damages to the cell 1, the cell 1 and a tip portion of the capillary 5 are placed in a droplet of a buffer generally used for cell culture and formed on an observation glass plate provided in the view field of the microscope. Therefore all of the operations described below are performed in the droplet.

As shown in step 2 in the figure, a cell membrane of the target cell 1 is broken with the tip 7 of the capillary 5 visually checking with a microscope.

Then in step 3, the capillary tip 7 is contacted to the cell membrane 4 visually checking the situation with a microscope. As indicated by the reference numeral 11, when it is recognized that capillary tip 7 has contacted the nuclear membrane 4, the capillary tip 7 is tightly pressed to the nuclear membrane 4. In this step, the driving device 9 should be operated carefully not to break the nuclear membrane 4. Then the micro syringe pump is driven to generate a negative pressure in the capillary 5. What is important in this step is a degree of negative pressure generated by the micro syringe pump. Sucking is performed with a pressure not breaking the nuclear membrane 4, but the operation should be performed carefully taking into consideration a type of a state of the cell monitoring with a microscope. With the careful operations as described above, tight contact between the capillary tip and the nuclear membrane is preserved. In this state, the capillary tip is kept in contact to the nuclear membrane for a prespecified period of time (for instance for 5 minutes) and sucking is performed. Then inside of the capillary 5 is restored to the normal pressure, and the capillary is quietly pulled off from the cell 1.

Then in step 4, a peripheral surface of the capillary is quickly washed with 15 mM NaOH and then with water to remove nucleic acid components or protein components deposited on the peripheral surface of the capillary 5.

Then an internal fluid in the capillary 5 conceivably containing mRNA having passed through the nuclear membrane 4 is exhausted into a well 12 on a 384 well micro plate.

With the operations described above, the mRNA having passed through the nuclear membrane 4 can be obtained.

Figure 76:
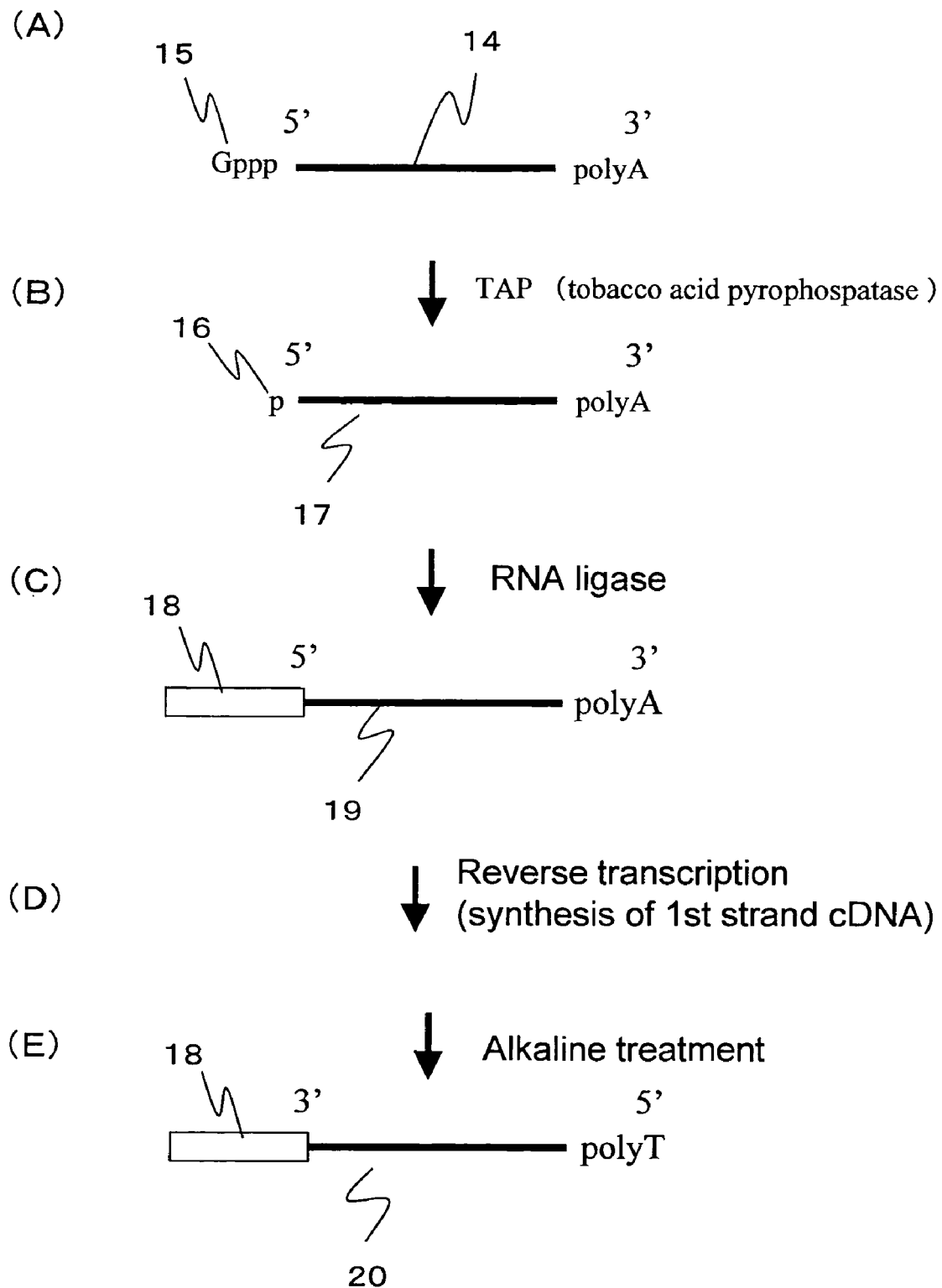
FIG. 76 is a view illustrating outline of a process for converting, of the mRNAs obtained in steps 1 to step 5 shown in FIG. 75, only those having the substantially full length to cDNAs.

FIG. 76 is a view showing outline of a process for converting, of the mRNAs obtained through the steps 1 to 5 shown in FIG. 75, those having the substantially full length to cDNA. The reaction employed for this process is that described in Y. Suzuki, K. Y. Nagayama, K. Murayama, A. Suyama, and S. Sugano, Gene 200, 146-156 (1997), and the reaction was slightly modified. Namely, in Example 1, it is conceivable that an amount of sampled mRNA is sub-picograms or below, a protocol for treating the ordinary mRNA at the scale of micrograms is not applicable to this process. Therefore, it is effective to minimize the reaction volume to the limit, and the process is performed based on this concept.

At first, shown in step A in the figure is a structure of mRAN 14 contained in the internal fluid of the capillary 5 obtained in step 5 and poured into the well 12 on the micro plate. Immediately 0.1 unit tobacco acid pyrophosphatase is reacted to the internal fluid in the capillary 5 (step B). The reaction is continued for 30 minutes in a 50 mM sodium acetate buffer solution (pH 5.5) containing 1 mM EDTA, 5 mM 2-melcaptoethanol and 1 unit of RNase which is a RNase inhibitor. The reaction volume is 0.5 µl In this processing, a cap structure 15 of mRNA 14 is removed, and mRNA 17 with the 5' terminal phosphorylated is obtained.

Then RNA ligase (10 units) is used against the mRNA 17 to obtain modified mRNA 19 with adaptor sequence 18 having been introduced therein (step C). The adaptor sequence is, for instance, (SEQ ID NO: 5)
5'-AGCAUCGAGUCGGCCUUGUUGGCCUACUGG-3':.

The reaction is performed in 5 mM 50 mM tris hydrochloric acid (Tris-HCl) buffer solution (pH 7.5) containing 5 mM MGCl$_2$ and 2-melcaptoethanol, 2 mM ATP, 25% PRG8000, and 1 unit of RNasin for 16 hours. The reaction volume is 5 µl. Then oligo DNA primer-added magnetic beads including 5-base length random sequence conjugated to 3' terminal of 26-base length poly T ($T_{26}$) (particle diameter: 2.1 um, amount of execution primer: 2 pml) and a reverse transcription enzyme are added to execute reverse transcription for 2 hours at 42° C., thus a $1^{st}$ strand cDNA being synthesized (step D). The random sequence is used in this step, because only poly T is insufficient for ensuring stability in hybridization of mRNA.

Then the reaction products are washed with 15 mM NaOH, and further the products are reacted in 15 mM NaOH for 10 minutes at 65° C. to remove RNA. With the operations described above, the $1^{st}$ strand cDNA 20 is obtained. 2 pmol adaptor sequence and 2 pmol random sequence-added poly T ($T_{26}$) are added according to the necessity to carry out PCR at 10 µl scale to obtain a double-stranded cDNA. When the random sequence poly T ($T_{26}$) without the magnetic beads added thereto is used, a large amount of cDNA-amplified products can be obtained in the solution. The cDNA obtained as described above is, in most cases, a full length cDNA including the cap structure up to the poly A sequence.

More specifically, in Example 1, mRNA passing through the nuclear membrane of a colon cancer cell is obtained as described below.

PCR amplification is carried out by using a portion of the adaptor sequence:

(SEQ ID NO: 6)
5'-AGCATCGAGTCGGCCTTGTTG-3' (Tm = 69° C.):

and a sequence specific to *Homo sapiens* tumor-associated calcium signal transducer 1 (TACSTD1):

(SEQ ID NO: 16)
5'-AAGCCACATCAGCTATGTCCACA-3' (Tm = 66° C.):

are used as primers against a mixture of single-stranded cDNA conceivably having the substantially full length. When full-length mRNA originated from TACSTD1 is included, it can be expected that a PCR product having the length of about 850 bp is obtained.

The Tm was computed using the Internet site; Tm Determination, Virtual Genome Center, prepared on 7 Aug. 1995, http://alces.med.umn.edu/rawtm.html programmed according to the method described in Breslauer et al., Proc. Nat. Acad. Sci. 83, 3746-50 (1986) and assuming the primer concentration of 200 nM and salt concentration of 50 mM. The sequence information for the TACSTD1 was searched using the mRNA code name NM_002354 from a web side of National Center for Biotechnology Information prepared by National Institute of Health (Revised: Jul. 16, 2004). The actual PCR is performed at the initial scale of 10 μl as described above and at the primer concentration of 200 nM 15 times with a reaction cycle of denaturing for 30 seconds at 94° C., annealing for 30 seconds at 60° C. and polymerase reaction for 2 minutes at 72° C.

Then 1 μl sample containing the amplification products is added to 50 μl of PCR reaction solution, and the mixture solution is subjected to 2-stage PCR amplification 35 times under the same conditions for reaction as those described above. The solution obtained through the PCR amplification is analyzed with i-chip (micro electrophoresis chip) obtainable from Hitachi Hi-Technology and Cosmo-i chip electrophoresis unit.

As a result, a plurality of bands are detected, and the electrophoretic separation band is observed at the position of 850 bp on one of the bands. This is the substantially same as the base-length of mRNA estimated from the database. The position of the primer on the sequence is complementary to the adaptor sequence introduced to the 5' terminal of the full length mRNA as well as to the segment from 796 to 818 bp on the mRNA sequence described in the code name NM_002354. This segmental sequence is in exon 6. From the NCBI data base described above, it is known that mRNA of the TACSTD1 has 1528-base length, which indicates that the sequence segment covers a half or more of the mRNA closer to the 5' terminal. A protocol for preparing a composition containing polyether when subjected to reverse transcription is used, so that, if the segment near the 5' terminal can be amplified like in Example 1, it may be considered that the substantially full-length cDNA has been obtained.

When contaminated with a precursor mRNA or a genome in the nuclear, PCR should be performed with a primer corresponding to the intron portion for determination. In this case, the amplification is tried with the primer SEQ No. 7 and the intron sequence:

(SEQ ID NO: 8)
AAGGAACAGTGATGCATGTAGATT (Tm = 61° C.):

positioned between the exon 5 and exon 6. The two-stage amplification was performed under the same conditions for PCR as described above, any peak was not detected at a position around 211 bp expected from the database.

Based on the result as described above, it may be said that the full length mRNA can efficiently be obtained by directly recovering the mRNA passing through the nuclear membrane 4 according to the method in Example 1. When a nuclear as a whole is grated, also precursor mRNA contained in the nuclear is recovered simultaneously, but with the method in Example 1, the problem can be evaded. Further, because the tip 7 of the capillary 5 only contacts (is pressed to) the nuclear membrane 4, so that the cell can be kept alive as it is. Further it is possible to pull off the capillary 5 once from the cell and to again insert the capillary 5 into the cell after a prespecified period of time for obtaining mRNA. The capability of obtaining mRNA without killing the cell is advantageous.

EXAMPLE 2

Figure 77:
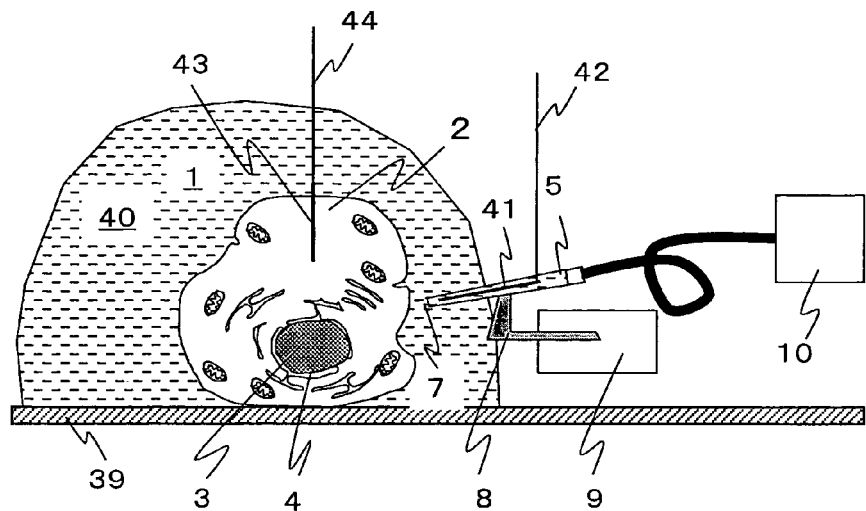
FIG. 77 is a schematic diagram showing an initial stage (step 1) of a process flow for acquiring matured mRNAs in Example 2.

FIG. 77 is a schematic diagram showing the initial state (step 1) of the process for obtaining matured mRNA in Example 2 of this embodiment. FIG. 77 corresponds to step 1 shown in FIG. 75, and as it is clearly understood from comparison between the two figures, the cell 1 and capillary 5 are placed on an observation glass plate 39 and also are included in a droplet 40. Further an electrode 41 is provided in the capillary 5, and a conductor 42 is connected to the electrode 41, and also an electrode 43 is placed in cytoplasm 2 of the cell 1. A conductor 44 is electrically insulated from the buffer droplet 40. Other steps in Example 2 corresponding to those in Example 1 are different only in addition of electrodes and conductors, and therefore the steps are steps are not shown.

In Example 2, the electrodes and conductors newly introduced are very effective in step 3 described in Example 1. Namely, in Example 1, the capillary tip 7 is only contacted to the nuclear membrane 4 visually monitoring with a microscope, but in Example 2, the electric conductivity between the electrode 41 and electrode 43 can be utilized, and therefore the electric conductivity can be monitored during the steps of contacting and pressing the capillary tip 7 to the nuclear membrane 4. Namely, while the tip 7 of the capillary 5 is within the cytoplasm 2, the electric conductivity between the electrode 41 and electrode 43 is extremely high (like short-circuited), but when the tip 7 of the capillary 5 contacts the nuclear membrane 4 of the cell 1, the electric conductivity between the electrode 41 and electrode 43 becomes larger. When the capillary tip 7 is tightly pressed to the nuclear membrane 4, the electric conductivity becomes further larger.

Therefore, in Example 2, contact and adhesion of the tip 7 of the capillary 5 to the nuclear membrane 4 of the cell 1 can be managed more easily by visually monitoring and controlling contact of the tip 7 of the capillary 5 to the nuclear 4 of the cell 1 and checking electric conductivity between the electrode 41 and electrode 43.

Further the electrodes 41 and 43 can also be used for sucking matured mRNA into the capillary 5. Namely, by setting the electrode 41 in the positive state and electrode 43 in the negative state and loading a voltage of about 10 V/cm to a section between the two electrodes 41 and 43, the mRNA originally having a negative charger can electrophoretically be sucked into the capillary 5. A voltage of about several tens mV is loaded to the cell, and sometimes the cell may be influenced, but mRNA can advantageously be recovered within a short period of time.

EXAMPLE 3

FIG. 78(a) to FIG. 78(c) are views each illustrating configuration of a tip portion of the capillary 5 which may be used in Example 1 or Example 2.

FIG. 78(a) shows a case where a partition 21 is provided inside the capillary 5 up to a position near a tip of the capillary 5. With this configuration, a flow path 22-1 and a flow path 22-2 separated from each other with the partition 21 are formed in the capillary 5. Therefore, when the micro syringe pump 10 is driven to generate a negative pressure in the capillary 5 in step 3 for sampling mRNA in the nuclear 3, the mRNA can be sampled by flowing a solution in the capillary 5 from one flow path to another flow path as indicated by the reference numeral 23. FIG. 78(b) shows a case in which a second capillary 26 is inserted up to a position near a tip of the capillary 5 to form a flow path 27-1 and a flow path 27-2. In step 3, the micro syringe pump is driven to generate a negative pressure in the capillary 5 for sampling mRNA in the nuclear 3. In this case the mRNA can be sampled by flowing a solution within the capillary from the outer flow path to the inner flow path as indicated by the reference numeral 28 using a gap in the tip portion. The second capillary 26 is required only to be inserted into the capillary 5, and is not required to be fixed. In this state the effect as described is achieved.

The FIG. 78(c) is similar to FIG. 78(b), and shows a case in which 5 capillaries 32-1 to 32-5 are provided in the capillary 5. In this case, for instance, during a sucking operation for 5 minutes, each of the capillaries 32-2 to 32-4 is set in the negative pressure state for one minute respectively for sucking, and a buffer solution is supplied form the capillary 32-1. Other capillaries are kept in the weak negative pressure state to substantially suppress migration of the fluid. With this configuration, mRNAs at different points of time are sucked into the four capillaries respectively.

Figure 79:
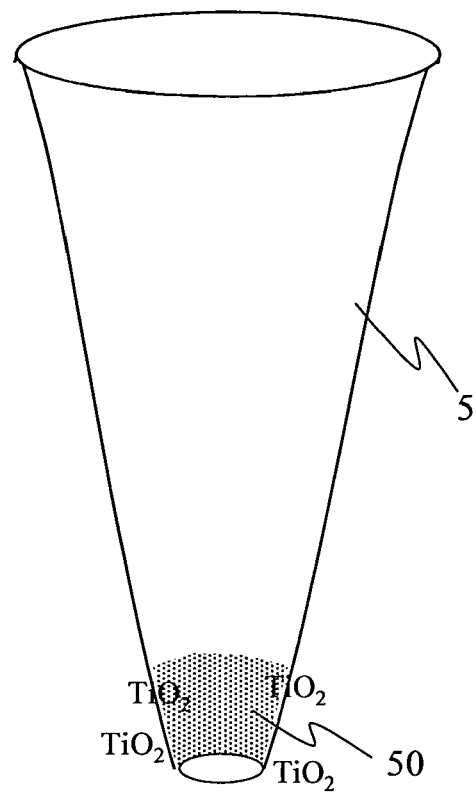
FIGS. 79(A) and 79(B) are views each illustrating a contrivance in an operation for inserting the capillary 5 into a cell, for reducing damages to the cell.
Figure 79:
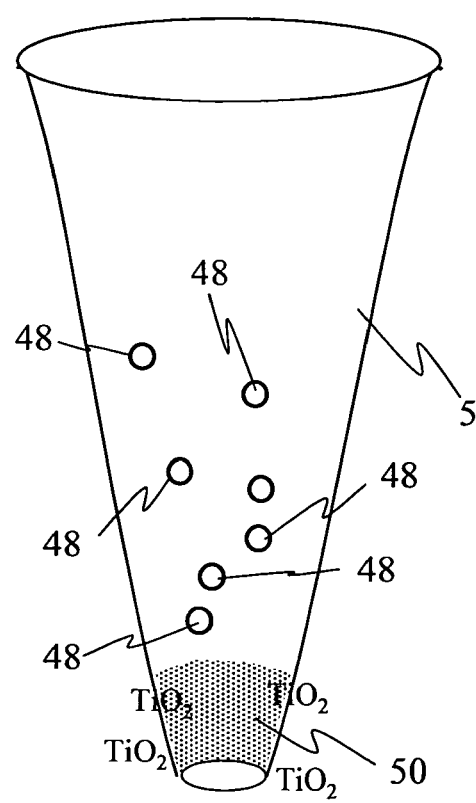

FIG. 79 is a view illustrating a contrivance for reducing damages given to a cell during an operation of inserting the capillary 5 into the cell.

FIG. 79(a) shows a case where a region 50 with titanium oxide $T_1O_2$ fixed thereto is provided at a tip portion of the capillary 5. With this configuration, when 335 nm UV ray is irradiated during an operation for inserting the tip portion of the capillary 5 into the cell 1, because of organic material decomposing activity of the titanium oxide coated thereon, the tip portion of the capillary 5 can easily be inserted into the cell 1 and damages given to the cell 1 are few. More specifically, the tip of the capillary 5 is passed through the cell membrane irradiating the US ray thereto. When the tip of the capillary 5 has passed through the cell membrane and reached the cytoplasm, irradiation of UV ray is stopped. Then the capillary tip is contacted to the nuclear membrane. When the capillary tip is contacted to the nuclear membrane, UV ray is not irradiated to prevent damages to the nuclear membrane. When the tip has reached the nuclear membrane, sucking is performed carefully as described in Example 1, and the capillary tip is tightly pressed to the nuclear membrane. The capillary tip is left in the state for 5 minutes to diffuse and recover the mRNA passing through the nuclear membrane inside the capillary 5.

FIG. 79(b) shows a case in which the region 50 with titanium oxide $T_1O_2$ fixed thereto is provided at a tip portion of the capillary 5 and further arginine 48 is fixed thereto. The arginine fixed thereto may be one amino acid, or that having the length of an octamer. For fixing arginine thereon, PNA (peptide nucleic acid) is added to the solution to be fixed at the molar ratio of 1/40, and the mixture solution is coated on the entire tip portion of the capillary 5. Also in this case, 335 nm UV ray is irradiated when the tip portion with $T_1O_2$ thereto passed through the cell membrane. Then irradiation of UV ray is stopped, and the capillary is further inserted into the cell until the tip portion reaches the nuclear membrane. Because of the mutual reaction between the arginine 48 and a phosphate base section in the lipid dual layer of the cell membrane, the capillary can smoothly be inserted into the cell.

It is needless to say that the tip portion of the capillary 5 described with reference to FIG. 79 may have the structure shown in FIG. 78(a) to FIG. 78(c).

The effect is provided also when only arginine is fixed to the tip portion of the capillary 5.

[XVI] Sixteenth Embodiment

A sixteenth embodiment discloses a novel technical means for separating an extremely small number of molecules having activity against a cell in a manner allowing a function of the cell to be traced from the viewpoint of not only separating a biochemical substance but also making the function of a cell clear.

The sixteenth embodiment is made by focusing on an analytical means known as the patch clamping method originally developed for researching a transporter and not having been related to the separation of a biochemical material so far, and by developing the means into a technique for separating a biochemical material.

As the patch clamping method, the following three types are generally used:

(1) the inside-out (the cytoplasm side of a cell membrane facing to the outside of a glass tubule) type in which a glass tubule having an opening with a tip thereof about 1 μm in diameter is pressed on a cell until electric resistance of the inside and outside of the glass tubule reaches a level of giga ohm to prepare a desired biochemical material;

(2) the whole-cell type in which a glass tubule sucks in while pressing a cell, and pierces a lipid bilayer formed in the glass tubule to obtain the whole cell attached onto the tip of the glass tubule; and (3) the outside-out (the outside of cytoplasm facing to the outside of a glass tubule) type in which, after forming the whole-cell type of a cell, the cell is removed, leaving behind a lipid bilayer in the proximity of a glass tubule, and an opening of the tubule is sealed making use of the lipid bilayer remaining in the periphery of the tubule opening to prepare a desired biochemical material.

The patch clamping method is a technique originally developed to research a transporter and measuring mobility of ion via a transporter as change in an electric current. Of the three types of the patch claming method developed as an analytical means, either type is means for preparation of a transporter itself with an operation using a glass tubule, and thus, has not been at all recognized as a device or technique for separating and preparing a biochemical material.

The sixteenth embodiment is made to solve the problems described above focusing attention on the patch clamping method. A transporter present in a cell membrane, a nuclear membrane or a mitochondrial membrane employed in the patch clamping method is used for separating a biochemical material. A transporter refers to a particular channel by which a specific chemical material passes through a cell membrane or the like. Such a transporter generally transports an amino acid including glutamic acid, oligopeptide including dipeptide and tripeptide, and various low molecule organic matters by making the materials pass through a cell membrane.

Examples of a transporter suited for applying to the sixteenth embodiment may be those listed in Table 1 described above. Nevertheless, not all transporters present in all cells are known, and actually, there is an orphan transporter whose existence is predicted from a genome sequence, there is a case where a transporter is unknown, and there are some substances capable of climbing over a cell membrane to transfer in and out of the cell without using a channel based on a concept as a specific transporter such as arginine oligomer described in the aforementioned Table 2. Therefore, the sixteenth embodiment can be implemented, like the second embodiment described above, if it is confirmed that there exists a function for transporting various substances.

Samples actually contain a diversified range of substances, and the types of the substances to be separated vary in many cases. Separation can be achieved by using a functional separation membrane including a transporter and employing a device with the transporter fixed thereon for collecting a separated materials. Alternatively, separation with a higher precision can be achieved by using a plurality of transporters to separate biochemical materials from a mixture sample, and more specifically, by connecting in series the membranes with the transporters embedded therein and separating biochemical material in stages. Medium in the sample is transferred by dispersion, electrophoresis or electro-osmotic flow, and a substance(s) having passed through the membranes is collected. In a case when membranes with the transporters embedded therein are connected in series to separate biochemical material in stages, biochemical materials captured between the adjoining membranes is collected. Alternatively, in the configuration where an outlet is provided each between the adjoining membranes, separation can be achieved by individually collecting a solution at each of the outlets.

Separation at a molecular level can be achieved by limiting an area of a membrane with a transporter embedded therein to several hundreds of $nm^2$ or less. Further, in this case, how many molecules pass through a transporter can be confirmed by measuring an electrical change in front and behind the membrane.

EXAMPLE 1

Figure 80:
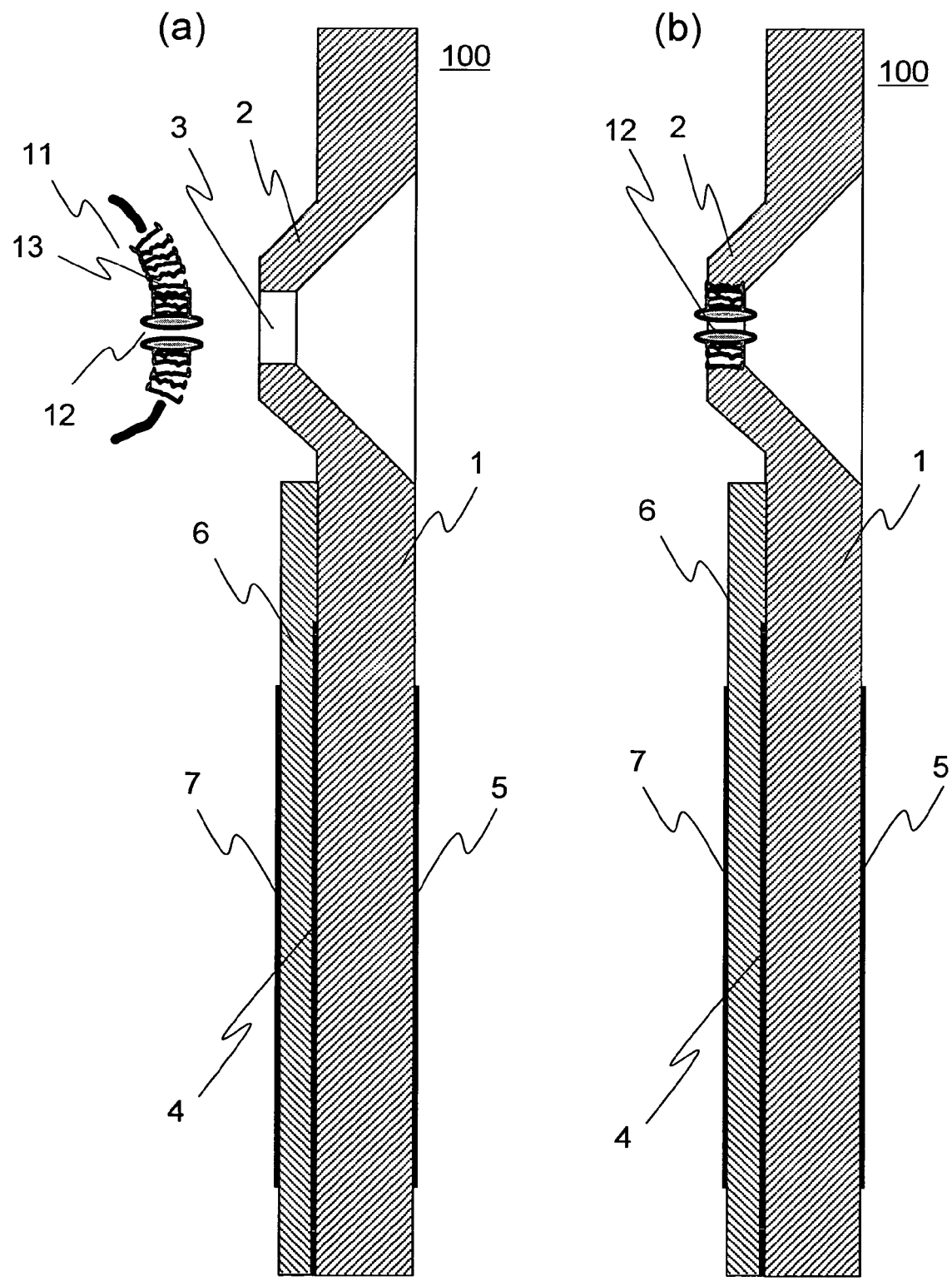

FIG. 80($a$) is a cross-sectional view showing outline of a method of preparing a biological material separation chip which can be used for a biochemical material separator related to Example 1 of a sixteenth embodiment, and FIG. 80($b$) is a cross-sectional view schematically showing an example of a structure of the completed biological material separation chip.

In FIG. 80, reference numeral 100 indicates a biological material separation chip. Reference numeral 1 indicates a substrate for a biological material separation chip, for instance, a silicon substrate. Size of the substrate is, for instance, 5 mm in the height direction in the figure, and 500 μm in the vertical direction in the same. Thickness of the substrate is, for instance, 100 μm. Height of a projection 2 formed on an end of the substrate 1 is, for instance, 5 μm, while the thickness thereof is, for instance, 2 μm. On the top of the projection is formed a pore 3. Size of the pore 3 is, for instance, 1~2 μmφ. On the both sides of a lower portion of the substrate are formed electrode layers 4, 5, and an insulating layer 6 is formed for covering all over the electrode layer 4, after which an electrode layer 7 is further formed thereon. The substrate 1 is created making use of the semiconductor technology, outline of creating the substrate 1 is described hereinafter with reference to FIG. 81.

The biological material separation chip 100 is completed after taking a transporter of a cell in a portion of the pore 3 thereon. Processing of taking a transporter of a cell in a portion of the pore 3 is described below.

Though not shown in the figure to avoid complications, the substrate 1 and a cell 11 are provided opposing to each other in a droplet of a buffer suitable for cell culture dropped down on an observation glass plate for a microscope. In this step, while observing with a microscope, a transporter 12 of the cell 11 is positioned to face to the pore 3 on the projecting side of the projection 2. It is to be noted that reference numeral 13 denotes a lipid bilayer of the cell 11. Further, a capillary connected to a microsyringe pump is temporarily attached to the concave portion side of the projection 2, so that inside of the capillary can be in the state of negative pressure. The buffer described above is filled inside the capillary. In addition, an electrode is provided inside the capillary, so that a lead wire connected to the electrode is drawn out, while another electrode is provided in a droplet portion, so that another lead wire connected to the electrode is drawn out. The latter lead wire is electrically isolated from the droplet of a buffer.

While observing with a microscope, a portion of the transporter 12 of the cell 11 is contacted to the pore 3 on the projection 2. In this step, while monitoring electrical conductivity between the two electrodes described above, before a portion of the transporter 12 of the cell 11 is contacted to the pore 3, an electrode in the capillary and another electrode in the droplet portion are short-circuited owing to a buffer, and by contrast, after the contact, the two electrodes are substantially isolated because the pore 3 is blocked off with the transporter 12 and the lipid bilayer 13 of the cell 11.

When it is confirmed by a visual observation with a microscope and a sharp decline in electrical conductivity between the two electrodes described above, a microsyringe pump connected to a capillary temporarily attached to the concave portion side of the projection 2 is operated, so that the inside of the capillary turns into the state of negative pressure. The cell 11 is kept being sucked at such a pressure as not piercing the lipid bilayer 13, and when the cell 11 is finally peeled off, a portion of the lipid bilayer 13 including the transporter 12 is left behind, being fixed onto the pore 3 on the projection 2. With this step, the biological material separation chip 100 is completed with a transporter of a cell taken in a portion of the pore 3 thereon, as shown in FIG. 80($b$). The chip having a transporter thereon shown in FIG. 80($b$) fixes the transporter in the form of inside-out. Descriptions are provided later for the electrode layers 4, 5 and electrode layer 7.

It should be understood that the completed biological material separation chip 100 is preserved in a buffer suitable for cell culture to avoid damages of the transporter fixed onto the pore 3.

Figure 81:
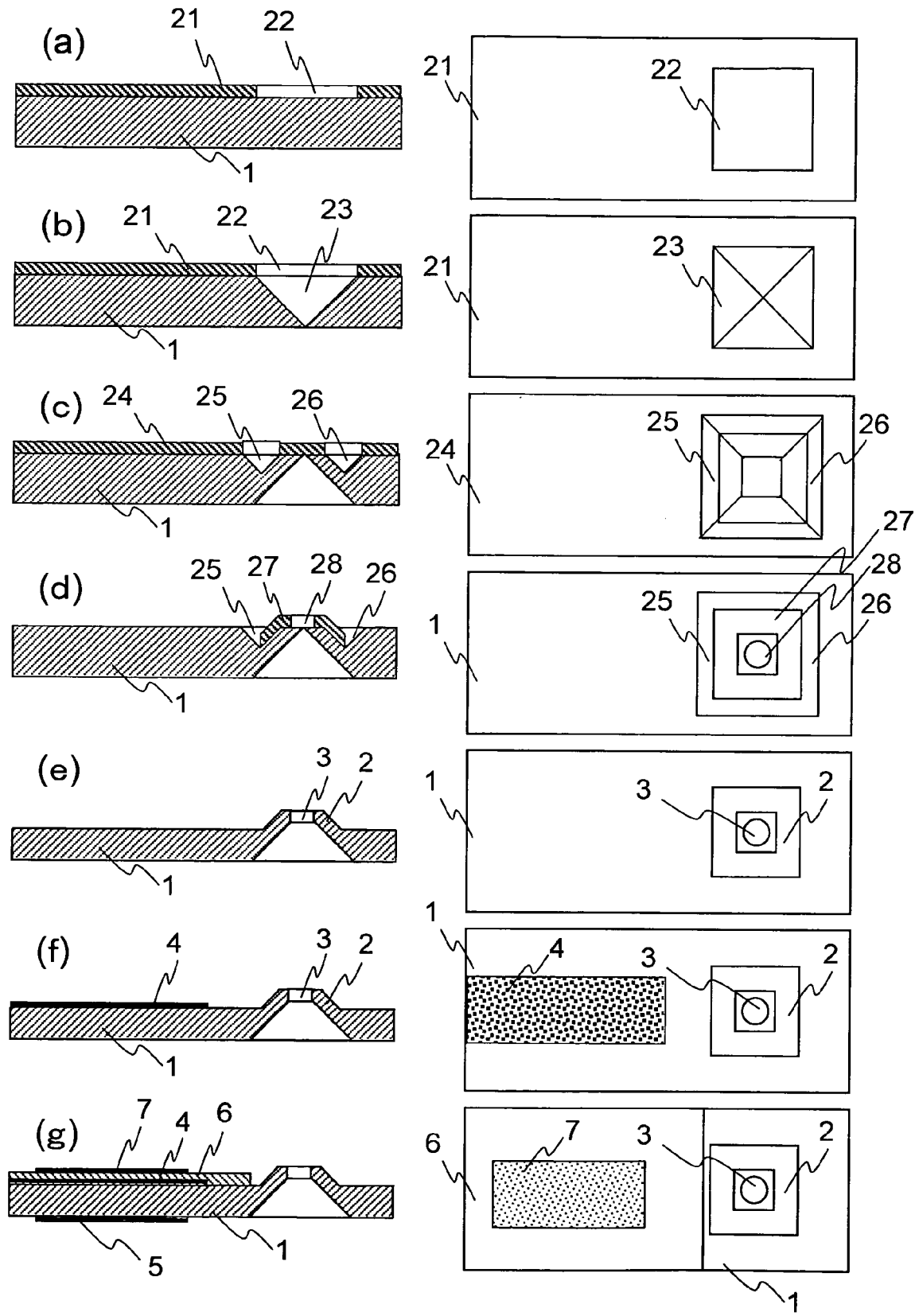
FIGS. 81(a) to 81(g) are views each schematically illustrating outline of a process for forming a substrate 1 of a biological-material separation-chip 100, and each view shows a cross section on the left side and a plan view corresponding to the cross section on the right side.

FIG. 81($a$) to FIG. 81($g$) are views each illustrating outline of a process of forming a substrate 1 for a biological material separation chip 100. In each of FIG. 81($a$) to FIG. 81($g$) are shown a cross section on the left side and a plan view corresponding to the cross section on the right side.

Firstly, as shown in FIG. 81($a$), a silicon substrate having a specified crystal axis is prepared, on one face of which is provided a mask 21, and a window 22 is formed by removing the mask 22 in a position where a projection 3 is to be created. As shown in FIG. 81($b$), a portion corresponding to a quadrangular pyramid 23 is removed with etching. Next, as shown in FIG. 81($c$), the mask 21 is removed, and a mask 24 is provided on another face of the silicon substrate 1 to form a window by removing the mask 24 in a position where a projection 3 is to be created, thereby concave sections 25, 26 each having a triangular cross section being formed. The concave sections 25, 26 are, as seen from the plane view, concaved and uninterrupted portions corresponding to the quadrangular pyramid 23. Then, as shown in FIG. 81(*d*), a window 28 is opened in a position surrounded by the concave sections 25, 26 by providing a mask 27. Next, as shown in FIG. 81(*e*), a pore 3 is opened in a position corresponding to the substrate 1 making use of the window 28. In this step, a projection 2 is also formed in the periphery of the concave sections 25, 26 on the substrate 1 by etching. Then, as shown in FIG. 81(*f*), an electrode 4 is formed on a face having a projection 2 on the substrate 1. The electrode 4 is made of an aluminum-deposited layer. Next, as shown in FIG. 81(*g*), the whole surface of the electrode 4 is covered with a polyimide insulating layer 6, on which an electrode 7 is formed. The electrode 7 is made of a platinum-deposited layer. After that, an electrode 5 is formed on another face of the substrate 1. The electrode 5 is also made of a platinum-deposited layer. Thus the formation of the substrate 1 for the biological material separation chip 100 is completed. Though detailed data on the semiconductor technology is omitted herein, those skilled in the art can easily implement the steps described above.

Figure 82:
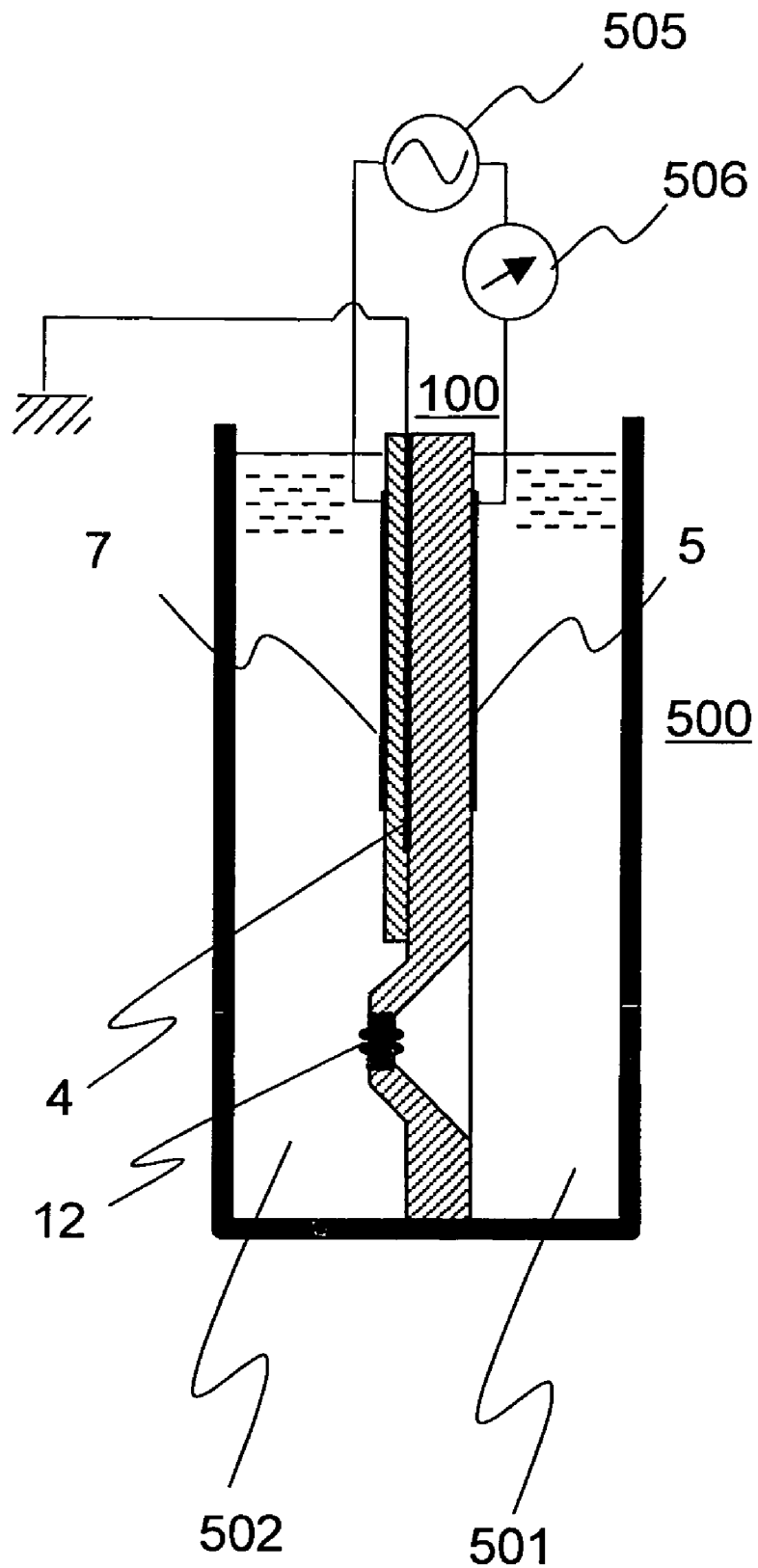
FIG. 82 is a view for illustrating an example of a biological-material separation by a biological material separation chip 100 with a transporter 12 fixed to a pore thereof.

FIG. 82 is a view illustrating an example of biological material separation by a biological material separation chip 100 with a glucose transporter 12 fixed onto a pore 3 thereon. In this case, a cell derived from cardiac muscle is employed as the cell 11 described in FIG. 80(*a*), and a lipid bilayer including a transporter capable of transporting glucose is fixed onto the pore 3. The use of cardiac muscle enables to obtain the chip 100 with a glucose transporter fixed thereon with a substantially high probability by means of the method described above. When the biological material separation chip 100 having a glucose transporter is created by means of the method described above, a number of other transporters are naturally fixed onto the pore 3.

The biological material separation chip 100 is provided turning a rear face thereof having the electrode 5 and a front face thereof having the electrode 7 to a space 501 and a space 502, respectively, each discretely provided in a vessel 500. The electrode 4 is earthed. The electrodes 5 and 7 are attached to a power source 505 and an ammeter 506 according to the necessity.

The spaces 501 and 502 are firstly filled with a solution of an M9 culture medium (pH 7.1) containing a 2 mM of calcium. Although the spaces 501 and 502 are seemingly large in the figure, there is actually a gap of several tens of μm between the spaces, so that the solution is put into the spaces using a capillary tube. At this point in time, the value indicated by the ammeter 506 is monitored. Next, the electric current value fluctuates when the M9 culture medium containing a 2% of glucose as a sample solution is added to the space 501 through the use of the capillary phenomenon. This demonstrates that glucose and some other ion are coupled to pass through a membrane. After a prespecified period of time, the solution on the side of the space 502 is collected.

The solutions collected from the space 502 and the original M9 culture medium are collected with a capillary, into which *Escherichia coli* bacteria suspended in an M9 culture medium is sucked one bacterium at a time. *E. coli* cultured in a solution collected from the space 502 divide after a lapse of 50 to 60 minutes, while in turn, *E. coli* cultured in a fresh M9 culture medium do not divide even after a lapse of 120 minutes and more. This shows that at least glucose is collected after passing through a transporter.

EXAMPLE 2

Figure 83:
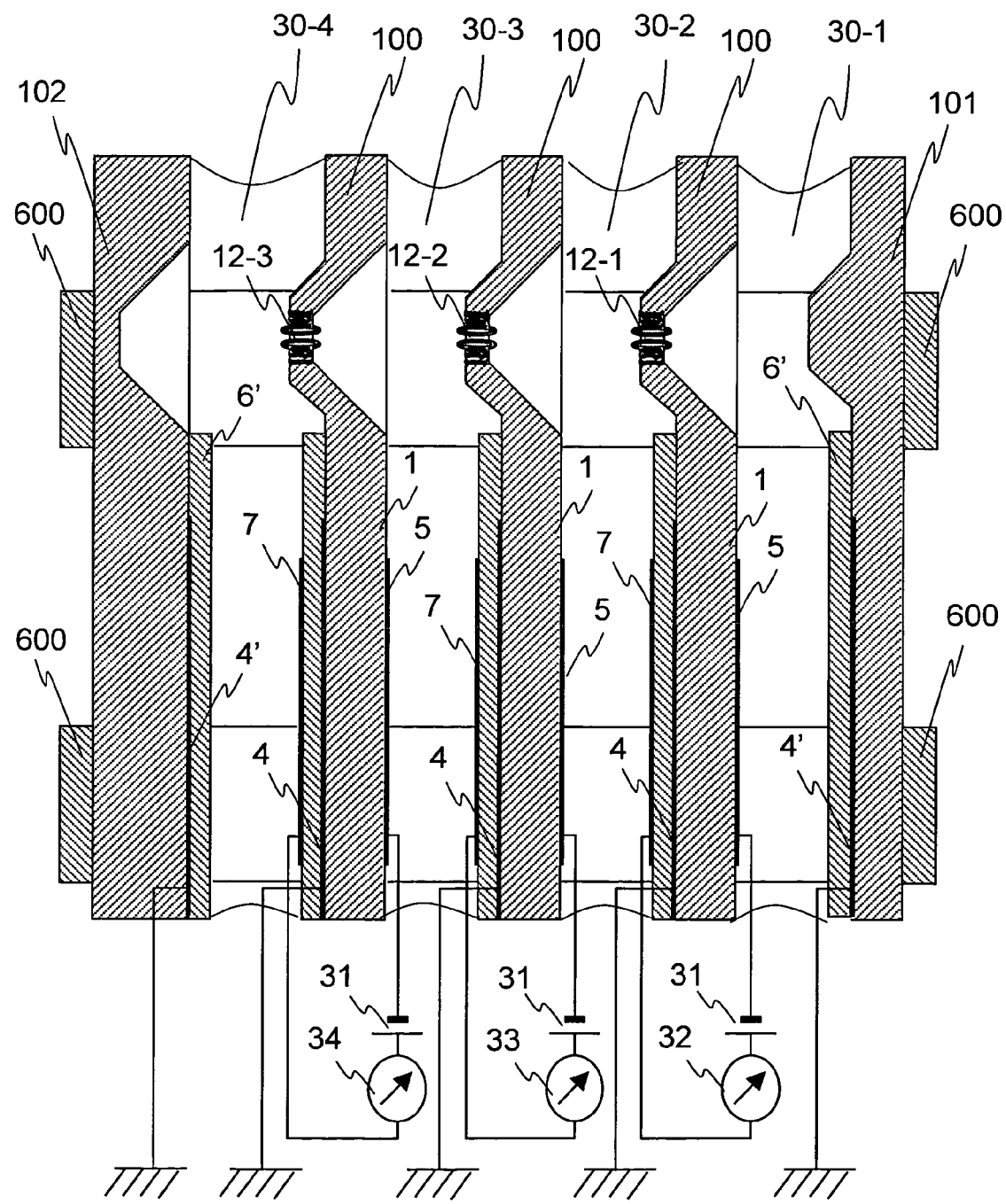
FIG. 83 is a cross-sectional view showing outline of a biological material separator in Example 2 in which three sheets of biological material separation chips 100 stored in a buffer suited to cell culture are combined with each other.

FIG. 83 is a cross-sectional view showing outline of a biological material separator in Example 2 in which three sheets of the biological material separation chips 100 preserved in a buffer suited to cell culture are combined with each other. The biological material separator according to Example 2 is assembled in a buffer suited to cell culture to avoid damages of a transporter 12 fixed onto a pore 3. More specifically, it is practical to assemble the separator under visual observation in droplets of a buffer dropped on an observation glass plate for a microscope and suited to cell culture. Herein, each of the biological material separation chips 100 fixes onto each pore 3 transporters from a plurality of types of cells present in a cell membrane, a nuclear membrane or the like and transporting a specific biological material.

Figure 84:
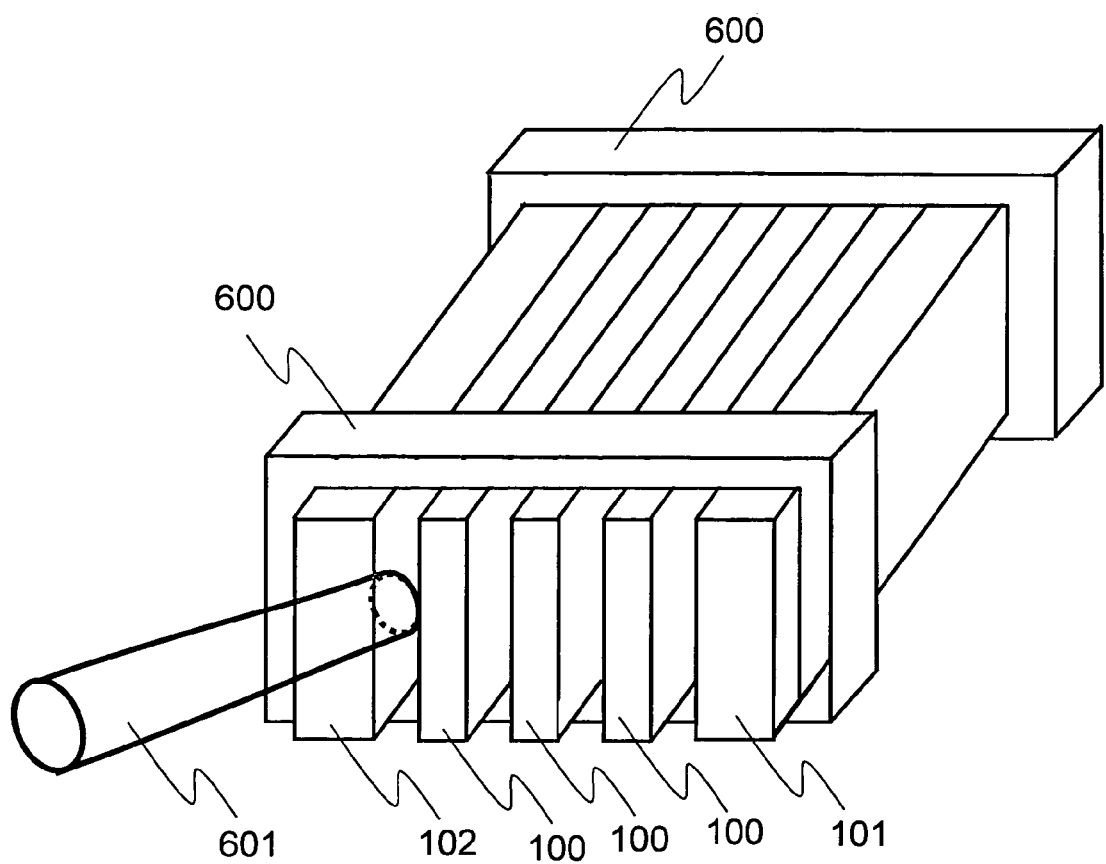
FIG. 84 is a perspective view showing an appearance of the biological material separator in Example 2 in which three sheets of biological material separation chips 100 are combined with each other.

In FIG. 83, reference numeral 100 indicates a biological material separation chip 100 shown in FIG. 80(*b*). Three sheets of the biological material separation chips 100 are arrayed at intervals of 100 to 500 μm, and sidewalls 101, 102 manufactured through the use of a silicon substrate are provided on both sides of the arranyed chips 100. On the side of the inner face of the sidewalls 101, 102 are provided an electrode 4' and an insulating layer 6' corresponding to the electrode 4 and the insulating layer 6 provided on the biological material separation chip 100, respectively. The sidewalls 101, 102 can be manufactured with the semiconductor technology, like the biological material separation chip 100. The biological material separation chips 100 herein are fixed with a clamp 600 whose external appearance is as shown in FIG. 84. In this step, a suitable spacer is inserted between the biological material separation chips 100 or between the biological material separation chip 100 and the sidewalls 101, 102, or the clamp 600 itself has a suitable spacer.

In FIG. 83, curved lines each drawn on the upper and lower ends between the biological material separation chips 100 as well as between the biological material separation chip 100 and the sidewalls 101, 102 indicate that a liquid filled in each space is maintained therein with the surface tension.

FIG. 84 is a perspective view showing an appearance of the biological material separator in Example 2 in which three sheets of the biological material separation chips 100 are combined with each other. As shown in the figure, each chip 100 and the sidewalls 101, 102 are fixed with a clamp 600. Clearances between each chip 100 are opened as 30-1, 30-2, 30-3 and 30-4 in FIG. 83. Gaps between each chip 100 are several tens of μm in distance, so that a liquid can be filled in or discharged from the gaps with a capillary tube using a capillary pipet 601. With the configuration as described above, different solutions can be filled in or discharged from each gap between the chips 100.

As shown in FIG. 83, a biological material separator assembled under visual observation in droplets of a buffer dropped on an observation glass plate for a microscope and suited to cell culture has the buffer between the biological material separation chips 100 and between the biological material separation chip 100 and the sidewalls 101, 102 when the assemble is completed.

In this state, a sample is fed in or taken out of the space between the biological material separation chips 100 and between the biological material separation chip 100 and the sidewalls 101, 102 using a capillary pipet 601, after both the electrodes 4 and 4' are earthed. This is for the purpose of shielding static electricity generated when a solution flows on the surface of the biological material separation chip 100 and the sidewalls 101, 102, and preventing current noise from being generated. A power source 31 and a current flowing therefrom are designed to be monitored so as to apply a specified voltage between the electrodes 5 and 7 on both sides of the biological material separation chip 100. When a transporter 12 is fixed onto a pore 3 in a stable manner, the current flowing from the power source 31 is substantially null, while in turn, when the transporter 12 is dropped off, a heavy electric current flows, which enables an easy detection of the state of the transporter 12.

Reference numerals 12-1, 12-2 and 12-3 indicate each of transporters 12 for each biological material separation chip 100 viewed from the side of the sidewall 101, and herein the transporter 12-1 is a transporter prepared from a neuron-derived cell membrane, the transporter 12-2 is a transporter prepared from a testicular cell membrane, and the transporter 12-3 is a lipid bilayer derived from a pulmonary cell membrane.

Firstly, a buffer at pH 6.5 is filled in all clearances of the separator, and an amino acid mixed solution including glutamic acid, aspartic acid, alanine and glutamine is fed in the clearance 30-1. Then a current at an about 100 nA is observed with an ammeter 32 and an ammeter 33, demonstrating that some kind of substrate transport takes place. A current flowing through an ammeter 34 is about one third of those observed with the other ammeters. Solutions in the clearances 30-2 to 30-4 are collected with the capillary phenomenon for amino-acid analysis using nano LC to find that glutamic acid and aspartic acid passes through the lipid bilayers 12-1 and 12-3 and are accumulated in the clearances 30-2 and 30-3. Glutamic acid and aspartic acid observed in the clearance 30-4 is at a level below the detection limit. Alanine and glutamine is detected in all of the clearances.

In fact, a transporter in the SLC 1 family related to amino acid transport is generally expressed in the cells described above according to the SLC new solute carrier superfamily proposed members (http://www.bioparadigms.org/slc/menu-.asp) described in HGNC Gene Grouping/Family Nomenclature (updated in June 2004), http://www.gene.ucl.ac.uk/nomenclature/genefamily.shtml in the transporter database (official website of HUGO), and acidic amino acid is expressed in neurons, testis, kidney, liver, heart and the like in large quantity, while alanine and glutamine, which is neutral amino acid, is expressed in a wide range of organs, these findings are consistent with the result described above.

Thus, by using the biological material separator and the method of separating biological material according to the sixteenth embodiment, an extremely trace quantity of biological material can be roughly classified depending on its property, and the difference analysis in which comparison of material transport among fixed cells is analyzed through the use of difference in material to be transported can be conducted by observing what kind of material is accumulated in each clearance.

EXAMPLE 3

Figure 85:
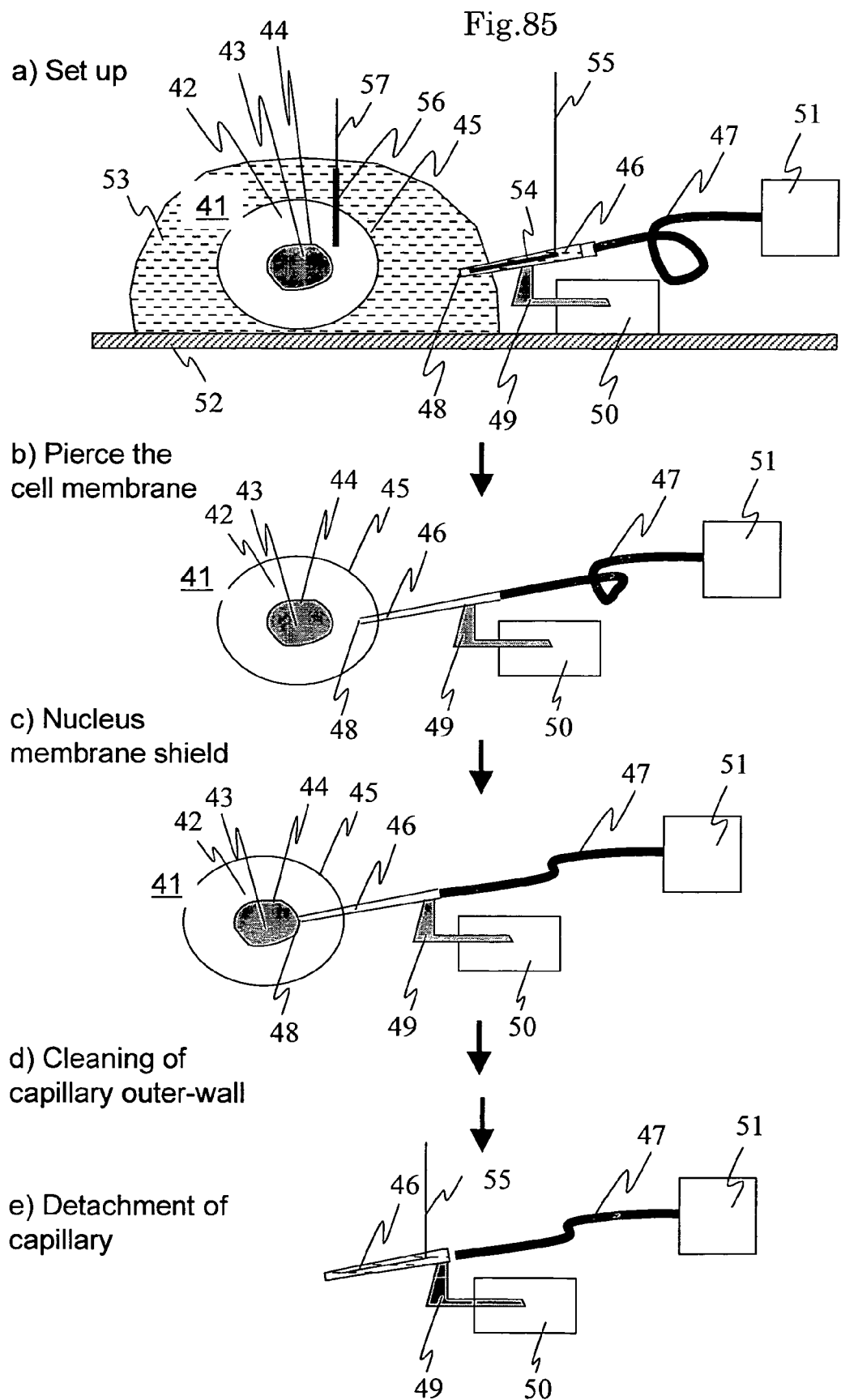
FIGS. 85(a) to 85(e) are views illustrating a procedure for preparing a biological material separation chip with a nucleic membrane fixed to a tip section of the capillary chip in Example 3.

In Example 3, a biological material separation chip having configuration in which a nuclear membrane is fixed onto the tip section of a capillary chip is described. FIG. 85(*a*) to FIG. 85(*f*) are views illustrating a procedure for preparing a biological material separation chip with a nucleic membrane fixed onto the tip section of a capillary chip thereof in Example 3. Herein is described an example of preparing an mRNA purified chip using a nuclear membrane of an oocyte of a *xenopus*.

FIG. 85(*a*) is a view showing a preparatory step and illustrating the outline when an oocyte of a *xenopus* for obtaining a nuclear membrane thereof and a capillary chip are provided within the field of a microscope for a visual observation. Designated at the reference numeral 41 is an oocyte of a *xenopus*, at 42 cytoplasm, at 43 a cell nucleus, at 44 a nuclear membrane partitioning cytoplasm from a nucleus, and at 45 a cell membrane. Reference numeral 46 indicates a capillary chip, whose tip 48 (a portion inserted into a cell) is about 400 μm in diameter and 20 mm in length in order to reduce a physical damage on a cell. The capillary 46 is attached to a fixture 49 capable of shifting the X, Y and Z axes thereof and changing the degree of the tip angle thereof. A buffer of the type used for cell culture is filled inside the capillary 46. The fixture 49 is attached to a drive unit 50 driven by hydraulic pressure. The driveline from the drive unit 50 to the fixture 49 utilizes hydraulic pressure. Further a microsyringe pump 51 is attached to the capillary 46, and the inside of the capillary 46 can be transformed between the states of positive and negative pressure with complete control. Reference numeral 47 indicates a tube for connecting the capillary 46 and the microsyringe pump 51.

To avoid damages to a cell 41, the cell 41 and the tip section of the capillary 46 are made to be always in droplets 53 of a buffer of a type used for culturing a cell formed on an observation glass plate 52 provided within the field of a microscope, and all of the following steps are taken in the droplets. Further, an electrode 54 is temporarily provided in the capillary 46, so that a lead wire 55 connected the electrode 54 is drawn out, while another electrode 56 is temporarily provided in the cytoplasm 42 of the cell 41, so that another lead wire 57 connected to the electrode 56 is drawn out. To avoid complications in the figure, representation of the observation glass plate 52, droplets 53, electrodes 54, 56 and lead lines 55, 57 are omitted in the following FIG. 85(*b*) to FIG. 85(*e*).

FIG. 85(*b*) shows a state where the cell membrane 45 of the cell 41 is pierced with the capillary 46, while visually observing with a microscope.

FIG. 85(*c*) shows a state where the tip 48 of the capillary 46 is contacted to the nuclear membrane 44, the microsyringe pump 51 is operated to obtain negative pressure inside the capillary 46, and thereby the tip 48 of the capillary 46 is closely adhered to the nuclear membrane 44. Then the degree of negative pressure by the microsyringe pump 51 is properly adjusted, and the capillary 46 is pulled out of the cell 41 keeping the state where the nuclear membrane 44 is adhered to the tip of the capillary chip, and, while sucking the nuclear membrane 44 at such pressure as not piercing the same. Thus a capillary chip 46 can be obtained having configuration in which the nuclear membrane 44 with the inside thereof facing to the outside of the chip is fixed onto the tip section 48 of the chip.

In addition to the contact of the capillary tip 48 to the nuclear membrane 44 while visually observing with a microscope, electrical conductivity between the electrode 54 and the electrode 56 can be utilized herein. Namely, the step of contacting and closely adhering the capillary tip 48 to the nuclear membrane 44 can be monitored with electrical conductivity. During the period when the tip 48 of the capillary 46 is in the cytoplasm 42, electrical conductivity between the electrode 54 and the electrode 56 is extremely high (short-circuited), however, when the tip 48 of the capillary 46 contacts the nuclear membrane 44 of the cell 41, the electrical conductivity drops (electric resistance increases), and moreover, the electrical conductivity further decreases when the contact becomes somewhat tighter.

Thus the contact and adhesion of the tip 48 of the capillary 46 to the nuclear membrane 44 of the cell 41 can be controlled more easily by controlling a contact of the tip 48 of the capillary 46 to the nuclear membrane 44 of the cell 41 under visual observation, and by checking electrical conductivity between the electrode 54 and the electrode 56.

After the tip 48 of the capillary 46 is closely adhered to the nuclear membrane 44 of the cell 41, while keeping nuclear membrane 44 onto the tip of the chip 48, the capillary 46 is pulled out from the cell 41.

FIG. 85(*d*) shows the step of cleaning the periphery of the capillary 46 having been pulled out from the cell 41 to remove nucleic acid ingredients and protein ingredients adhering to the periphery of the capillary 46.

FIG. 85(*e*) shows a state where a biological material separation chip with a nuclear membrane fixed onto the tip of a capillary chip thereof is completed. In this state, a buffer used for cell culture still remains in the capillary 46, though, it is desired that the entire chip is put in a buffer to preserve the nuclear membrane fixed on the tip of the capillary chip.

Figure 86:
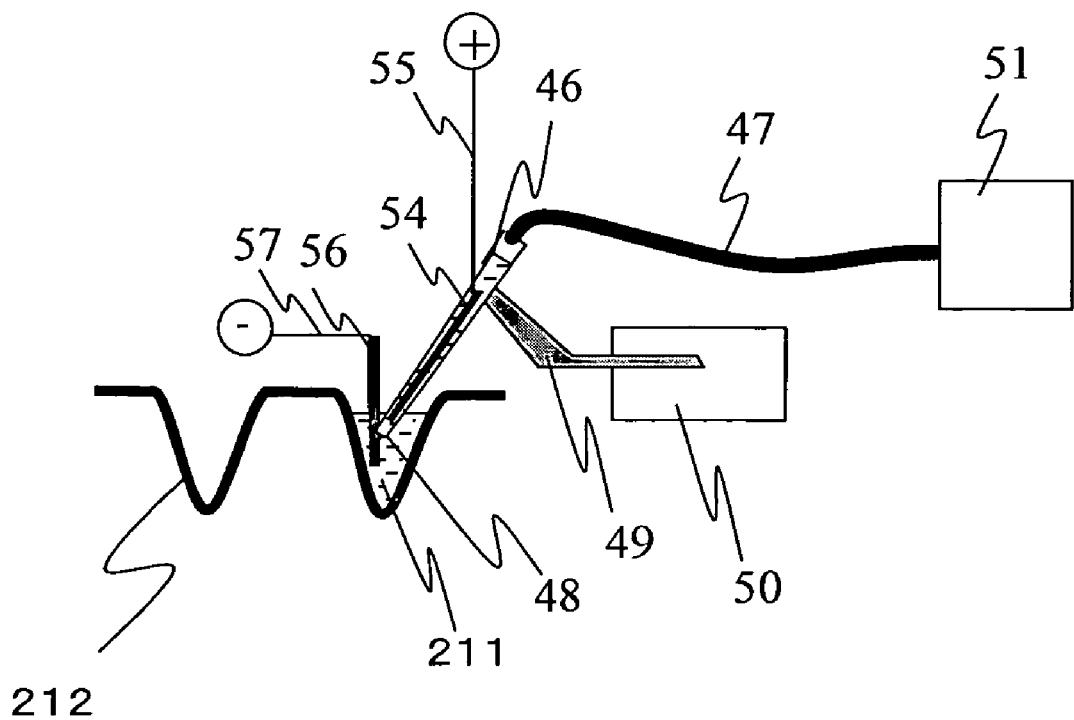
FIG. 86 is a view illustrating a specific example in which an mRNA is separated and acquired by using the biological material separation chip in Example 3.

FIG. 86 is a view illustrating a specific example in which mRNAs are prepared by using the biological material separation chip in Example 3.

For instance, liver tissue obtained from a *xenopus* is frozen, and is added to a phenol chloroform solution, and the mixture is immediately homogenized. After ethanol precipitation, a mixed pellet of the total RNAs and genome fragments is obtained. The mixed pellet is dissolved in 5 mM of a 50 mM Tris-HCl buffer solution (pH 7.5) to obtain a sample solution. The sample solution 211 is poured into a vessel 212. A configuration similar to that for preparing the biological material separation chip is used in which the biological material separation chip 46 is attached onto the tip of a tube 47 for a device comprising a fixture 49, a drive unit 50, a microsyringe pump 51 and a tube 47. In this step, the electrode 54 is provided in the biological material separation chip 46, and is connected to the positive pole of a direct current power source via the lead wire 55. In the meantime, the electrode 56 is immersed in the vessel 212 with the sample solution 211 put therein, and is connected to the negative pole of the direct current power source via the lead wire 57.

The tip of the biological material separation chip 46 is dipped in the vessel 212 with the sample solution 211 put therein, and electric field by 5 V/cm of direct current voltage is applied to a portion between the inside and the outside of the capillary chip 46 using the direct current power source described above. With this operation, mRNAs passing through the nuclear membrane fixed onto the tip of the biological material separation chip 46 and transferring to the inside of the capillary are collected.

The mRNAs obtained as described above and mRNAs in the solution remaining outside of the capillary chip are apparently different in size, that is, the mRNAs obtained from the solution in the capillary chip are mainly 1 k to 3 kb in size, while the mRNAs obtained from the solution outside of the capillary chip shows a smear band in a wide range up to several tens of kb. With the use of a device with a nuclear membrane fixed thereon employing the chip according to the sixteenth embodiment, mature mRNAs having a reduced size thereof by splicing with an mRNA mixture solution can be obtained.

Figure 78:
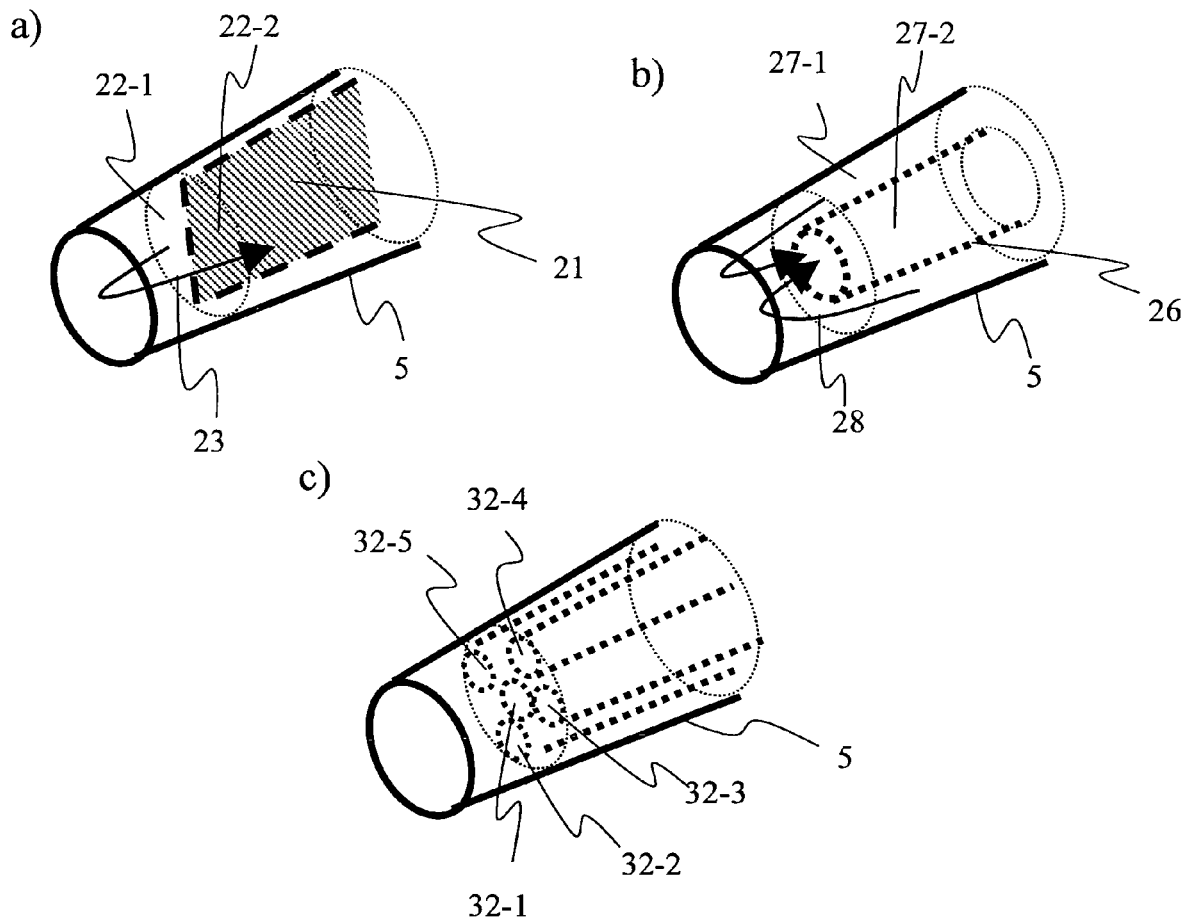
FIG. 78(a) to 78(c) are views each showing an example of configuration of a tip section of a capillary 5 which can be used in Example 1 or in Example 2.

The capillary chip having a nuclear membrane and used for Example 3 can use a configuration example described in the fifteenth embodiment with reference to FIG. 78, hence the description is omitted herein.

EXAMPLE 4

Figure 87:
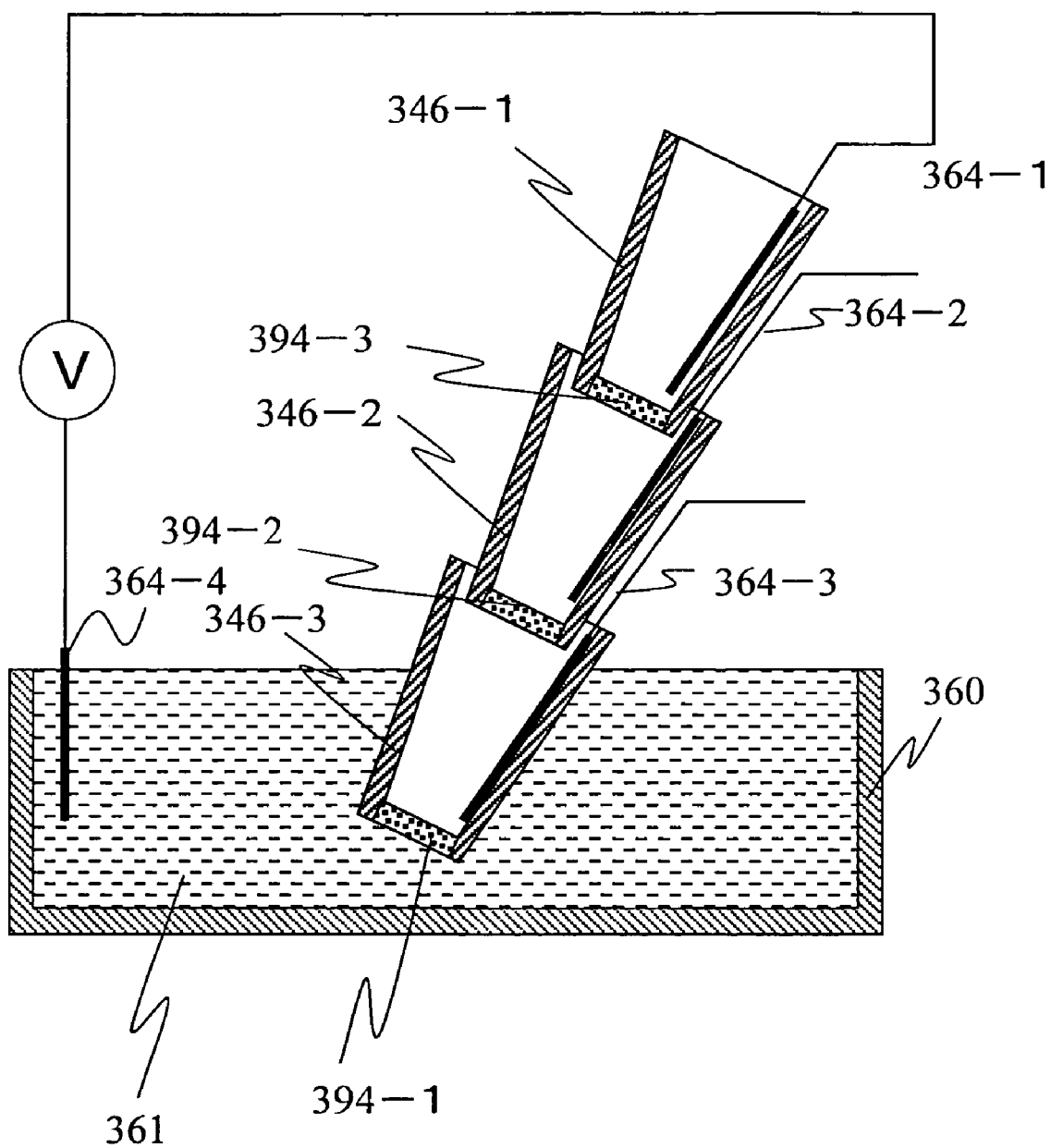
FIG. 87 is a view illustrating a simple method of realizing the example of triple structure in Example 2 with the glass capillary in Example 3.

FIG. 87 is a view illustrating a simple method of realizing the triple structure in Example 2 (Refer to FIG. 83) with the glass capillary shown in FIG. 78. The glass capillary is drawn out with a high frequency, and is tapered as shown in 346-1, 346-2 and 346-3 in FIG. 87. Electrodes 364-1, 364-2 and 364-3 are inserted between each capillary. As described with reference to FIG. 80, the tip of a capillary is pressed onto each cell membrane, and is then detached from a cell while lightly sucking the cell membrane. With this operation, the tip of the capillary with a portion of the cell membrane (lipid bilayer) 394-1, 394-2 and 394-3 attached thereon can be obtained. In this state, the lipid bilayer including transporters is fixed onto each capillary tip. The lipid bilayer having the same cell as that in Example 2 is fixed onto each capillary. Three capillaries are piled up in a buffer.

FIG. 87 is a cross-sectional view showing outline of biological material separation chips prepared as described above and arrayed in three cascades. Reference numerals 346-1 to 346-3 indicate biological material separation chips, on the tip of which are fixed nuclear membranes 394-1 to 394-3 respectively. The three biological material separation chips are connected with a slight clearance remained therebetween. As shown in FIG. 87, the tip of the chip is dipped in a sample solution 361 in a vessel 360. Electric field is herein applied to a portion between an electrode 364-1 and an electrode 364-4 provided in the sample solution in order to accelerate transfer of the substrate. Naturally, material transfer may be carried out in stages by switching the electrode 364-3, 364-2 and 364-1, and the electrode 364-4 in this order. After the lapse of a specified period of time, the capillaries are separated out, pressure is applied from the side of a capillary having a larger taper to pierce a lipid bilayer on the tip, and the solution inside can be collected.

[XVII] Seventeenth Embodiment

A seventeenth embodiment of the present invention discloses a method of establishing a technique for preventing outflow of contents in a cell, enabling insertion of a target substance into the cell, and recovering materials in the cell to facilitate an assay of a particular substance or production of a useful material. With this method, only a portion of cell membrane is made semipermeable. To make a portion of cell semipermeable, a chip based on a partition wall structure with small pores each smaller than an external diameter of a cell provided thereon is used. A cell is fixed on a face of this chip at a position where a pore is provided, and a cell membrane toxin such as streptolysin O is reacted from the other face through the pore to a portion of the cell to make the cell membrane at the pore position semipermeable. A substance is inserted into or taken out from the cell through this semipermeable membrane portion. Further by providing electrodes at both sides of the partition wall, ions passing through the cell membrane can be measured, or a substance can forcibly be inserted into or taken out from a cell by loading a voltage to the electrodes.

EXAMPLE 1

Figure 88:
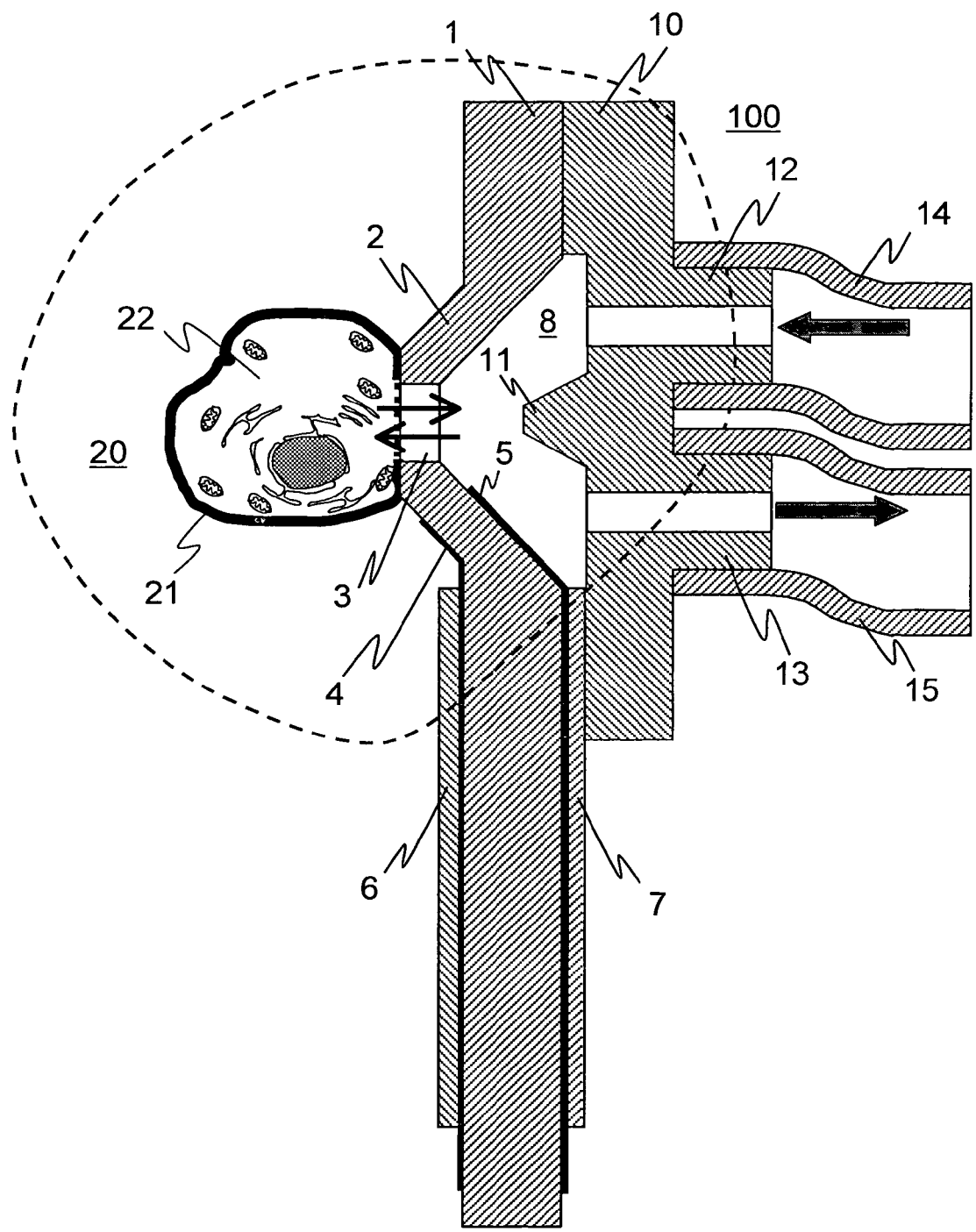
FIG. 88 is a cross-sectional view showing outline of the relation between a cell chip in Example 1 of a seventeenth embodiment of the present invention and a cell fixed to a pore portion thereof.

FIG. 88 is a cross-sectional view showing general relations between a cell chip in Example 1 and a cell fixed to a pore section thereof.

In FIG. 88, the reference numeral 100 indicates a cell chip. Reference numeral 20 indicates a cell. As described below, the cell 20 is fixed to a portion of a pore 3 on the cell chip 100.

Reference numeral 1 indicates a cell fixing substrate of the cell chip 100, and is made of, for instance, silicon. The size is 5 mm in the height and 500 μm in the vertical direction in the figure respectively. The thickness is, for instance, 100 μm. A projection 2 is provided at one edge portion of the cell fixing substrate 1. The height is, for instance, 5 μm, and thickness of the projection is, for instance, 2 μm. A pore 3 is formed at a top of the projection 2. The size is, for instance, in the range from 2 to 5 μmφ. Electrode layers 4, 5 are formed on both faces of a lower section of the cell fixing substrate 1. The electrodes 4, 5 are substantially covered with insulating layers, but portions near the projection 2 and near an edge of the cell fixing substrate 1 are exposed.

The reference numeral 10 is a rear plate, and is adhered to an entire portion of the rear surface of the projection 2 to form a buffer chamber 8 on the rear surface of the projection 2 of the cell fixing substrate 1. Thickness of the rear plate 10 is, for instance, 100 μm, but as shown in the figure, a projection 11 is formed at a position corresponding to the pore 3 on a surface of the cell fixing substrate 1, and further projections 12, 13 each having a throughhole are provided in both sides of the projection 11 on the external side face. Capillaries 14, 15 are attached to the projections 12, 13 respectively, and a micro syringe pump (not shown) can be communicated to each of the capillaries 14, 15. By circulating a buffer solution in the buffer chamber 8 making use of the capillaries 14, 15 as indicated by a bold line in the figure or sucking a buffer solution at a rate higher than a feed rate thereof, a negative pressure state can be generated inside the buffer chamber 8. The projection 11 disturbs a buffer solution supplied thereto and guides a flow of the buffer solution toward the pore 3.

Although portions relating to a microscope are not shown for simplification of the figure, a droplet of a buffer solution suited to cell culture is dripped onto an observation glass plate of the microscope, and the projection 2 of the cell fixing substrate 1 and the cell 20 are placed at positions opposite to each other in this droplet. In this step, the cell 20 is set at a position opposite to the pore 3 on the projection 2. Reference numeral 21 is a lipid dual layer of the cell 20, and reference numeral 22 indicates cytoplasm. In FIG. 88, a broken line surrounding the projection 2 of the cell fixing substrate 1 and the cell 20 indicates an image of a region immersed in the droplet. The buffer chamber 8 is included in the region surrounded by the broken line, but as described later, in the state where the cell 20 is fixed on the cell fixing substrate 1, the buffer chamber 8 is not communicated to the droplet. On the other hand, conductors are connected to the electrode layers 4, 5 exposed on edge portions of the cell fixing substrate 1 outside the droplet, and the conductors are also connected to a measuring instrument or a computer not shown in the figure.

The cell 20 is contacted to the pore 3 of the projection 2 observing the situation with the microscope. In this step, by monitoring the electric conductivity between the electrode layers 4, 5, it is observed that the electrode layer 5 exposed in the buffer chamber 8 and the electrode layer 4 exposed in the droplet are communicated to each other through the buffer solution before the cell is contacted to the pore 3 of the projection 2, but that, as the pore 3 is blocked with the lipid dual layer 21 of the cell 20 after the cell is contacted to the pore 3 of the projection 2, and therefore the two electrode layers 4, 5 are insulated against each other, thus contact to the cell 20 being confirmed. When contact of the cell 20 to the pore 3, by controlling a buffer solution through the capillaries 14, 15 connected to the projections 12, 13 to suck the buffer solution at a rate higher than a feed rage of the buffer solution, a negative pressure is generated in the buffer chamber 8, and therefore the cell 20 is tightly fixed to the pore 3.

Then streptolysin O is injected with the micro syringe pump communicated to the capillaries 14, 15 attached to the projections 12, 13 on the rear plate 10. The streptolysin O acts to a portion contacting the pore 3 of the lipid dual layer 21 of the cell 20 via the pore 3, so that only the portion is made semipermeable. In the semipermeable state, although the cell frame still remains, pores are opened in the lipid dual layer 21. Conditions for reaction of streptolysin, for instance, the technique disclosed in Kano, Y. Sako et al, Reconstruction of Brefeldin A-induced Golgi Tabulation and Fusion with the Endoplasmic Reticulum in Semi-Intact Chinese Hamster, Molecular Biology of the Cell 11, 3073-3087 (2000) may be modified according to a type of a cell. For instance, in a case of an ovarian cell, the cell is exposed to 25 mM HEPES buffer solution (pH 7.4) containing streptolysin O (60 ng/ml), 115 mM potassium acetate, 2.5 mM $MgCl_2$, 1 mM dithiothreitol, 2 mM EGTA for 10 minutes at 4° C. Then the cell is washed with the 25 mM HEPES buffer solution (pH 7.4) containing 115 mM potassium acetate, 2.5 mM $MgCl_2$, 1 mM dithiothreitol, 2 mM EGTA at 32° C. The cell 20 is kept in the droplet buffer during this step, so that the cell 20 is damaged little.

Descriptions are provided below for a method of using the cell chip 100 with a cell having a partially semipermeable membrane fixed thereto.

A short chain RNA which is a portion of a specific mRNA is led into the buffer chamber 8 from the capillary 14. A portion of this RNA is introduced into the cell 20 through the pore 3 on the semipermeable membrane. Usually, when RNA is introduced into the cell 20, the RNA is attacked by RNase and quickly disappears. In the cell chip 100 in Example 1, however, fresh RNA is constantly supplied through the capillary 14 into the buffer chamber 8, so that RNA in the cell 20 achieves equilibrium with those in the buffer chamber 8 through the semipermeable membrane as indicated by the thin arrow at the pore 3. Therefore, a constant volume of RNAs is always preserved in the cell. This phenomenon is not limited to the case of RNA, and also occurs in a case of DNA or a derivative of RNA.

Current value between the electrodes 4 and 5 is monitored before and after the RNA is introduced into the cell 20. If the RNA introduced into a cell gives influences to a transporter of the cell dual membrane 21, ion channels present in the cell dual membrane 21 couple to each other, so that fluctuation appears in ion transfer between the membrane, and a current flows between the electrode 4 and electrode 5. Namely, it is possible to introduce a substance into a cell and monitor influences by the substance over the cell. This technique is applicable also for measurement of influences by any chemical substance or a protein.

Further, it is possible to add various types of chemical substances in the side not exposed to streptolysin O in which the cell dual membrane 21 of the droplet side is present and introduce the chemical substances via a transporter into the cell 20, and possible to check influences of the introduced materials to the cell, for instance, by monitoring difference in electric potential between the electrodes 4 and 5. Namely a bioassay can be performed by making use of this technique.

Figure 89:
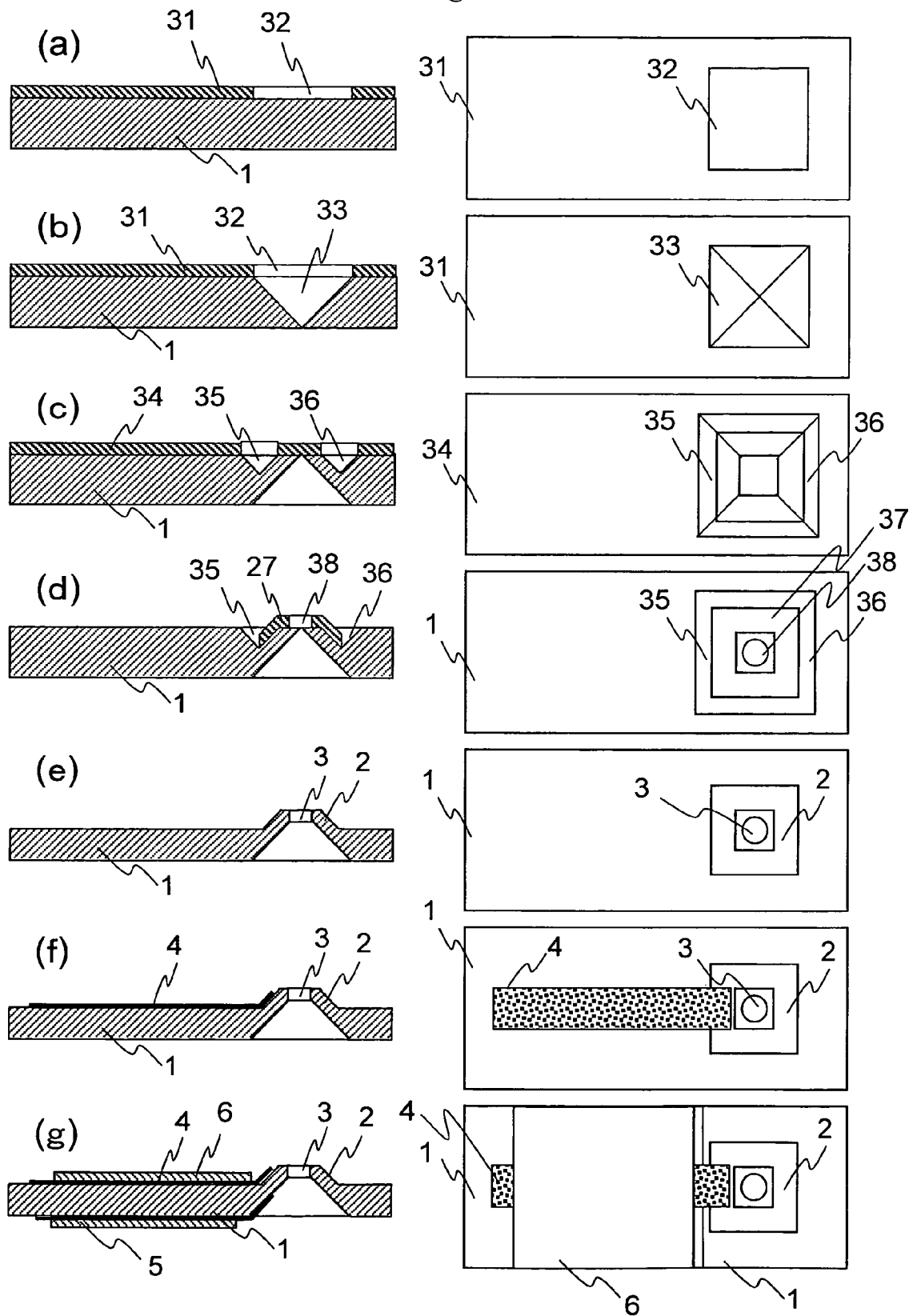
FIGS. 89(a) to 89(g) are views each illustrating outline of a process for forming a cell fixing substrate 1 in Example 1.

FIG. 89(*a*) to FIG. 89(*g*) are views each illustrating an outline of the processing for preparing the cell fixing substrate 1 in Example 1 by making use of the semiconductor technology. Each of FIG. 89(*a*) to FIG. 89(*g*) provides a cross-sectional view in the left side and a plan view corresponding to the cross-sectional view above in the right side.

At first, as shown in FIG. 89(*a*), a silicon substrate 1 having a prespecified crystal axis is prepared, and a mask 31 is provided on a surface thereof. Further a window 32 is formed by removing the mask 31 at a position where a projection 3 is to be formed. As shown in FIG. 89(*b*), etching is performed to remove a portion corresponding to a quadrangular pyramid 33. Then, as shown in FIG. 89(*c*), the mask 31 is removed and a mask 34 is provided on another surface of the silicon substrate 1. Then a window is formed by removing the mask 34 at a position where the projection 3 is to be formed, and with this operation, recesses 35 and 36 each having a triangular cross section are formed. The recesses 35, 36 are continuous ones corresponding to the quadrangular pyramid 33 as understood from the plan view. Then, as shown in FIG. 89(*d*), a mask 37 is provided at a position surrounded by the recesses 35, 36 to open a window 38. Then as shown in FIG. 89(*e*), the pore 3 is opened at a corresponding position on the substrate 1 by making use of this window 38. In this step, also the projection 2 is formed by etching on the substrate 1 around the recesses 35, 36. Then as shown in FIG. 89(*f*), the electrode 4 is formed on a surface of the substrate 1 with the projection 2 provided thereon. This electrode 4 is a deposition layer of aluminum. Then as shown in FIG. 89(*g*), the substantially entire surface excluding both edge sections of the electrode 4 is covered with a polyimide insulating layer 6. Then the electrode 5 is formed on another surface of the substrate 1. The electrode 5 is a platinum deposition layer, and the substantially entire surface excluding both edge sections of the electrode 5 is covered with a polyimide insulating layer 7. Thus the cell fixing substrate 1 of the cell chip 100 is formed. Detailed data concerning the semiconductor technology is not provided here, but those skilled in the art can easily carry out the technology.

Likely, also the rear plate 10 can be formed by machining a silicon substrate. By adhering the cell fixing substrate 1 to the rear plate 10, the cell chip 100 is assembled.

EXAMPLE 2

In Example 1, description was made for the cell chip allowing for a bioassay by fixing a single cell on a pore portion thereof and making the cell membrane semipermeable only at the pore portion. In a multicellular organisms, it is a rare case that a single cell functions by itself, and a cell generally functions in correlation with peripheral cells. It is conceivable that cells in the multicellular system transact information using various types of chemical substances. In most cases, a quantity of the chemical substance is extremely minute, and actually real time analysis of the chemical substance in a living cell is extremely difficult. In Example 2, there is proposed a cell chip enabling a simulated bioassay for a group of cells functioning with harmonization with peripheral cells. Example 2 is the same as Example 1 in the point that a cell is fixed to a pore portion and the cell membrane only at the pore portion is made semipermeable for carry out a bioassay.

Figure 90:
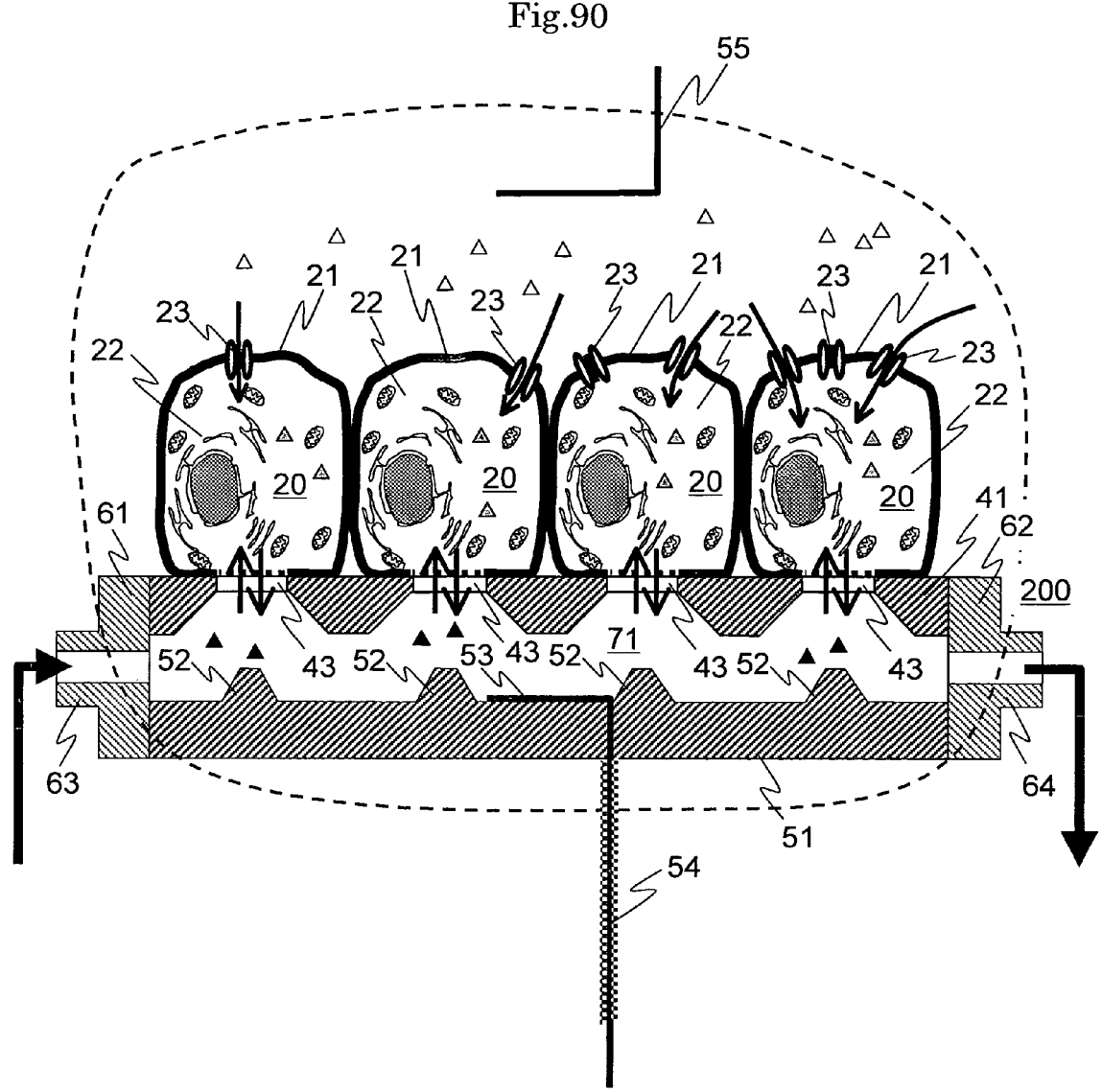
FIG. 90 is a cross-sectional view showing outline of the relation between the cell chip in Example 2 and a cell fixed to a pore portion thereof.

FIG. 90 is a cross-sectional view showing an outline of a relation between the cell chip and a cell fixed to the pore portion thereof in Example 2.

In FIG. 90, reference numeral 200 indicates a cell chip in Example 2, and the cell chip 200 includes a cell fixing substrate 41, a rear plate 51, and side wall plates 61, 62. The side wall plates are also provided behind and in front of the view plane. The space surrounded by the side wall plates forms a buffer chamber 71 like in Example 1. A pore 43 is formed on the cell fixing substrate 41. The cell fixing substrate 41 and the pore 43 correspond to the cell fixing substrate 1 and pore 3 in Example 1. Different from the cell fixing substrate 1 in Example 1, the projection 2 is not formed in the cell fixing substrate 41 in Example 2, and a number of pores 3 are provided thereon. A number of cells are arrayed on a surface of the cell fixing substrate 41 to form a group of cells functioning as a whole in harmonization with each other. In the case shown in the figure, four pores 43 are formed, but more pores may be provided. Size of the cell fixing substrate 41 is, for instance, about 10×10 mm. The thickness is, for instance, 100 μm. Diameter of the pore 43 is in the range from 2 to 5 μmφ, and the pores are arrayed with a pitch of 8 μm inbetween. The cells 20 are fixed to positions corresponding to the pores 3 on the cell fixing substrate 41. Namely the cells are arrayed with a pitch of 8 μm inbetween.

The rear plate 51 has the substantially same size as the cell fixing substrate 41, and is placed away from the cell fixing substrate 41 with a space of, for instance, 1 mm therefrom. The cell fixing substrate 41 and rear plate 51 are supported at the prespecified positions by the side wall plate behind and in front of the view plane, and the space surrounded with the side wall plates is a buffer 71. Like in Example 1, projections 63, 64 each having a throughhole are formed on the side wall plates 61, 62. Capillaries (not shown) can be attached to the projections 63, 64, and the capillaries are connected to a syringe pump respectively for feeding a buffer solution or the like. A projection 52 is formed at a position corresponding to the pore 43 on the rear plate 51. This projection 52 is provided to disturb a buffer solution supplied into the buffer chamber 71 to make it flow toward the pore 43, like the projection 11 in Example 1. An electrode 53 is provided on a surface of the rear plate 51 in the buffer chamber 71. An outgoing line from the electrode 52 is an insulated line, and is connected to outside of the buffer chamber 71.

Figure 91:
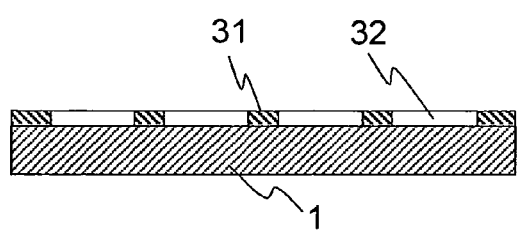
FIGS. 91(a) to 91(d) are views illustrating outline of a process for forming a cell fixing substrate 41 in Example 2.
Figure 91:
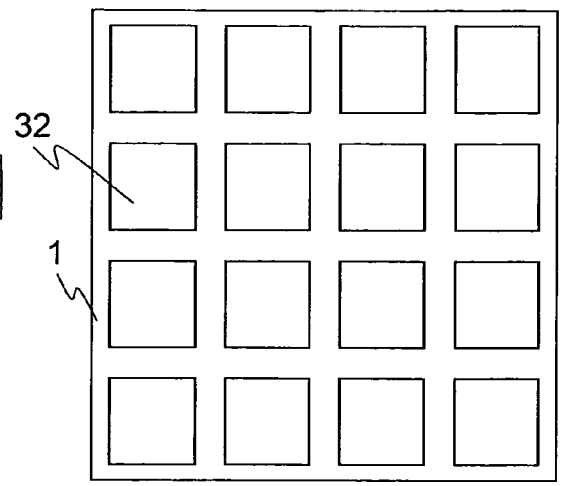
Figure 91:
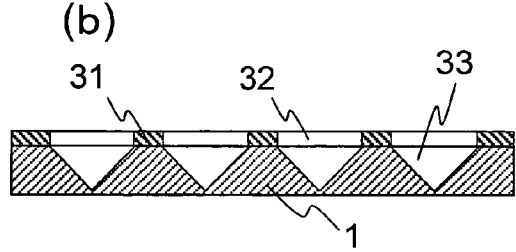
Figure 91:
Figure 91:
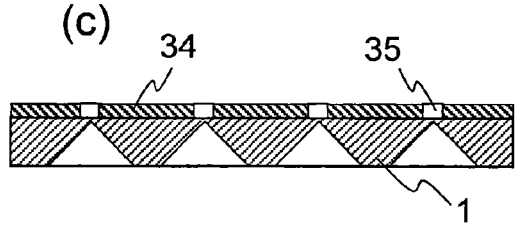
Figure 91:
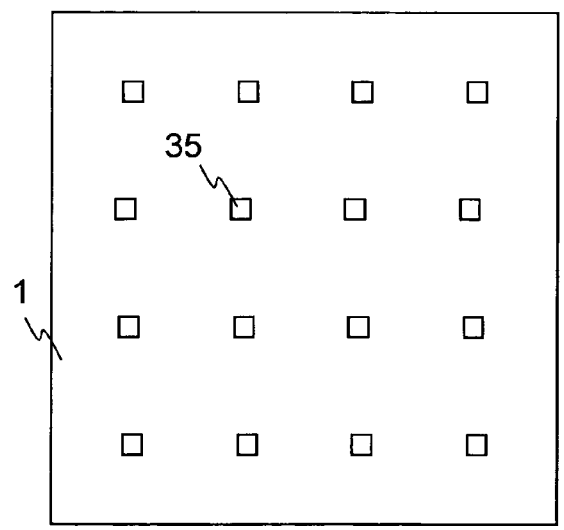
Figure 91:

FIG. 91(*a*) to FIG. 91(*d*) are views each illustrating an outline of the processing for forming the cell fixing substrate 41 in Example 2 by making use of the semiconductor technology. Each of the FIG. 91(*a*) to FIG. 91(*c*) shows a cross-sectional view in the left side and a plan view corresponding to the cross-sectional view in the right side. A plan view for FIG. 91(*d*) is the same as FIG. 4(*c*), and is omitted herefrom.

At first, as shown in FIG. 9(*a*), a silicon substrate 1 having a prespecified crystal axis is prepared, and a Mask 31 is provided on a surface thereof. Further a window 32 is formed by removing the mask 31 at a position where a projection 3 is to be formed. As shown in FIG. 91B, etching is performed to remove a portion corresponding to a quadrangular pyramid. Then, as shown in FIG. 91(*c*), the mask 31 is removed and a mask 34 is provided on another surface of the silicon substrate 1. Then a window 35 is formed by removing the mask 34 at a position where the pore 43 is to be formed. Then pores 43 are formed by etching as shown in FIG. 91(*d*). With the operation, the cell fixing substrate 41 of the cell chip 200 is formed. Herein detail data for the semiconductor technology is not provided, but those skilled in the art can easily use the technology.

Similarly, also the rear plate 51, side wall plates 61, 62 can be formed by machining a silicon substrate with the semiconductor technology. Then the cell fixing substrate 41, rear plate 51, and side wall plates 61, 62 are adhered to each other, thus the cell chip 200 being assembled.

As clearly understood from comparison of the plan view in FIG. 89(g) to that in FIG. 91(c), the cell chip 100 in Example 1 is used to perform a bioassay for a single cell, but the cell chip 200 in Example 2 enables a bioassay for 4×4 cells arrayed in a square form. The cell chip 200 is set on a culture plate and is immersed in a proper culture fluid. When the epithelial cells 20 are cultured on the cell fixing substrate 41 of the cell chip 200 in this state, a single-layered cell sheet is inevitably formed on the cell fixing substrate 41. FIG. 90 shows an image in which the cell chip 200 and a cultured cell sheet are within a region of a culture fluid indicated by the broken like and also shows the state with a cross-sectional view in which a monolayer cell sheet is formed on the cell fixing substrate 41 of the cell chip 200. The pores 43 are provided in correspondence to a pitch in a cell array, but when the pores 43 are provided at a sufficient density against a pitch between cells (such as, for instance, 8 µm) such as, for instance, 5 µm, the pores are allocated to substantially all of the cells in the monolayer cell sheet formed on the cell fixing substrate 41 regardless of the cell size. It is needless to say that cells may be fixed on a constant pitch and cultured on the cell fixing substrate 41 with the pores 43 each corresponding to the cell size arrayed thereon, for instance, with an agarose micro chamber arrays. Further any cell may be arrayed to form the cell sheet. It is to be noted that, in the cell 20 shown in FIG. 90, designated at reference numeral 22 is a cell dual membrane, at 22 cytoplasm, and at 23 a transporter present in the cell dual membrane.

Also in Example 2, at first, a buffer solution is supplied via the projections 63, 64 on the side wall plates 61, 62 into the buffer chamber 71 like in Example 1. In this state, electric conductivity between the electrode 55 immersed in a culture fluid on the culture plate and the electrode 53 in the buffer chamber 71 is monitored. When the cell sheet formed with the cells 20 is not tightly fixed on the cell fixing substrate 41, the electric conductivity between the electrode 55 immersed in the culture fluid on the culture plate and the electrode 54 exposed inside the buffer chamber 8 is relatively low due to the buffer solution. In this state, when a buffer solution supplied via the throughholes on the projections 61, 62 is controlled and sucked at a rate higher than a feed rate of the buffer solution as indicated by a bold line, a negative pressure is generated inside the buffer chamber 71 and the cell sheet is fixed to the cell fixing substrate 41.

Then streptolysin O is injected into the buffer chamber 71 like in Example 1. The streptolysin O acts via the pore 43 to a portion contacting the pore 43 on the lipid dual layer 21 of the cell 20 to make only the portion semipermeable. With this operation, a cell chip containing a cell having a semipermeable cell membrane only in the portion corresponding to the pore 43 is obtained.

Not descriptions are provided for a method of using the cell chip 200 with a cell having a partial semipermeable cell membrane fixed thereto prepared as described thereto.

Short chain RNA each as a portion of a specific mRNA is flown into the buffer chamber 71 as indicated by the bold line. A portion of the RNA is fetched through the semipermeable membrane into the cell 20. Generally, when introduced into the cell 20, RNA is attacked by RNase and quickly disappears. However, in the cell chip 200 in Example 2, fresh RNAs are sequentially supplied through the throughholes on the projections 61, 62, so that the RNAs inside the cell 20 achieve equilibrium via the semipermeable membrane with those in the buffer chamber 71 as indicated by a thin arrow in the figure. Therefore, a constant volume of RNAs is always preserved in the cell.

A current value between the electrode 54 and electrode 55 is monitored before and after the RNAs are introduced into the cell 20. If the RNA introduced into the cell constituting the cell sheet give influences to the transporter 23 for the cell dual membrane 21 ion channels in the cell dual membrane 21 couple to each other, so that fluctuations occur in transport of ions through the cell membrane, and therefore a current flows between the electrodes 54 and 55. Namely a substance can be introduced into a cell, and influences caused by the substance over the cell can be monitored. This technique can be used for measurement of influences not only by RNA, but also chemical substances and proteins. Further it is possible to add various types of chemical substances in a cell fluid in the side not exposed to streptolysin O where the cell dual membrane 21 in the culture plate side, introduce the chemical substance via a transporter into the cell 20, and check influences of the chemical substances over the cell, for instance, by detecting a different in electric potentials between the electrodes 54, 55. Namely a bioassay can be performed.

When a chemical substance indicated by a white triangle is added on the culture dish, the chemical substance is fetched into the cell via the transporter 23 as indicated by the solid black triangles in the figure. An arrow mark penetrating the transporter 23 indicates that the chemical substances passes therethrough. The fetched chemical substance passes through the semipermeable section of the cell membrane, and is eluted through the pore 43 into the buffer chamber 71 as indicated by the solid black triangle. By recovering the eluate via the through hole on the projection 62, reactions of the cell to the chemical substance can be assessed.

The biochemical substances as used in this specification include, but not limited to, amino acids, dipeptides, oligo peptides such as tripeptides, polypeptides such as proteins, nucleic acids, RNAs such as mRNAs, monosaccharide, disaccharide or oligosaccharide, sugars such as polysaccharide, hormones such as steroids, neurotransmitters such as noradrenaline, dopamine, and serotonin, other endocrine disrupters, various types of drugs, and other materials involving in the life phenomenon such as potassium, sodium, chloride ions, hydrogen ion. The biochemical substances have various types of characteristics. Therefore the possibility of assessing the influences of these materials through direction reactions with cells is extremely useful.

For instance, the aforementioned chip is prepared with a cell in which the SLC6A1 as a transporter is forcefully expressed, the chip is useful for detection on γ-amino butyric acid. The cell in which SLC6A2 is forcefully expressed may be used for noradrenaline, and that in which SLC6A4 may be used for measurement of serotonin. Further a cell in which SLCO3A1 can be used for measurement of prostaglandin, and a cell in which SLC6A5 is forcefully expressed can be used for measurement of glycine.

Further by using the chip according to the seventeenth embodiment, a material can be refined. For instance, cells each containing a transporter for dopamine forcefully expressed therein with the technique described above are arrayed on the chip 200 as shown in FIG. 90. Each of the cells has semipermeable cell membrane only at a potion thereof contacting the pore. In this state, a sample solution containing dopamine or a derivative thereof is added in the chip, and a voltage is loaded to the electrodes 54 and 55. Then dopamine as a target or homologues can be recovered through the cell membrane. A material having a completely different structure does not pass through the cell membrane. It is needless to say that other materials are recovered via the respective transporters, but a number of a transporter for the target material is substantially larger than those for other materials, so that the target material can substantially be recovered. The same refinement can also be performed for amino acids or sugars. Especially, by forcefully expressing a stereoisomer capable of being recognized by a transporter in a cell, for instance, only L-isomer can be refined from a synthetic amino acid (a mixture of D- and L-isomers) with small amount of energy.

As described above, the cell chip according to the seventeenth embodiment can be used not only for assay of chemical materials, but also for production of specific materials including refinement thereof.

[XVIII] Eighteenth Embodiment

An eighteenth embodiment of the present invention discloses a method of accurately counting a number of biomolecules, not only for separating the biological material, but also for separating an extremely small number of molecules having activity to a cell in the function traceable state to clarify functions of a cell. When a biomolecule moves, the biomolecule is always guided so that the biomolecule passes through a region with the space covered with the evanescent wave having a prespecified wavelength. As a result, when the molecule passes through the region, scattering of light occurs, and the scattered evanescent light goes out from the space, and therefore, by detecting this scattered light, a number of biomolecules can accurately be counted.

EXAMPLE 1

Figure 92:
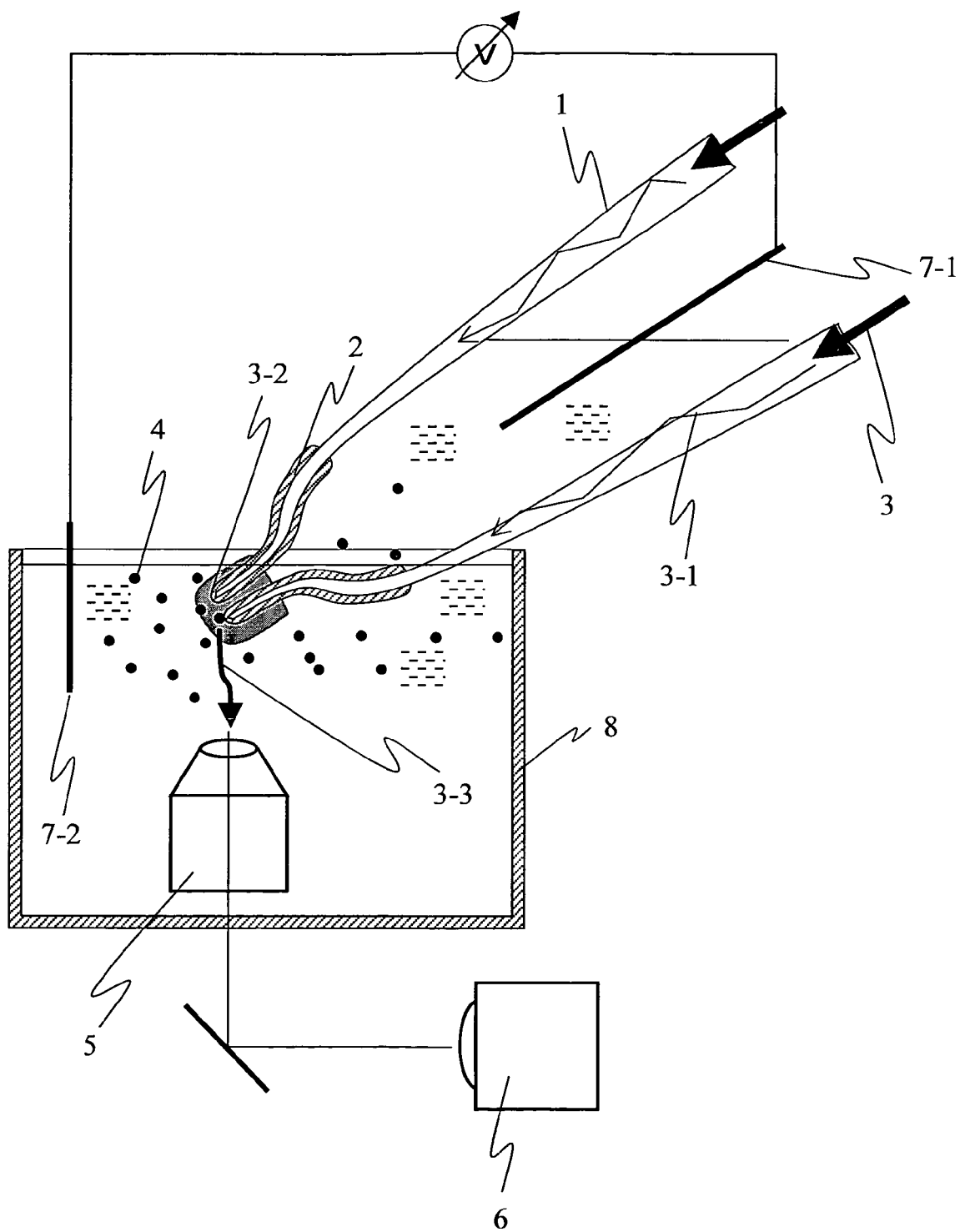
FIG. 92 is a conceptual diagram showing an example of a molecule measuring device based on detection of scattered light by making use of a resonance plasmon according to an eighteenth embodiment of the present invention.

FIG. 92 is a conceptual diagram showing an example of a molecule counter based on detection of scattered light by making use of resonant plasmon. Reference numeral 1 indicates a fine tube, and the material is fused silica with low light attenuation. The fine tube 1 is a detector. A diameter of an opening at a tip portion of the fine tune is in the range from 200 to 300 nm, and also the wall thickness is small. Inner and outer surfaces of the tip portion of the fine tune 1 at a portion near the opening are covered with a metal foil layer 2 to cause plasmon resonance when the evanescent waves go out of the opening at the tip portion of the fine tube. The best material for the metal foil layer 2 is gold. Wavelength of light introduced into the fine tube 1 should preferably be slightly larger than a diameter of the opening at the tip portion of the fine tube. Portions of fine tube other than the tip section may be thick, and when the wall thickness is sufficiently larger as compared to the wavelength of light described above, the light can be propagated by total reflection from the inlet portion to the opening of the tip portion of the fine tube. A diameter of the opening at the other edge of the tine tune is sufficiently larger as compared to the wavelength of light introduced into the fine tube 1.

The tip portion of the fine tube 1 can be thinned with any known method. For instance, by extending the fused silica tube by means of high-frequency heating, the tip portion can be thinned, and also the wall thickness of the tip portion can be reduced.

A sample solution containing a biomolecule 4 as a target for detection is put in a vessel 8 with a buffer solution filled therein, and the buffer solution is also introduced into the fine tube 1, and then the tip portion of the fine tube 1 is inserted into the vessel 8. When visible laser light 3 is irradiated from the thick wall section of the fine tube 1, the light propagates from the thick wall portion toward the tip portion by total reflection, and light having a prespecified wavelength goes out as evanescent light wave from a balled portion of the tip section to form a evanescent wave region 3-2. When the biomolecule 4 passes through the evanescent wave region 3-2, the resonant plasmon phenomenon occurs, and photons 3-3 springs out to outside of the evanescent region 3-3. The photons are focused with a lens 5 and counted with a photon counter 6, a number of biomolecules passing through the opening at the tip portion can be detected. The lens 5 is a water-submerged lens and is approached as much as possible to the evanescent wave region 3-2 at the tip portion of the fine tube 1 from which the scattered light goes out.

Electrophoresis is used for transport of a biological material. Namely electrodes 7-1 and 7-2 are placed inside the fine tube 1 functioning as a light guide and in a sample solution in which biomolecules are dispersed, and only a specified material can be introduced into the fine tube by loading a voltage on the electrodes 7-1 and 7-2. What is important in this step is a voltage applied to the electrodes 7-1 and 7-2. When a quantity of biological material is large, the photon counter 6 is saturated, and the photon pulses can not accurately be counted. In the situation as described above, the voltage is lowered so that a biomolecule passes through the evanescent wave regions 3-2 at the tip of the fine tube at a speed allowing for photon counting.

Figure 93:
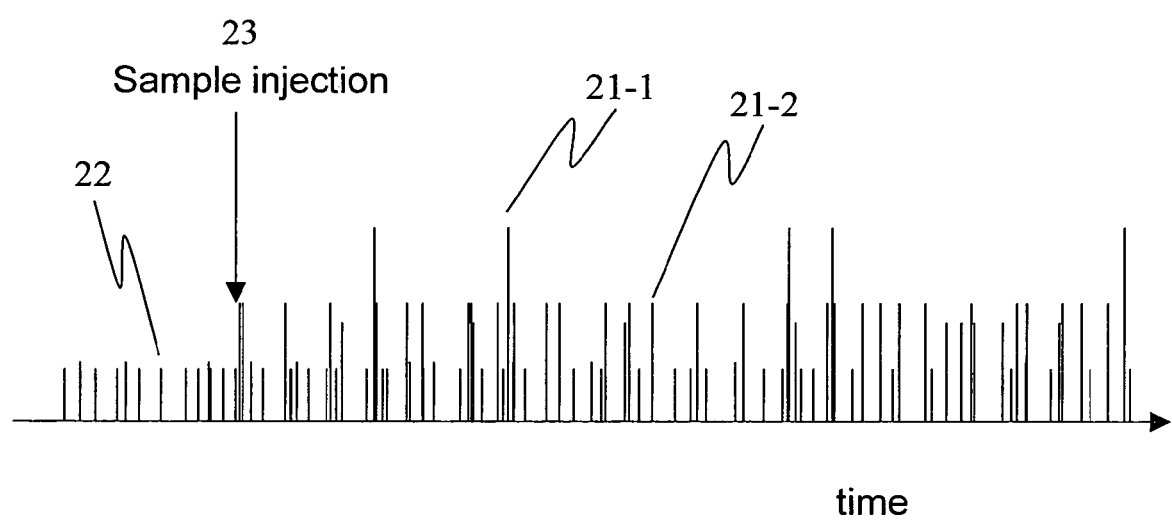
FIG. 93 is a conceptual diagram showing a result of measurement with a photon counter 6.

FIG. 93 is a conceptual view showing a result obtained by the photon counter 6. The horizontal axis indicates time, and the vertical axis indicates amplitude of light introduced into the photon counter 6. In the eighteenth embodiment, basically photon detection is performed, so that the background light should be removed as much as possible. When an electric field is loaded to the electrodes 7-1 and 7-2 so that the voltage at the electrode 7-1 is set to +15 V, a signal 22 is obtained. It is conceivable that this signal is generated by impurities contained in the buffer solution or by electric noises. Then transferrin, which is a type of protein, is added to outside of the fine tube 1 so that the concentration is 1 fM. Signals 21-1 and 22-2 having a clearly stronger amplitude than the signal 22, are detected. Namely, it is conceivable that the signal 22 is generated by noises and also that the signal 21-1 is generated by scattered light generated when transferrin passes through the evanescent wave region 3-2 at the tip of the fine tube. It is conceivable that the signal 21-2 indicates presence of other protein component contained in the transferrin solution, but the contents is unknown. Frequencies of the signals 21-1 and 21-2 increases when a quantity of added transferrin increases, and the frequencies drop when the quantity is reduced.

When a sample refined by chromatography using the DEAC cellulose column for transferring is used, a frequency of appearance of the signal 21-1 becomes higher as compared to that of the signal 21-2, and therefore the signal 21-1 is conceivably originated from the transferrin. The signal 21-2 can be considered as originated from other component contained in the transferring solution, but the substance is still unknown. Because an amplitude of scattered light indicated by the signal 21-2 is lower than that indicated by the signal 21-1, and therefore it may be guessed that this unknown substance has smaller size than transferrin.

EXAMPLE 2

FIG. 94(A) is a cross-sectional view showing a case where a measurement device described in Example 1 is formed with a substrate, and a chip-like detector placed on the substrate, while FIG. 94(B) is a plan view showing general relation between a substrate of the measurement device and the chip-like detector placed on the substrate. In this case, a pore for forming the evanescent wave region is provided on the chip.

Reference numeral 31 indicates the chip-like detector, and the chip has the width of 3 mm, length of 3 mm, and thickness of 200 μm. An opening with the diameter in the range from 200 to 300 nm is formed at a central portion thereof. A tip section 32 of the fine tube is curved and expanded by 100 μm, and a metal foil 33 is deposited on this curved section. An optical coupler 40 is fixed to an edge face of the chip-like detector 31. The optical coupler 40 is connected to an optical fiber 41, and a laser source 42 is set at a tip of the optical fiber 41. The laser light introduced from the laser source 42 into the chip-like detector 31 is totally reflected inside the chip-like detector, and reaches the tip portion 32 of the fine tube. The evanescent waves go out from the tip portion 32 of the fine tube to form the evanescent wave region 34. Electrodes 36-1 and 36-2 are provided on both surfaces of the chip at an edge section of the chip-like detector 31.

The chip-like detector 31 is attached to the substrate 30. A vessel 37 containing a buffer solution is formed on a top face of the substrate 30 at a position corresponding to the tip section 32 of the fine tube in the detector 31. The substrate 30 has the thickness of, for instance, 0.4 mm, and the thickness of the bottom section of the vessel 37 is 0.1 mm. When the detector 31 is attached to the substrate 30, the tip portion 32 of the curved fine tube is approached as much as possible to the bottom surface of the vessel 37. A buffer solution is put in the vessel 37.

A sample solution 35 is added through the opening into the chip-like detector 31 from the upper position. If there is a particle with the size of 10 nm in the sample droplet 35, when the particle passes through the evanescent wave region, scattering of light occurs, ad photons passes through a focusing lens 43 and reaches a photomultiplier 44 to provide a signal pattern as shown in FIG. 93 in Example 1. The electrode 36-1 in the detector 31 contacts the droplet 35, while the electrode 36-2 in the detector 31 contacts the buffer solution in the vessel 37, so that a molecule can be electrophoresed with a power source 505 to control a direction of the particle passing through the opening of the chip-like detector 31.

As indicated by the relation between the substrate and the chip-like detector placed on the substrate shown in FIG. 94(B), a hole 47 is provided on the substrate 30 at a position adjoining the chip-like detector 31. The hole 47 is communicated to the vessel 47 through a groove 48. Therefore, after the sample droplet is added from the top through the opening of the chip-like detector 31 and a prespecified measurement is performed, by sucking the buffer solution from the hole 47 with a dropping pipet, the buffer solution containing the particle moved into the buffer solution in the vessel 37 through the opening of the chip-like detector 31 can be taken out.

EXAMPLE 3

Figure 1:
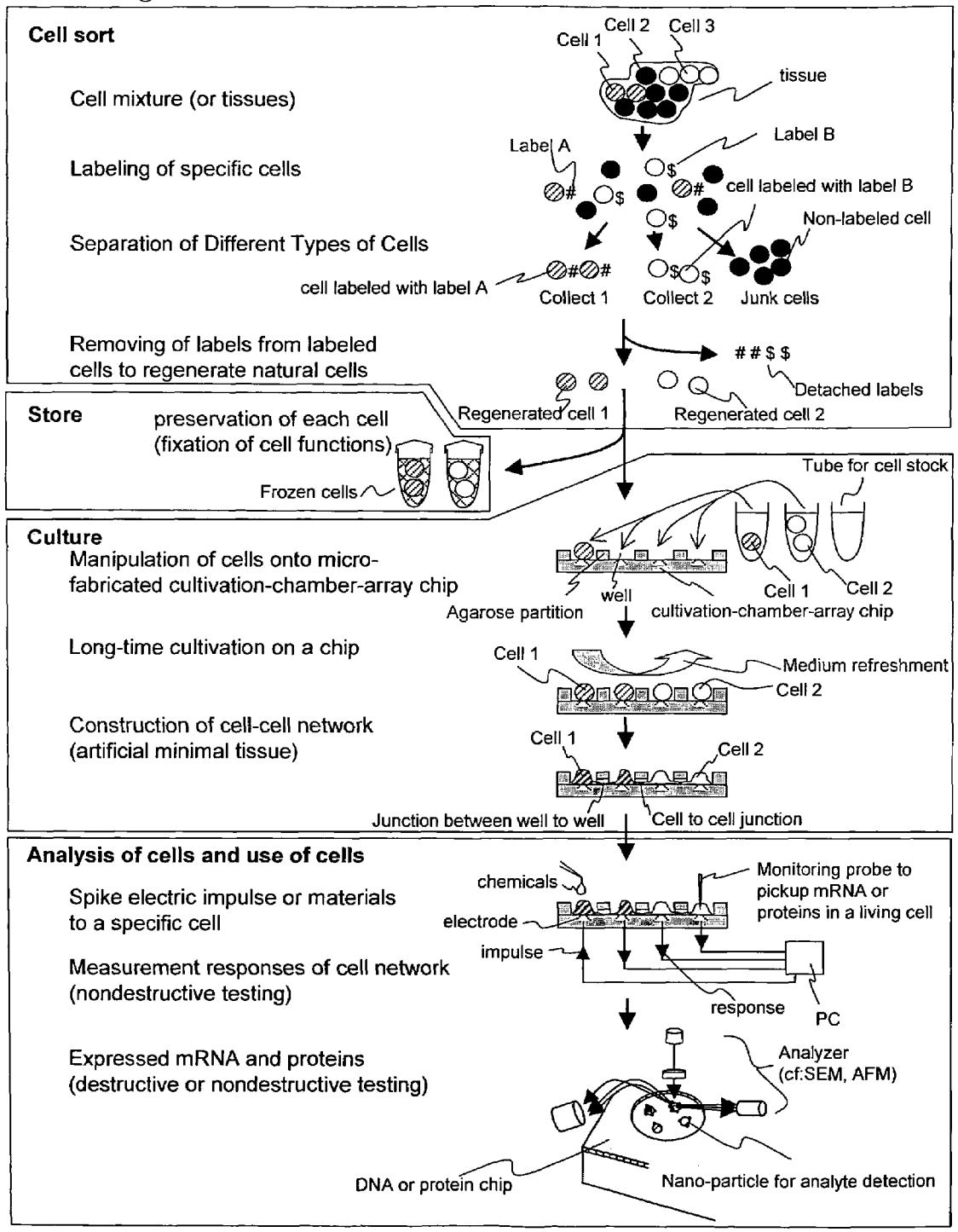
FIG. 1 is a diagram for illustrating a concept for a cellomics system according to the present invention.

Further, in the eighteenth embodiment, a specific biomolecule can be screen off and detected by attaching a chip 46 with a cell membrane including a transporter 45 selecting a biomolecule adhered to a top of the chip-like detector 31 described in Example 2. In this case, only the materials capable of passing through a transporter can advantageously be detected in the evanescent wave region 34. The transporter used in this case is, for instance, oocyte of *xenopus* (immature egg) in which a gene for a specific transporter is forcefully expressed. For instance, an mRNA sequence for a specific membrane protein is incorporated in an immature egg of *xenopus*, and a membrane is formed with cells in which the specific membrane protein is forcefully expressed. Then the cell membrane is cut off by patch clamping, and the cell membrane cut off as described may be adhered to the chip for use. More specifically, for instance, the transporter chip illustrated especially in FIG. 1 in Japanese Patent Application No. 2004-264866 filed by the present inventors may be used for this purpose.

Figure 94:
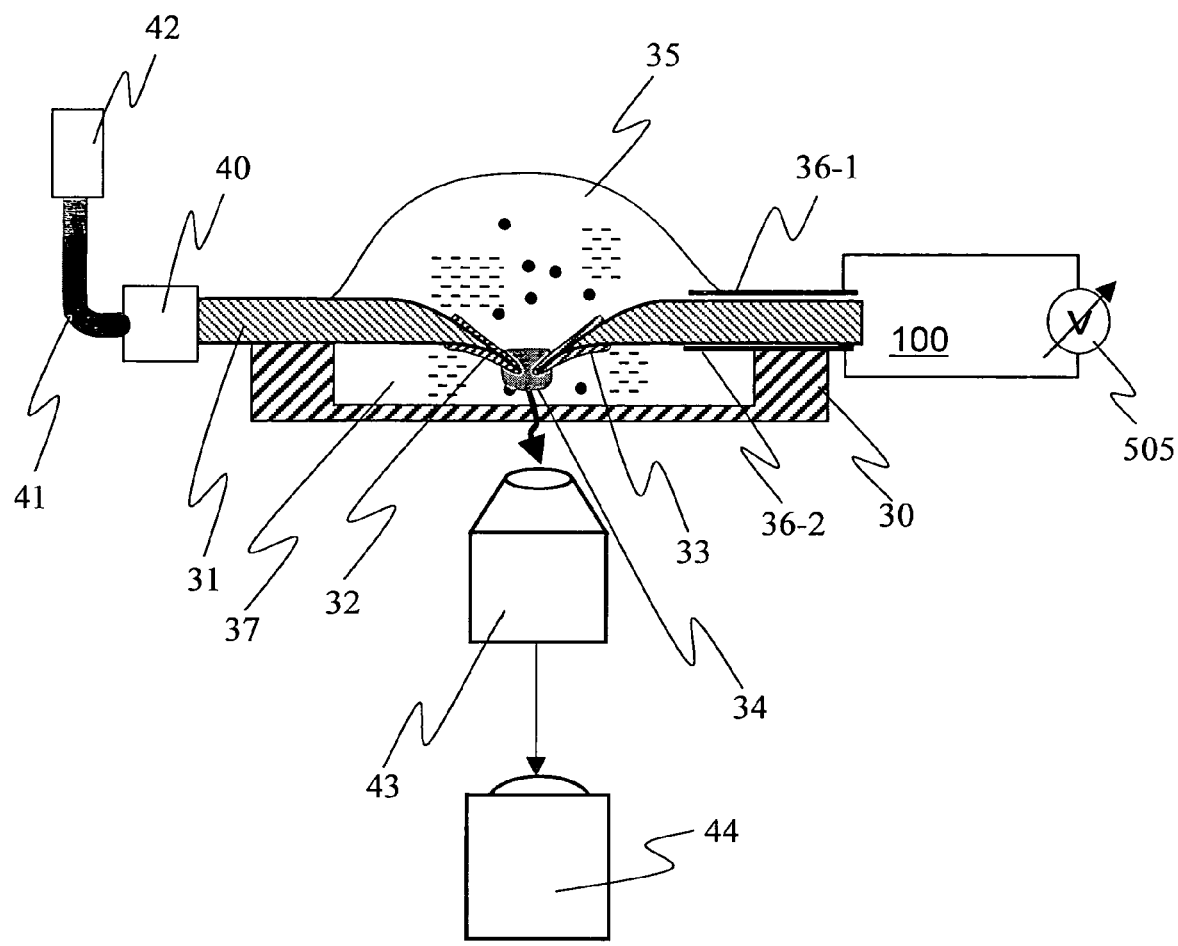
Figure 94:
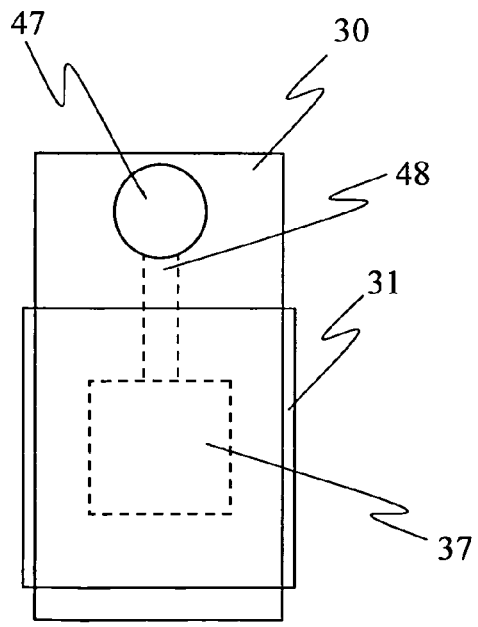
Figure 95:
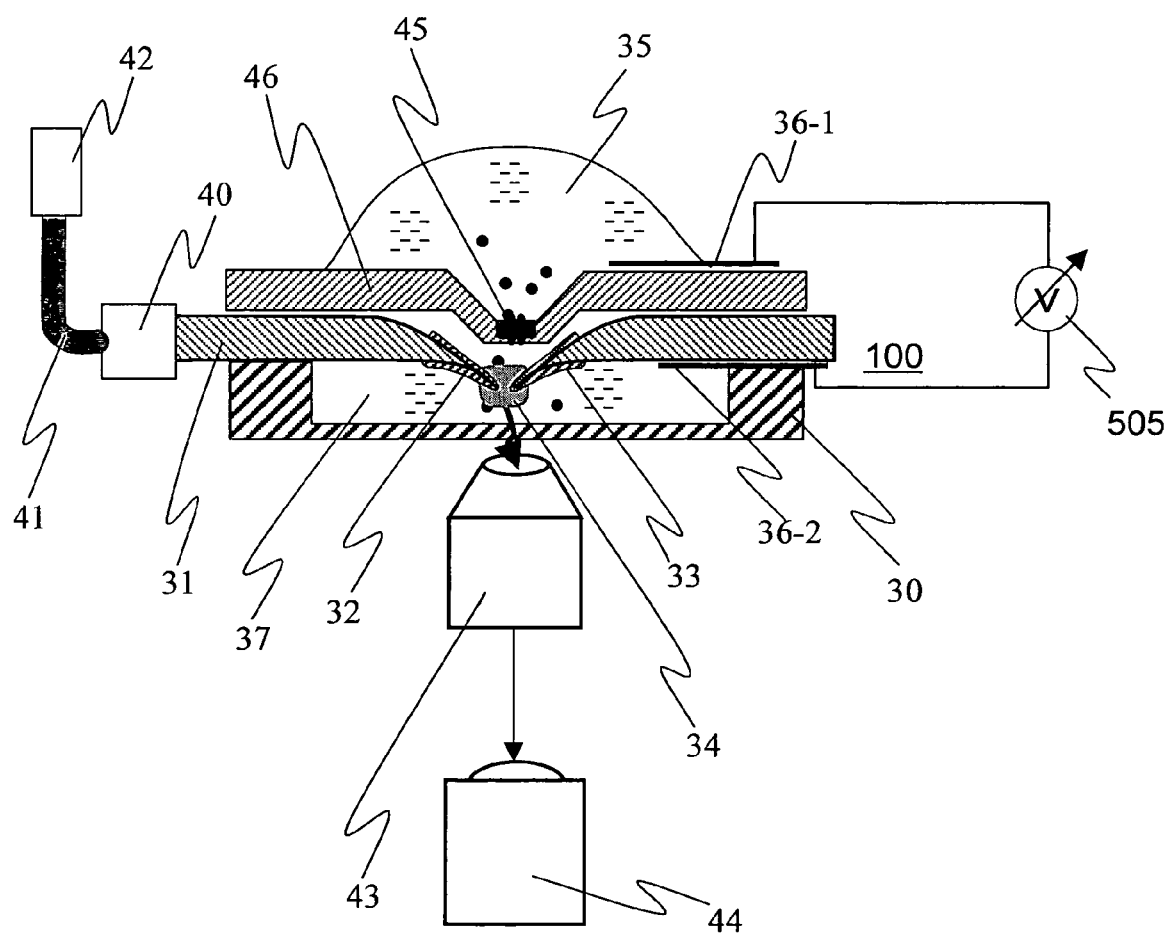
FIG. 95 is a cross-sectional view showing a measuring device in Example 3, in which a chip with a cell membrane including a transporter adhered thereon is placed on the chip-like detector of the measuring device described in Example 2.

FIG. 95 is a cross-sectional view showing a measurement device in Example 3 in which a chip with a cell membrane containing a transporter adhered thereon is placed on the chip-like detector of the measurement device described in Example 1. The plan view of the measurement device in Example 3 is the same as that in FIG. 94(B), and is omitted herefrom.

As clearly understood from comparison between FIGS. 95 and 94, FIG. 95 is the same as FIG. 94 excluding the points that a chip 46 with a cell membrane containing the transporter 45 selecting a biomolecule adhered thereon is placed on the chip-like detector 31, and that the electrode 36-1 is provided on the chip 46 with the cell membrane adhered thereon. Therefore, when the sample droplet 35 is dripped on a top surface of the chip 46 for measurement, only biomolecules capable of passing through the transporter 45 are introduced into the chip-like detector 31, so that passage of the biomolecules can be detected. Namely, in a case of the sample droplet 35 for a tissue piece containing a plurality of cells, or in a case of the sample droplet 35 containing a signal transmitter substance released from a particular cell in the cell chip on which cells are arrayed systematically, it is possible to previously select and measure the chip 46 with the cell membrane containing the transporter 45 selecting the biomolecule, which enables analysis of the state of each discrete cell in a multiple cell system.

EXAMPLE 4

Figure 96:
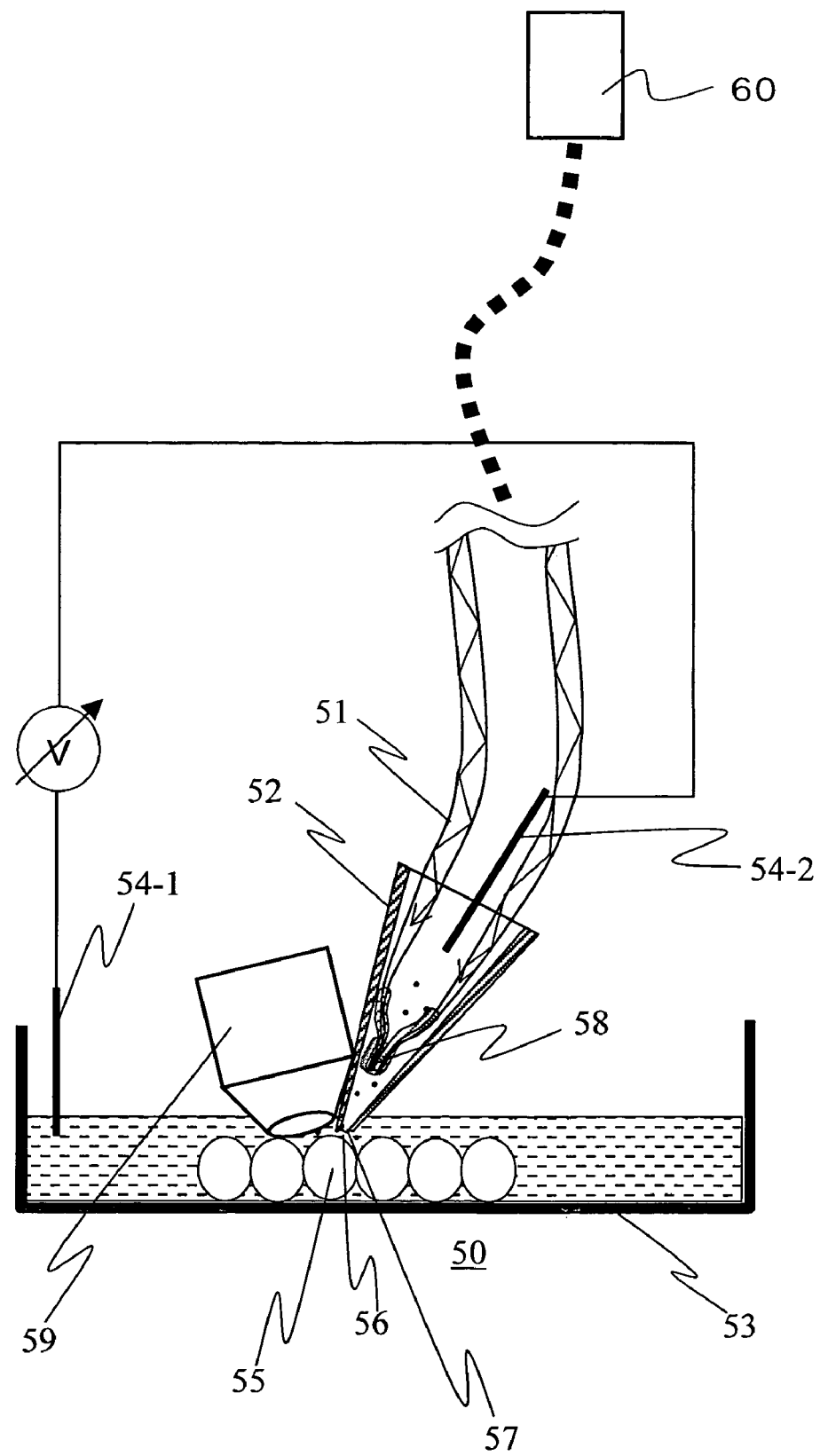
FIG. 96 is a cross-sectional view showing a measuring device in which a tubule with a cell membrane including a transporter adhered thereon is placed outside the chip-like detector of the measuring device described in Example 1.

In Example 3, the structure shown in FIG. 95 is employed for measurement with a droplet and improvement in productivity by employment of a chip, but this chip is not always convenient in use when it is difficult to make a droplet of a sample. Example 4 proposes a measurement device which can advantageously be used when it is difficult to make a droplet of a sample, or when a molecule released from a region where specific cells gather is to be detected. FIG. 96 is a cross-sectional view showing a measurement device in which a fine tube with a cell membrane containing a transporter is provided outside the chip-formed detector of the measurement device described in Example 1.

Also in Example 4, the fine tube with a cell membrane containing a transporter adhered thereon can be used in the transporter chip proposed by the present inventor and disclosed especially in FIG. 9 in Japanese Patent Application No. 2004-264866. Reference numeral 51 indicates a fine tube of the measurement device described in Example 1. An evanescent region 58 is formed at the tip section. Reference numeral 52 indicates a fine tube with a cell membrane containing a transporter adhered thereon. The fine tube 52 with a cell membrane containing a transporter covers the fine tube 51. Reference numeral 50 is a block of cells to be measured. A specific cell as a target for measurement is present in the block 50. The block 50 of cells is placed in the buffer solution in the vessel 53. An electrode 54-1 is set in the buffer solution in the vessel 53, while an electrode 54-2 is attached to inside of the fine tune 51 of the measurement device. A tip of the fine tube 52 is approached to the specific cell 55 in the cell block 50. A substance 56 released from the cell 55 is selectively fetched into the fine tube 52 via the transporter 57 attached to a tip portion of the fine tube 52 when an electric field is loaded to the electrode 54-1 and electrode 54-2. Materials not capable of passing through the transporter 57 are not fetched into the fine tube 52. A laser 60 as a light source is attached to the other edge of the fine tube 51. As described in Example 1, an evanescent region 84 is formed at the tip portion of the fine tube 51 as described in Example 1. Because of the configuration, cells having passed through the evanescent wave region 84 of the fine tube 51 are fetched into the fine tube one by one due to the electric field loaded to the electrode 54-1 and electrode 54-2, and the cells generate photons in this step. The photons are captured by a focusing lens 59 and counted with a photon counter (not shown).

In Example 4, as a tip of the measurement device is sharp, access to a specific region of a solid block of cells is easy.

[XIX] Nineteenth Embodiment

As a nineteenth embodiment, a method is described in which a polynucleotide chip and a protein chip both higher in density and better defined quantitatively and reproducibility than conventional chips are used, and also in which an atomic force microscope is used in detecting a shape of substance by tracing atomic force, in place of an optical detection which has a limitation in resolution in detecting captured DNA molecules. Although the atomic force microscope has a resolution fine enough for identifying DNA molecules in a state of a single-chain or a double-chain (approximately 3 nm in diameter), nanoparticles, which are easy to detect, are used as a marker for fast scanning.

EXAMPLE 1

Figure 97:
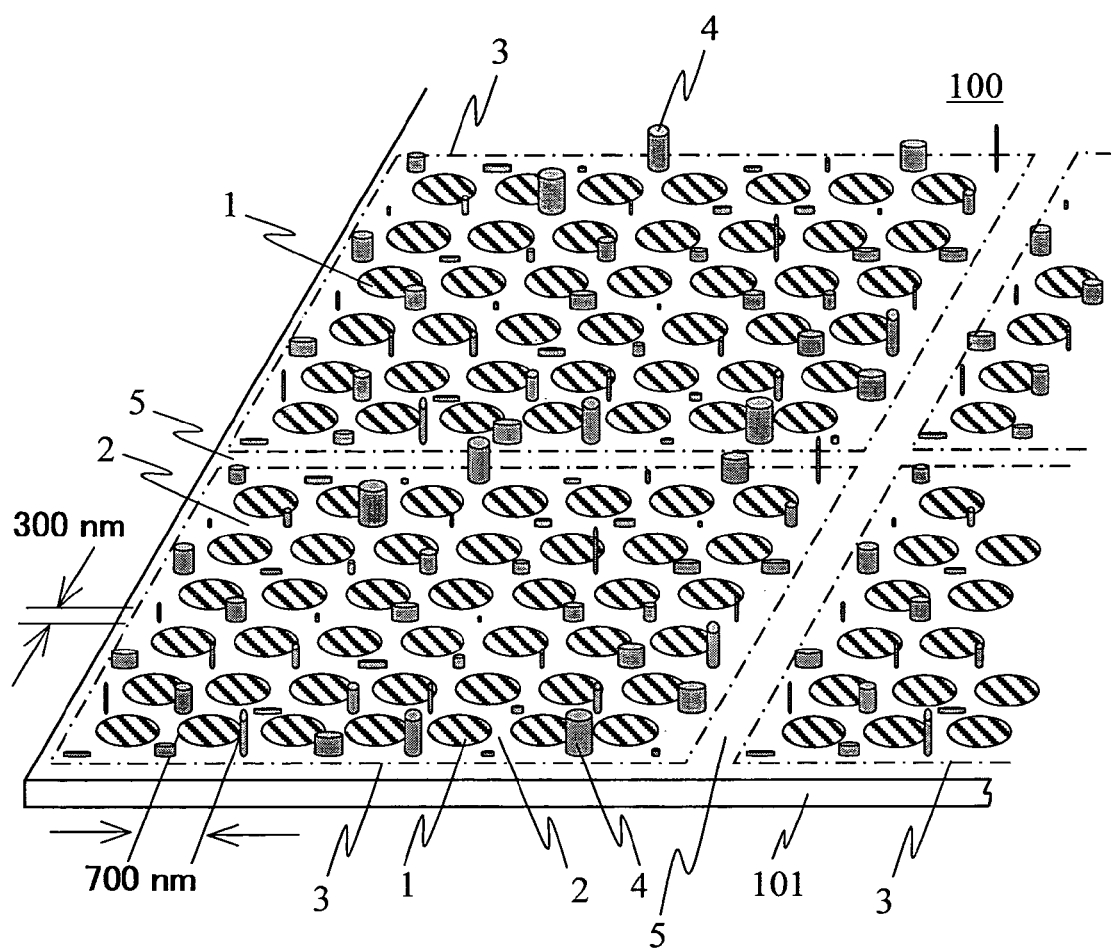
FIG. 97 is a perspective view conceptually showing a portion of a DNA chip in Example 1 of a nineteenth embodiment of the present invention.

FIG. 97 is a conceptual oblique perspective view showing part of a DNA chip according to a first example of the nineteenth embodiment. A chip 100 is formed on a silicon substrate 101 with oxidized film on the surface. Each element 1 has a form of a cylindrical column 700 nm in diameter. A spacing 2 between each element is 300 nm. This means that the elements are lined up at a distance of 1 µm. A group of 50×50 elements, as enclosed with a single-dotted line 3, forms an element group, and there are provided 20×20 element groups lined up on the chip. Between each element group 3 is a groove 5 40 nm in width and 20 nm in depth, and on each of four corners of each element is provided a pillar 4 for indexing. The pillar 4 between 2 elements is shared by both elements. The pillar 4 has a form of cylindrical column, with 17 different diameters starting from 50 nm at an increment of 10 nm, and with 17 different heights starting from 5 nm at an increment of 10 nm, and a combination of four pillars 4 at the four corners of each element is used for indexing, just like a bar code. There are therefore nine pillars 4 of the same shape in an element group 3, and the pillars are placed so that no adjoining pillars are of the same shape, and that the sizes of pillars are as randomly placed as possible.

Figure 98:
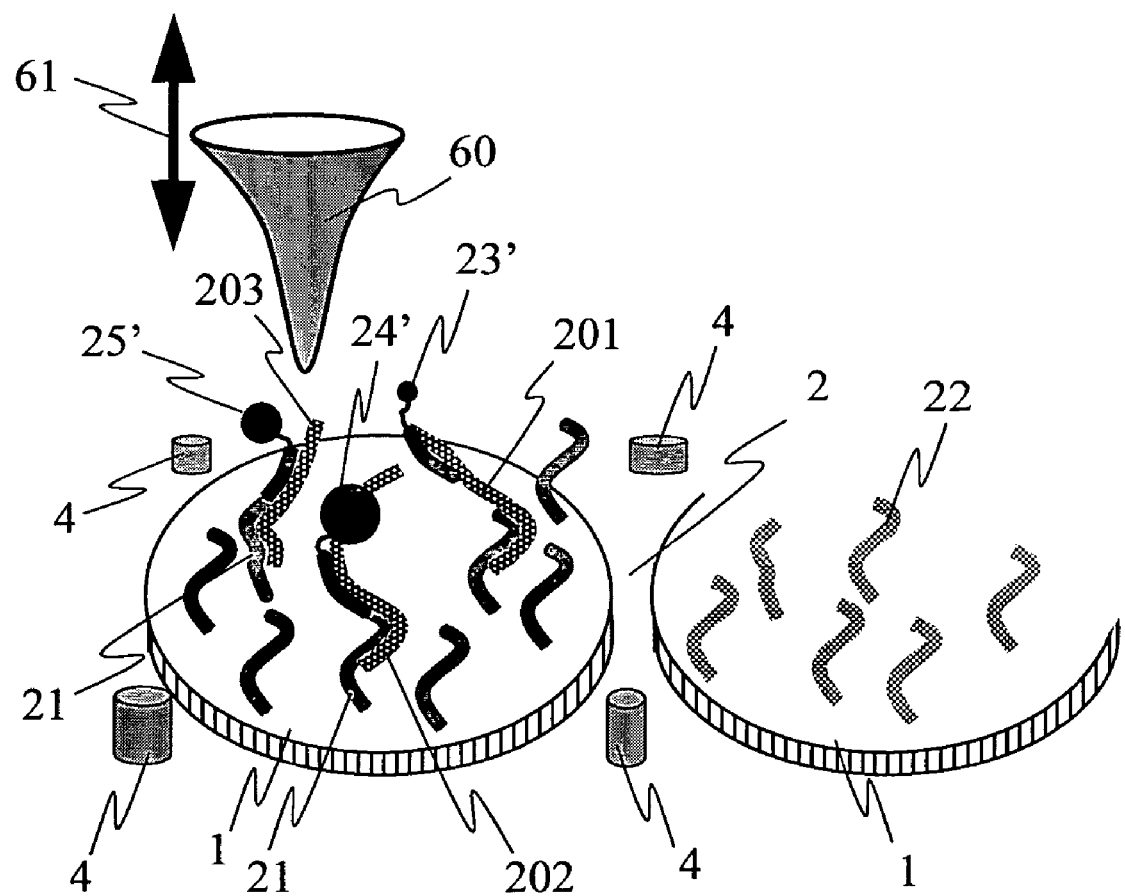
FIG. 98 is a view schematically showing a more detailed relation among DNA probes fixed on each element 1, a DNA piece prepared by hybridizing the DNA probe, and an AFM probe for detecting the DNA piece.

FIG. 98 is a pattern diagram showing more detailed relationship between the elements 1 each and the pillars 4 on the substrate 101 shown in FIG. 97, and relationship among DNA probes 21, 22 . . . , DNA fragments 201, 202 and 203 hybridized to the DNA probes, and an AFM probe 60 for detecting the DNA fragments. Each element 1 on the substrate 101 is provided at a raised level from the substrate surface. This means that there are grooves between each element, forming boundaries between each element. The element 1 is raised by 20 nm. DNA probes and others are described hereinafter.

Figure 99:
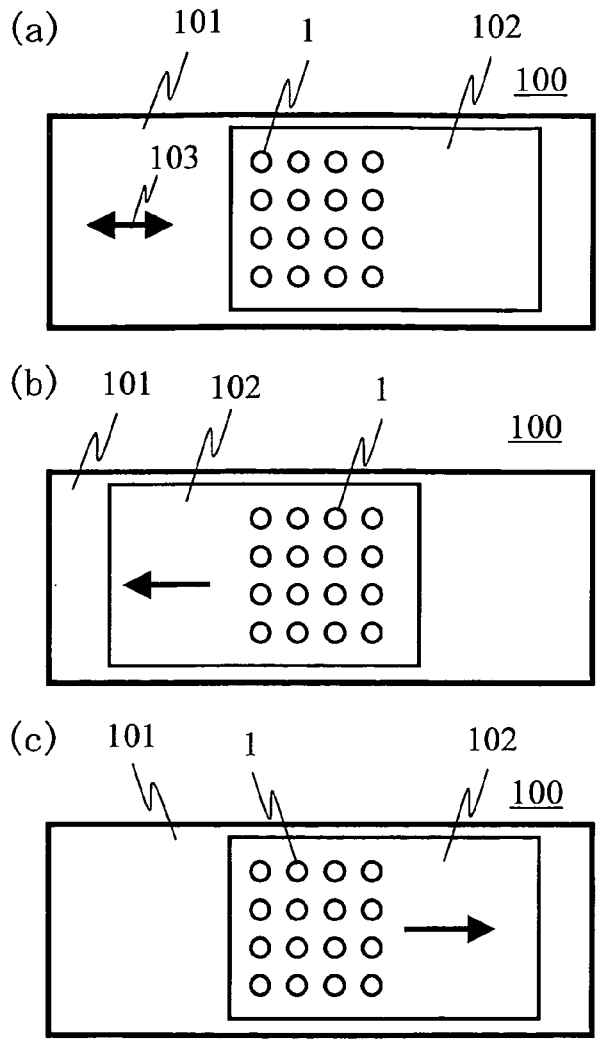
FIGS. 99(a) to 99(c) are views illustrating an effect of a pillar 4 for speeding up the probe hybridization.
Figure 100:
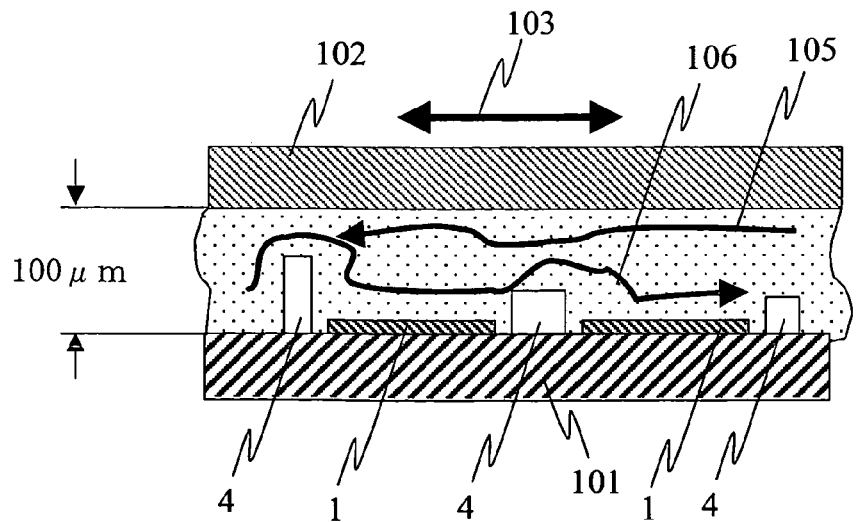
FIG. 100 is an explanatory view illustrating details of the effect provided by the pillar shown in FIG. 99.

The pillars 4, provided at the four corners of each element, are used for indexation, in addition for accelerating hybridization. FIGS. 99 (*a*), (*b*) and (C) are an overall view describing the effect of the pillars 4 for accelerating hybridization, and FIG. 100 is a detailed explanatory diagram showing the effect described in FIG. 99.

As shown in FIG. 99 (*a*), above the upper surface of the element 1 on the substrate 101 of the DNA chip 100 is provided an upper plate 102, at a gap of 100 µm, movable back and forth, as shown in an arrow 103, and between the upper plate 102 and the substrate 101 is sandwiched 1 µl of sample solution. As shown in FIG. 99 (*b*), the upper plate 102 is moved to the direction indicated by an arrow relative to the substrate 101. Thereafter the upper plate 102 is moved to the reverse direction relative to the substrate 101 indicated by an arrow as shown in FIG. 99(*c*). The upper plate 102 is moved back and forth at 1 Hz. Generally, in a micro device like the DNA chip, the solution tends to develop a laminar flow, resulting in poor agitation efficiency; the back-and-forth movement of the upper plate 102 over the substrate 101 disturbs the laminar flow, accelerating the hybridization. FIG. 100 is a cross-sectional view at a center position of two adjoining elements 1, with a pillar 4 visible beyond the center position. The back-and-forth movement of the upper plate 102 in the direction shown by an arrow 103 relative to the substrate 101 forces surface-direction movement of the solution as marked by reference numerals 105 and 106, and diffusion of the dissolved substance (DNA samples and marker probes in the example) in the direction of thickness only is known to be a determinant of hybridization speed (refer, for instance, to Japanese Patent Laid-Open No. 2004-144521). Hence, the sample solution is always altering on the surface of the elements 1 each, accelerating the hybridization. Further, in the 19th embodiment, as there are provided pillars effectively random in form between each of the elements 1, the solution forced to move in the surface direction is disturbed more effectively by the obstacle pillars 4, further accelerating the hybridization. As a result, the hybridization speed in the micro device is effectively close to the speed in a solution layer.

With reference to FIG. 98 again, on the upper surface of the elements 1 in the form of a cylindrical column 700 nm in diameter and 20 nm in height are each fixed mutually different DNA probes 21, 22 . . . . The DNA probes used here are of type PNA. The PNAs, unlike regular DNAs, do not have a negative charge originating from a phosphodiester bond, and hence there does not work an electrostatic repulsive force with target DNAs. This improves efficiency of the hybridization. In particular, in a micro device like a DNA chip in which probes are fixed on the solid phase of the elements in high density, if regular DNA probes are used, the target DNAs need to approach the probes through the barrier of the negative charge, which is disadvantageous in terms of reaction kinetics as well as thermodynamics. Also the DNA sample must be of single chain. The use of the PNA and the like without the negative charge results in lack of charges on the surface of the element, leading to a speedier hybridization speed and a better yield. Further, due to the characteristic of lack of the charge, an electrostatic repulsive force is not generated, so that PNAs can competitively enter between the two chains of DNAs and can competitively hybridize, even if the target DNAs are of double chain.

In the example 1, to the elements 1 each are fixed the DNA probes 21, 22 . . . , which are each a sequence of between 45 and 60 bases in length between a first exon and a second exon of human cDNA. This prevents false positive results and lower hybridization efficiency caused by hybridization of residual genomes. A commonly known method of fixing probes is used: probes are fixed with a silane coupling reaction. In the example, conditions of the hybridization such as composition of buffer fluid and the sample DNA probes are in accordance to a hybridization method described in Nucleic Acid Research (2002) 30, No. 16 e87. As a probe fixing method, a method described in the above document is employed, in which amino groups are introduced to an oxidized surface of the silicone substrate 101 processed with 3-aminopropyltrimethoxysilane. The amino group introduced on the surface and an SH group of the probe is bridged with N-(11-maleimidoundecanoxyloxy)succinimide. If probes about 50 bases in length are fixed with this method, the concentration of the probes is about a molecule per 15 nm$^2$. This means that there are some 25,000 probe molecules fixed on an element.

As the sample, $1^{st}$ strand cDNA is used, obtained by reverse-transcribing once mRNA originating from human leucocyte. Generally such a method as oligo-capping is employed to obtain full-length cDNA, but in the example, since it is desired to identify the quantity of mRNA in a cell, a method is used in which the cells are dripped into liquid helium little by little, resultant quick-frozen cells are drip-suspended in ultrasonic-agitated phenol together with the liquid helium, and the cells are destructed in an instant. Total RNAs are purified with a commonly known method. A reverse-transcription enzyme is worked on RNAs obtained from about 10 cells to produce the $1^{st}$ strand cDNAs.

The $1^{st}$ strand cDNAs obtained in the above-described manner are dissolved in 1 µl of 2×SSC and dripped on the DNA chip. At this state, there are included about $10^2$ molecules of rare $1^{st}$ strand DNAs and about $10^5$ molecules of abundant $1^{st}$ strand DNAs, and this matches the number of probes on the chip surface in terms of order.

The DNA chip is agitated for an hour at 45° C., as shown in FIGS. 99 and 100, to complete the hybridization process. Thereafter the upper plate 102 used for agitation as described in FIGS. 99 and 100 are removed and dried. In the example 1, since the PNA probes are used, it is not necessarily required to arrange a condition with high salt concentration as is the case with regular DNA chips. This is because it is not necessary to block the negative charges of the DNA probes and the sample DNAs with salt. On the contrary the results are usually better with low ionic strength.

In the example 1, single-chain $1^{st}$ strand cDNAs are used, but the hybridization can equally work with double-chain DNAs without first uncoiling them. In this case, the ironic strength should not be very high, as in this way, the sample double-chain DNAs are easier to uncoil due to the very own negative charges of the DNAs; the probes do not have negative charges and the hybridization process can proceed without problems. In this case, however, there is a competition between recoiling of the double-chain DNAs and hybridization with the probes, and the hybridization yield is inferior to the yield obtained with the hybridization of the $1^{st}$ strand cDNAs.

In the example 1, the hybridization process completes very fast even on the solid phase, due to the use of the PNA probes and sufficient agitation. With DNA probes according to the conventional technology, reaction efficiency is poor with the sample concentration and the probe quantity as described above, and the reaction does not complete even after 24 hours, due mainly to the electrostatic repulsion force.

FIG. 98 illustrates a state in which a sample DNA fragment 201 is hybridized with the probe 21 on the element 1.

Next, in order to identify different portion in complement sequences of the sample DNA fragments 201, 202 and 203 hybridized to the probes 21, second probes marked with gold nanoparticles 23', 24' and 25', the particles are to be hybridized with the sample DNA fragments 201, 202 and 203, is used. For the second probe, an exon different from the exon used in the capture probe 21 on the element 1 is employed. For instance, PNA probes corresponding to exon 3, exon 4 and exon 5 are prepared in advance. Each probe is about 30 to 50 bases in length. Each probe is introduced with a sulphide group (an SH group) at the 5' end at the time of synthesis. For probes corresponding to the exon 3, exon 4 and exon 5 each, gold nanoparticles with diameters 8.3 nm, 11 nm and 17 nm are mixed, respectively, and PNA probes marked with gold nanoparticles with different diameters are obtained. Each of the three gold nanoparticles-marked probes (23', 24' and 25') is mixed at 10 pmol/µl, each of the mixture is dripped on the DNA chip with hybridized sample DNAs, and the DNA chip is agitated for 15 minutes again with the method described in FIGS. 99 and 100.

After washing the chip with 2×SSC, the upper plate 102 for agitation described in FIGS. 99 and 100 are removed and dried. Thereafter, the surface of the chip 100 is scanned two-dimensionally while tapping an AFM probe 60 at 10 Hz, as shown with an arrow 61.

Figure 101:
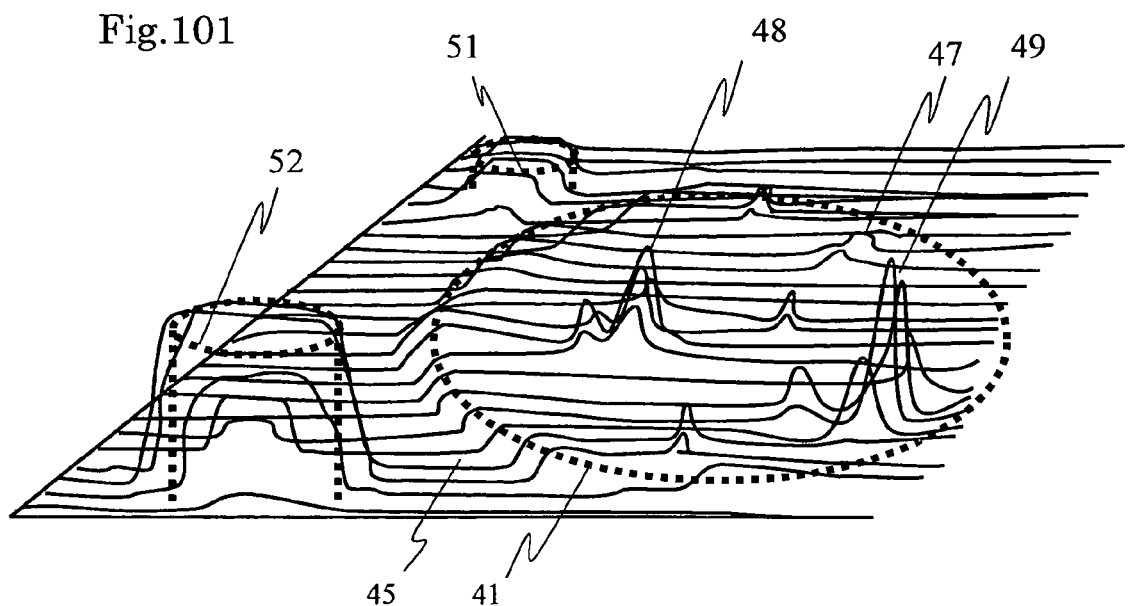
FIG. 101 is a view schematically showing a position signal for an AFM probe 60 obtained by scanning the chip 100 shown in FIG. 97 with the AFM probe 60 in the lateral direction.

FIG. 101 is a pattern diagram showing the position signal of the AFM probe 60 when the chip 100 as shown in FIG. 97 is scanned in lateral direction with the AFM probe 60. From the position signal of the AFM probe 60, it is known that the element 1 is located at a position shown with a dotted line 41, and the gap 2 between the elements 1 is located at an adjoining area 45. It is also known that the pillars with different sizes are located at positions indicated with dotted lines 51 and 52. Position signals corresponding to reference numerals 47, 48 and 49 indicate that the gold nanoparticles-marked PNA probes are hybridized to the second probes (23', 24' and 25' in FIG. 98) corresponding to the exon 3, exon 4 and exon 5, respectively, which are further hybridized to the PNA probes fixed on the element 1. Therefore, from the position signal of the AFM probe 60, the positions of elements and the markers can be identified.

EXAMPLE 2

Figure 102:
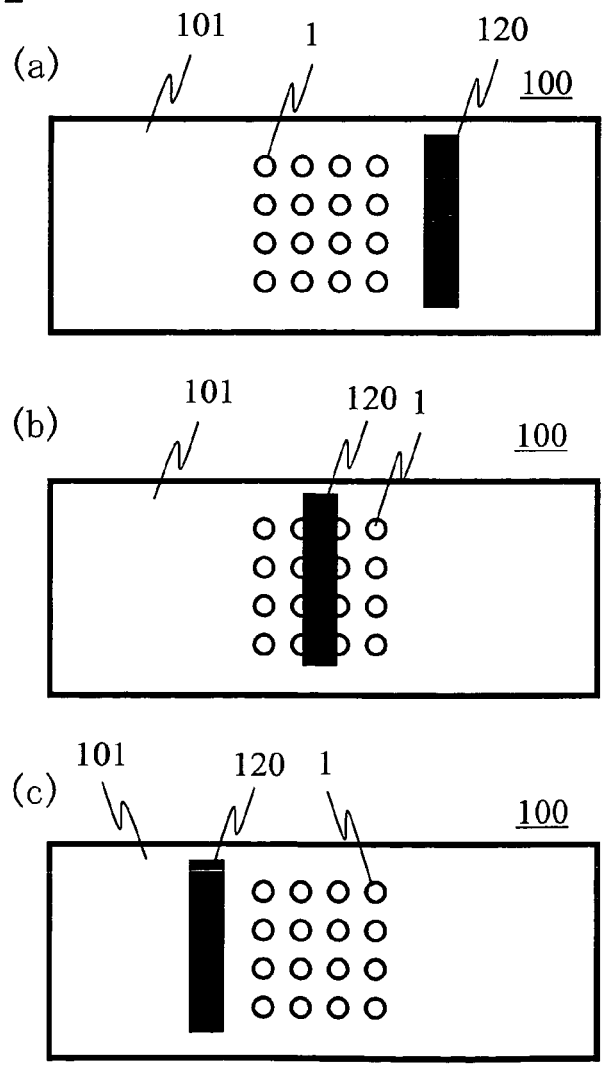
FIGS. 102(a) to 102(c) are views illustrating the effect of the pillar 4 in Example 2 for speeding up probe hybridization.
Figure 103:
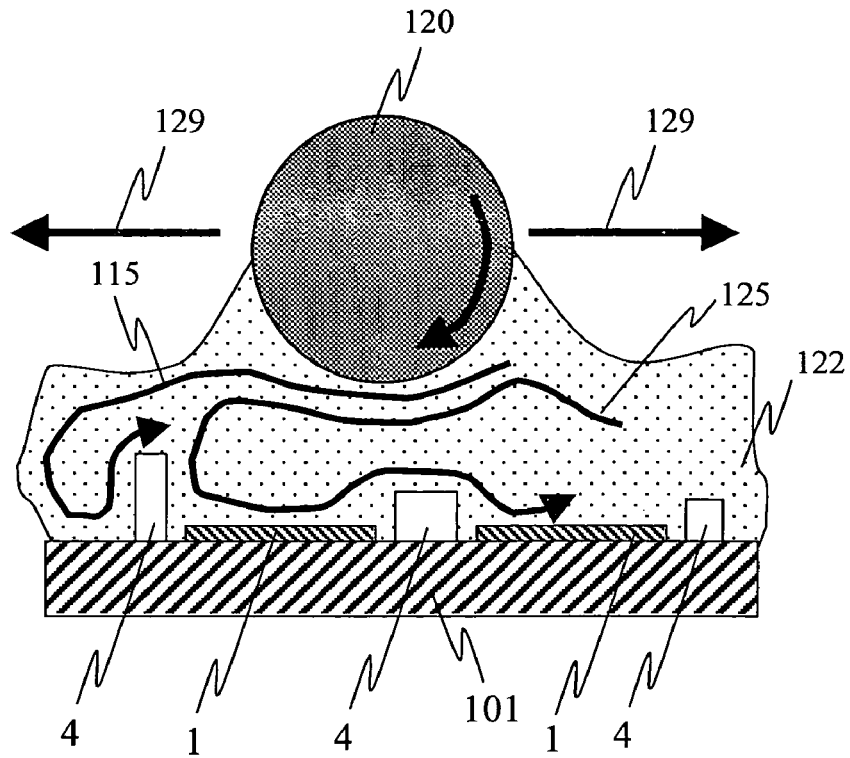
FIG. 103 is an explanatory view illustrating details of the effect shown in FIG. 102.

FIGS. 102 (*a*), (*b*) and (*c*) are an overall view showing another example of illustrating the effect of the pillars 4 for accelerating the probe hybridization, and FIG. 103 is a detailed explanatory diagram illustrating the effect described in FIG. 102.

It is known from comparison of FIGS. 102 (*a*), (*b*) and (*c*) with FIGS. 99 (*a*), (*b*) and (*c*) that there is a singular difference between the DNA chip 100 in the example 2 and the DNA chip 100 in the example 1, in that in place of the upper plate 102 located over the substrate 101, there is provided a rotating rod 120 with 100 µm in diameter. The rod 120 can be rotated at 200 rpm, touching the sample solution 122 on the substrate 101. There is a gap of 100 µm between the rod 120 and the chip element. While the rod 120 is rotated with a spindle motor, the stage on which is placed the chip is moved right and left once every 10 seconds. After 1 µl of sample solution or nanoparticles-marked probe solution is dripped on the substrate 101, the substrate 101 is moved from left to right while the rod 120 is rotated as illustrated in FIGS. 102 (*a*), (*b*) and (*c*), and from right to left if necessary (arrow 129: FIG. 103). The rotation of the rod 120 forces surface-direction movement of the solution as marked by heavy lines 115 and 125, and the solution is agitated well on the substrate 101. Hence, the sample solution is always altering on the surface of the elements 1 each, accelerating the hybridization. Further, also in the example 2, as there are provided pillars effectively-random in form between each of the elements 1, the solution forced to move in the surface direction is disturbed more effectively due to solution turbulence by the obstacle pillars 4, further accelerating the hybridization. In the example 2, due to interaction of the rotation of the rod 120 and the surface direction movement, the reaction liquid for hybridization is agitated well on the elements on the chip.

The size of the chip according to the nineteenth embodiment is described hereinafter. Generally, if optical means is used to identify substances, substances less than 400 to 500 nm cannot be identified with a numerical aperture of 0.8, as shown by the formula 1. If the size is smaller, even the existence of the substances cannot be identified. Practically, the minimum size is about 700 nm.

Formula 1:

$$\text{Resolution} = 0.61 \cdot \frac{\lambda}{n \cdot \sin\theta} \quad (1)$$

(where $n \cdot \sin\theta$ is the numerical aperture)

In the nineteenth embodiment, substances are identified by measuring the atomic force, and therefore substances can be identified without regard to wavelength. For this reason, the element 1 and the groove between the elements 1 can be identified even if the diameter of the element or the spacing between the elements are less than 700 nm. In the example 1, the element 1 has a diameter of 700 nm, and the spacing between the elements 1 is 300 nm, but the element 1 can be minuter, and the spacing between the elements can be shorter. For instance, if the element 1 has a diameter of less than 500 nm and the spacing is less than 300 nm, gold nanoparticles 8.3 nm in diameter and captured on the element 1 with the hybridization reaction can be quantitatively determined with the use of the atomic force microscope.

As for the minimum size of the element 1 or the spacing between the elements 1, about 70 nm is the minimum for reasons described hereinafter. Namely, it is described above that the concentration of the fixed probes is about a molecule per 15 nm$^2$, if probes of about 50 bases in length are used. On the other hand, a smallest size of nanoparticles generally available with the current technology is about 5 nm, which is about the same size with the concentration of the probes and serves as a decision standard for the minimum size. In practice, there must be at least 1,000 particles on an element 1 for quantitative determination. Hence, the minimum size of the element 1 is 15×1,000 nm$^2$. This means that the minimum diameter of the element 1 is about 70 nm. If the quantitative determination is not required, smaller elements may be used, and the area occupied by a probe molecule when fixed is the minimum. This means that the smallest possible diameter is 3 nm.

EXAMPLE 3

Protein chips are prepared in which affinity-purified anti-AFP antibody and anti-CEA antibody are fixed to different elements. Separately, SH groups are introduced to F(ab')$_2$ fragment obtained by papain-degradating the anti-AFP antibody and anti-CEA antibody. About 3 to 4 molecules of the SH group are introduced to a molecule of the F(ab')$_2$ fragment. Gold nanoparticles 20 nm in diameter is mixed, and particles with the F(ab')$_2$ fragment bonded on the surface is obtained. As samples, solution with AFP only with 1 zmol/μl in concentration, solution with CEA only with 5 zmol/μl in concentration, and a control without any substance are prepared. A PBS at pH 7.4 including 0.1% Tween 20 and 0.5% BAS is used as solvent. The protein chips are reacted with the solutions, and then with the gold nanoparticles-marked F(ab')$_2$. The reaction time is five minutes for the reaction with the samples, and another minutes for the reaction with the gold nanoparticles-marked F(ab')$_2$. After the reaction is completed, the chip is washed with buffer solution including 0.1% Tween 20 and 0.5% BAS, and scanned with the AFM.

The chip reacted with the AFP has 120 particles per element fixed with the anti-AFP antibody and 6 particles per element fixed with the anti-CEA antibody. The chip reacted with the CEA has 7 particles per element fixed with the anti-AFP antibody and 1,340 particles per element fixed with the anti-CEA antibody.

The chip reacted with the control has only 2 to 4 gold nanoparticles per element fixed with either of the antibodies.

The nineteenth embodiment may be applied in several forms as described above as examples, but in any of the forms, the hybridized sample DNAs and others are detected practically on a molecular basis and the embodiment offers a sensitivity far exceeding the conventional method. As an ultra small amount of DNAs or RNAs with an ultra small bulk can be detected, target DNAs or RNAs can be detected without PCR amplification as a pretreatment, which is not possible with the conventional method. Further, as the size and form of marker particles can be changed for identification, some 6 to 10 different samples can be multi-analyzed on the same element. This technique can be applied to conventional differential hybridization, as well as to the detection with different marker probes after sample polynucleotides are captured to the element with a single type of probe. The multi-analysis technology of the nineteenth embodiment offers an advantage of detecting alternative splicing and of typing a plurality of SNPs with a single element.

Figure 104:
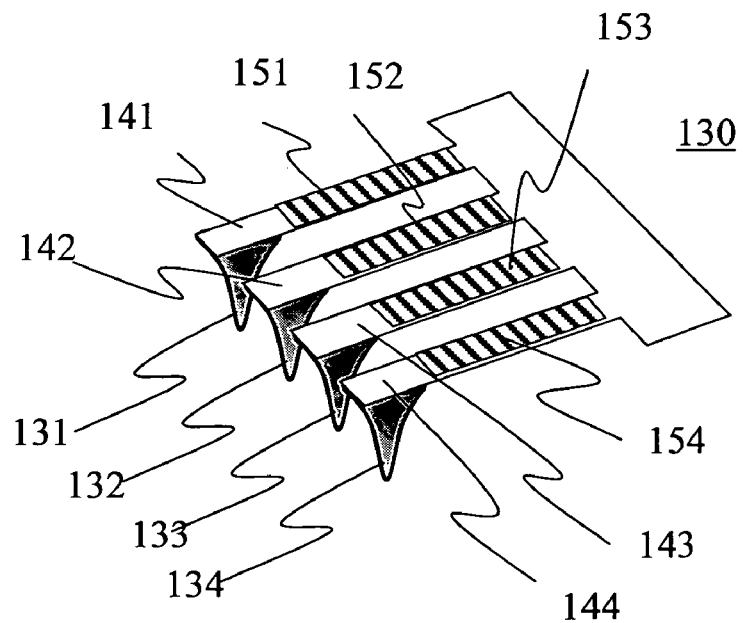
FIG. 104 is a perspective view showing an example of configuration of an AFM cantilever well suited to the nineteenth embodiment of the present invention.

FIG. 104 is an oblique perspective view illustrating construction of an AFM cantilever suitable for use with the nineteenth embodiment. The AFM cantilever 130 can be formed to have a plurality of needles 131-134 lined up in array. The needles 131-134 are independently fit to levers 141-144, each attached with a piezoelectric element 151-154, and with the up-and-down movement of the needles, electromotive force of the piezoelectric elements changes and can be detected. By using a cantilever with an array structure, a plurality of lines can be scanned at a time. Therefore nanoparticles captured on the chip can be detected very fast. Further, it is possible to take advantage of the speedy scan by scanning the same part a plurality of times, in order to reduce tracing errors of figuration. Specifically, by scanning N times, the measurement error in the direction of height can be reduced to 1/vN. In the embodiment according to the present invention, a cantilever with 10 needles is used and the scans are repeated 16 times to calculate values in the direction of depth. With this method, a 1 mm×1 mm chip with 10,000 elements can be scanned in 30 minutes.

[XX] Twentieth Embodiment

A twentieth embodiment of the present invention describes a method for detecting a DNA molecular captured by a chip with high resolution like the nineteenth embodiment, but using a scanning electron microscope which detects a shape of a substance by tracing with an electric beam instead of the atom force microscope employed in the nineteenth embodiment. Though the scanning electron microscope can resolve and discriminate between a single-stranded DNA and a double-stranded DNA (with around 3 nm in diameter), the scanning electron microscope uses a nanoparticle as a marker which is easier to detect for enabling scanning at a higher speed.

Figure 105:
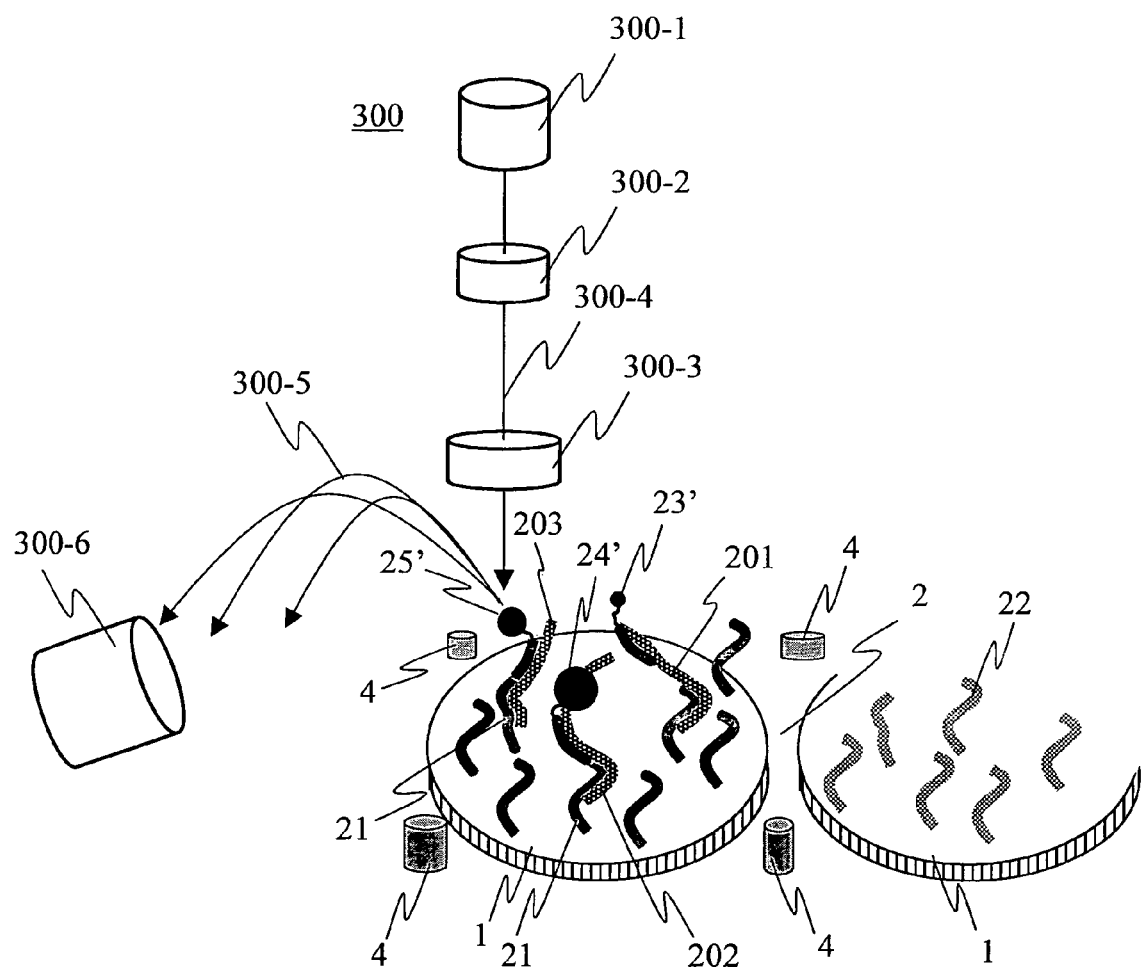
FIG. 105 is a view schematically showing each relation among DNA probes fixed on each element, a DNA piece obtained by hybridizing the DNA probe, and a scanning electron microscope detecting the DNA piece and the DNA probe in a twentieth embodiment of the present invention.

FIG. 105 is a view schematically showing a more detailed relation between the element 1 and the pillar 4 on the substrate 101 illustrated in FIG. 97, and also the relations among DNA probes 21, 22, . . . fixed on each element 1, DNA pieces 201, 202, and 203 obtained by hybridizing the DNA probes above, and a scanning electron microscope 300. The scanning electron microscope 300 includes an electron gun 300-1, a condenser lens 300-2, a scanning coil 300-3, a detector 300-6, and the like. Electrons of an electron beam 300-4 irradiated from the electron gun collide with specimens (gold particles coupled to the DNA pieces 201, 202, or 203), then the specimens release secondary electrons 300-5, and then the detector 300-6 captures the secondary electrons. Each element 1 on the substrate 101 is at a higher position than a surface level of the substrate 101. Namely the elements 1 each with the height of 20 nm are divided and bordered by a groove.

As understood from comparison of FIG. 105 to FIG. 98, the twentieth embodiment is equal to the nineteenth embodiment except for the tracing method for which the twentieth embodiment uses the electron beam 300-4 in place of the exploring needle 60 of the atom force microscope employed in the nineteenth embodiment. Therefore the DNA chip preferable to the twentieth embodiment is the same DNA chip used in the nineteenth embodiment shown in FIG. 97. Similarly the same method described in the nineteenth embodiment is applicable to the twentieth embodiment in the preparation for DNA probe and specimen.

Figure 106:
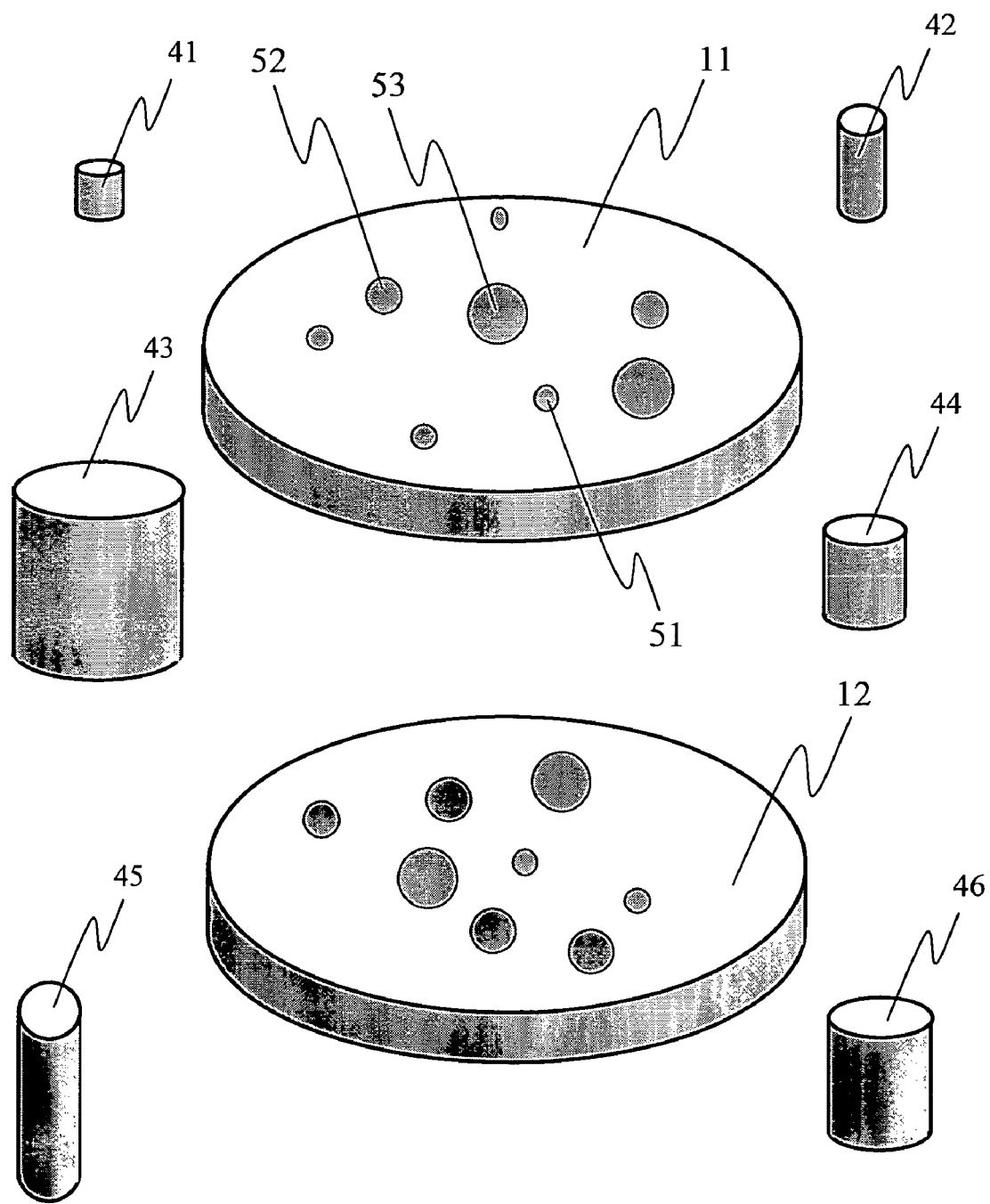
FIG. 106 is a view schematically showing a scanning electron microscope image obtained by two-dimensionally scanning the chip 100 shown in FIG. 97 with a scanning electron microscope.

FIG. 106 is a view schematically showing a scanning electron microscope image obtained by two-dimensionally scanning with the electron beam 300-4 of the scanning electron microscope 300. Reference numerals 11 and 12 indicate elements corresponding to the element 1 shown in FIG. 105. Reference numerals 41, 42, . . . , 46 indicate pillars arranged at the four corners of the elements 11 and 12, corresponding to the pillar 4 described in FIG. 105, different from each other in size. Reference numerals 51, 52, and 53 indicate gold nanoparticles, with 8.3 nm, 11 nm, and 17 nm in size respectively. Although there are other gold particles without any reference numeral, in the figures only the gold particles each with a reference numeral are shown. The scanning electron microscope used in the twentieth embodiment builds up an image only from substances emitting secondary electrons when exposed to the electron beam, and substances not emitting secondary electrons do not appear in the image. Therefore the pillar, the element, and the gold nanoparticles appear in the image built up by the electron microscope in the twentieth embodiment, while the probe, the DNA pieces hybridized thereto, and a polymer molecule or salt contained in the hybridization buffer do not appear in the image.

With the twentieth embodiment, substances can be detected by detecting the secondary electron due to exposure to the electron beam, so that the substances can be measured independent of the wavelength. Therefore in a case where the element 1 or the gap between elements is 700 nm or below, the microscope can detect the element and the edge thereof. Though in Example 1, the element 1 is 700 nm φ and the gap between the elements is 300 nm, a structure with the finer element 1 or gap therebetween is acceptable. For instance even in a case where the element 1 is 500 nm or below or the gap therebetween is 300 nm or below, the gold particles with 8.3 nm in size on the element 1 captured through the hybridization reaction can be detected by the scanning electron microscope with a fixed quantity.

The lower limit of the element 1 and the gap therebetween is 70 nm because of the reason described below. As described above in a case where a probe with around 50 bases is fixed, the probe fixing density is around one molecule in 15 nm². While a lower limit of a nanoparticle used for detection is 5 nm in size, based on the lower limit in size to be available in common under the current state of the art, which is approximately equal to the value of the probe fixing density. This value is recognized to be a criterion for the lower limit. Though in an actual case, in the light of the fixed quantity detection, at least 1000 particles are required to be placed on the element 1. Namely, the lower limit of the element 1 is 15×1000 nm² in size, and the diameter of the round element 1 is at least 70 nm. Needless to say in a case not considering the fixed quantity detection, the smaller element can be used. In this case the lower limit becomes an area where one molecule of the probe to be fixed occupies, indicating that the smallest unit of the element is 3 nm.

[XXI] Twenty-First Embodiment

A twenty-first embodiment discloses a DNA probe chip speeding up hybridization on the surface of a solid chip, capable of measurement in a short time, highly sensitive, and having less pseudopositive hybridization, a method of making the same, and a method of hybridization on the DNA probe chip.

Specifically, this embodiment suggests;

1) The probe should be fixed on the surface of the electrode configured to concentrate the target polynucleotide adjacent to the electrode on which the probe is fixed, and 2) The probe should be configured to have negatively dissociated residues on the free end so that the probe rises quickly when the target polynucleotide concentrated adjacent to the electrode is diffused.

In addition to the above, as a further improved embodiment;

3) By making the fixed end of the probe to be GC-rich, the probe allows the hybridization of the target polynucleotide to the risen probe to advance from the board side to the free end side. This restrains steric hindrance by adjacent probes and solid surfaces, and 4) In order for the target polynucleotide easily to hybridize the probe by using a probe removed of the negative charge from the principal chain, The probe speeds up hybridization on the surface of a solid chip, is capable of measurement in a short time and highly sensitive, and having less pseudopositive hybridization.

With consideration of the hybridization process of the probe and the target polynucleotide, in order to implement the hybridization effectively, the following points must be considered.

1) According to the DNA probe chip, the probe is fixed on the solid surface and the hybridization of the probe and the target polynucleotide is substantially a complementary strand coupling reaction on the solid-liquid interface. For this reason, in order for the target polynucleotide in solution to collide the probe, the target polynucleotide must be diffused to reach the solid-liquid interface.

It is necessary to sufficiently stir the solution or to add a concentration gradient to the target polynucleotide to increase the concentration in the area adjacent to the solid-liquid interface until the target polynucleotide reaches the diffusion zone on the surface of the solid. Nevertheless, because simply stirring the solution depends on the diffusion coefficient of the target polynucleotide, it takes much time to attain thorough diffusion.

According to the twenty-first embodiment, the surface of the DNA probe chip (the solid surface where the probe is fixed) has the positive charge to electrostatically draw the target polynucleotide having negative charge to the surface of the DNA probe chip. This results in the concentration gradient of the target polynucleotide directing from the solid-liquid interface between the surface of the DNA probe chip and the sample solution including the target polynucleotide to the sample solution. Namely, the closer it is to the surface of the DNA probe chip, the higher the concentration of the target polynucleotide is. The positive charge of the surface of the DNA probe chip can be achieved by either preparation by introducing the positively dissociating residue (positive charge) to the surface of the DNA chip or providing electrodes on the surface of the DNA probe chip and in a portion of the sample solution away from the surface of the DNA probe chip and applying voltage thereto so that the surface of the DNA chip has the positive charge.

2) The probe on the DNA probe chip and the target polynucleotide are both negatively charged polymers. It is considered that, in the process of forming the hybridization, a portion of the probe and target polynucleotide most easily hybridized becomes a core to form the hybridization, and that full hybridization is completed by spreading the region. What must be considered in this case are the effect by the surface of the DNA probe chip and the steric hindrance by the probe.

For instance, comparing known Nucleic Acids Research, 29, 5163-5168 (2001) and Langmuir, 16, 4984-4992 (2000), it can be understood that having more probes is thermally advantageous for hybridization under the condition where the probes are sufficiently non-dense, but that the repulsive force of the charge on the adjacent probe reduces the efficiency of hybridization where the density is 7 nm or lower. Also, though not described therein, the steric hindrance reduces the efficiency of hybridization.

From a macro viewpoint, there will be an optimal probe density. However, according to the twenty-first embodiment, since the target polynucleotide is forced to exist in a high density adjacent to the probe to hit the probe, there will not exist the optimal probe density as observed from the macro viewpoint. Namely, in the twenty-first embodiment, the hybridization starts from the state where the target polynucleotide has reached the probe on the surface of the chip. Therefore, it is noticeable that the hybridization efficiency varies depending on whether the tip of the probe becomes the core of hybridization or the foot of the probe (surface of the chip) becomes the core.

Namely, in the case where the tip (free end) of the probe becomes the core of the hybridization, a huge molecule of the target polynucleotide may sterically disadvantageously collide an adjacent probe or surface of the chip in the process of looping around the probe DNA (forming a double strand) to slow down looping. On the contrary, in the case where the foot of the probe (surface of the chip) becomes the core of the hybridization, the target polynucleotide loops around the probe (forming a double strand) away from the chip surface. In this case, there is little steric hindrance because the hybridization advances in the direction away from the surface of the chip. Further, because an adjacent probe does not have the target polynucleotide looped around the tip, there is little hindrance.

With reference to drawings, the embodiment is described more specifically below.

EXAMPLE 1

Figure 107A:
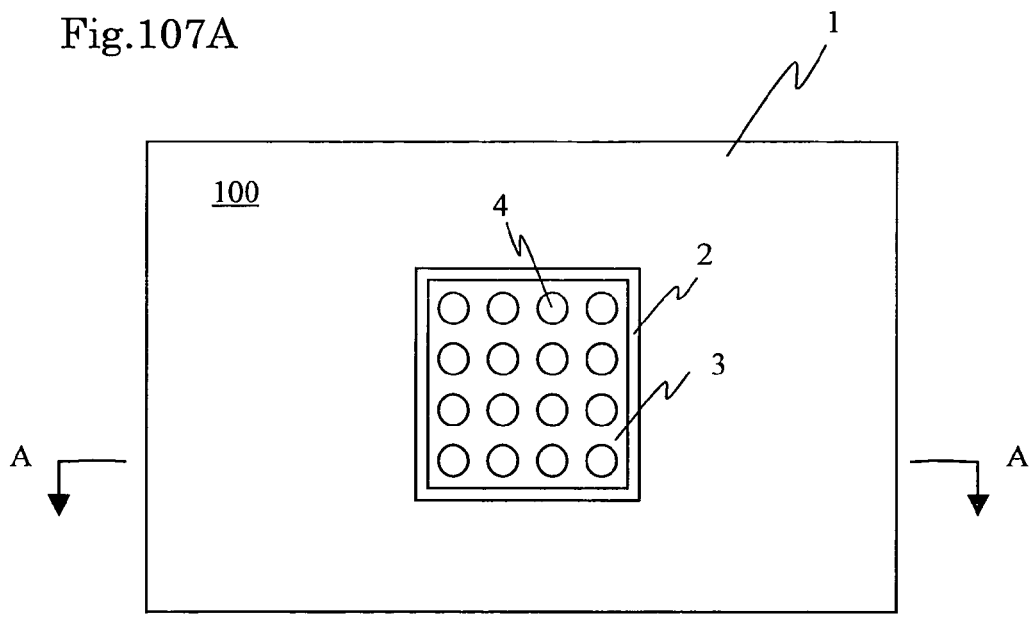
FIG. 107A is a plan view showing a DNA probe chip advantageously applicable to a twenty first embodiment of the present invention.
Figure 107B:
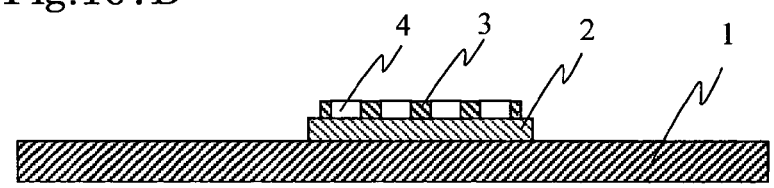
FIG. 107B is a cross-sectional view showing the DNA probe chip 100 shown in FIG. 107A taken along the line A-A and viewed in the direction indicated by the arrow.

FIG. 107A is a plan view showing a DNA probe chip 100 advantageously applicable to a twenty-first embodiment of the present invention, and FIG. 107B is a cross-sectional view showing the DNA probe chip 100 shown in FIG. 107A taken along the line A-A and viewed in the direction indicated by the arrow.

The reference numeral 1 is a float glass (20×40 mm) used as a DNA probe chip substrate. The reference numeral 2 is an electrode deposited on the surface of the substrate 1. The electrode is made of ITO (Indium-Tin Oxide) with the size of 10×10 mm and 10 nm thick. The reference numeral 3 is a 10-nm thick fluorinated surface coating formed on the surface of the ITO electrode 2. The reference numeral 4 is a probe-fixing region where the surface of the electrode 2 is exposed by periodically removing the fluorinated surface coating. While the probe-fixing region 4 is indicated by 4×4 pieces of large circles on FIG. 107A, the actual size of the probe-fixing region 4 is regarded to be about 30 μmφ diameter and, for instance, 100×100 regions are provided. Two adjacent probe-fixing regions 4 are spaced from each other by about 60 μm and the fluorinated surface coating is provided between the adjacent probe-fixing regions 4 to establish independency of each probe-fixing region 4.

The fluorinated surface coating 3 provided on the surface of the electrode 2 is introduced in order to prevent a cross-contamination between the adjacent probe-fixing regions 4. Since prespecified probe solution is applied to each probe-fixing region 4 by a pin array device in the order of several hundred pl, the fluorinated surface coating must be water repellent so that the probe solution will not run off from the region. The probe-fixing region 4 can be produced by ashing by oxygen plasma using a mask and removing the fluorinated surface coating from the surface having the fluorinated surface coating 3 applied thereto by the printing technique. The probe-fixing region 4 is produced by the oxygen plasma ashing, and the ITO electrode 2 exposed in the region is hydrophilic.

There is described below a method of fixing the probe on the surface of the ITO electrode 2 in the probe-fixing region 4. Since the surface of the ITO electrode 2 is in the oxidation state, the DNA probe is fixed using the silane coupling reaction. The condition for implementation of the DNA probe fixing, or the composition of the buffering solution and the sample DNA probe follows a method of hybridization described in Nucleic Acids Research (2002) 30, No. 16 e87. For the method of fixing the probe, based on the reference described above, the ITO electrode 2 is processed by 3-aminopropyl-trimethoxysilane and the amino group is introduced to the surface. The amino group introduced to the surface is bridged to the SH group on the probe using N-(11-maleimidoundecanoxyloxy)succinimide. When a probe of about 50 bases is fixed by this method, the probe fixing density is about one molecule per 15 nm$^2$.

Otherwise, according to another method by A. Kumar, et al. as described in (Nucleic Acids Research (2000) 28, No. 14 e71), the probe may be fixed by applying the silanized DNA probe having the trimethoxysilane residue introduced in advance to the 5' end of synthetic oligonucleotide to the surface of the ITO electrode 2 in the probe-fixing region 4.

EXAMPLE 2

Figure 108A:
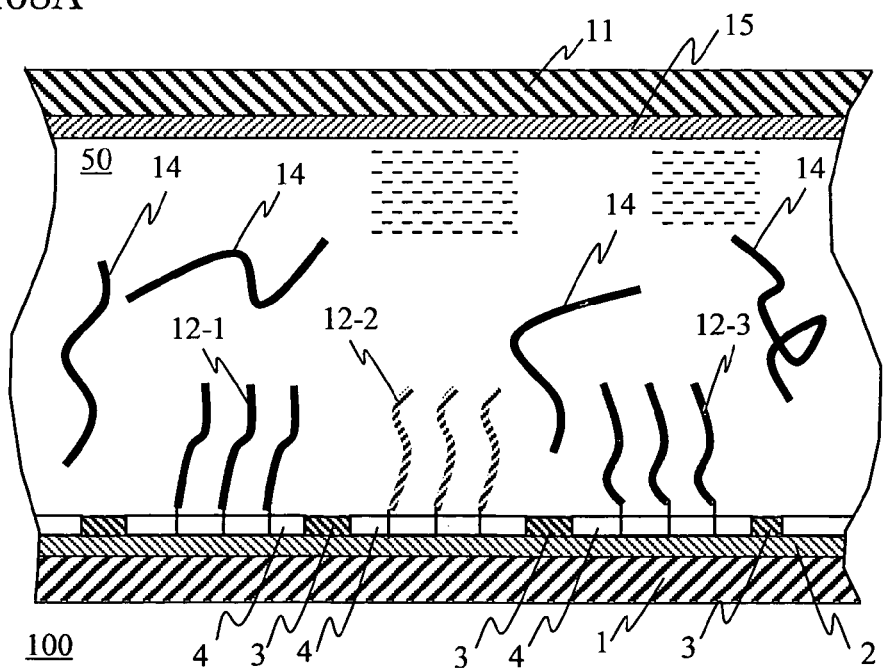
FIG. 108A is a view showing the state in which a sample liquid including a target polynucleotide is introduced on a surface of the DNA probe chip 100 described with reference to FIGS. 107A and 107B.
Figure 108B:
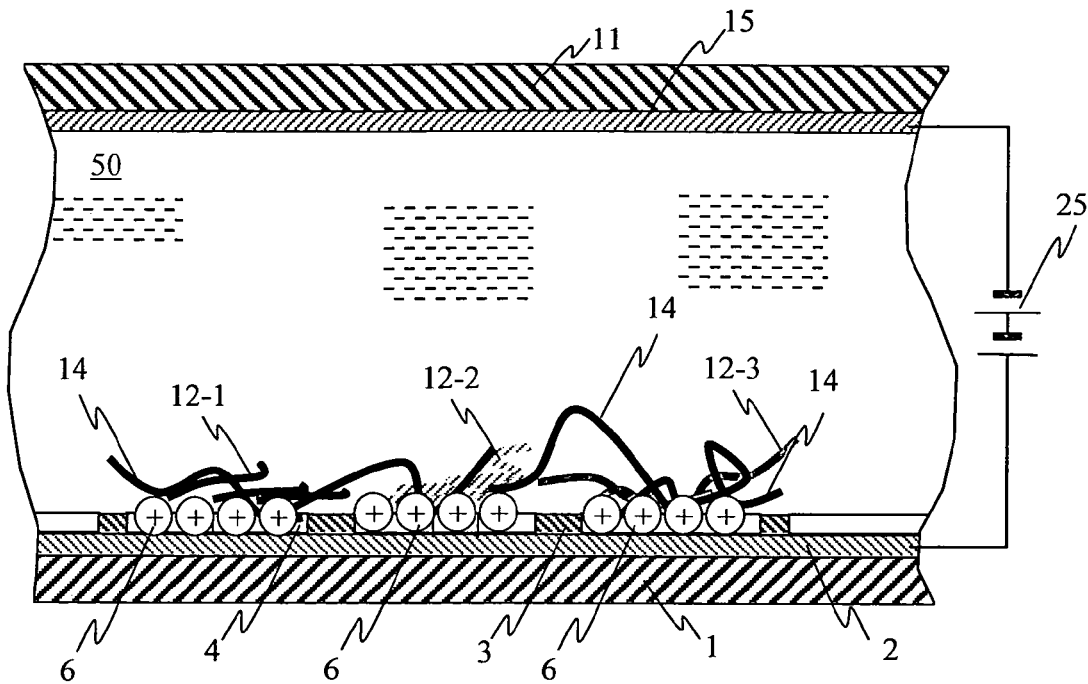
FIG. 108B is a view showing the state in a step of process for forming a concentration gradient of the target polynucleotide on a surface of the DNA probe chip 100.
Figure 108C:
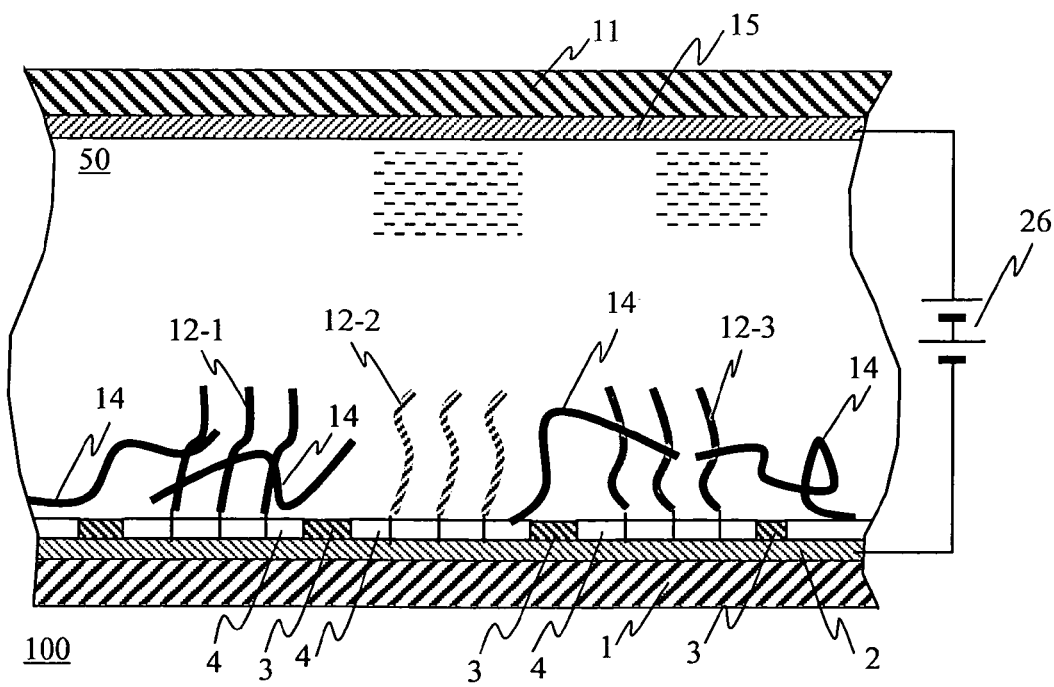
FIG. 108C is a view showing the state in the next step for forming the concentration gradient as a cross-sectional view.

FIG. 108A is a view showing the state in which a sample liquid including a target polynucleotide is introduced on a surface of the DNA probe chip 100 described with reference to FIGS. 107A and 107B, FIG. 108B is a view showing the state in a first step of a process for forming a concentration gradient of the target polynucleotide from a solid-liquid interface between a surface of the DNA probe chip 100 and of a sample liquid toward a sample liquid, and FIG. 108C is a view showing the state in the next step for forming the concentration gradient as a cross-sectional view.

A suitable spacer (not shown) is inserted onto the surface of the DNA probe chip 100 to provide a 0.1-mm gap and a cover glass 11 is placed thereon. A 100-nm thick ITO electrode 15 is provided on the internal surface of the cover glass 11. 40 microliter of mRNA sample solution 50 is applied to the gap between the surface of the DNA probe chip 100 and the cover glass 11. The sample solution 50 allows a slide glass to reciprocate at a constant speed to be stirred thereby. FIG. 108A shows such a state, and each reference numeral 12-1, 12-2 and 12-3 is a probe fixed on the probe-fixing region 4. The reference numeral 14 is a target polynucleotide diffused in the sample solution 50. In this state, the target polynucleotide only diffuses based on the diffusion coefficient of the target polynucleotide.

FIG. 108B is a view showing the state where the electric field is applied between the electrode 2 on the DNA probe chip 100 and the electrode 15 on the cover glass 11 by a power supply 25 achieve +15 V/cm (substantially 0.15 V between the electrodes) so that the electrode 2 is positive. As a result, by achieving the positive charge on the surface side of the DNA probe chip, the target polynucleotide 14 and probes 12-1, 12-2 and 12-3 having the negative charge are electrostatically attracted to the surface of the DNA probe chip. The electrode 15 does not have to be stuck on the cover glass 11 but has only to be located apart from the surface side of the DNA probe chip in the sample solution 50.

FIG. 108C is a view showing the state where the electric field is applied between the electrode 2 on the DNA probe chip 100 and the electrode 15 on the cover glass 11 by a power supply 26 to achieve +15 V/cm (substantially 0.15 V between the electrodes) 30 seconds after the power supply 25 applies voltage so that the electrode 2 is negative and stirring is continued 0 to 30 minutes. Since the electrode 2 becomes negative, the target polynucleotide 14 and probes 12-1, 12-2 and 12-3 having the negative charge and electrostatically attracted to the surface of the DNA probe chip leave from the surface of the DNA probe chip. The probes 12 leave in a short time due to the shortness, and the target polynucleotide 14 takes time to leave, and therefore the concentration of the target polynucleotide 14 in the sample solution 50 is higher on the side of the surface of the DNA probe chip.

Namely, as shown in FIG. 108C, when the electric field inverts, there occurs a repulsive force against the negative charge in the probe 12 and the negative charge in the target polynucleotide 14, which works in the direction away from the surface of the DNA probe chip. The probe 12 tries to move away faster because of the shortness (smallness) compared with the target 14, but, being fixed on one end, the probe molecule quickly rises from the chip surface as a straight chain. On the contrary, the target polynucleotide has so large a molecule that the motion is slow and the target polynucleotide stays on the surface of the DNA probe chip for a longer time. Namely, the concentration of the target polynucleotide is higher in an area adjacent to the fixed end of the probe than in an area adjacent to the tip.

Namely, FIG. 108C shows the state before the hybridization starts, where the probability of the hybridization of the target polynucleotide with the probe is higher at the root of the probe than at the tip. Thus it is more likely to randomly form the core of the hybridization in a portion of the probe close to the chip surface, the hybridization advances in the direction from a portion of the probe close to the substrate to the tip, and the target polynucleotide effectively hybridizes with the probe on the surface of the DNA probe chip.

Figure 109:
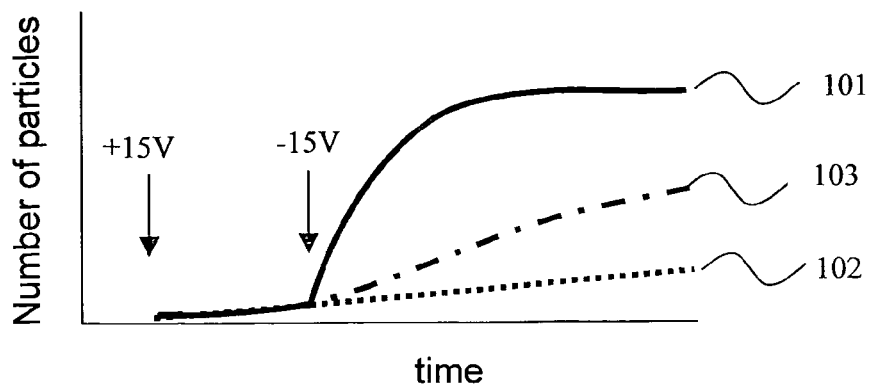
FIG. 109 is a diagram showing the effect in Example 2.

FIG. 109 is a view showing the effect in Example 2. In order to evaluate the target polynucleotide captured by the probe 12 as described with reference to FIGS. 108A, 108B and 108C, the target polynucleotide is coupled with gold particles and observed varying the time to capture the target polynucleotide using a condition of the electric field applied to the DNA probe chip as a parameter. After cleaning and drying the chip, the number of the gold particles left on the surface was counted using a scanning electron microscope. A lateral axis indicates the time of applying the electric field, and the longitudinal axis indicates the counted number of the gold particles.

A characteristic curve 101 indicates the result of the DNA probe chip capturing the target polynucleotide when −15 V/cm electric field is applied between the electrodes 2 and 15 by the power supply 26 after +15 V/cm electric field is applied by the power supply 25, a characteristic curve 102 indicates the result of the DNA probe chip capturing the target polynucleotide when no electric field is applied as a control, and a characteristic curve 103 indicates the result of the DNA probe chip capturing the target polynucleotide when +15 V/cm is applied by the power supply 25 but −15 V/cm is not applied by the power supply 26, respectively. The time of applying the first +15 V/cm in the cases of 101 and 103 herein are the same.

As clarified by the characteristic curve 101, firstly the +15 V/cm electric field is applied between the electrodes 2 and 15 by the power supply 25 to electrostatically attract the target polynucleotide 14 and probes 12-1, 12-2 and 12-3 having negative charge to the surface of the DNA probe chip. Next, −15 V/cm electric field is applied between the electrodes 2 and 15 by the power supply 26 to detach the target polynucleotide 14 and probes 12-1, 12-2 and 12-3 having negative charge from the surface of the DNA probe chip. By this procedure, the concentration of the target polynucleotide 14 in the sample solution 50 is higher on the side of the surface of the DNA probe chip, which results in indicating that the target polynucleotide has been efficiently captured. As also seen from the drawing, since the capturable target polynucleotide becomes saturated as the hybridization advances to a certain degree, it is unworthy to continue the hybridization reaction for a long time.

While this embodiment uses gold nanoparticles as a marker, a sequence code 11 labeled by Cy3 fluorescent material may be used as a sample to result in the similar tendency. Namely, in the case the fluorescent marker is used, the longitudinal axis in FIG. 109 may be replaced by the relative fluorescence intensity.

By only applying +15 V/cm electric field between the electrodes 2 and 15 by the power supply 25 to electrostatically attract the target polynucleotide 14 and probes 12-1, 12-2 and 12-3 having negative charge to the surface of the DNA probe chip, even if the electric field is removed, the attracted probes do not line up in order as shown in FIG. 108C, therefore it is difficult to advance the hybridization reaction.

When no voltage is applied, since there does not occur the concentration gradient of the target polynucleotide 14 in the sample solution 50, the capture rate of the target polynucleotide 14 is naturally low.

In order to charge the surface of the DNA probe chip positive, it is achievable not only by disposing the electrodes on the surface of the DNA probe chip and in a portion of the sample solution away from the surface of the DNA probe chip and applying voltage to charge the surface of the DNA probe chip positive as described above, but also by preparation by introducing the positively dissociated residue (positive charge) to the surface of the DNA probe chip. A reference numeral 6 in FIG. 108B (an indication of + and a surrounding circle) indicates the positively dissociated residue (positive charge). In the case where the surface of the DNA probe is charged positively by introducing the positively dissociated residue (positive charge) to the surface of the DNA probe chip, the electric field applied from the outside may be only an electric field for inversion as shown in FIG. 108C.

EXAMPLE 3

In Example 3, hybridization of a probe with a target polynucleotide is illustrated. In this example hybridization is performed taking into consideration an effect of a nuclear for hybridization and a direction of the hybridization.

Figure 110A:
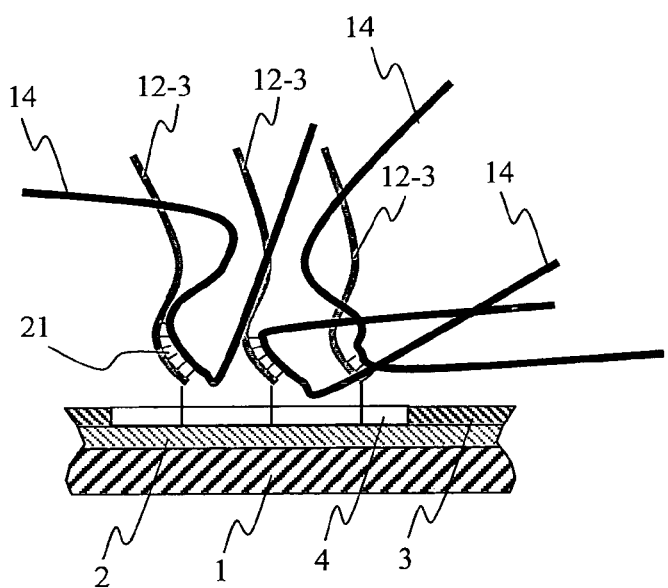
FIG. 110A is a view schematically showing the situation in which a probe 12-3 and a target polynucleotide 14 hybridize with each other using a root portion of the probe 12-3 (a portion close to a surface of the DNA probe chip) as a nuclear for hybridization.
Figure 110B:
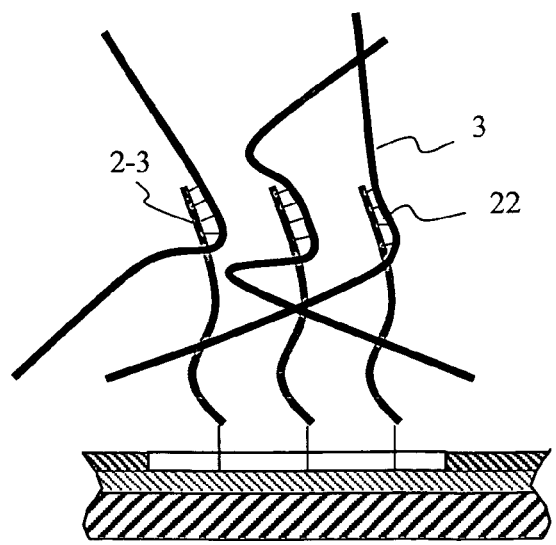
FIG. 110B is a view schematically showing the situation in which the probe 12-3 and the target polynucleotide 14 hybridize with each other using a tip portion of the probe 12-3 (a portion close to a free edge of the DNA probe chip) as a nuclear for hybridization.

FIG. 110A is a view schematically showing the situation in which a probe 12-3 and a target polynucleotide 14 hybridize with each other using a root portion of the probe 12-3 (a portion close to a surface of the DNA probe chip) as a nuclear for hybridization, and FIG. 110B is a view schematically showing the situation in which the probe 12-3 and the target polynucleotide 14 hybridize with each other using a tip portion of the probe 12-3 (a portion close to a free terminal of the DNA probe chip) as a nuclear for hybridization.

In FIGS. 110A and 110B, reference numerals 21 and 22 indicates a portion which functions as a nuclear for hybridization. With reference to FIG. 110A, when a side where the probe is fixed, namely a root portion (a surface of the tip) of the probe is used as a nuclear for hybridization, the target polynucleotide twists around the probe (forming a double strand) at a direction of spacing away from the surface of the tip. In this case, there is little steric interruption since hybridization is developed to the direction of spacing away from the surface of the tip. Further, it could be well understood that there is little interruption also from a situation that the target polynucleotide is not twisted around a tip portion of nearest-neighbor prove. On the other hand, with reference to FIG. 110B, when the tip portion (a free terminal) is used as a nuclear for hybridization, macromolecule of the target polynucleotide collides with a nearest-neighbor probe or the surface of the tip under a process of twisting around the probe DNA (forming a double strand) and it could be well understood that twisting speed becomes slow due to this steric interruption.

For making a root portion (a surface of the tip) of the probe function as a nuclear for hybridization, it is useful to draw the target polynucleotide 14 in the sample liquid 50 to the surface of the DNA probe tip, and also to make larger the concentration gradient of the target polynucleotide 14 in the sample liquid 50 near the surface of the DNA probe tip as described. In this example, descriptions are provided for an example in which the root portion (a surface of the tip) of the probe is used as a nuclear for hybridization by devising a sequence of the probe.

As a probe, a sequence of 50-base length from human mRNA sequence is extracted for use. The 20-base segment near a substrate and another sequence segment having more than 15% GC content different from the remaining portion are used preferentially. Namely GC content near the 20-base segment is made higher. If this kind of modification is impossible in the sequence, the probe sequence is designed with a sequence mismatching the cDNA sequence forming a template from a position around the 10th base up to a position around the 30th base each from the free terminal or a blank sequence not forming a stable complementary strand with any ACGT is used for designing the probe sequence. But the mismatch sequence and the blank sequence can be inserted at maximum two places in this range because excessive insertion lowers the stability. It is important to control the stability of hybridization in the manner as described above for forming a nuclear for hybridization near a fixed terminal of the probe.

As a specific example, a complementary sequence (SEQ No. 10) for the segment sequence of bases 918 to 967 of mRNA of PON1 (*Homo sapiens* paraoxonase 1) is used as a probe sequence:

As a specific example, a complementary sequence (SEQ No. 10) for the segment sequence of bases 918 to 967 of mRNA of PON1 (*Homo sapiens* paraoxonase 1) is used as a probe sequence:

```
                                          (SEQ ID NO: 9)
5'-AAAAUCUUCU UCUAUGACUC AGAGAAUCCU CCUGCAUCAG

AGGUGCUUCG-3':

(SEQ ID NO: 10)
5'-CGAAGCACCT CTGATGCAGG AGGATTCTCT GAGTCATAGA

AGAAGATTTT-3':
```

In this example, in order to compare a case in which a nuclear for hybridization is formed near a surface of the substrate to a case in which a nuclear for hybridization is formed far from a surface of the substrate, a probe having the base sequence of SEQ No. 10 is fixed at the 5' terminal thereof to the probe fixed domain 4 of one DNA probe chip using any of the methods described above. At the same time, a probe having a base sequence of the same SEQ No. 10 is fixed at the 3' terminal to the probe fixed area 4 of other DNA probe chip. When a sequence of the probe 2 is divided to units each including 10 bases and GC % in each unit including 10 bases is calculated, it is observed that the CG % is 60%, 60%, 40%, 40% and 20% from the side of 5' terminal. Namely, when this probe is fixed at the 5' terminal thereof and is used for hybridization, 20 mer in the side of the 5' terminal is hybridized first, and the hybridization area extends from the portion above as a nuclear for hybridization to the 3' terminal of the probe. On the other hand, this probe is fixed at the 3' terminal and is used for hybridization, 20 mer in the 5' terminal, namely in the free terminal of the probe hybridizes first, and hybridization area extends to the side of the 3' terminal (a surface of the tip) of the probe using this area as a nuclear.

A method for preparing a sample for hybridization will be described below. A synthetic single-stranded DNA is used as a sample. The model employed in this example has the full length of 90 bases and has a complementary sequence for SEQ No. 2 at the core portion and the core portion is conjugated at both terminals thereof to poly A (indicating as $A_{20}$) including 20 bases.

```
                                          (SEQ ID NO: 11)
5'-A20-AAAATCTTCT TCTATGACTC AGAGAATCCT CCTGCATCAG

AGGTGCTTCG-A20-3':
```

Gold nanoparticle having a diameter of 10 nm is conjugated to either the 5' terminal or 3' terminal. The gold nanoparticle can be labeled by introducing alkane SH into either the 5' terminal or 3' terminal when a sample is synthesized.

Figure 111:
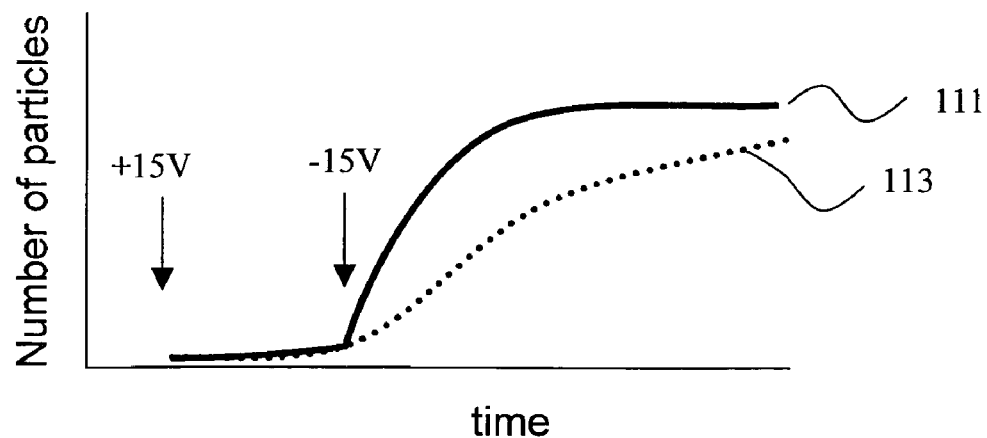
FIG. 111 is a diagram showing a comparison of hybridizations under the state of being formed a concentration gradient of the target polynucleotide on a surface of a substrate.

FIG. 111 is a view showing a comparison between a result obtained when a sample with SEQ No. 11 is processed with the DNA probe chip with the probe with SEQ No. 10 fixed at the 5' terminal thereof (as indicated by a characteristic curve 111) and a result obtained when the sample with SEQ No. 10 is fixed at the 3' terminal thereof (as indicated by a characteristic curve 113). The conditions employed in this comparison are the same as those in FIG. 109 showing a result of Example 2 excluding the conditions for applying an electric field.

Namely, when the probe with SEQ No. 10 is fixed at the 5' terminal thereof, 20 mer at side of 5' terminal (a surface of DNA probe chip) is hybridized first, and then the hybridization area extends a side of probe 3' terminal using this area as a nuclear, thus hybridization being developed rapidly as described in FIG. 110A. On the other hand, when this probe is fixed at the 3' terminal thereof and is used for hybridization, the 5' terminal, namely the free terminal of the probe of 20 mer is hybridized first, and then using this point as a nuclear, the hybridization area extends to the side of the 3' terminal of the probe (a surface of the tip), thus hybridization being developed slowly as described in FIG. 110B.

FIG. 111 specifically illustrates the above statement.

In this example, gold nanoparticle is used for a labelling, but when the SEQ No. 11 labeled with Cy3 fluorescent material is used as a sample, a result indicating the same tendency can be obtained.

EXAMPLE 4

For forming a nuclear for hybridization in the neighborhood of the substrate more easily, as described in the Example 2, it is one of the important items to make a probe act quickly. Example 4 relates to the probe which is designed based on this viewpoint.

Figure 112:
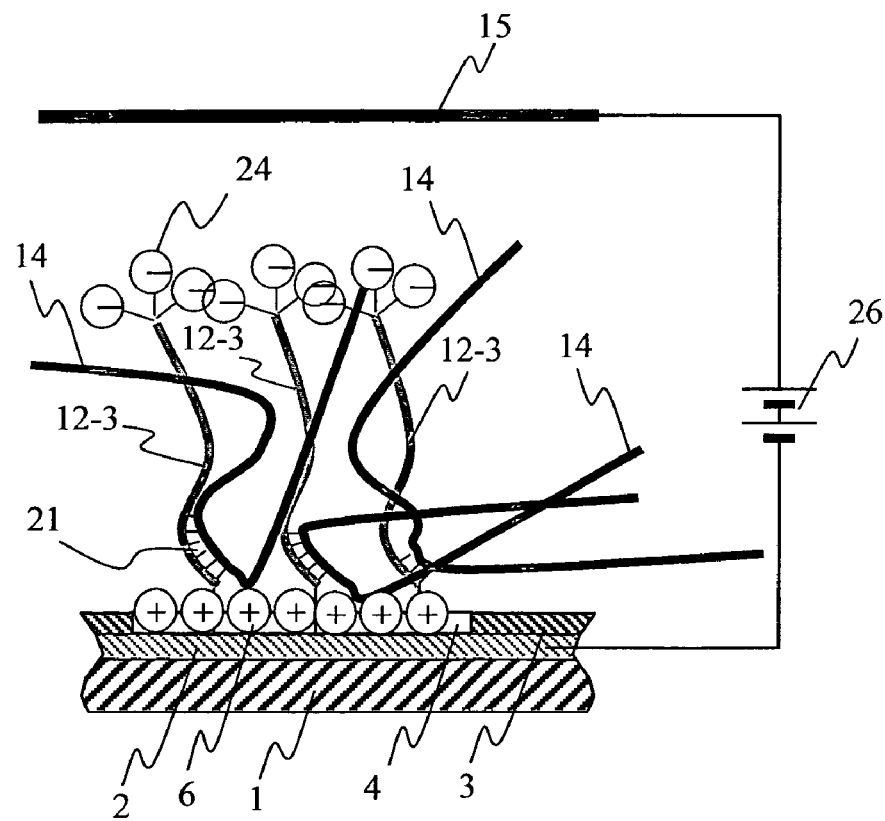
FIG. 112 is a view showing a case where the probe in Example 4 is used in the case shown in FIG. 110A showing the situation in which a probe 12-3 and a target polynucleotide 14 hybridize with each other using a root portion of the probe 12-3 (a portion close to a surface of the DNA probe chip) as a nuclear for hybridization.

FIG. 112 is a view schematically showing a case of where the probe in Example 4 is used in the case shown in FIG. 110A showing the situation in which a probe 12-3 and a target polynucleotide 14 hybridize with each other using a root portion of the probe 12-3 (a portion close to a surface of the DNA probe chip) as a nuclear for hybridization.

In Example 4, an excessive amount of dissociation group 24 is introduced into the terminal in the opposite side (free terminal) against to the fixed terminal where the probe 12-3 is fixed on the surface of the DNA probe chip. As the dissociation group 24, a negatively charged group such as sulfuric acid group or phosphoric acid group may be used. A larger effect can be obtained by using molecules or particles containing a large amount of minus residue of the dissociation group 24. Because the free terminal of the probe 12-3 has a minus charge, as described in FIG. 108B, after attracting the target polynucleotide 14 and the probe 12-3 to the surface portion of the DNA probe chip electrostatically by the surface portion of the DNA probe chip positively charged, an electric field is reversed by the power source 26, and then a stronger repelling force acts with the negative charge 24 at the probe tip, so that the probe 12-3 acts quickly.

Also when the positively charged residue 6 is constantly introduced to the surface portion of the DNA probe, the same effect is obtained. So long as any specific operation is not performed to the surface portion of the chip, as the surface portion is always kept with a positive charge because of the introduced positive static charge, the probe and the target polynucleotide 14 are absorbed on the surface portion as described in FIG. 108B. In this situation, by adding minus charge that is more than that enough for canceling the positive charge on the surface of the electrode 2 as well as the opposite electrode 15 on the chip surface, the probe with an excessive amount of minus charge introduced to the fee terminal side quickly acts. The target oligonucleotide 14 has the larger size than the probe 12-3 and moves more slowly, so that a nuclear for hybridization is formed at a position closer to the probe substrate, and hybridization develops towards the probe tip.

For making the system described above act effectively, it is preferable that the probe should preferably have the 30 to 50-base length.

EXAMPLE 5

In order to make the twenty-first embodiment of the present invention more effective, it is preferable to eliminate a charge of probe itself and introduce a large amount of minus charge to the free terminal of the probe. For instance, PNA (Peptide Nucleic Acid) in which a phosphodiester bond of synthetic oligonucleotide is changed to a peptide bond, or CAS (Cysteine Antisense Compound) which includes S-carboxydimethyl-L-cysteine as a base frame may be used as a non-charged probe.

Since main chains of the polymer PNA and CAS have no charge, an electrostatic repelling force does not work with the target polynucleotide. As they have amino group and carboxyl group on the terminals thereof respectively, when an amino group is used at the fixed terminal, the fee terminal is naturally changed to a negatively charged carboxyl group. Further it is possible to make the probe act quickly in response to the electrode on the surface of the substrate by introducing a large amount of minus charge with residues having minus charge like in Example 4. As the PNA and CAS do not have an electric charge in the main chain, a repelling force does not work with the target polynucleotide. When a space for hybridization is provided by making the probe act, the probe is quickly hybridized with the target polynucleotide 14.

When the PNA and CAS are fixed as a probe, the following process is employed. An activate silanol group is formed by hydrolysis of a methoxy group by keeping 0.5% solution of 3-glycidoxypropyltrimethoxysilane for 30 minutes at the room temperature (25° C.) (0.5% of acetic acid is included as a catalyst. When the silane coupling agent cannot be dissolved, acetic acid is added until the silane coupling agent is dissolved). This activate silanol solution is coated on the substrate surface and keep at the room temperature for 45 minutes. A substrate having an ITO-electrode with glycidoxypropyl group introduced therein with covalent bond is obtained by blowing off remained solution on the substrate after washing it with pure water and then heating the substrate at 105° C. for 30 minutes in the air. A part of the atomic group constituting the introduced glycidoxypropyl group is epoxy group with high reactivity with an amino group. A mixed solution containing 10 pmol/µl of PNA or CAS having the amino group and 25 to 100 µM of Lys, pH 10 is coated on the substrate. Lys is mixed in the solution for the purpose to fix the PNA or the CAS on the substrate uniformly and also to prevent the fixing density of the PNA or the CAS from being too high (when only the PNA or the CAS is mixed in the solution without Lys, the substance attacks a surface of ITO, and places with high mixing density and low mixing density are generated as islands). The solution is reacted for one hour at 50° C. With the reaction described above, a probe chip with the PNA or the CAS fixed thereon can be obtained.

A substrate surface obtained from the above probe fixation is electrically neutral. Next, a method for preparing a positively charged is described below. 25 to 100 µM arginine oligomer (L-Arg)$_6$ (SEQ ID NO: 17) is mixed in and reacted to the DNA probe used in the method described above. When the probe is the PNA or the CAS, arginine oligomer is added in place of Lys. Thereby, a probe chip having a positively charged substrate surface can be obtained.

Even when controlling the electrode by applying an electric field thereto like in Example 2, an effect of the electric field is not remarkable since a probe to be fixed has no electric charge. However, when a sulfonic acid group is introduced to the free terminal of probe, the same effect is obtained as that obtained by introduction of an excessive mount of dissociation group 24 described in Example 4, and an extremely high speed hybridization can be carried out. When a sample liquid is added, the target polynucleotide having minus charge in the sample liquid is condensed on the ITO-electrode surface with the probe fixed thereon because of the plus charge on the substrate surface. When the electric field is reversed, minus charge of the sulfonic acid group introduced into the fee terminal of the probe repels the electric field, so that the probe acts quickly. Also in this example, like in Example 3, when the probe is fixed to be GC rich near the substrate, hybridization progresses faster with the yield higher.

[XXII] Twenty-Second Embodiment

A twenty-second embodiment of the present invention provides a device of and a method of preparing a DNA probe chip having the features of improved hybridization rate performed on a surface of a solid-state chip, as described in a twenty-first embodiment above, being measured in a shorter time, having higher sensitivity, and having less possibility of performing pseudo-positive hybridization, and a method of performing hybridization in the DNA probe chip thereof. In the twenty-first embodiment, the improvement can be achieved mainly by adding dissociation groups each having negative charge to one end of the DNA probe which is the opposite to the other end fixed to the probe fixed area of the DNA probe. In this twenty-second embodiment, an improvement can be achieved by dividing a whole DNA probe area into three areas and modifying the base sequence of the area closest to a fixed end of the DNA probe thereof so that the base sequence thereof becomes complementary to the base sequence of the target polynucleotide thereof. Apart from this feature, the twenty-second embodiment is the same as the twenty-first embodiment.

Figure 113:
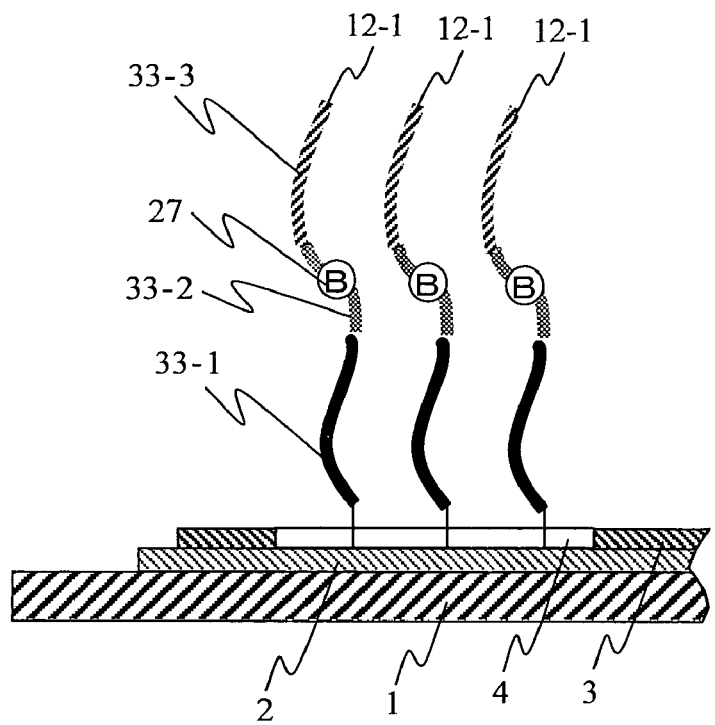
FIG. 113 is a view schematically showing the state in which an edge of a probe 12-1 is configured based on the concept according to a twenty-second embodiment of the present invention.

FIG. 113 is a view schematically illustrating a status that one end of probe 12-1 is fixed to a probe fixed area 4 according to the twenty-second embodiment. The DNA probe 12-1 is divided into areas in order from the probe fixed area 4. The sequence of the probe is divided into at least three areas, and the hybridization stability of each area is independently controlled. More specifically, modifications are made so that the hybridization stability of the area closest to the probe fixed 4 should be higher than that of any other areas. The length of a first area 33-1 which is closest to the probe fixed area 4 is approximately 15 to 20 bases long, and the sequence of the area is substantially complementary to the base sequence of the target polynucleotide thereof. The length of a second area 33-2 is 15 to 20 bases long, and at least one third of this area included therein are base sequence, indicated by the reference numeral 27, that would not form any complementary hydrogen bonding with any of A, C, G, and T base sequence or should be non-complementary to the target polynucleotide thereof. The base sequence of a third area 33-3 is substantially complementary to the target polynucleotide thereof. But it is important that the hybridization stability of the third area should be lowered than that of the first area, for instance, by making the length of the third area shorter than that of the first area.

In the probe 12-1 that has been modified as described above, the hybridization stability of the first area is higher than that of the second and third areas. The base sequence in the third area 33-3 is substantially complementary to the target polynucleotide thereof, so hybridization is to be performed there. But, as mentioned above, the hybridization stability of the first area is higher than that of the third area, eventually, the hybridization is to be started in the first area first.

Because of this feature, in general, the hybridization with the target polynucleotide thereof can be started in the probe fixed area 4 of the probe first. But when the probe specificity and probe stability are taken into consideration, it is noted that the appropriate length of such probes should be in the range between 40 to 60 bases long. When the length of the first area is too long, it might become difficult to perform hybridization in or around the probe fixed area 4 first. And there is another problem when the length of the second area is too long. It is still acceptable if the sequence of the second area is more AT-rich than that of the first area. But otherwise, it is then necessary to introduce some bases that would not perform hybridization with the target polynucleotide thereof or the other mismatch bases into the second area. This modification might affect the hybridization specificity thereof. It might be important to limit the number of bases to be modified to 1 to 3 bases out of every 9 bases. Because of this feature, the base length of the second area should be approximately 20 bases long at the maximum. The third area 33-3 has the role to increase the hybridization stability of the first area higher than that of any other areas while the whole base length of the probe is to be adjusted as previously determined. Namely, it is most preferable that the hybridization stability level of each area should be arranged as follows: the first area>the third area>the second area. The length of the base sequence of the probe as a whole should be in the range between 30 to 50 bases long.

In one example, the sequence of 940 through 989 base portion (SEQ. ID. NO. 12) of the mRNA of PON1 (*Homo sapiens* paraoxonase 1) is used as the probe sequence. Obviously, the probe should be prepared chemically.

(SEQ ID NO: 12)
5'-AGAATCCTCC TGCATCAGAG GTGCTTCGAA TCCAGAACAT

TCTAACAGAA-3':.

The 5' end of the probe having the SEQ. ID. NO. 12 is fixed to the probe fixed area 4. The sequence of the probe is divided into sections every 10 bases, and the GC-percent of each section is calculated. The results of the GC-percent of those sections from the 5' end are 50%, 50%, 50%, 40%, and 30% respectively. Therein, the first 20 bases at the 5' end, the next 21 to 30 bases, and 31 to 50 bases are defined herein as the first area 33-1, the second area 33-2, and the third area 33-3 respectively. The GC-amount in the second area is so large that the possibility that the hybridization performed in the first area first may be decreased and the possibility that the hybridization performed in the second are first may be then increased. To correct it, the bases thereof are changed to lower the hybridization stability in the range between $20^{th}$ and $30^{th}$ bases thereof. In addition, the bases in the second area are apt to have a palindrome structure, so the bases are changed so as not to constitute such palindrome structure. The probe sequence after being changed as described above is given below as SEQ. ID. NO. 13.

(SEQ ID NO: 13)
5'-AGAATCCTCC TGCATCAGAG GTGBTTBGAA TCCAGAACAT

TCTAACAGAA-3':

Therein, the base "B" should be either a pseudo-base that would not form a stable complimentary chain with any bases or a base non-complementary to the target polynucleotide thereof. For instance, either a spacer consisting of only sugar chains without having any base section therein or a pseudo-base with atoms having large atomic radius in the base section introduced therein such as 2-thiouracil is to be used. The 2-thiouracil would not be able to form a stable hydrogen bonding with Cytosine which lies in the opposite base in the sequence of the target polynucleotide thereof. The atomic radius of sulfur atoms introduced in the bases thereof is so large that it may be impossible to form hydrogen bonding with Guanine. When base "A" is introduced as the base "B", it may cause mis-hybridization with base "C", so base "A" can not be used. In this case, however, it is practical to change the base into "T" or 2-Thiouracil as the base "B". To prepare mismatch bases, change the bases in the probe so that the A-G, A-A, C-C, or T-T mismatching should be prepared.

The sequence of the probe having modified sequence of SEQ. ID. NO. 13 is divided into sections every 10 bases in order, and the GC-percent of each section is calculated. The results of the GC-percent of those sections from the 5' end are 50%, 50%, 30%, 40%, and 30% respectively. When the hybridization is to be performed with the modified probe, the hybridization starts in the 20 bases at 5' end, and then the hybridization expands its range to the 3' end of the probe thereof.

A method of preparing a sample for the hybridization is provided below. A synthetic single-stranded DNA is used as the sample. As a model, the sequence complementary to SEQ. ID. NO. 12 is used as the core section thereof, and Poly A (referred to as $A_{20}$ hereinafter) consisting of 20 bases are bonded before and after the sequence thereof to prepare 90 bases long sequence as a whole.

(SEQ ID NO: 11)
5'-$A_{20}$-TTCTGTTAGA ATGTTCTGGA TTCGAAGCAC CTCTGATGCA

GGAGGATTCT-$A_{20}$-3'

Therein, the 5' end of the probe is coupled with the Sulforhodamine 101, the fluorescent dye, which used to assay the hybridization.

Therein, two cases are prepared: one case is that the hybridization start on or around the surface of the probe fixed area 4, and the other case is that the hybridization start far from the surface of the probe fixed area 4. To compare the effects of hybridization between two DNA probe chips, two different DNA probe chips are prepared. Namely, the 5' end of the probe with the base sequence of SEQ. ID. NO. 13 included therein is fixed at the probe fixed area 4 of one DNA probe chip is prepared by one of the above-mentioned methods. Simultaneously, the 5' end of the probe with the base sequence of SEQ. ID. No. 12 included therein is fixed at the probe fixed area 4 of the other DNA probe chip is also prepared.

With above two different DNA probe chip, the following experiment is conducted. 0.1 mm gap is created with a spacer and a cover glass is put on the chip, and 40 micro litter of DNA for fluorescent labeling according to the SEQ. ID. NO. 11 is added thereto. The sample is stirred by pumping the slide glass with the sample included therein with a constant rate. Then the electric field is applied so that the electric field at electrode 4-1 between the electrode 2 and the opposite electrode 3 becomes +15V/cm (effectively 0.15 V between those electrodes). The mRNA in the sample solution is swiftly pulled to the ITO electrode section on a substrate. After 30 seconds, −15V/cm of electric field is applied to the electrode 4-1, and the mixing continues for the period between 0 and 30 min. It is cleaned and the fluorescence (excited 545 nm, fluorescent 520 nm or more) intensity from the element surface is measured.

Figure 114:
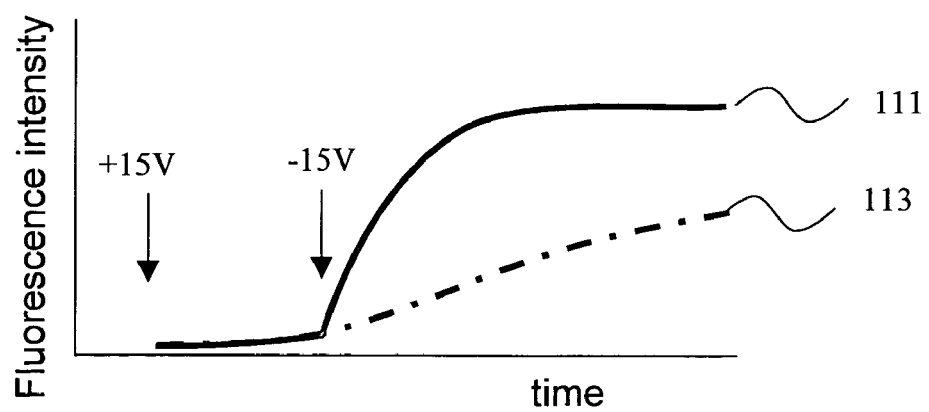
FIG. 114 is a diagram showing a comparison between a result obtained when a sample with SEQ No. 11 is processed with a DNA probe chip with a probe with SEQ. No. 13 fixed to the 5' terminal thereof (as indicated by a characteristic curve 111) and a result obtained when the sample with SEQ No. 11 is processed with a DNA probe chip with SEQ. No. 13 fixed to the 3' terminal thereof (as indicated by a characteristic curve 113)

FIG. 114 is a view illustrating the comparison of results between two cases; one case is that the sample with the sequence of SEQ. ID. NO. 11 included therein is processed with the DNA probe chip with the probe having the sequence of SEQ. ID. NO. 13 fixed at the 5' thereof (shown in the characteristic curve 111), and the other case is that the same sample is processed with the DNA probe chip with the probe having the sequence of SEQ. ID. NO. 12 fixed at the 5' thereof (shown in the characteristic curve 113). Therein, other conditions such as applied electron field are the same as those in FIG. 109 showing the results of Example 2. Obviously, the fluorescent intensity 111 from the element with the probe with the sequence of SEQ. ID. NO.13 fixed thereto can increase faster than the fluorescent intensity 113 from the element with the probe with the sequence of SEQ. ID. NO. 12 fixed thereto. This result also shows that, when stable hybridization could be performed at the 5' end with the probe fixed thereto more easily than any other areas, the rate of the hybridization thereof would become faster. In other words, when the bases on and around the 5' end fixed to the probe fixed area 4 is more GC-rich than bases on and around 3' end, the hybridization can start in the bases around the substrate and proceeds to the free end without being largely affected by the steric hindrance or the solid surface. And this is important when the DNA probe chips are designed.

[XXIII] Twenty-Third Embodiment

A twenty-third embodiment of the present invention discloses, like in twenty-first embodiment and twenty-second embodiment, a DNA chip enabling a higher speed hybridization on a solid chip surface and measurement within a short period of time and also rarely inducing quasi-positive hybridization, a method of preparing the DNA chip, and a method of inducing hybridization on the DNA probe chip. In the twenty-first embodiment, improvement is provided mainly by adding an dissociation group having a negative charge to a terminal different from that fixed to a probe fixing area on the DNA probe, and in the twenty-second embodiment, improvement is provided by using a DNA probe consisting of three areas and providing a sequence substantially complementary to the target polynucleotide at the area closest to the fixed edge of the DNA probe. In contrast, in the twenty-third embodiment, the improvement is provided mainly by making larger a probe fixing area of the DNA probe. Other features are the same as those in the twenty-first and twenty-second embodiments.

The twenty-third embodiment is described in detailed with reference to the related drawings.

EXAMPLE 1

Figure 115A:
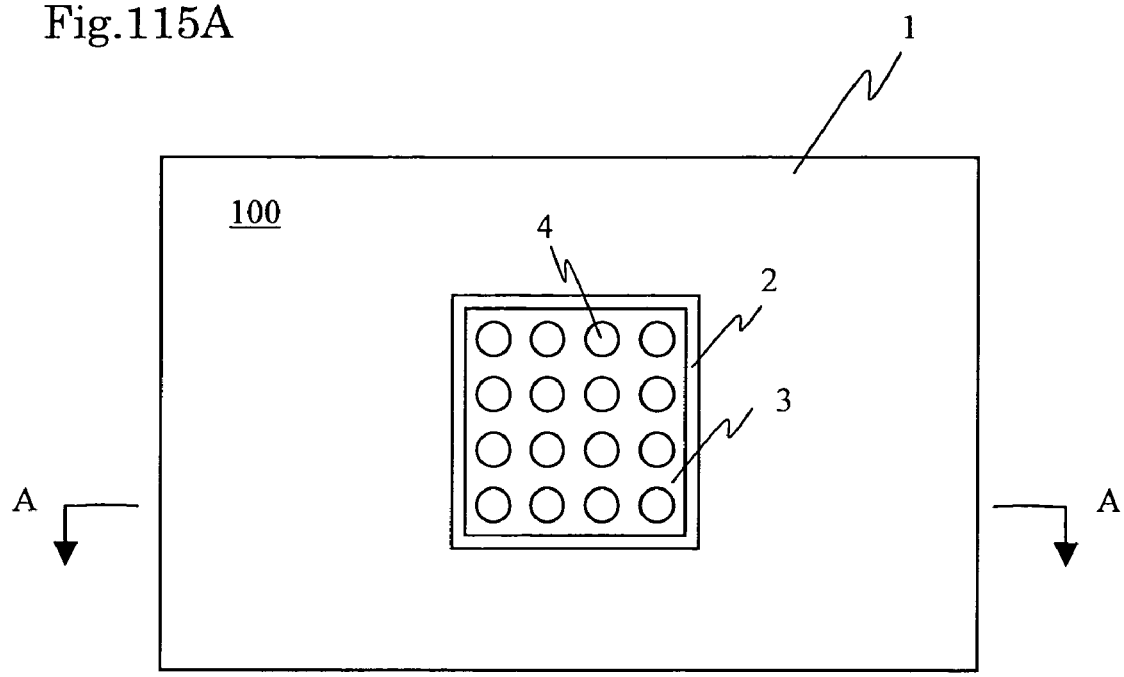
FIG. 115A is a plan view showing the DNA probe chip 100 advantageously applicable in a twenty third embodiment of the present invention.
Figure 115B:
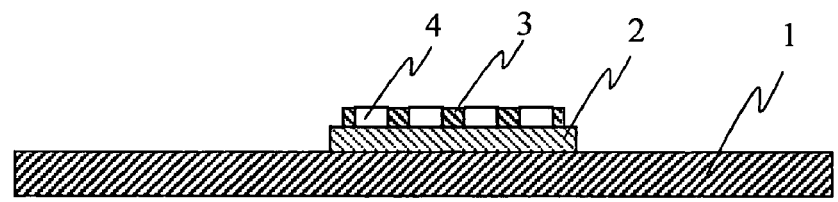
Figure 115C:
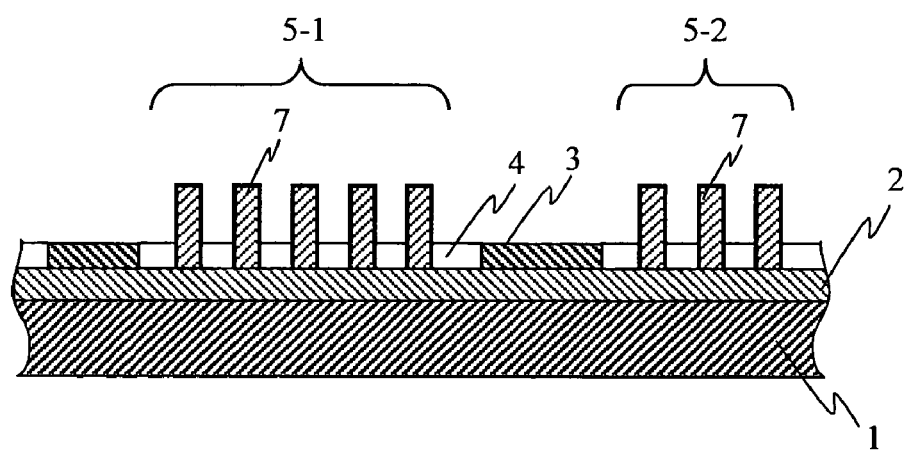

FIG. 115A is a plan view showing outline of a DNA probe chip advantageously available for carrying out the twenty-third embodiment; FIG. 115B is a cross-sectional view showing the outline shown in FIG. 115A taken along the line A-A and viewed in the direction indicated by the arrow; and FIG. 115C is a cross-sectional view showing details of a probe fixing area of the DNA probe chip advantageously available for carrying out the twenty-third embodiment.

Reference numeral 1 indicates a fused quartz-glass sheet (20×40 mm) as a DNA probe chip. Reference numeral 2 indicates and electrode, which is deposited on a surface of the substrate 1. The electrode is ITO (Indium-Tin Oxide) having the size of 10×10 mm and the thickness of 300 nm. Reference numeral 3 is a fluorine surface coating with the thickness of 10 nm formed on a surface of the ITO electrode 2. The fluorine surface coating 3 is provided to prevent cross contamination between the adjoining probe fixing areas 4. A prespecified probe solution is applied on each of the probe fixing areas 4 with a pin array device with the order of several hundreds pl, and therefore the water-repulsive characteristic is required for the fluorine surface coating 3 to prevent the probe solution from overflooding from the area. The probe fixing area 4 can be prepared by ashing a surface of the fluorine surface coating 3 applied by printing using a mask with oxygen plasma to remove the fluorine surface coating. For preparing the probe fixing area 4 by means of oxygen plasma ashing, the ITO electrode 2 exposed in this area is required to be hydrophilic.

FIG. 115A shows a large disk consisting of 4×4 probe fixing areas 4, but the actual probe fixing area 4 has a diameter of around 30 μmφ, so that, for instance, 100×100 probe fixing areas 4 may be provided. A space between the adjoining probe fixing areas 4 is about 60 μm, and further the adjoining probe fixing areas 4 are separated from each other by the fluorine surface coating.

Reference numeral 7 indicates a pillar. To raise the reaction speed or reaction yield, it is preferable to use as many probes as possible in the probe fixing area 4, but when the probe density is raised, the hybridization efficiency drops due to the electrostatic repulsive force. In Example 1, probes are fixed with the average space inbetween of 10 to 30 nm. A density higher than this level is not preferable in use of the ordinary polynucleotide probe, and when a probe length is as long as 50-bases polynucleotide, the density is preferably in the range from 10 to 60 nm. In the twenty-third embodiment, the probe density is not made higher, but the pillar 7 is provided on a surface of the electrode 2 forming the probe fixing area 4 to enlarge the substantial area of the probe fixing area 4, and with this configuration, it is possible to increase a number of probes fixed thereon.

The pillar 7 is formed on a surface of the ITO electrode in the probe fixing area 4 by applying the epoxy-based rein SU8 with a spinner on a surface of the substrate 1 having the fluorine surface coating 3 thereon and irradiating light thereon with a mask. Height of the pillar 7 is 50 μm and a diameter of the base section is 10 μm. A space between the pillars 7 is 15 μm. As compared to the case in which probes are fixed without providing the pillars, the probe fixing area can be increased about 7 times. Reference numerals 5-1, 5-2 are elements each indicating a group of pillars 7 formed on the probe fixing area 4.

It is conceivable to employ the sand blast method to increase a surface of the probe fixing area 4 in stead of providing the pillars 7, but in this case the aspect ratio can not be made larger, and the can be increased at most two times.

Two methods of fixing probes on a surface of the ITO electrode 2 in the probe fixing area 4 are described below. In the first method, oxygen plasma is irradiated, and then polylysine is coated with UV rays irradiated thereto to introduce an amino group into a surface of the pillar 7. For fixing the DNA probe, a bivalent reagent is used. For instance, when N-(8-maleimidocaproyloxy)sulfosuccinimide is reacted, the sulfosuccinimide at pH 8 ester portion reacts to an amino group in lysine, so that a maleimido group is introduced into a surface of the pillar 7. When a synthetic DNA probe with an SH group introduced to the 5' terminal is added at pH 6.5, the SH group present in the DNA probe reacts the maleimido group, and therefore the DNA probe is fixed on a surface of the pillar 7. Alternatively, after polylysine is coated, the surface is modified with succinic acid anhydride to introduce a carboxylic group into the amino group. N-hydroxysuccinimide is ester-bonded thereto to convert the carboxylic group to an active ester. A synthetic DNA probe having an amino group at the 5' terminal may be added to fix the probes on a surface of the pillars by means of peptide bond. In the second method, the pillars formed with SU8 are processed with oxygen plasma, and then a functional group is introduced by making use of the silane coupling reaction. When SU8 is subjected to processing with oxygen plasma, an OH group or radial oxygen is generated on the surface. These are unstable residues and decrease with elapse of time, so that the chip is immediately immersed in 0.5% N-(β-aminoethyl)-γ-aminopropyltrimethoxysilane (previously kept at the room temperature for 30 minutes to provide an activated silane coupling solution) and left in the state for one hour. After rinsed with deionized water, the reaction product is dried at a temperature in the range from 105 to 110° C. With this operation, an amino group is introduced also to the pillar section coated with SU8. The amino group is modified with succinic acid anhydride to introduce a carboxyl group into the amino group. N-hydroxysuccinimide is conjugated thereto by ester bond to convert the carboxyl group to an active ester. A synthetic DNA probe having an amino group at the 5' terminal is added to fix the probes to a surface of the pillar by peptide bond.

EXAMPLE 2

Figure 116A:
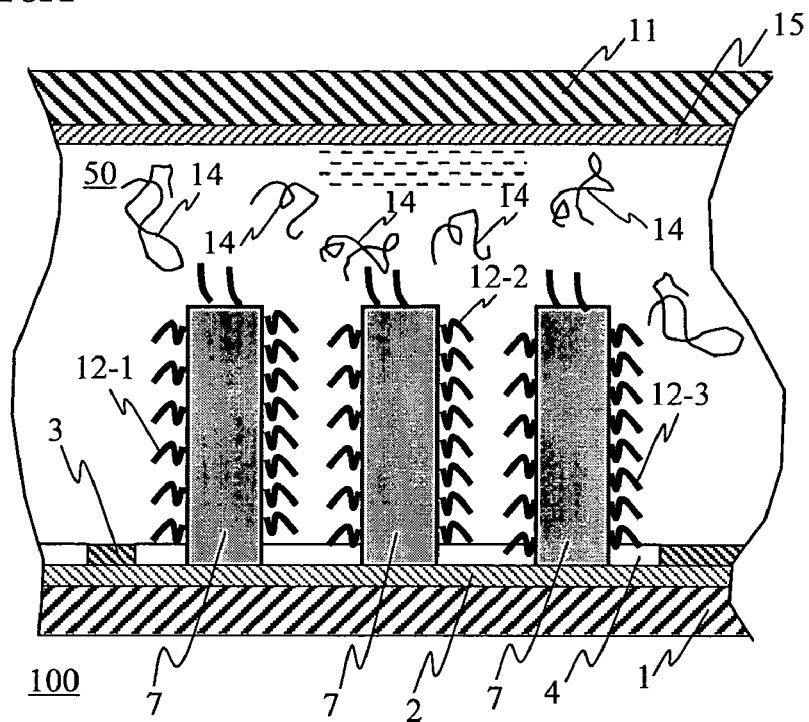
Figure 116B:
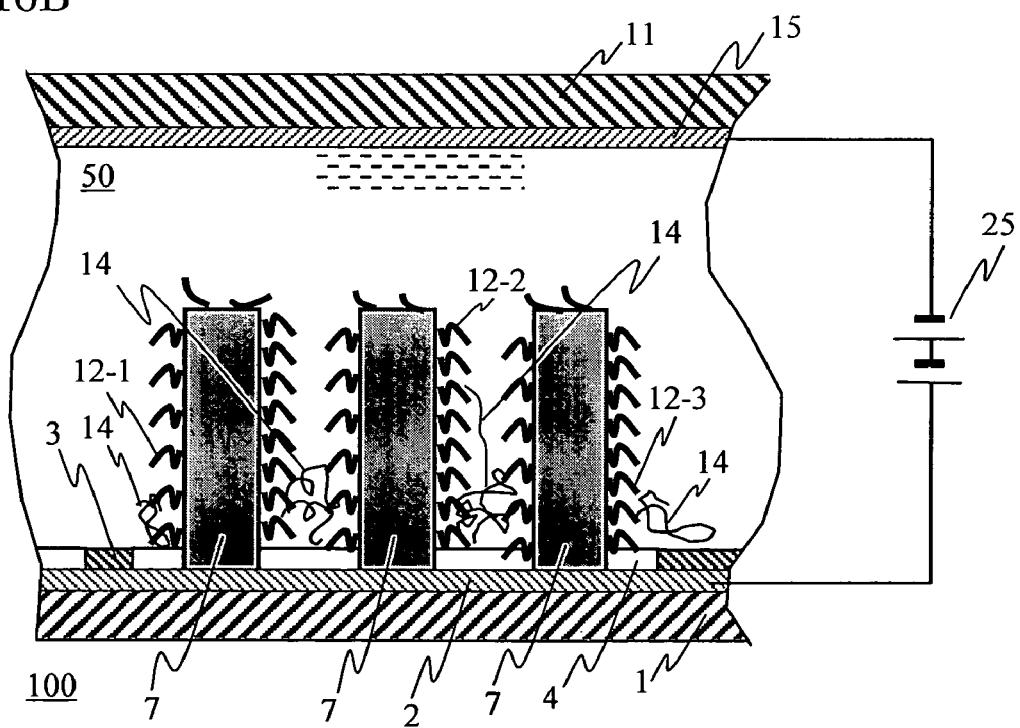
Figure 116C:
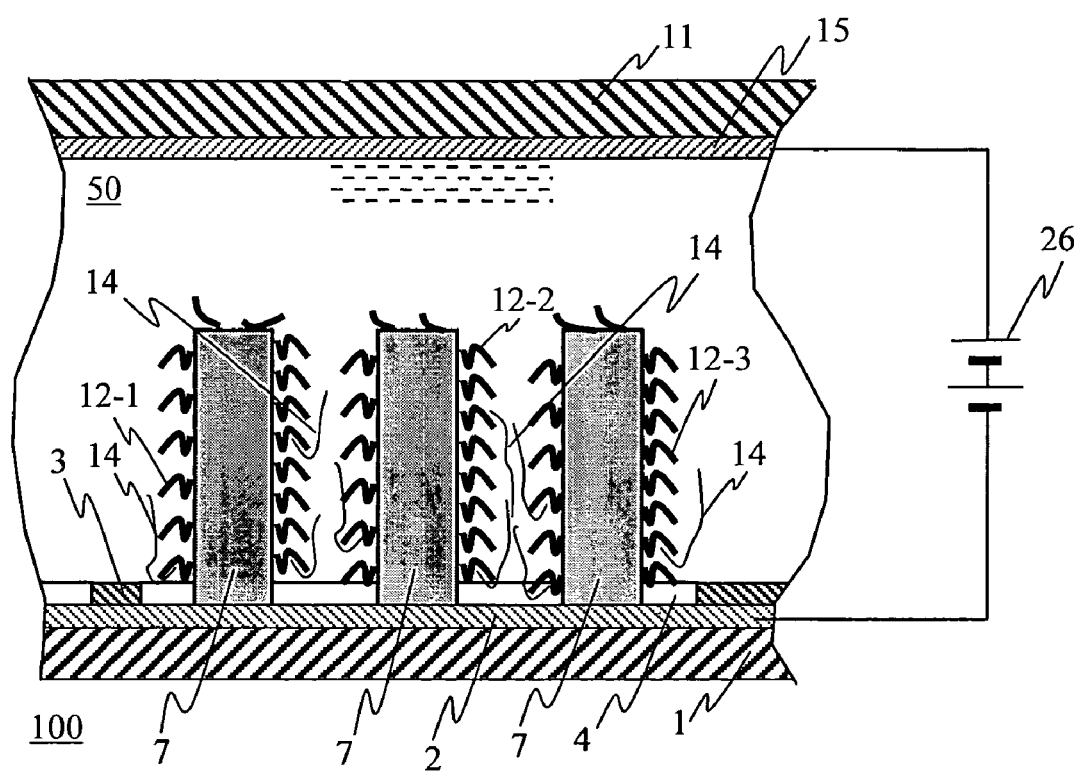

FIG. 116A shows the state in which a sample solution containing a target polypeptide therein is introduced into a surface of the DNA probe chip 100 described with reference to FIG. 115A to FIG. 115C; FIG. 116B shows the state in which the first step for forming the concentration gradient of the target polypeptide from an solid-liquid interface between a surface of the DNA probe chip 100 and the sample solution toward the sample solution; and FIG. 116C shows the state in which the next step for forming the concentration gradient of the target polypeptide is executed. Each state shown in the figures above is shown as a cross-sectional view.

A proper spacer (not shown) is set on a surface of the DNA probe chip 100 and a glass cover is placed over the spacer with a gap of 0.1 mm. An ITO electrode 15 with the thickness of 100 nm is provided on an inner surface of the cover glass 11. 40 μl of mRNA sample solution 50 is added between a gap between the surface of the DNA probe chip 100 and the cover glass 11. The sample solution 50 is agitated by reciprocally moving the slide glass at a constant speed. FIG. 116A is a cross-sectional view showing the state, and reference numerals 12-1, 12-2, and 12-3 indicate probes fixed on a surface of the pillar 7 on the probe fixing area 4. Reference numeral 14 indicates target polypeptide distributed in the sample solution 50. In this state, the target polypeptide is diffused according to a diffusion coefficient of the target polypeptide.

FIG. 116B is a cross-sectional view showing the state an electric field (actually 0.15 V between the electrodes) is applied by the power source 25 to a section between the electrode 2 on the DNA probe chip 100 and the electrode 15 on the cover glass 11 so that the electrode 2 is positively charged with +15 V/cm. As a result, the surface of the DNA probe chip 100 is positively charged, so that also the probes 12-1, 12-2, and 12-3 attracting the negatively charged target polypeptide 14 electrostatically to a recess between pillars 7 on the probe fixing area 4 (on a surface of DNA probe chip) are attracted to the electrode, and therefore it is conceivable that, as one terminal of a probe molecule is sized, a free terminal thereof is attracted to the electrode and the probe molecule extends along a side face of the pillar. The electrode 15 is not always required to be adhered to the cover glass 11, and is required only to be off from a surface of the DNA probe chip in the sample solution 50.

FIG. 116C is a cross-sectional view showing the state in which an electric field (actually 0.15 V between electrodes) is applied, in 30 seconds after a voltage is applied by the power source 25, to a section between the electrode 2 on the DNA probe chip 100 and the electrode 15 on the cover glass 11 by the power source 26 so that the electrode 2 is charged with −15 V/cm and agitation is performed for 0 to 30 minutes. Because the electrode 2 is negatively charged, the negatively charged target polypeptide 14 having been electrostatically attracted to recess between the pillars 7 on the probe fixing area 4 (on the surface of the DNA probe chip) starts moving from the recess between the pillars 7 (on the surface of the DNA probe chip) toward the electrode 15.

In other words, as shown in FIG. 116C, when the electric field is reversed, a repulsive force works between a negative charge of the electrode 2 and that of the target polypeptide 14, and therefore the target polypeptide 14 moves away from the surface of the DNA probe chip. In this step, the target polypeptide is larger and moves slowly, so that the provability of hybridization between the target polypeptide and the DNA probe fixed on a surface around a recess between the pillars 7 becomes higher.

Figure 117:
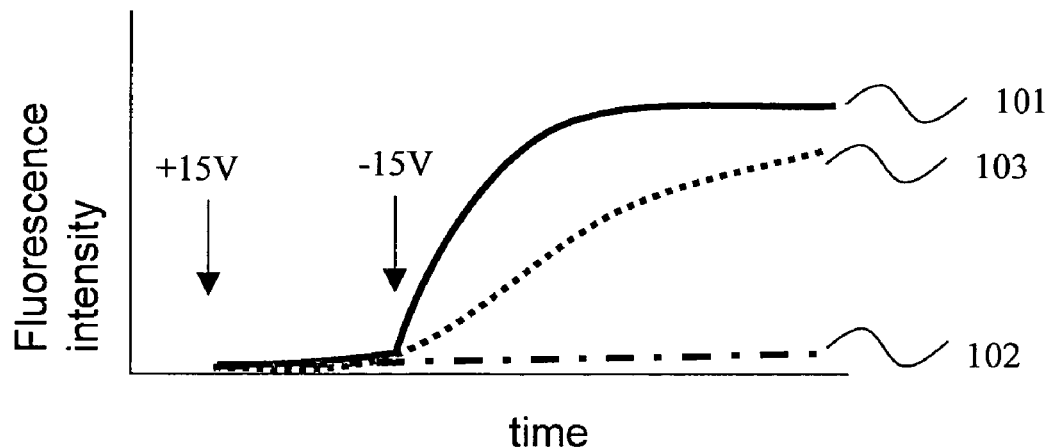

FIG. 117 is a view showing the effects provided in Example 2. For assessing the target polypeptide captured by the probe 12 as described with reference to FIGS. 116A, 116B, and 116C, a fluorescent coloring matter is used for labeling the target polypeptide to detect the fluorescence. Also nanoparticles such as gold colloid may be used for labeling and a number of particles is directly counted, and in this case, the tomographic technique may be used for reorganizing a plurality of images with a scan electronic microscope.

Changing a period of time for capturing the target polypeptide, amplitude of fluorescence emitted from the substrate after cleaning is examined with reference to conditions of an electric field applied to the DNA probe chip as a parameter. This figure is plotted with the horizontal axis for a period of time for application of an electric field and with the vertical axis for fluorescence amplitude.

The characteristic curve 101 in FIG. 117 shows a result of capturing of target polypeptide by the DNA probe chip when an electric field of +15V/cm is applied by the power source 25 to a section between the electrodes 2 and 15 and then an electric field of −15V/cm is applied by the power source 26 to the section between the electrode 2 and electrode 15; the characteristic curve 102 shows a result of capturing of target polypeptide by the DNA probe chip when no electric field is applied as a control; and the characteristic curve 103 shows a result of capturing of target polypeptide by the DNA probe chip when an electric field of +15V/cm is applied by the power source 25 to a section between the electrodes 2 and 15 and but an electric field of −15V/cm is not applied by the power source 26 to the section between the electrodes 2 and 15. In the cases indicated by the characteristics curves 101 and 103, the +15V/cm is applied for the same period of time.

As clearly indicated by the characteristic curve 101, at first an electric field of +15V/cm is applied by the power source 25 to a section between the electrodes 2 and 15 to electrostatically attract the negative charged target polypeptide 14 to the recess between pillars 7 (on a surface of the DNA probe chip). Then an electric field of −15V/cm is applied by the power source 26 to the section between the electrodes 2 and 15 to electrostatically separated the negatively charged target polypeptide 14 having been attracted to the recess between the pillars 7 (on a surface of the DNA probe chip) from the recess between the pillars 7 (on a surface of the DNA probe chip). By carrying out the steps above, the target polypeptide 14 in the sample solution 50 has the density gradient higher at a position closer to the recess between the pillars 7 (on a surface of the DNA probe chip). This result indicates that the target polypeptide is captured efficiently. Also as understood from the figures, at a point of time when hybridization proceeds to some extent, the DNA probe chip is saturated with captured target polypeptide, so that the hybridization reaction is not required to be executed for a long time.

When the negatively charged target polypeptide 14 is electrostatically attracted to the recess between the pillars 7 (on a surface of the DNA probe) by applying the electric field of +15V/cm to the section between the electrodes 2 and 15 with the power source 25, even if the electric field is removed, the attracted target polypeptide 14 is not distributed on a surface of the pillar 7 as shown in FIG. 116C, and in this case the hybridization reaction does not smoothly proceed.

When no voltage is applied, the density gradient of the target polypeptide 14 is not generated in the sample solution 50, and naturally the target polypeptide 14 is not captured so well.

In the example described above, a direction in which an electric field is applied is reversed only once, but may be reversed several times. In this case the states shown in FIGS. 116B and 116C are repeatedly reproduced, and the target polypeptide 14 not hybridized yet is distributed at a higher density around the DNA probe on the surface of the pillar 7, so that the provability of capturing the target polypeptide 14 can be improved.

EXAMPLE 3

In Example 2, there is provided no comment on with which form the DNA probe and target polypeptide should preferably hybridize with each other, but also in the twenty-third embodiment, hybridization proceeds more smoothly when a root portion of the DNA probe is used as a nuclear for hybridization. In this example, descriptions are provided for contrivance for utilization of a root portion of the DNA probe as a nuclear for hybridization.

To utilize a root (chip surface) of a probe as a nuclear for hybridization, it is effective, as described above, to attract the target polypeptide 14 in the sample solution 50 to the surface of the DNA probe chip to realize the density gradient of the target polypeptide 14 in the sample solution 50 higher at position closer to a surface of the DNA probe chip. In this example, descriptions are provided for contrivance for utilization of a root portion (chip surface) of the DNA probe as a nuclear for hybridization.

A sequence with 50-base length is extracted from human mRNA and used as a probe. The segment of 20 based near the substrate and other sequence segments with the GC rate of 15% higher than other portions are preferentially used. Namely the GC content is made higher at a position closer to the substrate. When this is impossible on the sequence, a probe sequence is designed by inserting a sequence mismatching the cDNA sequence functioning as a template or a blank sequence not forming a stable complementary chained at any of ACGT in a section from about 10th base up to about 30th base from a free edge thereof. However, when the mismatch sequence or blank sequence is inserted, the stability lowers, so that the places for insertion are at most two in this range. It is important to control stability of hybridization with the methods as described above for forming a nuclear for hybridization near a fixed edge of a probe.

Figure 118:
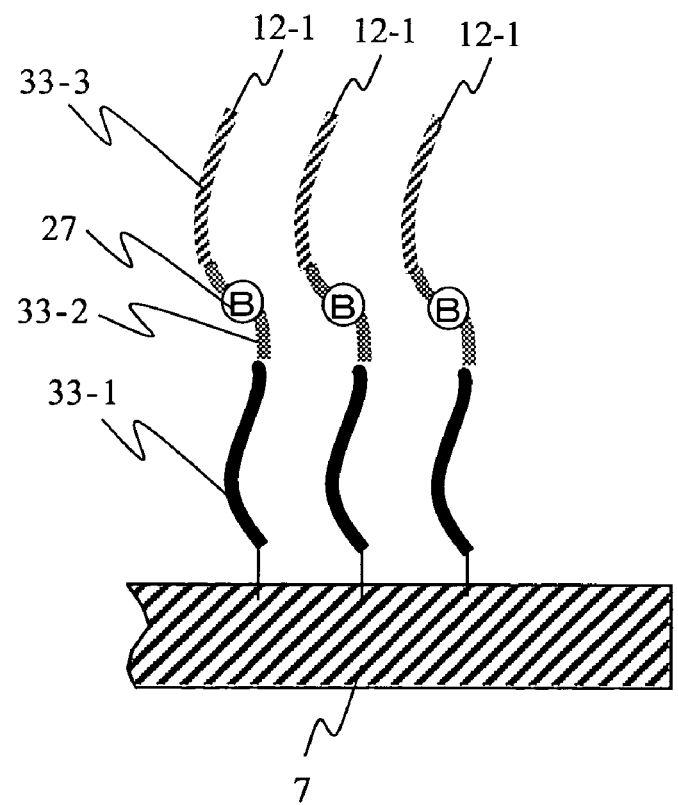

FIG. 118 is a view schematically showing the state in which a terminal of the probe 12-1 is constructed based on the concept according to the twenty-third embodiment and is fixed on a surface of the pillar 7. When the probe having the construction as described above is used, the same effects as those provided in the twenty-second embodiment can be obtained.

[XXIV] Twenty-Fourth Embodiment

A twenty-fourth embodiment of the present invention, just like the twenty-third embodiment, discloses a DNA-probe chip which improves the hybridizing rate on the surface of a solid chip, is capable of measuring in a short time, has a high sensitivity, and has only a small amount of pseudopositive hybridization, and a method of manufacturing the same; and the twenty-fourth embodiment discloses a hybridization method of the DNA probe chip. As is the case with the twenty-third embodiment, the twenty-fourth embodiment improves a probe fixing region mainly by enlarging it. The other points are the same as those of the twenty-first embodiment and the twenty-second embodiment.

While referring to the views, more specific descriptions will be given below.

EXAMPLE 1

The same kind of DNA probe chip illustrated in FIG. 107 describing DNA probe chip can be adopted as a chip suitable to the twenty-fourth embodiment.

Figure 119:
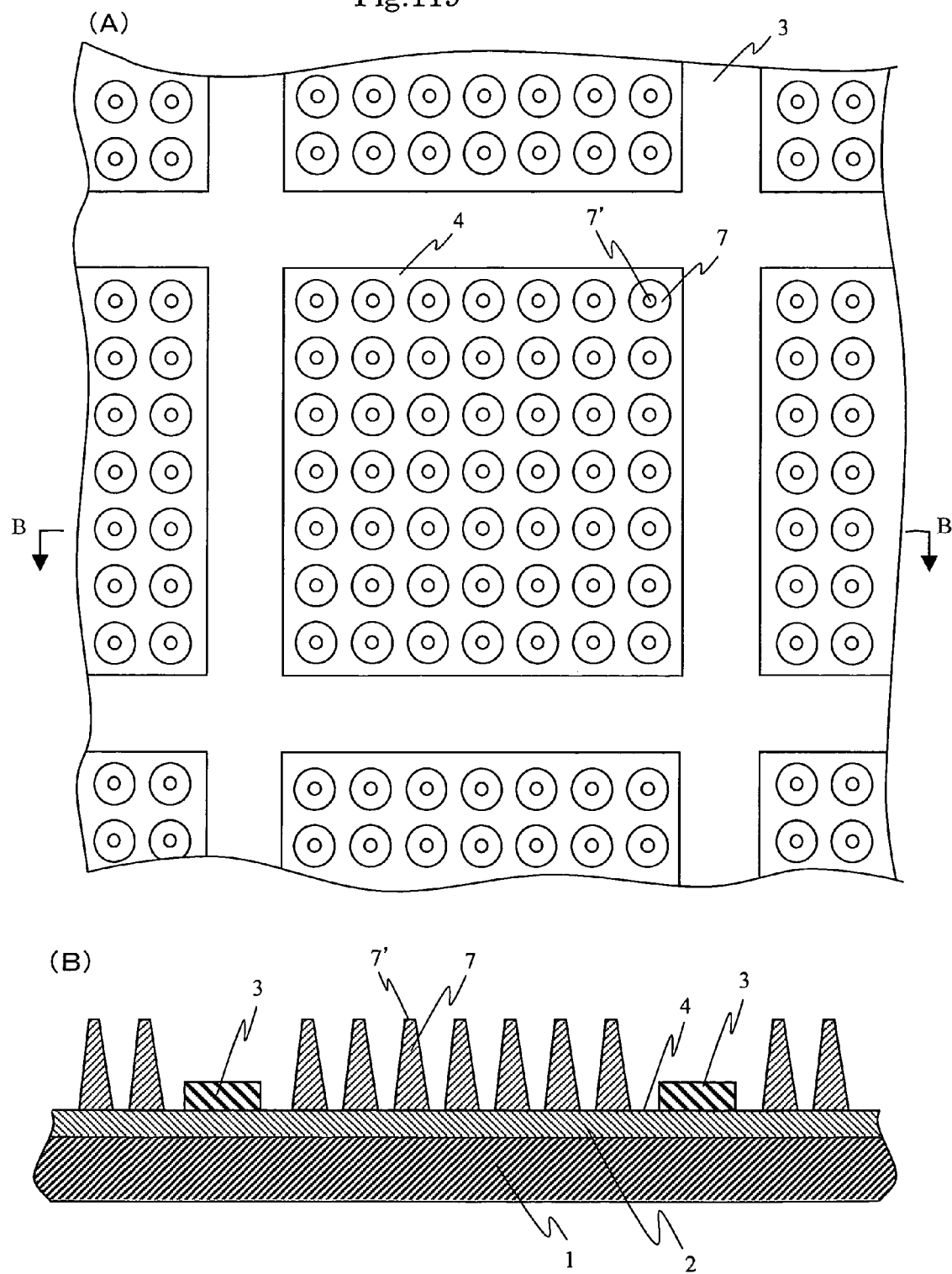

FIGS. 119 (A), (B) and 120 (A), (B) each shows a plan view or a cross-sectional view by focusing on and enlarging one of the probes in the probe fixing region 4 described in FIG. 107. In this embodiment, the probe fixing region 4 has a square shape of 100×100 μm. The reference numeral 7 indicates a pillar having a square shape with its bottom surface measuring 10×10 μm or a cone shape with a diameter of 10 μmφ. There are 7×7 pillars formed in the probe fixing region 4 with a pitch of 15 μm. The pillar 7 has a top face of 7' and a height of 50 μm. In FIG. 119, the pillar 7 is a truncated cone; in FIG. 120, the pillar 7 is a truncated square pyramid. In both FIGS. 119 and 120, two cross sections of the pillar are the same. There is no need to form a top face of the pillar 7; the top face of the pillar 7 may be left sharp. When the top face of the pillar 7 is left sharp, the pillar 7 becomes a cone in FIG. 119, and a square pyramid in FIG. 120. According to the examples of the size described here, compared with the case in which the probe fixing region 4 is a simple flat face, the truncated cone can obtain about 3.5 to 8 times the area of the probe fixing region and the truncated square pyramid can obtain about 4.4 to 10 times the area of the probe fixing region. These figures are calculated assuming that no probes are joined to the polar zone at the bottom of the pillar.

The number of probes fixed on the probe fixing region 4 may be increased in order to raise reaction rate or reaction yield; however, as described above, when the probe density is raised, hybridization efficiency goes down by electrostatic repulsion. Fixing probes at high density is no good as long as ordinary polynucleotide probes are used; when a probe length is as long as 50-bases polynucleotide, it is better to have a probe length of as sparse as 10 to 40 nm. In the twenty-fourth embodiment, the probe density itself is not raised, but the area of the probe fixing region 4 is enlarged to increase the number of the probes fixed to the probe fixing region 4. Therefore, the probe fixing density doesn't have to be raised, but by fixing probes, for example, with a pitch of 10 to 20 nm on average, more probes can be fixed.

There are several methods of producing the pillar 7. First, a method of using glass or silicon is to be described. A glass or silicon piece with a thickness of 100 μm is put together on the substrate 1 with an electrode 2 formed with vacuum evaporation and abraded to its prescribed thickness with spattering or etching. Alternatively, spattering is used to form a glass or a silicon layer with a thickness of 20 nm. After that, existing techniques are made full use of to produce a pyramid or a truncated pyramid depending on the convergence conditions of spattering electrons, while using a plurality of masks. An object of the twenty-fourth embodiment is just to enlarge an area of the probe fixing region 4; therefore, the pillar 7 does not have to be a complete cone, the pillar 7 may be curled on the side a little. Even when a micro array producing method, a known technique, is used to produce a mountain with a high aspect ratio, the effect of the twenty-fourth embodiment can be obtained.

A method of producing a pillar made of plastic is described hereinafter. The surface of the electrode 2, coated with a fluorine surface coating 3, is coated with an epoxy resin with a spinner to a thickness of 50 to 100 μm, pressed with a quartz mold into the shape of FIG. 119 or FIG. 120 and irradiated with ultraviolet rays for polymerization.

The quartz mold is removed after polymerization. At this point, due to poor adhesiveness between the mold and the electrode 2, a thin resin layer still remains on the bottom of the pillar 7, that is, on the electrode surface 2. Due to this resin layer, when the mold is removed, the molded pillar 7 remains on the electrode 2 together with this thin resin layer. The electrode is exposed to oxygen plasma for exposure in order to remove the thin resin layer on the electrode. At this time, the tip of the pillar becomes a little round and the pillar becomes short; however, there is no problem in carrying out the twenty-fourth embodiment. Alternatively, by contriving so that the plasma is intensively irradiated on the valley portion of the pillar using the mask, a more precise circular cone, truncated cone, pyramid and truncated pyramid can be formed.

From the perspective of the concentration of the sample DNA and the contact on the pillar sides, it doesn't matter whether the side of the cone of the pillar 7 is round or the tip thereof is round; rather, it reduces the problems of sample DNA particles getting stuck on the tip.

On the other hand, measurement is performed by projecting the pillar 7 vertically from the top surface to the bottom face; from the perspective of measurement, it is advantageous for the side of the cone to be inclined to a certain degree. For example, assuming the pillar 7 is in a shape of a hemisphere with its bottom placed upward, the side close to the bottom face of the cone is nearly vertical; when projected in the vertical direction, a large number of DNA molecules are overlapped. On the other hand, the side of the cone gently describes an arc at the tip of the cone; therefore, only a small number of DNA molecules are overlapped. Considering fluorescence detection in such a cone, even when DNA molecules are caught at a certain density, the foot of the pillar and the tip thereof each has a different fluorescent density; therefore it is better that the side of the cone is not round. However, either case has both advantages and disadvantages; therefore, the detailed structure of the pillar is not taken into consideration in this embodiment.

A method of fixing the probe on the surface of the pillar 7 is to be described. First, when a pillar material is glass or silicon, the method disclosed by T. Pastinen et al., Genome Research (1997) 7, 606-614 is revised to be used in this embodiment. With NN-disopropylethylamine used as a catalyst, 3-glycidoxypropyltrimetoxysilane is reacted at 80° C. for 16 hours in xylene solvent to introduce a glycidoxy group on the pillar surface. Alternatively, about 0.5% of acetic acid is added into a 2% solution of 3-glycidoxypropyltrimetoxysilane as a catalyst and left for thirty minutes; after activating a silanol group, the activated silanol group is applied on the surface of the pillar 7, left for thirty minutes, rinsed with pure water and dried at 105° C. for thirty minutes so that a glycidoxy group can be introduced on the surface of the pillar 7. Next, a fifty-base-long probe DNA having an amino group at 5' end is reacted at pH 9 to 10 for two hours with a thickness of 50 μM. The probe DNA is then rinsed to obtain a DNA chip with the probe fixed on the surface of the pillar 7.

When the surface of the pillar 7 is made of an epoxy resin, oxygen plasma or UV ozone is used to treat the surface. An OH group or oxygen radical is generated on the surface of the pillar 7. Because the OH group and oxygen radical are unstable residues, they are reduced over time; therefore, the surface of the pillar 7 is immediately dipped in a 0.5% N-(β-aminoethyl)-γ-aminopropyltrimethoxysilane solution (left at room temperature for thirty minutes to become an activated silane coupling solution) and left for one hour. After rinsing in pure water, the surface of the pillar 7 is dried in the air at 105 to 110° C. In this way, the amino group can be obtained on the surface of the pillar 7 made of an epoxy resin. The amino group is modified with succinic anhydride to introduce a carboxyl group to the amino group. N-hydroxysuccinimide is esterified in order to make the carboxyl group an activated ester. A synthetic DNA probe with the amino group at 5' end is added, and the probe is fixed on the surface of the pillar 7 with peptide binding.

EXAMPLE 2

The following figures each shows the state thereof in a cross-sectional view: FIG. 121A shows the state in which a sample solution including a target polynucleotide is introduced on the surface of a DNA probe chip 100; FIG. 121B shows the state in which a first step is taken for forming a concentration gradient of the target polynucleotide from the solid-liquid interface between the surface of the DNA probe chip 100 and the sample solution toward the sample solution; FIG. 121C shows the next step for forming the concentration gradient. Hatching of the pillar 7 in the sense of a cross section is omitted because hatching makes it hard to see the views.

On the surface of the DNA probe chip 100, a gap of 0.1 mm is made by putting an appropriate spacer (not shown) and a cover glass 11 is placed on it. An ITO electrode 15 with a thickness of 100 nm is provided on the inner face of the cover glass 11. Forty micro liters of an mRNA sample solution 50 is added into the space between the surface of the DNA probe chip 100 and the cover glass 11. The sample solution 50 is agitated by moving the slide glass back and forth at a certain rate. FIG. 121A is a view showing this state; the reference numeral 12 indicates a probe fixed on the surface of the pillar 7 in the probe fixing region 4. The reference numeral 14 indicates the target polynucleotide dispersed in the sample solution 50. In this state the target polynucleotide 14 only diffuses corresponding to a diffusion coefficient of the target polynucleotide.

FIG. 121B is a view showing a state in which an electric field (effectively 0.15 V between the electrodes) is applied so that, between an electrode 2 of the DNA probe chip 100 and the electrode 15 of the cover glass 11, the electrode 2 turns positive +15V/cm with a power source 25. As a result, by making the surface of the DNA probe chip have a positive potential, the target polynucleotide 14 having a negative charge is electrostatically drawn to the valley of the pillar 7 (the surface of the DNA probe chip) in the probe fixing region 4. At this time, a probe 12 is also drawn to the electrode; therefore, because one end of the probe 12 is fixed, a free end of the probe 12 is drawn to the electrode; the probe 12 is supposed to extend along the surface of the pillar 7. The surface of the pillar 7 is electrically neural or slightly has a negative charging; therefore, the probe 12 is not adsorbed in the surface of the pillar 7, but has a certain freedom. Because of that, the probe 12 has a capability of causing hybridization when the target polynucleotide 14 clashes. In fact, when the target polynucleotide 14 is attracted by the electrode 2, as an arrow with the reference mark 17 shows, the target polynucleotide 14 collides on the surface of the pillar 7. Because of that, as the reference mark 18 shows, some target polynucleotide 14 is hybridized with the probe 12 even at this step.

An electrode 15 does not have to be attached to a cover glass 11; it may be placed away from the surface of an electrode 12 of the DNA probe chip 100 inside the sample solution 50.

FIG. 121C is a view showing the state in which, thirty seconds after a voltage is applied from a power source 25, the electric field of −15V/cm (effectively 0.15 V between the electrodes) is impressed between an electrode 2 of the DNA probe chip 10 and the electrode 15 of the cover glass 11 from a power source 26 so that the electrode 2 turns negative. Because the electrode 2 turns negative, the target polynucleotide 14, having a negative charging and electrostatically drawn to the valley of the pillar 7 (the surface of the DNA probe chip) in the probe fixing region 4, starts to move toward the electrode 15 from the valley of the pillar 7 (the surface of the DNA probe chip).

In other words, as shown in FIG. 121C, when the electric field is inverted, repulsion between the electrode 2 and a negative charging of the target polynucleotide 14 works; therefore, the electrode 2 and the target polynucleotide 14 move in the direction away from the surface of the DNA probe chip. In this case, because a molecule of the target polynucleotide is big, it is slow to move; therefore, there is a high probability of the target polynucleotide hybridizing with the DNA probe fixed on the surface surrounding the valley of the pillar 7. Further, the hybridization efficiency can be raised by turning on and off of the power source repeatedly.

A series of views of Figs. (A) to (F) describe the effect of Example 2. In order to assay the target polynucleotide caught by the probe 12 according to the way described in FIGS. 121A, 121B and 121C, the target polynucleotide is made a label by using a fluorescent dye. The fluorescence of the fluorescent dye is to be detected. A nanoparticle like a gold colloid may be made a label to count particles directly; this case can be realized by using a tomography method which reconstructs a plurality of images with a scanning electron microscope.

Figure 122:
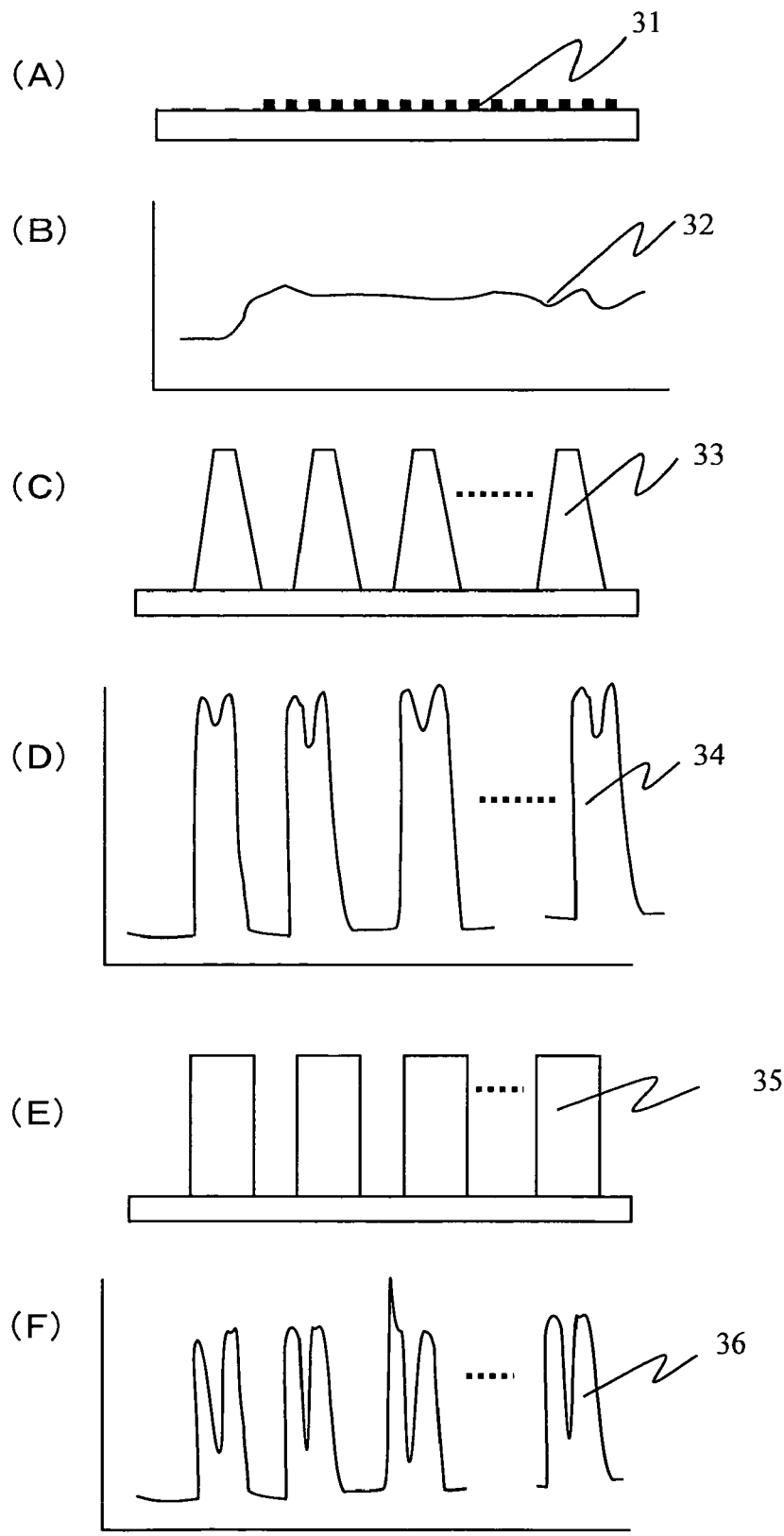

FIG. 122 (A) is a view showing a probe fixing position 31, hybridized with the target polynucleotide with a fluorescent label, on the conventional flat type DNA probe chip. An incident-light fluorescence microscope is used for capturing a fluorescent image; and image processing software is used for fluorescent profiling. FIG. 122 (B) indicates a fluorescence profile 32 obtained at this time. It can be seen that the fluorescence intensity of the probe fixing position rises a little above the background level.

The fluorescence profiles, the detection results with the DNA chip provided with the pillar on the cone of the twenty-fourth embodiment, are described hereinafter.

FIG. 122 (C) is a view showing the position of the pillar for fixing the probe. Both FIGS. 122 (A) and 122(C) have the same scale size. As shown in FIG. 122 (D), a strong fluorescence is observed at the pillar position of a fluorescence profile 34 obtained with the DNA chip provided with the pillar on the cone. Because no probe is fixed on the electrode portion, the fluorescent intensity is almost on the background level. Compared with fixing the probe simply on a flat surface, the high strength can be obtained, the hybridization efficiency goes up, and the high sensitivity is realized. The strength of the apex of the pillar decreases compared with that of the side of the pillar.

FIG. 122 (E) is a view showing the position of a cylinder pillar for comparing with the pillar of the twenty-fourth embodiment. Both FIGS. 122 (C) and 122(E) have the same scale size. As shown in FIG. 122 (E), the pillar is of a cylindrical form; therefore, the hybridization caused by colliding of the target polynucleotide and the probe occurred when the sample polynucleotide is drawn to the bottom face of the pillar in the electric field, as described in FIG. 121 B, is unlikely to happen: and because each side of the pillar is juxtaposed vertically, the optical stacking takes place. Such phenomena, compared with the pillar with a taper, make the hybridization efficiency decrease, or handicap the optical characteristics at the time of measurement; therefore, the fluorescence intensity of the obtained fluorescence profile 35 remarkably decreases compared with that of FIG. 122 (D). The fluorescence intensity drop of the cylinder apex is striking.

FIG. 123 is a view showing an example of the result obtained by checking the fluorescence intensity by variously changing the time to capture the target polynucleotide, using the condition of the electric field for applying on the DNA probe chip as a parameter. The horizontal axis indicates the time to apply the electric field, while the vertical axis indicates the fluorescence intensity.

A characteristic curve 101 shows a result of capturing the target polynucleotide of the DNA probe chip when the electric field of −15V/cm is applied between the electrodes 2 and 15 from the power source 26, after the electric field of +15V/cm is applied between the electrodes 2 and 15 from the power source 25, with the chip provided with the truncated cone pillar. A characteristic curve 102 shows a result of capturing the target polynucleotide of the DNA probe chip with the chip provided with the same truncated cone pillar when no electric field is applied, as a control. A characteristic curve 103 shows a result of capturing the target polynucleotide of the DNA probe chip when the electric field of −15V/cm is applied from the power source 26 after the electric field of +15V/cm is applied from the power source 25, with the chip provided with the cylindrical pillar. The time to apply the first +15V/cm in the characteristic curves 101 and 103 is the same. Both characteristic curves show an average fluorescence value in the probe fixing region.

As evidently shown in the characteristic curves 101, first, the electric field of +15V/cm is applied between the electrodes 2 and 15 from the power source 25 to electrostatically draw the target polynucleotide 14 having a negative charge to the valley of the pillar 7 (the surface of the DNA chip). At this time, the hybridization has already started, so the fluorescence intensity increases over time. After that, the electric field of −15V/cm is applied between the electrodes 2 and 15 from the power source 26 to release the target polynucleotide 14 with a negative charge, electrostatically drawn to the valley of the pillar 7 (the surface of the DNA chip), from the valley of the pillar 7 (the surface of the DNA chip). By following this step, the closer to the valley of the pillar 7 (the surface of the DNA chip), the higher gradient the density of the target polynucleotide 14 inside the sample 50 has; therefore, the target polynucleotide can be captured efficiently. As can be seen from the view, after the prescribed time has passed, the target polynucleotide moves away from the pillar; therefore it is no use applying more voltage.

A fluorescence intensity 103 obtained with the cylindrical pillar is low due to the reasons described above.

When no voltage is applied, there occurs no density gradient of the target polynucleotide 14 inside the sample 50; therefore, it is natural that a capturing rate of the target polynucleotide 14 is low.

In this example, the direction of the electric field is changed once; however, this step may be repeated several times. When it is repeated several times, the states in FIGS. 121 B, 121C are to be repeated; because many of the unhybridized target polynucleotides 14 are distributed near the DNA probe on the surface of the pillar 7, the capturing rate of the target polynucleotide 14 can be increased.

EXAMPLE 3

FIG. 124 is a cross-sectional view showing the DNA chip of Example 3 for enlarging the surface area by producing many wells on the substrate; like Examples 1, 2, the side of the well has a taper so that more reaction efficiency can be obtained and the optical measurement can be easily performed. A silicon substrate 51 is provided with the electrode 52 thereon, on the electrode 52 exists a component 54 made of a well 53. The electrode of the well 53 is exposed on the bottom surface thereof. Chromium is evaporated on the surface of the silicon substrate 51 to turn it to be the electrode 52. Platinum is evaporated on the electrode 52. Just like Example 1, the epoxy layer is formed on the platinum to form a well using plasma processing. An amino group is introduced on the surface with silane processing; and following the method of Example 1, the probe DNA is fixed. By combining the DNA chip, with an electrode, composed of the probe fixing area having many wells, produced as described above, and the fluorescence detection, the detection sensitivity at least ten times as strong as that of the conventional flat DNA probe chip can be obtained.

Further, it is possible to hybridize the target polynucleotide with a 5 nm-gold particle labeled and to detect a fixed quantity of gold particles with a scanning electron microscope. This case has an advantage which makes it possible to measure on the single molecular level in about one minute of the measuring time. On the side of the cylindrical well, the gold particles bound with the hybridization reaction vertically overlap; therefore, detection is hard even with the scanner electron microscope because the particles each overlaps on top of each other. According to the twenty-fourth embodiment for making the well have a taper, the particles each bound on the side of the well can be measured without overlapping on top of each other so much. Therefore, the twenty-fourth embodiment is useful as a DNA probe chip of a single molecule measuring type which uses nanoparticles and the scanner electron microscope.

[XXV] Twenty-Fifth Embodiment

A twenty-fifth embodiment of the present invention discloses a multi-detection method of a labeling substance for labeling dozens or thousands of sample molecules in the same probe section divided into a minimum size, and a biological material using this labeling substance, in a wide-ranging biological material detection method including DNA probe array.

The twenty-fifth embodiment uses a nanoparticle made by changing a ratio of different elements of a labeling substance as a label. For example, a gold based substance blended with a trace of palladium and chromium is used below to describe this label. When a composition ratio of palladium and chromium is changed eight gradations, sixty-four kinds of nanoparticles of gold can be obtained. When three kinds of elements are added to gold, 512 kinds of nanoparticles of gold can be obtained. When a particle diameter is changed into about five kinds between 10 nm and 50 nm each every 10 nm stage, about 2500 kinds of nanoparticles of gold with different composition and size can be obtained.

Because this particle is a conductor, the location and the size thereof can be easily detected by irradiating electrons on the particles using a scanning electronic microscope, measuring the energy distribution of secondary electron beams, and obtaining the SEM image with the location and the size of the particle identified. Further, the location and the size of the particle can be obtained by using an energy dispersive character X-ray detector to obtain the element analyzed images of character X-rays generated when electrons are irradiated on the particles using the scanning electronic microscope. This method makes it possible to detect the size of a nanoparticle, the kind of element included therein and the location of the particle on the substrate section. By making the particles each with different composition and diameter become the structures each having a probe DNA binding to each different DNA sequence, it is possible to detect thousands of target DNA pieces on the same level.

Because nanoparticles are mainly composed of gold, the probe can be fixed on the particle surface by using a. DNA probe with alkylsulphide group.

The twenty-fifth embodiment is basically based on the alloy manufacturing technique, so various kinds of elements can be blended; further, it is possible to combine four or more kinds of elements. For example, combining five elements makes it possible to obtain thirty some thousand nanoparticles of different composition equivalent to the number of sections of the existing DNA chips. Or, putting 250 kinds of combination of three elements into one group, and preparing a plurality of groups composed of the combination of the other elements enable distinction and detection of several thousand kinds of DNA. To change composition thereof, three to five elements are selected from the combination of elements consisting of gallium, aluminum, yttrium, erbium, horonium, cesium, cobalt, titan, nickel, iron and the like. In order to fix the probe, in addition to the gold and the SH group reaction, a functional group is introduced using a silane coupling reaction when the probe has an oxidized surface.

As described above, the twenty-fifth embodiment of the present invention overturns the conventional concept of DNA chips which have to fix different types of probes on a great many number of section elements. It is possible to analyze the mRNA expression in a short time simply by trapping mRNA on the chip with poly T fixed thereon, hybridizing each mRNA with the synthetic DNA probe having complementary sequences with nanoparticles each having different composition labeled thereon, and by analyzing with the scanning electronic microscope.

An analyzing method of analyzing thousands of different kinds of epitopes at once is to be established by using an antibody instead of the DNA probe and using it on a biological substance (for instance, protein) fixed on the substrate.

EXAMPLE 1

FIG. 125 is a conceptual drawing showing a portion of the DNA chip according to an example 1 of the twenty-fifth embodiment in a diagrammatic perspective view. Chip 1 is formed on a silicon substrate 101 having an oxidized membrane surface. The chip 1 has a size of 20×20 mm. A probe fixing region 102 is the only one for fixing the DNA probe and has 10 mmφ. The surrounding portion thereof is coated with a water shedding resin 103, a kind of Teflon (registered trademark). The coating is about 50 μm thick. In a probe fixing region 102, the 3' end of poly T with 26-base lengths is bound together with the 5' end of random sequence oligo-DNA with 5-base lengths. It is because the Poly T alone cannot fully secure the stability of mRNA hybridization. The probe is made of PNA, peptide nucleic acid, so that the probe can be easily interacted with the intracellular mRNA. Similar to ordinary DNA, PNA does not have any negative charging originated from phosphodiester bond; therefore, electrostatic repulsion does not occur between the target DNA and PNA, which improves the efficiency of hybridization.

Further, using PNA for the probe to have a property without the charging does not generate electrostatic repulsion; therefore, hybridization proceeds without performing denaturation because even if a poly A portion of the target mRNA forms a partial duplex with another site in the cell, the probe can competitively get inside the duplex, and hybridize the duplex competitively.

A method disclosed by A. Kumar et al. (Nucleic Acids Research (2000) 28, No. 14 e71) is revised to make the probe fixing method used here. In this method, a silanized DNA probe, with the trimethoxysilane residue introduced to the amino end of synthetic PNA in advance, is coated on the element portion of the chip substrate to fix the probe. The silanized DNA probe, for example, can be obtained by binding a glycidoxy group of 3-glycidoxypropyltrimethoxysilane to the amino end of PNA.

For example, a 50 μl of total RNA solution extracted from the tissue pieces of intestinal cancer removed in accordance with the known method is blended with a 0.1% (w/v) solution of gold based nanoparticles (10 μm) with a ratio of gallium, aluminum, yttrium and chromium altered so that about forty base sequences complementary to each mRNA can be distinguished; and then the solution is added to the probe fixing region 102 of the chip 1 without performing any special treatment. The chip is preheated at 45° C. About 1-mm gap is provided, and a 40 mmφ of glass plate is placed on the top surface of the probe fixing region; the glass plate, while being decentered, is moved in circles so that the edge of the probe fixing region 102 matches that of the glass plate. The glass plate is moved once every five seconds, which makes it possible to hybridize at a high rate. In the probe fixing region 102 of the chip 1, a probe fixed on the chip 1, an mRNA and a particle labeling probe are bound in that order in a sandwich structure. An unreacted particle labeling probe or RNA is washed and removed.

FIG. 126 is a conceptual view illustrating how the probe chip 1 described in FIG. 125 is observed using the scanning electron microscope.

Many probes are fixed on the surface of the probe fixing region 102 of the chip 1; this example is performed using a simplified method in which DNA pieces 201-204 are hybridized on each of the fixed probes 11-14; and these DNA pieces are labeled with gold particles 21-24. Each of the gold particles 21, 22, 23 and 24 is to have a ratio of (1:1:1:0), (1:1:0:1), (1:0:1:1), (1:1:1:1) for gallium, aluminum, yttrium and chromium, respectively. A maximum ratio of each metal blended into gold is 20% because binding between gold and alkanethiol introduced at a 5' end of the probe is to be used in order to fix an mRNA specific probe on the surfaces of nanoparticles. Gold and thiol are vulnerable to oxidative conditions or exposure to UV rays, but under ordinary hybridization conditions gold and thiol can obtain very stable binding force. Therefore, in Example 1 the alkanethiol previously introduced at the 5' end of the probe and the gold are blended at a ratio of 10 to 1 to obtain a string of gold nanoparticles with mRNA specific probes fixed on the surfaces thereof.

An electron gun 300-1, a convergent lens 300-2 and a scanner coil 300-3 of a scanning electron microscope 300 for detecting the gold particles are provided on the surface of the probe fixing region 102 of the chip 1. The electron of an electron ray 300-4 shot from the electron gun 300-1 clashes against the gold particles 21, 22, 23 and 24, and then the gold particles emit an electron ray 300-5. This secondary electron is captured by a detector 300-6. Based on the secondary electrons captured by the detector 300-6, so called SEM images can be obtained to identify the location and the size of the gold particles.

On the other hand, the twenty-fifth embodiment is provided with an energy dispersive character X-ray detector 300-8 for detecting an X-ray 300-7 with a wavelength specific to elements constituting the gold nanoparticles emitted from the gold particles 21, 22, 23 and 24 when the electron of the electron ray 300-4 clashes against the gold particles 21, 22, 23 and 24. Thus, analyzed images of elements can be obtained from wavelength signals corresponding to the structural elements detected by the energy dispersive character X-ray detector 300-8.

The analyzed images of elements obtained by the energy-dispersive-character X-ray detector 300-8 is to have the data of locations and structural elements of the gold particles. Therefore, when the SEM image and the analyzed image of elements are matched, mRNA particles hybridized by the gold particle labeling probe can be identified.

FIG. 127 is a conceptual view illustrating a method of identifying the mRNA particles hybridized by the gold particle labeling probe by comparing the SEM image with the analyzed image of elements.

As an example, oligo PNA (28 bases) having a sequence corresponding to an mRNA sequence of EpCAM, oligo PNA (26 bases) having a sequence corresponding to an mRNA sequence of CD44, an expression which is also said to increase in a cancer cell, and oligo PNA (29 bases) having a sequence corresponding to an mRNA sequence of CEA, each of them is fixed on the surface of the probe fixing region as a probe. A method of adding a gold particle (with a diameter of 10 nm), as a label, each including gallium, aluminum, yttrium and chromium with a ratio of (1:1:1:0), (1:1:0:1), (1:0:1:1), (1:1:1:1) respectively to the amino end hybridizing to these probes is described below.

In FIG. 127, the reference numeral 30 indicates the SEM image. The SEM image has all the particles images. The reference numeral 31, 32, 33, 34 each indicates a gallium image, an aluminum image, an yttrium image and a chromium image respectively. Comparing a SEM image 30 with the gallium image 31, aluminum image 32, yttrium image 33 and chromium image 34 shows that the SEM image 30 is the same with the gallium image 31, but the aluminum image 32, yttrium image 33 and chromium image 34 each fails to display a location particle by dotted lines shown against the SEM image 30. In other words, because gallium is included in all of the particles used as labels, the gallium image 31, like the SEM image 30, shows all the particles. The aluminum image 32 does not show a location particle shown by dotted lines. It means that an mRNA hybridized to the probe in this location indicates a CEA molecule labeled by a gold nanoparticle including no aluminum. This indicates a gold particle shown as the reference numeral 37 in the SEM image 30. Similarly, the yttrium image 33 does not display two particles in the location shown by dotted lines. In other words, an mRNA hybridized to the probe in this location indicates a CD 44 molecule labeled by a gold particle including no yttrium. This is a gold particle shown as the reference numeral 36 in the SEM image 30. Further, the chromium image 34 does not display three particles in the location shown by dotted lines. In other words, an mRNA hybridized to the probe in this location indicates an EpCAM molecule labeled by a gold particle including no chromium. This indicates a gold particle shown as the reference numeral 35 in the SEM image 30.

In FIG. 127, all the particles were regarded to have the same size in order to simplify the description; however, when the particles of different sizes are used together with the particles of the same size, more substances can be identified. Of course it is needless to say that this identification can be performed with an image processing of a calculator.

Using the twenty-fifth embodiment makes it possible to distinguish and quantitatively measure a plurality of mRNAs on the DNA chip with an mRNA having a poly-A tail simply captured. Because the energy dispersive X-ray detector attached to SEM can identify an element ratio of a few percent, it can identify the same element by about eight gradations. When four kinds of elements are used, it is possible to identify 4096 kinds of particles. When five kinds of elements are used, 32768 kinds of particles can be identified by shooting only five images.

As described above, using the particles with the element ratio altered according to the twenty-fifth embodiment enables the mRNA profiling of a single molecule level without using a probe chip made with a conventional section separation method but with using a particle counting method. The probe chip made with a conventional section separation method has such a complicated structure that it is troublesome to manufacture the probe chip.

EXAMPLE 2

An example 2 describes the multi-detection method of a biological substance with an antigen-antibody reaction. In this example, the same substrate described by referring to FIG. 25 is used. In the example 2, the probe fixing region 102 is used as a reaction portion; an IgG fraction with antihuman antiserum affinity purified is fixed in a reaction portion 102. The serum to be measured contains a large amount of human albumin or human IgG; therefore it is necessary to remove an antibody to human albumin and an antibody to human IgG from the reaction portion 102 in advance so that they may not react. Therefore, the IgG fraction with an affinity purified antihuman antiserum IgG fraction absorbed by human albumin and human IgG is prepared; the IgG fraction is fixed in the reaction portion 102 and a surplus absorption place is masked with phosphatidylcholine compound. Next, the reaction portion 102 is washed with 0.15M NaCl, 50 mM sodium phosphate buffer (PBS: pH7.4) including 10 mg/ml of bovine serum albumin to remove unreacted human IgG.

When 100 µl of human serum sample is added to the reaction portion 102, and agitated for ten minutes just like the process in Example 1, the protein existing inside the serum causes an antigen antibody reaction, and the protein is trapped by the antibody on the reaction portion 102.

Aside from this, a nanoparticle labeling antibody is prepared. For example, an SH group is introduced to an F(ab')$_2$ fragment obtained with papain degradation of affinity purified polyclonal anti-AFP antibody and anti-CEA antibody. The SH group to be inserted has 3 to 4 molecules per one F(ab')$_2$ molecule. Gold (20 nmφ)-based palladium and chromium with a ratio of (20:80) and gold particles with a ratio of (30:70) are blended with F(ab')$_2$ derived from the anti-AFP antibody and anti-CEA antibody including the SH group prepared as described above to obtain gold particles with F(ab')$_2$ bound on the surface thereof.

AFP alone with a concentration of 1 zmol/µl, CEA alone with a concentration of 5 zmol/µl and a control with nothing therein are prepared to make a sample. PBS (pH 7.4) including 0.1% Tween 20 and 0.5% BAS is used as a solvent.

Each solution is reacted with the protein chip, and then the gold nanoparticle labeling F(ab')$_2$ is reacted with the protein chip. The reaction time for the first sample reaction is five minutes, and the reaction time for the gold nanoparticle labeling F(ab')$_2$ is five minutes. After the reaction ends, the chip is washed with the buffer solution including 0.1% Tween 20 and 0.5% BAS; the gold nanoparticles are detected using the scanning electronic microscope and the energy dispersive character X-ray detector, and then AFP and CEA molecules are counted from the abundance ratio of palladium and chromium.

When AFP alone is reacted with the protein trapped by the antibody on the above mentioned reaction portion 102, 120 particles/µm$^2$ of gold nanoparticles which can recognize the AFP bound with protein and two particles/µm$^2$ of the other gold nanoparticles are detected. Similarly, when CEA alone is reacted, 1580 particles/µm$^2$ of gold nanoparticles which can recognize the CEA bound with protein and six particles/µm$^2$ of the other gold nanoparticles are detected. Only two to four particles/µm$^2$ of gold nanoparticles can be detected from the control solution.

In the twenty-fifth embodiment, the metal or semiconductor constituting an alloy particle which is to be a label is selected from either one of transition metals with any atomic number up to 79 of the periodic table excluding atomic number 43, either one of metals with atomic numbers 13, 31, 32, 49, 50, 51, 81, 82, 83, and either one of semiconductors with atomic numbers 14, 33, 34, 52.

As described above, the twenty-fifth embodiment can be carried out in several examples; in any example, a hybridized DNA sample and the like are detected practically by every molecule; therefore, the sensitivity obtained using this method far exceeds the sensitivity obtained using a conventional method. An infinitesimal DNA (RNA) can be detected by an infinitesimal volume; therefore, it is now possible to detect a target DNA (RNA) without carrying out any pretreated amplifications, which was impossible using a conventional method. Because a labeling particle size or form for detection can be changed, it is now possible to perform multi analysis of different samples from about six to ten kinds on the same element. In addition to using this technique to the conventional differential hybridization, this technique makes it possible to trap a sample polynucleotide in an element using the same probe and perform detection using a different label probe. The multi-analysis technique according to the twenty-fifth embodiment has the advantages of detecting alternative splicing or performing typing of a plurality of SNPs using one element.

[XXVI] Twenty-Sixth Embodiment

As with the twenty-fifth embodiment, a twenty-sixth embodiment of the present invention discloses a labeling material capable of identifying, in a minimized probe zone, several tens to several thousands sample molecules in the same zone and a multiplex examination method for examining biological materials with the labeling material. In the twenty-sixth embodiment, different from the twenty-fifth embodiment in which a probe is fixed to a probe zone, indexing particles each with a probe fixed thereto are prepared. In other points, the twenty-sixth embodiment is the same as the twenty-fifth embodiment.

In a first aspect of the twenty-sixth embodiment, nanoparticles having different elemental compositions respectively are used as labeling materials. Descriptions are provided below for a case in which nanoparticles of gold with minute quantities of palladium and chromium mixed therein are used as labeling materials. Sixty-four types of gold nanoparticles can be obtained by changing a content of palladium and that of chromium with 8 steps respectively. If three elements are added in the nanoparticles of gold, 512 types of gold nanoparticles can be obtained. If the particle diameter is changed by 5 stages with a 10-nm step in the range from 10 nm to 50 nm, about 2500 types of nanoparticles of gold having different compositions and sizes can be obtained.

The particles are conductive, the position and size of each particle can easily be detected by irradiating the particles with electrons under a scanning electron microscope and measuring an energy distribution of secondary electron beam to obtain a SEM image identifying positions and sizes of the particles. Further a position and size of each particle can be detected by irradiating electrons with a scanning electron microscope to the particles to obtain an elemental analysis image for the characteristic X-ray generated by each particle with an energy-dispersive-characteristic X-ray detector. With the operations above, a position of each nanoparticle on the substrate can be detected, and at the same time the elements contained in the particle and size thereof can be detected. With a structure having a number of different probe DNAs to which particles having different compositions and sizes conjugate respectively, even several thousands target DNA fragments can be detected on the same plane.

The main ingredient of the nanoparticle is gold, so that the probe cab be sided to a surface of the particle by using a DNA probe having an alkyl sulfide group.

The twenty-sixth embodiment is basically dependent on the alloy manufacturing technology, and various types of elements may be mixed in the particle. If necessary, four or more types of elements may be mixed in the particle. For instance, when five types of elements, nanoparticles based on thirty thousands or more compositions equivalent to a number of the existing DNA chips can be obtained. Alternatively, by preparing 250 types of compositions with three types of elements and then preparing other several elements to be mixed in each of the 250 types of compositions, several thousands of DNA probes can be discriminated and detected.

As elements available for preparing various compositions, three to five types of elements may be selected from the group including gallium, aluminum, yttrium, erbium, polonium, cesium, cobalt, titanium, nickel, and iron. To fix a probe, in addition to a reaction between gold and an SH group, in a case of an alloy having an oxidized surface, the probe DNA can be fixed by introducing a functional group using the silane coupling reaction.

As described above, a concept of the twenty-sixth embodiment of the present invention is completely different from the ordinary concept for a DNA chip in which different probes are required to be fixed in an extremely large number of zone elements. An expression of mRNA can be analyzed within a short period of time by simply trapping mRNAs on a chip with poly T fixed thereon, hybridizing synthetic DNA probes with nanoparticles having different compositions respectively labeled thereon to the mRNAs, and analyzing the reaction products with a scanning electron microscope.

Using the chip with DNA probes changed to antibodies for biological materials (such as proteins) fixed on the substrate, several thousand epitopes can be analyzed all at once.

In a second aspect of the twenty-sixth embodiment as a development of the configuration in the first embodiment, particles prepared with differential elemental compositions respectively are prepared and used for fixing specific probes. That is, a particle having a specific elemental composition can be used for fixing a specific probe. On the other hand, target DNA fragments to be hybridized to probes fixed on the particles are labeled with particles of gold for counting. The probes are hybridized to the target DNA fragments by mixing the particles with the probed fixed thereon and the target DNA fragments in a solution. This processing is performed in a specified zone in a vessel or in a specified zone, and then the particles are washed and recovered. To wash and recover the particles, centrifugation may be employed, or the supernatant may be replaced. When the particles contain any magnetic material, the particles may be recovered with a magnet with the supernatant replaced. After the processing, the particles are dried and fixed on a prespecified zone on the substrate. As a result, the target DNA fragments can be assessed by indexing the particles and counting the gold particles used for labeling.

In this second aspect, hybridization of probes fixed on particles and target DNA fragments can be performed in the state where the particles are suspended in a solution, so that such problems associated with hybridization occurring on an interface between a solid phase and a liquid phase as heterogeneous reactions, low reaction speed due to dispersion of molecules, and low reaction rate are substantially alleviated. As treated as a suspension, specific vessels and pipets and any special technique are not required, which is advantageous. The technique used to the labels for the target object materials may be applied to this particle indexing. In other words, by directing electros to the particles under a scanning electron microscope to obtain an SEM image identifying positions and sizes of the particles, and also by sensing the characteristic X ray generated when the particles are irradiated by electrons with an energy dispersive X ray detector to obtain an elemental analysis image, and particles fixed on a zone on the substrate are indexed by comparing the two images above with each other. The particles are fixed on the zone on the substrate. Descriptions of this example above assume use of the energy-dispersive X-ray detector, but a method with high sensitivity such as the wavelength dispersive X-ray spectroscopy (WDX) may be employed. Rather the wavelength dispersive X-ray spectroscopy may be more adapted to the twenty-sixth embodiment because the method is excellent in X-ray wavelength resolution.

When an object for measurement is a protein or a sugar chain, the immunoassay technique is employed. In other words, indexing particles each with an antibody molecule reactive to a particular epitope and antibodies fixed to nano-particles of gold for labeling are used. In this case, both of the antibodies fixed to the indexing particles and particles for labeling contain an antigen molecule sandwiched with an antibody specific to an object for measurement and form hybrids of indexing particle, antigen, and gold nanoparticle for labeling. Alternatively the antigen is sandwiched with a second antibody universally reacting to the indexing particle with a specific antibody fixed thereon and an antibody not labeled. In any method, a number of antigens are indexed in use for quantitative detection.

To fix the hybrids of indexing particle, mRNA, and gold nanoparticles for labeling or the indexing particle-antigen-gold nanoparticles for labeling hybrid onto the substrate, a suspension of each hybrid may be dripped and dried thereon, or more reasonably a magnetic substance is used for the indexing particle, and the indexing particle is attracted onto the substrate with a magnet, and then the solution is scattered off with a blower or the like for drying.

As described above, the concept of this embodiment is completely different from the concept for ordinary DNA probe chip that different probes must be fixed in a number of zone elements. The concept of this embodiment provides a analyzing technique capable of analyzing types and quantities of several thousands to several tens of thousands of mRNAs or proteins all at once by making the indexing particles, samples, and labeling particles reacting to each other and observing the reacting situation with a scanning electron temperature.

The DNA chip 1 according to the twenty-fifth embodiment shown in FIG. 125 may be employed as the DNA chip in the twenty-sixth embodiment.

An aspect in which probes are fixed on the DNA chip according to the twenty-sixth embodiment and indexing particles conjugated to the samples captured by the probes are observed with a scanning electron microscope is the same as that of the twenty-fifth embodiment shown in FIGS. 126 and 127, and therefore description thereof is omitted here.

An SEM with low resolution or an X-ray detector with the resolution of about 0.1 μm may be used as a simple version for detection when indexing particles conjugated to the captured samples are observed under a scanning electron microscope. The device with low resolution as described above is so compact that the device can be installed on a desk, and in addition, the price is lower than an SEM with the ordinary X-ray detector. Alternatively, en electron probe X-ray microanalyser (EPMA) based on an electron beam microprobe capable of performing elemental analysis within a range of 1 $\mu m^2$ may be used, and the method is described below. With the resolution of about 0.1 μm, nanoparticles of gold can not be counted, nor can be obtained an elemental analysis image thereof. In this case, an elemental analysis value for each element within the range irradiated by X ray is obtained. In this example, too many types of elements can not be used for labeling each DNA probe, and only two to three elements may be used for labeling one particle, and allowable elemental compositions are about three types. When a particle is labeled with one element, variation in labeling is allowable according to a number of used elements, and in this case, several tens of DNAs or biological materials can be analyzed simultaneously.

EXAMPLE 1

FIG. 128 is a diagram showing a concept for measurement of a biological sample in the twenty-sixth embodiment. This measurement is characterized by using indexing particles. No probe is fixed on the silicon substrate 101. The silicon substrate 101 is a vessel for measurement only having a prespecified area, and is used for fixing indexing particles in measurement. The size is 20×20 mm. There is only one indexing particle fixing area 102, and the diameter is 3 mm. SU8 is applied on the silicon substrate 101, and a bank 103 is formed by curing SU8 with UV ray. Needless to say, the bank 103 may be formed by directly engraving the base. There is not restriction over a structure of the bank 103 so long as a liquid is contained therein, but because sometimes an aqueous solution containing 70% alcohol may be contained therein, and in this case the height should preferably be 150 μm or more.

Reference numerals 41 to 44 are indexing particles composed with elemental compositions different from one another. The indexing particles correspond to the nanoparticles of gold 21-24 for labeling with different elemental compositions respectively in the first aspect, but are different from the latter in the following points. In the first aspect, the gold nanoparticles 21-24 for labeling have different elemental compositions respectively, and specific biological materials (such as, for instance, target DNA fragments) are detected by directing electrons to the gold nanoparticles to check X-rays having different wavelengths specific to elemental compositions of the gold nanoparticles for identifying each discrete nanoparticles of gold. In contrast, in the second aspect, the indexing particles 41 to 44 are directly used each for fixing a probe thereon, and in addition, particles for labeling are used for counting specific biological materials captured by the probe. That is, in the second aspect, positions of indexing particles are identified by making use of the fact the indexing particles 41 to 44 irradiated with electron beams generate X-rays having different wavelengths specific to elemental compositions of the particles 41 to 44 respectively and then specific biological materials captured by the indexing particles are detected. Particles including, in addition to gold, a plurality of elements are used for indexing, and gold nanoparticles are used for counting.

A particle as a base for the indexing particle is made of polystyrene not to prevent detection of elements for labeling in the indexing particles during the process of elemental analysis. Alternatively, polystyrene magnetic particles with a paramagnetic material such as iron or cobalt embedded therein may be used. In this case an element for labeling is deposited and fixed on a surface of the particle. There are variable methods available for preparing particles for labeling in addition to deposition of an element. For instance, a prespecified number of elements may be kneaded in a polystyrene sphere as a nanoparticle. In this case, an element signal from each particle can be obtained by raising energy of the emitted electron beam so that the electron beam reaches inside the polystyrene sphere.

When magnetic particles are used, there is provided the advantage that operations for reactions and those for detecting particles can advantageously be performed with a magnet. In a case of the ordinary polystyrene, operations can smoothly be performed by recovering particles by centrifugation or with a filter.

The solid black circle attached to each of the indexing particles 41 to 44 is a labeling particle for counting. As described below, this is a labeling particle for a specific biological material captured by a probe fixed on each of the indexing particles 41 to 44. The indexing particles 41 to 44 are fixed on the indexing particle fixing area 102 (with a diameter of 3 mm) on the silicon substrate 101. After the specific biological materials are captured by the probes fixed to the indexing particles 41 to 44 by mixing the indexing particles 41 to 44 and a sample containing the target biological material labeled with a labeling particle in a solution, and then the mixture solution is dripped by a prespecified volume onto the probe fixing area 102 and dried to fix the indexing particles to the indexing particle fixing area 102.

When a base for the indexing particle is a polystyrene particle, after 1 µl of the mixture solution is dripped onto the probe fixing area 102 and dried in the depressurized state to fix the indexing particles. For this purpose, it is necessary to add a mechanism for holding a droplet in the indexing particle fixing area 102, and in Example 3, SU8 is applied on the substrate 101 and then the bank 103 is prepared by curing with UV ray. Needless to say, the bank 103 may directly be formed on the substrate 101 by etching. There is no specific restriction over a structure of the bank 103 so long as a liquid can be preserved therein, but as described below, sometimes an aqueous solution containing 70% alcohol must be preserved therein, and in this case the height is required to be at least 150 µm.

In the state where the indexing particles have been fixed on the indexing particle fixing area 102, like in Example 1, the substrate 101 is set in a scanning electron microscope 300 having an energy dispersive X-ray detector or a wavelength dispersive X-ray spectrometer. The scanning electron microscope 300 has an electron gun 300-1, a focusing lens 300-2, and a scanning coil 300-3, and electrons emitted from the electron gun 300-1 collide against the indexing particles 41-44, which emit the second electrons 300-5. The secondary electrons are captured by the detector 300-6. The so-called SEM image is made based on the secondary electrons detected by the detector 300-6, so that positions and sizes of the indexing particles 41 to 44 are identified. Further, the labeling particles coupled to surfaces of the indexing particles 41 to 44 are detected. There is also provided an energy dispersive X-ray detector or a wavelength dispersive X-ray spectrometer 300-8 for detecting X-ray 300-7 having wavelength specific to elements constituting each indexing particle. That is, an elemental analysis image is obtained from the wavelength signals corresponding to the constituent elements detected by the energy dispersive X-ray detector or a wavelength dispersive X-ray spectrometer 300-8. With this configuration, the indexing particles can indicate types of probes fixed on the surfaces thereof with the size and constituent element.

FIG. 129 is a diagram illustrating the operations for identifying positions and sizes of the indexing particles 41 to 44 from an SEM image obtained with the detector 300-6 as well as from an elemental analysis image obtained by the energy dispersive X-ray detector 300-8 and assessment of the specific biological materials with the labeling particles hybridized to the indexing particles 41 to 44 added thereto. In the following descriptions, the elemental compositions (gallium:aluminum:yttrium:chromium) of the indexing particles 41 to 44 are (1:1:1:0) in the indexing particle 41, ((1:1:0:1) in the indexing particle 42, ((1:0:1:1) in the indexing particles 43, and (0:1:1:1) in the indexing particle 44, and also it is assumed in the following descriptions that diameters of the particles are in the range from 0.5 to 5 µm.

In FIG. 129, reference numeral 50 indicates an SEM image. All of the indexing particles 41 to 44 and labeling particles for the specific biological materials captured on the indexing particles 41 to 44 are shown in the SEM image. Reference numerals 51, 52, 53, and 54 are elemental analysis images for a chromium image, an yttrium image, an aluminum image, and a gallium image respectively. Comparing the SEM image 50 to the chromium image 51, yttrium image 52, aluminum image 53, and gallium image 54, it is understood that an particle image at a position corresponding the indexing particle 41 indicated by a broken line is not shown in the chromium image 51. Likewise, particles image at positions corresponding to the indexing particles 42, 43, and 44 shown in the SEM image 30 are not shown in the yttrium image 52, aluminum image 53, and gallium image 54. That is, the indexing particles 41, 42, 43, and 44 do not include chromium, yttrium, aluminum, and gallium each as a constituent element for each particle respectively, so that the images are not shown in the elemental analysis image. When the labeling particles are gold nanoparticles, the particle image is principally not shown in the elemental analysis image. When the labeling particles is irradiated with electron beams and emit X-rays having the specific wavelength close to that emitted from the constituent elements in the indexing particles, the particle images are shown in the elemental analysis image. Therefore, noise is included more as compared to the SEM image 50, but the noise does not substantially spoil execution of the elemental analysis.

Therefore the indexing particles 41 to 44 are discriminated and identified by comparing the SEM image 50 to the elemental analysis images 51 to 54. Further, because the labeling particles are shown in the SEM image 50, by counting the particles and integrating the counts with a result of identification of the indexing particles 41 to 44 for assessment, how many labeling particles are included in each of the indexing particles, in other words, which specific biological material is present in the sample can be accessed. For simplification, the descriptions above assume a case in which four particles each having the same size are used for checking whether a particular element is present in a particle or not, but by preparing indexing particles having different diameters at a level where the sizes can be identified in an SEM image and also changing the elemental compositions of the indexing particles to various values at a level where the indexing particles can be recognized in the elemental analysis images, a number of types of indexing particles can be increased according to a product of a particle diameter×a number of elemental compositions×a quantity of each constituent element. For instance, when indexing particles with different diameters in four stages in the range from 0.5 to 5 μm and also with different elemental compositions in 10 stages, 40,000 types of indexing particles can be obtained.

Descriptions are provided below of elements that may be used as indexing particles. Elements that can be analyzed with the energy dispersive characteristic X-ray detector 300-8 ranges from B, a fifth element up to U, a $92^{nd}$ element in the periodic table. Any element in this range can be detected if the element is contained by 1% or more. Resolution of a device or spectrum ascription can be classified to about 10 grades in the range from 1% to about 20% in the determination characteristic analysis. When a magnetic particle is used as a base particle, elements involving in magnetism cannot be employed for indexing. Therefore, Fe, Co, and Ni cannot be used for indexing. C, N, and O are also contained in polystyrene, so that the elements cannot be used. The elements Fe, Co, Ni, C, N, and O exist a lot in the nature, and the elements may be introduced as a result of contamination from the outside, so that the elements should not be used. For the same reason, alkali metals (group I) and alkali earth metals (group II), and other metals in groups, 15, 16, and 17 up to As should be excluded, and elements belonging to group 18 are gases, so that the elements should be excluded. Al, Si, Mo, Sn exist a lot in the ordinary environment. V belong to family 5 is excluded because the element existing in living organisms relatively a lot. Also Tc, Pm, Ac, Pa, and U having no or few stable isotopes should be excluded. Hg itself exists as a liquid. Elements other those listed above may be used for indexing. That is, the elements available for indexing are Sc, Ti, Ga, Ge, Y, Zr, Nb, Ru, Rh, Pd, Ag, Cd, In, Sb, La, Ce, Pr, Nd, Sm, Eu, Gd, Tb, Dy, Ho, Er, Tm, Yb, Lu, Hf, Ta, W, Re, Os, Ir, Pt, Au, Tl, Bi, and Th.

FIG. 130(A) is a diagram schematically showing the indexing particles 41 to 44 and probes 41*a*, 42*a*, 43*a*, and 44*a* fixed on surfaces of the indexing particles 41 to 44, FIG. 130(B) is a view schematically showing specific biological materials 41*b*, 42*b*, 43*b*, and 44*b* hybridized to the probes 41*a*, 42*a*, 43*a*, and 44*a* each with a labeling particle added thereto, and FIG. 130(C) is a diagram schematically showing the situation in which the probes and specific biological materials hybridize with each other. The following descriptions assume a case in which a DNA probe is used as a probe.

As shown in FIG. 130(A), specific probes are fixed to surfaces of the indexing particles 41 to 44 respectively. Any known method may be used for fixing the probes to the indexing particles. For instance, oxygen plasma is directed to the indexing particles to generate an active group on the surface thereof, then 3-aminoethyl aminopropyl trimethoxysilane is reacted to the indexing particles to introduce an amino group into the surface, the amino group is converted to a carboxylic group with succinic acid anhydride, this carboxylic group is changed to succinimide ester, and a probe DNA having an amino group at the 5' terminal may be fixed thereto. When PNA is used as a probe DNA, the amino terminal of the probe DNA is used to fix the probe on the surface as above. Needless to say, the specific biological materials 41*b*, 42*b*, 3*b* and 44*b* hybridized to the probes 41*a*, 42*a*, 43*a*, and 44*a* shown in FIG. 130(B) have sequences complementary to the probes 41*a*, 42*a*, 43*a*, and 44*a*. The specific biological materials with labeling particles such as nanoparticles of gold (20 nm) fixed thereon are prepared by preparing a sequence having an SH group at the 5' terminal and mixing the sequence with the nanoparticles of gold. The indexing particles 41 to 44 are mixed with a sample solution containing the specific biological materials to hybridize the specific biological materials to the probes 41*b*, 42*b*, 3*b* and 44*b*. Then the hybrid is dripped at a certain amount onto the indexing particle fixing area on the substrate 101, dried and scanned under the scanning electron microscope 300 as described above to obtain an SEM image and elemental analysis images as described above. The assessment is performed with the method described with reference to FIG. 129.

EXAMPLE 2

Descriptions are provided for a case in which the technique described in Example 1 is applied for quantitatively detecting specific biological materials directly from a mixture of mRNA or by cDNA converted.

FIG. 131(A) is a view schematically showing the indexing particles 41 to 44 and probes 41*a*, 42*a*, 43*a*, and 44*a* fixed onto surfaces of the indexing particles 41 to 44; FIG. 131(B) is a view schematically showing a specific biological material with poly A hybridizing to each of the probes 41*a*, 42*a*, 43*a*, and 44*a*; and FIG. 131(C) is a view schematically showing the poly T hybridizing to the poly A.

As shown in FIG. 131(A), also in Example 4, configuration of each of the indexing particles 41 to 44 is the same as that described in Example 3. Namely specific probes 41*a*, 42*a*, 43*a*, and 44*a* are fixed to the indexing particles 41 to 44 respectively. As shown in FIG. 131(B), poly A is added to the specific biological materials 41*b*, 42*b*, 43*b*, and 44*b*. It is needless to say that the probes 41*a*, 42*a*, 43*a*, and 44*a* are complementary to the specific biological materials 41*b*, 42*b*, 43*b*, and 44*b* respectively, but when mRNA is directly detected, 1) a sequence complementary to a 30- to 50-base sequence ranging from the exon closest the poly-A terminal of mRNA to the second exon thereof is used as a probe. 2) When measuring as a cDNA, if a single-stranded cDNA (prepared by removing mRNA sequence, after cDNA is synthesized, with RNase, and complementary to the mRNA) is used as a sample, the 30- to 50-base sequence ranging from the exon closest the poly-A terminal of mRNA to the second exon thereof in the same side as the mRNA is used as a probe. In this case, a probe based on a sequence complementary to cDNA is used in the probes in place of probes 41*a*, 42*a*, 43*a*, and 44*a* shown in FIG. 131(A); a single-stranded cDNA is used in place of the specific biological materials 41*b*, 42*b*, 43*b*, and 44*b* shown in FIG. 131(B); and a poly A is used in place of the poly T conjugated to the labeling particle shown in FIG. 131(C) each as a probe. 3) When a double-stranded dDNA is used as a sample, a portion of the sequence close to the 3' terminal (30 to 50 bases) from the poly-A terminal of human mRNA sequence to the site where the first MboI sequence appears is used as a probe. In this case, a combination of a probe having the same sequence as that of the mRNA and poly T conjugated to the labeling particle shown in FIG. 131(C) is used in places of the probes 41a, 42a, 43a shown in FIG. 131(A), or a combination of a probe having the sequence complementary to that of the mRNA and poly A conjugated to the labeling particle shown in FIG. 131(C) is used in places of the probes 41a, 42a, 43a shown in FIG. 131(A). When a double-stranded dDNA is used, any desired synthetic DNA can be introduced to the MboI-cut-off-terminal of the dDNA by a ligation reaction using the DNA ligase. In the case, a sequence complementary to the synthetic DNA in place of the poly T is conjugated to a labeling particle shown in FIG. 131(C).

Descriptions are provided below for the case 1) as a representative case. For fixing probes to the indexing particles shown in FIG. 131(A), any known method may be used. For instance, oxygen plasma is irradiated to the indexing particles to generate an active group on a surface thereof, then an amino group is introduced to the surface by reacting 3-aminoethyl aminopropyl trimethoxysilane thereto, then the amino group is converted to a carboxylic group with a succinic acid anhydride, the carboxylic group is converted to succinimide ester, and a probe DNA having an amino group may be added to the 5' terminal of the ester. When PNA is used as a probe DNA, the amino terminal of the probe DNA is processed according to the same procedure.

As shown in FIG. 131(C), poly T-gold nanoparticles with poly T (T30) (SEQ ID NO: 18) fixed thereto (with the size of 20 nm) is prepared. For fixing poly T to the gold nanoparticles, a sequence having an SH group at the 5' terminal is synthesized, and the sequence is mixed with the gold nanoparticles.

The mixture solution containing the sample mRNA shown in FIG. 131(B) (containing the RNase inhibitor), a suspension of indexing particles shown in FIG. 131(A), and a suspension of the poly T-gold nanoparticles shown in FIG. 131(C) are mixed and a mixture solution is heated to 70° C. 0.1 to 1-M NaCl and 50-mM citric acid (pH 7) containing a surface active agent as a dispersant are used as the reaction liquid. The reaction liquid is mildly agitated for one hour at 45° C. to always keep the particles in the suspended state. In this step, the mRNAs 41b, 42b, 43b, and 44b are captured by the indexing particles 41 to 44 having the complementary probes 41a, 42a, 43a, and 44a, and the poly T-gold nanoparticles are conjugated to the poly A portions of the captured mRNAs.

FIG. 132 is a view schematically showing a result of operations for mixing particles, a sample, and labeling particles to obtain hybrids among the DNA probes 41a, 42a, 43a, and 44a, mRNAs 41b, 42b, 43b, and 44b, and poly T-gold nanoparticles. In each hybrid, the indexing particle correspond to a probe on the surface, and further the probe corresponds to each mRNA. In this case, poly T in some poly T-gold nanoparticles may be conjugated to poly A in mRNA in the reverse direction, or off by one base, but these phenomena do not give substantial damages to the effect provided in the twenty-sixth embodiment. In FIG. 132, the probes 41a, 42a, 43a, and 44a fixed to the indexing particles 41 to 44 respectively at the 3' terminal thereof and gold nanoparticles with poly T fixed at the 5' terminal are used. For the reason described above, the complex structure as shown in FIG. 132 is provided, but also indexing particles 41 to 44 with the probes 41a, 42a, 43a, and 44a fixed thereto at the 5' terminal may be used.

The substrate having the hybrids obtained in Example 2 can be assessed by irradiating an electron beam to the substrate with the scanning electron microscope 300 for scanning to obtain an SEM image and an elemental analysis image, and according to the method described with reference to FIG. 129.

FIG. 133 is a view showing the situation during processing expected to provide an assessment result with higher precision as compared to the result provided by the homogeneous reaction described with reference to FIG. 132 in which the indexing particles, sample mRNAs, and poly T-gold nanoparticles are simultaneously reacted. At first, the DNA probes 41a, 42a, 43a, and 44a fixed on the indexing particles 41 to 44 are reacted to the mRNAs 41b, 42b, 43b, and 44b to prepare hybrids between the indexing particles and the sample mRNAs and unnecessary components are washed away. Then the hybrids may be reacted to the poly T-gold nanoparticles shown in FIG. 132.

In Examples 1 and 2, a plurality of biological materials contained in the sample can simultaneously be discriminated and detected by the indexing particles with specific probes fixed thereto. In this step, the reaction between the samples and indexing particles can be performed in batch in the suspended state, so that, different from the DNA microarrays or protein arrays in which a reaction is performed on a surface of the substrate, the reaction can be carried out homogeneously and the reaction speed is faster because the particles are dispersed in the solvent, which advantageously enables simultaneous measurement for multiple items.

For instance, a colon cancer tissue piece cut off from the affected area is frozen with liquid nitrogen, and the frozen piece is directly added to phenol chloroform and homogenized, and then the total RNA is extracted in the examples described above, but in this example, 0.1% (W/V) solution of magnetic particles (2.8 µm) containing gallium, yttrium, cesium, osmium, and platinum with various probes fixed thereto at 8 different contents mixed in 50 µl of total RNA solution is added as indexing particles for discriminating sequences having about 40-base length complementary to various mRNAs. Under the conditions of salt concentration of 1 M and citric acid concentration of 50 mM, the reactants are left for one minutes at 70° C. and mildly agitated at 45° C. for hybridization. Then a magnet is approached from outside of the vessel to attract magnetic particles with the supernatant removed, and then the reaction products are washed with 1M NaCl and 50 mM citric acid buffer solution (pH 7). The gold nanoparticles are suspended in the buffer solution and the mixture solution is agitated for one hour at the room temperature.

The indexing particle-mRNA-gold nanoparticle-labeled poly T complex produced through the hybridization reaction is collected on a wall of the vessel using a magnet and washed with 1-M Na Cl and 50-mM citric acid buffer solution (pH 7), and then is washed with a 70% ethanol aqueous solution, and is suspended in 100 µl of 70% ethanol. 1 µl of the mixture solution is dripped onto the vessel 102 (See FIG. 128) in Example 1, and is dried for 3 hours in the depressurized state. A substantially long period is consumed for drying in the depressurized state so that high vacuum in the scanning electron microscope will not be affected.

The particle hybrids prepared as described above are observed with a scanning electron microscope. In this step, the number of gold colloidal particles captured on surfaces of the magnetic particles can be counted. Then the operating mode is switched to the detection mode with the energy dispersive characteristic X-ray detector. When the electron beam 300-4 collides the indexing particles, X-rays having various wavelengths specific to elements on the surfaces of the indexing particles are generated. The X-rays with specific wavelengths are detected with the energy dispersive characteristic X-ray detector or wavelength dispersive characteristic X-ray detector 300-8 to perform elemental analysis. With this operation, the magnetic particles coupled to the gold nanoparticles can be indexed, and quantities of mRNA molecules with the corresponding gold nanoparticle-labeled probes hybridized thereto can be identified. In this state, one gold nanoparticle corresponds to one mRNA molecule.

When the indexing particles with different concentrations of gallium, cesium, osmium, and platinum each as an element for indexing at 8 grades are used, 25000 types of human mRNAs can be measured in batch.

As described above, by using particles with various contents of various elements according to the twenty-sixth embodiment, it is possible to profile each mRNA at a single molecule level without using the prior art-based probe chips having a complicated structure and very difficult to be manufactured and also by using the particle counting technique.

EXAMPLE 3

In Examples 1 and 2, particles for detection and quantification having the poly T having the same sequence as that of the indexing particles each with a discrete probe DNA fixed thereto are used. But in Example 3, for further raising the specificity, it is possible to develop a system in which the indexing particles 41 to 44 having discrete sequence probes 41a, 42a, 43a, and 44a respectively and labeling particles having the probes 41d to 41d corresponding to the indexing particles 41 to 44 respectively are used. Descriptions are provided below for this system.

FIG. 134(A) is a view schematically showing the discrete probes 41a, 42a, 43a, 44a and 45a similar to examples 1, 2; FIG. 134(B) is a view schematically showing the state in which the probes 41c, 42c, 43c, and 44c are further added to the specific biological materials 41b, 42b, 43b, and 44b each having poly A hybridizing to the probes 41a, 42a, 43a, and 44a respectively as samples having mRNA sequences to be measured; and FIG. 134(C) is a view schematically showing a case in which the synthetic oligonucleotides (with the 20- to 50-base length) 41d, 42d, 43d, and 44d complementary to the probes 41c, 42c, 43c, 44c, and 45c having the sequence described above (the specific material 45c is not included in the samples shown in FIG. 134(B) are labeled with gold nanoparticles (20 nm). FIG. 134(D) is a view showing the state of the indexing particles, samples, and oligonucleotides labeled with gold nanoparticles after hybridization.

The indexing particles 41 to 45 with the probes 41a, 42a, 43a, 44a, and 45a fixed thereon are reacted to the samples with mRNA mixed in shown in FIG. 134(B) to selectively capture the probes with the probes 41b, 42b, 43b, and 44b of the sample mRNAs onto the indexing particles, and then gold nanoparticles (20 nm) having synthetic oligonucleotides 41d, 42d, 43d, and 44d (with the 20 to 50 base length) having sequences complementary to the sequences corresponding to the indexing particles, namely to other portions 41c, 42c, 43c, and 44c of the same mRNAs are reacted thereto. Magnetic particles are used as the indexing particles. At first, indexing particles for the mRNA existing a lot such as β-globin or β-actin included in the mRNA are added, and only the reacted ones are attracted with a magnet to remove it. In this step, only unnecessary mRNAs are removed, and therefore the time required for hybridization may be short, for instance, 15 minutes. Then indexing particles for mRNA to be measured are added and reacted for 30 minutes, and then particles not reacted yet are removed by washing. Further gold nanoparticles having probes for the mRNAs are added and reacted for 30 minutes. What is important in this step is that the synthetic oligonucleotides 41d, 42d, 43d, 44d, and 44d labeled with gold nanoparticles are mixture materials. Therefore, gold nanoparticles 46 are detected only in the hybrids 41e, 42e, 43e, and 44e among the obtained particle hybrids, and the gold nanoparticles are actually not detected in the 45e not including a target material therein.

Merits provided in Example 3 are as described below. Assume, for instance, that mRNA has a similar sequence. Also assumes a case in which the mRNA 41b shown in FIG. 134(B) hybridizes not only to the probe 41a fixed on the indexing particles, but also the probe 42a. This types of phenomenon often occurs in DNA hybridization. In other words, in addition to the mRNA having the target sequence 42b, also mRNA having the sequence 41b is sometimes captured as an artifact on a surface of the indexing particle 42. In this step, by reacting a group of probes containing the sequence 41d and a group of probes containing the sequence 42d shown in FIG. 134(C) discretely, it is possible to separate and count even the mRNA which can not be separated and identified with the probe sequence on the indexing particles by remarking the difference in the probe sequences as shown in FIG. 134(C). In a group of indexing particles each having a sequence corresponding to an indexing bead with gold nanoparticle not added thereto, the gold nanoparticles are not coupled to the surface of the indexing particle 42a, so that the gold nanoparticle is not detected.

EXAMPLE 4

Figure 135:
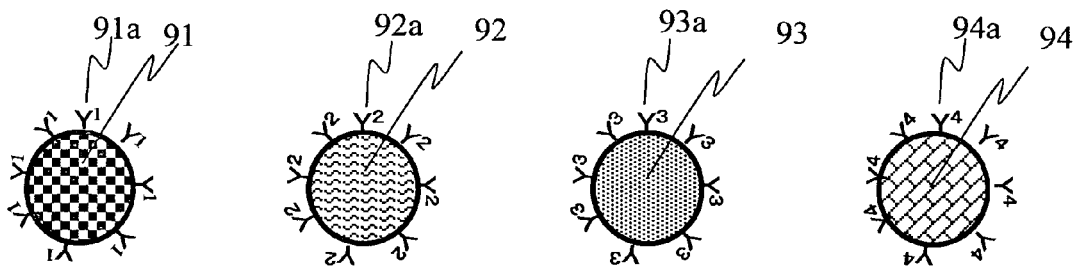
Figure 135:
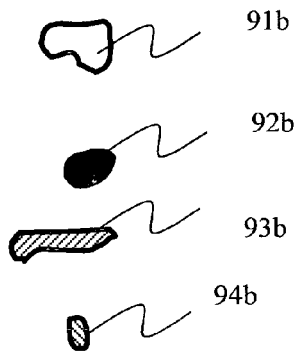
Figure 135:
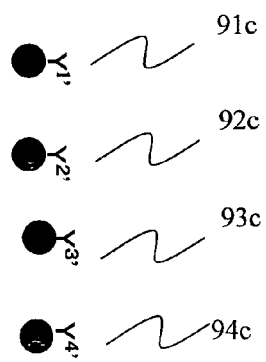
Figure 135:
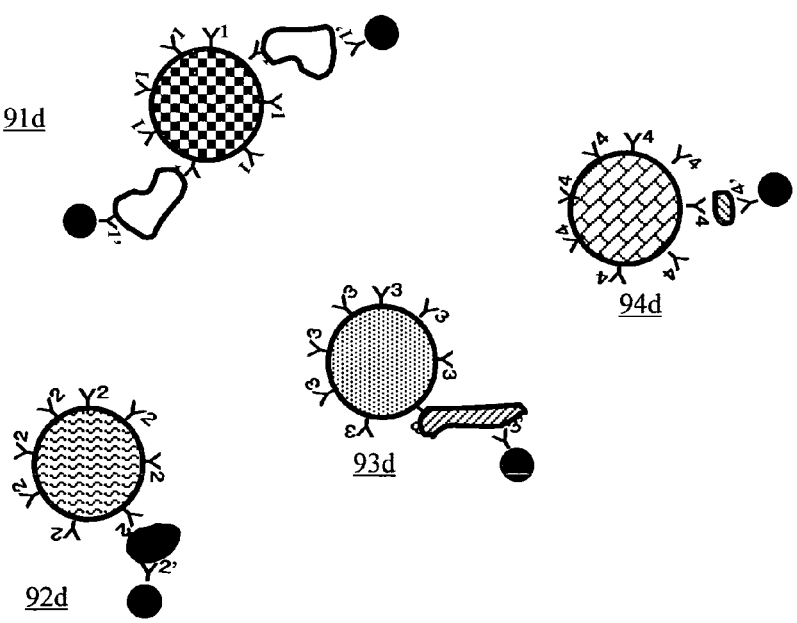

In Example 4, detection of multiple biological materials through the antigen-antibody reaction is described with reference to FIG. 135.

At first the F(ab')$_2$ fragment is prepared by decomposing various types of monoclonal antibodies with papain. Magnetic particles (3 μm) coated with polystyrene containing Hf, Pt, and Ce each at the concentrations of 0, 1, 2, 3, 4, 6, 8, and 10 weight percents respectively are prepared as indexing particles. Different F(ab')$_2$ fragments 91a, 92a, 93a, and 94a are fixed to the indexing particles 91, 92, 93, and 94 to obtain the F(ab')$_2$ fragment-labeled indexing particles. Any known method may be employed for fixing the F(ab')$_2$ fragment. For instance, a minute quantity of a monomer with a functional group introduced therein is mixed in polystyrene and the functional monomer exposed on the surface may be used for fixing the F(ab')$_2$ fragment, or the surface is oxidized by oxygen plasma so that 3-aminoethyl aminopropyl trimethoxysilane is reacted with the amino group introduced into the surface thereof, then the amino group is converted to a carboxylic group with succinic acid anhydride, then the carboxylic group is changed to a form of succinimido ester. Then a probe DNA having an amino group at the 5' terminal can be fixed thereto. As the F(ab')$_2$ fragment, for instance, antibodies to AFP91b, CEA92b, EpCAM93b and the like may be used. The F(ab')$_2$ fragment mixture is coated with sphingolipids. Serums (from healthy people and those suffering from liver cancer) doubly diluted with 2×PBS (1×PBS: 0.15M NaCl, 50 mM sodium phosphate buffer solution (pH 7.4)) containing 0.2% Tween 20 is added to the F(ab')$_2$-labeled indexing particle mixture. After agitated for 10 minutes at 37° C., the indexing particles are attracted with a magnet to the vessel wall, and the supernatant is discarded. The reaction product is washed with PBS containing 0.1% Tween 20. Monoclonal antibodies labeled with gold nanoparticles 91c, 92c, 93c, and 94c are added to the monoclonal antibodies for antigens to be measured (those having different epitopes from the F(ab')$_2$ fragments fixed on the indexing particles). Also the monoclonal antibodies are labeled with the F(ab')$_2$ fragment respectively, and about three SH groups are introduced for molecule with iminothiolan, and the SH group is labeled with the gold nanoparticles (20 nmφ). Reference numeral 91c indicates a gold nanoparticles-labeled antibody to AFP, reference numeral 92c indicates a gold nanoparticles-labeled antibody to CEA, reference numeral 93c indicates a gold nanoparticles-labeled antibody to EpCAM, and reference numeral 94c indicates a gold nanoparticles-labeled antibody to other antigens. The reacting materials are left for 10 minutes at 37° C. to obtain indexing particle-antigen-gold nanoparticle particle hybrids 91d, 92d, 93d, and 94d with the supernatant discarded, and the hybrids is washed with PBS containing 0.1% Tween 20, and is then washed with 50% ethanol dissolved in deionized water. In this step, proteins are denatured, but the indexing particle-antigen-gold nanoparticle particle hybrids do not collapse. 1 µl of the solution is added on the vessel 102 shown in FIG. 128 and dried in the depressurized state. Then recognition of the forms and elemental analysis are performed with a scanning electron microscope.

As a result, 64 gold nanoparticles are found on a surface of the indexing bead for AFP in a serum from healthy people, and 3200 gold nanoparticles in a serum from people suffering from cancer, which indicates that more gold nanoparticles are found in serums from people suffering from cancer. There is no substantial fluctuation in CEA or EpCAM, and in any of the samples, only about 30 to about 100 gold nanoparticles are obtained on surfaces of indexing beads to the antigens.

As described, the twenty-sixth embodiment of the present invention can be carried out in various forms, and in any case, hybridized sample DNA molecules or the like are detected one by one, so that the sensitivity substantially higher than that provided by the conventional methods is provided. An extremely minute quantity of DNA (RNA) can be detected with an extremely small volume of samples, and therefore a target DNA (RNA) can be detected without performing pre-amplification with PCR as required in the conventional techniques. Further labeling particle used for detection can be changed in its size and form, so that 6 to about 10 different types of samples can be analyzed in batch with the same element. This technique can be applied not only to the differential hybridization, but also to a method in which sample nucleotides are captured with the same probe and detected with different labeling probes. With the multiplex analysis method according to the twenty-sixth embodiment of the present invention, detection of alternative splicing or typing of a plurality of SNPs can advantageously be performed with one element.

[XXVII] Twenty-Seventh Embodiment

A twenty-seventh embodiment discloses a gel plate having the shape designed to reliably collect a separated substance of high purity from a separation gel spot for two-dimensional electrophoresis gel after the separation by electrophoresis, an electrophoretic separated substance collecting device, and a method of collecting an electrophoretic separated substance for collecting the separation gel spot while observing the same.

Considering the technique for collecting an electrophoretic separated substance to date, one will find that there is a problem in cutting out gel after separation. When the technique is automated, a separated band is recognized to cut out a position corresponding to the band; however, it is often difficult to cut it out while observing because a cut-out jig obstructs the view. Though it is typical to capture images and conduct a cut-out based on the image data, a delicate cut-out is difficult to cut out tender gel. When an electrophoretic separated substance is collected using an electrode, the electrode is moved to a spot position referring to captured images, as the electrode forms an obstacle.

In the twenty seventh embodiment, an electrophoretic separated substance included in a gel spot is collected while confirming the position and shape of the gel spot. For this purpose, gel is collected after being melted with the photothermal conversion using light. It is desirable that gel turns to be a thin layer with the thickness of 0.5 mm or less, preferably 0.2 mm or less, and is configured to contact a substrate in order to prevent a melted range from broadening owing to thermal diffusion. Convergence light is employed because the irradiated light is required to be sufficiently small as compared to a spot. In addition, as light needs to convert into heat, laser at 1480 nm is employed. Laser is absorbed into water in gel to generate heat. As it is necessary for gel to be melted by heat, gel used herein includes agarose, linear polyacrylamide, dimethylcellulose and the like including agarose, copolymers of agarose and linear polyacrylamide, dimethylcellulose and the like. When protein is to be separated, in particular, the aforementioned gel including low melting point agarose having a melting point of 60° C. or less is used.

EXAMPLE 1

FIG. 136 is a view schematically showing the situation in which a separated band is formed by electrophoresis in Example 1. FIGS. 137(A), 137(B) and 137(C) are views schematically showing melting and collection of the separated band with heat described in FIG. 136. Herein descriptions are provided for an example of separating a PCR product with the one-dimensional electrophoresis.

A sample used herein is amplified products form cDNA of human mRNA prepared by PCR amplification using synthetic oligo DNAs (concentration: 0.2 pmol/µl) having the sequence identification No. 1 and No. 2 as primers respectively, which is according to the conventional technology. In the PCR, a cycle of denaturation at 94° C. for 5 seconds, and annealing at 55° C. for 10 seconds and at 72° C. for 10 seconds is repeated 35 times. The quantity of a reaction solution is 2 µl. The base length of the PCR product predicted from the database is 233 bp.

```
CTGAGCGAGT GAGAACCTAC TG:        (SEQ ID NO: 1)

AGCCACATCA GCTATGTCCA:           (SEQ ID NO: 2)
```

In FIG. 136, reference numeral 1 indicates a glass substrate. On the glass substrate 1 is applied 2% agarose gel 2, 10 cm square and 0.1 mm thick. The agarose gel has a thickness of 0.2 mm and a size of 90×90 mm. On the agarose gel is provided a slit 3 allowing addition of a sample. The size of the slit 3 is 5 mm in width and 0.5 mm in the electrophoretic direction. In the figure, though a plane view is omitted, a plurality of the slits 3 is provided at suitable regular intervals, for instance, at an interval of 10 mm, so that a plurality of samples can be subjected to electrophoresis.

Gel is configured to connect a negative electrode 5-1 and a positive electrode 5-2 via sponges 4-1 and 4-2 containing a buffer also serving as an electrolysis solution of Tris-acetic acid (pH 8.2). 0.5 µl of a sample solution is filled in the slit 3 with capillary phenomenon, and is put in a wet box, to which is impressed electric field by immediately connecting the electrodes 5-1 and 5-2 to a power source. Of course, electrophoresis may be conducted, like the conventional submarine electrophoresis, by immersing gel in an electrolysis solution. The electrophoresis is carried out with the electric field intensity of 15 V/cm, and, for instance, for 30 minutes.

At this point of time, a prespecified amount of ethidium bromide is put in the gel, in addition to the electrolysis solution. Ethidium bromide is put in a sample; however, the electrolysis solution is not. Ideally, a PCR product dissolved in water is preferable, but a PCR solution diluted with water twofold or more may be used. This intends the stacking effect when a PCR product in a sample solution penetrates the gel. Ethidium bromide produces fluorescence when intercalated in a duplex DNA and excited with YAG laser at 545 nm, so that existence of ethidium bromide can be easily confirmed. Reference numerals 6-1 to 6-4 in the figure indicate separated bands separated with electrophoresis as described above. Herein the band 6-3 is the target band to be melted and collected.

As shown in FIG. 137(A), laser light 7 at a wavelength of 1480 nm is irradiated. Laser beams thereof are narrowed down to 50 μmφ. If the diameter of a spot for an electrophoretic separated band is smaller than this, laser beams are needed to be further narrowed down, and in this case, an objective lens for a microscope of about 10 magnifications may be used. Reference numeral 13 indicates a lens when such an objective lens is inserted. It is to be noted that a fluorescent observation of gel in a wide range is not possible in this case, because the objective lens is inserted. Only a portion of an electrophoretic separated band targeted to be cut out can be confirmed; nevertheless, laser irradiation can be executed while moving a stage and confirming a target spot, not causing any problem. Generally, it is often the case that the objective lens 13 is not used.

When laser beams 7 are irradiated, temperature of the gel in the band 6-3 portion of the gel 3 rises within an extremely short period of time, and the gel is melted. Reference numeral 9 is a pipet, which interlocks a syringe pump 14 to allow sucking of the melted gel. As shown in FIG. 137(B), this operation opens a hole 8, in which the separated band 6-3 has once existed, and the separated band 6-3 is sucked in the pipet as shown with reference numeral 6-3'.

Then, as shown in FIG. 137(C), the pipet 9 is moved, and the syringe pump 14 is operated to discharge the separated band 6-3' from the pipet 9 to a plate 10, so that the resultant separated band 6-3' can be collected as a dot of separated band as indicated at reference numeral 11.

FIGS. 138(A) and 138(B) are waveform diagrams each showing a dot 11 of the separated band obtained as described above and the result of analysis of a solution obtained by PCR amplification before separation. Herein the figures are the waveform diagrams demonstrating the result analyzed with an i-chip (micro electrophoretic chip) and a cosmo i-chip electrophoresis device produced by Hitachi, Ltd.

As shown in FIG. 138(A), the result of analyzing the dot 11 of the separated band provides a substantially single electrophoretic separated band at a position of 230 bp. When the result of analyzing the dot 11 of the separated band is examined in comparison with the database, it can be understood that a predicted base length of the PCR product does not represent any band other than the peak 20-3' at 233 bp. Peaks 20-1, 20-2, 20-3 and 20-4 corresponding to a plurality of bands are detected from the PCR product before separation.

EXAMPLE 2

In Example 2, descriptions are provided for an example of separating and collecting a protein separation spot separated by the two-dimensional electrophoresis with the device according to the twenty seventh embodiment.

Electrophoresis in one dimension is the isoelectric focusing electrophoresis. In the isoelectric focusing electrophoresis, 0.5% agarose gel containing carry ampholyte (pH 4-7) in a glass tube 1 mm in diameter and 8 cm long is used for migration at 400 V for 8 hours. After finishing the migration, the gel is pushed out from the glass tube, and is placed at a position 10 mm from the negative pole side of the gel of the second dimension 90×90×0.2 mm in size. The gel of the second dimension is 2% agarose. Tris-acetic acid buffer (pH 8.5) is used as a buffer solution in the second dimension. Staining is conducted with Coomassie brilliant blue R250 in compliance with appropriate information to find that a protein separated band is stained blue.

FIG. 139 is a schematic view showing configuration of a device for recovering a specific band separated by two-dimensional electrophoresis.

The present device has a general observation optical system 200 on the upper surface of separation gel 100 and a laser heating optical system 300 on the under surface of separation gel 100, in order to heat with convergence light while observing a protein spot separated on the two-dimensional electrophoretic separation gel 100.

Firstly, the general observation optical system 200 is configured as described below. Light irradiated from a light source 170 is irradiated to the electrophoretic separation gel 100. The irradiated light passes through an objective lens 205 and a filter 206 to reach a CCD camera 207. Image data obtained in the CCD camera 207 is sent to an image processing analysis device 161 and is used for detecting and aligning a spot and monitoring the state of laser heating.

In the laser heating optical system 300, light irradiated from a laser light source 141 is selected based on a wavelength, according to, for instance, a laser irradiation signal given by a user upon viewing a monitor screen, and then, the irradiated light is induced to an objective lens 305 by a dichroic mirror 310 to converge on the gel 100. When a converging point is needed to shift, the dichroic mirror 310 is moved accordingly to shift the convergence position of laser within a plane surface of the gel 100. Gel present at the site where laser convergence light is irradiated is melted, which is observable as a light emitting point with the optical system 200. Laser irradiation by the objective lens 305 is sent to the image processing analysis device 161 via the dichroic mirror 310, mirror 144, lens 145 and filter 146. The image processing analysis device 161 sends a signal for stopping laser irradiation to the laser light source 141 upon information on laser irradiation.

Image data obtained in the camera 207 is analyzed with the image processing analysis device 161. The movable dichroic mirror 310, and a motor for moving stage 162 for freely moving in the X-Y direction in order to control the position of a movable XY stage 304 with the gel substrate mounted thereon having a temperature regulating plate 101 can be controlled based on various results of analysis. This enables recognition of the shape of a protein separated spot or tracking of laser irradiation after the recognition. Alternatively, it is possible to continually recognize a spot to subject the same to laser heating in sequence, or shifting a position of the pipet 9 to collect melted agarose by moving the syringe 14.

After finishing the laser irradiation, the pipet 9 immediately shifts to the position where a spot has once existed to suck the melted agarose. A heater is attached to the pipet 9, so that the temperature thereof can be maintained in a range from 30° C. to 65° C. if necessary. As the melted agarose is re-solidified over time, access to the pipet 9 should be made without delay. The pipet 9 accesses the proximity of the laser irradiation optical axis during laser irradiation, and immediately after finishing the laser irradiation, shifts to a portion where agarose is melted to suck the melted agarose. Though not shown in the figure, the pipet 9 is attached to an arm capable of moving in the X-Y direction as well as in the vertical direction, and quickly shifts to a spot position following the directions from the image processing analysis device 161, as indicated with the arrows 210.

Agarose sucked in the pipet is analyzed similarly as described in Example 1.

EXAMPLE 2

FIG. 140 is a view showing a collecting method in Example 2 which is different from the method of collecting thermally melted gel of the electrophoretic spot portion melted by being heated with converged light, as described in Example 1 and a structure of a pipet used in the method. The present method is described as a method in which a pipet used herein substitutes the pipet 14 for the device of collecting a specific band separated with the two-dimensional electrophoresis, and protein is collected from a protein separation spot two-dimensionally developed by the electrophoresis.

A chip 401 is attached to a pipet 400. The chip 401 is used as disposable. Firstly, a cylinder 400' of the pipet is operated to fill the pipet with an electrolysis solution 440. A first electrode 402 is attached to the inside of the pipet 400. The pipet 400 sucks gel melted with convergence light in the same way as Example 1. At this point of time, temperature of the gel drops, and the gel is gelated again in the pipet chip 401. Then the tip of the chip 401 is immersed in a prespecified amount of an electrolysis solution in a vessel 406. A second electrode 403 is attached to the vessel 406. Electric field is impressed between the first electrode 402 as negative pole and the second electrode 403 as positive pole at 15 V/cm. Thus separated protein contained in the gel 405 solidified in the chip 401 is eluted in the electrolysis solution by electrophoresis. This operation enables to collect a target protein in the vessel 406.

[XXVIII] Twenty-Eighth Embodiment

As a twenty-eighth embodiment, a new technique is described which, expanding on the scope of a conventional method of simply isolating biochemical substances, isolates molecules active to a cell and found only in very small quantity in a functionally traceable manner, in order to clarify functionality of a cell. For this purpose, a solution including a small number of cells or cell masses are placed on a basal plate as a liquid droplet, and a focused light beam is irradiated on the liquid droplet on the basal plate.

Figure 141:
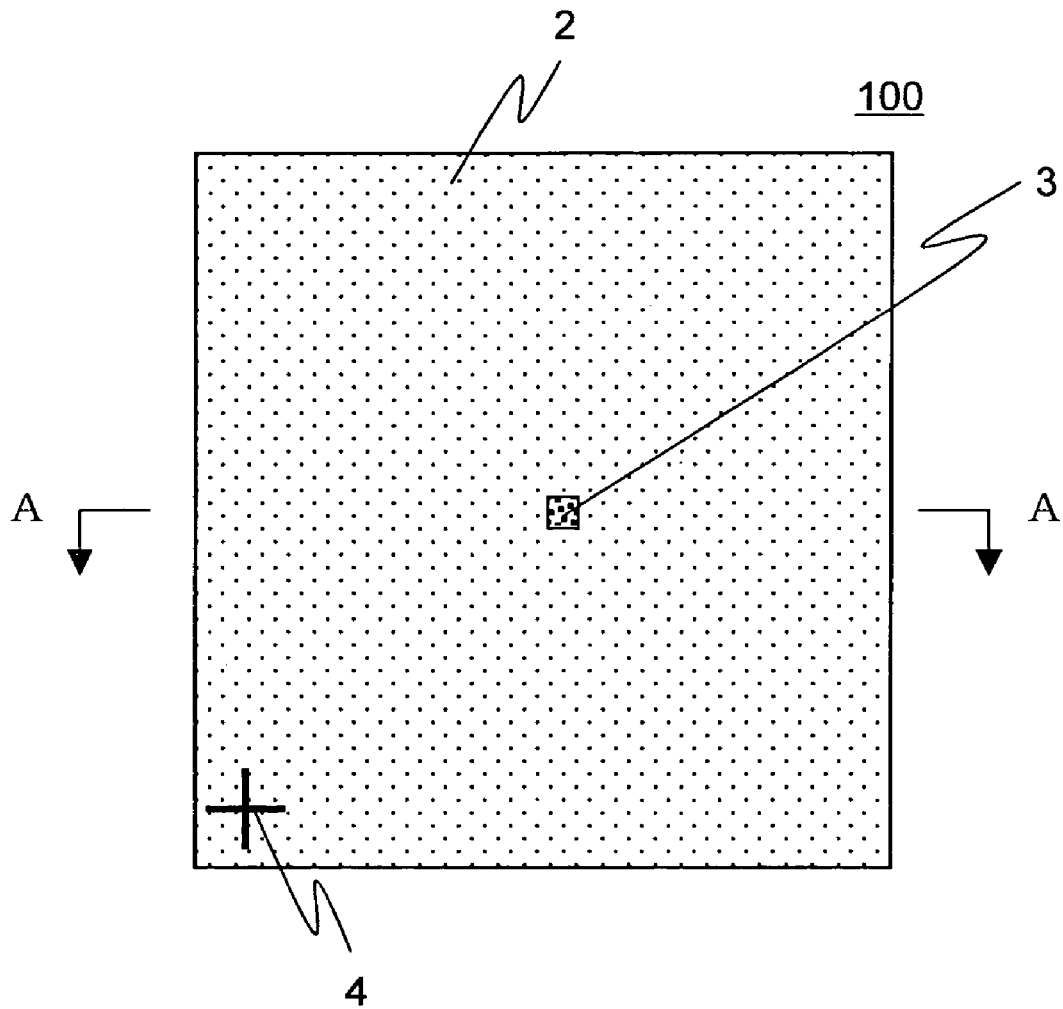
Figure 141:
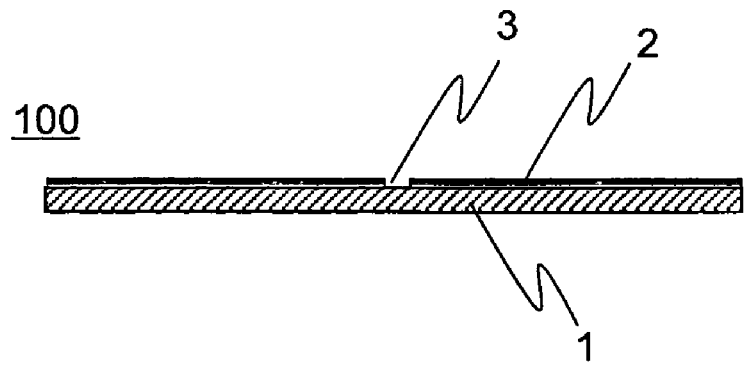

FIG. 141 (A) is a plan view of a cell-holding basal plate 100 suitable for the 28th embodiment of the present invention, and FIG. 141 (B) is a cross-sectional view of the plan view viewed at the A-A line on the plan view to the direction of the arrow. A reference numeral 1 indicates a silicon basal plate with, for example, a size of 20 mm×20 mm and a thickness of 1 mm. On the surface of the basal plate 1 is a hydrophobic area 2, and in the hydrophobic area 2 are provided an array of hydrophilic areas 3. A size of a hydrophilic area 3 is small enough in comparison to a size of a diameter of the liquid droplet to be placed on the hydrophilic area 3. A reference numeral 4 refers to a marker for positioning, and is formed on a side of the silicon basal plate 1.

For the creation of the hydrophilic area and the hydrophobic areas, an upper surface of the silicon basal plate may, for example, first be oxidized, generating a hydrophilic $SiO_2$ thin film on the entire surface. Thereafter, the $SiO_2$ thin film is dissolved and removed from areas intended to be hydrophobic with hydrofluoric acid. Alternatively, if on the surface of the material for the basal plate 1 is formed the $SiO_2$ thin film in advance and the surface is therefore hydrophilic, the hydrophobic area may be formed by placing hydrophobic material such as fluorine resin or silicon resin thereon. In this case, the hydrophilic areas in the hydrophobic area are depressed by a thickness of the hydrophobic material. FIG. 141 is an example in which the hydrophobic area 2 is formed with the latter method.

FIG. 142 (A) is a conceptual diagram illustrating an example of a system configuration for forming a liquid droplet containing a cell on the hydrophilic area 3 on the cell-holding basal plate 100 suitable for the 28th embodiment of the present invention, and FIG. 142 (B) is a cross-sectional view showing a liquid droplet containing a cell formed on a hydrophilic area 3 of the cell-holding basal plate 100.

In FIG. 142 (A), a liquid droplet containing a cell 12 is formed on the hydrophilic area 3 on the cell-holding basal plate 100 while a liquid droplet at a tip of a pipette 11 for forming a liquid droplet containing a cell 12 is being monitored optically. A reference numeral 19 indicates a stage driven in the X-Y direction, and a reference numeral 27 is a driving device for the stage 19. On an upper surface of the stage 19 is placed the cell-holding basal plate 100. Over the cell-holding basal plate 100 is provided the pipette 11 having sucked up and contained suspension 13 containing the cell 12 for containment in the liquid droplet. To a base of the pipette 11 is connected a syringe pump 31 via a tube 30, and to the syringe pump 31 is connected a driving device 32. When the syringe pump 31 is driven by the driving device 32, the suspension 13 contained in the pipette 11 is squeezed out together with the cell 12. In the FIG. 142 (A), the base of the pipette 11 and the connection part of the tube 30 are illustrated as not contacting each other, but this is simply for the purpose of showing the pipette 11 enlarged.

At the tip of the pipette 11 is placed a tip of another pipette 20 for supplying culture fluid to the tip of the pipette 11. To a base of the pipette 20 is connected a syringe pump 35 via a tube 34, and to the syringe pump 35 is connected a driving device 36. When the syringe pump 35 is driven by the driving device 36, the culture fluid contained in the pipette 20 is squeezed out.

There is also provided a vertical driving device 37 for driving the pipette up and down for transferring the liquid droplet formed at the tip of the pipette 11 to the hydrophilic area 3 on the cell-holding basal plate 100. In this example, the vertical driving device is connected to the pipette 11. If a user issues an instruction for lowering the pipette 11 to the vertical driving device 37, the pipette 11 moves downward, and the liquid droplet formed at the tip of the pipette 11 is transferred to the hydrophilic area 3 on the cell-holding basal plate 100. If the user issues an instruction for restoring a position of the pipette 11 to the vertical driving device 37, the pipette 11 returns to the original position as shown in FIG. 142 (B). The restoring of the pipette 11 to the position shown in FIG. 142 (B) may be controlled with a personal computer 26 sequentially from the time of the lowering operation. A dot-dash line 39 indicates that the vertical driving device 37 is connected to the pipette 11.

Further, a light source 16 and a light-condensing lens 17 are provided, forming an optical system for monitoring a size of the liquid droplet to be formed inside the pipette 11 near the tip or at the tip thereof, and a collimate lens 18 and a monitor 25 are provided below the cell-holding basal plate 100 facing the light source 16 and the light-condensing lens 17. For this reason, the cell-holding basal plate 100 and the stage 19 need to be transparent optically. The reference numeral 26 indicates a so-called personal computer, and supplies an appropriate control signal to the driving devices 27, 32, 36 and 37, generated from a program stored in advance in response to an input signal from the monitor 25, or based on an input-operation signal 28 of the user watching the image on the screen of the monitor 25. It is not shown in the FIG. 142 (A), but it is convenient if an identical image detected and shown by the monitor 25 is also shown on the monitor of the personal computer 26. In this configuration, a small CCD camera may be used as the monitor 25. The input-operation signal 28 is given with an input device of the personal computer 26.

If the cell-holding basal plate 100 and the stage 19 are not transparent optically, the light may be irradiated from above, and reflected light may be monitored. This means that the collimate lens 18 and the monitor 25 are provided on the same side as the light source 16 above the basal plate, and the reflected image is observed. For example, the light may be irradiated diagonally, and the image is observed from the right angle.

A size of the pipette 11 is described hereinafter. It is necessary that the pipette 11 is such that a liquid droplet can be formed at the tip thereof with an appropriate size for containing a required number of cells. The pipette 11 is used after sucking the suspension 13 containing the cells into inside the pipette 11 with the functionality of the pipette 11, and upon forming a liquid droplet 21, the cells passing through the tip of the pipette 11 must be detected without error with the monitor 25. Therefore the diameter of the pipette 11 at the tip thereof must be large enough to allow a cell, or a cell mass containing a prespecified number of cells to pass, but not too large to allow too many cells exceeding the counting capability to pass at once. This means that the pipette must not be culture pipettes generally used at present with a large diameter, but a transparent pipette with a diameter of 20 to 100 μm for general animal cells and one with a diameter of about 5 μm for bacteria and other microorganisms.

An operation for forming the liquid droplet 21 containing the cell 12 on the hydrophilic area 3 on the cell-holding basal plate 100 is described hereinafter. Upon start-up of the system, the user positions the cell-holding basal plate 100 for a prespecified start-up position with the help of the marker 4 described in FIG. 141 (A). Next, the stage 19 is moved with the driving device 27 based on the input-operation signal 28 for moving the point on the cell-holding basal plate 100 for forming the liquid droplet 21 containing the cells 12 to a position corresponding to the tips of the pipettes 11 and 20. When the cell-holding basal plate 100 is moved to the prespecified position, an operation is performed for squeezing out the cell suspension liquid 13 in the pipette 11 together with the cells 12. At the time of the operation, the outside of the tip of the pipette 11 and the inside near the tip thereof are monitored with the optical system consisting of the light source 16 and the monitor 25. Output from the monitor 25 is fed to the personal computer 26, and, based on a picture image calculation result of the personal computer 26, the driving device 32 may be operated for controlling liquid sent by the syringe pump 31.

While monitoring the tip of the pipette 11 with the monitor 25, the driving device 32 is operated, the syringe pump 31 is driven, the suspension 13 containing the cells 12 is squeezed out of the tip of the pipette 11, and the liquid droplet 21 is formed at the tip of the pipette. When the personal computer 26 recognizes through the monitor 25 that a prespecified number of cells are inserted into the liquid droplet 21, the personal computer 26 issues a halt instruction to the driving device 32 and the syringe pump 31 is stopped.

In order to make a description simpler, the number of cells 12 inserted into the liquid droplet 21 is assumed to be one hereinafter, although the number of cells may be set at the discretion of the user. For instance, it may be set that 10 cells are inserted to the liquid droplet 21. The cell 12 may be recognized directly in the liquid droplet 21 at the tip of the pipette 11, but more effectively, the cell 12 moving inside the pipette 11 may be monitored with the monitor 25, the position and the moving speed of the cell inside the pipette may be calculated with the personal computer 26, the timing that the cell is squeezed out to the liquid droplet 21 from the tip of the pipette 11 may be forecast, and the syringe pump 31 may be controlled accordingly. The latter recognition method is advantageous if, for instance, a plurality of cells are moving inside the pipette with a short interval and only one cell is to be inserted into the liquid droplet.

If the cell concentration in the cell suspension 13 is low, it is possible to start forming the liquid droplet 21 just prior to the cell is squeezed out of the tip of the pipette 11 and stop forming the liquid droplet after a prespecified time, for forming the liquid droplet 21 of a desired size. When it is not desired to form the liquid droplet, the liquid squeezed from the tip of the pipette 11 can be, for example, blown away with a blower. Alternatively, the liquid may be discharged to a drain formed outside the basal plate 1.

If, on the other hand, the cell concentration in the cell suspension 13 is high, the volume of liquid squeezed out of the pipette 11 varies. Namely, the frequency with which the cell 12 is squeezed out from the pipette rises, and if the time for squeezing out the liquid is fixed at a prespecified length, there is a possibility that a next cell is inserted into the liquid droplet 21. The pipette 20 is used in this case. The pipette 20 and the syringe pump 35 connected thereto are filled with culture fluid or cell diluting fluid only. When the personal computer 26 recognizes through the monitor 25 that a cell 12 is squeezed out into the liquid droplet 21, the personal computer 26 issues a halt instruction to the driving device 32 and the syringe pump 31 is stopped, and the personal computer 26 further calculates a cubic volume of the liquid droplet 21 at that time from a movement distance of the syringe pump 31 for forming the liquid droplet 21. The personal computer 26 further calculates a difference between the cubic volume of the liquid droplet 21 and a desired cubic volume. Based on a result of the calculation, the culture fluid or the cell diluting fluid is added from the pipette 20 to the liquid droplet 21 already formed by that time with a signal sent from the personal computer 26 to the driving device 36, driving the syringe pump 35 and adding the fluid with the pipette 20 until the cubic volume of the liquid droplet 21 reaches the prespecified volume.

It is desired that the tip of the pipette 20 is thin enough for the cell not to pass, for instance 0.2 μmφ in diameter, so that the cell in the liquid droplet does not flow upstream to the pipette 20. Alternatively, the pipette 20 may be formed to have a filtering structure of 0.2 μm in diameter at the tip.

The liquid droplet 21 containing a cell formed in the manner described above is brought in contact with the hydrophilic area 3 on the basal plate 1 placed on the stage 19 by the vertical driving device 37 of the pipette 11, and the liquid droplet 21 is transferred to the hydrophilic area 3 on the basal plate 1. The liquid droplet 21 is shed by the hydrophobic area 2, and is fixed to the energy-stable position at the hydrophilic area 3 in a self-forming manner. The operator finishes the operation when it is confirmed that the liquid droplet 21 containing the cell 12 is transferred to the hydrophilic area 3 on the basal plate 1, that is, the hydrophilic area 3 on the cell-holding basal plate 100.

FIG. 142 (B) is a cross-sectional view of the liquid droplet containing a cell placed in the hydrophilic area 3 on the cell-holding basal plate 100, formed with the system for forming a liquid droplet containing a cell on the cell-holding basal plate 100 as described with reference to FIG. 142 (A). On the hydrophilic area 3 of the basal plate 1 is placed a cell 12, and a liquid droplet 15 is formed, enclosing the cell.

FIG. 143 is a oblique perspective view illustrating an outline of an example device for destroying a cell in a liquid droplet, targeting the liquid droplet 15 formed on the basal plate as described above with reference to FIGS. 141 and 142. The device described in FIG. 143 is an independent device, but it is convenient if the device is formed combined with the system for forming the liquid droplet as described with reference to FIG. 142 above and placed next to each other, and the personal computer 26 controls the movement of the cell-holding basal plate 100 by controlling the stage 19, and irradiation of a laser beam.

In FIG. 143, the liquid droplet on the cell-holding basal plate 100 can be irradiated with light from both above and below. The light from the light source 41 placed above is first adjusted to a specific wavelength with a filter 42, concentrated with a condenser lens 43, and irradiated to the liquid droplet 15. The irradiated light is led through an objective lens 47, a dichroic mirror 48, a mirror 49 and a filter 51 to a camera 52 as transmitted light, and the transmitted light image of inside the liquid droplet 15 is formed on a light receiving surface of the camera 52. For this reason, it is desirable that the cell-holding basal plate 100 and the stage 19 are made of optically transparent material, as with the system for forming the liquid droplet. Specifically, glass such as borosilicate glass or silica glass, or resin such as polystyrene or plastic, or a solid basal plate such as a silicon basal plate, is suitable. If a silicon basal plate is used for the basal plate 1 of the cell-holding basal plate 100, the wavelength of the light from the light source 41 described above should be 900 nm or longer.

Light irradiated from a light source 47 placed below is first wavelength-selected with the filter 46, then led to the objective lens 47 through the dichroic mirror 48, and is used as excitation light for fluorescence for observing inside the liquid droplet 15. The fluorescent light generated inside the liquid droplet is observed with the objective lens 47 again, and the fluorescent light after the excitation light is removed with the filter 51 can be observed with the camera 52.

By adjusting a combination of the filters 42, 46 and 51, it is possible to observe just the transmitted light with the camera 52, just the fluorescent light, or both the transmitted light image and the fluorescent light image at the same time with the camera 52.

The picture image data obtained with the camera are analyzed with the personal computer 26, and the stage 19 can be controlled accordingly so that laser beam 63 may be focused on the liquid droplet 15. If the laser beam 63 is of type ultraviolet laser, it is dangerous to observe the light directly, and the CCD camera 52 is used for observation. Again, although it is not illustrated in FIG. 143, it is convenient to display the picture image data being detected with the CCD camera 52 on the monitor of the personal computer 26.

A reference numeral 61 indicates a laser beam source and a reference numeral 62 refers to a filter for wavelength selection: in an example 1, the laser can irradiate a third harmonic component of a YAG laser at 355 nm in wavelength. Intensity of the laser beam 63 is over around 200 µJ, and the beam is concentrated for radiation to the cell. In FIG. 143, the laser beam 63 is irradiated from the laser beam source 61 directly to the liquid droplet 15; it is also possible to place mirrors in the path of the laser beam 63 as appropriate for leading the laser beam, if structural constraints make it impossible to irradiate the liquid droplet 15 directly. The irradiation from the laser beam source 61 may be controlled with the personal computer 26. The user can also control the irradiation from the laser beam source 61 by inputting an operation signal 28 to the personal computer.

When the laser beam 63 is focused on the cell 12 in the liquid droplet 15 and a laser pulse of 200 µJ is irradiated to the cell under observation with a microscope, it is observed that membrane of the cell is destroyed instantaneously and cell contents are splashed. Since the laser in the example is an ultraviolet laser, all the optical components in the laser irradiation system are compatible with ultraviolet. If the size of the liquid droplet is large, or if there are many cells in the liquid droplet, the intensity of the laser beam 63 may be strengthened. It is easy to attain an output power of around 5 mJ.

The selection of the wavelength of the light and the way to irradiate the light are important. If a wavelength is used for which the water has light absorptivity, the water, or the solvent itself, is evaporated. A wavelength should therefore be selected which is absorbed by the cell but absorptivity of which by water is ignorable. Specifically, one method is to use a wavelength in an ultraviolet band, which biochemical substances, proteins and nucleic acids absorb for conversion to heat. Alternatively, certain visible light can destroy the cell, although the mechanism is not known. It is known that the cell can be killed and destroyed instantaneously if the light is irradiated to the cell as converged light.

The purpose of the twenty-eighth embodiment of the present invention is to destroy a very small number of cells, such as a single cell, effectively and analyze or collect the contents efficiently thereafter, and for this purpose the cell is contained in a liquid droplet, so that dilution and splash of cell contents at the time of cell destruction are prevented by containing them in the liquid droplet. Generally, the cell and the water used as solution have slightly different light-absorptivity characteristics, and therefore, light with a wavelength, which is little adsorped by water but is absorbed well by cell organs, is irradiated on the liquid droplet, thereby heating and destroying the cell only and retaining the contents of the destroyed cell in the liquid droplet. If the light absorption and temperature increase are slow, the temperature of the water, a component of the solution, rises as well. It is therefore important to irradiate a strong light for an instance, thereby realizing a faster temperature increase for the cell with light absorptivity than the temperature increase for the solution, and solubilizing the cell.

FIG. 144 is a conceptual diagram illustrating a concrete example of collecting biological substances directly from suspension containing fragments of the destroyed cell in the liquid droplet 15 according to the method described in the embodiment above. A prespecified quantity (0.1 µl) of fluorescent intercalator CYBR Green II for RNA is added to the suspension containing fragments of the destroyed cell in the liquid droplet 15. This is directly infused to the liquid droplet 15 with a capillary tube. To the liquid droplet 15 are contacted a platinum electrode 71 and a capillary 72 with an inner diameter of 50 μm filled with electrophoretic separation medium containing linear dimethylpolyacrylamide as a main ingredient. The other end of the capillary 72 is dipped into buffer fluid in a container 73. One end of a platinum electrode 74 is also dipped into the buffer fluid. An electric field of 50 v/cm is applied to the capillary 72 for 10 seconds between the platinum electrode 71 as a negative electrode and the platinum electrode 74 as a positive electrode. Thereafter, 50 μl of electrophoretic buffer fluid (Tris-HCl) is added to the liquid droplet 15, and an electric field of 200 v/cm this time is applied, continuing the process of electrophoresis. Aragon laser from an argon laser source 75 of 488 nm, located at 10 cm from the liquid droplet 15, is irradiated to the liquid droplet 15, and resulted fluorescence is monitored with a detector 76.

It is omitted in FIG. 144, but it is desired that the electrode 71 and the capillary 72 are held in an arm manipulator with the tip thereof movable to a desired position, like the vertical driving device 37 described with reference to FIG. 142, which is controlled with the personal computer 26.

FIG. 145 is a electropherogram illustrating an example of an electrophoretic pattern observed in the electrophoresis. The horizontal axis represents the electrophoretic time, while the vertical axis represents fluorescence intensity. Two sharp peaks 81 and 82 represents two types of rRNAs, a broad band 83 originates from mRNA, and a reference numeral 84 corresponds to a polymer genome. As is observable from FIG. 145, the biological substances as described above are discharged from the other end of the capillary 72 to the container 73 after a period corresponding to the electrophoresis time. This means that biological substances can be collected from a very small number of cells with a method according to the twenty-eighth embodiment of the present invention. Furthermore, as these biological substances are obtained by destroying the cell in the liquid droplet, it is obvious that conditions of the biological substances in the cell at the time of cell destruction are stably fixed.

[XXIX] Twenty-Ninth Embodiment

A twenty-ninth embodiment discloses a reaction tracking device of extremely small amount which enables rapid reaction tracking using a different principle from a conventional stopped-flow principle. This embodiment utilizes a phenomenon in which a solvent mainly composed of water becomes a liquid droplet and rolls on a water-repellent substrate. The liquid droplet can move to any position by a slight external force. Making use of this phenomenon, a plurality of extremely small amount of liquids including dissolved substances for reaction are arranged on the substrate as liquid droplets in order to start a rapid reaction by making each of the liquid droplets colliding against one another. The liquid droplet weighs basically between a submicroliter and several microliters, making it possible to start the reaction instantly.

Example 1

Example 1 uses the twenty-ninth embodiment in order to track a DNA hybridization process.

Figure 146:
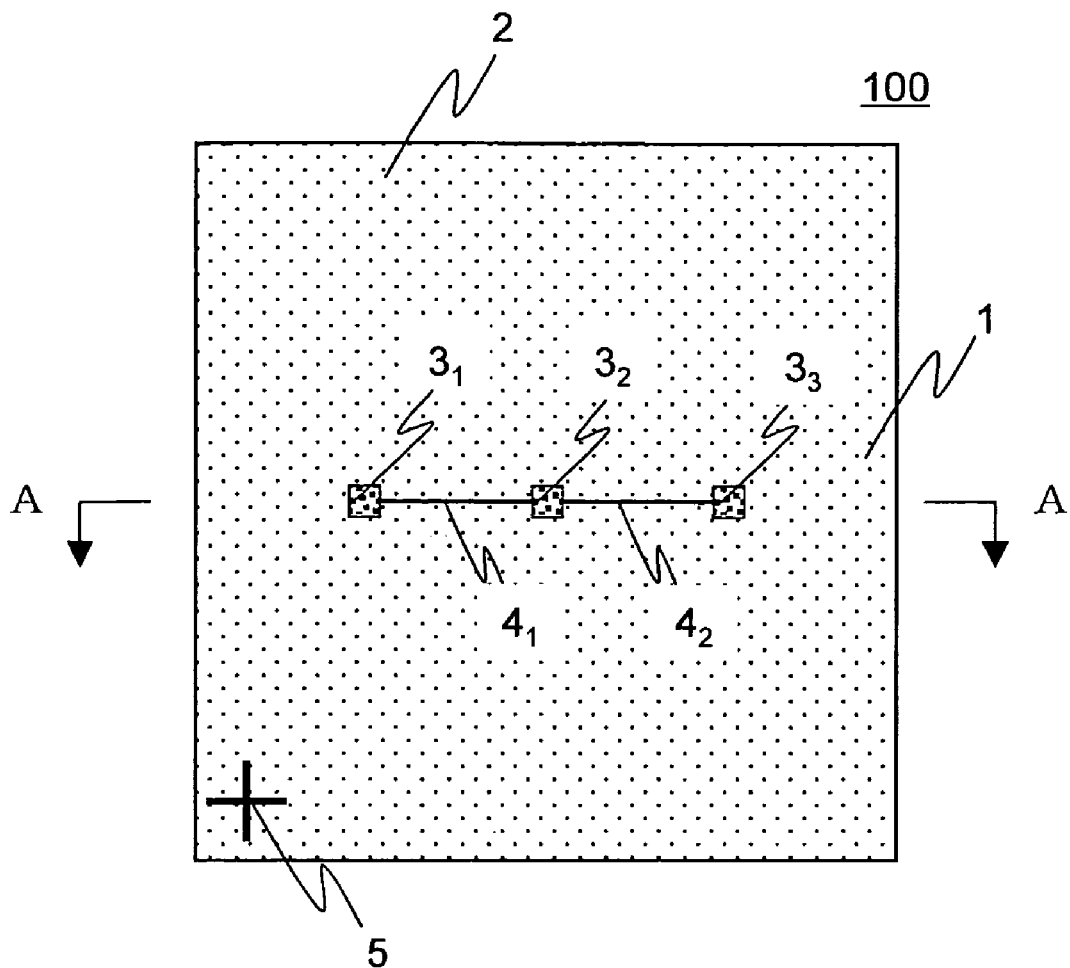
Figure 146:
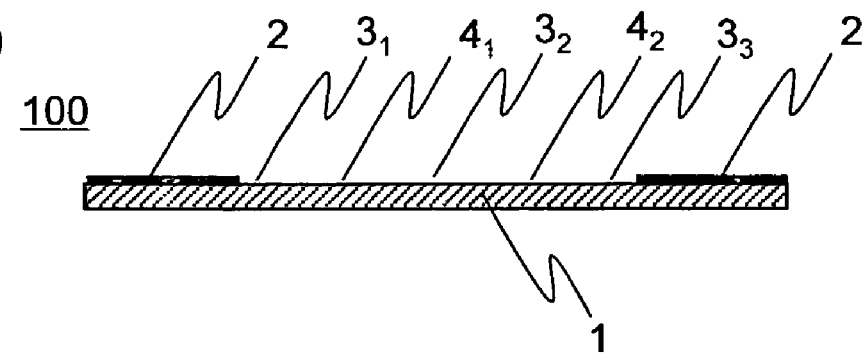

FIG. 146 (A) is a flat view of a reaction substrate 100 suitable for implementing the twenty-ninth embodiment; FIG. 146 (B) is a cross-sectional view of the flat view taken along the line A-A and viewed in the direction indicated by the arrow. The reference numeral 1 indicates a silicon substrate, for example, with a thickness of 1 mm and a size of 20 mm×20 mm. The surface of the substrate 1 is a hydrophobic region 2, in which three hydrophilic regions $3_1$, $3_2$ and $3_3$ are arrayed. The dimension of the hydrophilic region 3 is small enough compared with a diameter of the liquid droplet to be held in this hydrophilic region, for example, a dimension of 0.01 $mm^2$. Three hydrophilic regions $3_1$, $3_2$ and $3_3$ are connected by narrow hydrophilic grooves $4_1$ and $4_2$, for example with a width of 2 μm. The reference numeral 5 is a marker for positioning, and formed all over the silicon substrate 1.

In FIG. 146 (B) the entire central portion of the substrate 1 has become a hydrophilic region, because the cross-sectional surface thereof is positioned in three hydrophilic regions $3_1$, $3_2$ and $3_3$ and the hydrophilic grooves $4_1$ and $4_2$ for connecting these hydrophilic regions. A method of producing the hydrophilic region and the hydrophobic region is, for example, oxidizing a top surface of the hydrophobic silicon substrate 1 to make the entire region a hydrophilic thin film of $SiO_2$ once. After that, the $SiO_2$ thin film in the region to become hydrophobic is dissolved and removed using fluorine to produce a hydrophobic region. Alternatively, when the surface of the substrate 1 is hydrophilic with the $SiO_2$ thin film formed thereon in advance, the hydrophobic region is formed by arraying a hydrophobic substance such as a fluoride resin and a silicon resin thereon. In this case, the hydrophilic region existing in the hydrophobic region has become low in accordance with a thickness of the hydrophobic substance. FIG. 146 shows an example of using the latter method to form the hydrophobic region 2.

In Example 1, the liquid droplets including substances for reaction to the hydrophilic regions $3_1$ and $3_3$ are formed in advance; and each of the liquid droplets is guided through the hydrophilic grooves $4_1$ and $4_2$ to move each droplet to the hydrophilic region $3_2$ and to collide in the hydrophilic region $3_2$.

Figure 147:
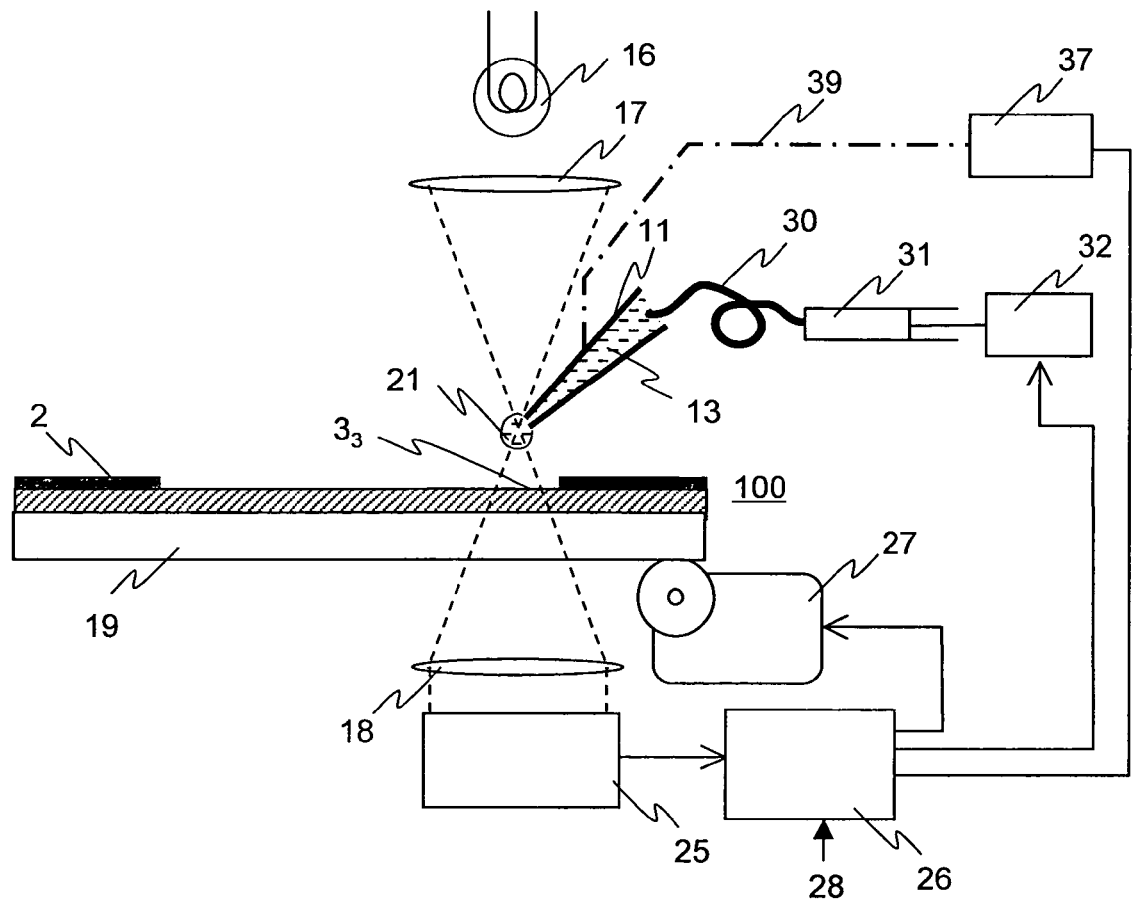
Figure 147:
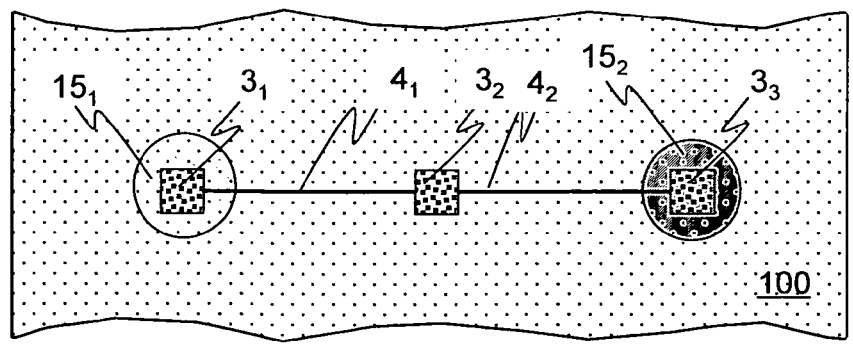

FIG. 147 (A) is a conceptual diagram describing an example of a system construction for constructing the liquid droplet including the substance for reaction to the hydrophilic regions $3_1$ and $3_3$ of the reaction substrate 100 suitable for implementing the twenty-ninth embodiment; FIG. 147 (B) is a plan view showing a portion of the reaction substrate 100 on which the liquid droplet including the substance for reaction to the hydrophilic regions $3_1$ and $3_3$ is formed in the hydrophilic region 3 of the reaction substrate 100.

In FIG. 147 (A), while optically monitoring the liquid droplet at the end of a pipette 11 for forming the liquid droplet including the substance for reaction, the liquid droplet including the substance for reaction to the hydrophilic regions $3_1$ and $3_3$ of the reaction substrate 100 is formed. The reference numeral 19 indicates a stage driven in the direction of XY; and the reference numeral 27 is a drive unit of the stage 19. The reaction substrate 100 is placed on the top surface of the stage 19. The pipette 11 with a suspension 13, which is to be included in the liquid droplet and includes the substance for reaction, siphoned up and maintained beforehand is placed on top of the reaction substrate 100. A syringe pump 31 is provided at the bottom of the pipette 11 through a tube 30; and a drive unit 32 is installed on the syringe pump 31. When the syringe pump 31 is driven with the drive unit 32, the suspension 13 inside the pipette 11 is pushed out together with the substance for reaction. In the figure, the joint of the base of the pipette 11 and the tube 30 looks apart, because the pipette 11 is enlarged for display; therefore the joint is not separated.

A pipette vertical drive unit 37 is provided for transferring the liquid droplet formed at the end of the pipette 11 to the hydrophilic regions $3_1$ and $3_3$ of the reaction substrate 100. In this example, the vertical drive unit 37 is linked to the pipette 11. When a signal to lower the pipette 11 is given to the vertical drive unit 37 by a user, the pipette 11 moves down, transferring the liquid droplet formed at the end of the pipette 11 to the hydrophilic regions $3_1$ and $3_3$ of the reaction substrate 100. When a signal to restore the pipette 11 is given to the vertical drive unit 37 by a user, the pipette 11 returns to the position shown in the figure. Restoring the pipette 11 to the position shown in the figure may be performed time sequentially using a personal computer 26 starting from the downward operation. A dashed line 39 indicates the link between the vertical drive unit 37 and the pipette 11.

A light source 16 and a collective lens 17 constituting an optical system are provided to monitor the dimension of the liquid droplet formed inside the neighborhood of and at the end of the pipette 11; and in the opposite position, a collimate lens 18 and a monitor 25 are provided in the lower part of the reaction substrate 100. Therefore, the reaction substrate 100 and the stage 19 need to be optically transparent. The reference numeral 26 indicates a personal computer for giving a control signal obtained from a prescribed program stored beforehand in accordance with an input signal from the monitor 25 and a personal computer for giving a necessary signal to the drive units 27, 32 and 37 in accordance with an operation input signal 28 given by the user while watching the display of the monitor 25. Although not shown here, it is convenient to display the same screen as the screen detected by the monitor 25 on the monitor of the personal computer 26. By doing this, the monitor 25 can become a small size CCD camera. The operation signal 28 is given through the input device of the personal computer 26.

When the reaction substrate 100 and the stage 19 are not optically transparent, the reflection of the light illuminated from the top surface is used as a monitor.

The size of the pipette 11 is described hereinafter. The pipette 11 needs to construct, at the end thereof, a liquid droplet with a suitable size including the substance for reaction. On the other hand, the suspension 13 including the substance for reaction is siphoned up with the pipette 11 before using the suspension 13; therefore, the pipette 11 needs to be big enough to be able to hold the suspension 13 with a volume necessary to construct a liquid droplet 21.

A method of forming the liquid droplet 21 including the substance for reaction to the hydrophilic region 3 of the reaction substrate 100 is described herein after. First, when the system starts, the user chooses a position so that the reaction substrate 100 is in the prescribed start position, focusing attention on the marker 5 described in FIG. 146 (A). Next, in accordance with the operation input signal 28 for transferring the position of the liquid droplet 21 including the substance for reaction to the position corresponding to the end of the pipette 11, the stage 19 is operated using the drive unit 27. When the reaction substrate 100 comes to the prescribed position, an operation for discharging the suspension 13 including the substance for reaction inside the pipette 11 is performed. At this time, the outside of the end of the pipette 11 and the inside of the neighborhood of the end of the pipette 11 are monitored with the optical system consisting of the light source 16 and the monitor 25. The liquid pumping with the syringe pump 31 can be controlled by inputting the output of the monitor 25 into the personal computer 26 and by operating the drive unit 32 based on the image computing result of the personal computer 26.

While the tip of the pipette 11 is monitored with the monitor 25, the liquid droplet 21 is formed at the tip of the pipette by operating the drive unit 32, activating the syringe pump 31, discharging the suspension 13 including the substance for reaction from the tip of the pipette 11. At this time the personal computer 26 recognizes that the liquid droplet has reached the prescribed size through the monitor 25 and gives the stop command to the drive unit 32 to stop the syringe pump 31.

The liquid droplet 21 of the suspension including the substance for reaction, which is produced according to the above-mentioned method, is contacted with the hydrophilic region $3_3$ on the substrate 1 placed on the stage 19 using the vertical drive unit 37 on the pipette 11, and transferred to the hydrophilic region $3_3$ of the reaction substrate 100. The liquid droplet 21 is repelled by the hydrophobic region 2 and is fixed, in a self-generated manner, in the position of hydrophilic region $3_3$ which is energetically stable. When it is confirmed that the liquid droplet 21 including the substance for reaction is transferred to the hydrophilic region $3_3$ of the reaction substrate 100, the user transfers the stage 19, going on to the next operation of placing the liquid droplet 21 on the hydrophilic region $3_1$ of the reaction substrate 100. This operation can be performed by exchanging the pipette 11, suctioning the suspension including other substances for reaction therein and repeating the above-mentioned operations.

FIG. 147 (B) is a plan view showing the result in which the liquid droplet including the substance which is to be reacted to the hydrophilic region $3_1$ and $3_3$ of the reaction substrate 100 is placed by using the system for forming the liquid droplet including the substance reacted to the reaction substrate 100, as described referring to the FIG. 147 (A). Droplets $15_1$ and $15_2$ including the substance to be reacted to the hydrophilic region $3_1$ and $3_3$ of the reaction substrate 100 are arranged.

Figure 148:
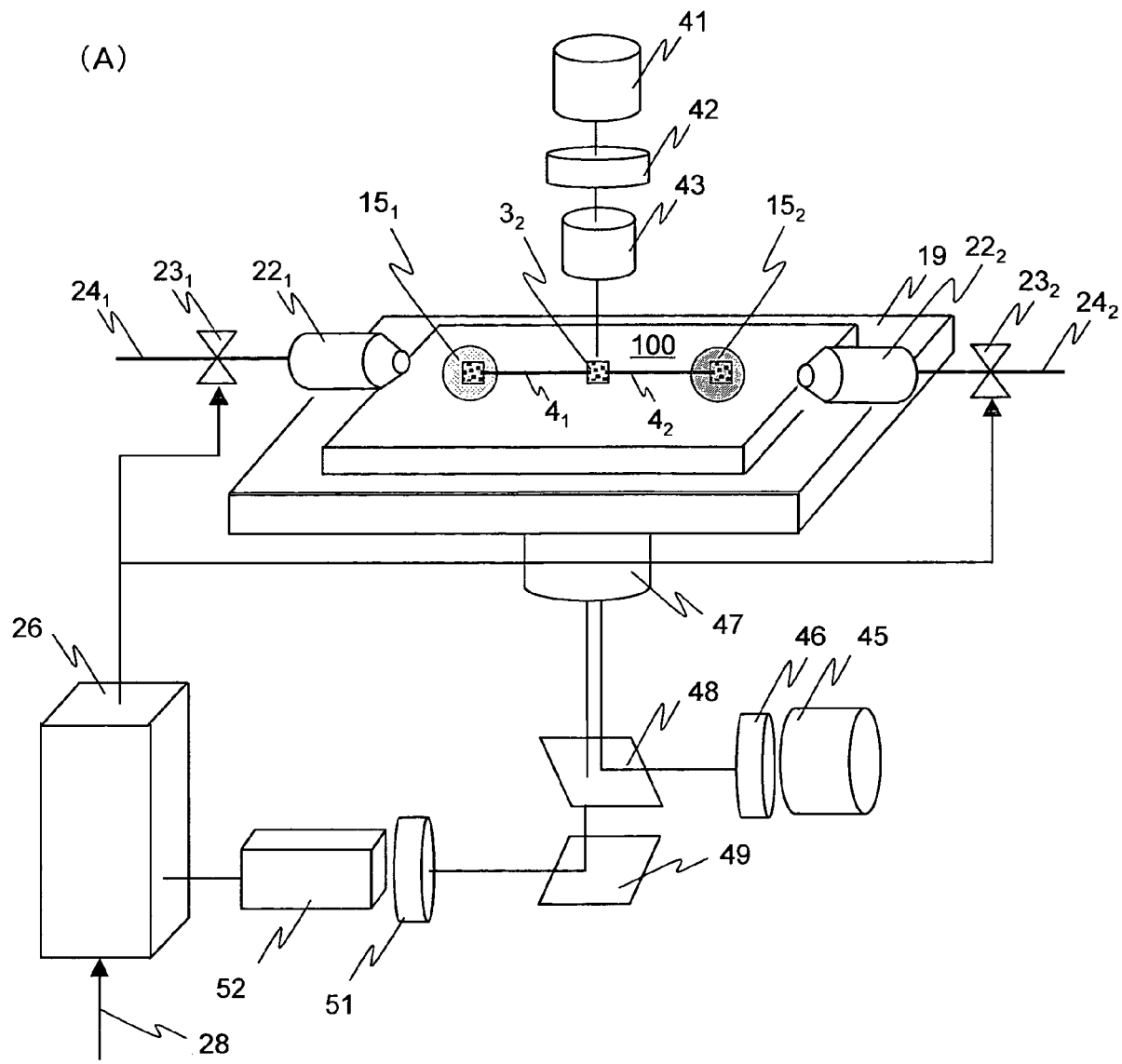
Figure 148:
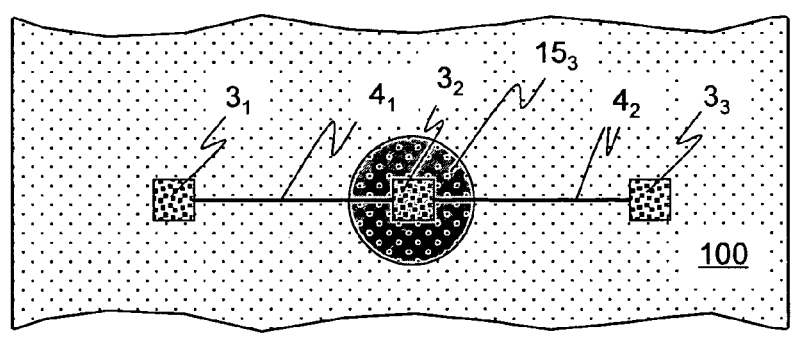

FIG. 148 (A), as shown in FIG. 147 (B), is a perspective view showing an outline of the example of the device for reacting the two droplets $15_1$ and $15_2$ formed on the reaction substrate 100 by making each of the two droplets collide against each other; and FIG. 148 (B) is a view showing a frame format of an aspect in which the two droplets $15_1$ and $15_2$ have turned into one droplet after colliding against each other. The device described in FIG. 148 is in the independent form; however, it is advantageous to be in the form which is unified with and adjacent to the system constituting the liquid droplet described in FIG. 147, so that the device can control the transfer of the reaction substrate 100 with the stage 19, the gas injection for moving the two droplets $15_1$ and $15_2$ and the like using the personal computer 26.

In FIG. 148 (A), each of the top and the bottom of the reaction substrate 100 is provided with the optical system for monitoring the liquid droplet and the reaction thereof. Gas injection nozzles $22_1$ and $22_2$ are provided on an extension of hydrophilic grooves $4_1$ and $4_2$ for connecting the two liquid droplets $15_1$ and $15_2$ with these. Each of the gas injection nozzles $22_1$ and $22_2$ is connected to tubes $24_1$ and $24_2$ which are connected to a gas pressure tank, so that the gas injection with the gas injection nozzles $22_1$ and $22_2$ can be controlled by opening or closing valves $23_1$ and $23_2$. When gas is injected from the gas injection nozzles $22_1$ and $22_2$, the liquid droplets $15_1$ and $15_2$ are guided by the hydrophilic grooves $4_1$ and $4_2$ and move to the hydrophilic region $3_2$, colliding on the hydrophilic region $3_2$.

FIG. 148 (B) shows a state in which the two liquid droplets $15_1$ and $15_2$ move on the hydrophilic grooves $4_1$ and $4_2$, collide on the hydrophilic region $3_2$ and is unified.

In FIG. 148 (A), the light irradiated from a light source 41 on top is modulated to the prescribed wavelength with a filter 42, condensed with a condenser lens 43 and irradiated on the hydrophilic region $3_2$. The irradiated light is led to a camera 52, as transmitted light, through an objective lens 47, a dichroic mirror 48, a mirror 49 and a filter 51; and a transmitted light image on the hydrophilic region $3_2$ is focused onto the acceptance surface of the camera 52. In other words, it can be confirmed that the hydrophilic region $3_2$ is in the prescribed position. Therefore, as is the case with forming liquid droplets, it is preferable that the reaction substrate 100 and the stage 19 are made of optically transparent materials. More specifically, it is suitable to use glass like borosilicate glass and quartz glass, resin and plastic like polyethylene, or a solid substrate like a silicon substrate. When a silicon substrate is used for the substrate 1 of the reaction substrate 100, a light source 41 on top may emit light with a wavelength of 900 nm or more.

When it is confirmed that the hydrophilic region $3_2$ is in the prescribed position; namely, the two liquid droplets $15_1$ and $15_2$ and the gas injection nozzles $22_1$ and $22_2$ are aligned on the line, the user gives the operation signal 28 to the personal computer 26, pulse-opens the valves $23_1$ and $23_2$ to inject gas from the gas injection nozzles $22_1$ and $22_2$. When gas is injected from the gas injection nozzles $22_1$ and $22_2$, the liquid droplets $15_1$ and $15_2$ are guided through the grooves $4_1$ and $4_2$ to move to the hydrophilic region $3_2$ and collide on the hydrophilic region $3_2$.

In this example, the liquid droplets $15_1$ and $15_2$ are supposed to be of the same size; however, depending on the reaction of the measurement thereof, each size may be different. In this case, gas injected from the gas injection nozzles $22_1$ and $22_2$ must be controlled, so that the two liquid droplets $15_1$ and $15_2$ collide on the hydrophilic region $3_2$. For this reason, it is natural for the personal computer to have a suitable program so that when the sizes of the two liquid droplets $15_1$ and $15_2$ are inputted into the personal computer 26, the personal computer 26 gives a suitable signal. This issue is not limited to the size; there can be a possibility that this issue needs to be considered depending on the substance which is included in the liquid droplet and which needs to be reacted.

The case of the reaction on the hydrophilic region $3_2$ in which the two liquid droplets $15_1$ and $15_2$ collide on the hydrophilic region $3_2$, turning into the liquid droplet $15_3$ can be measured not only by the above-mentioned optical system but also by the optical system described below.

After the wavelength of the light irradiated from a light source 45 at the lower side is selected with the filter 46, the light irradiated from a light source 45 is led to the objective lens 47 with the dichroic mirror 48 and is used for excitation light for observing the reaction inside the liquid droplet $15_3$. Fluorescence emitted from inside the liquid droplet $15_3$ is observed with the objective lens 47 again; and fluorescence emitted after excitation light is cut with the dichroic mirror 48 and a filter 51 can be observed with a camera 52.

At this time, by adjusting a combination of the dichroic mirror 48, the filters 42, 46 and 51, transmitted light alone can be observed with the camera 52; or fluorescence alone is observed; or transmitted light image and fluorescence image can be observed with the camera 52 at the same time.

Image data obtained with a camera are analyzed with the personal computer 26. The CCD camera 52 carries out observation. Although not shown here, it is convenient to display the image signal detected by the CCD camera 52 on the monitor of the personal computer 26.

Specific examples are described below regarding tracking of the DNA hybridization process. Liquid A and liquid B each is a 28-base-long synthetic single-stranded DNA complementary to each other with a concentration of 0.2 pmol/µl. A solvent thereof is 10 mM of Tris-HCl (pH 8.0) including 500 mM of NaCl. Ethidiumhomodimer intercalated specifically to the double-stranded DNA is added in either of the liquid A and the liquid B. 1 µl of the liquid A is put on the hydrophilic region $3_1$ on the reaction substrate 100 to form the liquid droplet $15_1$. 1 µl of the liquid B is put on the hydrophilic region $3_3$ to form the liquid droplet $15_2$. Two of the liquid droplets are made to roll and collide against each other on the hydrophilic region. The two collided liquid droplets turn into one liquid droplet $15_3$; the liquid droplet $15_3$ is anchored to the hydrophilic region $3_2$ and stays in that position stably; therefore, the hybridization process with the liquid A and the liquid B proceeds.

The aspect in which the two liquid droplets $15_1$ and $15_2$ collide on the hydrophilic region $3_2$ can be monitored and detected with the optical system on the upper side; hybridization by the liquid A and the liquid B coalesced into one liquid droplet $15_3$ can be monitored with the optical system on the lower side; and fluorescence intensity in the neighborhood of 560 nm can be dispersed and measured.

FIG. 149 is a waveform diagram showing change over time of the fluorescence intensity obtained by monitoring the fluorescence intensity of the liquid droplet $15_3$. After a threshold 61 of several dozen milliseconds after the collision of the liquid droplets, the fluorescence intensity rapidly increases. The fluorescence intensity increases because each of the single-stranded DNAs hybridizes with one another to become a double-stranded DNA to which ethidiumhomodimer is intercalated. The reaction takes place in at least three steps of 62, 63 and 64; it is considered that hybridization takes place with the portion of a single-stranded DNA as a core in which it is easier for each single-stranded DNA to hybridize with one another; and sequentially hybridization proceeds within a molecule.

Example 1 uses a reaction system similar to a stopped flow system in which flow is stopped for measurement by blending reaction liquid with collision; therefore, the data similar to those from the existing stopped flow system can be easily obtained. Because very small amount of liquid is used, the use of a precious sample can be reduced. In respect to reaction, spectroscopic change on the collision face of the liquid droplets may be tracked using microspectroscopy; similarly, spectroscopic change on the collision face of the liquid droplets may be tracked by driving a small droplet into a big droplet. It is effective to disperse light of the entire liquid droplet by irradiating ultrasonic waves for just a moment, agitating and blending to start the reaction, although this technique has a problem of promoting the reaction by giving energy from outside.

Other Examples

FIG. 150 is a plan view showing an example of the reaction substrate 100 suitable for spectroscopic measurement using a microspectroscopic device. As can be seen easily in contrast with FIG. 146 (A), in this example, there are many combinations of the hydrophilic regions $3_1$, $3_2$ and $3_3$ and the hydrophilic grooves $4_1$ and $4_2$ on the substrate 1. Therefore, a variety of liquid droplets including reactants of the A group are arrayed on the hydrophilic regions $3_1$; a variety of liquid droplets including reaction medium of the B group reacting to a variety of liquid droplets including reactants of the A group are arrayed on the hydrophilic region $3_3$; by making the liquid droplets of the liquid droplet array of the B group sequentially collide against the liquid droplets of the A group array, a variety of reactions start by time interval to perform measurement. For that purpose, the number of the pairs of the gas injection nozzles $22_1$ and $22_2$ should be the same as that of the pairs of the hydrophilic regions $3_1$, $3_2$ and $3_3$ and the hydrophilic grooves $4_1$ and $4_2$; and it is necessary to operate controls in which each valve is sequentially opened or closed with the personal computer 26, or by moving the stage 19 bit by bit with the personal computer 26, the valve is opened or closed every time the stage 19 reaches the prescribed position.

In Example 1, two liquid droplets are collided with the pair of the hydrophilic regions $3_1$, $3_2$ and $3_3$ and the hydrophilic grooves $4_1$ and $4_2$; however, for example, when a pair having the same construction with the pair of the hydrophilic regions $3_1$, $3_2$ and $3_3$ and the hydrophilic grooves $4_1$ and $4_2$ is formed with the hydrophilic region $3_2$ overlapped, and the gas injection nozzles $22_1$ and $22_2$ are provided corresponding to it, it is possible to observe the reaction caused by the collision of the four liquid droplets.

It is also possible to observe an influence on a cell by dissolving a plurality of reactive precursors for causing reaction in each of the different liquid droplets, making it collide or react, or by dissolving a liquid droplet with a cell inserted therein and a liquid droplet including an active substance of a different cell into a different liquid droplet, making it collide or react.

[XXX] A Thirtieth Embodiment

A thirtieth embodiment of the present invention disclosed herein provides a spectroscopic system and a spectroscopic method capable of advantageously testing even a very small amount of sample without any cuvette device to solve the problem associated with the needs for measuring a minute amount of sample. This embodiment uses the known phenomenon that a solvent containing water as a main ingredient is apt to form a droplet having the form of substantially perfect circle on a water-repelling substrate. In this embodiment, a droplet is formed on a substrate having the water-repelling property. On the substrate, a hydrophilic line on which the droplet can be moved along is formed. The droplets are transferred on this line successively. A detection system is provided so that the direction of the system intersects the direction of the hydrophilic line, and the absorbance and fluorescence intensity of the droplet is measured when the droplet moves across the detector direction of the system. White light or excitation light is projected to the droplet on the hydrophilic line, and the absorbance is measured by the spectroscopy measurement with the light transmitted through the droplet, or the fluorescence level is measured. The light path length necessary for measurement of the absorbance and fluorescence can be obtained by measuring the size of the droplet.

Example 1

Detailed descriptions are provided below by referring to measurement of a concentration of a protein as an example. Herein, a quantification of a protein is performed using 280-nm wavelength known as a typical protein absorption band. As the protein, chicken egg white lysozyme is used and the molecular extinction coefficient $E^{1\%}_{280}$ is 26.6. The concentration of the protein is previously adjusted in the range between 0.05 mg/ml and 10 mg/ml and the sample solution is used as a diluted solution.

Figure 151:
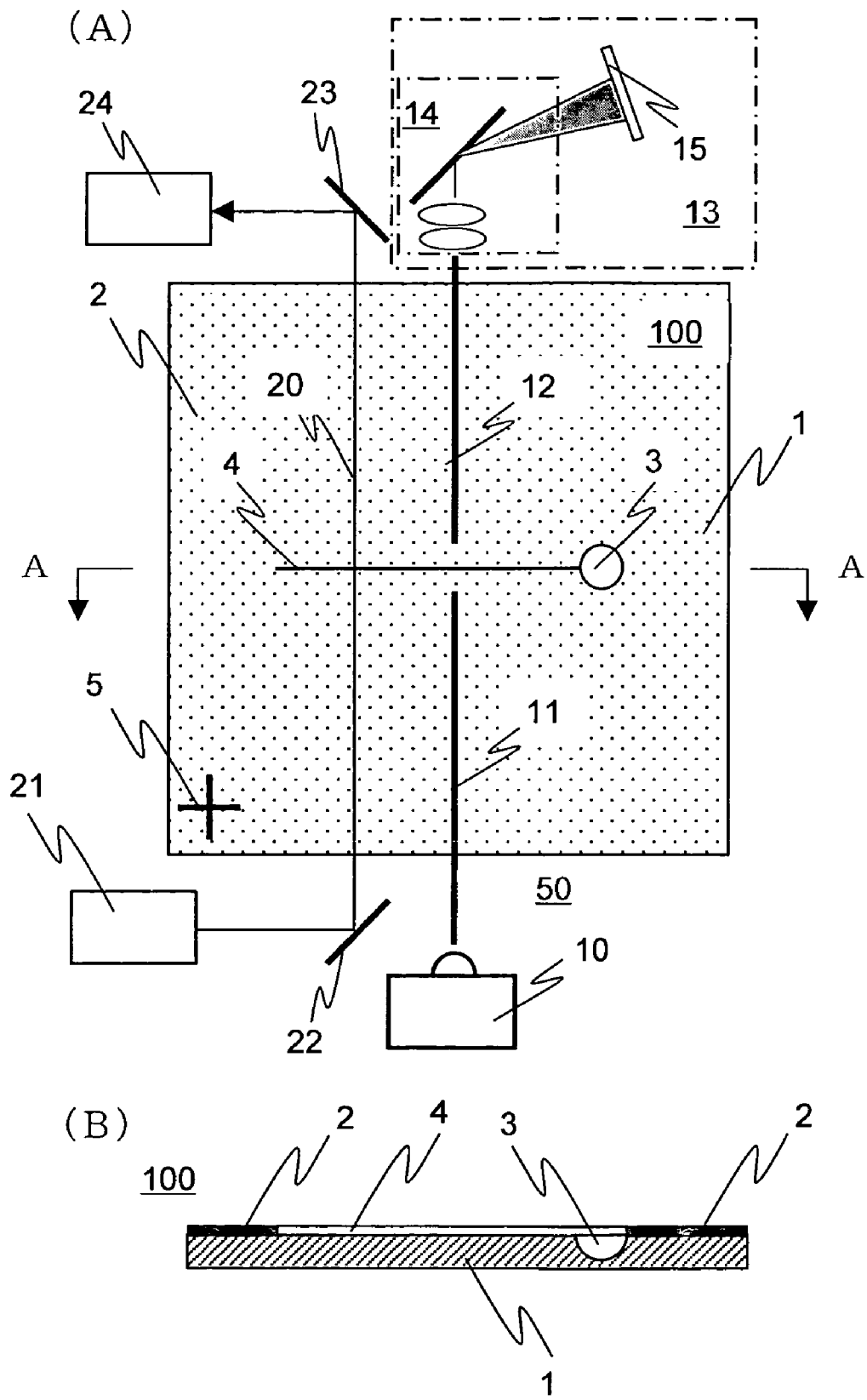

FIG. 151 (A) is a plan view illustrating a measuring substrate 100 advantageously applicable to the Example 1, and is also a conceptual view illustrating the measurement system with the measuring substrate configured therein as a fundamental component. FIG. 151 (B) is a cross-sectional view of the measuring substrate 100 taken at the line A-A and viewed in the direction indicated by the arrow. Reference numeral 1 denotes a silicon substrate with, for instance, 1 mm thickness and the size of 40 nm×40 nm. The surface of the silicon substrate 1 is regarded as a hydrophobic region 2. On the region, a hydrophilic line 4 is formed. The length of the hydrophilic line 4 may be, for instance, 20 mm with 0.01 mm wide. At the terminal point of the hydrophilic line 4, a droplet stopper 3 is formed. Numeral reference 5 denotes an alignment marker formed on one surface of the silicon substrate 1. As described below, a droplet is formed on the left end of the hydrophilic line 4 and is moved on the hydrophilic line 4 to the droplet stopper 3 at the predefined velocity. The size in the figure is shown in the deformed state for simplifying for convenience of illustration.

A measurement system 50 is provided approximately at an intermediate position of the both ends of the hydrophilic lines 4 so that the measurement system intersects the hydrophilic line. The measurement system 50 includes a wide range light source 10 capable of emitting lights in the ultraviolet to visible regions, an optical fiber 11 for guiding the white light outputted from the wide range light source 10 and irradiating the white light to a droplet moving on a hydrophilic line 4 in parallel to a surface of the measuring substrate 100, an optical fiber 12 provided at a position opposite to the optical fiber 11 across the hydrophilic line 4 and capable of receiving the white light transmitted though the droplet, and a detector 13 receiving the white light transmitted through the droplet and guided though the optical fiber 12. It is needless to say that the headers of both the optical fibers 11 and 12 are placed opposite to each other across the hydrophilic line 4 so that the headers do not contact with any droplet moving on the hydrophilic line 4. The detector 13 includes a spectroscope 14 and a CCD line sensor 15.

A laser beam 20 is projected in parallel to the surface of the measuring substrate 100 and passes across the hydrophilic line 4 to the left side of the measurement system 50. Numeral reference 21 denotes a laser source. Numeral reference 22 and 23 denote reflection mirrors for reflecting the laser beam 20, and numeral reference 24 denotes a detector for detecting the laser beam 20. This laser beam 20 is used for measuring a diameter of the droplet moving on the hydrophilic line 4. Because of this feature, the laser beam 20 may be projected to the right side of the measurement system 50.

In FIG. 151 (B), the cross section is taken at the position of the hydrophilic line 4, and therefore the entire central portion on the substrate 1 are indicated as a hydrophilic region. The droplet stopper 3 is provided at the right edge section of the hydrophilic line 4.

For forming the hydrophilic line 4 (hydrophilic region) and the hydrophobic region, the top surface of a hydrophilic silicon substrate 1 is once oxidized to create a hydrophilic $SiO_2$ thin film across the whole region once. Then the $SiO_2$ thin film of the region is removed by melting the $SiO_2$ thin film with a fluorinated acid to form a hydrophobic region. Alternatively, when the hydrophilic material is previously used on the surface of the substrate 1 with the $SiO_2$ thin film formed thereon, a hydrophobic material such as fluorinated resin and silicon resin can be placed on the hydrophilic surface to form a hydrophobic region. In this case, the height of the hydrophilic region provided in the hydrophobic region becomes shorter than the height of the hydrophobic region by the height of the hydrophilic region thereof. FIGS. 151 (A) and (B) show an example where the hydrophobic region 3 and the hydrophilic line 4 are formed by the latter method described above.

In Example 1, a droplet of a fluid to be measured can be formed at the left end of the hydrophilic line 4 once. Then the droplet is moved to the right on the hydrophilic line 4 with predefined speed. In the moving process, the size of the droplet can be measured to analyze the droplet.

FIG. 152 is a schematic diagram illustrating a sample of a system configuration preferable to the thirty embodiment of the present invention capable of forming a droplet at the left end of the hydrophilic line 4 on the measuring substrate 100.

First, descriptions are provided below for operations of forming a droplet 36 at the left end of the hydrophilic line 4 on the measuring substrate 100. When the system is started up, a user checks the position of the alignment marker 5 described with reference to FIG. 151(A), and gives an operation signal 28 to a personal computer 26 to control a driving unit 27 to position the stage 19 so that the measuring unit 100 can be placed in the predetermined start-up position. The stage 19 can be moved in X and Y directions in response to the signal inputted thereto. Next, for adjusting the position that the droplet 36 is located (the position at the end of the hydrophilic line 4) to the position that the header portion of the Pipet 33, the user gives an operation signal 28 to the personal computer 26 to control the driving unit 27, thereby the stage 19 is positioned. In this case, if necessary, the user can adjust the position more accurately by sending a feedback signal for positioning to the personal computer 26 while monitoring the header portion of a Pipet 33. Then a fluid to be measured is aspirated into the Pipet 33.

When the measuring substrate 100 is moved to the predefined position, in other words, when the position of the header portion of the Pipet 33 corresponds to the left end of the hydrophilic line 4, this event can be detected or the user may give a direction to the personal computer 26 to send a signal to the driving unit 32 so as to eject a fluid 34 to be measured. And then a syringe pump 31 is driven so as to eject the fluid to be measured from the inside of the Pipet 33 to form a droplet 36 at the header portion of the Pipet 33. The size of the droplet 36 formed at the header portion of the Pipet 33 can be determined according to the conditions such as the density and gravity of the fluid to be measured and the size of the header portion of the Pipet 33. And after the droplet grows to have a certain size, the droplet can be dropped off to the left end of the hydrophilic line 4. It is not always necessary to control to stop the syringe pump 31 and it is allowable if a program to stop the syringe pump 31 is stored in the personal computer.

When the user would prefer the method including the control of the syringe pump, it is allowable to monitor the droplet 36 formed at the header portion of the Pipet 33 with an optical device. And either in response to the signal outputted from the device, the driving unit 32 is controlled so that the status that the droplet grows to have predefined size could be detected, or in response to the operator's instruction, the operation of the syringe pump 31 can be stopped, and the Pipet 33 can be held down (it is not shown but it is necessary to have a driving unit here like the driving unit 37 to control the Rod 41 as described hereinafter) so that the droplet 36 formed at the header portion of the Pipet 33 could be contacted with the left end of the hydrophilic line 4 on the measuring substrate 100 to be placed on the hydrophilic line 4. The reason why it is illustrated as the elementary part of the Pipet 33 is separated from a tube 30 herein is to enlarge the scale of the Pipet 33 for illustrative purpose only.

Next, the descriptions are provided below for the measurement of the droplet 35 of the fluid to be measured placed on the left end of the hydrophilic line on the measuring substrate 100. In this case, 1 µl of solution including protein (50 mM of phosphoric acid buffer solution with pH 7.4 including 150 mM of NaCl) is used as the fluid to be measured. Next, a Rod 41 with 0.1-mm diameter having a header made of hydrophilic glass and side surface made of hydrophobic Polyimide is contacted with the top surface of the droplet 35. Therein, it is regarded that the Rod 41 could work with the driving unit 37 capable of moving the Rod 41 in the vertical and horizontal directions on the hydrophilic line 4. When the Rod 41 is placed on the left end of the hydrophilic line 4, if the user gives a signal to the personal computer 26 to lower the position of the Rod 41, the Rod 41 is moved downward by the driving unit 37. When the header portion of the Rod 41 touches the droplet 35, the downward movement of the driving unit 37 is stopped. Then the Rod 37 is moved to the right over the hydrophilic line 4 with the predefined speed. Accordingly, the droplet 35 on the hydrophilic line 4 on the measuring substrate 100 can be moved on the hydrophilic line 4 horizontally to the right side with the predefined speed to drop into the droplet stopper 3.

In the moving process on the hydrophilic line 4 horizontally to the right side with the predefined speed, the droplet 35 can be passed through the laser beam 20 to be measured the diameter of the droplet 35 thereof. For instance, if the Rod 41 is moved at the speed of 2 mm/sec, the droplet 35 can stick to the header of the Rod 41, and move at the same speed. Namely, the droplet 35 can also be moved at 2 mm/sec, the same moving speed of the Rod 41. When the droplet 35 passes through the laser beam 20, the laser light is refracted on the boundary surface on the droplet 35, changing the amount of light that reaches the detection unit 24. After the droplet 35 passes through the laser beam 20, the amount of light can be restored to the previous level. If it would take 1.22 sec for the droplet to pass through the laser beam, the diameter of the droplet 35 could be obtained by the calculation of 0.61 (=1.22/2) mm at the crossing position of the laser beam. This method assumes that the height of the laser beam 20 from the measuring substrate 100 is previously adjusted to the half of the diameter of the droplet 35 before the measurement. Because of this feature, it might be necessary to adjust the height of the laser beam 20 from the measuring substrate 100 if the diameter of the droplet 35 changes largely.

Next, the droplet 35 passes through the position where the optical fibers 11 and 12 of the detection device placed opposite each other. In this case, since the height of the optical fibers 11 and 12 from the measuring substrate 100 is adjusted to the same height of the laser beam 20 from the measuring substrate 100, the light pass length of fluid to be measured becomes 0.61 mm. The maximum absorbance when the droplet passes through the position between the optical fibers 11 and 12 of the detection device can be measured and then converted into the value when the light pass length is 1 cm.

The FIG. 153 is a characteristic drawing in which the measured absorbance values according to the Example 1 are plotted thereon. The characteristics having a linear portion 21 and non-linear portion 22 can be obtained as shown in this FIG. 153. The non-linear portion 22 can be described as a typical phenomenon caused by too high lysozyme concentration level. When the values of the measurement result can be compared to the values in the public domain of the well-known protein concentration, they can be well matched each other.

In the measurements according to Example 1, the droplet 35 dropped into the droplet stopper 3 would be just passed through the laser beam 20 and then while light projected from the optical fiber 11 of the detection unit without receiving any operations that could induce any chemical changes of the droplet therein. Because of this feature, it is allowable to aspirate the droplet 35 dropped into the droplet stopper 3 and use it in the other measurement.

Further, in the measurement according to Example 1, what might be contaminated by the measurements is just the hydrophilic line 4 on the measuring substrate 100. Because of this feature, even if the droplet of a new sample is dropped on the left end of the hydrophilic line 4 and then the measurements are to be repeated, the droplet of the new sample would not be contaminated by the sample previously measured. Accordingly, it is allowable to place all the series of sample droplets sequentially on the hydrophilic line 4 on the measuring substrate 100 to measure them sequentially to improve the throughput thereof.

According to the thirty embodiment of the present invention, the requirements of the measurements described above would be the possibility of measuring the spectral instantly and the property of the laser light to be projected to the samples that should have fairly constant intensity in terms of the wavelength component over time. Because of the limited requirements above, the measurement can be done even in an open space. Obviously, it is also allowable to use a light having a single wavelength after the spectroscopy to project to the droplet and use a conventional spectroscopy optical system to measure the absorbance. But in this case, it may not be allowable to use in an open space and, instead, the measurement may have to be done inside a dark box.

Further, since a cuvette is not substantially used in the above-mentioned measurements, the light used therein passes thorough the droplet and air only. Because of this feature, the spectroscopy measurements even using a waveform that could be absorbed by a cuvette can be advantageously performed. For instance, when the amount of protein is measured by using the absorbance method with 210 nm wavelength light, it is not practical to use a typical glass cuvette or plastic cuvette. It might be practical if a cuvette made of expensive fused silica could be used. But, with the thirty embodiment of the present invention, it would be possible to exclude such an expensive fused silica cuvette.

Example 2

Example 2 in the 30th embodiment of the present invention describes an example to conduct a fluorescence measurement. This example includes the preprocessing to mix the reagent with a liquid to be measured and make a reaction before the measurement.

FIG. 154 (A) is a plan view of the measuring substrate 200 preferred for the Example 2, and a schematic diagram of the measuring system comprising the components based on the measuring system. FIG. 154 (B) is a cross-sectional diagram of the measuring substrate 100, viewed in the direction of indicated by the arrow, at the position of A-A in the plan view of measuring substrate 200. The sizes of the drawings are deformed for the purpose of explanation.

The measuring substrate 200 is similar to the measuring substrate 100 in the Example 1. Reference numeral 1 indicates a silicon substrate, for instance, having the thickness of 1 mm and the size of 40 mm×40 mm. The surface of silicon substrate 1 is made to a hydrophobic region, and hydrophilic regions 52 to 54 and hydrophilic lines 56 to 59 are set up therein to retain droplets. The liquid receiver 3 has been formed on the end edge (at the far right) of the hydrophilic line 59. The size of the hydrophilic regions 52 to 55 are decided depending on the size of the retained droplet in this region, for instance, however, it is approximately 400 μm×400 μm. The width of hydrophilic lines 56 to 59 is approximately 0.1 mm. The reference numeral 5 indicates the marker for positioning, and which is formed on one side of silicon substrate 1. The reference numeral 8 indicates a temperature control plate, and which is formed on the back side of silicon substrate 1. The sizes of the drawings are deformed for the purpose of explanation.

A measuring system 51 is installed with the shape that intersects with hydrophilic line 59. The measurement system 51 is comprised optical fiber 11, optical fiber 12 and detector 13. Optical fiber 11 guides laser source 10' for fluorescent excitation and laser beam of the laser source 10', and the laser beam is exposed to the droplet in parallel to the surface of measuring substrate 100, neighboring the droplet moving on the hydrophilic line 59. Optical fiber 12 is installed across the hydrophilic line 59, and opposing position with optical fiber 12 to receive fluorescent exposed by the droplet. Detector 13' has an input of fluorescent exposed by the droplet guided by optical fiber 12. Optical fiber 12 is set up to have a 120 degree of angle with optical fiber 11, so that the reflected light on the surface of the droplet of the laser beam, which is exposed on the droplet, will not be entered into the optical fiber 12. Optical fiber 12 here is also set up at opposing position with optical fiber 11, having a certain distance that the tips do not contact with the droplet which moves on the hydrophilic line 59.

In the same way as the description referring to FIG. 152 in the Example 1 in the 30th embodiment of the present invention, each droplet is formed in the hydrophilic regions 52 to 54. A droplet containing a single stranded cDNA mixture, which is reverse-transcribed from mRNA, is formed in the hydrophilic region 54. A droplet comprising 60 base probe solution, which hybridizes to specific cDNA, in the hydrophilic region 53. A droplet comprising cyber green I solution, which intercalates specifically to the double stranded, is formed in the hydrophilic region 52. Each droplet is 0.5 μl. Examine 5 pmol/μl of complementary probe and non-complementary probe per cDNA 0.2 pmol/μl here as a model system. The solvent is 10 mM of Tris-HCl (pH 8.0) containing 50 mM of NaCl.

Firstly, the droplets formed both in hydrophilic region 53 and 54 are transported in the same method as Example 1 in the 30th embodiment of the present invention, and mixed here. Rod 41 used for transporting droplets can mix the droplets by rotating for the axial direction. Of course, a piezoelectric element should be formed in advance on the back face of the silicon substrate 1, which is located at the position that hydrophilic region 55 is formed, and the droplets may be stirred by contact-free after reaction of the ultrasonic wave caused by the piezoelectric element with the droplet placed in the hydrophilic region 55. After stirring the droplets for 30 seconds, the droplet formed in the hydrophilic region 52 is added in the droplets stirred in the hydrophilic region 55, and then the mixed droplets are stirred again. After 30 seconds, the droplets comprising three different liquid droplets stirred in the hydrophilic region 55, are transported with the prespecified speed, for instance, 2 mm/second, on the hydrophilic line 59. The droplet transporting on the hydrophilic line 59 produces fluorescence in receipt of the laser beam of the laser source 21', when the droplet transporting on the hydrophilic line 29 passes through the betweenness of the tips of the optical fiber 12, which is set up opposing to optical fiber 11. The fluorescence intensity at this point is measured by detector 13' through optical fiber 12.

When the complementary cDNA with probe exists in the liquid for the sample, the strength of fluorescence is obtained in accordance with the amount of cDNA. If there is no complementary cDNA at all, the fluorescence strength is less or equal to 1/20.

Since it is better to manage the size of the droplet in a rigorous manner in the Example 2 than the Example 1 in the 30th embodiment of the present invention, it is better to measure with a CCD camera using the optical system (not shown in the drawing), to input the data in the personal computer 26, to make a prespecified process and to control driving device 32 of the syringe pump 31 when the droplet is formed described for FIG. 152.

This optical system may be, to be short, the system which can monitor the fore-end part of the pipet 33. Moreover, the optical system should control the temperature control plate 8 that is set up on the back surface of the measuring substrate 200, and operate the system in the state that the temperature of the measuring substrate 200 ranges 42° C. to 46° C. and in the wet condition that the ambient atmosphere of 45° C. Since the fluctuation of the size of the droplet will change the inclusive concentration of cDNA, it is better to control by monitoring the movement of the droplet or size of the droplet after stirring with an optical system CCD camera that the diameter of the droplet will not fluctuate 10% and above by feedback control on the temperature control plate 8 in the case there is a fluctuation in size of the droplet diameter.

In the Example 2 in the 30th embodiment of the present invention, because the droplet formed in the hydrophilic region 54 and the droplet formed in the hydrophilic region 53 are transported to the hydrophilic region 55 in the same method as the Example 1 in the 30th embodiment of the present invention, and preprocessing before the reaction is carried out by mixing the droplets at this point, and then the processes are integrated by a reaction of the droplet formed in the hydrophilic region 52 with the mixed droplets, it is possible to avoid the above-mentioned human error. In addition, this process is made on one measuring substrate 200, it is better to make the measuring substrate 200 as a chip, which measures immediately after the reaction and is disposable type used only for one time, in order to prevent from any contamination.

It can be used for the purpose of detecting reaction products by combining with various reactions, and can resolve the problem by making it as system-on-chip, that the sample reaction and detection is integrated. The reactive precursor should be divided by several droplets, and each droplet on the hydrophilic line is reacted by collision and coalition in the predefined order. The reaction time is that, for instance, a hydrophilic region with approximately 2 to 4 times of line width diameter may be set up on the hydrophilic line so that the droplet can stay therein, or it is possible to solve by making a slightly bent part so that the droplet can stay therein for a predefined time.

Other Examples

Example 30 can be performed in various systems not limited to a configuration of the aforementioned examples.

For instance, a migration of droplet by the rod 41 described with reference to FIG. 152 can be replaced to by gas injection. As an example, a gas injection nozzle is provided on an extension of the hydrophilic line 4 and the gas injection nozzle has a tube connected to a gas pressure tank and a valve, and then a migration of the droplet 35 may be controlled with gas injection using the gas injection nozzle by opening and closing the valve. Assuming that a size and weight of the droplet is considered to gas injection, the droplet 35 migrates on the hydrophilic line 4 with prespecified speed guided by the hydrophilic line 4, and drops into a liquid tank 3. A migration from the hydrophilic area 55 to the liquid tank 3 in Example 2 can be also performed in the same manner. When using gas injection for migration of the droplet, since physical facilities migrating on the upper side of the measuring substrate 200 is reduced, a configuration of device becomes simpler.

A surface elastic wave can be used for migrating a droplet. FIG. 155 is a conceptual diagram illustrating an example of configuration of a system for preparing a droplet at a left edge of the hydrophilic line 4, migrating the droplet with surface elastic wave, and measuring the migration. A surface elastic wave generator comprising of the piezoelectric element 205 and the comb electrodes 206 is provided under the hydrophobic line 4 on which the droplet of the substrate 1 migrates. As the comb electrodes, lithium compounds such as lithium 4-borale, lithium tantalate or lithium niobate can be used. Surfaces of the piezoelectric element 205 and the comb electrodes 206 are coated with hydrophobic coating, and the hydrophilic line 4 is provided to a direction of transporting droplet as described in the aforementioned Example 1. By applying a voltage between the comb electrodes 206 facing each other, a surface electric wave having uniform phases can be generated along the hydrophilic line 4. The droplet 202 migrates on the surface electric wave. Then, the comb device is provided at the upper section of the hydrophilic line 4 generating a droplet. A piezoelectric substrate section may be provided at all over the hydrophilic line 4 of the substrate 1 or may be provided only close to areas in which the droplet 202 is dropped as illustrated in FIG. 155. By applying a voltage between the comb electrodes, a surface elastic wave is generated and a droplet flies and migrates to a direction of the arrow 204.

Conventionally, a sample used for measuring absorbance is generally abandoned. If a volume of liquids for the measurement is large, samples will become wastes.

For example, a high through-put can be achieved by the system described in FIG. 151; a plurality of the systems for the hydrophilic line 4 and the liquid tank 3 are provided in parallel, a droplet made from a sample liquid to be measured is provided at a left edge of each hydrophilic line 4, and each droplet is sequentially rolled to a detecting section for measurement by gas injection. In this case, it is practical that only one system of gas injection is provided and the stage 19 is moved.

A force for migrating a droplet is, in another system, that one miniature magnet is put into a droplet and the droplet is migrated by moving the miniature magnet from a back side of a substrate to a magnetic field. In this case, the miniature magnet should have hydrophilic property for clinging the droplet thereto. A size of the miniature magnet makes less than half of a diameter of the droplet so that measuring absorbance in later can not be interrupted.

The present invention can be realized with the following configurations in accordance with each embodiment as described previously besides the configurations described in the claims.

First Embodiment

1. A centrifugal separator comprising:
a motor for rotating a rotating plate;
a rotating plate rotating about a shaft rotated by the motor; and
a chip for centrifugal separation attached to a face of the rotating plate;
the chip for centrifugal separation including:
flow paths fed with a plurality of solutions each having different specific gravity;
a separation chamber with the flow path converged thereon; and
a plurality of flow paths branching out from the separation chamber;

wherein reservoirs are provided at each end of the flow paths for feeding solutions to the separation chamber and the plurality of flow paths branching out from the separation chamber, a solution having prespecified specific gravity is reserved in the reservoir communicating to the flow path for feeding solutions to the separation chamber, and a sample to be separated is supplied in one of the reservoirs.

2. The centrifugal separator according to paragraph 1, wherein the centrifugal separator has configuration in which the reservoir communicating to the flow path fed with a plurality of solutions each having different specific gravity is positioned at an equal distance from the rotational shaft, and the reservoir communicating to the plurality of flow path branching out from the separation chamber is positioned at an equal distance from the rotational shaft.

3. A method of separation performed by a centrifugal separator comprising:

a motor for rotating a rotating plate;

a rotating plate rotating about a shaft rotated by the motor; and a chip for centrifugal separation attached to a face of the rotating plate;

the chip for centrifugal separation including:

flow paths fed with a plurality of solutions each having different specific gravity;

a separation chamber with the flow path converged thereon; and a plurality of flow paths branching out from the separation chamber;

wherein reservoirs are provided at each end of the flow paths for feeding solutions to the separation chamber and the plurality of flow paths branching out from the separation chamber, a solution having prespecified specific gravity is reserved in the reservoir communicating to the flow path for feeding solutions to the separation chamber, a sample to be separated is supplied in one of the reservoirs, and a solution transferred from the reservoir to the separation chamber by centrifugal separation forms layers corresponding to the specific gravity to separate the sample to be separated according to the specific gravity.

4. A chip for centrifugal separation applicable to a centrifugal separator comprising:

a motor for rotating a rotating plate;

a rotating plate rotating on an axis rotated by the motor; and a chip for centrifugal separation attached to a face of the rotating plate;

the chip for centrifugal separation including:

flow paths fed with a plurality of solutions each having different specific gravity;

a separation chamber with the flow path converged thereon; and a plurality of flow paths branching out from the separation chamber;

wherein reservoirs are provided at each end of the flow paths feeding solutions to the separation chamber and the plurality of flow paths branching out from the separation chamber.

5. A chip for centrifugal separation, the centrifugal separator configured to have a position of the reservoir communicating to the flow paths feeding solutions to the separation chamber at an equal distance from the rotational shaft, and to have a position of the reservoir communicating to each end portion of the plurality of flow paths branching out from the separation chamber at an equal distance from the rotational shaft.

6. The chip for centrifugal separation according to paragraph 3, wherein the reservoir is provided on a face opposite to a substrate with the flow path for the chip for centrifugal separation and the separation chamber provided thereon, and an end of the reservoir and an end of the flow path are communicated by a hole penetrating the substrate.

7. The chip for centrifugal separation according to paragraph 3, wherein the reservoir communicating to one end of the flow path fed with a plurality of solutions each having a different specific gravity has a partly cut out separation wall for separating a plurality of reservoirs in a position opposite to the communicating hole.

Second Embodiment

1. A cell separation chip comprising:

a flow path introducing a fluid containing a target cell with a specific substance for labeling identification intaked into a cell separation area via a transporter, and a sample hole connected to the flow path for feeding a fluid containing a target cell;

a buffer flow path provided in parallel with the flow path with a fluid containing a target cell in the cell separation area introduced therein, and a buffer hole connected to the flow path for feeding a buffer;

a flow path located on the downstream side from the position in which the flow path introducing a fluid containing a target cell in the cell separation area and the buffer flow path converge, for observing a cell in the fluid in which the liquid containing a target cell and a buffer-combined fluid flow as a laminar flow;

the cell separation area comprising: two openings for gel electrodes formed on the downstream side of the flow path for observing a cell, facing to each other on both sides of the flow path, and placed in a position slightly deviated from the flow direction; a target cell collecting flow path located in an imaginary line extended from the flow path; and a cell discharge flow path branching out from the flow path;

a hole for feeding the gel electrodes with a gel electrode material;

a hole connected to the cell discharging flow path for accommodating a liquid containing a discharged cell;

a cell dialysis section provided on the downstream side of the target cell collecting flow path; and a collecting flow path passing therethrough a fluid containing a target cell having passed through the cell dialysis section and a hole connected to the collecting flow path for accommodating a fluid containing the collected cell;

the cell separation chip including:

a buffer retention bath for feeding a buffer provided in a common communication with the sample hole for feeding a fluid containing a target cell and a buffer hole for feeding a buffer;

a buffer retention bath provided in communication with the hole for accommodating a fluid containing a fluid containing a discharged cell, for accommodating a discharged cell and a buffer; and a buffer retention bath provided in communication with the hole for accommodating a fluid containing a collected cell, for accommodating a target cell and a buffer;

the cell dialysis section including:

a dialysis area for dialyzing the collected cell via a prespecified porous membrane to discharge a specific material for labeling identification;

a buffer retention bath for feeding a buffer not containing a specific material for labeling identification in the dialysis area; and a buffer retention bath for collecting a buffer after dialysis.

2. The cell separation chip according to paragraph 1, comprising:

a substrate having a prespecified thickness and size;

each of the flow paths and the gel electrodes formed on the bottom face of the substrate;

a hole communicating with each of the flow paths and the gel electrodes formed the bottom face of the substrate and penetrating the substrate;

a translucent thin film attached onto the bottom face of the substrate, a retention bath communicating with the flow path provided on the top face of the substrate;

the cell dialysis section including a flow path provided between a flow path in the downstream region of the cell separation area and the hole, and communicating from the bottom face to the top face of the substrate; and a porous membrane provided on the top face of the substrate in the cell dialysis section, a space for circulating a buffer not containing a specific material for labeling identification for dialyzing the collected cell, and a retention bath for feeding the space with buffer.

3. A cell separator comprising:

a flow path with introduced in a cell separation area a fluid containing a target cell with a specific material for labeling identification intaked therein via a transporter, and a sample hole connected to the flow path for feeding a fluid containing a target cell;

a buffer flow path provided in parallel with the flow path with a fluid containing a target cell introduced into the cell separation area, and a buffer hole connected to the flow path for feeding a buffer;

a flow path located on the downstream side from a position in which the flow path with a fluid containing a target cell introduced into the cell separation area and the buffer flow path converge, for observing a cell in the fluid in which the fluid containing a target cell and a buffer are combined to flow as a laminar flow;

the cell separation area comprising: two openings for gel electrodes formed on the downstream side of the flow path for observing a cell, facing to each other on both sides of the flow path, and provided in a position deviated from the flow; a target cell collecting flow path located in an imaginary line extended from the flow path; and a cell discharging flow path branching out from the flow path;

a hole for feeding the gel electrodes with a gel electrode material;

a hole connected to the cell discharging flow path for accommodating a fluid containing a discharged cell;

a cell dialysis section provided on the downstream side of the target cell collecting flow path;

a collecting flow path passing therethrough a fluid containing a target cell having passed through the cell dialysis section and a hole connected to the collecting flow path for accommodating a fluid containing a collected cell;

a buffer retention bath provided in a common communication with the sample hole for feeding a fluid containing a target cell and a buffer hole for feeding buffer;

a buffer retention bath provided in communication with the hole for accommodating a fluid containing the discharged cell, for accommodating a discharged cell and a buffer; and a buffer retention bath provided in communication with the hole for accommodating a fluid containing the collected cell, for accommodating a target cell and a buffer;

the cell dialysis section including: a dialysis area for dialyzing the collected cell via a prespecified porous membrane to discharge a specific material for labeling identification via a transporter; a buffer retention bath for feeding the dialysis area with a buffer not containing a specific material for labeling identification; and a buffer retention bath for collecting the buffer after dialysis, in addition to a cell separation chip; and an optical system for detecting a cell flowing down in the flow path for observing a cell on the cell separation chip, the optical system determining whether a cell flowing down in the flow path is a target cell or not, and determining according to the result of determination whether voltage is applied to the gel electrodes or not.

4. The cell separator according to paragraph 3, wherein voltage is applied to the gel electrodes when it is determined that a cell flowing down in the flow path is not a target cell.

5. The cell separator according to paragraph 3, wherein a plurality of the cell separation chips are arrayed on the same plane; and a certain number of the cell separation chips are commonly provided with plumbing for feeding a buffer not containing a specific material for labeling identification and with plumbing for collecting a buffer after dialysis to feed a buffer to transit the buffers via each retention; and each buffer is relayed by respective detention baths to feed the dialysis area of the cell dialysis section with a buffer not containing a specific material for labeling identification.

Third Embodiment

1. A method of cytotechnology comprising the steps of:

binding for identification, polynucleotide specifically binding to a surface antigen expressed in a cancer-derived cell and having a structure binding to a labeled substance with covalent bonding, to the surface antigen expressed in the cancer-derived cell in a group of sample cells to separate the cells; and subjecting the separated cells to action of nuclease for decomposing the polynucleotide binding to the surface antigen expressed in the cancer-derived cell to obtain the cancer-derived cell, thereby determining the presence of cancer.

2. A method of cytotechnology comprising the steps of:

binding for identification, polynucleotide specifically having EpCAM bound to a surface antigen in a cancer-derived cell and having a structure binding to a labeled substance with covalent bonding, to a EpCAM bound surface antigen in the cancer-derived cell in a group of sample cells to separate the cells; and subjecting the separated cell to action of nuclease for decomposing the polynucleotide having EpCAM bound to the surface antigen with the cancer-derived cell to obtain the cancer-derived cell, thereby determining the presence of cancer.

3. A method of identifying a cell comprising the steps of:

preparing an identification element having a configuration in which a labeled substance is bonded to an identification substance with covalent bonding, the labeled substance being polynucleotide specifically binding to a specific antigen present on a surface of a specific cell;

mixing a group of sample cells and the identification element to bind the polynucleotide to the antigen in the specific cell in the group of sample cells; and employing the identification substance to identify the specific cell having the specific antigen;

wherein nuclease discomposing the polynucleotide is used as a reagent.

4. A method of cytotechnique or cell identification according to any of paragraphs 1 to 3, wherein the identification substance of the identification element is a fluorescent substance, and fluorescent detection is used for identifying a cell with the labeled substance in the identification element bonded thereto.

5. A method of cytotechnique or cell identification according to any of paragraphs 1 to 3, wherein the identification substance of the identification element is a particle or a magnetic particle, and particle imaging, scattered light detection or magnetic detection is used for identifying a cell with the labeled substance in the identification element bonded thereto.

Fourth Embodiment

1. A sample freezing device comprising: a pressure-resistant vessel having a cylinder with a solution containing a sample accommodated therein; a piston capable of engaging with the cylinder; a pressurizing unit capable of pushing the piston into the cylinder; and a control unit for controlling the pressurizing unit to control the rate of pushing the piston into the cylinder, the control unit applying pressure to a solution while keeping a temperature of the solution in the cylinder within a range from the phase transition point between the ice-I area and the liquid water area up to plus 4° C., and releasing pressure when the temperature reaching the state of almost the lowest temperature in the relationship between the ice-I area and the liquid water area.

2. The sample freezing method according to paragraph 1, wherein the cylinder is tapered on an end face of the pressure-resistance vessel, and an operation of engaging the piston with the cylinder is conducted in the state where a solution containing a sample to be accommodated in the cylinder overflows from the top of the cylinder.

3. A sample freezing device comprising the steps of:
cooling a sample at high pressure keeping the state of a solution thereof; and
flash-freezing the sample by rapid pressure reduction.

4. The sample freezing method according to paragraph 3, wherein a solution containing a sample is pressurized in the range from 0.1 to 0.2 GPa while keeping a temperature thereof in the range from the phase transition point between the ice-I area and the liquid water area up to plus 4° C. in the state where a gas phase the solution is not present, and is then subjected to a rapid pressure reduction.

Fifth Embodiment

1. A cell aliquoting device comprising:
a pipet capable of retaining a solution containing a plurality of cells and having a diameter of a tip opening thereof suited for passing through a prespecified size of a cell or a cell agglomerate;
a means for observing a cell on the tip of the pipet;
a means for pushing out a solution containing cells on the tip of the pipet to form a liquid droplet; and
a means for determining that a prespecified cell is contained in the liquid droplet to become a prespecified size of the liquid drop;
wherein each of the liquid droplets formed on the tip of the pipet is dropped and arrayed in a prespecified position on a substrate.

2. A cell culture system comprising: a means for forming a liquid droplet containing a prespecified number of cells; a means for controlling the size of the liquid droplet; a substrate for setting each of the liquid droplets in array; and a solvent layer formed on the substrate, having specific gravity smaller than a solvent of the liquid droplet, and being substantially unfused with the liquid droplet.

3. A cell culture system comprising: a means for forming a liquid droplet containing a prespecified number of cells; a means for controlling the size of the liquid droplet; a substrate for setting the liquid droplet in array; and a solvent layer formed on the substrate, having specific gravity smaller than a solvent of the liquid droplet, and being substantially unfused with the liquid droplet; a means for replacing a solvent of a liquid droplet on the substrate; a means for controlling a temperature of the liquid droplet during cultivating the cell; a means for observing a cell in a liquid droplet set in array on the substrate; and a means for collecting the cell after cultivating for a prespecified period of time.

4. A cell culture chip comprising: a substrate with a face thereof having a prespecified size provided as a hydrophobic area, the hydrophobic area being formed thereon a plurality of discrete hydrophilic areas with a prespecified clearance; and a wall formed on the substrate surrounding the plurality of hydrophilic areas, the cells contained in prespecified droplets being arrayed in the hydrophilic areas, and being covered with a solvent layer having specific gravity smaller than the solvent of the liquid droplet and being substantially unfused with the solvent of the liquid droplet.

5. A cell culture chip according to paragraph 4, wherein the solvent layer is previously provided, and then each cell included in a prespecified liquid droplet is arrayed in the plurality of hydrophilic areas on the substrate.

6. The cell aliquoting device according to paragraph 1, wherein the means of forming a liquid droplet containing a prespecified number of cells is arranged in such a way that a tip of a pipet for feeding a suspension containing the cells and a tip of a pipet for feeding a culture solution are faced to each other, and the size of a liquid droplet is controlled by controlling a quantity of each liquid.

7. The cell culture system according to paragraph 2 or paragraph 3, wherein the means of forming a liquid droplet containing a prespecified number of cells is arranged in such a way that a tip of a pipet for feeding a suspension containing the cells and a tip of pipet for feeding a culture solution are faced to each other, and the size of a liquid droplet is controlled by controlling a quantity of each liquid.

8. The cell aliquoting device according to paragraph 6, wherein the flow path associated with the two pipets is formed in a single pipet.

9. The cell culture system according to paragraph 7, wherein the flow path associated with the two pipets is formed in a single pipet.

Sixth Embodiment

1. A droplet operation device comprising:
an insulating substrate with one surface thereof being water-repellent;
a plurality of hydrophilic droplet retention areas formed on the water-repellent surface of the substrate;
a hydrophilic droplet transfer line formed by extending the hydrophilic droplet retention areas on the substrate;
a droplet forming device for forming a droplet in the hydrophilic drop retention areas on the substrate;
a charging device for selectively charging a droplet retained in the hydrophilic drop retention area on the substrate; and
a joy stick for making a charge having the same polarity as that of the charged droplet act to cause repulsion force against a charge of the charged droplet;
wherein the specific droplet retention area in the hydrophilic droplet retention area on the substrate is configured to allow a droplet to be subjected to charging and discharging.

2. The droplet operation device according to paragraph 1, wherein the charging device for selectively charging a droplet retained in the hydrophilic droplet retention area on the substrate comprises: a first electrostatic electrode not directly contacting to the droplet on an insulating substrate with a droplet contacted thereto; and a second electrode configured to directly contact an in-capillary liquid with a capillary for retaining a liquid capable of contacting the solution; wherein the portion of a droplet is charged by polarizing a droplet and a liquid in the capillary.

3. The droplet operation device according to paragraph 1, wherein the configuration of the specific droplet retention area in the hydrophilic drop retention area on the substrate capable of discharging a charge of a droplet is by earthing an electrode provided in the drop earth retention area.

4. The droplet operation device according to paragraph 2 or paragraph 3, wherein further provided is a switchboard placed in the lower portion of the substrate for earthing the electrode provided in the hydrophilic droplet retention area, when the substrate is set up on the switchboard.

5. The droplet operation device according to paragraph 1, wherein the charging device for selectively charging a droplet retained in the hydrophilic droplet retention area on the substrate is a device for selectively launching charged particles into the droplet.

6. A droplet operation method comprising the steps of: charging a plurality of droplets formed on a hydrophilic pattern on an insulating substrate with water repellency; and making a movable stick charged and having the same polarity as that of the droplet come close to the charged droplet to move the droplet along the pattern by means of repulsing force between the two.

7. The droplet operation method according to paragraph 6, wherein the moved drop is discharged in a prespecified position, and is incorporated with other drops moved to the prespecified position.

8. A substrate for a droplet operation comprising:
an insulating substrate with one surface thereof being water-repellent;
a plurality of hydrophilic droplet retention areas formed on the water-repellent surface on the substrate;
a hydrophilic droplet transfer line for hydrophilic liquid formed by extending the hydrophilic droplet retention area on the substrate;
an electrostatic electrode provided in the hydrophilic droplet retention area on the substrate via an insulating layer; and
an electrode formed on another surface on the substrate, associated with the electrode provided in the hydrophilic droplet retention area, and electrically connected to the latter electrode.

9. A switchboard used by placing a substrate for a droplet operation, the substrate comprising:
an insulating substrate with one surface thereof being water-repellent;
a plurality of hydrophilic droplet retention areas formed on the water-repellent surface on the substrate;
a hydrophilic droplet transfer line formed by extending the hydrophilic drop retention areas on the substrate;
an electrostatic electrode provided in the hydrophilic droplet retention area on the substrate via an insulating layer; and
an electrode formed on another surface on the substrate, associated with the electrode provided in the hydrophilic droplet retention area, and electrically connected to the electrode;
wherein the electrode provided in the hydrophilic droplet retention area on the substrate is earthed.

Seventh Embodiment

1. A controller for the size of a droplet comprising: a means for generating a droplet; a substrate with a pattern of a hydrophilic area retaining the generated droplet on a water-repellent surface thereof provided thereon; a temperature regulator contacting the substrate; a means for measuring the size of a droplet formed on the substrate; and a control unit for controlling a temperature of the temperature regulator based on the size of the measured droplet.

2. The controller for the size of a droplet according to paragraph 1, wherein the temperature regulator is discretely provided for each of a plurality of drops, and is capable of discretely regulating the temperature of each drop.

3. A controller for the size of a droplet comprising: a means for generating a droplet; a substrate with a pattern of a hydrophilic area retaining the generated droplet on a water-repellent surface thereof provided thereon; a means for transferring a droplet from one hydrophilic area to another hydrophilic area on the hydrophilic pattern; a temperature regulator contacting the substrate; a means for measuring the size of a droplet formed on the substrate; and a control unit for controlling a temperature of the temperature regulator based on the size of the measured droplet.

4. The controller for the size of a droplet according to paragraph 3, wherein the hydrophilic pattern includes at least a hydrophilic line segment, and comprises a hydrophilic line segment on the substrate.

5. The controller for the size of a droplet according to paragraph 3, wherein the temperature regulator is capable of discretely regulating a temperature with respect to each hydrophilic area on the substrate on which the droplet can stay.

6. The controller for the size of a drop according to paragraph 3, wherein the means of transferring a droplet is a means for generating a droplet to which another droplet is contacted.

7. A method of controlling the size of a droplet comprising the steps of:
placing a droplet formed in a hydrophilic area on a substrate, in an environment humidified at a prespecified humidity; and controlling a temperature of the substrate with the droplet retained thereon to control the size of the droplet.

Eighth Embodiment

1. A cell culture microarray having an electrode in a groove or a tunnel for connecting a plurality of minute compartments capable of retaining a cell one by one.

2. A neuron culture microchamber having on a substrate a plurality of compartment walls for keeping a cell in a specific spatial configuration, a plurality of electrode patterns for measuring an electrical change in a cell being provided between each cell, and an optically-transparent semipermeable membrane and a culture solution bath being provided on the compartment walls.

3. A cell culture microarray on a substrate, made of agarose, having a plurality of compartments for keeping a cell in a specific spatial configuration, and provided with an electrode in a tunnel for connecting each compartment.

4. A cell culture microarray provided on a substrate, made of agarose or its derivative, having a plurality of compartments for keeping a cell in a specific spatial configuration, and having a configuration in which a cell is retained substantially one by one in each compartment; in order to obtain interaction between the cells, agarose is locally overheated with convergence light in a given direction to form a tunnel; and one or more electrodes are always provided in each tunnel.

5. A cell culture microarray according to paragraph 3 or paragraph 4, wherein a culture solution bath capable of replacing a solution therein is provided on the top face of agarose.

6. A method of electrically measuring a cell comprising the steps of: providing on a substrate a plurality of compartments made of agarose or its derivative for keeping a cell in a specific spatial configuration; retaining substantially a single cell in each compartment; locally overheating the agarose with convergence light for the purpose of discretionally prescribing the direction in which each cell extends axon or the like for securing intercellular interaction, to form a tunnel to connect each compartment with respect to one another; and measuring an electrical change caused by the intercellular interaction employing an electrode provided in each tunnel.

7. A method of electrically measuring a cell comprising the steps of: providing on a substrate a plurality of compartments made of agarose for keeping a cell in a specific spatial configuration; retaining substantially a single cell in each compartment; locally overheating the agarose with convergence light for the purpose of discretionally prescribing the direction in which each cell extends axon or the like for securing intercellular interaction, to form a tunnel to connect each compartment with respect to one another; giving electric stimulation to intercellular space using an electrode provided in each tunnel; and measuring an electrical change caused by a response from a cell.

8. The method of electrically measuring a cell employing a cell culture microarray according to paragraph 6 or paragraph 7 comprising the steps of: adding to a cell a biological material such as peptide and amino acid or a chemical material suspected of being an endocrine disrupting chemical or having toxicity; and measuring an electrical change caused by a response from the cell.

9. A method of electrically measuring a cell comprising the steps of: employing a neuron culture microchamber having a plurality of compartment walls and tunnels for connecting the compartment walls on a substrate for keeping a cell in a specific spatial configuration, a plurality of electrode patterns for measuring an electrical change in a cell being provided in each of the tunnels, and an optically transparent semipermeable membrane and a culture solution bath being provided on the compartment walls; giving electric stimulation to intercellular space using an electrode provided in each tunnel; and measuring an electrical change caused by a response from the cell.

Ninth Embodiment

1. A cell reconstruction device comprising: a plurality of microchambers each having an electrode for incubating a prespecified number of cells; and a tunnel or a groove communicating between the plurality of microchambers with the cell not capable of passing therethrough but with a culture solution capable of passing therethrough, a cell provided in the microchambers on both sides of the tunnel or groove being a heterogeneous cell.

2. A cell reconstruction device comprising: a plurality of microchambers each having an electrode for incubating a prespecified number of cells; a tunnel or a groove communicating between the plurality of microchambers with the cell not capable of passing therethrough but with a culture solution capable of passing therethrough; and a culture solution bath in which a culture solution for a cell provided in the microchambers on both sides of the tunnel or groove is discretely replaceable.

3. A cell reconstruction device having on a substrate a plurality of compartments for keeping a cell in a specific spatial configuration; a tunnel or a groove communicating between the plurality of compartments with the cell not capable of passing therethrough but with a culture solution capable of passing therethrough; a plurality of electrode patterns for measuring an electrical change in a cell; and an optically transparent semipermeable membrane and a culture solution bath being placed on the compartments; wherein a culture solution bath is designed so that a culture solution for the cell provided in the compartments on both sides of the tunnel or groove can be discretely replaced.

4. A cell reconstruction device having on a substrate a plurality of compartments for keeping a different cell in a specific spatial configuration; a tunnel or a groove communicating between the plurality of microchambers with the cell not capable of passing therethrough but with a culture solution capable of passing therethrough; a plurality of electrode patterns for measuring an electrical change in a cell; and an optically transparent semipermeable membrane and a culture solution bath being placed on the compartments; wherein a culture solution bath is designed so that a culture solution for the cell provided in the compartments on both sides of the tunnel or groove can be discretely replaced.

5. A bioassay chip comprising:
a plurality of microcompartments each retaining a prespecified number of heterogeneous cells;
a groove or a tunnel for connecting between the plurality of microcompartments and those adjacent thereto; and
a means for feeding a different culture solution to each cell in a microcompartment connected with the groove or tunnel.

6. A cell bioassay chip comprising:
a plurality of microcompartments each retaining a single cell of heterogeneous cells one by one;
a group of microcompartments for retaining homogenous cells in the plurality of microcompartments and for retaining homogenous cells connected with a groove or a tunnel to each other between the adjoining microcompartments;
a groove or a tunnel for connecting groups for connecting between the microcompartments groups for retaining homogenous cells; and
a means for feeding different culture solutions to each of microcompartment groups.

7. A bioassay: employing a cell reconstruction device comprising, a plurality of microchambers each having an electrode for incubating a prespecified number of cells, a tunnel or a groove communicating between the plurality of microchambers with the cell not capable of passing therethrough but with a culture solution capable of passing therethrough, and a culture solution bath capable of discretely replacing a culture solution for a cell provided in the microchambers on both sides of the tunnel or groove; adding a testing sample to the culture solution for a cell in a microchamber on one of the tunnel or groove side; and observing a change in electrical potential or shape of a cell in a microchamber on the other of the tunnel or groove.

8. A bioassay: employing a cell reconstruction device provided with a plurality of compartments having a substrate, agarose gel provided on the substrate, and an electrode for keeping two or more types of heterogeneous cells formed on the agarose gel in a specific spatial configuration; locally overheating the agarose gel with convergence light for the purpose of discretionally prescribing the direction in which a substantially single cell retained in each of the compartment extends a portion thereof for securing intercellular interaction, to form a tunnel or a groove; giving stimulation to a specific cell using the electrode; and measuring a response of a different cell.

Tenth Embodiment

1. A cell culture method comprising the steps of: incubating a cell on a cellulose membrane; and, after the incubation, decomposing the cellulose membrane using cellulase to collect a cultured cell.

2. A cell culture method comprising the steps of: incubating a cell on the cellulose membrane of a cell culture support having a bottom face inside thereof, forming a plurality of beams with the upper portion thereof opened on the bottom face, and configured to have a cellulose medium attached to the upper edge of the beams; and, after the incubation, injecting cellulose into a flow path formed in a portion of the beams to decompose the cellulose membrane.

3. A cell culture method comprising the steps of: in order to incubate a cell on a cellulose membrane on a cell culture support having a bottom face inside thereof, forming a plurality of beams with the upper portion thereof opened on the bottom face, and configured to have a cellulose membrane attached to the upper edge of the beams; circulating a culture solution in a flow path formed in a portion of the beams; injecting, after the incubation, cellulase in the flow path formed in a portion of the beams; decomposing the cellulose membrane by making cellulase act on the cellulose membrane; and collecting a cell or a sheet of cells.

4. A cell culture method comprising the steps of: in order to incubate a cell on a cellulose membrane on a cell culture support having a bottom face inside thereof, forming a plurality of beams with the upper portion thereof opened on the bottom face, and configured to have a cellulose membrane attached to the upper edge of the beams; circulating a culture solution in a flow path formed in a portion of the beams; injecting, after the incubation, cellulase in the flow path formed in a portion of the beams; decomposing the cellulose membrane by making cellulase act on the cellulose membrane; collecting a cell or a sheet of cells; and further, putting a previously-collected sheet of cells on top of another sheet of cells newly formed with the procedure to incubate the cells; decomposing the cellulose membrane by making cellulase act on the cellulose membrane; and collecting the two-ply sheet of cells.

5. The cell culture method according to paragraph 4 further comprising the step of: putting the two-ply sheet of cells on top of another newly formed sheet of cells.

6. A cell culture support having a bottom face inside thereof, forming a plurality of beams with the upper portion thereof opened on the bottom face, and configured to have a cellulose membrane attached to the upper edge of the beams.

7. The cell culture support according to paragraph 6, having a cover used by putting on top of the culture support, wherein the cover is provided with a tube for supplying or sucking a solution supplied to between the plurality of beams or sucked from between the same.

8. The cell culture support according to paragraph 6, having a cover used by putting on top of the culture support, wherein the cover provided with a tube for supplying or sucking a solution supplied to between the plurality of beams or sucked from between the same; and a plate adjoining the tube for blocking a flow of the solution is provided.

Eleventh Embodiment

1. A microchamber for cell culture comprising:
a semipermeable membrane;
a gel membrane formed on the semipermeable membrane and made of agarose or a derivative thereof; and
a plurality of compartments formed on the gel membrane for keeping a cell in a specific spatial configuration.

2. A microchamber for cell culture comprising:
a semipermeable membrane;
a gel membrane formed on the semipermeable membrane and made of agarose or a derivative thereof; and
a plurality of compartments formed on the gel membrane for keeping a cell in a specific spatial configuration, spaces between the plurality of compartments being capable of forming a groove by locally heating an agarose gel membrane with convergence light in the discretional direction.

3. The microchamber for cell culture according to paragraph 1 or paragraph 2, wherein the semipermeable membrane is a cellulose membrane.

4. A method of building the structure of a cell comprising the steps of:
placing a microchamber for cell culture configured to form an agarose gel membrane on a semipermeable membrane;
forming a prespecified number of cell compartments on the agarose gel membrane by means of convergence light heating;
inserting a cell into the cell compartment to incubate the same;
irradiating, during the cell culture, laser convergence light at a wavelength absorbable by water to the agarose gel membrane present between the cell compartments in a prespecified order in the direction desirable for binding the cells to one another to link any cell compartments to one another with a groove; and
making cellulase act on the semipermeable membrane, after a cell assembly with the cells conjugated therein is formed, to remove the semipermeable membrane.

5. A microchamber for cell culture comprising:
a semipermeable membrane;
a thin plate attached to the semipermeable membrane and having an opening in the center thereof;
a gel membrane formed on the opening on the thin plate and made of agarose or a derivative thereof supported by the semipermeable membrane; and
a plurality of compartments formed on the gel membrane for keeping a cell in a specific spatial configuration.

6. A microchamber kit for cell culture comprising:
a pool having an upper portion thereof opened and capable of retaining a solution;
a fine structure substrate having a plurality of beams formed in the pool at prespecified intervals; and
a microchamber for cell culture comprising: a semipermeable membrane; a thin plate attached to the semipermeable membrane and having an opening corresponding to the pool in the center thereof; a gel membrane formed on the opening on the thin plate and made of agarose or a derivative thereof supported by the semipermeable membrane; and a plurality of compartments formed on the gel membrane for keeping a cell in a specific spatial configuration.

7. The microchamber kit for cell culture according to paragraph 6, wherein the microchamber for cell culture is provided with an opening communicating with the pool at both ends of the opening.

8. A cell culture device comprising:
a pool having an upper portion thereof opened and capable of retaining a solution;

a fine structure substrate having a plurality of beams formed in the pool at prespecified intervals; and a microchamber for cell culture comprising: a semipermeable membrane; a thin plate attached to the semipermeable membrane and having an opening corresponding to the pool in the center thereof; a gel membrane formed on the opening on the thin plate and made of agarose or a derivative thereof supported by the semipermeable membrane; and a plurality of compartments formed on the gel membrane for keeping a cell in a specific spatial configuration, the microchamber for cell culture being provided with an opening communicating to the pool at both ends of the opening to supply or discharge a culture solution to the pool via a tube communicating with the pool through the opening.

9. The cell culture device according to paragraph 8, wherein, when the cell culture reaches a prespecified stage, cellulase at a prespecified concentration is supplied to the pool via a tube communicating with the pool through the opening to dissolve and remove the semipermeable membrane.

10. The cell culture device according to paragraph 4, wherein the formation of a groove on the agarose gel membrane is conducted by, in the step of cell culture, irradiating laser convergence light to a portion of a microneedle contacting the agarose gel membrane to locally heat a portion of the microneedle.

Twelfth Embodiment

1. A cardiac muscle cell bioassay chip comprising:
a means for arranging a network constituting four or more pulsating myocardial cells in the state where each cell is observable;
a means for controlling and measuring electrical stimulation or response of each cell one by one; and
a means for preventing conditions during incubation from changing by means of spatial configuration of each cell.

2. A cardiac muscle cell bioassay chip comprising:
a means for arranging a network constituting not fewer than 4 nor more than 32 pulsating myocardial cells in the state where each cell is observable;
a means for controlling and measuring electrical stimulation or response of each cell one by one; and
a means for preventing conditions during incubation from changing by means of spatial configuration of each cell.

3. A cardiac muscle cell bioassay chip comprising:
a plurality of microcompartments each capable of retaining a single pulsating myocardial cell one by one;
a groove or a tunnel for connecting between the plurality of microcompartments and those adjacent thereto;
not fewer than 4 adjoining microcompartments each with a single cell having been inserted therein in advance; and
a means for supplying each of the microcompartments with a culture solution for pulsating myocardial cells.

4. A cardiac muscle cell bioassay chip comprising:
a substrate;
a plurality of microcompartments provided with four or more pulsating myocardial cells arranged to adjoin one another on the substrate;
a groove or a tunnel for connecting each of the microcompartments; and
a means for supplying each of the microcompartments with a culture solution for pulsating myocardial cells.

5. A cardiac muscle cell bioassay chip comprising:
a plurality of microcompartments each capable of retaining a single pulsating myocardial cell one by one;
a groove or a tunnel for connecting between the plurality of microcompartments and those adjacent thereto;
not fewer than 4 nor more than 32 adjoining microcompartments each with a single cell having been inserted therein in advance; and
a means for supplying each of the microcompartments with a culture solution for pulsating myocardial cells.

6. A cardiac muscle cell bioassay chip comprising:
a substrate;
a plurality of microcompartments provided with not fewer than 4 nor more than 32 pulsating myocardial cells arranged to adjoin one another on the substrate;
a groove or a tunnel for connecting each of the plurality of microcompartments; and
a means for supplying each of the microcompartments with a culture solution for pulsating myocardial cells.

7. A cardiac muscle cell bioassay chip according to any of paragraphs 1 to 6, wherein the material forming the plurality of microcompartments is agarose.

8. An aggregated cell microarray having on a substrate a groove or a tunnel for connecting between a plurality of microcompartment walls in order to adjoin four or more pulsating myocardial cells one another and to keep the cells in a specific spatial configuration, and a plurality of electrical patterns for measuring an electrical change of a cell in each groove or tunnel, and an optically transparent semipermeable membrane and a culture solution bath being provided on the microcompartment walls.

9. A bioassay accommodating a single pulsating myocardial cell in each of a plurality of microcompartments formed on a substrate and connected with a groove or a tunnel to one another, adding a testing sample to each of eight or more microcompartments adjacent to the plurality of microcompartments, and observing a change in electrical potential or shape of the cell each accommodated in the microcompartments.

10. The bioassay according to paragraph 9, wherein the testing sample is a biological material such as peptide and amino acid or a chemical material suspected of being a endocrine disrupting chemical or having toxicity.

11. A bioassay: employing an aggregated cell microarray having on a substrate a groove or a tunnel for connecting between a plurality of microcompartment walls in order to adjoin four or more pulsating myocardial cells one another and to keep the cells in a specific spatial configuration, and a plurality of electrical patterns for measuring an electrical change of a cell in each groove or tunnel, and an optically transparent semipermeable membrane and a culture solution bath being provided on the microcompartment walls; giving electric stimulation to intercellular space using an electrode provided in each groove or tunnel; and measuring a change in electrical potential or shape caused by a response from a cell.

Thirteenth Embodiment

1. A biological sample chip for collecting a specific biological material in a cell, the biological sample chip having a biological sample chip tip section with a needle configuration having a sharp-pointed tip, and fixed thereto a material having an affinity to the specific biological material in a probe area inserted into a cell in the biological sample chip tip section.

2. The biological sample chip according to paragraph 1, wherein $TiO_2$ is fixed onto a portion where a cell is inserted into the endmost portion of the biological sample chip tip section.

3. The biological sample chip according to paragraph 1, wherein, in addition to the material having an affinity to the specific biological material, $(Arg)_n$ (n: 1~8) is fixed to a probe area inserted into a cell in the biological sample chip tip section.

4. The biological sample chip according to paragraphs 1 to 3, wherein the biological sample chip tip section has a holder in a root portion thereof, and the holder is connected to an operation substrate.

5. A method of measuring a specific material in a cell comprising the steps of:

sticking into a cell a probe area in the biological sample chip tip section with a material having an affinity to the specific biological material fixed thereon;

capturing in the probe area a material having an affinity to the material fixed to the probe area on the biological sample chip;

making a nanoparticle labeled probe react to the biological material in the cell captured in the probe area for hybridization; and counting the number of nanoparticles of the probe hybridized with the biological material in the cell captured in the probe area.

6. A method of measuring a specific material in a cell comprising the steps of:

sticking into a cell a probe area in a biological sample chip tip section with a material having an affinity to the specific biological material and $(Arg)_n$ (n: 1~8) fixed thereon;

capturing in the probe area a material having an affinity to the material fixed to the probe area on the biological sample chip;

making a nanoparticle labeled probe react to the biological material in the cell captured in the probe area for hybridization; and counting the number of nanoparticles of the probe hybridized with the biological material in the cell captured in the probe area.

7. The method of measuring a specific material in a cell according to paragraph 5 or paragraph 6, wherein the specific biological material is mRNA.

8. The method of measuring a specific material in a cell according to paragraph 5 or paragraph 6, wherein the specific biological material is protein.

9. The method of measuring a specific material in a cell according to any of paragraphs 5 to 8, wherein a position for sticking the biological sample chip tip section is the nucleus of a cell.

10. The method of measuring a specific material in a cell according to any of paragraphs 5 to 8, wherein a position for sticking the biological sample chip tip section is cytoplasm of a cell.

Fourteenth Embodiment

1. A method of collecting a biological material comprising the steps of:

sticking into a living cell a needle with a material having an affinity to a specific biological material fixed on a tip section thereof;

pulling out the needle from the living cell after a prespecified period of time; and collecting the specific biological material from the tip section.

2. A method of collecting a biological material comprising the steps of:

sticking into a living cell a needle with a material having an affinity to a specific biological material and $(Arg)_n$ (n: 1~8) fixed onto a tip section thereof;

capturing the material having an affinity in the tip section of the needle; and collecting the specific biological material contained in the cell as the cell remains alive.

3. A method of collecting a biological material comprising the steps of:

sticking into a living cell a needle with a material having an affinity to a specific biological material and $TiO_2$ fixed onto a tip section thereof;

capturing the material having an affinity in the tip section of the needle; and collecting the specific biological material contained in the cell as the cell remains alive.

4. The method of collecting a biological material according to paragraph 1 or paragraph 2, wherein the specific biological material is mRNA.

5. A method of collecting a biological material comprising the steps of:

sticking into a living cell a needle with a probe having a derivative with a poly T sequence having an affinity to a poly A portion of mRNA fixed onto a tip section thereof;

pulling out the needle from the cell after a prespecified period of time;

collecting the mRNA captured in the tip section of the needle; and amplifying the collected mRNA with the PCR to obtain cDNA of a specific gene.

6. The method of collecting a biological material according to paragraph 1 or paragraph 2, wherein the specific biological material is protein.

7. A method of collecting a biological material comprising the steps of:

sticking into a living cell a needle with a material having an affinity to a specific biological material fixed onto a tip section thereof;

pulling out the needle from the living cell after a prespecified period of time;

collecting the specific biological material from the tip section;

further sticking, after a prespecified period of time, into the cell a needle with a material having an affinity to a specific biological material fixed onto a tip section thereof;

pulling out the needle from the cell after a prespecified period of time; and collecting the specific biological material from the tip section.

Fifteenth Embodiment

1. An mRNA aliquotting device for collecting mature mRNA comprising:

a chip tip section having a hollow capillary structure with a tip section thereof contacted to the nuclear membrane of a cell;

a means for applying negative pressure to the inside of the chip;

a means for visually observing a contact state between the nuclear membrane of a cell and the chip tip section having a hollow capillary structure; and a means for regulating a position of the chip tip section having a hollow capillary structure under the control of visual observation of the contact state between the nuclear membrane of a cell and the chip tip section having a hollow capillary structure.

2. An mRNA aliquotting device for collecting mature mRNA according to paragraph 1 further comprising:

a means for measuring electric conductivity between a buffer retained in the chip tip section having a hollow capillary structure and a portion of the cell.

3. A method of aliquotting mRNA comprising the steps of:

sticking a hollow capillary into a cell with mRNA thereof to be collected;

making a tip of the hollow capillary firmly adhere to the nuclear membrane in the cell; and collecting mRNA passing through the nuclear membrane of the cell into the hollow capillary.

4. The method of aliquotting for collecting mature mRNA of a cell according to paragraph 3 comprising the step of:

filling the hallow capillary with a buffer before sticking a hollow capillary into a cell with mRNA thereof to be collected.

5. A hollow capillary employed in the method of aliquotting mRNA comprising the steps of: sticking a hollow capillary into a cell with mRNA thereof to be collected; making a tip of the hollow capillary firmly adhere to the nuclear membrane in the cell; and collecting mRNA passing through the nuclear membrane of the cell into the hollow capillary, the tip section of the hollow capillary having an $(Arg)_n$ (n: 1~8) fixed onto an outer wall thereof.

6. A hollow capillary with $TiO_2$, in place of the $(Arg)_n$ (n: 1~8), fixed onto the tip section thereof according to paragraph 5.

7. A hollow capillary with $TiO_2$, in addition to the $(Arg)_n$ (n: 1~8), fixed onto the tip section thereof according to paragraph 5.

8. A hollow capillary according to paragraphs 5 to 7, wherein the hollow capillary has a chip tip section configured to have inside thereof at least two systems of hollows separated with the same axle or partition; a buffer is flown from one or more of at least two systems of the hollows separated with the partition; and mRNA is continuously collected from the other hollow(s).

9. A method of aliquotting mRNA according to paragraph 3 or paragraph 4, wherein the collected mRNA is amplified with the PCR to obtain cDNA of a specific gene.

10. A method of aliquotting mRNA to collect mRNA passing through the nuclear membrane of the cell into hollow capillary by:

sticking a hollow capillary into a cell with mRNA thereof to be collected;

making a tip of the hollow capillary firmly adhere to the nuclear membrane in the cell; and making mRNA transfer by applying positive voltage to an electrode provided in the hollow capillary and applying negative voltage to an electrode provided in the cell nucleus outside the hollow capillary.

Sixteenth Embodiment

1. A biochemical material separator comprising:

a member with a lipid bilayer containing a transporter fixed in a micropore thereof;

a mechanism provided on one side of the micropore for adding a sample; and a mechanism provided on the other side of the micropore for collecting a biochemical material passing the micropore.

2. A biochemical material separator providing with a plurality types of separation members comprising a lipid bilayer having a transporter present in a cell membrane, nuclear membrane and the like, configured to hierarchically arrange the separation members each for partitioning an anterior vessel thereof, and having a means for collecting the separated biochemical material from between each of the separation members.

3. A biochemical material separator configured to fix a lipid bilayer having a transporter present in a cell membrane, nuclear membrane and the like and passing through a different biological material, onto an inlet of each collecting port of a vessel comprising one sample adding port and a plurality of collecting ports.

4. A biochemical material separator configured to fix a plurality types of lipid bilayers discretely having a plurality types of transporters present in a cell membrane, nuclear membrane and the like and passing through a specific biochemical material, onto an inlet of each collecting port of a vessel comprising one sample adding port and a plurality of collecting ports; and having a means for collecting a specific biochemical material passing through each transporter.

5. A biochemical material separator having the element configuration of fixing a lipid bilayer discretely having a plurality types of transporters present in a cell membrane, nuclear membrane and the like and passing through a specific biochemical material, onto an inlet of each collecting port of a vessel comprising one sample adding port and a plurality of collecting ports; and having a mechanism for collecting a transporter present in an element making a specific biochemical material pass through.

6. The separator according to paragraphs 1 to 5, having a mechanism of making a biochemical material transfer with the electrophoresis or electroosmosis and pass through a transporter.

7. A method of separating a biochemical material to separate a plurality of biochemical materials comprising the steps of:

adding a biological sample solution to a front portion of a micropore in a biochemical material separation comprising: a member with a plurality of transporters and lipid bilayers discretely fixed onto a micropore thereof; a mechanism for adding a sample to one of a front portion or a rear portion of each micropore; and a mechanism for collecting a biochemical material passing through each micropore on the other portion; and making a biochemical material transfer to separate the same into a material passing through a micropore and that not passing through a micropore.

8. A method of separating a transporter comprising the steps of:

adding a specific biological sample solution to a front portion of a micropore in a biochemical material separation comprising: a member with a plurality of transporters and lipid bilayers discretely fixed onto a micropore thereof; a mechanism for adding a sample to one of a front portion or a rear portion of each micropore; and a mechanism for collecting a biochemical material passing through each pore on the other portion;

detecting an element in which a specific biochemical material passes through a micropore; and collecting a transporter present in the element in which a specific biochemical material passes through a micropore.

9. The separation method according to paragraph 7 or paragraph 8, wherein a means for making a biochemical material transfer is the electrophoresis or electroosmosis.

10. An mRNA aliquotting chip, the chip being a biological material chip for collecting mature mRNA, having a chip tip section with a hollow capillary structure, and configured to fix a nuclear membrane onto the biological material chip tip section with the inside of the nuclear membrane turned to the outside of the chip.

11. An mRNA separation method comprising the steps of: immersing the biological material chip tip section for collecting the mature mRNA according to paragraph 10, in a sample solution; and collecting the mRNA passing through a nuclear membrane fixed onto the chip tip section, in the biological material chip.

Seventeenth Embodiment

1. A cell chip comprising: a cell fixing substrate having one face thereof as a face for fixing a cell; a micropore provided in a cell fixing portion of the substrate and having a diameter smaller than the cell; and a buffer chamber configured on the reverse of the face for fixing a cell at a position of the micropore on the cell fixing substrate, liquid such as a buffer capable of continuously being fed to the buffer chamber.

2. The cell chip according to paragraph 1, wherein, when a cell is fixed by adding a droplet in a position of the micropore on the face for fixing a cell on the cell fixing substrate, an electrode for measuring electrical conductivity or current passing between the droplet and the buffer chamber is provided.

3. The cell chip according to paragraph 2, wherein the electrode is formed each on both sides of the cell fixing substrate.

4. The cell chip according to paragraph 1 or 2, having a plurality of the micropores, and having clearances between the micropores smaller than those between the cells fixed on the cell fixing substrate.

5. A method of altering a cell comprising the steps of:
placing in a buffer solution a cell fixed onto a cell fixing substrate of a cell chip, the cell chip comprising: a cell fixing substrate having one face thereof as a face for fixing a cell; a micropore provided in a cell fixing portion of the substrate and having a diameter smaller than the cell; and a buffer chamber configured on the reverse of the face for fixing a cell at a position of the micropore on the cell fixing substrate, liquid such as a buffer capable of continuously being fed to the buffer chamber; and
feeding streptolysin O into the buffer chamber to make a lipid bilayer of a cell in a position of the micropore into a semipermeable membrane.

6. The method of altering a cell according to paragraph 5, further comprising the step of: after the feed of streptolysin O, adding any DNA or RNA or a derivative thereof to the buffer chamber.

7. A method of collecting a chemical material comprising the steps of:
placing in a buffer solution a cell fixed onto a cell fixing substrate of a cell chip, the cell chip comprising: the cell fixing substrate having one face thereof as a face for fixing a cell; a micropore provided in a cell fixing portion of the substrate and having a diameter smaller than the cell; and a buffer chamber configured on the reverse of the face for fixing a cell in a position of the micropore on the cell fixing substrate, liquid such as a buffer capable of continuously being fed to the buffer chamber;
altering a cell by feeding streptolysin O to the buffer chamber to make a lipid bilayer of a cell in a position of the micropore into a semipermeable membrane;
adding any chemical material to a buffer surrounding the altered cell; and
collecting a chemical material passing through a lipid bilayer of the cell from the semipermeable membrane-turned lipid bilayer into the buffer chamber.

8. A cell chip comprising: a cell fixing substrate having one face thereof as a face for fixing a cell; a micropore provided in a cell fixing portion of the substrate and having a diameter smaller than the cell; and a buffer chamber configured on the reverse of the face for fixing a cell at a position of the micropore on the cell fixing substrate, electrodes being provided in the buffer chamber and on the side of the face for fixing the cell, and liquid such as a buffer capable of continuously being fed to the buffer chamber, a cell fixed onto the cell fixing substrate of the cell chip being placed in a buffer solution, streptolysin O being fed to the buffer chamber to alter the cell by making a lipid bilayer of the cell at a position of the micropore into a semipermeable membrane, a cell chip with a given peptide expressed therein being prepared by adding mRNA encoding any membrane protein or a vector encoding the mRNA sequence into the cell, any chemical material being added to a buffer surrounding the altered cell, and a chemical material having an affinity to the membrane protein being detected by means of the electrodes.

9. A cell chip comprising: a cell fixing substrate having one face thereof as a face for fixing a cell; a micropore provided in a cell fixing portion of the substrate and having a diameter smaller than the cell; and a buffer chamber configured on the reverse of the face for fixing a cell at a position of the micropore on the cell fixing substrate, electrodes being provided in the buffer chamber and on the side of the face for fixing the cell, and liquid such as a buffer capable of continuously being fed to the buffer chamber, a cell fixed onto the cell fixing substrate of the cell chip being placed in a buffer solution, streptolysin O being fed to the buffer chamber to alter the cell by making a lipid bilayer of the cell at a position of the micropore into a semipermeable membrane, voltage being applied between the electrodes, and a chemical material passing through the fixed cell continuously being collected from the buffer chamber.

Eighteenth Embodiment

1. A biomolecule detecting tubule, being a tubule having one end thereof for an opening in diameter smaller than a prespecified wavelength of light and the other end thereof for another opening in diameter sufficiently larger than the prespecified wavelength of light, and forming a light guide configured to deposit metal on at least an inner wall and an outer wall in the proximity of the tip section opening of the tubule.

2. A biomolecule detector comprising:
a biomolecule detecting tubule, being a tubule having a tip section thereof for an opening in diameter smaller than a prespecified wavelength of light and the other end thereof for another opening in diameter sufficiently larger than the prespecified wavelength of light, and forming a light guide configured to deposit metal on at least an inner wall and an outer wall in the proximity of the tip section opening of the tubule;
two electrodes for applying prespecified voltage;
a laser light source for irradiating light at the prespecified wavelength from the sufficiently large opening of the biomolecule detecting tubule forming the light guide; and
a photon counter provided in the tip section of the tubule for counting light, an evanescence wave area being formed in the proximity of the tip section opening of the tubule by irradiating the laser light, the tip section of the biomolecule detecting tubule being placed in a solution containing a biomolecule, and, when the biomolecule traverses the evanescence wave area and passes the tip section opening of the tubule due to an electric field by the two electrodes, scattered wave generated by the biomolecule being detected with the counter.

3. A biomolecule detector comprising:
a biomolecule detecting chip with a curved and projecting opening in diameter smaller than a prespecified wavelength of light formed in the center portion thereof to form a light guide configured to deposit metal on both faces in the proximity of the opening in the center portion thereof;

two electrodes for applying prespecified voltage;

a laser light source for irradiating light at the prespecified wavelength from one edge face of a chip forming the light guide;

a substrate having a vessel provided on the side of a face with the chip opening being curved and projecting thereon;

a photon counter provided outside a bottom face of the vessel on the substrate, an evanescence wave area being formed in the proximity of the central section opening of the chip by irradiating the laser light; a buffer being put into the vessel; a droplet containing a biomolecule being placed on the opposite side to the side of the vessel of the biomolecule detecting chip; and, when the biomolecule traverses the evanescence wave area and passes the tip section opening of the chip due to electric field generated by the two electrodes, scattered wave caused by the biomolecule being detected with the counter.

4. The biomolecule detector according to paragraph 2, further comprising: a second tubule with a tip section of the biomolecule detector included therein and with a membrane passing a prespecified material provided in the tip opening section thereof.

5. The biomolecule detector according to paragraph 4, wherein the membrane provided in the tip opening section of the second opening and passing a prespecified material includes a transporter passing a prespecified material.

6. The biomolecule detector according to paragraph 3, further comprising: a second chip with an opening section having a membranes passing a prespecified material on a top face of the biomolecule detector.

7. The biomolecule detector according to paragraph 4, wherein the membrane provided in the opening section of the second chip and passing a prespecified material includes a transporter passing a prespecified material.

8. The biomolecule detector according to paragraph 2 or 3, wherein the metal is gold.

9. The biomolecule detector according to paragraph 4, wherein the membrane passing a specific biomolecule is a membrane in which an mRNA sequence of a specific membrane protein is incorporated into an immature ovum of a platanna, and thereby the specific membrane protein is forced to be expressed.

10. The biomolecule detector according to paragraph 6, wherein the membrane passing a specific biomolecule through is a membrane in which an mRNA sequence of a specific membrane protein is incorporated into an immature ovum of a platanna, and thereby the specific membrane protein is forced to be expressed.

11. A method of detecting a biomolecule comprising the steps of:

forming an evanescence wave area in the opening section in diameter smaller than a prespecified wavelength of light;

passing a biomolecule to be detected through the evanescence wave area; and detecting a scattered wave caused by passage of the biomolecule.

12. The method of detecting a biomolecule according to paragraph 11, wherein the biomolecule to be detected is supplied through a membrane allowing passage of a prespecified material.

13. The method of detecting a biomolecule according to paragraph 12, wherein the membrane allowing passage of a prespecified material is a membrane in which an mRNA sequence of a specific membrane protein is incorporated into an immature ovum of a platanna, and thereby the specific membrane protein is forced to be expressed.

Nineteenth Embodiment

1. A biological sample analysis chip with a different probe fixed on each area of a plurality of areas discretely provided on a substrate thereof, each of the plurality of discrete areas having an area not more than that of a circle 700 nm$\phi$ and not less than that of a circle 3 nm$\phi$.

2. A biological sample analysis chip with a different probe fixed on each area of a plurality of areas discretely provided on a substrate thereof, providing structures each having a specific shape on the four corners in each of the plurality of discrete areas, and each of the structures having a specific shape provided on the four corners being different from one another in each of the plurality of discrete areas respectively.

3. The biological sample analysis chip according to paragraph 1 or 2, wherein the areas having as a unit a prespecified number of the plurality of discrete areas are each provided via a groove formed between the areas.

4. The biological sample analysis chip according to paragraph 1 or 2, wherein the areas having as a unit a prespecified number of the plurality of discrete areas are provided at a prespecified distance or farther.

5. An analysis method by means of a biological sample analysis chip comprising the steps of:

dropping a sample solution on a biological sample analysis chip with a different probe fixed on each of a plurality of areas discretely provided on a substrate thereof, each of the plurality of discrete areas having an area not more than that of a circle 700 nm$\phi$ and not less than that of a circle 3 nm$\phi$;

placing a thin plate or a rod rotating at a prespecified speed on the top face of the biological sample analysis chip; and moving the plate or rod from side to side on the substrate to accelerate hybridization between the probe and a sample in the sample solution.

6. An analysis method by means of a biological sample analysis chip comprising the steps of:

dropping a sample solution on a biological sample analysis chip with a different probe fixed on each area of a plurality of areas discretely provided on a substrate thereof, a structure having a specific shape being provided on each of the four corners in the plurality of discrete areas, and each of the structures having a specific shape provided on the four corners being different from one another with respect to each of the plurality of discrete areas;

placing a thin plate or a rod rotating at a prespecified speed on the top face of the biological sample analysis chip; and moving the plate or rod from side to side on the substrate to accelerate hybridization between the probe and a sample in the sample solution.

7. A method of analyzing a biological sample comprising the steps of:

tracing with a probe for an atomic force microscope a biological sample analysis chip with a different probe fixed on each area of a plurality of areas discretely provided on a substrate thereof, each of the plurality of discrete areas having an area not more than that of a circle 700 nm$\phi$ and not less than that of a circle 3 nm$\phi$; and detecting a sample hybridized with the probe.

8. A method of analyzing a biological sample comprising the steps of:

tracing with a probe for an atomic force microscope a biological sample analysis chip with a different probe fixed on each area of a plurality of areas discretely provided on a substrate thereof, a structure having a specific shape being provided on each of the four corners in the plurality of discrete areas, and each of the structures having a specific shape provided on the four corners being different from one another with respect to each of the plurality of discrete areas; and detecting a sample hybridized with the probe.

9. The method of analyzing a biological sample according to paragraph 7 or 8, wherein the sample hybridized with the probe reacts to a labeling probe labeling particles each having a different particle diameter to an oligo probe hybridized with a sequence portion complementary to and different from a DNA fragment having been hybridized.

Twentieth Embodiment

1. An analysis method by means of a biological sample analysis chip comprising the steps of:

labeling by means of conductive microparticles a DNA fragment hybridized with a probe of a biological sample analysis chip with a different probe fixed on each area of a plurality of areas discretely provided on a substrate thereof, a structure having a specific shape being provided on each of the four corners in the plurality of discrete areas, each of the structures having a specific shape provided on the four corners being different from one another with respect to each of the plurality of discrete areas, and areas having as a unit a prespecified number of the plurality of discrete areas being provided via a groove formed between the areas; and detecting the conductive microparticle with a scanning electron microscope.

2. The analysis method by means of a biological sample analysis chip according to paragraph 1 further comprising the steps of:

dropping a sample solution on the biological sample analysis chip;

placing a thin plate or a rod rotating at a prespecified speed on the top face of the biological sample analysis chip; and moving the plate or rod from side to side on the substrate to accelerate hybridization between the probe and a sample in the sample solution.

3. An analysis method by means of a biological sample analysis chip comprising the steps of:

labeling by means of conductive microparticles a DNA fragment hybridized with a probe of a biological sample analysis chip with a different probe fixed on each area of a plurality of areas discretely provided on a substrate thereof, each of the plurality of discrete areas having an area not more than that of a circle 700 nmϕ and not less than that of a circle 3 nmϕ; and detecting the conductive microparticles with a scanning electron microscope.

4. An analysis method by means of a biological sample analysis chip comprising the steps of:

labeling by means of conductive microparticles a DNA fragment hybridized with a probe of a biological sample analysis chip with a different probe fixed on each area of a plurality of areas discretely provided on a substrate thereof, a structure having a specific shape being provided on each of the four corners in the plurality of discrete areas, and each of the structures having a specific shape provided on the four corners being different from one another with respect to each of the plurality of discrete areas; and detecting the conductive microparticles with a scanning electron microscope.

Twenty-First Embodiment

1. A DNA probe chip comprising:
a substrate;
an electrode formed on the substrate and having a plurality of discrete probe fixing areas formed thereon; and
prespecified DNA probes each fixed on respective probe fixing areas with covalent bonding,
wherein the DNA probe being configured to cause hybridization with a complementary strand DNA from the terminus side fixed onto the probe fixing area.

2. A DNA probe chip comprising:
a substrate;
an electrode formed on the substrate and having a plurality of discrete probe fixing areas formed thereon; and
prespecified DNA probes each fixed on respective probe fixing areas with covalent bonding,
wherein a dissociative group having a negative charge on the terminus different from that fixed on the probe fixing area being added to each of the DNA probes.

3. The DNA probe chip according to paragraph 1, wherein the electrode with a plurality of discrete probes formed thereon is an ITO electrode, and a water repellent surface coating is applied to the area other than the probe fixing areas.

4. The DNA probe chip according to paragraph 1, wherein an electrode surface in the plurality of discrete probe fixing areas is prepared by introducing a residue dissociating positive.

5. The DNA probe chip according to paragraph 1, wherein the DNA probe is a PNA whose main chain is composed with the peptide bond, or a CAS having S-carboxymethyl-L-cysteine as a basic skeleton.

6. The DNA probe chip according to paragraph 1, wherein the DNA probe is designed to have a sequence complementary to that having a prespecified base length starting from an mRNA sequence having a sequence to be hybridized with the DNA probe, and the DNA probe is selected from an area in which the quantity of GC fixed onto the plurality of discrete probe fixing areas on the terminus side is higher than that on the free end side.

7. The DNA probe chip according to paragraph 1, wherein the DNA probe has a sequence complementary to that having a prespecified base length starting from an mRNA sequence having a sequence to be hybridized with the DNA probe, and the DNA probe has a configuration in which, between the terminus side fixed onto the plurality of discrete probe fixing areas and the free end side is inserted a sequence mismatched with a sequence to be hybridized with the DNA probe between the position about 10 bases and that about 30 bases from the free end, or a blank sequence not forming a stable complementary strand with any of ACGT.

8. A method of controlling DNA hybridization comprising the steps of:

adding a sample solution containing a target polynucleotide to between a DNA probe chip comprising: a substrate; an electrode with a plurality of discrete probe fixing areas formed on the substrate formed thereon; and prespecified DNA probes each fixed on respective probe fixing areas with covalent bonding, a dissociative group having a negative charge on the terminus different from that fixed on the probe fixing area being added to the DNA probe: and a member provided opposing to a surface of the DNA probe chip;

applying prespecified electric field to between the electrode and the sample solution site to condense the polynucleotide in the proximity of the surface of the DNA probe chip; and inverting the electric field for applying to between the electrode and the sample solution site to start hybridization in the state where the probe is stretched.

9. The method of controlling DNA hybridization according to paragraph 7, wherein a DNA probe chip is employed in which the electrode formed thereon a plurality of discrete probe is an ITO electrode, and a water repellent surface coating is applied to the area other than the probe fixing areas.

10. The method of controlling DNA hybridization according to paragraph 7, wherein a DNA probe chip is employed in which an electrode surface in the plurality of discrete probe fixing areas is prepared by introducing a residue dissociating positive.

11. The method of controlling DNA hybridization according to paragraph 7, wherein a DNA probe chip is employed in which the DNA probe is a PNA whose main chain is composed with the peptide bond, or a CAS having S-carboxymethyl-L-cysteine as a basic skeleton.

12. A DNA probe chip comprising:
a substrate;
an electrode with a plurality of discrete probe fixing areas formed on the substrate formed thereon; and
prespecified DNA probes each fixed on respective probe fixing areas with covalent bonding,
wherein the DNA probe being configured to form more stable hybridization on the terminus side fixed onto the probe fixing area than on the free end side.

13. The DNA probe chip according to paragraph 1, wherein the DNA probe with one end thereof fixed on a substrate has a sequence complementary to that having a prespecified base length starting from an mRNA sequence having a sequence to be hybridized with the DNA probe, and the DNA probe is selected from an area in which the quantity of GC fixed onto the plurality of discrete probe fixing areas on the terminus side is higher than that on the free end side.

Twenty-Second Embodiment

1. A DNA probe chip comprising: a substrate; an
electrode with a plurality of discrete probe fixing areas formed on the substrate formed thereon; and prespecified DNA probes each fixed on respective probe fixing areas with covalent bonding, the DNA probe constituting at least three areas in the order viewed from the side of the probe fixing area with the DNA probe fixed thereon: a first area being a base sequence substantially complementary to a target polynucleotide; a second area being a base sequence including a base not forming the hydrogen bond complementary to any base among ACGT in the target polynucleotide; and a third area being a base sequence substantially complementary to the target polynucleotide and having a base length thereof equal to or shorter than that of the first area.

2. The DNA probe chip according to paragraph 1, wherein the second area includes at least one third or more base sequence noncomplementary to a target polynucleotide.

3. The DNA probe chip according to paragraph 1, wherein the second area includes a base sequence capable of forming the hydrogen bonding with a target polynucleotide, though unstable in terms of energy as compared to AG or CT base pair.

4. The DNA probe chip according to any of paragraphs 1 to 3, wherein stability of hybridization with a target polynucleotide in the first area, second area and third area declines in the order of the first area, third area and second area.

5. The DNA probe chip according to paragraph 1, wherein a dissociative group having a negative charge on the terminus different from that fixed on the probe fixing area is added to the DNA probe.

6. A method of controlling DNA hybridization comprising the steps of:
adding a sample solution containing a target polynucleotide to between: a DNA probe chip comprising: a substrate; an electrode with a plurality of discrete probe fixing areas formed on the substrate formed thereon; and prespecified DNA probes each fixed on respective probe fixing areas with covalent bonding, the DNA probe constituting at least three areas in the order viewed from the side of the probe fixing area with the DNA probe fixed thereon, a first area being a base sequence substantially complementary to a target polynucleotide; a second area being a base sequence including a base not forming the hydrogen bond complementary to any base among ACGT in the target polynucleotide; and a third area being a base sequence substantially complementary to the target polynucleotide and having a base length thereof equal to or shorter than that of the first area: and a member provided opposing to a surface of the DNA probe chip;
applying prespecified voltage to between the electrode and the sample solution site to condense the polynucleotide in the proximity of a surface of the DNA probe chip; and
inverting electric field for applying to between the electrode and the sample solution site to start hybridization in the state where the probe is stretched.

Twenty-Third Embodiment

1. A DNA probe chip comprising: a substrate; an electrode with a plurality of discrete probe fixing areas formed on the substrate formed thereon; and prespecified DNA probes each fixed with covalent bonding on respective faces of a plurality of pillars in array formed on the electrode face.

2. A DNA hybridization chip having: a structure having probe fixing areas each with a plurality of different DNA probes fixed on the substrate; a structure in which pillars in array are present on each of the probe fixing areas, and space between the pillars forms a valley; a structure of an electrode forming each of the probe fixing areas; and a structure with one end of the DNA probe fixed on a surface of the pillar with covalent bonding.

3. The DNA probe chip according to paragraph 1 or 2, wherein the DNA probe constitutes at least 3 areas in the order viewed from the pillar surface side with the DNA probe fixed thereon, a first area being a base sequence substantially complementary to a target polynucleotide; a second area being a base sequence including a base not forming the hydrogen bond complementary to any base among ACGT in the target polynucleotide; and a third area being a base sequence substantially complementary to the target polynucleotide with a base length thereof and having equal to or shorter than that of the first area.

4. The DNA probe chip according to paragraph 3, wherein the second area includes at least one third or more base sequence noncomplementary to a target polynucleotide.

5. The DNA probe chip according to paragraph 4, wherein the second area includes a base sequence capable of forming the hydrogen bonding with a target polynucleotide, though unstable in terms of energy as compared to AG or CT base pair.

6. The DNA probe chip according to any of paragraphs 3 to 5, wherein stability of hybridization with a target polynucleotide in the first area, second area and third area declines in the order of the first area, third area and second area.

7. A method of controlling DNA hybridization comprising the steps of:

adding a sample solution containing a target polynucleotide to between: a DNA probe chip comprising: a substrate; an electrode with a plurality of discrete probe fixing areas formed on the substrate formed thereon; and prespecified DNA probes each fixed with covalent bonding on respective faces of a plurality of pillars in array formed on the electrode face: and member provided opposing to a surface of the DNA probe chip;

applying prespecified voltage to between the electrode and the sample solution site to condense the polynucleotide into a valley of the pillar on a surface of on the DNA probe chip; and inverting electric field applied to between the electrode and the sample solution site to start hybridization of the target polynucleotide with a probe on the surface of the pillar.

Twenty-Fourth Embodiment

1. A DNA probe chip having a prespecified DNA probe fixed onto a surface of each of the pillars with covalent bonding; a multitude of the pillars being shaped like a cone, truncated cone, or pyramid or truncated prism, and formed on a separate probe fixing area on a substrate; and having an electrode in a valley of the bottom face of each pillar.

2. A DNA probe chip having a prespecified DNA probe fixed onto a surface of each of wells with covalent bonding, a multitude of the wells being shaped like a cone, truncated cone, or pyramid or truncated prism, and formed on a separate probe fixing area on a substrate; and having an electrode on the bottom face of each well.

3. A method of DNA hybridization comprising the steps of:

adding a sample solution containing a target polynucleotide to between: a DNA probe chip having a substrate forming a plurality of pillars shaped like a cone, truncated cone, or pyramid or truncated prism on a plurality of separate probe fixing areas formed on the substrate, having an electrode in a valley formed with each pillar, and also having a prespecified DNA probe fixed onto a surface of each of the pillars with covalent bonding; and a member provided opposing to a surface of the DNA probe chip;

applying prespecified electric field to between the electrode and the sample solution site to condense the polynucleotide into a valley of the pillar on a surface of the DNA probe chip; and inverting the electric field applied to between the electrode and the sample solution site to conduct hybridization of the target polynucleotide with a probe on a surface of the pillar.

4. A method of DNA hybridization comprising the steps of:

adding a sample solution containing a target polynucleotide to between: a DNA probe chip having a substrate, forming a plurality of wells shaped like a cone, truncated cone, or pyramid or truncated prism on a plurality of separate probe fixing areas formed on the substrate configured to provide an electrode on the bottom face of each well, and also having a prespecified DNA probe fixed onto a surface of each of the wells with covalent bonding; and a member provided opposing to a surface of the DNA probe chip;

applying prespecified electric field to between the electrode and the sample solution site to condense the polynucleotide into a well on the DNA probe chip; and inverting the electric field applied to between the electrode and the sample solution site to conduct hybridization of the target polynucleotide with a probe on a surface of the pillar.

Twenty-Fifth Embodiment

1. A biological sample labeling substance being particles for labeling DNA or protein, and made of an alloy of at least two types of transition metal or semiconductor.

2. The biological sample labeling substance according to paragraph 1, wherein each of the particles has a size in a range from 10 nmφ to 50 nmφ.

3. The biological sample labeling substance according to paragraph 1, wherein each of the particles has a size in a range from 10 nmφ to 50 nmφ; and the ratio of elemental composition of the alloy constituting the particles varies, thereby enabling the particles to be classified into a number of different labeling substances in combination with the size thereof.

4. A biological sample labeling substance, being particles for labeling DNA, made of an alloy of at least two types of metal or semiconductor alloy, being a set of particles each having a varied ratio of elemental composition of the alloy, and used by one-to-one correspondence with respect to each sequence of a DNA probe.

5. A biological sample labeling substance, being particles for labeling DNA, made of an alloy of at least two types of metal or semiconductor alloy, being a set of particles each having a varied ratio of elemental composition of the alloy, being used by one-to-one correspondence with respect to an antigen reactive to a prespecified epitope.

6. A method of labeling a biological substance comprising the step of: labeling a biological substance capable of bonding to a biological sample fixed onto a substrate with particles made of an alloy of at least two types of transition metal or semiconductor.

7. A method of testing a biological substance comprising the steps of:

fixing a biological sample on a substrate;

labeling a biological substance capable of bonding to the biological sample with particles made of an alloy of at least two types of transition metal or semiconductor;

subjecting the biological substance labeled with the alloy particles to a reaction with the biological sample; and conducting elemental analysis with respect to each of the alloy particles labeling the biological substance bonding to the biological sample on the substrate.

8. A method of testing a biological substance comprising the steps of:

fixing a biological sample on a substrate;

labeling a biological substance capable of bonding to the biological sample with particles made of an alloy of at least two types of transition metal or semiconductor;

subjecting the biological substance labeled with the alloy particles to a reaction with the biological sample;

scanning the alloy particles labeling the biological substance bonding to the biological sample on the substrate by means of electron beams of a scanning electron microscope for measuring an energy distribution of secondary electron beams derived from a specific element to identify the position and size of the particles; and detecting characteristic X-ray radiated by the particles subjected to the electron beam scanning with a energy dispersive characteristic X-ray detector to obtain the result of elemental analysis.

9. The biological sample labeling substance according to any of paragraphs 1 to 5, wherein the metal or semiconductor is any of transition metal with the atomic number up to 79 other than 43 in the periodic table, metal with the atomic number 13, 31, 32, 49, 50, 51, 81, 82 and 83, and semiconductor with the atomic number 14, 33, 34 and 52.

10. The method of labeling a biological substance according to paragraph 6 to paragraph 7, wherein the metal or semiconductor is any of transition metal with the atomic number up to 79 other than 43 in the periodic table, metal with the atomic number 13, 31, 32, 49, 50, 51, 81, 82 and 83, and semiconductor with the atomic number 14, 33, 34 and 52.

11. The method of testing a biological substance according to paragraph 8, wherein the metal or semiconductor is any of transition metal with the atomic number up to 79 other than 43 in the periodic table, metal with the atomic number 13, 31, 32, 49, 50, 51, 81, 82 and 83, and semiconductor with the atomic number 14, 33, 34 and 52.

Twenty-Sixth Embodiment

1. A method of testing a biological substance comprising the steps of:
obtaining a secondary electron by scanning with electron beams a plurality of particles with a plurality of elements contained therein to obtain an electron beam scanning line image of the particles from the obtained secondary electron;
obtaining an elemental analysis image from the secondary electron obtained by scanning with electron beams a plurality of particles with a plurality of elements contained therein, based on X-ray at a specific wavelength depending on composition element of the particles;
comparing the electron beam scanning image and the elemental analysis image to identify each of the plurality of particles and a position thereof.

2. A biological sample labeling substance using particles with a plurality of elements contained therein as particles for labeling DNA or protein, the plurality of elements being at least two types of transition metal or semiconductor.

3. The biological sample labeling substance according to paragraph 2, wherein each of the particles has a size in a range from 10 nm$\phi$ to 50 nm$\phi$.

4. The biological sample labeling substance according to paragraph 2, wherein each of the particle has a size in a range from 10 nm$\phi$ to 50 nm$\phi$, the ratio of element composition of the alloy constituting the particles varies, thereby enabling particles to be classified into a number of different labeling substances in combination with the size thereof.

5. A biological sample labeling substance having particles for labeling DNA, the particles containing at least two types of transition metal or semiconductor, having a varied ratio of the element composition, and used by one-to-one correspondence with respect to each sequence of a DNA probe.

6. A biological sample labeling substance having particles for labeling DNA, the particles containing at least two types of transition metal or semiconductor, having a varied ratio of the element composition, and used by one-to-one with respect to each sequence of a specific epitope.

7. A method of labeling a biological substance, a biological substance capable of bonding a biological sample fixed on a substrate being labeled with particles containing at least two types of transition metal or semiconductor.

8. A method of testing a biological substance comprising the steps of:
fixing a biological sample on a substrate;
labeling a biological substance capable of bonding the biological sample with particles containing at least two types of transition metal or semiconductor;
subjecting the biological substance labeled with the alloy particles to a reaction with the biological sample; and conducting elemental analysis of the particles labeling the biological substance bonded to the biological sample on the substrate with respect to each particle.

9. A method of testing a biological substance comprising the steps of:
fixing a biological sample on a substrate;
labeling a biological substance capable of bonding the biological sample with particles containing at least two types of transition metal or semiconductor;
subjecting the biological substance labeled with the alloy particles to a reaction with the biological sample;
scanning the particles labeling the biological substance bonded to the biological sample on the substrate with electron beams of a scanning electron microscope for measuring an energy distribution of a secondary electron beam derived from a specific element to identify the position and size of the particles; and
detecting characteristic X-ray generated by the particles scanned with the electron beams utilizing an energy dispersive characteristic X-ray spectrometer to obtain the result of elemental analysis.

10. The biological sample labeled substance according to any of paragraphs 2 to 6, wherein the metal or semiconductor is any of transition metal with the atomic number up to 79 other than 43 in the periodic table, metal with the atomic number 13, 31, 32, 49, 50, 51, 81, 82 and 83, and semiconductor with the atomic number 14, 33, 34 and 52.

11. The method of labeling a biological substance according to paragraph 7 or paragraph 8, wherein the metal or semiconductor is any of transition metal with the atomic number up to 79 other than 43 in the periodic table, metal with the atomic number 13, 31, 32, 49, 50, 51, 81, 82 and 83, and semiconductor with the atomic number 14, 33, 34 and 52.

12. The method of testing a biological substance according to paragraph 9, wherein the metal or semiconductor is any of transition metal with the atomic number up to 79 other than 43 in the periodic table, metal with the atomic number 13, 31, 32, 49, 50, 51, 81, 82 and 83, and semiconductor with the atomic number 14, 33, 34 and 52.

13. Particles for testing a biological substance, the particles having a prespecified size, including a mixture of at least two types of transition metal or semiconductor, and having a surface thereof with a probe having a base sequence complementarily bonded to a biological sample to be detected fixed thereon.

14. The particles for testing a biological substance according to paragraph 13, wherein different probes are fixed onto each of a plurality of the particles having different ratio of elemental composition respectively.

15. The particles for testing a biological substance according to paragraph 13 or paragraph 14, wherein the size of the particles is in a range from 0.5 μm to 5 μmm.

16. The particles for testing a biological substance according to paragraph 14, wherein each of a plurality of the particles is in one-to-one correspondence with respect to an antibody reactive to a specific epitope in a biological sample.

17. A method of testing a biological substance comprising the steps of:
labeling, with respect to each of a plurality of particles having different ratio of elemental composition composed of a prespecified size of a particle including a mixture of at least two types of transition metal or semiconductor, a first group of particles fixed in one-to-one correspondence to various types of ligands having affinity to different biological substance depending on each of the particles, and the biological substance with a second group of particles to complementarily bond each ligand;

scanning each particle of the first group of particles with electron beams to obtain an electron beam scanning line image of the particles from the obtained secondary electron;

obtaining an elemental analysis image from the secondary electron obtained by scanning the first group of particles with electron beams, based on X-ray at a specific wavelength depending on composition element of the particles;

comparing the electron beam scanning image and the elemental analysis image to identify each of the first group of particles and a position thereof; and counting the number of the second group of particles to evaluate the quantity of the biological substance being in the state of ligand to each of the first group of a plurality of particles.

18. Particles for testing a biological substance according to paragraph 13, wherein a plurality types of elements used for a prespecified size of the particles including a mixture of at least two types of transition metal or semiconductor are any of Sc, Ti, Ga, Ge, Y, Zr, Nb, Ru, Rh, Pd, Ag, Cd, In, Sb, La, Ce, Pr, Nd, Sm, Eu, Gd, Tb, Dy, Ho, Er, Tm, Yb, Lu, Hf, Ta, W, Re, Os, Ir, Pt, Au, Tl, Bi and Th.

19. A method of testing a biological substance comprising the steps of:

labeling, with respect to each of a plurality of particles having different ratio of elemental composition composed of a prespecified size of particles including a mixture of at least two types of transition metal or semiconductor, a first group of particles fixed in one-to-one correspondence to various types of ligands having affinity to different biological substance depending on each of the particles, and the biological substance with a second group of particles to complementarily bond each ligand to thereby remove the biological substance together with the first group of particles;

labeling, with respect to each of a plurality of particles having different ratio of elemental composition of a prespecified size of particles including a mixture of at least two types of transition metal or semiconductor, a second group of particles fixed in one-to-one correspondence to various types of ligands having affinity to biological substances different from the various types of ligands having affinity to biological substances for the first group of particles, and the biological substance with a third group of particles to complementarily bond each ligand;

scanning each particle of the first group of particles with electron beams to obtain an electron beam scanning image of the particles from the obtained secondary electron;

obtaining an elemental analysis image from the secondary electron obtained by scanning the second group of particles with electron beams, based on X-ray at a specific wavelength depending on composition element of the particles;

comparing the electron beam scanning image and the elemental analysis image to identify each of the second group of a plurality of particles and a position thereof; and counting the number of the third group of particles to evaluate the quantity of the biological substance being in the state of ligand to each of the second group of a plurality of particles.

Twenty-Seventh Embodiment

1. A method of collecting an electrophoretic separated substance comprising the steps of:

irradiating convergence light to a specific electrophoretic separation band portion of the electrophoretic separation band developed on heat-melting gel; and melting the electrophoretic separation band portion to collect the same.

2. A device for collecting an electrophoretic separated substance comprising: a means for holding an electrophoretic separation gel substrate having a electrophoretic separation band developed on heat-melting gel; a means for detecting a specific electrophoretic separation band portion of the electrophoretic separation band; a means for irradiating convergence light to the detected electrophoretic separation band portion to heat the same; and a means for sucking gel melted by the heating.

3. The device for collecting an electrophoretic separated substance according to paragraph 2, wherein the means for holding an electrophoretic separation gel substrate holds a means for regulating temperature.

4. The device for collecting an electrophoretic separated substance according to paragraph 2, wherein the means for sucking gel melted by the heating is provided with a means for accessing a pipet and a specific electrophoretic separation band portion with the pipet melted thereon.

5. The device for collecting an electrophoretic separated substance according to paragraph 2, wherein the heat-melting gel contains agarose in a quantity at least sufficient to maintain a gel structure thereof.

6. The device for collecting an electrophoretic separated substance according to paragraph 2, wherein the melting point of agarose for the heat-melting gel is 60° C. or below.

7. A heat-melting gel substrate applied to a method of collecting an electrophoretic separated substance comprising the steps of: irradiating convergence light to a specific electrophoretic separation band portion of the electrophoretic separation band developed on heat-melting gel; and melting the electrophoretic separation band portion to collect the same, the heat-melting gel being fixed onto a glass substrate with a thickness of the heat-melting gel not less than 0.02 mm nor more than 0.2 mm.

8. A device for collecting an electrophoretic separated substance configured to have the means for sucking gel melted by heating capable of impressing electric field with a pipet with a first electrode attached to the inside thereof between the first electrode and another electrode provided in a vessel outside.

9. A method of collecting an electrophoretic separated substance comprising the steps of:

filling the pipet with an electrolysis solution in advance;

sucking gel melted by convergence light;

lowering the temperature of the gel sucked in the pipet to turn the same into gel again;

contacting a pipet chip tip section with a vessel filled with an electrolysis solution;

impressing electric field between a first electrode contacting the electrolysis solution in the pipet and a second electrode in the vessel, taking the second electrode as positive pole, to subject an electrophoretic separated substance contained in the gel solidifying in the pipet chip to electrophoresis to elute the same in the electrolysis solution in the vessel.

Twenty-Eighth Embodiment

1. A cell crushing device comprising: a substrate for holding a droplet including a prespecified cell on a surface thereof; and an optical system for irradiating convergence light including a band absorbed by the cell to the droplet.

2. The cell crushing device according to paragraph 1, wherein the substrate for holding a droplet including a prespecified cell in a hydrophilic area thereof is configured to have a hydrophilic area surrounded by a water-repellent area and having a range smaller than the size of the droplet.

3. A cell crushing device comprising: a pipet capable of holding a solution with a plurality of cells included therein, and having a tip opening in a diameter suited for a prespecified size of a cell or a cell mass to pass therethrough; a means for observing a cell on the pipet tip; a means for pressing out the solution including a plurality of cells on the pipet tip section from the inside of the pipet to form a droplet; a means for determining the formation of a droplet including a prespecified cell and having a prespecified size; a unit for dropping the droplet formed on the pipet chip section to a prespecified position on the substrate; and an optical system irradiating convergence light including a band absorbed by the cell to the droplet.

4. A method of crushing a cell comprising the steps of:

holding a droplet including a cell in a hydrophilic area on a substrate, the hydrophilic area surrounded by a water repellent area and having an area smaller than the size of the cell; and irradiating convergence light including a band optically absorbed by a cell in the droplet.

Twenty-Ninth Embodiment

1. A high speed trace quantity reactor comprising: a means for transferring droplets each containing different reaction precursors respectively to collide to one another; and a detecting means for tracking reaction of the collided droplets.

2. A high speed trace quantity reactor comprising: a means for transferring droplets each containing different reaction precursors respectively to collide to one another; a means for stirring the collided droplets; and a detecting means for tracking reaction of the collided droplets.

3. A method of trace quantity reaction comprising the steps of:

dissolving a plurality of reaction precursors targeted to be reacted, in respective different droplets;

putting each of the droplets in different positions on a substrate; and making each of the droplets collide to one another on the substrate to cause reactions.

4. A method of trace quantity reaction comprising the steps of:

putting each of a droplet with a cell inserted therein and a droplet including a heterologous cell active substance in different positions on a substrate; and making each of the droplets collide to one another on the substrate to observe effects on the cell.

Thirtieth Embodiment

1. An absorption spectroscopy system comprising: a means for forming a droplet containing solute on a substrate; a means for transferring the droplet as crossing a beam of light; a source of the beam of light; and a light detector for detecting a signal obtained when the droplet crosses the beam of light.

2. An absorption spectroscopy system comprising: a means for forming a droplet containing solute on a substrate; a means for focusing a beam of light on the droplet; and a light detector for detecting intensity of light passing through the droplet.

3. A fluorescence spectroscopy system comprising: a means for forming a droplet containing solute on a substrate; a means for transferring the droplet as crossing a beam of light; a source of the beam of light; and a light detector for detecting a signal obtained when the droplet crosses the beam of light.

4. An absorption spectroscopy system comprising: a substrate with hydrophilic patterns for holding a droplet on a water repellent face provided thereon; a means for transferring the droplet formed on the substrate as the droplet crosses a beam of light on the hydrophilic patterns; a source of the beam of light; a light detector for detecting a signal obtained when the droplet crosses the beam of light; a measuring means for measuring the size of the droplet transferring as crossing the beam of light on the hydrophilic patterns; and a computing device for computing the light path length based on the measured size of the droplet.

5. An spectroscopy system comprising: an absorption spectroscopy system comprising; a substrate with hydrophilic patterns for holding a droplet on a water repellent face provided thereon, a means for transferring the droplet formed on the substrate utilizing a surface acoustic wave as the droplet crosses a beam of light on the hydrophilic patterns, a source of the beam of light, and a light detector for detecting a signal obtained when the droplet crosses the beam of light; and a computing device for estimating the size of the droplet by a temporal change of a position of the droplet to compute the light path length.

6. The spectroscopy system according to paragraph 5, wherein a means for generating the surface acoustic wave is a piezoelectric substrate provided in a droplet transfer path, and a comb-shaped electrode made of lithium tetraborate or lithium tantarate or lithium niobate.

7. The absorption spectroscopy system according to paragraph 4, wherein the substrate is equipped with a temperature control plate contacting thereto.

8. A spectroscopic method comprising the steps of:

providing a droplet on a line of a substrate with hydrophilic line patterns for holding a droplet on a water repellent face provided thereon;

transferring the droplet along the hydrophilic line patterns; detecting a signal including information on the droplet obtained when the droplet is transferred as crossing a beam of light irradiated from a light source; measuring the size of the droplet from the signal; computing the light path length of the light passing through the droplet based on the seize of the measured droplet; and measuring light absorption or fluorescence of the droplet.

9. The spectroscopy system for measuring light absorption or fluorescence of a droplet according to paragraph 5, wherein the hydrophilic line patterns have a pattern with a plurality of hydrophilic lines converge thereon, and each droplet held on a plurality of the hydrophilic lines are mixed at a convergent point of the pattern.

10. The spectroscopic method for measuring light absorption or fluorescence of a droplet according to paragraph 6, wherein the hydrophilic line patterns have a pattern with a plurality of hydrophilic lines converge thereon, have another convergent point downstream of the convergent point described above, and have patterns allowing a plurality of times of time-series mixing at a convergent point of each of the droplets held in the plurality of hydrophilic lines.

What is claimed is:

1. A method of separating a target cell comprising the steps of:

incubating cells with a specific labeling material so that the specific labeling material is taken into a target cell by a transporter;

optically detecting said specific labeling material taken into the target cell; and separating the target cell based on the detecting of the specific labeling material taken into target cell, wherein said specific labeling material is optically detectable, and wherein said step of separating the target cell based on the detecting of the specific labeling material taken into the target cell comprises a cell separation chip, wherein said chip comprises;

a flow path for introducing a fluid containing a target cell with a specific labeling material taken into a cell separation area by a transporter, and a sample hole connected to the flow path for feeding a fluid containing the target cell;

a buffer flow path provided in parallel with the flow path with a fluid containing the target cell in the cell separation area introduced therein, and a buffer hole connected to the flow path for feeding a buffer;

a flow path located on the downstream side from the position in which the flow path introducing a fluid containing the target cell in the cell separation area and the butter flow path converge, for observing a cell in the which the liquid containing a target cell and a buffer-combined fluid flow as a laminar flow;

the cell separation area comprising: two openings for gel electrodes formed on the downstream of the flow path for observing a cell, facing to each other on both sides of the flow path, and placed in a position slightly deviated from the flow direction; a target cell collecting flow path located in an imaginary line extended from the flow path; and a cell discharge flow path branching out from the flow path;

a hole for feeding the gel electrodes with a gel electrode material;

a hole connected to the cell discharging flow path for accommodating a liquid containing a discharged cell;

a cell dialysis section provided on the downstream side of the target cell collecting flow path;

a collecting flow path passing therethrough a fluid containing a target cell having passed through the cell dialysis section and a hole connected to the collecting flow path for accommodating a fluid containing the collected cell;

a buffer retention bath for feeding a buffer provided in a common communication with the sample hole for feeding a fluid containing a target cell and a buffer hole for feeding a buffer;

a buffer retention bath provided in communication with the hole for accommodating a fluid containing a fluid containing a discharged cell, for accommodating a discharged cell and a buffer; and a buffer retention bath provided in communication with the hole for accommodating a fluid containing a collected cell, for accommodating target cell and a buffer;

the cell dialysis section comprising;

a dialysis area for dialyzing the collected cell via a pre-specified porous membrane to discharge a specific labeling material;

a buffer retention bath for feeding a buffer not containing a specific labeling material in the dialysis area; and a buffer retention bath for collecting a buffer after dialysis.

2. The method of separating a target cell according to claim 1, wherein said step of incubating cells with a specific labeling material comprises step of cultivating said cells under a pre-specified condition for a pre-specified period of time; and said step of separating the target cell based on the detecting of the specific labeling material taken into the target cell comprises a step of exposing the target cell to a solution which does not contain the specific labeling material for a pre-specified period of time.

3. The method of separating a target cell according to claim 1, wherein said step of incubating cells with a specific labeling material is conducted using a tissue fragment with said target cell contained therein, and then, dispersing the cells.

4. The method of separating a target cell according to claim 1, wherein said cell separation chip comprises:

a substrate having a pre-specified thickness and size;

each of the flow paths and the gel electrodes formed on the bottom face of the substrate;

a hole communicating with each of the flow paths and the gel electrodes formed the bottom face of the substrate and penetrating the substrate;

a translucent thin film attached onto the bottom face of the substrate, a retention bath communicating with the flow path provided on the top face of the substrate;

the cell dialysis section including a flow path provided between a flow path in the downstream region of the cell separation area and the hole, and communicating from the bottom face to the top face of the substrate; and a porous membrane provided on the top face of the substrate in the cell dialysis section, a space for circulating a buffer not containing a specific labeling material for dialyzing the collected cell, and a retention bath for feeding the space with buffer.

5. The method of separating a target cell according to claim 1, wherein said specific labeling material is selected from the group consisting of a sugar, an amino acid, an oligopeptide and a medicament; and wherein said specific labeling material is labeled with a fluorescent material.

6. The method of separating a target cell according to claim 5, wherein said specific labeling material is selected from the group consisting of glucose, fructose, galactose, glycine, glutamic acid, aspartic acid, alanine, serine, threonine, cystein, glutamine, asparagine, arginine, β-aminobutyric acid, Y-aminobutylic acid, dipeptide, tripeptide, $(Arg)_n$ (n=6~8), noradrenaline, dopamine, serotonin, lactoferrin, fibroblast growth factor, Herpes simplex virus type 1 protein 22, Herpes simplex virus type 1 transactivator protein, Engrailed, thiamine, folic acid, eicosanoids, prostaglandin, L-ascorbic acid, and a nucleoside.

7. The method of separating a target cell according to claim 5, wherein said fluorescent material is a derivative of 6-(N-(7-nitrobenz-2-oxa-1.3-diazol-4-yl) or a derivative of 4,4-difluoro-4-bora-3a,4a-diaza-s-indacene.

* * * * *